(12) United States Patent
Singh et al.

(10) Patent No.: US 7,582,648 B2
(45) Date of Patent: *Sep. 1, 2009

(54) METHODS OF TREATING OR PREVENTING AUTOIMMUNE DISEASES WITH 2,4-PYRIMIDINEDIAMINE COMPOUNDS

(75) Inventors: Rajinder Singh, Belmont, CA (US); Ankush Argade, Foster City, CA (US); Hui Li, Millbrae, CA (US); Holger Keim, Menlo Park, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 285 days.

This patent is subject to a terminal disclaimer.

(21) Appl. No.: 11/539,142

(22) Filed: Oct. 5, 2006

(65) Prior Publication Data

US 2008/0312438 A1  Dec. 18, 2008

Related U.S. Application Data

(63) Continuation of application No. 10/903,263, filed on Jul. 30, 2004.

(60) Provisional application No. 60/572,246, filed on May 18, 2004, provisional application No. 60/531,598, filed on Dec. 19, 2003, provisional application No. 60/491,641, filed on Jul. 30, 2003.

(51) Int. Cl.
*C07D 239/48* (2006.01)
*C07D 403/12* (2006.01)
*C07D 403/14* (2006.01)
*A61K 31/506* (2006.01)
*A61P 19/02* (2006.01)

(52) U.S. Cl. .................. 514/275; 544/323; 544/324

(58) Field of Classification Search .................. 544/323, 544/324; 514/275
See application file for complete search history.

(56) References Cited

U.S. PATENT DOCUMENTS

| | | | |
|---|---|---|---|
| 3,159,547 A | 12/1964 | Hollis et al. |
| 3,320,256 A | 5/1967 | Duschinsky et al. |
| 4,166,452 A | 9/1979 | Generales, Jr. et al. |
| 4,256,108 A | 3/1981 | Theeuwes |
| 4,265,874 A | 5/1981 | Bonsen et al. |
| 4,713,388 A | 12/1987 | Ezer et al. |
| 4,866,048 A | 9/1989 | Calverley et al. |
| 4,968,781 A | 11/1990 | Seitz et al. |
| 4,983,608 A | 1/1991 | Effland et al. |
| 5,147,876 A | 9/1992 | Mizuchi et al. |
| 5,179,204 A | 1/1993 | Effland et al. |
| 5,194,431 A | 3/1993 | Deluca et al. |
| 5,200,400 A | 4/1993 | Teramoto et al. |
| 5,206,229 A | 4/1993 | Calverley et al. |
| 5,223,505 A | 6/1993 | Hargreaves et al. |
| 5,246,948 A | 9/1993 | Takatani et al. |
| 5,292,728 A | 3/1994 | Neef et al. |
| 5,420,129 A | 5/1995 | Breu et al. |
| 5,446,035 A | 8/1995 | Neef et al. |
| 5,521,184 A | 5/1996 | Zimmerman |
| 5,532,228 A | 7/1996 | Neef et al. |
| 5,585,381 A | 12/1996 | Yanaka et al. |
| 5,700,904 A | 12/1997 | Baker et al. |
| 5,728,536 A | 3/1998 | Ihle et al. |
| 5,840,893 A | 11/1998 | Bukrinsky et al. |
| 5,859,032 A | 1/1999 | Nishino et al. |
| 5,863,924 A | 1/1999 | Berger et al. |
| 5,958,935 A | 9/1999 | Davis et al. |
| 5,985,856 A | 11/1999 | Stella et al. |
| 6,004,985 A | 12/1999 | Kochanny et al. |
| 6,022,884 A | 2/2000 | Mantlo et al. |
| 6,048,866 A | 4/2000 | Hutchings et al. |
| 6,069,141 A | 5/2000 | Barbachyn et al. |
| 6,080,747 A | 6/2000 | Uckun et al. |
| 6,080,748 A | 6/2000 | Uckun et al. |
| 6,080,858 A | 6/2000 | Schumacher |
| 6,093,716 A | 7/2000 | Davis et al. |
| 6,127,376 A | 10/2000 | Davey et al. |
| 6,133,305 A | 10/2000 | Tang et al. |
| 6,177,433 B1 | 1/2001 | Uckun et al. |
| 6,197,779 B1 | 3/2001 | Andries et al. |
| 6,200,977 B1 | 3/2001 | Cushing et al. |
| 6,210,654 B1 | 4/2001 | Ihle et al. |

(Continued)

FOREIGN PATENT DOCUMENTS

AU  748087 B2  8/1999

(Continued)

OTHER PUBLICATIONS

Wolff Manfred E. "Burger's Medicinal Chemistry, 5ed, Part 1", John Wiley & Sons, 1995, pp. 975-977.*

(Continued)

*Primary Examiner*—Venkataraman Balasubramanian
(74) *Attorney, Agent, or Firm*—McDonnell Boehnen Hulbert & Berghoff LLP

(57) ABSTRACT

The present invention provides methods of treating or preventing autoimmune diseases with 2,4-pyrimidinediamine compounds, as well as methods of treating, preventing or ameliorating symptoms associated with such diseases. Specific examples of autoimmune diseases that can be treated or prevented with the compounds include rheumatoid arthritis and/or its associated symptoms, systemic lups erythematosis and/or its associated symptoms and multiple sclerosis and/or its associated symptoms.

3 Claims, 3 Drawing Sheets

U.S. PATENT DOCUMENTS

Figure 1:
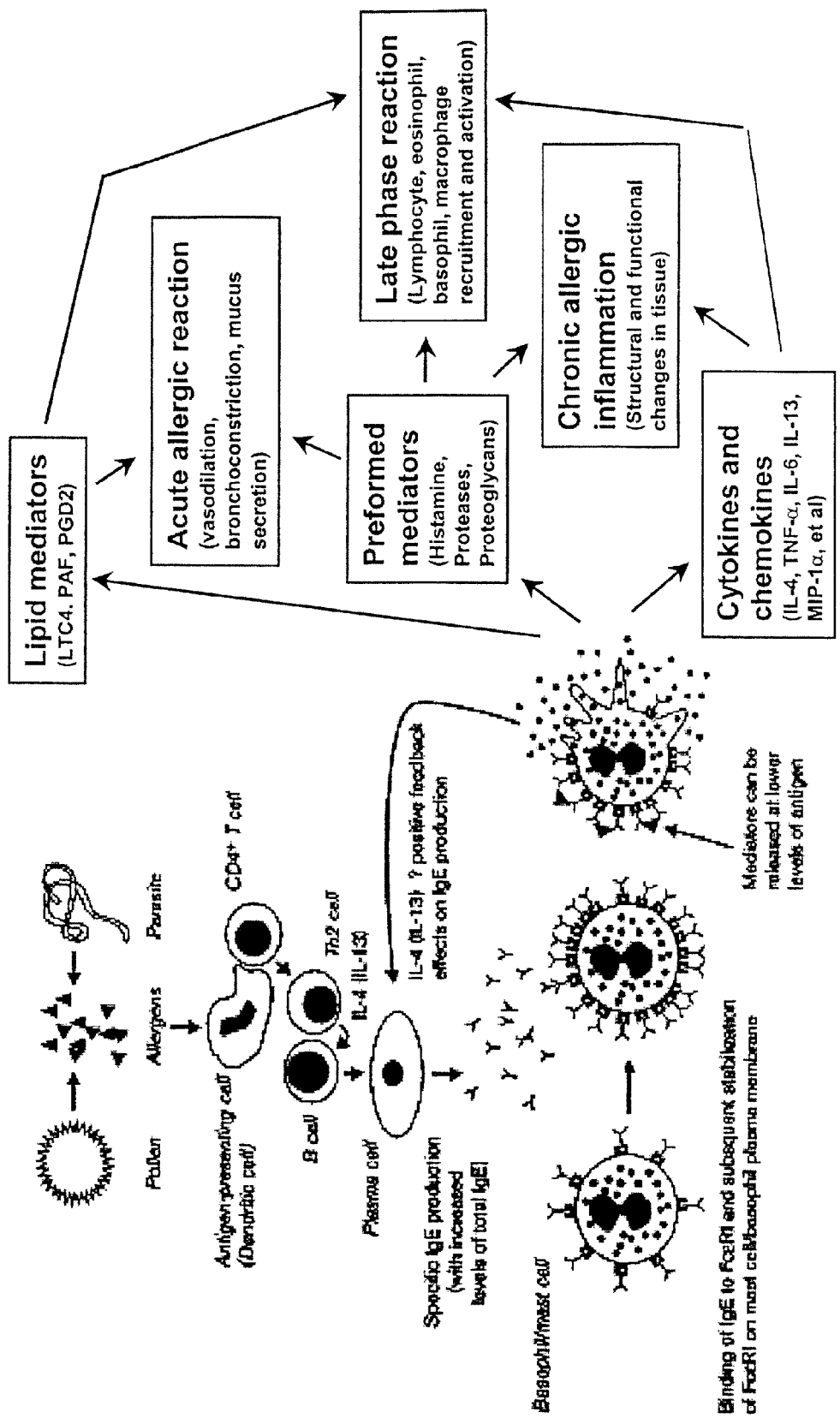

| | | |
|---|---|---|
| 6,235,746 B1 | 5/2001 | Davis et al. |
| 6,242,434 B1 | 6/2001 | Bishop et al. |
| 6,284,730 B1 | 9/2001 | Dietrich et al. |
| 6,313,130 B1 | 11/2001 | Uckun et al. |
| 6,316,635 B1 | 11/2001 | Tang et al. |
| 6,337,335 B1 | 1/2002 | Hutchings et al. |
| 6,342,503 B1 | 1/2002 | Aldrich et al. |
| 6,372,751 B1 | 4/2002 | Davey et al. |
| 6,432,963 B1 | 8/2002 | Hisamichi et al. |
| 6,433,018 B1 | 8/2002 | Siddiqui et al. |
| 6,440,986 B2 | 8/2002 | Andries et al. |
| 6,448,401 B1 | 9/2002 | Chen et al. |
| 6,486,185 B1 | 11/2002 | McMahon et al. |
| 6,489,333 B2 | 12/2002 | Pitts et al. |
| 6,506,763 B2 | 1/2003 | Tang et al. |
| 6,525,051 B2 | 2/2003 | Davey et al. |
| 6,528,509 B1 | 3/2003 | Hale et al. |
| 6,528,513 B2 | 3/2003 | Cushing et al. |
| 6,531,279 B1 | 3/2003 | Blumenfeld |
| 6,534,524 B1 | 3/2003 | Kania et al. |
| 6,573,295 B2 | 6/2003 | Shakespeare et al. |
| 6,579,983 B1 | 6/2003 | Batchelor |
| 6,586,594 B1 | 7/2003 | Butters et al. |
| 6,593,326 B1 | 7/2003 | Bradbury et al. |
| 6,593,357 B1 | 7/2003 | Green et al. |
| 6,608,048 B2 | 8/2003 | Tsou et al. |
| 6,610,688 B2 | 8/2003 | Liang et al. |
| 6,635,651 B2 | 10/2003 | Uckun |
| 6,673,908 B1 | 1/2004 | Stanton |
| 6,677,368 B2 | 1/2004 | Cui et al. |
| 6,683,082 B2 | 1/2004 | Tang et al. |
| 6,696,448 B2 | 2/2004 | Tang et al. |
| 6,699,865 B2 | 3/2004 | Hale et al. |
| 6,710,052 B2 | 3/2004 | Pease et al. |
| 6,762,179 B2 | 7/2004 | Cochran et al. |
| 6,777,417 B2 | 8/2004 | Liang et al. |
| 6,777,441 B2 | 8/2004 | Wang et al. |
| 6,784,195 B2 | 8/2004 | Hale et al. |
| 6,815,439 B2 | 11/2004 | Harris et al. |
| 6,825,190 B2 | 11/2004 | Moon et al. |
| 6,835,722 B1 | 12/2004 | Kang et al. |
| 6,849,641 B1 | 2/2005 | Tang et al. |
| 6,897,207 B2 | 5/2005 | Cox et al. |
| 6,897,208 B2 | 5/2005 | Edwards et al. |
| 6,908,920 B2 | 6/2005 | Thomas et al. |
| 6,939,874 B2 | 9/2005 | Harmange et al. |
| 6,949,580 B2 | 9/2005 | Hale et al. |
| 6,969,760 B2 | 11/2005 | Ihle et al. |
| RE38,934 E | 1/2006 | Gutman et al. |
| 6,998,391 B2 | 2/2006 | Lyons et al. |
| 7,056,944 B2 | 6/2006 | Hale et al. |
| 7,060,827 B2 | 6/2006 | Singh et al. |
| 7,070,996 B2 | 7/2006 | Rossi et al. |
| 7,074,793 B2 | 7/2006 | Hudkins et al. |
| 7,105,529 B2 | 9/2006 | Davis et al. |
| 7,105,530 B2 | 9/2006 | Boloor et al. |
| 7,115,617 B2 | 10/2006 | Buchanan et al. |
| 7,122,542 B2 | 10/2006 | Singh et al. |
| 7,122,552 B2 | 10/2006 | Ledford |
| 7,153,964 B2 | 12/2006 | Pease et al. |
| 7,279,469 B2 | 10/2007 | Pierce et al. |
| 7,321,041 B2 | 1/2008 | Cywin et al. |
| 2001/0007033 A1 | 7/2001 | Tang et al. |
| 2002/0115173 A1 | 8/2002 | Ben-Sasson |
| 2002/0137141 A1 | 9/2002 | Ben-Sasson |
| 2003/0134838 A1 | 7/2003 | Bornemann et al. |
| 2003/0165873 A1 | 9/2003 | Come et al. |
| 2003/0171359 A1 | 9/2003 | Dahmann et al. |
| 2004/0029902 A1 | 2/2004 | Singh et al. |
| 2004/0043388 A1 | 3/2004 | Come et al. |
| 2004/0063737 A1 | 4/2004 | Lucking et al. |
| 2004/0097504 A1 | 5/2004 | Ebethiel et al. |
| 2004/0102455 A1 | 5/2004 | Burns et al. |
| 2004/0102630 A1 | 5/2004 | Brumby et al. |
| 2004/0106615 A1 | 6/2004 | Cochran et al. |
| 2004/0122029 A1 | 6/2004 | Liu et al. |
| 2004/0142404 A1 | 7/2004 | Wilks et al. |
| 2004/0142947 A1 | 7/2004 | Cox et al. |
| 2004/0147507 A1 | 7/2004 | Ledeboer et al. |
| 2004/0198750 A1 | 10/2004 | Green et al. |
| 2005/0004152 A1 | 1/2005 | Cochran et al. |
| 2005/0009876 A1 | 1/2005 | Bhagwat et al. |
| 2005/0026914 A1 | 2/2005 | Buchanan et al. |
| 2005/0038243 A1 | 2/2005 | Singh et al. |
| 2005/0054732 A1 | 3/2005 | Meguro et al. |
| 2005/0113398 A1 | 5/2005 | Argade et al. |
| 2005/0176743 A1 | 8/2005 | Luecking et al. |
| 2005/0192301 A1 | 9/2005 | Li et al. |
| 2005/0209230 A1 | 9/2005 | Singh et al. |
| 2005/0209246 A1 | 9/2005 | Ueda et al. |
| 2005/0234049 A1 | 10/2005 | Singh et al. |
| 2005/0272753 A1 | 12/2005 | Nagashima et al. |
| 2006/0025410 A1 | 2/2006 | Singh et al. |
| 2006/0035891 A1 | 2/2006 | Li et al. |
| 2006/0035916 A1 | 2/2006 | Singh et al. |
| 2006/0047135 A1 | 3/2006 | Chadwick et al. |
| 2006/0058292 A1 | 3/2006 | Singh et al. |
| 2006/0058525 A1 | 3/2006 | Singh et al. |
| 2006/0111378 A1 | 5/2006 | Cleve et al. |
| 2006/0135543 A1 | 6/2006 | Singh et al. |
| 2006/0167249 A1 | 7/2006 | Argade et al. |
| 2006/0167254 A1 | 7/2006 | Cooper et al. |
| 2006/0178407 A1 | 8/2006 | Argade et al. |
| 2006/0211657 A1 | 9/2006 | Singh et al. |
| 2006/0234983 A1 | 10/2006 | Singh et al. |
| 2006/0270694 A1 | 11/2006 | Wong |
| 2006/0293311 A1 | 12/2006 | Li et al. |
| 2007/0004626 A1 | 1/2007 | Masuda et al. |
| 2007/0060603 A1 | 3/2007 | Singh et al. |
| 2007/0129360 A1 | 6/2007 | Bhamidipati et al. |
| 2007/0129362 A1 | 6/2007 | Bhamidipati et al. |
| 2007/0191405 A1 | 8/2007 | Noronha et al. |
| 2007/0197782 A1 | 8/2007 | Clough et al. |
| 2007/0203161 A1 | 8/2007 | Argade et al. |
| 2007/0203162 A1 | 8/2007 | Li et al. |
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299095 A1 | 12/2007 | Singh et al. |
| 2008/0039622 A1 | 2/2008 | Singh et al. |
| 2008/0194603 A1 | 8/2008 | Li et al. |
| 2008/0221089 A1 | 9/2008 | Argade et al. |
| 2008/0260754 A1 | 10/2008 | Li et al. |
| 2008/0279867 A1 | 11/2008 | Atuegbu et al. |

FOREIGN PATENT DOCUMENTS

| | | |
|---|---|---|
| CA | 2542492 | 4/2005 |
| DE | 4029650 A1 | 3/1992 |
| EP | 0 139 613 | 8/1984 |
| EP | 0 248 348 | 5/1987 |
| EP | 0 432 893 | 6/1991 |
| EP | 0 525 768 A1 | 2/1993 |
| EP | 1 056 742 B1 | 12/2000 |
| GB | 2373186 | 9/2002 |
| JP | 63008387 | 1/1988 |
| JP | 03/127790 A | 5/1991 |
| JP | 04178385 | 6/1992 |
| SU | 1499883 A1 | 10/1991 |
| WO | WO 90/12790 A1 | 11/1990 |
| WO | WO 91/18887 A1 | 12/1991 |
| WO | WO 95/03701 A1 | 2/1995 |
| WO | WO 95/19358 A1 | 7/1995 |

| | | | | | | | |
|---|---|---|---|---|---|---|---|
| WO | WO 97/19065 A1 | 5/1997 | | WO | WO 03/000186 A2 | 1/2003 |
| WO | WO 98/33798 | 8/1998 | | WO | WO 03/000688 | 1/2003 |
| WO | WO 98/41512 A1 | 9/1998 | | WO | WO 03/000695 | 1/2003 |
| WO | WO 99/15500 A1 | 4/1999 | | WO | WO 03/002542 A1 | 1/2003 |
| WO | WO 99/24874 A1 | 5/1999 | | WO | WO 03/002544 A1 | 1/2003 |
| WO | WO 99/31073 | 6/1999 | | WO | WO 03/016306 A1 | 2/2003 |
| WO | WO 99/33846 | 7/1999 | | WO | WO 03/018022 A1 | 3/2003 |
| WO | WO 99/41253 A1 | 8/1999 | | WO | WO 03/020698 | 3/2003 |
| WO | WO 99/47529 | 9/1999 | | WO | WO 03/108021 A1 | 3/2003 |
| WO | WO 99/50249 A2 | 10/1999 | | WO | WO 03/026664 A1 | 4/2003 |
| WO | WO 99/50250 A1 | 10/1999 | | WO | WO 03/026665 A1 | 4/2003 |
| WO | WO 99/50251 A2 | 10/1999 | | WO | WO 03/026666 A1 | 4/2003 |
| WO | WO 99/61437 A1 | 12/1999 | | WO | WO 03/030909 A1 | 4/2003 |
| WO | WO 00/00202 A1 | 1/2000 | | WO | WO 03/032994 A2 | 4/2003 |
| WO | WO 00/10981 A1 | 3/2000 | | WO | WO 03/032997 A1 | 4/2003 |
| WO | WO 00/12485 A1 | 3/2000 | | WO | WO 03/040141 A1 | 5/2003 |
| WO | WO 00/27802 | 5/2000 | | WO | WO 03/045923 A1 | 6/2003 |
| WO | WO 00/27825 A1 | 5/2000 | | WO | WO 03/048133 A1 | 6/2003 |
| WO | WO 00/27826 A1 | 5/2000 | | WO | WO 03/048162 A1 | 6/2003 |
| WO | WO 00/33844 A1 | 6/2000 | | WO | WO 03/055489 A1 | 7/2003 |
| WO | WO 00/39101 A1 | 7/2000 | | WO | WO 03/062225 A1 | 7/2003 |
| WO | WO 00/47583 A1 | 8/2000 | | WO | WO 03/063794 A2 | 8/2003 |
| WO | WO 00/51587 A2 | 9/2000 | | WO | WO 03/066601 A1 | 8/2003 |
| WO | WO 00/55159 A2 | 9/2000 | | WO | WO 03/074515 A1 | 9/2003 |
| WO | WO 00/56714 | 9/2000 | | WO | WO 03/076437 A1 | 9/2003 |
| WO | WO 00/58305 A1 | 10/2000 | | WO | WO 03/078404 A1 | 9/2003 |
| WO | WO 00/59893 A1 | 10/2000 | | WO | WO 03/080047 | 10/2003 |
| WO | WO 00/63182 A2 | 10/2000 | | WO | WO 03/094920 A1 | 11/2003 |
| WO | WO 00/76980 A1 | 12/2000 | | WO | WO 03/101989 A1 | 12/2003 |
| WO | WO 00/78731 A1 | 12/2000 | | WO | WO 03/106416 A2 | 12/2003 |
| WO | WO 01/09134 A1 | 2/2001 | | WO | WO 2004/002964 A1 | 1/2004 |
| WO | WO 01/22938 A1 | 4/2001 | | WO | WO 2004/014382 A1 | 2/2004 |
| WO | WO 01/23362 A2 | 4/2001 | | WO | WO 2004/014384 | 2/2004 |
| WO | WO 01/23389 A2 | 4/2001 | | WO | WO 2004/016597 A2 | 2/2004 |
| WO | WO 01/30782 | 5/2001 | | WO | WO 2004/039359 A2 | 5/2004 |
| WO | WO 01/42246 A2 | 6/2001 | | WO | WO 2004/041789 A1 | 5/2004 |
| WO | WO 01/45641 A2 | 6/2001 | | WO | WO 2004/041810 A1 | 5/2004 |
| WO | WO 01/47897 A1 | 7/2001 | | WO | WO 2004/041814 A1 | 5/2004 |
| WO | WO 01/52852 | 7/2001 | | WO | WO 2004/043467 A1 | 5/2004 |
| WO | WO 01/52892 A2 | 7/2001 | | WO | WO 2004/043953 A1 | 5/2004 |
| WO | WO 01/56993 A2 | 8/2001 | | WO | WO 2004/046112 A2 | 6/2004 |
| WO | WO 01/57022 A2 | 8/2001 | | WO | WO 2004/046118 A2 | 6/2004 |
| WO | WO 01/60816 A1 | 8/2001 | | WO | WO 2004/046120 | 6/2004 |
| WO | WO 01/64654 A1 | 9/2001 | | WO | WO 2004/047843 A1 | 6/2004 |
| WO | WO 01/64655 A1 | 9/2001 | | WO | WO 2004/048343 A1 | 6/2004 |
| WO | WO 01/64656 A1 | 9/2001 | | WO | WO 2004/050068 A1 | 6/2004 |
| WO | WO 01/72744 A1 | 10/2001 | | WO | WO 2004/052359 | 6/2004 |
| WO | WO 01/72758 A1 | 10/2001 | | WO | WO 2004/054617 A1 | 7/2004 |
| WO | WO 01/85699 A2 | 11/2001 | | WO | WO 2004/056786 A2 | 7/2004 |
| WO | WO 01/85700 A2 | 11/2001 | | WO | WO 2004/058749 A1 | 7/2004 |
| WO | WO 02/00661 A1 | 1/2002 | | WO | WO 2004/058753 A2 | 7/2004 |
| WO | WO 02/04429 A1 | 1/2002 | | WO | WO 2004/069812 A1 | 8/2004 |
| WO | WO 02/16306 | 2/2002 | | WO | WO 2004/074244 A2 | 9/2004 |
| WO | WO 02/22601 A1 | 3/2002 | | WO | WO 2004/074261 A1 | 9/2004 |
| WO | WO 02/43735 A1 | 6/2002 | | WO | WO 2004/074262 A1 | 9/2004 |
| WO | WO 02/45652 A2 | 6/2002 | | WO | WO 2004/080980 A1 | 9/2004 |
| WO | WO 02/48336 A2 | 6/2002 | | WO | WO 2004/085388 | 10/2004 |
| WO | WO 02/50066 A2 | 6/2002 | | WO | WO 2004/092154 | 10/2004 |
| WO | WO 02/059110 A1 | 8/2002 | | WO | WO 2004/099159 A1 | 11/2004 |
| WO | WO 02/059112 A2 | 8/2002 | | WO | WO 2004/101549 A1 | 11/2004 |
| WO | WO 02/060492 A1 | 8/2002 | | WO | WO 2004/101564 A1 | 11/2004 |
| WO | WO 02/060927 A1 | 8/2002 | | WO | WO 2005/007621 A2 | 1/2005 |
| WO | WO 02/062789 A1 | 8/2002 | | WO | WO 2005/007646 A1 | 1/2005 |
| WO | WO 02/064096 A2 | 8/2002 | | WO | WO 2004/009957 A1 | 2/2005 |
| WO | WO 02/066461 A1 | 8/2002 | | WO | WO 2005/009980 A1 | 2/2005 |
| WO | WO 02/066480 A2 | 8/2002 | | WO | WO 2005/012262 A1 | 2/2005 |
| WO | WO 02/066481 | 8/2002 | | WO | WO 2005/012294 | 2/2005 |
| WO | WO 02/068409 | 9/2002 | | WO | WO 2005/012304 A2 | 2/2005 |
| WO | WO 02/096888 A1 | 12/2002 | | WO | WO 2005/012307 A1 | 2/2005 |
| WO | WO 02/096905 | 12/2002 | | WO | WO 2005/013982 | 2/2005 |
| WO | WO 02/096909 A1 | 12/2002 | | WO | WO 2005/013996 | 2/2005 |
| WO | WO 02/102313 A2 | 12/2002 | | WO | WO 2005/016344 A1 | 2/2005 |
| WO | WO 02/102800 A1 | 12/2002 | | WO | WO 2005/016893 A2 | 2/2005 |

| WO | WO 2005/016894 A1 | 2/2005 |
| --- | --- | --- |
| WO | WO 2005/026130 A1 | 3/2005 |
| WO | WO 2005/026158 A1 | 3/2005 |
| WO | WO 2005/027848 A2 | 3/2005 |
| WO | WO 2005/028467 A1 | 3/2005 |
| WO | WO 2005/028475 A2 | 3/2005 |
| WO | WO 2005/028479 A2 | 3/2005 |
| WO | WO 2005/033107 A1 | 4/2005 |
| WO | WO 2005/037800 | 4/2005 |
| WO | WO 2005/051366 A2 | 6/2005 |
| WO | WO 2005/061458 A2 | 7/2005 |
| WO | WO 2005/066156 A1 | 7/2005 |
| WO | WO 2005/075468 A2 | 8/2005 |
| WO | WO 2005/080393 A1 | 9/2005 |
| WO | WO 2005/107760 A1 | 11/2005 |
| WO | WO 2005/118544 | 12/2005 |
| WO | WO 2006/021454 | 3/2006 |
| WO | WO 2006/026274 | 3/2006 |
| WO | WO 2006/034872 | 4/2006 |
| WO | WO 2006/074057 | 7/2006 |
| WO | WO 2006/078846 | 7/2006 |
| WO | WO 2006/133426 | 12/2006 |
| WO | WO 2007/006926 | 1/2007 |
| WO | WO 2007/014846 | 2/2007 |
| WO | WO 2007/032263 | 3/2007 |
| WO | WO 2007/053452 | 5/2007 |
| WO | WO 2007/059611 | 5/2007 |
| WO | WO 2007/085540 | 8/2007 |
| WO | WO 2007/085833 | 8/2007 |
| WO | WO 2007/098507 | 8/2007 |
| WO | WO 2007/124589 | 8/2007 |
| WO | WO 2008/014108 | 1/2008 |

OTHER PUBLICATIONS

Banker, G.S. et al, "Modern Pharmaceutices, 3ed.", Marcel Dekker, New York. 1996, pp. 451 and 596.*
U.S. Appl. No. 11/539,013, filed Oct. 5, 2006, Singh et al.
U.S. Appl. No. 11/539,018, filed Oct. 5, 2006, Singh et al.
U.S. Appl. No. 11/539,147, filed Oct. 5, 2006, Singh et al.
U.S. Appl. No. 11/539,520, filed Oct. 6, 2006, Singh et al.
U.S. Appl. No. 11/555,222, filed Oct. 31, 2006, Payan.
5-[(4-chlorophenyl)sulfonyl]pyrimidine-2,4-diamine,commercially available from Maybridge, Cornwall, England, catalog #KM 00680.
2,4-Pyrimidinediamine, 6-(4-chlorophenyl)-, commercially available from Maybridge, Cornwall, England, catalog #GK 01237.
2,4-Pyrimidinediamine, 6-(1,1-dimethylethyl)-, commercially available from Maybridge, Cornwall, England, catalog #GK 01685.
Benzenesulfonamide, N-[2-amino-6-(4-fluorophenyl)-4-pyrimidinyl]-4-(trifluoromethyl)-, commercially available from Maybridge, Cornwall, England, catalog #GK 01714.
N4-(3-pyridylmethyl)-6-methylpyrimidine-2,4-diamine, commercially available from Maybridge, Cornwall, England, catalog #RDR 02058.
N4-(3,4-dimethoxyphenethyl)-6-methylpyrimidine-2,4-diamine, commercially available from Maybridge, Cornwall, England, catalog #RDR 02059.
Arutyunyan et al. 1970, "Reaction of uracils with phosphoric acid amides" *Izvestiya Akademii Nauk SSSR, Seriya Khimicheskaya* 4:904-909.
Banks 1944, "Arylaminoheterocycles. II. Arylaminopyrimidines" *Journal of American Chemical Society* 66:1131.
Biressi et al. 1966, "SU Alcune 5-Fluoro-6-Anilino-Amminopirimidine" *Bolletino Chimico Farmaceutico* 105(9):660-665.
Breault et al. 2003, "Cyclin-Dependent Kinase 4 Inhibitors as a Treatment for Cancer. Part 2: Identification and Optimization of Substituted 2,4-Bis Anilino Pyrimidines" *Bioorg. Med. Chem. Lett.* 13(18):2961-2966.
Britkova et al. 1966, "Derivatives of Orotic Acid and its Analogs IV, Synthesis and Properties of Amino Acid Derivatives of the Lactone of 5-(Hydroxymethyl)pyrimidine-4-carboxylic Acid" *Khimiya Geterosiklichesikikh Soedinenii* 2(5):783-790 (as translated in *Chemistry of Heterocyclic Compounds*, 1968 The Faraday Press, pp. 606-611).
Brown 1954, "Improved Syntheses in the Pyrimidine Series. III. 5-Amino-4-(methylamino)pyrimidine" *J. Appl. Chem.* 4:72-75.
Chemical Abstracts 64:27547, compound 5177-26-4, 1954.
Chemical Abstracts 66:2531, compound 13150-23-7P, 1966.
Chemical Abstracts 67:64344, compound 15783-61-6P, 1996.
Chemical Abstracts 67:64344, compound 15783-79-6P, 1996.
Chemical Abstracts 71:81300, compound 19144-75-3P, 1967.
Chemical Abstracts 71:81300, compound 19144-76-4P, 1967.
Chemical Abstracts 72:111409, compound 26857-80-7P, 1969.
Chemical Abstracts 73:35322, compound 28458-89-1, 1944.
Chemical Abstracts 74:141685, compound 31796-90-4, 1970.
Chemical Abstracts 74:141685, compound 31796-91-5, 1970.
Chemical Abstracts 74:141685, compound 31796-99-3, 1970.
Chemical Abstracts 74:141685, compound 31797-00-9, 1970.
Chemical Abstracts 74:141685, compound 31797-01-0, 1970.
Chemical Abstracts 74:141685, compound 31797-09-8, 1970.
Chemical Abstracts 74:3577, compound 29935-92-0, 1970.
Chemical Abstracts 74:3577, compound 29935-93-1, 1970.
Chemical Abstracts 74:3577, compound 29935-94-2, 1970.
Chemical Abstracts 74:3577, compound 29935-98-6, 1970.
Chemical Abstracts 74:3577, compound 29935-99-7, 1970.
Chemical Abstracts 74:51826, compound 31414-49-0, 1970.
Chemical Abstracts 74:51826, compound 31414-50-3, 1970.
Chemical Abstracts 74:3577, compound 29935-96-4, 1970.
Chemical Abstracts 74:3577, compound 29935-97-5, 1970.
Chemical Abstracts 75:5843, compound 30953-40-3P, 1970.
Chemical Abstracts 75:5843, compound 32090-58-7P, 1970.
Chemical Abstracts 75:5843, compound 32090-59-8P, 1971.
Chemical Abstracts 78:97592, compound 40423-75-4, 1971.
Chemical Abstracts 78:97592, compound 40423-76-5P, 1971.
Chemical Abstracts 78:97592, compound 40423-83-4P, 1971.
Chemical Abstracts 78:97592, compound 40423-84-5P, 1971.
Chemical Abstracts 78:97592, compound 40505-53-1P, 1971.
Chemical Abstracts 78:97592, compound 40864-28-6P, 1971.
Chemical Abstracts 79:39197, compound 29935-97-5, 1970.
Chemical Abstracts 83:126278, compound 40423-75-4, 1971.
Chemical Abstracts 86:89050, compound 61763-95-9, 1976.
Chemical Abstracts 86:89050, compound 61798-30-9, 1976.
Chemical Abstracts 88:151697, compound 66229-55-8P, 1978.
Cherkasov et al. 1970, "Aminolysis of 2,4-dichloro-5-nitro-6-aminopyrimidine" *Ukrainskii Khimicheskii Zhurnal (Russian Edition)* 36(7):694-696.
Chkhikvadze et al. 1967, "Preparation of 7-Substituted 5,6-Dihydropyrrolo[2,3-d] pyrimidines or its derivatives" *Khimiko-Farmatsevticheskii Zhurnal* 2:5-12.
Chkhikvadze et al. 1969, "5-Substituted pyrimidines. II. Synthesis of 5,6-dihydropyrrolo[2,3-d]pryimidines(5,7-diazaindolines)" *Khimiya Geterotsiklicheskikh Soedinenii* 1:138-144.
Coates et al. 1979, "Correlation analysis of pyrimidine folic acid antagonists as antibacterial agents, I." *Eur. J. Med. Chem. Chimica Therapeutica* pp. 261-270.
Cook et al. 1978, "Fluorinated Pyrimidine Nucleosides. 2 reaction of 2,2'-anhydro-1-b-D-Arabinofuranosyl-2-fluorocytosine Hydrochloride with Nitrogen and Sulfur Nucleophiles" *J. Org. Chem.* 43(21):4200-4206.
Das et al. 2004, Roles of Conformational and Positional Adaptability in Structure-Based Design of TMC 125-R165335 (Etravirine) and Related Non-Nucleoside Reverse Transcriptase Inhibitors that are "Highly Potent and Effective Against Wild-Type and Drug-Resistant HIV-1Variants" *J. Med. Chem.* 47(10):2550-2560.
El-Kerdawy et al. 1986, "2,4-Bis(Substituted)-5-Nitropyrimidines of Expected Diuretic Action" *Egypt J. Chem.* 29(2):247-251.
Ghosh & Mukhehjee 1967, "2,4-Bis(arylamino)-5-methylpyrimidines as Antimicrobial Agents" *J. Med. Chem.* 10:974-975.
Ghosh 1981, "2,4-Bis(Arylamino)-6-Methyl Pyrimidines as Antimicrobial Agents" *J. Indian Chem. Soc.* 58:512-513.
Grigoreva et al. 1979, *Chemico-Pharm. J.* 13(3):5-10.
Grigoreva et al. 1980, *Chemico-Pharm. J.* 14(8):7-11.

Hare et al. 2004, "CORES: An Automated Method for Generating Three-Dimensional Models of Protein/Ligand Complexes" *J. Med. Chem.* 47(19):4731-4740.

Karn et al. 1983, *Khimiko-Farmatsevtsevtichesskii Zhurnal* 17(11):1281-1282, 1304-1307.

Karn et al. 1984, "Synthesis and Antiinflammatory Properties of O-Carboxyphenylamino Pyrimidines" *Kiev Scientific-Research Institute of Pharmacology and Toxicology Plenum Publishing Corporation*, pp. 777-779 (as translated from Karn et al. 1983, *Khimkoframatsevticheskii Zhurnal* 17(11):1304-1307).

Kokorin et al. 1976, "EPR study of the conformation of triazine series nitroxyl biradicals" *Izvestiya Akademii Nauk SSSR, Seriya Khimicheskaya* 9:1994-1999.

Kuz'menko and Protscnko 1973, "Chemistry of Heterocyclic Compounds, 2-and 4-Substituted 5-Fluropyrimidines" *Kiev Scientific-Research Institute of Pharmacology and Toxicology* 1:104-107 (as translated from Kuz'menko and Protscnko 1971, "2- and 4-Substituted 5-Fluoropyrimidines" *Khimiya Geterotsiklicheskikh Soedinenii* 1:117-119).

Ludovici et al. 2001, "Evolution of Anti-HIV Drug Candidates. Part 3: Diarylpyrimidine (DAPY) Analogues" *Bioorg. Med. Chem. Lett*, 11:2235-2239.

Lyne et al. 2004, "Identification of Compounds with Nanomolar Binding Affinity for Checkpoint Kinase-1 Using Knowledge-Based Virtual Screening" *J. Med. Chem.* 47(8):1962-1968.

Machon & Jasztold-Howorko 1976, "Synthesis of 2,4-Disubstituted 5-Aminopyrimidine-6- Carboxylic Acids Derivatives Part I." *Polish Journal of Pharmacology and Pharmacy* 28(1):61-67.

Mamaev & Sedova 1965, "Pyrimidines. III. Dehydrogenation of 4-phenylbenzo[h]quinazoline derivatives" *Khimiya Geterotsiklicheskikh Soedinenii* 4:608-615.

Manesiotis et al. 2005, "Improved Imide Receptors by Imprinting Using Pyrimidine-Based Fluoroscent Reporter Monomers" *J. Org. Chem.* 70:2729-2738.

Mashkovsky 1993, *Meditsina* 1:8.

Mokhort 1970, "Search for Non-steroid Antiinflammatory Substances among Heterocyclic Anthranilic Acid Derivatives" *Farmatsevtichnii Zhurnal (Kiev)* 25(4):76.

Paegle et al. 1971, "Synthesis and Properties of N-(2-chloro-5-fluoro-4-pyrimidyl)- and N-(2-thylthio-5-fluoro-4pyrimidyl)amino Acids" *Khimiya Geterotsiklicheskikh Soedinenii* 7(2):258-261.

Polis 1970, "Mechanism of C-N Bond Breaking in Substituted Amines" *Khimiya Geterotsiklicheskikh Soedinenii* 4(571).

Popova et al. 1996A, "Study of Reactions of 2,4,6-Trifluoropyrimidines and 2- and 4-Aminodifluoropyrimidines with Ethylamine" *J. Org. Chem.* 32(5):749-755, as translated from *Zhurnal Organicheskoi Khimii* 32(5):781-787.

Popova et al. 1996B, "Synthesis and Properties of 2- and 4-Aminosubstituted Difluoropyrimidines" *J. Org. Chem.* 32(9):1424-1429, as translated from *Zhurnal Organicheskoi Khimii* 32(9):1418-1423.

Portnyagina & Danilenko 1971, "Guanidine derivatives of pyrimidine" *Khimiko-Farmatsevticheskii Zhurnal* 5(4):15-17.

Protsenko et al. 1966, "Derivatives of pyrimidine. III. Bis(ethylenimino)pyrimidines" *Ukrainskii Khimicheskii Zhurnal (Russian Edition)* 32(8):867-871.

Protsenko et al. 1970, "Reaction of ethyleniminopyrimidines with hydrogen chloride" *Ukrainskii Khimicheskii Zhurnal (Russian Edition)* 36(10):1043-1047.

Radinov et al. 1975, "Fiziologicheski Aktivnye Veshchestva" 7:68-72.

Ryabukha & Mokhort 1970, "Relation between structure and pharmacological action in guanidino derivatives of pyrimidine" *Farmakologiya i Toksikologiya (Kiev)* 5:64-67.

Smirnov et al. 1969, "Products of the reaction of cyanuric trichloride with diiminoisoindoline" *Izvestiya Vysshikh Uchebnykh Zavedenii, Khimiya I Khimicheskaya Tekhnologiya* 12(10):1420-1423.

Strote et al. 1998, "Chemotherapy for Onchocerciassis: Results of in vitro Experiments with Promising New Compounds" *Tropical Medicine and International Health* 3(5):397-407.

Taylor et al. 1998, "1-Alkylcarbonyloxymethyl Prodrugs of 5-Fluorouracil (5-FU): Synthesis, Physicochemical Properties, and Topical Delivery of 5-FU" *J. Pharm. Sci.* 87:5-20.

Tret'yakova et al. 1972, "Physiological activity of some amino- and chloropyrimidines" *Fiziologicheski Aktivnye Veschestva* 4:93-95.

Tret'yakova et al. 1980, *Phys. Active Substances* 12:63-67.

Trinus et al. 1970, "Correlation Between the Chemical Structure and Pharmacological Activity of Nitrogen-Containing Heterocyclic Guanidine Derivatives" *Farmatsevtichinii Zhurnal (Kiev)* 25(6):66-68.

Tumkevicius et al. 1998, "Synthesis and Hypolipidemic Activity of 6-Alkyl (Aryl)Amino-2-Chloropyrimidine-4-Carboxylic Acid Esters" *Chemija Chemistry*, ISSN 0235-7216, pp. 90-92.

Zagulyaeva et al. 1978, "Relative reactivity of chlorine atoms in 2,4-dichloropyrimidine in reactions with ammonia and amines in isooctane and ethanol" *Zhurnal Organicheskoi* 14(2):409-13.

U.S. Appl. No. 11/539,074, filed Oct. 5, 2006, Singh et al.
U.S. Appl. No. 11/943,506, filed Nov. 20, 2007, Bhamidipati et al.
U.S. Appl. No. 12/028,581, filed Feb. 8, 2008, Argade et al.
U.S. Appl. No. 12/030,031, filed Feb. 12, 2008, Li et al.
U.S. Appl. No. 12/175,441, filed Jul. 17, 2008, Singh et al.
U.S. Appl. No. 12/193,627, filed Aug. 18, 2008, Li et al.
U.S. Appl. No. 12/199,705, filed Aug. 27, 2008, Singh et al.
U.S. Appl. No. 12/268,235, filed Nov. 10, 2008, Singh et al.
U.S. Appl. No. 12/268,218, filed Nov. 10, 2008, Singh et al.
U.S. Appl. No. 12/273,357, filed Nov. 18, 2008, Singh et al.

Atkins et al. 2003, "RANKL expression is related to the differentiation state of human osteoblasts" *J. Bone Miner. Res.* 18(6):1088-1098.

Bean-Knudsen et al. 1989, "Porcine mast cell leukemia with systemic mastocytosis" *Vet. Pathol.* 26(1):90-92.

Blair et al. 1997 "Lack of expression of Thy-1 (CD90) on acute myeloid leukemia cells with long-term proliferative ability in vitro and in vivo." *Blood* 89(9):3104-3112.

Boutry et al. 2003, "Trabecular bone structure of the calcaneus: preliminary in vivo MR imaging assessment in men with osteoporosis" *Radiology* 227(3):708-717.

Casanova et al. 1999, PubMed Abstract May 1999, Rev. Neurol. 28(9):909-15.

Catlett-Falcone et al. 1999, "Constitutive activation of Stat3 signaling confers resistance to apoptosis in human U266 myeloma cells." *Immunity* 10(1):105-115.

Denoto et al. 1981, "Human growth hormone DNA sequence and mRNA structure: possible alternative splicing" *Nucleic Acids Res.* 9(15):3719-3730.

Frank 1999, "STAT signaling in the pathogenesis and treatment of cancer." *Mol. Med.* 5(7):432-456.

Garcia-Bustos et al. "PIK1, an essential phosphatidylinositol 4-kinase associated with the yeast nucleus." *EMBO J.* 13(10):2352-2361 (1994).

Garnero et al. 2001, "Evaluation of a fully automated serum assay for C-terminal cross-linking telopeptide of type I collagen in osteoporosis" *Clin. Chem.* 47(4):694-702.

Hiles et al. 1992, "Phosphatidylinositol 3-kinase: structure and expression of the 110 kd catalytic subunit." *Cell* 70(3):419-429.

Hill et al. 1989, "The preparation of monoclonal antibodies which react preferentially with human bone alkaline phosphatase and not liver alkaline phosphatase" *Clin. Chim. Acta* 186(2):315-320.

Hough et al. 1998, "A model for spontaneous B-lineage lymphomas in IgHmu-HOX11 transgenic mice" *Proc. Natl. Acad. Sci. USA* 95(23):13853-13858.

Jiang et al. 2000, "Micro CT and Micro MR imaging of 3D architecture of animal skeleton" *J. Musculoskelet. Neuronal. Interact.* 1(1):45-51.

Jiang et al. 2003, "Recombinant human parathyroid hormone (1-34) [teriparatide] improves both cortical and cancellous bone structure" *J. Bone Miner. Res.* 18(11):1932-1941.

Jilka et al. 1996, "Linkage of decreased bone mass with impaired osteoblastogenesis in a murine model of accelerated senescence" *J. Clin. Invest.* 97(7):1732-1740.

Jurlander, J. et al. 1997 "Characterization of interleukin-10 receptor expression on B-cell chronic lymphocytic leukemia cells." *Blood* 89(11):4146-4152.

Katznelson et al. 1996, "Increase in bone density and lean body mass during testosterone administration in men with acquired hypogonadism" *J. Clin. Endocrin. Metab.* 81(12):4358-4365.

Knighton et al. 1991, "Crystal structure of the catalytic subunit of cyclic adenosine monophosphate-dependent protein kinase." *Science* 253(5018):407-414.

Kunz et al. 1993, "Target of rapamycin in yeast, TOR2, is an essential phosphatidylinositol kinase homolog required for G1 progression" *Cell* 73(3):585-596 (1993).

The Non-Hodgkin's Lymphoma Pathologic Classification Project 1982, "National Cancer Institute sponsored study of classifications of non-Hodgkin's lymphomas: summary and description of a working formulation for clinical usage" *Cancer* 49(10):2112-2135.

National Institutes of Health 1994, "NIH Consensus Statement; Optimal Calcium Intake" Jun. 6-8 12(4):1-30.

Neer et al. 2001, "Effect of parathyroid hormone (1-34) on fractures and bone mineral density in postmenopausal women with osteoporosis" *N. Engl. J. Med.* 344(19): 1434-1441.

Nielsen et al. 1997, "Constitutive activation of a slowly migrating isoform of Stat3 in mycosis fungoides: tyrphostin AG490 inhibits Stat3 activation and growth of mycosis fungoides tumor cell lines." *Proc. Nat. Acad. Sci. USA* 94(13):6764-6769.

Pak et al. 1995, "Treatment of postmenopausal osteoporosis with slow-release sodium fluoride. Final report of a randomized controlled trial" *Ann. Inter. Meg.* 123(6):401-408.

Pak et al. 1996, "Slow-release sodium fluoride in osteoporosis" *J. Bone Miner. Res.* 5:561-564.

Passegue et al. 2003, "Normal and leukemic hematopoiesis: are leukemias a stem cell disorder or a reacquisition of stem cell characteristics?" *Proc. Natl. Acad. Sci.* USA 100(Suppl 1):11842-11849.

Ringe et al. 1999, "Therapy of established postmenopausal osteoporosis with monofluorophosphate plus calcium: dose-related effects on bone density and fracture rate" *Osteop. Int.* 9(2):171-178.

Rosen and Bilezikian 2001, "Clinical review 123: Anabolic therapy for osteoporosis" *J. Clin. Endocrinol. Metab.* 86(3):957-964.

Roskam et al. 1979, "Molecular cloning and nucleotide sequence of the human growth hormone structural gene" *Nucleic Acids Res.* 7(2):305-320.

Rowe 2004, "The wrickkened pathways of FGF23, MEPE and PHEX" *Crit. Rev. Oral Biol. Med.* 15(5):264-281.

Sewon et al. 2004, "Salivary calcium reflects skeletal bone density of heavy smokers" *Arch. Oral Biol.* 49(5):355-358.

Simone 1996 "Oncology: Introduction", Cecil Textbook of Medicine 20th Ed., 1:1004-1010.

Spangler et al. 2001, "Smokeless tobacco and osteoporosis: a new relationship?" *Med. Hypotheses* 56(5):553-557.

Todd et al. 2003, "Osteoporosis and exercise" *Postgrad. Med. J.* 79(932):320-323.

Turhan et al. 1995 "Highly purified primitive hematopoietic stem cells are PML-RARA negative and generate nonclonal progenitors in acute promyelocytic leukemia" *Blood* 85(8):2154-2161.

Weinstein et al. 1998, "Inhibition of osteoblastogenesis and promotion of apoptosis of osteoblasts and osteocytes by glucocorticoids. Potential mechanisms of their deleterious effects on bone" *J. Clin. Invest.* 102(2):274-282.

Anderson et al. 2003, "Imidazo[1,2a]pyridines: A potent and selective class of cyclin-dependent dinase inhibitors identified through structure-based hybridisation" *Bioorganic & Medicinal Chemistry Letters* 13(18):3021-3026.

Bamborough et al. 2007, "N-4-Pyrimidinyl-1H-indazol-4-amine inhibitors of Lck: Indazoles as phenol isosteres with improved pharmacokinetics" *Bioorganic & Medicinal Chemistry Letters* 17(15):4363-4368.

Balant et al. 1995, "Metabolic Considerations in Prodrug Design" Burger's Medicinal Chemistry and Drug Discovery, Fifth Ed. 1:949-982.

Bansal et al. 1981A, "N-hydroxymethyl derivatives of nitrogen heterocycles as possible prodrugs I: N-hydroxymethylation of uracils" *J. Pharm. Sci.* 70(8):850-854.

Bansal et al. 1981B, "N-hydroxymethyl derivatives of nitrogen heterocycles as possible prodrugs II: possible prodrugs of allopurinol, glutethimide, and phenobarbital" *J. Pharm. Sci.* 70(8):855-857.

Boloor et al. 2002, CAPLUS Abstract 137:140534.

Bundgaard 1985, "Design of prodrugs: Bioreversible derivatives for various functional groups and chemical entities" *Design of Prodrugs*, Elsevier Science Publishers B.V., Introduction, p. 1.

Bundgaard et al. 1989, "A novel solution-stable, water-soluble prodrug type for drugs containing a hydroxyl or an NH-acidic group." *J. Med. Chem.* 32(12):2503-2507.

Carreras et al. 1993, "Activated T cells in an animal model of allergic conjunctivitis" *Br. J. Ophthalmol* 77(8):509-514.

Catalog No. 0122-0021, 4-methyl-N-(4-t-butylphenyl)-6-(3,5-dimethylpyrazole)-2,pyrimidinamine, commercially available from Contact Services/Chemdiv, San Diego, CA, Feb. 28, 2002.

Catalog No. 0781-2697, N2,N4-Bis(4-hydroxy-2-methylphenyl)-6-methyl-5-nitro,2,4-pyrimidinediamine, commercially available from Contact Services/Chemdiv, San Diego, CA, Mar. 1, 2002.

Catalog No. 1079-1249, N2-(4-hydroxyphenyl)-N4-(4-methoxyphenyl)-6-methyl-2,4-diaminopyrimidine, commercially available from Contact Services/Chemdiv, San Diego, CA, Feb. 28, 2002.

Catalog No. 1142-0021, N2,N4-Bis(3-chlorophenyl)-5-fluoro-2,4-pyrimidinediamine, commercially available from Contact Services/Chemdiv, San Diego, CA, Mar. 1, 2002.

Catalog No. 1142-0024, N2,N4-Bis(2,5-dimethylphenyl)-5-fluoro-2,4-pyrimidinediamine, commercially available from Contact Services/Chemdiv, San Diego, CA, Mar. 1, 2002.

Catalog No. 1142-0026, N2,N4-Bis(4-ethoxyphenyl)-5-fluoro-2,4-pyrimidinediamine, commercially available from Contact Services/Chemdiv, San Diego, CA, Mar. 1, 2002.

Catalog No. 1142-0027, N2,N4-Bis(3,4-dimethylphenyl)-5-fluoro-2,4-pyrimidinediamine, commercially available from Contact Services/Chemdiv, San Diego, CA, Mar. 1, 2002.

Catalog No. 1142-0031, N2,N4-Bis(2-methoxyphenyl)-5-fluoro-2,4-pyrimidinediamine, commercially available from Contact Services/Chemdiv, San Diego, CA, Feb. 28, 2002.

Catalog No. 1142-0033, N2,N4-Bisphenyl-5-fluoro-2,4-pyrimidinediamine, commercially available from Contact Services/Chemdiv, San Diego, CA, Mar. 28, 2002.

Catalog No. 1142-0035, N2,N4-Bis(2,4-dimethylphenyl)-5-fluoro-2,4-pyrimidinediamine, commercially available from Contact Services/Chemdiv, San Diego, CA, Mar. 1, 2002.

Catalog No. 1142-0059, N2,N4-Bis(3-bromophenyl)-5-fluoro-2,4-pyrimidinediamine, commercially available from Contact Services/Chemdiv, San Diego, CA, Mar. 1, 2002.

Catalog No. 1690-0003, N2,N4-Bis(4-methoxyphenyl)-5-fluoro-2,4-pyrimidinediamine, commercially available from Contact Services/Chemdiv, San Diego, CA, Feb. 28, 2002.

Catalog No. 1690-0005, N2,N4-Bis(4-chlorophenyl)-5-fluoro-2,4-pyrimidinediamine, commercially available from Contact Services/Chemdiv, San Diego, CA, Mar. 1, 2002.

Catalog No. 1690-0007, N2,N4-Bis(2-chlorophenyl)-5-fluoro-2,4-pyrimidinediamine, commercially available from Contact Services/Chemdiv, San Diego, CA, Feb. 28, 2002.

Catalog No. 1690-0013, N2,N4-Bis(3-methylphenyl)-5-fluoro-2,4-pyrimidinediamine, commercially available from Contact Services/Chemdiv, San Diego, CA, Feb. 28, 2002.

Catalog No. RJF 00403, N4-(2,4-difluorophenyl)-6-methyl-2,4-pyrimidinediamine hydrochloride, commercially available from Maybridge, Cornwall, England, Feb. 27, 2002.

Cetkovic-Cvrlje 2004, "Therapeutic potential of Janus kinase 3 (JAK3) inhibitors." *Current Pharmaceutical Design* 10(15):1767-1784.

Chan et al. 2001 "Expression of interleukin-4 in the epidermis of transgenic mice results in a pruritic inflammatory skin disease: an experimental animal model to study atopic dermatitis" *J. Invest. Dermatol.* 117(4):977-983.

Changelian 2003, "Prevention of organ allograft rejection by a specific Janus kinase 3 inhibitor." *Science* 302(5646):875-878.

Claman et al. 1990, "Immunoglobulin dysregulation in murine graft-vs-host disease: a hyper-IgE syndrome" *Clin. Immunol. Tmmunopathol.* 56(1):46-53.

Clemens et al. 1997, "Evidence that serum NTx (collagen-type I N-telopeptides) can act as an immunochemical marker of bone resorption" *Clin. Chem.* 43(11):2058-2063.

Corral et al. 1998, "Dissociation between bone resorption and bone formation in osteopenic transgenic mice" *Proc. Natl. Acad. Sci.* USA 95(23):13835-13840.

Damasio 1996 "Alzheimer's Disease and Related Dementias" Cecil Textbook of Medicine, 20th Ed., 2:1992-6.

Demo et al. 1999, "Quantitative measurement of mast cell degranulation using a novel flow cytometric annexin-V binding assay" *Cytometry* 36(4):340-348.

Demoulin et al. 1996, "A single tyrosine of the interleukin-9 (IL-9) receptor is required for STAT activation, antiapoptotic activity, and growth regulation by IL-9." *Mol. Cell. Biol.* 16(9):4710-4716.

Dempster et al. 2001, "Effects of daily treatment with parathyroid hormone on bone microarchitecture and turnover in patients with osteoporosis: a paired biopsy study" *J. Bone Miner. Res.* 16(10):1846-1853.

Erion et al. 2004, "Design, synthesis, and characterization of a series of cytochrome P(450) 3A-activated prodrugs (HepDirect prodrugs) useful for targeting phosph(on)ate-based drugs to the liver" *J. Am. Chem. Soc.* 126(16):5154-5163.

Ettmayer et al. 2004, "Lessons learned from marketed and investigational prodrugs" *J. Med. Chem.* 47(10):2393-2404.

Foster 1995, "The pathophysiology of ocular allergy: current thinking" *Allergy* 50(21Suppl):6-9; discussion 34-38.

Fox et al. 1998, "A single amino acid substitution makes ERK2 susceptible to pyridinyl imidazole inhibitors of p38 MAP kinase" *Protein Science* 7(11):2249-2255.

Ghiron et al. 1995, "Effects of recombinant insulin-like growth factor-I and growth hormone on bone turnover in elderly women" *J. Bone Miner. Res.* 10(12):1844-1852.

Ghosh 1966, "2, 4-Bis(arylamino)pyrimidines as Antimicrobial Agents" *Journal of Medicinal Chemistry* 9:423-424.

Guillory 1999, "Generation of Polymorphs, Hydrates, Solvates and Amorphous Solids" Polymorphism in Pharmaceutical Solids, Brittain ed, Marcel Dekker, Inc, pp. 183-226.

Hakim et al. 1996, "A nine-amino acid peptide from IL-1beta augments antitumor immune responses induced by protein and DNA vaccines" *J. Immunol.* 157(12):5503-5511.

Halleen et al. 1999, "Intracellular fragmentation of bone resorption products by reactive oxygen species generated by osteoclastic tartrate-resistant acid phosphatase" *J. Biol. Chem.* 274(33):22907-22910.

Halleen et al. 2001, "Serum tartrate-resistant acid phosphatase 5b is a specific and sensitive marker of bone resorption" *Clin. Chem.* 47(3):597:-600.

Hanks et al. 1995, "Protein kinases 6. The eukaryotic protein kinase superfamily: kinase (catalytic) domain structure and classification." *FASEB J.* 9(8):576-596.

Henrotin et al. 2001, "Strontium ranelate increases cartilage matrix formation" *J. Bone Miner. Res.* 16(2):299-308.

Janckila et al. 2003, "Disease-specific expression of tartrate-resistant acid phosphatase isoforms" *J. Bone Miner. Res.* 18(10):1916-1919.

Kagari et al. 2002, "The importance of IL-1 beta and TNF-alpha, and the noninvolvement of IL-6, in the development of monoclonal antibody-induced arthritis" *J. Immunol.* 169(3):14591466.

Kaneko et al. 1997, "Rescue by cytokines of apoptotic cell death induced by IL-2 deprivation of human antigen-specific T cell clones" *Clin. Exp. Immun.* 109(1):185-193.

Kawaguchi et al. 1994, "Nasal mast cells in experimentally induced allergic rhinitis in guinea-pigs" *Clin. Exp. Allergy* 24(3):238-244.

Kawakami et al. 2003, "A Ras activation pathway dependent on Syk phosphorylation of protein kinase C" *Proc. Natl. Acad. Sci. USA* 100(16):9470-9475.

Kaye 1964, "Substituted pyrido[2,3-b]pyrazines" *Journal of Medicinal Chemistry* 7(2), 240-241.

Khan et al. 1989, "Aqueous degradation of N-(hydroxymethyl)phthalimide in the presence of specific and general bases. Kinetic assessment of N-hydroxymethyl derivatives of nitrogen heterocycles as possible prodrugs"*J. Pharmaceutical and Biomedical Analysis* 7(6):685-691.

Kirken 2001, "Targeting Jak3 for immune suppression and allograft acceptance" *Transpl. Proc.* 33(7-8):3268-3270.

Kleinau et al. 2000, "Induction and suppression of collagen-induced arthritis is dependent on distinct fcgamma receptors" *J. Exp. Med.* 191:1611-1616.

Kluba and Zwierzak (1978) "Tertra-n-butylaminium Di-t-butyl Phospahte. A New Effective Phophorylating Agent for Alkyl Bromides" Synthesis 1978:770-771.

Konishi et al. 2002, "Platelets activated by collagen through immunoreceptor tyrosine-based activation motif play pivotal role in initiation and generation of neointimal hyperplasia after vascular injury" *Circulation* 105:912-916.

Krise et al. 1999, "Novel prodrug approach for tertiary amines: synthesis and preliminary evaluation of N-phosphonooxymethyl prodrugs"*J. Med. Chem.* 42(16):3094-3100.

Kudlacz et al. 2004, "The novel JAK-3 inhibitor CP-690550 is a potent immunosuppressive agent in various murine models." *Am. J. Transplant* 4(1):51-57.

Kunert et al. 2001, "Alteration in goblet cell numbers and mucin gene expression in a mouse model of allergic conjunctivitis" *Invest. Ophthalmol. Vis. Sci.* 42(11):2483-2489.

Kuno 2001, et al. "Constitutive kinase activation of the TEL-Syk fusion gene in myelodysplastic syndrome with t(9;12)(q22;p12)" *Blood* 97(4):1050-1055 (2001).

Lai et al. 2003, "Potent small molecule inhibitors of spleen tyrosine kinase (Syk)" *Bioorg. Med. Chem. Lett.* 13(18):3111-3114.

Lau et al. 2003, "Osteoblastic tartrate-resistant acid phosphatase: its potential role in the molecular mechanism of osteogenic action of fluoride" *J. Bone Miner. Res.* 18(10):1897-1900.

Layzer 1996 "Degenerative diseases of the Nervous System" Cecil Textbook of Medicine, 20th Ed., 1996, 2:2050-7.

Leonard et al. 2000, "Cytokine receptor signaling pathways." *J. Allergy Clin. Immunol.* 105(5):877-888.

Lin et al. 1998, "Heterogeneity of trabecular bone structure in the calcaneus using magnetic resonance imaging" *Osteoporos Int.* 8:16-24.

Lubec et al. 1996, "Evidence for McKusick's hypothesis of deficient collagen cross-linking in patients with homocystinuria" *Biochim. Biophys. Acta* 1315(3):159-162.

Macinnis et al. 2003, "Determinants of bone density in 30- to 65-year-old women: a co-twin study" *J. Bone Miner. Res.* 18(9):1650-1656.

Mackie et al. 1952, "Influence of groups in the molecule 2,3-dihydro-3-keto-1,4-benzothiazine on its effect on liver fluke (Fasciola hepatica) in vitro". *British Journal of Pharmacology and Chemotherapy*, 7:219-22.

Malaviya et al. 1999, "Targeting Janus kinase 3 in mast cells prevents immediate hypersensitivity reactions and anaphylaxis" *J. Biol. Chem.* 274(38):27028-28038.

Malaviya et al. 1999, "Genetic and biochemical evidence for a critical role of Janus kinase (JAK)-3 in mast cell-mediated type I hypersensitivity reactions"*Biochem. Biophys. Res. Commun.* 257(3):807-813.

Mantyla et al. 2002, "A novel synthetic route for the preparation of alkyl and benzyl chloromethyl phosphates" *Tet. Lett.* 43(21):3793-3794.

Maruyama et al. 1996, "Physical and functional association of cortactin with Syk in human leukemic cell line K562" *J. Biol. Chem.* 271(12):6631-6635.

Mawatari et al. 2000, "Effect of vitamin K2 on three-dimensional trabecular microarchitecture in ovariectomized rats" *J. Bone Miner. Res* 15(9):1810-1817.

McCoy et al. 2002, "The role of prostaglandin E2 receptors in the pathogenesis of rheumatoid arthritis" *J. Clin. Invest.* 110(5):651-658.

Meunier et al. 2002, "Strontium ranelate: dose-dependent effects in established postmenopausal vertebral osteoporosis—a 2-year randomized placebo controlled trial" *J. Clin. Endocrinol. Metab.* 87(5):2060-2066.

Mizuno et al. 2000, "Transgenic mice overexpressing soluble osteoclast differentiation factor (sODF) exhibit severe osteoporosis" *J. Bone Miner. Metab.* 20(6):337-344.

Mocsai et al. 2002, "Syk is required for integrin signaling in neutrophils" *Immunity* 16(4):547-558.

Monteiro & Van De Winkel 2003, "IgA Fc receptors" Annu. Rev. Immunol. 21:177-204.

Muller-Ladner et al. 2000, "Activation of the IL-4 STAT pathway in rheumatoid synovium." *J. Immunol.* 164(7):3894-3901.

Nakamura et al. 1996, "An epidermal growth factor receptor/Jak2 tyrosine kinase domain chimera induces tyrosine phosphorylation of Stat5 and transduces a growth signal in hematopoietic cells." *J. Biol. Chem.* 271(32):19483-19488.

Nakasato et al. 1999, "Clinical significance of immunoassays for type-5 tartrate-resistant acid phosphatase" *Clin. Chem.* 45(12):2150-2157.

Neunhoeffer et al. 1990, "1,4-Dioxino[2,3-b] pyridines and 1,4-oxathiino[2,3-b] pyridines" *Chemische Berichte* 123(12):2453-2454.

Nomiyama et al. 2005, "Identification of genes differentially expressed in osteoclast-like cells" *J. Interferon. Cytokine. Res.* 25(4):227-231.

O'Keefe et al. 1987, Systemic mastocytosis in 16 dogs, *J. Vet. Intern. Med.* 1(2):75-80.

O'Shea et al. 2004, "A new modality for immunosuppression: targeting the JAK/STAT pathway." *Nature Reviews Drug Discovery* 3(7):555-564.

Ohmori et al. 1990, "Novel a-Amino-3-hydroxy-5-methylisozazole-4-propionate Receptor Antagonists: Synthesis and Structure-Activity Relationships of 6-(1H-Imidazol-1-yl)-7-nitro-2,3(1H,4H)-pyrido[2,3-b]pyrazinedione and Related compounds" *J. Med. Chem.* 39:1331-1338.

Peters et al. 1996, "Syk, activated by cross-linking the B-cell antigen receptor, localizes to the cytosol where it interacts with and phosphorylates alpha-tubulin on tyrosine" *J. Biol. Chem.* 271(9):4755-7462.

Petersen et al. 2000, "Identification of osteoblast/osteocyte factor 45 (OF45), a bone-specific cDNA encoding an RGD-containing protein that is highly expressed in osteoblasts and osteocytes" *J. Biol. Chem.* 275(46):36172-36180.

Rajinder et al. 2005, CAPLUS Abstract 124:219300.

Reginster 2002, "Strontium ranelate in osteoporosis" *Curr. Pharm. Des.* 8(21):1907-1916.

Robins et al. 1994, "Direct, enzyme-linked immunoassay for urinary deoxypyridinoline as a specific marker for measuring bone resorption" *J. Bone Miner. Res.* 9(10):1643-1649.

Rosenquist et al. 1998, "Serum CrossLaps One Step ELISA. First application of monoclonal antibodies for measurement in serum of bone-related degradation products from C-terminal telopeptides of type I collagen" *Clin. Chem.* 44(11):2281-2289.

Ruzzene et al. 1996, "SH2 domains mediate the sequential phosphorylation of HS1 protein by p72syk and Src-related protein tyrosine kinases" *Biochemistry* 35(16):5327-5332.

Sada et al. 2001, "Structure and function of Syk protein-tyrosine kinase" *J. Biochem.* (Tokyo) 130(2):177-186.

Saiga et al. 1992, Clinical and cytologic aspects of ocular late-phase reaction in the guinea pig, *Ophthalmic Res.* 24(1):45-50.

Sammond et al. 2005, "Discovery of a novel and potent series of dianilinopyrimidineurea and urea isostere inhibitors of VEGFR2 tyrosine kinase" *Bioorganic & Medicinal Chemistry Letters* 15(15):3519-3523.

Seidel et al. 2000, "Pharmaceutical intervention in the JAK/STAT signaling pathway." *Oncogene* 19(21):2645-2656.

Seyedin et al. 1993, "Immunoassay for urinary pyridinoline: the new marker of bone resorption" *J. Bone Miner. Res.* 8(5):635-641.

Shiotani et al. 2002, "Regulation of osteoclast differentiation and function by receptor activator of NFkB ligand and osteoprotegerin" *Anat. Rec.* 268(2):137-146.

Shiraki et al. 2000, "Vitamin K2 (menatetrenone) effectively prevents fractures and sustains lumbar bone mineral density in osteoporosis" *J. Bone Miner. Res.* 15(3):515521.

Shridhar et al. 1985, "Synthesis and anthelmintic activity of some new 6- and 7-iosothiocyanato-2H-1,4-benzoxa(thia)zin-3(4H)-ones and benzoxa(thia)zin-3(4H)-thiones." *Indian Journal of Chemistry, Section B: Organic Chemistry including Medicinal Chemistry*, 24B(12):1263-7.

Silverman 1992, "Prodrugs and drug delivery systems", *The Organic Chemistry of Drug Design and Drug Action*, Academic Press, Inc., pp. 352-400.

Singh et al. 2004, CAPLUS Abstract 140:199334.

Sudbeck et al. 1999, "Stucture-based design of specific inhibitors of Janus kinase 3 as apoptosis-inducing antileukemic agents" *Clin. Cancer Res.* 5(6):1569-1582.

Sugimoto et al. 2000, "A new model of allergic rhinitis in rats by topical sensitization and evaluation of H(1)-receptor antagonists" *Immunopharmacology* 48(1):1-7.

Suto et al. 1999, "NC/Nga mice: a mouse model for atopic dermatitis" *Int. Arch. Allergy Immunol.* 120(Suppl 1):70-75.

Suzuki et al. 2000, "Role of common cytokine receptor gamma chain (gamma(c))- and Jak3-dependent signaling in the proliferation and survival of murine mast cells" *Blood* 96(6):2172-2180.

Svensson et al. 1998, "B cell-deficient mice do not develop type II collagen-induced arthritis (CIA)." *Clin. Exp. Immunol.* 111:521-526.

Szalai et al. 2000, "The Arthus reaction in rodents: species-specific requirement of complement" *J. Immunol.* 164(1):463-468.

Szelenyi et al. 2000, "Animal models of allergic rhinitis" *Arzneimittelforschung* 50(11):1037-1042.

Takahashi et al. 2002, "S 12911-2 inhibits osteoclastic bone resorption in vitro" *J. Bone Miner. Res.* 18(6):1082-1087.

Tamura et al. 1993, "New resorption assay with mouse osteoclast-like multinucleated cells formed in vitro" *J. Bone Miner. Res.* 8(8):953-960.

Terato et al. 1992, "Induction of arthritis with monoclonal antibodies to collagen" *J. Immunol.* 148(7):2103-2108.

Traxler 1997 "Protein Tyrosine Kinase inhibitors in cancer treatment" *Exp. Opin. Ther. Patents* 7(6):571-588.

Trieu et al. 2000, "A specific inhibitor of janus kinase-3 increases survival in a transgenic mouse model of amyotrophic lateral sclerosis" *Biochem Biophys. Res. Commun.* 267(1):22-25.

Tumas et al. 2001, "Anti-IgE efficacy in murine asthma models is dependent on the method of allergen sensitization" *J. Allergy Clin. Immunol.* 107(6):1025-1033.

Turner et al. 2000, "Tyrosine kinase SYK: essential functions for immunoreceptor signalling" *Immunology Today* 21:148-154.

Ueda et al. (2003) "Phosphonooxymethyl Prodrugs of the Broad Spectrum Antifungal Azole, Ravuconazole: Synthesis and Biological Porperties" Bioorganic & Medicinal Chemistry Letters 13:3669-3672.

Ulrich 2002, "Crystallization" *Kirk-Othmaer Encyclopedia of Chemical Technology*, John Wiley & Sons, Inc., Chapter 4: Crystal Characteristics.

Wang et al. 1999, "G(s)alpha repression of adipogenesis via Syk" *J. Biol Chem.* 274(45):32159-32166.

Watson & Gibbons 1998, "Collagen receptor signalling in platelets: extending the role of the ITAM" *Immunol. Today* 19:260-264.

Weinstein et al. 1997, "The effects of androgen deficiency on murine bone remodeling and bone mineral density are mediated via cells of the osteoblastic lineage" *Endocrinology* 138(9):4013-4021.

Wong et al. 2004, "Targeting Syk as a treatment for allergic and autoimmune disorders" *Expert Opin. Investig. Drugs* 13(7):743-762.

Yu 1997, "Constitutive activation of the Janus kinase-STAT pathway in T lymphoma overexpressing the Lck protein tyrosine kinase." *J Immunol.* 159(11):5206-5210.

Zwierzak and Kluba (1974) "Organophosphorus Esters-I* t-Butyl as Protecting Group in Phosphorylation Via Nucleophilic Displacement" Tetrahedron 27:3163-3170.

Braselmann et al. 2006, "R406, an orally available spleen tyrosine kinase inhibitor blocks Fc receptor signaling and reduces immune complex-mediated inflammation." *J. Pharmacology and Experimental Therapeutics*, 319(3):998-1008.

Cha et al. 2006, "A novel spleen tyrosine kinase inhibitor blocks c-Jun N-Terminal kinase-mediated gene expression in synoviocytes." *J. Pharmacology and Experimental Therapeutics*, 317(2):571-578.

Vippagunta et al. (2001) "Crystalline solids." *Advanced Drug Delivery Reviews*, 48:3-26.

West (1988) "Solid solutions." *Solid State Chemistry and Its Applications*, John Wiley & Sons, Inc., pp. 358 & 365.

\* cited by examiner

Mast Cell FceR1 Signaling Pathway

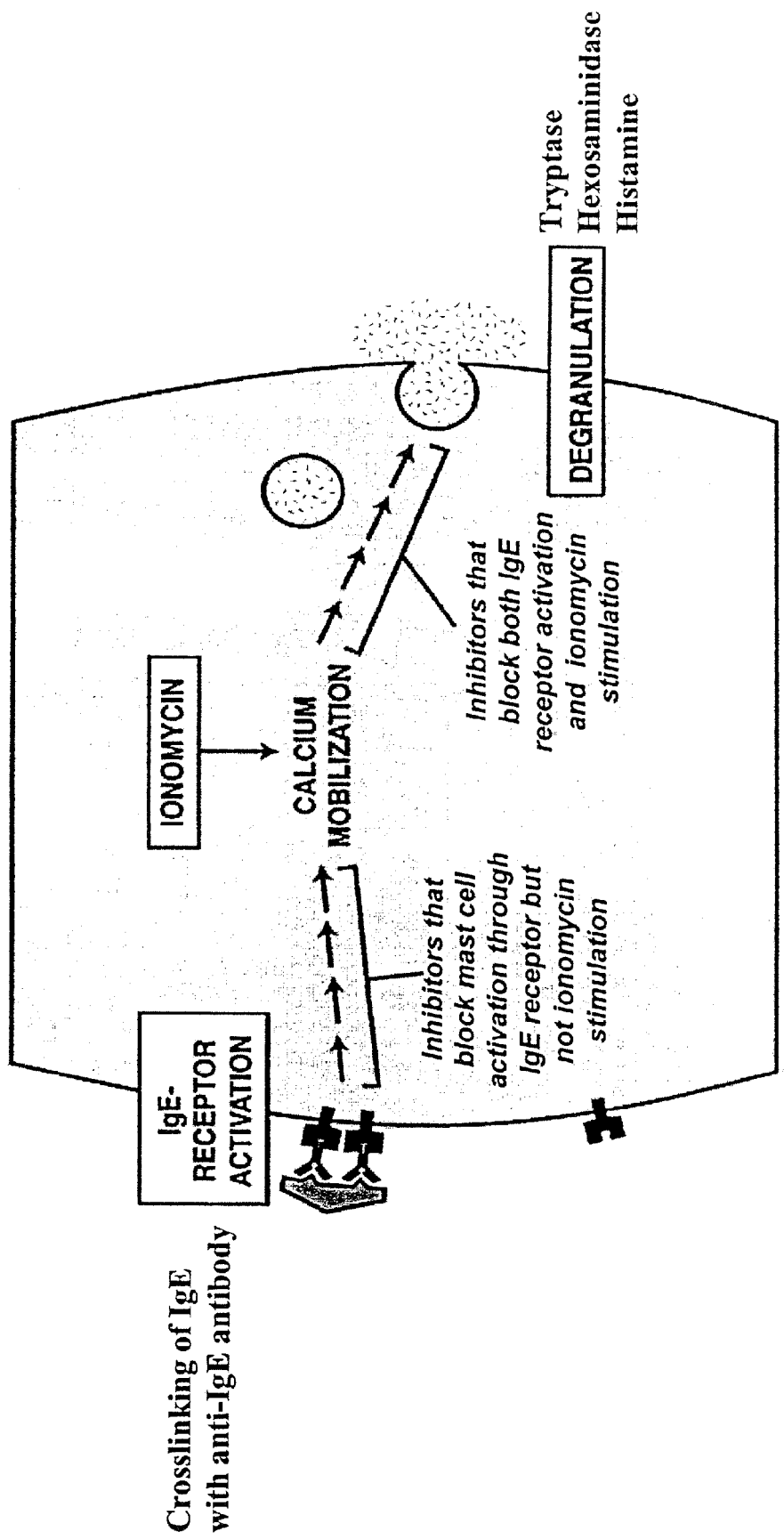

METHODS OF TREATING OR PREVENTING AUTOIMMUNE DISEASES WITH 2,4-PYRIMIDINEDIAMINE COMPOUNDS

1. CROSS REFERENCE TO RELATED APPLICATION

This application is a continuation of U.S. application Ser. No. 10/903,263 filed Jul. 30, 2004, which claims benefit under § 119(e) to application Ser. No. 60/491,641, filed Jul. 30, 2003, Ser. No. 60/531,598, filed Dec. 19, 2003 and Ser. No. 60/572,246, filed May 15, 2004, the disclosures of which are incorporated herein by reference in their entirety.

2. FIELD OF THE INVENTION

The present invention relates generally to 2,4-pyrimidinediamine compounds, pharmaceutical compositions comprising the compounds, intermediates and synthetic methods of making the compounds and methods of using the compounds and compositions in a variety of contexts, such as in the treatment or prevention of autoimmune diseases and/or the symptoms associated therewith.

3. BACKGROUND OF THE INVENTION

Crosslinking of Fc receptors, such as the high affinity receptor for IgE (FcϵRI) and/or the high affinity receptor for IgG (FcγRI) activates a signaling cascade in mast, basophil and other immune cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Additional mediators that are synthesized and released upon crosslinking Fc receptors include cytokines and nitric oxide.

The signaling cascade(s) activated by crosslinking Fc receptors such as FcϵRI and/or FcγRI comprises an array of cellular proteins. Among the most important intracellular signal propagators are the tyrosine kinases. And, an important tyrosine kinase involved in the signal transduction pathways associated with crosslinking the FcϵRI and/or FcγRI receptors, as well as other signal transduction cascades, is Syk kinase (see Valent et al., 2002, *Intl. J. Hematol.* 75(4):257-362 for review).

As the mediators released as a result of FcϵRI and FcγRI receptor cross-linking are responsible for, or play important roles in, the manifestation of numerous adverse events, the availability of compounds capable of inhibiting the signaling cascade(s) responsible for their release would be highly desirable. Moreover, owing to the critical role that Syk kinase plays these and other receptor signaling cascade(s), the availability of compounds capable of inhibiting Syk kinase would also be highly desirable.

4. SUMMARY OF THE INVENTION

In one aspect, the present invention provides novel 2,4-pyrimidinediamine compounds that, as will be discussed in more detail below, have myriad biological activities. The compounds generally comprise a 2,4-pyrimidinediamine "core" having the following structure and numbering convention:

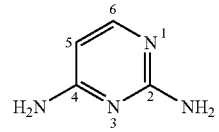

The compounds of the invention are substituted at the C2 nitrogen (N2) to form a secondary amine and are optionally further substituted at one or more of the following positions: the C4 nitrogen (N4), the C5 position and/or the C6 position. When substituted at N4, the substituent forms a secondary amine. The substituent at N2, as well as the optional substituents at the other positions, may range broadly in character and physico-chemical properties. For example, the substituent(s) may be a branched, straight-chained or cyclic alkyl, a branched, straight-chained or cyclic heteroalkyl, a mono- or polycyclic aryl a mono- or polycyclic heteroaryl or combinations of these groups. These substituent groups may be further substituted, as will be described in more detail below.

The N2 and/or N4 substituents may be attached directly to their respective nitrogen atoms, or they may be spaced away from their respective nitrogen atoms via linkers, which may be the same or different. The nature of the linkers can vary widely, and can include virtually any combination of atoms or groups useful for spacing one molecular moiety from another. For example, the linker may be an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH═CH—CH$_2$—, and the like), a monocyclic or polycyclic heteroaryl bridge (e.g., [3,4] furano, pyridino, thiopheno, piperidino, piperazino, pyrazidino, pyrrolidino, and the like) or combinations of such bridges.

The substituents at the N2, N4, C5 and/or C6 positions, as well as the optional linkers, may be further substituted with one or more of the same or different substituent groups. The nature of these substituent groups may vary broadly. Non-limiting examples of suitable substituent groups include branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities may be protected or unprotected, as is well-known in the art.

In one illustrative embodiment, the 2,4-pyrimidinediamine compounds of the invention are compounds according to structural formula (I):

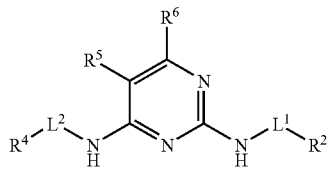

including salts, hydrates, solvates and N-oxides thereof, wherein:

$L^1$ and $L^2$ are each, independently of one another, selected from the group consisting of a direct bond and a linker;

$R^2$ and $R^4$ are described infra;

$R^5$ is selected from the group consisting of $R^6$, (C1-C6) alkyl optionally substituted with one or more of the same or different $R^8$ groups, (C1-C4) alkanyl optionally substituted with one or more of the same or different $R^8$ groups, (C2-C4) alkenyl optionally substituted with one or more of the same or different $R^8$ groups and (C2-C4) alkynyl optionally substituted with one or more of the same or different $R^8$ groups;

each $R^6$ is independently selected from the group consisting of hydrogen, an electronegative group, —$OR^d$, —$SR^d$, (C1-C3) haloalkyloxy, (C1-C3) perhaloalkyloxy, —$NR^cR^c$, halogen, (C1-C3) haloalkyl, (C1-C3) perhaloalkyl, —$CF_3$, —$CH_2CF_3$, —$CF_2CF_3$, —CN, —NC, —OCN, —SCN, —NO, —$NO_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)NR^cR^c$, —$OS(O)_2NR^cR^c$, —$C(O)R^d$, —$C(O)OR^d$, —$C(O)NR^cR^c$, —$C(NH)NR^cR^c$, —$OC(O)R^d$, —$SC(O)R^d$, —$OC(O)OR^d$, —$SC(O)OR^d$, —$OC(O)NR^cR^c$, —$SC(O)NR^cR^c$, —$OC(NH)NR^cR^c$, —$SC(NH)NR^cR^c$, —$[NHC(O)]_nR^d$, —$[NHC(O)]_nOR^d$, —$[NHC(O)]_nNR^cR^c$ and —$[NHC(NH)]_nNR^cR^c$, (C5-C10) aryl optionally substituted with one or more of the same or different $R^8$ groups, phenyl optionally substituted with one or more of the same or different $R^8$ groups, (C6-C16) arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;

$R^8$ is selected from the group consisting of $R^a$, $R^b$, $R^a$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m—R^b$, —$(CHR^a)_m—R^b$, —O—$(CH_2)_m—R^b$, —S—$(CH_2)_m—R^b$, —O—$CHR^aR^b$, —O—$CR^a(R^b)_2$, —O—$(CHR^a)_m—R^b$, —O—$(CH_2)_m—CH[(CH_2)_m—R^b]R^b$, —S—$(CHR^a)_m—R^b$, —$C(O)NH—(CH_2)_m—R^b$, —$C(O)NH—(CHR^a)_m—R^b$, —O—$(CH_2)_m—C(O)NH—(CH_2)_m—R^b$, —S—$(CH_2)_m—C(O)NH—(CH_2)_m—R^b$, —O—$(CHR^a)_m—C(O)NH—(CHR^a)_m—R^b$, —S—$(CHR^a)_m—C(O)NH—(CHR^a)_m—R^b$, —NH—$(CH_2)_m—R^b$, —NH—$(CHR^a)_m—R^b$, —NH$[(CH_2)_m—R^b]$, —N$[(CH_2)_mR^b]_2$, —NH—C(O)—NH—$(CH_2)_m—R^b$, —NH—C(O)—$(CH_2)_m—R^b$, —NH—C(O)—$(CH_2)_m—CHR^bR^b$ and —NH—$(CH_2)_m—C(O)—NH—(CH_2)_m—R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ and —$[NR^aC(NR^a)]_nNR^cR^c$;

each $R^c$ is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^d$ is independently a protecting group or $R^a$;

each m is independently an integer from 1 to 3; and each n is independently an integer from 0 to 3.

In one embodiment, $R^5$ is F and $R^6$ is hydrogen.

In another aspect, the present invention provides prodrugs of the 2,4-pyrimidinediamine compounds. Such prodrugs may be active in their prodrug form, or may be inactive until converted under physiological or other conditions of use to an active drug form. In the prodrugs of the invention, one or more functional groups of the 2,4-pyrimidinediamine compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs of the invention include special types of protecting groups, termed "progroups," masking one or more functional groups of the 2,4-pyrimidinediamine compounds that cleave under the conditions of use to yield an active 2,4-pyrimidinediamine drug compound. Functional groups within the 2,4-pyrimidinediamine compounds that may be masked with progroups for inclusion in a promoiety include, but are not limited to, amines (primary and secondary), hydroxyls, sulfanyls (thiols), carboxyls, carbonyls, phenols, catechols, diols, alkynes, phosphates, etc. Myriad progroups suitable for masking such functional groups to yield promoieties that are cleavable under the desired conditions of use are known in the art. All of these progroups, alone or in combinations, may be included in the prodrugs of the invention. Specific examples of promoieties that yield primary or secondary amine groups that can be included in the prodrugs of the invention include, but are not limited to amides, carbamates, imines, ureas, phosphenyls, phosphoryls and sulfenyls. Specific examples of promoieties that yield sulfanyl groups that can be included in the prodrugs of the invention include, but are not limited to, thioethers, for example S-methyl derivatives (monothio, dithio, oxythio, aminothio acetals), silyl thioethers, thioesters, thiocarbonates, thiocarbamates, asymmetrical disulfides, etc. Specific examples of promoieties that cleave to yield hydroxyl groups that can be included in the prodrugs of the invention include, but are not limited to, sulfonates, esters and carbonates. Specific examples of promoieties that yield carboxyl groups that can be included in the prodrugs of the invention included, but are not limited to, esters (including silyl esters, oxamic acid esters and thioesters), amides and hydrazides.

In one illustrative embodiment, the prodrugs of the invention are compounds according to structural formula (I) in which the protecting group of $R^c$ and $R^d$ is a progroup.

In another illustrative embodiment, the prodrugs of the invention are compounds according to structural formula (II):

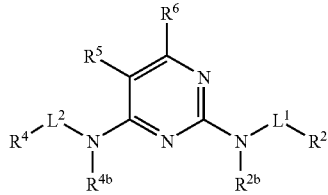

including salts, hydrates, solvates and N-oxides thereof, wherein:

$R^2$, $R^4$, $R^5$, $R^6$, $L^1$ and $L^2$ are as previously defined for structural formula (I);

$R^{2b}$ is a progroup;

$R^{4b}$ is progroup or an alkyl group, e.g., methyl, and as further defined by the examples.

In another aspect, the present invention provides compositions comprising one or more compounds and/or prodrugs of the invention and an appropriate carrier, excipient or diluent. The exact nature of the carrier, excipient or diluent will depend upon the desired use for the composition, and may range from being suitable or acceptable for veterinary uses to being suitable or acceptable for human use.

In still another aspect, the present invention provides intermediates useful for synthesizing the 2,4-pyrimidinediamine compounds and prodrugs of the invention. In one embodiment, the intermediates are 4-pyrimidineamines according to structural formula (III):

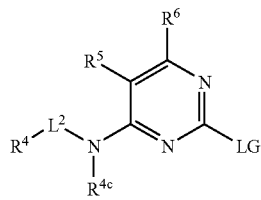

including salts, hydrates, solvates and N-oxides thereof, wherein $R^4$, $R^5$, $R^6$ and $L^2$ are as previously defined for structural formula (I); LG is a leaving group such as, for example, —S(O)$_2$Me, —SMe or halo (e.g., F, Cl, Br, I); and $R^{4c}$ is hydrogen, a progroup, an alkyl group or as described herein.

In another embodiment, the intermediates are 2-pyrimidineamines according to structural formula (IV):

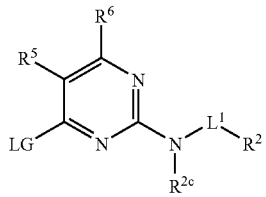

including salts, hydrates, solvates and N-oxides thereof, wherein $R^2$, $R^5$, $R^6$ and $L^1$ are as previously defined for structural formula (I); LG is a leaving group, such as, for example, —S(O)$_2$Me, —SMe or halo (e.g., F, Cl, Br, I) and.

In yet another embodiment, the intermediates are 4-amino- or 4-hydroxy-2-pyrimidineamines according to structural formula (V):

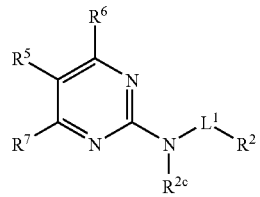

including salts, hydrates, solvates and N-oxides thereof, wherein $R^2$, $R^5$, $R^6$ and $L^1$ are as previously defined for structural formula (I), $R^7$ is an amino or hydroxyl group and $R^{2c}$ is hydrogen or a progroup.

In another embodiment, the intermediates are N4-substituted cytosines according to structural formula (VI):

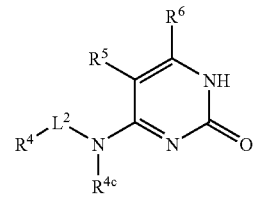

including salts, hydrates, solvates and N-oxides thereof, wherein $R^4$, $R^5$, $R^6$ and $L^2$ are as previously defined for structural formula (I) and $R^{4c}$ is as previously defined in formula (III).

In yet another aspect, the present invention provides methods of synthesizing the 2,4-pyrimidinediamine compounds and prodrugs of the invention. In one embodiment, the method involves reacting a 4-pyrimidineamine according to structural formula (III) with an amine of the formula HR$^{2c}$N—L$^1$—R$^2$, where L$^1$, R$^2$ and R$^{2c}$ are as previously defined for structural formula (IV) to yield a 2,4-pyrimidinediamine according to structural formula (I) or a prodrug according to structural formula (II).

In another embodiment, the method involves reacting a 2-pyrimidineamine according to structural formula (IV) with an amine of the formula $R^4$—$L^2$—NHR$^{4c}$ where $L^4$, $R^4$ and $R^{4c}$ are as previously defined for structural formula (III) to yield a 2,4-pyrimidinediamine according to structural formula (I) or a prodrug according to structural formula (II).

In yet another embodiment, the method involves reacting a 4-amino-2-pyrimidineamine according to structural formula (V) (in which $R^7$ is an amino group) with an amine of the formula $R^4$—$L^2$—NHR$^{4c}$, where $L^2$, $R^4$ and $R^{4c}$ are as defined for structural formula (III), to yield a 2,4-pyrimidinediamine according to structural formula (I) or a prodrug according to structural formula (II). Alternatively, the 4-amino-2-pyrimidineamine may be reacted with a compound of the formula $R^4$—$L^2$—LG, where $R^4$ and $L^2$ are as previously defined for structural formula (I) and LG is a leaving group.

In still another embodiment, the method involves halogenating a 4-hydroxy-2-pyrimidineamine according to structural formula (V) ($R^7$ is a hydroxyl group) to yield a 2-pyrimidineamine according to structural formula (IV) and reacting this pyrimidineamine with an appropriate amine, as described above.

In yet another embodiment, the method involves halogenating an N4-substituted cytosine according to structural formula (VI) to yield a 4-pyrimidineamine according to structural formula (III) and reacting this pyrimidineamine with an appropriate amine, as described above.

The 2,4-pyrimidinediamine compounds of the invention are potent inhibitors of degranulation of immune cells, such as mast, basophil, neutrophil and/or eosinophil cells. Thus, in still another aspect, the present invention provides methods of regulating, and in particular inhibiting, degranulation of such cells. The method generally involves contacting a cell that degranulates with an amount of a 2,4-pyrimidinediamine compound or prodrug of the invention, or an acceptable salt, hydrate, solvate, N-oxide and/or composition thereof, effective to regulate or inhibit degranulation of the cell. The method may be practiced in in vitro contexts or in in vivo contexts as a therapeutic approach towards the treatment or prevention of diseases characterized by, caused by or associated with cellular degranulation.

While not intending to be bound by any theory of operation, biochemical data confirm that the 2,4-pyrimidinediamine compounds exert their degranulation inhibitory effect, at least in part, by blocking or inhibiting the signal transduction cascade(s) initiated by crosslinking of the high affinity Fc receptors for IgE ("FcεRI") and/or IgG ("FcγRI"). Indeed, the 2,4-pyrimidinediamine compounds are potent inhibitors of both FcεRI-mediated and FcγRI-mediated degranulation. As a consequence, the 2,4-pyrimidine compounds may be used to inhibit these Fc receptor signalling cascades in any cell type expressing such FcεRI and/or FcγRI receptors including but not limited to macrophages, mast, basophil, neutrophil and/or eosinophil cells.

The methods also permit the regulation of, and in particular the inhibition of, downstream processes that result as a consequence of activating such Fc receptor signaling cascade(s). Such downstream processes include, but are not limited to, FcεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a 2,4-pyrimidinediamine compound or prodrug of the invention, or an acceptable salt, hydrate, solvent, N-oxide and/or composition thereof, effective to regulate or inhibit the Fc receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present invention provides methods of treating and/or preventing diseases characterized by, caused by or associated with the release of chemical mediators as a consequence of activating Fc receptor signaling cascades, such as FcεRI and/or FcγRI-signaling cascades. The methods may be practiced in animals in veterinary contexts or in humans. The methods generally involve administering to an animal subject or human an amount of a 2,4-pyrimidinediamine compound or prodrug of the invention, or an acceptable salt, hydrate, solvate, N-oxide and/or composition thereof, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods of the invention.

For example, in mast cells and basophil cells, activation of the FcεRI or FcγRI signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods of the invention.

Additional diseases which can be treated or prevented according to the methods of the invention include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD) and diseases of the gut such as inflammatory bowel syndrome (spastic colon).

The 2,4-pyrimidinediamine compounds of the invention are also potent inhibitors of the tyrosine kinase Syk kinase. Thus, in still another aspect, the present invention provides methods of regulating, and in particular inhibiting, Syk kinase activity. The method generally involves contacting a Syk kinase or a cell comprising a Syk kinase with an amount of a 2,4-pyrimidinediamine compound or prodrug of the invention, or an acceptable salt, hydrate, solvate, N-oxide and/or composition thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro contexts or in in vivo contexts as a therapeutic approach towards the treatment or prevention of diseases characterized by, caused by or associated with Syk kinase activity.

Figure 2:
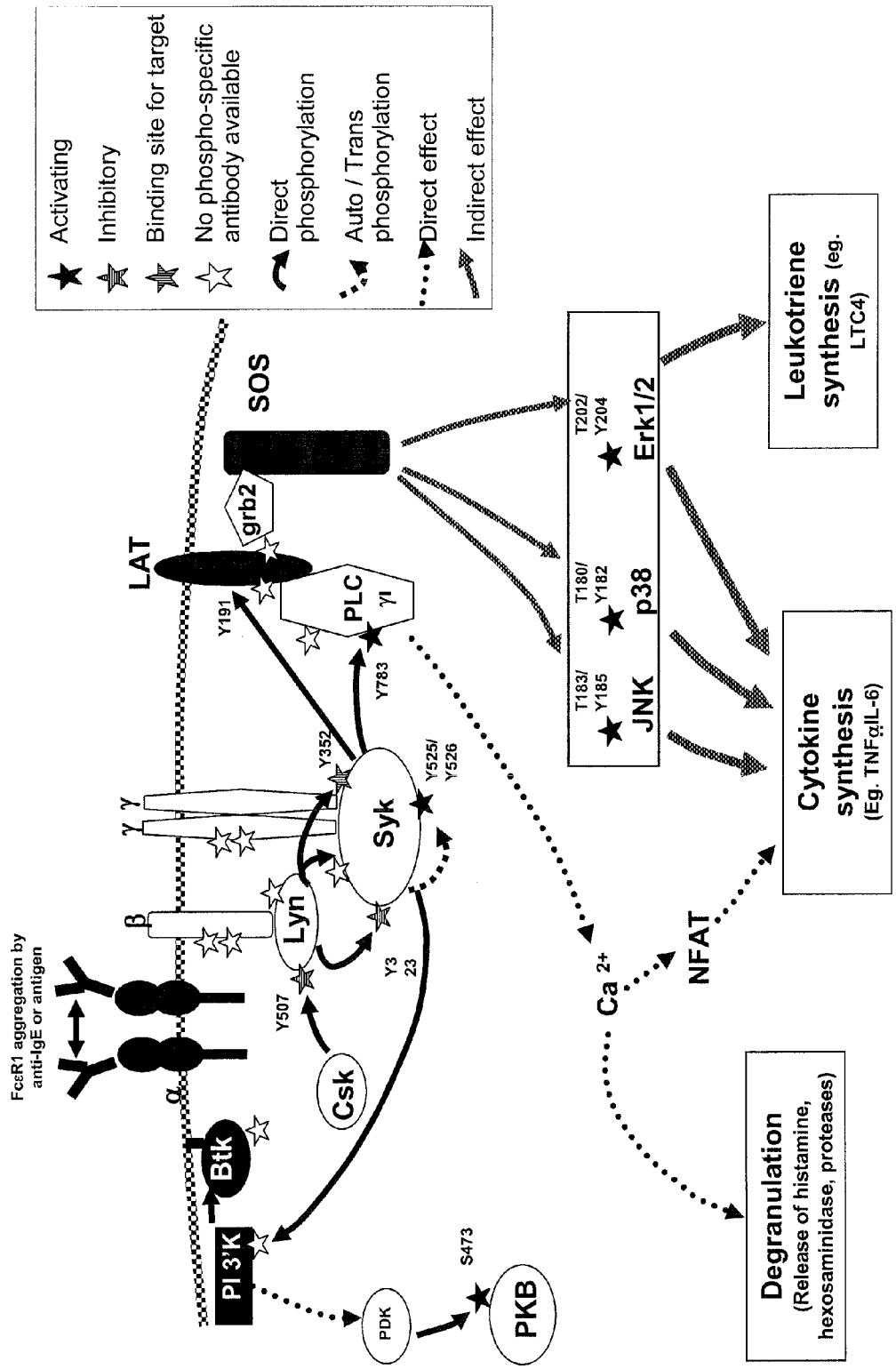

While not intending to be bound by any particular theory of operation, it is believed that the 2,4-pyrimdinediamine compounds of the invention inhibit cellular degranulation and/or the release of other chemical mediators primarily by inhibiting Syk kinase that gets activated through the gamma chain homodimer of FcεRI (see, e.g., FIG. 2). This gamma chain homodimer is shared by other Fc receptors, including FcγRI, FcγRIII and FcαRI. For all of these receptors, intracellular signal transduction is mediated by the common gamma chain homodimer. Binding and aggregation of those receptors results in the recruitment and activation of tyrosine kinases such as Syk kinase. As a consequence of these common signaling activities, the 2,4-pyrimidinediamine compounds described herein may be used to regulate, and in particular inhibit, the signaling cascades of Fc receptors having this gamma chain homodimer, such as FcεRI, FcγRI, FcγRIII and FcαRI, as well as the cellular responses elicited through these receptors.

Syk kinase is known to play a critical role in other signaling cascades. For example, Syk kinase is an effector of B-cell receptor (BCR) signaling (Turner et al, 2000, Immunology Today 21:148-154) and is an essential component of integrin beta(1), beta(2) and beta(3) signaling in neutrophils (Mocsai et al., 2002, Immunity 16:547-558). As the 2,4-pyrimidinediamine compounds described herein are potent inhibitors of Syk kinase, they can be used to regulate, and in particular inhibit, any signaling cascade where Syk plays a role, such as, fore example, the Fc receptor, BCR and integrin signaling cascades, as well as the cellular responses elicited through these signaling cascades. The particular cellular response regulated or inhibited will depend, in part, on the specific cell type and receptor signaling cascade, as is well known in the art. Non-limiting examples of cellular responses that may be regulated or inhibited with the 2,4-pyrimidinediamine compounds include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, the present invention provides methods of regulating, and in particular inhibiting, signal transduction cascades in which Syk plays a role. The method generally involves contacting a Syk-dependent receptor or a cell expressing a Syk-dependent receptor with an amount of a 2,4-pyrimidinediamine compound or prodrug of the invention, or an acceptable salt, hydrate, solvate, N-oxide and/or composition thereof, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal transduction cascade where Syk is not known or later discovered to play a role. The methods may be practiced in in vitro contexts or in in vivo contexts as a therapeutic approach towards the treatment or prevention of diseases characterized by, caused by or associated with activation of the Syk-dependent signal transduction cascade. Non-limited examples of such diseases include those previously discussed.

Cellular and animal data also confirm that the 2,4-pyrimidinediamine compounds of the invention may also be used to treat or prevent autoimmune diseases and/or symptoms of such diseases. The methods generally involve administering to a subject suffering from an autoimmune disease or at risk of developing an autoimmune disease an amount of a 2,4-pyrimidinediamine method or prodrug of the invention, or an acceptable salt, N-oxide, hydrate, solvate or composition thereof, effective to treat or prevent the autoimmune disease and/or its associated symptoms. Autoimmune diseases that can be treated or prevented with the 2,4-pyrimidinediamine compounds include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

5. BRIEF DESCRIPTION OF THE FIGURES

FIG. 1 provides a cartoon illustrating allergen-induced production of IgE and consequent release of preformed and other chemical mediators from mast cells;

FIG. 2 provides a cartoon illustrating the FcεRI signal transduction cascade leading to degranulation of mast and/or basophil cells; and FIG. 3 provides a cartoon illustrating the putative points of action of compounds that selectively inhibit upstream FcεRI-mediated degranulation and compounds that inhibit both FcεRI-mediated and ionomycin-induced degranulation.

6. DETAILED DESCRIPTION OF THE PREFERRED EMBODIMENTS

6.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain alkyldiyl saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active 2,4-pyrimidinediamine compound (drug) that requires a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking a functional group in the 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active 2,4-pyrimidinediamines compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Nitrogen protecting groups and nitrogen pro-drugs of the invention may include lower alkyl groups as well as amides, carbamates, etc. Other specific examples of suitable progroups and their respective promoieties will be apparent to those of skill in the art.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Fc Receptor" refers to a member of the family of cell surface molecules that binds the Fc portion (containing the specific constant region) of an immunoglobulin. Each Fc receptor binds immunoglobulins of a specific type. For example the Fcα receptor ("FcαR") binds IgA, the FcεR binds IgE and the FcγR binds IgG.

The FcαR family includes the polymeric Ig receptor involved in epithelial transport of IgA/IgM, the mycloid specific receptor RcαRI (also called CD89), the FcαRI and at least two alternative IgA receptors (for a recent review see Monteiro & van de Winkel, 2003, Annu. Rev. Immunol, advanced e-publication. The FcαRI is expressed on neutrophils, eosinophils, monocytes/macrophages, dendritic cells and kupfer cells. The FcαRI includes one alpha chain and the FcR gamma homodimer that bears an activation motif (ITAM) in the cytoplasmic domain and phosphorylates Syk kinase.

The FcεR family includes two types, designated FcεRI and FcεRII (also known as CD23). FcεRI is a high affinity receptor (binds IgE with an affinity of about $10^{10}M^{-1}$) found on mast, basophil and eosinophil cells that anchors monomeric IgE to the cell surface. The FcεRI possesses one alpha chain, one beta chain and the gamma chain homodimer discussed above. The FcεRII is a low affinity receptor expressed on mononuclear phagocytes, B lymphocytes, eosinophils and platelets. The FcεRII comprises a single polypeptide chain and does not include the gamma chain homodimer.

The FcγR family includes three types, designated FcγRI (also known as CD64), FcγRII (also known as CD32) and FcγRIII (also known as CD16). FcγRI is a high affinity receptor (binds IgG1 with an affinity of $10^8M^{-1}$) found on mast, basophil, mononuclear, neutrophil, eosinophil, deudritic and phagocyte cells that anchors nomomeric IgG to the cell surface. The FcγRI includes one alpha chain and the gamma chain dimer shared by FcαRI and FcεRI.

The FcγRII is a low affinity receptor expressed on neutrophils, monocytes, eosinophils, platelets and B lymphocytes. The FcγRII includes one alpha chain, and does not include the gamma chain homodimer discussed above.

The FcγRIII is a low affinity (bindes IgG1 with an affinity of $5 \times 10^5 M^{-1}$) expressed on NK, eosinophil, macrophage, neutrophil and mast cells. It comprises one alpha chain and the gamma homodimer shared by FcαRI, FcεRI and FcγRI.

Skilled artisans will recognize that the subunit structure and binding properties of these various Fc receptors, cell types expressing them, are not completely characterized. The above discussion merely reflects the current state-of-the-art regarding these receptors (see, e.g., Immunobiology: The Immune System in Health & Disease, $5^{th}$ Edition, Janeway et al., Eds, 2001, ISBN 0-8153-3642-x, FIG. 9.30 at pp. 371), and is not intended to be limiting with respect to the myriad receptor signaling cascades that can be regulated with the compounds described herein.

"Fc Receptor-Mediated Degranulation" or "Fc Receptor-Induced Degranulation" refers to degranulation that proceeds via an Fc receptor signal transduction cascade initiated by crosslinking of an Fc receptor.

"IgE-Induced Degranulation" or "FcεRI-Mediated Degranulation" refers to degranulation that proceeds via the IgE receptor signal transduction cascade initiated by crosslinking of FcεR1-bound IgE. The crosslinking may be induced by an IgE-specific allergen or other multivalent binding agent, such as an anti-IgE antibody. Referring to FIG. 2, in mast and/or basophil cells, the FcεRI signaling cascade leading to degranulation may be broken into two stages: upstream and downstream. The upstream stage includes all of the processes that occur prior to calcium ion mobilization (illustrated as "$Ca^{2+}$" in FIG. 2; see also FIG. 3). The downstream stage includes calcium ion mobilization and all processes downstream thereof. Compounds that inhibit FcεRI-mediated degranulation may act at any point along the FcεRI-mediated signal transduction cascade. Compounds that selectively inhibit upstream FcεRI-mediated degranulation act to inhibit that portion of the FcεRI signaling cascade upstream of the point at which calcium ion mobilization is induced. In cell-based assays, compounds that selectively inhibit upstream FcεRI-mediated degranulation inhibit degranulation of cells such as mast or basophil cells that are activated or stimulated with an IgE-specific allergen or binding agent (such as an anti-IgE antibody) but do not appreciably inhibit degranulation of cells that are activated or stimulated with degranulating agents that bypass the FcεRI signaling pathway, such as, for example the calcium ionophores ionomycin and A23187.

"IgG-Induced Degranulation" or "FcγRI-Mediated Degranulation" refers to degranulation that proceeds via the FcγRI signal transduction cascade initiated by crosslinking of FcγRI-bound IgG. The crosslinking may be induced by an IgG-specific allergen or another multivalent binding agent, such as an anti-IgG or fragment antibody. Like the FcεRI signaling cascade, in mast and basophil cells the FcγRI signaling cascade also leads to degranulation which may be broken into the same two stages: upstream and downstream. Similar to FcεRI-mediated degranulation, compounds that selectively inhibit upstream FcγRI-mediated degranulation act upstream of the point at which calcium ion mobilization is induced. In cell-based assays, compounds that selectively inhibit upstream FcγRI-mediated degranulation inhibit degranulation of cells such as mast or basophil cells that are activated or stimulated with an IgG-specific allergen or binding agent (such as an anti-IgG antibody or fragment) but do not appreciably inhibit degranulation of cells that are activated or stimulated with degranulating agents that bypass the FcγRI signaling pathway, such as, for example the calcium ionophores ionomycin and A23187.

"Ionophore-Induced Degranulation" or "Ionophore-Mediated Degranulation" refers to degranulation of a cell, such as a mast or basophil cell, that occurs upon exposure to a calcium ionophore such as, for example, ionomycin or A23187.

"Syk Kinsase" refers to the well-known 72 kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al, 2001, J. Biochem. (Tokyo) 130:177-186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as $Ca^{2+}$ mobilization and mitogen-activated protein kinase (MAPK) cascades (see, e.g., FIG. 2) and degranulation. Syk kinase also plays a critical role in integrin signaling in neutrophils (see, e.g., Mocsai et al. 2002, Immunity 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK accession no. gi|21361552|ref|NM_003177.2|, gi|496899|emb|Z29630.1|HSSYKPTK[496899] and gi|15030258|gb|BC011399.1|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role and biological responses effected by such Syk mimics and Syk mimic-dependent signaling cascades may be regulated, and in particular inhibited, with the 2,4-pyrimidinediamine compounds described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

6.2 The 2,4-Pyrimidinediamine Compounds

The compounds of the invention are generally 2,4-pyrimidinediamine compounds according to structural formula (I):

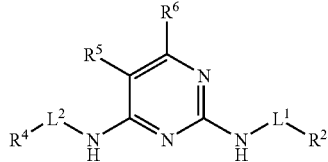

including salts, hydrates, solvates and N-oxides thereof, wherein:

$L^1$ and $L^2$ are each, independently of one another, selected from the group consisting of a direct bond and a linker;

$R^2$ and $R^4$ are as described in the following embodiments and examples;

$R^5$ is selected from the group consisting of $R^6$, (C1-C6) alkyl optionally substituted with one or more of the same or different $R^8$ groups, (C1-C4) alkanyl optionally substituted with one or more of the same or different $R^8$ groups, (C2-C4) alkenyl optionally substituted with one or more of the same or different $R^8$ groups and (C2-C4) alkynyl optionally substituted with one or more of the same or different $R^8$ groups;

each $R^6$ independently is selected from the group consisting of hydrogen, an electronegative group, —$OR^d$, —$SR^d$, (C1-C3) haloalkyloxy, (C1-C3) perhaloalkyloxy, —$NR^cR^c$, halogen, (C1-C3) haloalkyl, (C1-C3) perhaloalkyl, —$CF_3$, —$CH_2CF_3$, —$CF_2CF_3$, —CN, —NC, —OCN, —SCN, —NO, —$NO_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$OC(O)R^d$, —$SC(O)R^d$, —$OC(O)OR^d$, —$SC(O)OR^d$, —$OC(O)NR^cR^c$, —$SC(O)NR^cR^c$, —$OC(NH)NR^cR^c$, —$SC(NH)NR^cR^c$, —$[NHC(O)]_nR^d$, —$[NHC(O)]_nOR^d$, —$[NHC(O)]_nNR^cR^c$ and —$[NHC(NH)]_nNR^cR^c$, (C5-C10) aryl optionally substituted with one or more of the same or different $R^8$ groups, phenyl optionally substituted with one or more of the same or different $R^8$ groups, (C6-C16) arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;

$R^8$ is selected from the group consisting of $R^a$, $R^b$, $R^a$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—$(CH_2)_m$—$R^b$, —O—$CHR^aR^b$, —$CR^a(R^b)_2$, —O—$(CHR^a)_m$—$R^b$, —O—$(CH_2)_m$—$CH[(CH_2)_m$—$R^b]R^b$, —S—$(CHR^a)_m$—$R^b$, —$C(O)NH$—$(CH_2)_m$—$R^b$, —$C(O)NH$—$(CHR^a)_m$—$R^b$, —O—$(CH_2)_m$—$C(O)NH$—$(CH_2)_m$—$R^b$, —S—$(CH_2)_m$—$C(O)NH$—$(CH_2)_m$—$R^b$, —O—$(CHR^a)_m$—$C(O)NH$—$(CHR^a)_m$—$R^b$, —S—$(CHR^a)_m$—$C(O)NH$—$(CHR^a)_m$—$R^b$, —NH—$(CH_2)_m$—$R^b$, —NH—$(CHR^a)_m$—$R^b$, —NH$[(CH_2)_m$ $R^b]$, —$N[(CH_2)_mR^b]_2$, —NH—$C(O)$—NH—$(CH_2)_m$—$R^b$, —NH—$C(O)$—$(CH_2)_m$—$CHR^bR^b$ and —NH—$(CH_2)_m$—$C(O)$—NH—$(CH_2)_m$—$R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ and —$[NR^aC(NR^a)]_nNR^cR^c$;

each $R^c$ is independently $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which is optionally substituted with one or more of the same or different $R^a$ or suitable $R^b$ groups;

each $R^d$ is independently $R^a$;

each m is independently an integer from 1 to 3; and each n is independently an integer from 0 to 3.

In the compounds of structural formula (I), $L^1$ and $L^2$ represent, independently of one another, a direct bond or a linker. Thus, as will be appreciated by skilled artisans, the substituents $R^2$ and/or $R^4$ may be bonded either directly to their respective nitrogen atoms or, alternatively, spaced away from their respective nitrogen atoms by way of a linker. The identity of the linker is not critical and typical suitable linkers include, but are not limited to, (C1-C6) alkyldiyls, (C1-C6) alkanos and (C1-C6) heteroalkyldiyls, each of which may be optionally substituted with one or more of the same or different $R^8$ groups, where $R^5$ is as previously defined for structural formula (I). In a specific embodiment, $L^1$ and $L^2$ are each, independently of one another, selected from the group consisting of a direct bond, (C1-C3) alkyldiyl optionally substituted with one or more of the same or different $R^a$, suitable $R^b$ or $R^9$ groups and 1-3 membered heteroalkyldiyl optionally substituted with one or more of the same or different $R^a$, suitable $R^b$ or $R^9$ groups, wherein $R^9$ is selected from the group consisting of (C1-C3) alkyl, —$OR^a$, —$C(O)OR^a$, (C5-C10) aryl optionally substituted with one or more of the same or different halogens, phenyl optionally substituted with one or more of the same or different halogens, 5-10 membered heteroaryl optionally substituted with one or more of the same or different halogens and 6 membered heteroaryl optionally substituted with one or more of the same or different halogens; and R$^a$ and R$^b$ are as previously defined for structural formula (I). Specific R$^9$ groups that may be used to substitute L$^1$ and L$^2$ include —OR$^a$, —C(O)OR$^a$, phenyl, halophenyl and 4-halophenyl, wherein R$^a$ is as previously defined for structural formula (I).

In another specific embodiment, L$^1$ and L$^2$ are each, independently of one another, selected from the group consisting of methano, ethano and propano, each of which may be optionally monosubstituted with an R$^9$ group, where R$^9$ is as previously defined above.

In all of the above embodiments, specific R$^a$ groups that may be included in R$^9$ groups are selected from the group consisting of hydrogen, (C1-C6) alkyl, phenyl and benzyl.

In still another specific embodiment, L$^1$ and L$^2$ are each a direct bond such that the 2,4-pyrimidinediamine compounds of the invention are compounds according to structural formula (Ia):

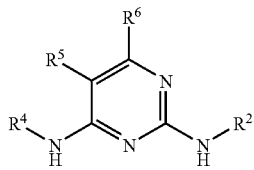

including salts, hydrates, solvates and N-oxides thereof, wherein R$^2$, R$^4$, R$^5$ and R$^6$ are as previously defined for structural formula (I). Additional specific embodiments of the 2,4-pyrimidinediamine compounds of the invention are described below.

In a first embodiment of the compounds of structural formula (I) and (Ia), L$^1$, L$^2$, R$^5$, R$^6$, R$^8$, R$^a$, R$^b$, R$^c$, R$^d$, m and n are as previously defined, R$^2$ is

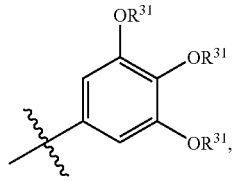

wherein each R$^{31}$, independently of the others, is methyl or (C1-C6) alkyl and R$^4$ is

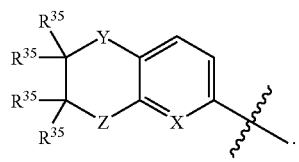

X is selected from the group consisting of N and CH, Y is selected from the group consisting of O, S, SO, SO$_2$, SONR$^{36}$, NH, NR$^{35}$ and NR$^{37}$, Z is selected from the group consisting of O, S, SO, SO$_2$, SONR$^{36}$, NH, NR$^{35}$ and NR$^{37}$. Each R$^{35}$ is, independently of the others, selected from the group consisting of hydrogen and R$^8$, or, alternatively, two R$^{35}$ bonded to the same carbon atom are taken together to form an oxo (=O), NH or NR$^{38}$ group and the other two R$^{35}$ are each, independently of one another, selected from the group consisting of hydrogen and R$^8$. Each R$^{36}$ is independently selected from the group consisting of hydrogen and (C1-C6) alkyl. Each R$^{37}$ is independently selected from the group consisting of hydrogen and a progroup. R$^{38}$ is selected from the group consisting of (C1-C6) alkyl and (C5-C14) aryl.

In particular, Y is O, Z is NH and X is N. R$^5$ can be halogen and R$^6$ is a hydrogen.

In a second embodiment of the compounds of structural formula (I) and (Ia), L$^1$, L$^2$, R$^5$, R$^6$, R$^8$, R$^a$, R$^b$, R$^c$, R$^d$, m, n, X, Y and Z are as previously defined, R$^2$ is

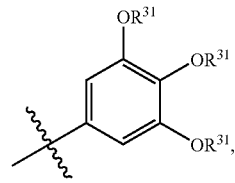

wherein each R$^{31}$, independently of the others, is methyl or (C1-C6) alkyl and R$^4$ is

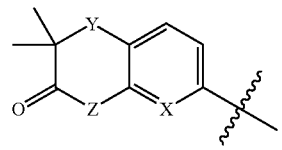

In particular, Y is O, Z is NH and X is N. R$^5$ can be halogen and R$^6$ is a hydrogen. In one particular aspect, Y is O, Z is NH, X is N and each R$^{31}$ is methyl.

In a third embodiment of the compounds of structural formula (I) and (Ia), L$^1$, L$^1$, R$^5$, R$^6$, R$^8$, R$^a$, R$^b$, R$^c$, R$^d$, m, n, R$^{31}$, R$^{35}$, R$^{36}$, R$^{37}$, R$^{38}$, X, Y and Z are as previously defined, R$^2$ is

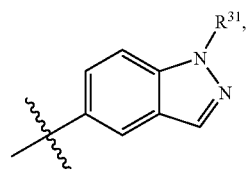

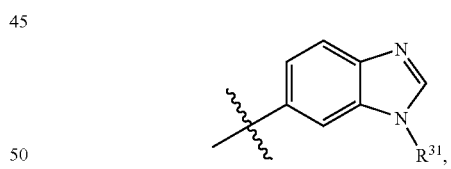

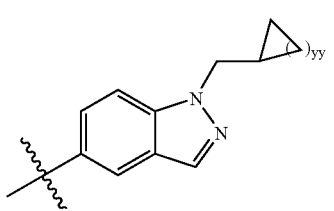

or

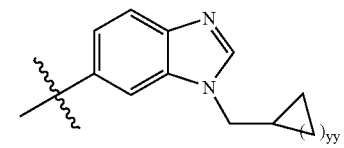

and R$^4$ is

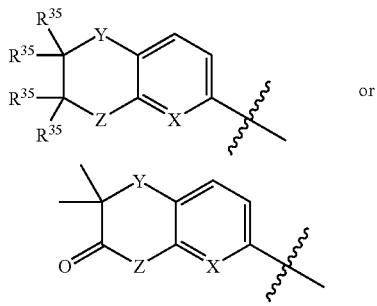

and yy is 1-6. In particular, Y is O, Z is NH and X is N. $R^5$ can be halogen and $R^6$ is a hydrogen.

In a fourth embodiment of the compounds of structural formula (I) and (Ia), $L^1$, $L^2$, $R^5$, $R^6$, $R^8$, $R^a$, $R^b$, $R^c$, $R^d$, m, n, $R^{35}$, $R^{36}$, $R^{37}$, $R^{38}$, Y and Z are as previously defined, $R^2$ is

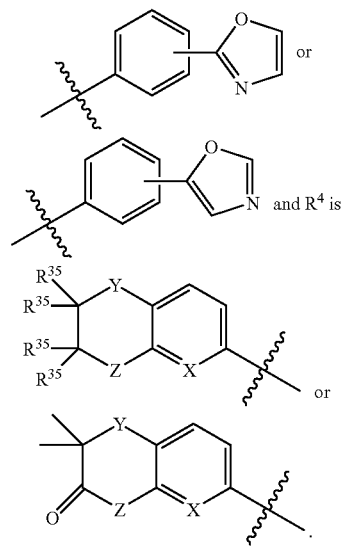

Substitution about the $R^2$ phenyl ring can be at the 2, 3, 4, 5 or 6 positions. In particular, Y is O, Z is NH and X is N. $R^5$ can be halogen and $R^6$ is a hydrogen.

In a fifth embodiment of the compounds of structural formula (I) and (Ia), $L^1$, $L^2$, $R^5$, $R^6$, $R^8$, $R^a$, $R^b$, $R^c$, $R^d$, m, n, $R^{35}$, $R^{36}$, $R^{37}$, $R^{38}$, X, Y and Z are as previously defined, $R^2$ is a phenyl group disubstituted with two $R^b$ groups and $R^4$ is

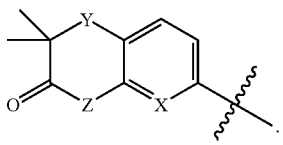

Substitution about the $R^2$ phenyl ring can be at the 2,3, 2,4, 2,5, 2,6, 3,4, 3,5, 3,6, 4,5, 4,6 or 5,6 positions, with the proviso that the following compounds are not included:

N4-(2,2-Dimethyl-3-oxo-4H-5-pyrid[1,4]oxazin-6-yl)-N2-(3-chloro-4-methoxyphenyl)-5-fluoro-2,4-pyrimidinediamine;

N4-(2,2-Dimethyl-3-oxo-4H-5-pyrid[1,4]oxazin-6-yl)-N2-(3,5-dimethoxyphenyl)-5-fluoro-2,4-pyrimidinediamine;

N2-(3,4-Dichlorophenyl)-N4-(2,2-dimethyl-3-oxo-4H-5-pyrid[1,4]oxazin-6-yl)-5-fluoro-2,4-pyrimidinediamine;

N4-(2,2-dimethyl-3-oxo-4H-5-pyrid[1,4]oxazin-6-yl)-N2-(3-fluoro-4-methoxyphenyl)-5-fluoro-2,4-pyrimidinediamine;

N2-(3,5-Dichlorophenyl)-N4-(2,2-dimethyl-3-oxo-4H-5-pyrid[1,4]oxazin-6-yl)-5-fluoro-2,4-pyrimidinediamine; and N2-(3-Chloro-4-trifluoromethoxyphenyl)-N4-(2,2-dimethyl-3-oxo-4H-5-pyrid[1,4]oxazin-6-yl)-5-fluoro-2,4-pyrimidinediamine.

In particular, Y is O, Z is NH and X is N. $R^5$ can be halogen and $R^6$ is a hydrogen. In certain aspects, each $R^b$ independently is selected from (C1-C6) alkoxy, (C1-16) alkyl, (C1-C6) perhaloalkyls, halogens, carboxylic acid, carboxylic ester, carboxamides, sulfonamides and imidazoles.

In a sixth embodiment of the compounds of structural formula (I) and (Ia), $L^1$, $L^2$, $R^5$, $R^6$, $R^8$, $R^a$, $R^b$, $R^c$, $R^d$, m, n, $R^{35}$, $R^{36}$, $R^{37}$, $R^{38}$, X, Y and Z are as previously defined, $R^2$ is a phenyl group trisubstituted with three $R^b$ groups and $R^4$ is

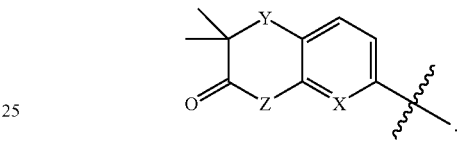

Substitution about the $R^2$ phenyl ring can be at the 2,3,4, 2,3,5, 2,3,6, 2,4,5, 2,4,6, 2,5,6, 3,4,5, 3,4,6, 3,5,6, or 4,5,6 positions, with the proviso that the following compounds are not included:

N2-(3-Chloro-4-methoxy-5-methylphenyl)-N4-(2,2-dimethyl-3-oxo-4H-5-pyrid[1,4]oxazin-6-yl)-5-fluoro-2,4-pyrimidinediamine;

N2-(3-Chloro-4-hydroxy-5-methylphenyl)-N4-(2,2-dimethyl-3-oxo-4H-5-pyrid[1,4]oxazin-6-yl)-5-fluoro-2,4-pyrimidinediamine; and N2-(3,5-Dimethyl-4-methoxyphenyl)-N4-(2,2-dimethyl-3-oxo-4H-5-pyrid[1,4]oxazin-6-yl)-5-fluoro-2,4-pyrimidinediamine.

In particular, Y is O, Z is NH and X is N. $R^5$ can be halogen and $R^6$ is a hydrogen. In certain aspects, each $R^b$ independently is selected from (C1-C6) alkoxy, (C1-16) alkyl, (C1-C6) perhaloalkyls, halogens, carboxylic acid, carboxylic esters, carboxamides, sulfonamides In certain embodiments, the compounds disclosed in U.S. patent application Ser. Nos. 10/631,029, filed on Jul. 29, 2003 and 10/355,543, filed Jan. 31, 2003, respectively, are not included within the scope of the present application.

In a seventh embodiment of the compounds of structural formula (I) and (Ia), $R^5$, $R^6$, $L^1$ and $L^2$ are as previously defined, $R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups, $R^4$ is

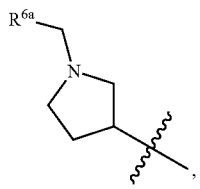

$R^{6a}$ is (C5-C10) aryl optionally substituted with one or more of the same or different $R^8$ groups or phenyl optionally substituted with one or more of the same or different $R^8$ groups and $R^8$ is as previously defined.

In an eighth embodiment of the compounds of structural formulae (I) and (Ia), $R^5$, $R^6$, $R^8$, $L^1$ and $L^2$ are as previously defined, $R^2$ is selected from the group consisting of

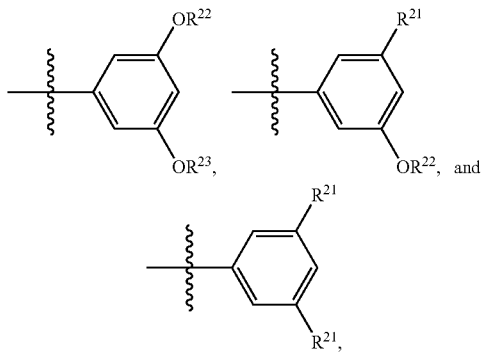

wherein each $R^{21}$ is independently a halogen atom or an alkyl optionally substituted with one or more of the same or different halo groups, $R^{22}$ and $R^{23}$ are each, independently of one another, a hydrogen atom, methyl or ethyl group optionally substituted with one or more of the same or different halo groups and $R^4$ is a (C3-C8) cycloalkyl optionally substituted with one or more of the same or different $R^8$ groups.

In a ninth embodiment of the compounds of structural formulae (I) and (Ia), $R^5$, $R^6$, $R^8$, $L^1$ and $L^2$ are as previously defined, $R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups, $R^4$ is

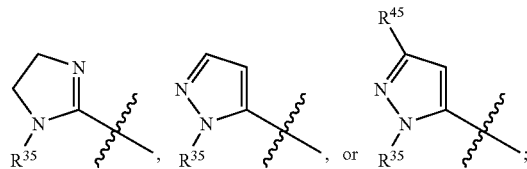

$R^{35}$ is a hydrogen or $R^8$; and $R^{45}$ is a (C3-C8) cycloalkyl optionally substituted with one or more of the same or different $R^8$ groups.

In a tenth embodiment compounds of structural formulae

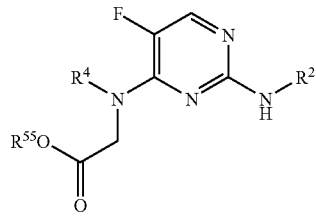

$R^2$ selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups, $R^4$ is selected from the group consisting of hydrogen, (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups, and $R^{55}$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups.

In an eleventh embodiment of the compounds of structural formulae (I) and (Ia), $R^5$, $R^6$, $R^8$, $L^1$ and $L^2$ are as previously defined, $R^2$ is

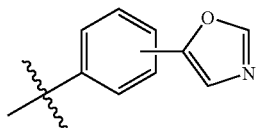

and $R^4$ is selected from the group consisting of hydrogen, (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups.

In a twelfth embodiment of the compounds of structural formulae (I) and (Ia), $R^5$, $R^6$, $R^8$, $L^1$ and $L^2$ are as previously defined, $R^2$ is

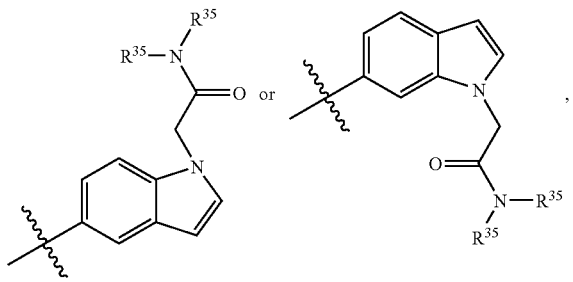

$R^4$ is selected from the group consisting of hydrogen, (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups and each $R^{35}$ individually is a hydrogen or a suitable $R^8$.

In a thirteenth embodiment of the compounds of structural formulae (I) and (Ia), $R^5$, $R^6$, $R^8$, $L^1$ and $L^2$ are as previously defined, $R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups, $R^4$ is

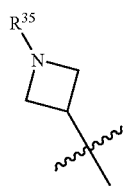

and $R^{35}$ is a hydrogen or a suitable $R^8$.

In a fourteenth embodiment, the compounds of structural formulae (I) and (Ia), $R^5$, $R^6$, $R^8$, $L^1$ and $L^2$ are as previously defined, $R^4$ is a substituted phenyl group, substituted with the same or different $R^8$ groups and $R^2$ is

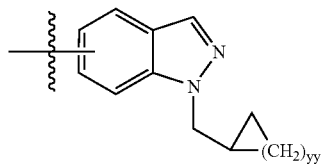

wherein "yy"=1 to 6. In one aspect, the $R^4$ phenyl group is di or tri substituted with the same or different $R^8$ groups, and in particular, halogen atoms. In particular, $R^4$ can be substituted at the 3 and 4 positions relative to attachment to the N4 amine, particularly with halogen atoms and/or alkoxy groups.

In a fifteenth embodiment, the compounds of structural formulae (I) and (Ia), $R^5$, $R^6$, $R^8$, $L^1$ and $L^2$ are as previously defined, $R^4$ is a substituted phenyl group, substituted with the same or different $R^8$ groups and $R^2$ is

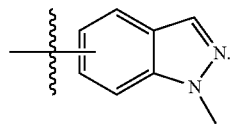

In one aspect, the $R^4$ phenyl group is di or tri substituted with the same or different $R^8$ groups, and in particular, halogen atoms. In particular, $R^4$ can be substituted at the 3 and 4 positions relative to attachment to the N4 amine, particularly with halogen atoms and/or alkoxy groups.

In a sixteenth embodiment, the compounds of structural formulae (I) and (Ia), $R^5$, $R^6$, $R^8$, $L^1$ and $L^2$ are as previously defined, $R^4$ is a substituted phenyl group, substituted with the same or different $R^8$ groups and $R^2$ is

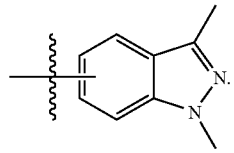

In one aspect, the $R^4$ phenyl group is di or tri substituted with the same or different $R^8$ groups, and in particular, halogen atoms. In particular, $R^4$ can be substituted at the 3 and 4 positions relative to attachment to the N4 amine, particularly with halogen atoms and/or alkoxy groups.

In a seventeenth embodiment, the compounds of structural formulae (I) and (Ia), $R^5$, $R^6$, $R^8$, $L^1$ and $L^2$ are as previously defined, $R^4$ is a substituted phenyl group, substituted with the same or different $R^8$ groups and $R^2$ is

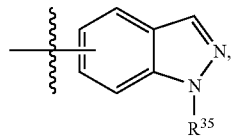

wherein $R^{35}$ is an alkylalkoxy group, and in particular is

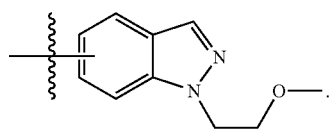

In one aspect, the $R^4$ phenyl group is di or tri substituted with the same or different $R^8$ groups, and in particular, halogen atoms. In particular, $R^4$ can be substituted at the 3 and 4 positions relative to attachment to the N4 amine, particularly with halogen atoms and/or alkoxy groups.

In a eighteenth embodiment, the compounds of structural formulae (I) and (Ia), $R^5$, $R^6$, $R^8$, $L^1$ and $L^2$ are as previously defined, $R^4$ is a substituted phenyl group, substituted with the same or different $R^8$ groups and $R^2$ is

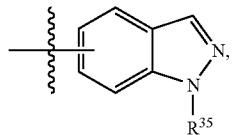

wherein $R^{35}$ is an alkyl group, and in particular is

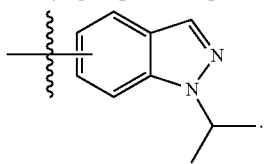

In one aspect, the $R^4$ phenyl group is di or tri substituted with the same or different $R^8$ groups, and in particular, halogen atoms. In particular, $R^4$ can be substituted at the 3 and 4 positions relative to attachment to the N4 amine, particularly with halogen atoms and/or alkoxy groups.

In a nineteenth embodiment, the compounds of structural formulae (I) and (Ia), $R^5$, $R^6$, $R^8$, $L^1$ and $L^2$ are as previously defined $R^4$ is

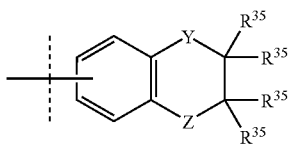

and $R^2$ is

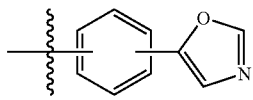

and in particular, is substituted at the 3 or 4 position with the isoxazole. Y is selected from the group consisting of O, S, SO, $SO_2$, $SONR^{36}$, NH and $NR^{37}$. Z is selected from the group consisting of O, S, SO, $SO_2$, $SONR^{36}$, NH and $NR^{37}$. Each $R^{35}$ is, independently of the others, selected from the group consisting of hydrogen and $R^8$, or, alternatively, two $R^{35}$ bonded to the same carbon atom are taken together to form an oxo (=O), NH or $NR^{38}$ group and the other two $R^{35}$ each, if present, independently of one another, are selected from the group consisting of hydrogen and $R^8$. Each $R^{36}$ is independently selected from the group consisting of hydrogen and (C1-C6) alkyl. Each $R^{37}$ is independently selected from the group consisting of hydrogen and a progroup. $R^{38}$ is selected from the group consisting of (C1-C6) alkyl and (C5-C14) aryl.

In certain aspects, $R^{37}$ is selected from the group consisting of aryl, arylalkyl, heteroaryl, $R^a$, $R^b$—$CR^aR^b$—O—C(O)$R^8$, —$CR^aR^b$—O—PO(O$R^8$)$_2$, —$CH_2$—O—PO(O$R^8$)$_2$, —$CH_2$—PO(O$R^8$)$_2$, —C(O)—$CR^aR^b$—N(CH$_3$)$_2$, —$CR^aR^b$—O—C(O)—$CR^aR^b$—N(CH$_3$)$_2$, —C(O)$R^8$, —C(O)CF$_3$ and —C(O)—$NR^8$—C(O)$R^8$ In one aspect, Y is oxygen, Z is NH and one or more of $R^{35}$ is an alkyl group, and in particular, a methyl group. In certain, two $R^{35}$'s form a gem dialkyl moiety, in particular, a gem dimethyl moiety adjacent to the NH depicted as

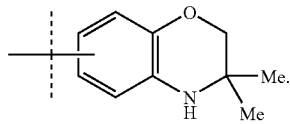

In a twentieth embodiment, the compounds of structural formulae (I) and (Ia), $R^5$, $R^6$, $R^8$, $L^1$ and $L^2$ are as previously defined, $R^4$ is

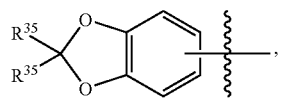

wherein each $R^{35}$ are as defined above, and in particular are both halogen atoms, e.g., fluorine, and $R^2$ is a substituted phenyl group, substituted with the same or different $R^8$ groups. In one aspect, the $R^2$ phenyl group is di or tri substituted with the same or different $R^8$ groups, and in particular, halogen atoms. In particular, $R^2$ can be substituted at the 3 and 5 positions relative to attachment to the N2 amine, particularly with halogen atoms and/or alkoxy groups.

In a twenty first embodiment, the compounds of structural formulae (I) and (Ia), $R^5$, $R^6$, $R^8$, $L^1$ and $L^2$ are as previously defined, $R^4$ is

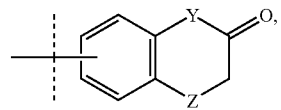

wherein Y and Z are defined as above and $R^2$ is

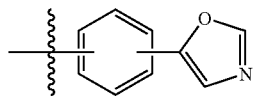

and in particular is substituted at the 3 or 4 position with the isoxazole. In one aspect of the thirty ninth embodiment with regard to $R^4$, Y is NH and Z is O e.g.,

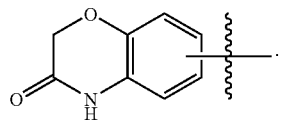

In a twenty second embodiment the compounds of structural formulae (I) and (Ia), $R^5$, $R^6$, $R^8$, $L^1$ and $L^2$ are as previously defined, $R^4$ is

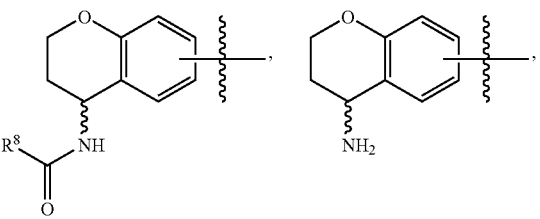

-continued

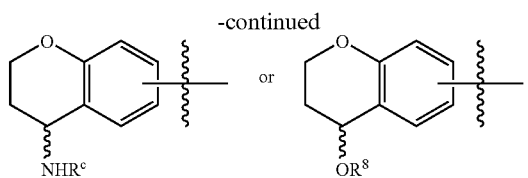

wherein $R^8$ and $R^c$ are as defined above and $R^2$ is a phenyl group substituted at the 3 or 4 position with

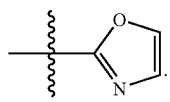

In one aspect —$OR^8$, $R^8$ is a hydrogen atom.

In a twenty third embodiment, the compounds of structural formulae (I) and (Ia), $R^5$, $R^6$, $R^8$, $L^1$ and $L^2$ are as previously defined, $R^4$ is

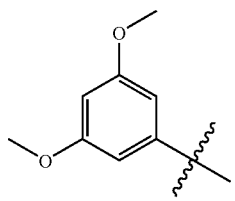

and $R^2$ is a substituted phenyl group, substituted with at least two of the same or different $R^8$ groups as defined above. Suitable examples include compounds 340, 343, 349, 350 and 351.

In a twenty fourth embodiment, the compounds of structural formulae (I) and (Ia), $R^5$, $R^6$, $R^8$, $L^1$ and $L^2$ are as previously defined, $R^4$ is

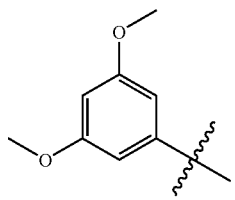

and $R^2$ is

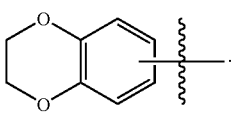

In a twenty fifth embodiment, the compounds of structural formulae (I) and (Ia), $R^5$, $R^6$, $R^8$, $L^1$ and $L^2$ are as previously defined, $R^4$ is

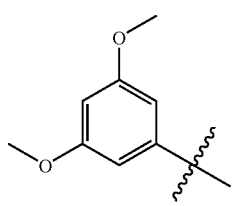

and $R^2$ is

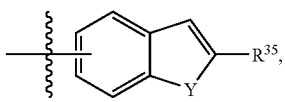

wherein Y and $R^{35}$ are as defined above. Suitable examples include compounds 368, 381, 382, 383 and 384.

In a twenty sixth embodiment, the compounds of structural formulae (I) and (Ia), $R^5$, $R^6$, $R^8$, $L^1$ and $L^2$ are as previously defined, $R^4$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups and $R^2$ is

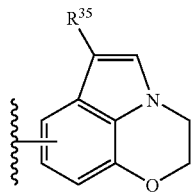

wherein $R^{35}$ is as defined above. Suitable examples include compounds 205 and 206.

In a twenty seventh embodiment the compounds of structural formulae (I) and (Ia), $R^5$, $R^6$, $R^8$, $L^1$ and $L^2$ are as previously defined, $R^4$ is

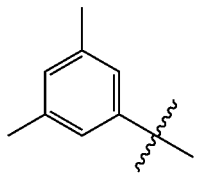

and $R^2$ is a phenyl group substituted with one or more of the same $R^8$ groups. Suitable examples include compounds 328, 329, 330, 341, 553, 554, 555, 556, 559 and 560.

In a twenty eighth embodiment, the compounds of structural formulae (I) and (Ia), $R^5$, $R^6$, $R^8$, $L^1$ and $L^2$ are as previously defined, $R^4$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups and $R^2$ is

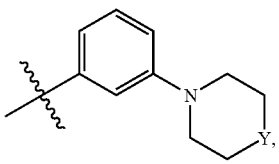

wherein Y is as defined above or is NR³⁵ and R³⁵ is as defined above. Suitable examples include compounds 1070, 1071, 1073, 1074, 1075, 1076, 1078, 1080, 1085, 1091 and 1092.

In a twenty ninth embodiment, the compounds of structural formulae (I) and (Ia), $R^5$, $R^6$, $R^8$, $L^1$ and $L^2$ are as previously defined, $R^4$ is

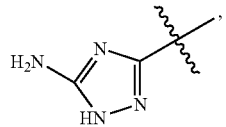

wherein $R^2$ is a substituted phenyl group or an indazole, substituted with one or more of the same or different $R^8$ groups as defined above. Suitable examples include compounds 1251, 1252, 1253, 1254 and 1255.

In a thirtieth embodiment, the compounds of structural formulae (I) and (Ia), $R^5$, $R^6$, $R^8$, $L^1$ and $L^2$ are as previously defined, $R^4$ is

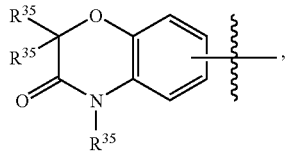

wherein each $R^{35}$ independently is as described above and $R^2$ is

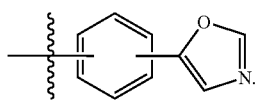

Suitable examples include compounds 217, 218, 219, 220, 221, 222, 223, 224, 225, 226, 227, 228, 229, 230, 231, 232, 233, 234, 236, 237, 238, 239, 240, 241, 242, 243, 244, 245, 246, 247, 1281, 1283, 1283, 1284, 1285, 1287, 1288, 1289, 1290 and 1291.

In a thirty first embodiment, the compounds of structural formulae (I) and (Ia), $R^5$, $R^6$, $R^8$, $L^1$ and $L^2$ are as previously defined, $R^4$ is

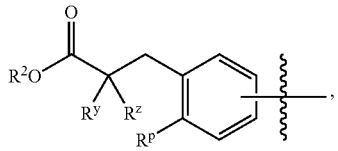

wherein $R^z$ is a hydrogen or lower alkyl group, $R^x$ and $R^y$ are each independently lower alkyl groups, or taken together form a cycloalkyl and $R^p$ is a halogen atom or a lower alkyl group and $R^2$ is as defined above. Suitable examples include compounds 402, 403, 407, 408, 409 and 410.

In a thirty second embodiment, the compounds of structural formulae (I) and (Ia), $R^5$, $R^6$, $R^8$, $L^1$ and $L^2$ are as previously defined, $R^2$ is

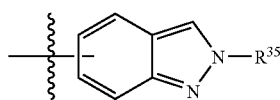

and $R^4$ is

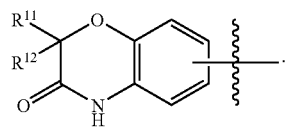

$R^{11}$ and $R^{12}$ are each, independently of one another, selected from the group consisting of alkyl, alkoxy, halogen, haloalkoxy, aminoalkyl and hydroxyalkyl;

In a thirty third embodiment, the compounds of structural formulae (I) and (Ia), $R^5$, $R^6$, $R^8$, $L^1$ and $L^2$ are as previously defined, $R^2$ is selected from (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups.

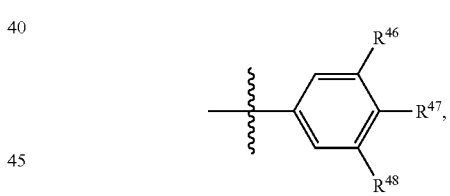

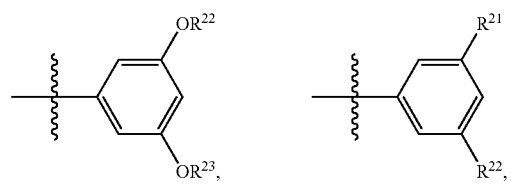

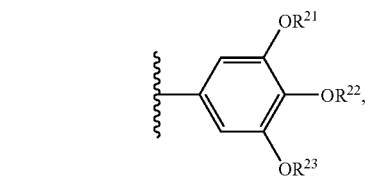

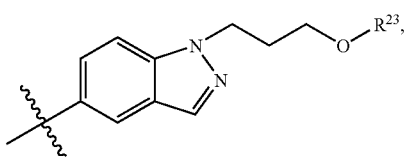

-continued

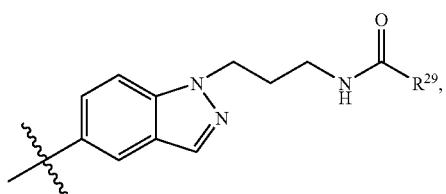

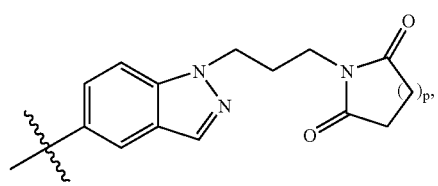

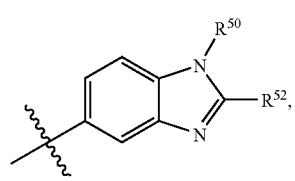

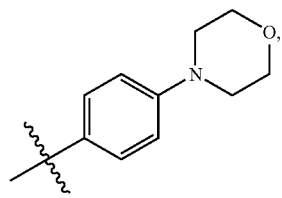

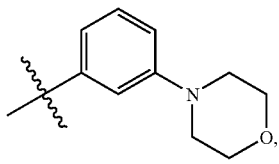

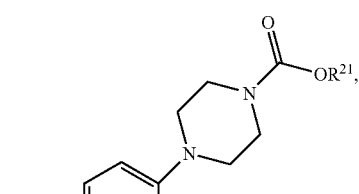

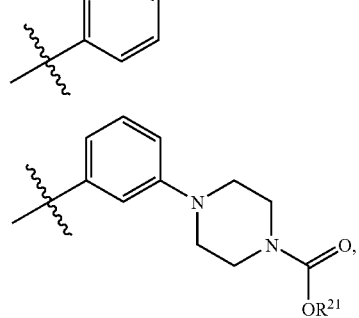

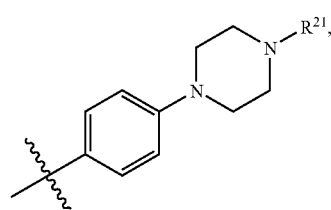

-continued

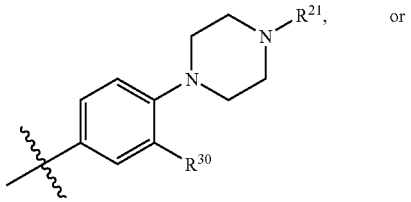

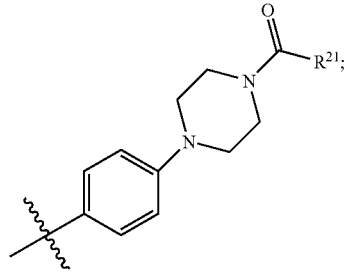

$R^4$ is

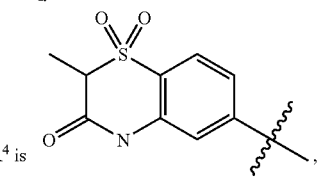

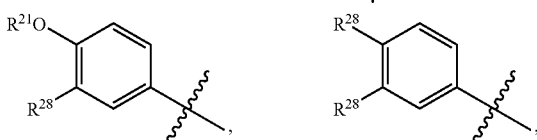

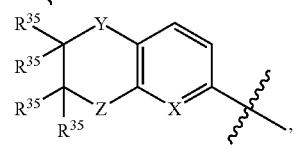

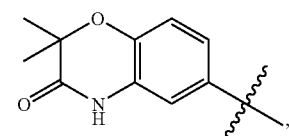

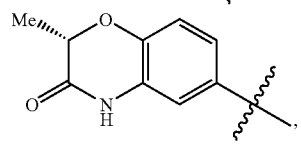

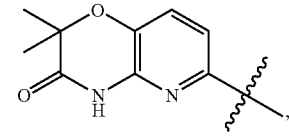

$R^5$, $R^6$, $R^8$, $R^a$, $R^b$, $R^c$, $R^d$, m and n are as described above;
each $R^{21}$, $R^{22}$ and $R^{23}$ are each, independently of one another, as described above and in particular, an alkyl group;
each $R^{28}$ individually is a halogen or alkoxy;
$R^{29}$ is a (C1-C6) alkyl or (C3-C9) cycloalkyl;
$R^{30}$ is an alkyl group or a halogen;
X is selected from the group consisting of N and CH;

Y, Z, $R^{35}$, $R^{36}$, $R^{37}$ and $R^{38}$ are as described above;

each $R^{46}$, $R^{47}$ and $R^{48}$ independently is selected from the group consisting of a hydrogen, alkyl, alkoxy, hydroxyl, halogen, isoxazole, piperazino, N-alkyl piperazine, morpholino and CH$_3$NHC(O)CH$_2$O—, with the proviso that $R^{46}$, $R^{47}$ and $R^{48}$ are all not hydrogen and when one of $R^{46}$, $R^{47}$ or $R^{48}$ is isoxazole, piperazino, N-alkyl piperazine, morpholino or CH$_3$NHC(O)CH$_2$O—, then the remaining $R^{46}$, $R^{47}$ or $R^{48}$ are hydrogen;

$R^{50}$ is an alkyl group or —(CH$_2$)$_q$OH;

q is an integer from 1 to 6;

$R^{52}$ is an alkyl group or a substituted alkyl group p is 1, 2 or 3; and x=1-8.

In a thirty fourth embodiment of the compounds of structural formulae (I) and (Ia), $R^2$, $R^4$, $R^5$, $L^1$ and $L^2$ are as previously described for their respective structures (I) and (Ia), with the proviso that $R^2$ is not 3,4,5-trimethoxyphenyl, 3,4,5-tri(C1-C6) alkoxyphenyl or

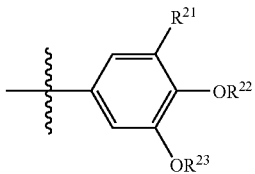

where $R^{21}$, $R^{22}$ and $R^{23}$ are as defined for $R^1$, $R^2$ and $R^3$, respectively of U.S. Pat. No. 6,235,746, the disclosure of which is incorporated by reference. In a specific embodiment of this first embodiment, $R^{21}$ is hydrogen, halo, straight-chain or branched (C1-C6) alkyl optionally substituted with one or more of the same or different $R^{25}$ groups, hydroxyl, (C1-C6) alkoxy optionally substituted with one or more of the same or different phenyl or $R^{25}$ groups, thiol (—SH), (C1-C6) alkylthio optionally substituted with one or more of the same or different phenyl or $R^{25}$ groups, amino (—NH$_2$), —NHR$^{26}$ or —NR$^{26}$R$^{26}$; $R^{22}$ and $R^{23}$ are each, independently of one another, a (C1-C6) straight-chain or branched alkyl optionally substituted with one or more of the same or different $R^{25}$ groups; $R^{25}$ is selected from the group consisting of halo, hydroxyl, (C1-C6) alkoxy, thiol, (C1-C6) alkylthio, (C1-C6) alkylamino and (C1-C6) dialkylamino; and each $R^{26}$ is independently a (C1-C6) alkyl optionally substituted with one or more of the same or different phenyl or $R^{25}$ groups or a —C(O)R$^{27}$, where $R^{27}$ is a (C1-C6) alkyl optionally substituted with one or more of the same or different phenyl or $R^{25}$ groups.

In another specific embodiment, $R^{21}$ is methoxy optionally substituted with one or more of the same or different halo groups and/or $R^{22}$ and $R^{23}$ are each, independently of one another, a methyl or ethyl optionally substituted with one or more of the same or different halo groups.

In a thirty fifth embodiment, the compounds of structural formulae (I) and (Ia), $R^5$, $R^6$, $R^8$, $L^1$ and $L^2$ are as previously defined:

$R^2$ is

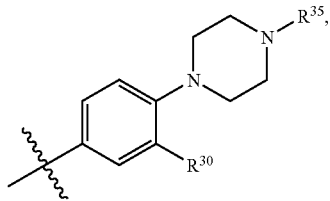

$R^4$ is

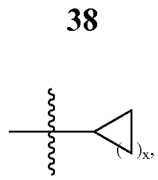

$R^5$, $R^6$, $R^{30}$, $R^{35}$ and x are as defined above. In certain embodiments, x is 2 through 4. In other embodiments, $R^{35}$ is a methyl group. In still additional embodiments, $R^{30}$ is chlorine, methyl or trifluoromethyl. In still other embodiments, $R^5$ is fluorine and $R^6$ is hydrogen.

In a thirty sixth embodiment the 2,4-pyrimidinediamine includes those compounds according to structures I and I(a) wherein $R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups. $R^4$ is

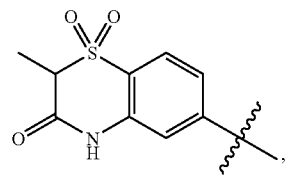

$R^5$, $R^6$ and $R^8$ are described as above. In certain embodiments, $R^5$ is a fluorine atom and $R^6$ is a hydrogen atom. In certain embodiments, $R^2$ is a di or tri-substituted phenyl group.

In a thirty seventh embodiment, the invention pertains to 2,4-pyrimidinediamine compounds according to structures I and I(a) wherein $R^2$ is

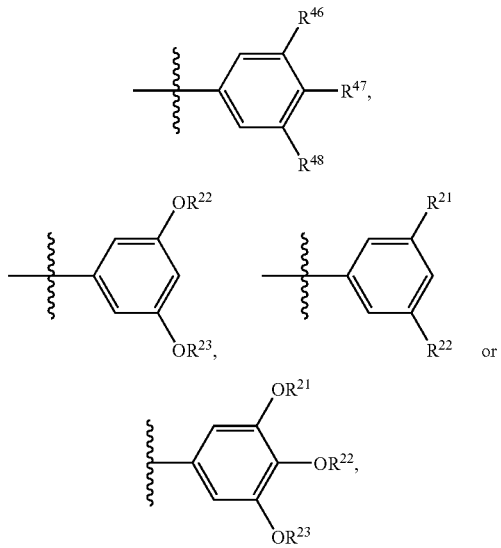

-continued

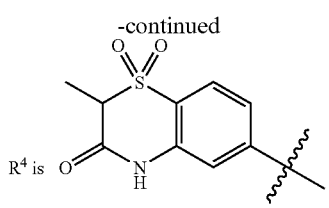

and $R^5$, $R^6$, $R^{22}$ and $R^{23}$, $R^{46}$, $R^{47}$ and $R^{48}$ are as defined above, each $R^{21}$, independently of one another, is an alkyl group. In certain embodiments, $R^5$ is a fluorine atom and $R^6$ is a hydrogen atom.

In a thirty eighth embodiment, the present invention relates to 2,4-pyrimidinediamine compounds according to structures I and I(a) wherein $R^2$ is

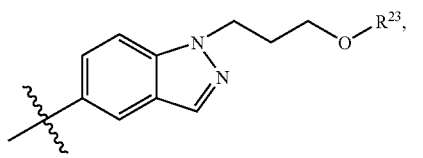

$R^4$ is,

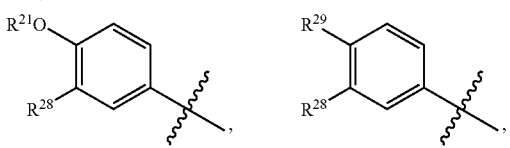

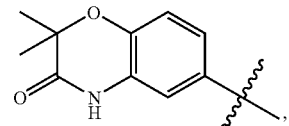

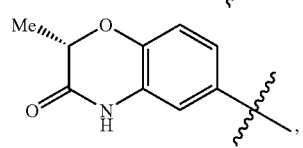

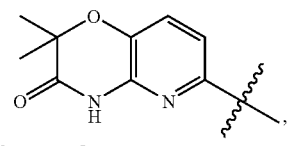

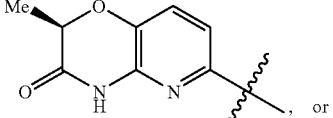

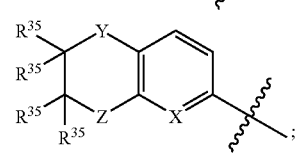

$R^5$, $R^6$, $R^8$, $R^{21}$, $R^{23}$, $R^{28}$, $R^{35}$, $R^{36}$, $R^{37}$, $R^{38}$, Y, Z, $R^a$, $R^b$, $R^c$, $R^d$, and n are as described above, and X is selected from the group consisting of N and CH. In a particular embodiment, $R^{28}$ is a methoxy. In another embodiment, $R^{23}$ is methyl. In particular embodiments, $R^{21}$ is a methyl group. In other embodiments, each $R^{28}$ is chlorine. In still additional embodiments, $R^{21}$ is a methyl group and at least one $R^{28}$ is a chlorine. In another embodiment, $R^{28}$ is a methoxy.

In a thirty ninth embodiment, the present invention provides pyrimidinediamine compounds according to structures I and I(a) wherein $R^2$ is

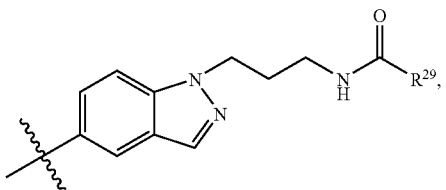

$R^4$ is,

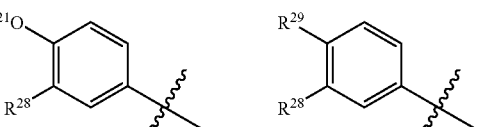

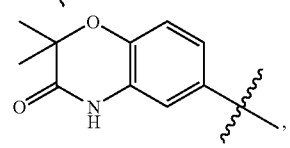

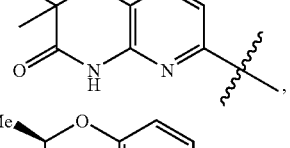

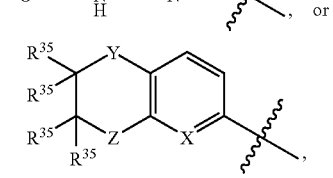

, or

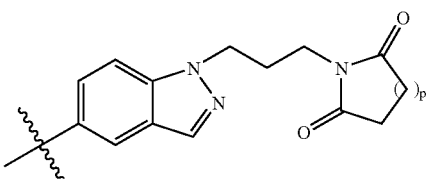

$R^5$, $R^6$, $R^8$, $R^{21}$, each $R^{28}$, $R^{29}$, $R^a$, $R^b$, $R^c$, $R^d$, and n, X, Y, Z, each $R^{35}$ each $R^{36}$ each $R^{37}$ and $R^{38}$ are as described above.

In certain embodiments, $R^{29}$ is a t-butyl group. In other embodiments, $R^{21}$ is a methyl group. In certain embodiments, each $R^{28}$ is a chlorine. In still another embodiment, $R^{21}$ is a methyl group and at least one of $R^{28}$ is a chlorine.

In a fortieth embodiment, the invention pertains to 2,4-pyrimidinediamine compounds according to structures I and I(a) wherein $R^2$ is

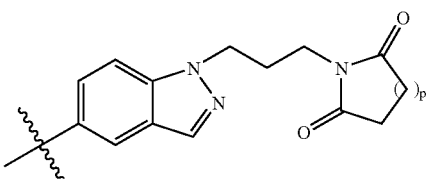

$R^4$ is

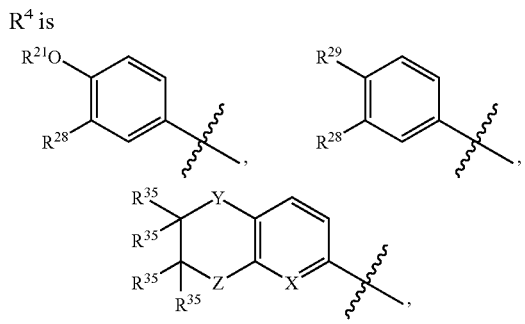

$R^5$, $R^6$, $R^8$, $R^{21}$, each $R^{28}$, $R^a$, $R^b$, $R^c$, $R^d$, m, n, p, X, Y, Z, each $R^{35}$, each $R^{36}$, each $R^{37}$ and $R^{38}$ are as described above. In particular embodiments, $R^{21}$ is a methyl group. In other embodiments, each $R^{28}$ is a chlorine. In still other embodiments, $R^{21}$ is a methyl group and at least one of $R^{28}$ is a chlorine. In still another aspect, p is 1 or 2.

In a forty first embodiment, the invention relates to 2,4-pyrimidinediamine compounds according to structures I and I(a) wherein $R^2$ is

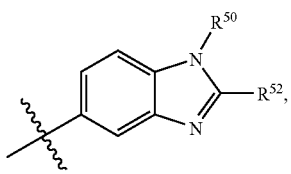

$R^4$ is

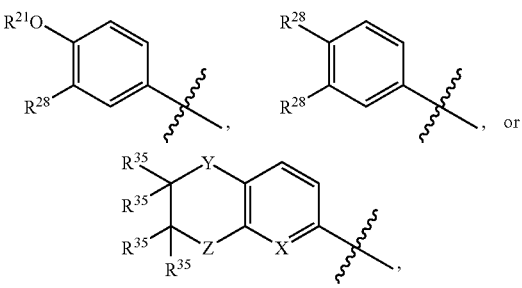

$R^5$, $R^6$, $R^8$, $R^{21}$, each $R^{28}$, $R^a$, $R^b$, $R^c$, $R^d$, m, n, q, X, Y, Z, $R^{35}$, $R^{36}$, $R^{37}$, $R^{38}$, $R^{50}$, and $R^{52}$ are as described above.

In certain aspects, $R^{50}$ is —CH$_2$CH$_2$—OH or methyl. In another aspect, $R^{52}$ is trifluoromethyl. In still another aspect, at least one $R^{28}$ is a chlorine. In yet another aspect, $R^{50}$ is a methyl and at least one $R^{28}$ is a chlorine.

In a forty second embodiment, applicable to the first through forty first embodiments, $R^5$ of the pyrimidine ring is a halogen atom, such as fluorine, and $R^6$ of the pyrimidine ring is a hydrogen atom.

In a forty third embodiment, $L^1$ and $L^2$ are covalent bonds for the above-identified embodiments.

Also specifically described are combinations of the above first through forty third embodiments.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. Indeed, many of the active 2,4-pyrimidinediamine compounds described in TABLE 1, include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamines that include ester moieties may be considered prodrugs of their corresponding carboxylic acid, regardless of whether the ester form is pharmacologically active. Referring to TABLE 1, numerous ester-containing 2,4-pyrimidinediamines of the invention are active in their ester, "prodrug" form.

In the prodrugs of the invention, any available functional moiety may be masked with a progroup to yield a prodrug. Functional groups within the 2,4-pyrimidinediamine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

In one illustrative embodiment, the prodrugs of the invention are compounds according to structural formula (I) in which $R^c$ and $R^d$ may be, in addition to their previously-defined alternatives, a progroup.

Those of skill in the art will appreciate that many of the compounds and prodrugs of the invention, as well as the various compound species specifically described and/or illustrated herein, may exhibit the phenomena of tautomerism, conformational isomerism, geometric isomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the compounds and prodrugs of the invention may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. In cases of limited rotation around the 2,4-pyrimidinediamine core structure, atropisomers are also possible and are also specifically included in the compounds of the invention.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives for $R^b$ can be used to substitute an alkyl group, certain of the alternatives, such as =O, cannot be used to substitute a phenyl group. It is to be understood that only possible combinations of substituent-group pairs are intended.

The compounds and/or prodrugs of the invention may be identified by either their chemical structure or their chemical name. When the chemical structure and the chemical name conflict, the chemical structure is determinative of the identity of the specific compound.

Depending upon the nature of the various substituents, the 2,4-pyrimidinediamine compounds and prodrugs of the invention may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, cycloalkylsulfonic acids (e.g., camphorsulfonic acid), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion), an ammonium ion or coordinates with an organic base (e.g., ethanolamine, diethanolamine, triethanolamine, N-methylglucamine, morpholine, piperidine, dimethylamine, diethylamine, etc.).

The 2,4-pyrimidinediamine compounds and of the invention, as well as the salts thereof, may also be in the form of hydrates, solvates and N-oxides, as are well-known in the art.

6.3 Methods of Synthesis

The compounds and prodrugs of the invention may be synthesized via a variety of different synthetic routes using commercially available starting materials and/or starting materials prepared by conventional synthetic methods. Suitable exemplary methods that may be routinely adapted to synthesize the 2,4-pyrimidinediamine compounds and prodrugs of the invention are found in U.S. Pat. No. 5,958,935, U.S. patent application Ser. No. 10/355,543, filed Jan. 31, 2003 (US Publication US20040029902-A1), WO 03/063794, published Aug. 1, 2003, U.S. patent application Ser. No. 10/631,029, filed Jul. 29, 2003 and WO 2004/014382, published Feb. 19, 2004, the disclosures of which are incorporated herein by reference. All of the compounds of structural formulae (I), (Ia) and (II) may be prepared by routine adaptation of these methods.

A variety of exemplary synthetic routes that can be used to synthesize the 2,4-pyrimidinediamine compounds of the invention are described in Schemes (I)-(XI), below. In Schemes (I)-(XI), like-numbered compounds have similar structures. These methods may be routinely adapted to synthesize the prodrugs according to structural formula (II).

In one exemplary embodiment, the compounds can be synthesized from substituted or unsubstituted uracils or thiouracils as illustrated in Scheme (I), below:

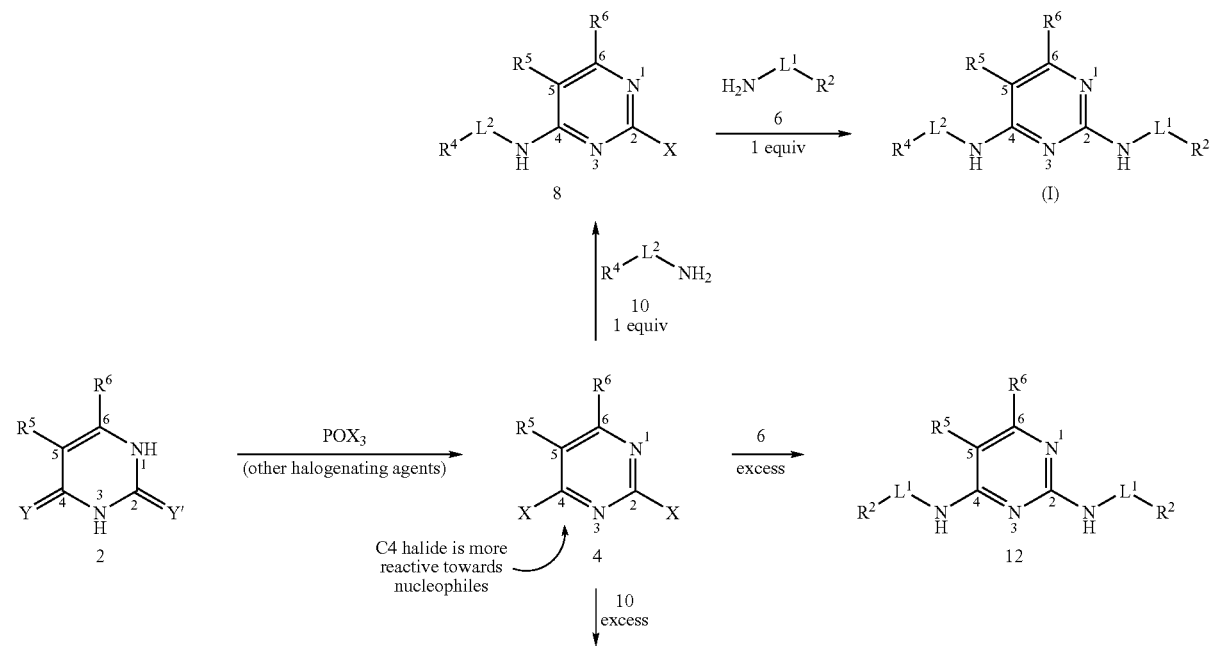

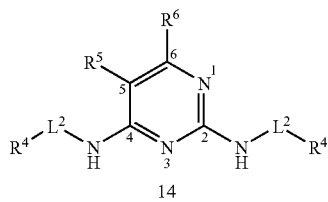

14

In Scheme (I), $R^2$, $R^4$, $R^5$, $R^6$, $L^1$ and $L^2$ are as previously defined for structural formula (I), X is a halogen (e.g., F, Cl, Br or I) and Y and Y' are each, independently of one another, selected from the group consisting of O and S. Referring to Scheme (I), uracil or thiouracil 2 is dihalogenated at the 2- and 4-positions using standard halogenating agent $POX_3$ (or other standard halogenating agent) under standard conditions to yield 2,4-bishalo pyrimidine 4. Depending upon the $R^5$ substituent, in pyrimidine 4, the halide at the C4 position is more reactive towards nucleophiles than the halide at the C2 position. This differential reactivity can be exploited to synthesize 2,4-pyrimidinediamines according structural formula (I) by first reacting 2,4-bishalopyrimidine 4 with one equivalent of amine 10, yielding 4N-substituted-2-halo-4-pyrimidineamine 8, followed by amine 6 to yield a 2,4-pyrimidinediamine according structural formula (I). 2N,4N-bis(substituted)-2,4-pyrimidinediamines 12 and 14 can be obtained by reacting 2,4-bishalopyrimidine 4 with excess 6 or 10, respectively.

In most situations, the C4 halide is more reactive towards nucleophiles, as illustrated in the Scheme. However, as will be recognized by skilled artisans, the identity of the $R^5$ substituent may alter this reactivity. For example, when $R^5$ is trifluoromethyl, a 50:50 mixture of 4N-substituted-4-pyrimidineamine 8 and the corresponding 2N-substituted-2-pyrimidineamine is obtained. Regardless of the identity of the $R^5$ substituent, the regioselectivity of the reaction can be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry) in a sealed tube (at 20 bar pressure).

The uracil or thiouracil 2 starting materials may be purchased from commercial sources or prepared using standard techniques of organic chemistry. Commercially available uracils and thiouracils that can be used as starting materials in Scheme (I) include, by way of example and not limitation, uracil (Aldrich #13,078-8; CAS Registry 66-22-8); 2-thiouracil (Aldrich #11, 558-4; CAS Registry 141-90-2); 2,4-dithiouracil (Aldrich #15, 846-1; CAS Registry 2001-93-6); 5-acetouracil (Chem. Sources Int'l 2000; CAS Registry 6214-65-9); 5-azidouracil; 5-aminouracil (Aldrich #85, 528-6; CAS Registry 932-52-5); 5-bromouracil (Aldrich #85, 247-3; CAS Registry 51-20-7); 5-(trans-2-bromovinyl)-uracil (Aldrich #45,744-2; CAS Registry 69304-49-0); 5-(trans-2-chlorovinyl)-uracil (CAS Registry 81751-48-2); 5-(trans-2-carboxyvinyl)-uracil; uracil-5-carboxylic acid (2,4-dihydroxypyrimidine-5-carboxylic acid hydrate; Aldrich #27, 770-3; CAS Registry 23945-44-0); 5-chlorouracil (Aldrich #22, 458-8; CAS Registry 1820-81-1); 5-cyanouracil (Chem. Sources Int'l 2000; CAS Registry 4425-56-3); 5-ethyluracil (Aldrich #23,044-8; CAS Registry 4212-49-1); 5-ethenyluracil (CAS Registry 37107-81-6); 5-fluorouracil (Aldrich #85, 847-1; CAS Registry 51-21-8); 5-iodouracil (Aldrich #85, 785-8; CAS Registry 696-07-1); 5-methyluracil (thymine; Aldrich #13, 199-7; CAS Registry 65-71-4); 5-nitrouracil (Aldrich #85, 276-7; CAS Registry 611-08-5); uracil-5-sulfamic acid (Chem. Sources Int'l 2000; CAS Registry 5435-16-5); 5-(trifluoromethyl)-uracil (Aldrich #22, 327-1; CAS Registry 54-20-6); 5-(2,2,2-trifluoroethyl)-uracil (CAS Registry 155143-31-6); 5-(pentafluoroethyl)-uracil (CAS Registry 60007-38-3); 6-aminouracil (Aldrich #A5060-6; CAS Registry 873-83-6) uracil-6-carboxylic acid (orotic acid; Aldrich #0-840-2; CAS Registry 50887-69-9); 6-methyluracil (Aldrich #D11, 520-7; CAS Registry 626-48-2); uracil-5-amino-6-carboxylic acid (5-aminoorotic acid; Aldrich #19, 121-3; CAS Registry #7164-43-4); 6-amino-5-nitrosouracil (6-amino-2,4-dihydroxy-5-nitrosopyrimidine; Aldrich #27, 689-8; CAS Registry 5442-24-0); uracil-5-fluoro-6-carboxylic acid (5-fluoroorotic acid; Aldrich #42, 513-3; CAS Registry 00000-00-0); and uracil-5-nitro-6-carboxylic acid (5-nitroorotic acid; Aldrich #18, 528-0; CAS Registry 600779-49-9). Additional 5-, 6- and 5,6-substituted uracils and/or thiouracils are available from General Intermediates of Canada, Inc., Edmonton, Alberta, Calif. (www.generalintermediates.com) and/or Interchim, France (www.interchim.com), or may be prepared using standard techniques. Myriad textbook references teaching suitable synthetic methods are provided infra.

Amines 6 and 10 may be purchased from commercial sources or, alternatively, may be synthesized utilizing standard techniques. For example, suitable amines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines 6 and 10 and/or substituents $R^5$ and/or $R^6$ on uracil or thiouracil 2 may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

A specific embodiment of Scheme (I) utilizing 5-fluorouracil (Aldrich #32, 937-1) as a starting material is illustrated in Scheme (Ia), below:

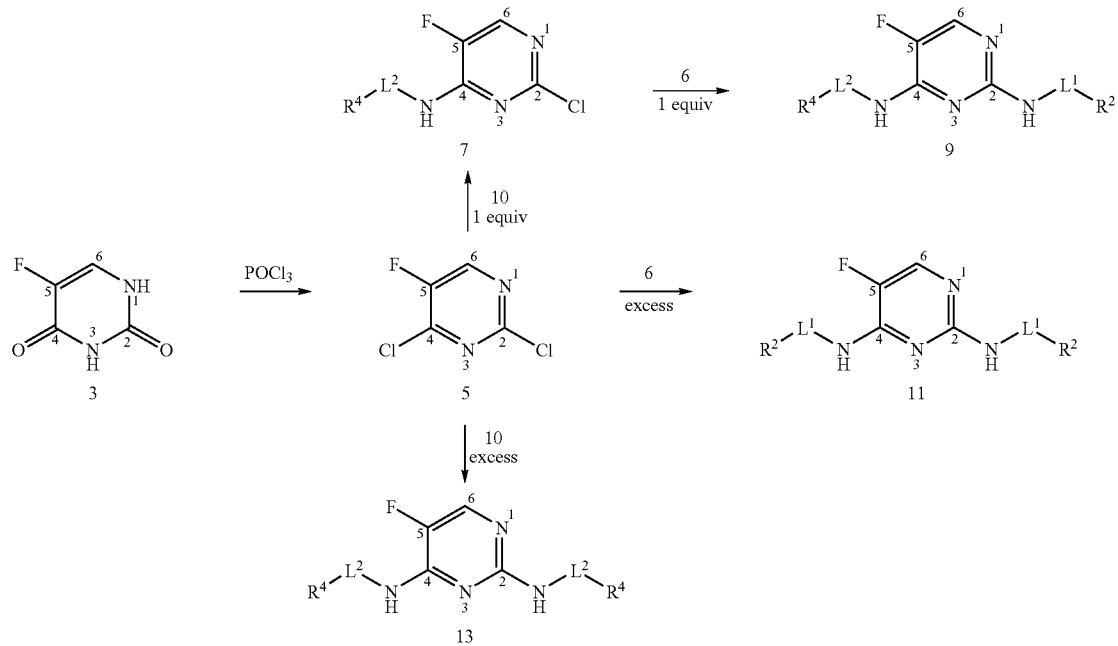

In Scheme (Ia), $R^2$, $R^4$, $L^1$ and $L^2$ are as previously defined for Scheme (I). According to Scheme (Ia), 5-fluorouracil 3 is halogenated with $POCl_3$ to yield 2,4-dichloro-5-fluoropyrimidine 5, which is then reacted with excess amine 6 or 10 to yield N2,N4-bis substituted 5-fluoro-2,4-pyrimidinediamine 11 or 13, respectively. Alternatively, non-bis 2N,4N-disubstituted-5-fluoro-2,4-pyrimidinediamine 9 may be obtained by reacting 2,4-dichloro-5-fluoropyrimidine 5 with one equivalent of amine 10 (to yield 2-chloro-N4-substituted-5-fluoro-4-pyrimidineamine 7) followed by one or more equivalents of amine 6.

In another exemplary embodiment, the 2,4-pyrimidinediamine compounds of the invention may be synthesized from substituted or unsubstituted cytosines as illustrated in Schemes (IIa) and (IIb), below:

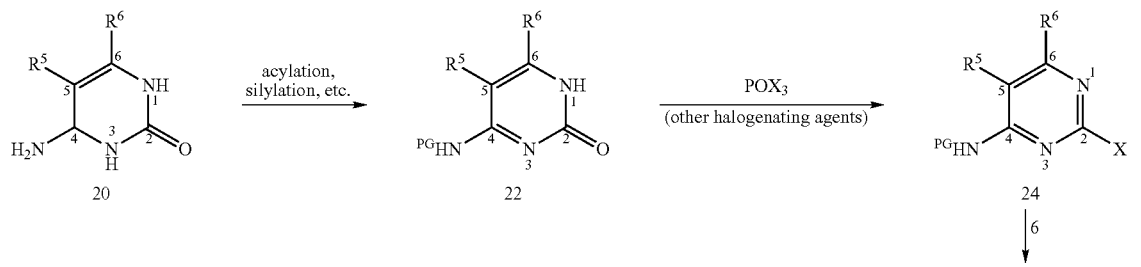

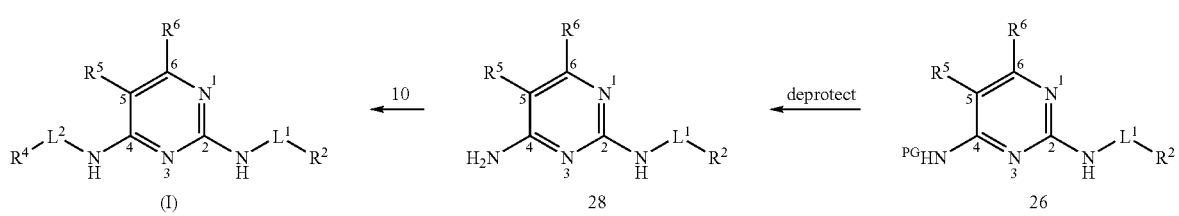

Scheme (IIb)

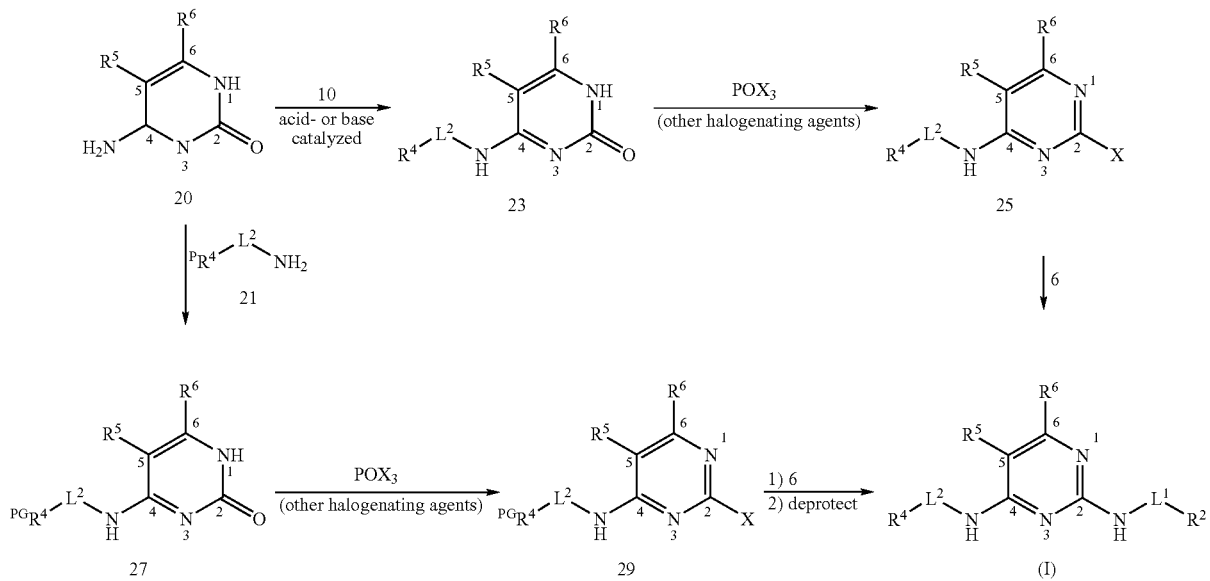

In Schemes (IIa) and (IIb), $R^2$, $R^4$, $R^5$, $R^6$, $L^1$, $L^2$ and X are as previously defined for Scheme (I) and PG represents a protecting group. Referring to Scheme (IIa), the C4 exocyclic amine of cytosine 20 is first protected with a suitable protecting group PG to yield N4-protected cytosine 22. For specific guidance regarding protecting groups useful in this context, see Vorbrüggen and Ruh-Pohlenz, 2001, *Handbook of Nucleoside Synthesis*, John Wiley & Sons, NY, pp. 1-631 ("Vorbrüggen"). Protected cytosine 22 is halogenated at the C2 position using a standard halogenation reagent under standard conditions to yield 2-chloro-4N-protected-4-pyrimidineamine 24. Reaction with amine 6 followed by deprotection of the C4 exocyclic amine and reaction with amine 10 yields a 2,4-pyrimidinediamine according to structural formula (I).

Alternatively, referring to Scheme (IIb), cytosine 20 may be reacted with amine 10 or protected amine 21 to yield N4-substituted cytosine 23 or 27, respectively. These substituted cytosines may then be halogenated as previously described, deprotected (in the case of N4-substituted cytosine 27) and reacted with amine 6 to yield a 2,4-pyrimidinediamine according to structural formula (I).

Commercially-available cytosines that may be used as starting materials in Schemes (IIa) and (IIb) include, but are not limited to, cytosine (Aldrich #14, 201-8; CAS Registry 71-30-7); $N^4$-acetylcytosine (Aldrich #37, 791-0; CAS Registry 14631-20-0); 5-fluorocytosine (Aldrich #27, 159-4; CAS Registry 2022-85-7); and 5-(trifluoromethyl)-cytosine. Other suitable cytosines useful as starting materials in Schemes (IIa) are available from General Intermediates of Canada, Inc., Edmonton, Alberta, Calif. (www.generalintermediates.com) and/or Interchim, France (www.interchim.com), or may be prepared using standard techniques. Myriad textbook references teaching suitable synthetic methods are provided infra.

In still another exemplary embodiment, the 2,4-pyrimidinediamine compounds of the invention may be synthesized from substituted or unsubstituted 2-amino-4-pyrimidinols as illustrated in Scheme (III), below:

Scheme (III)

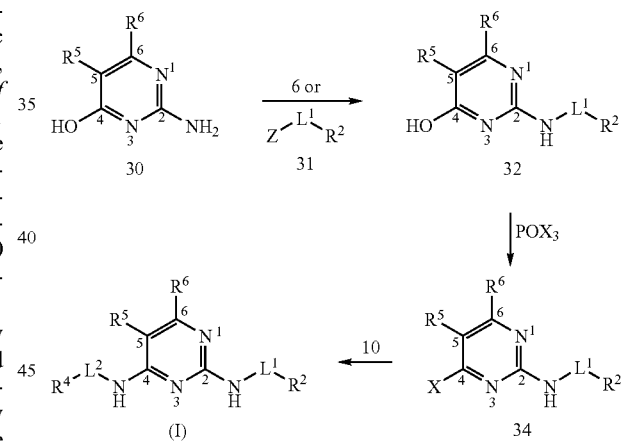

In Scheme (III), $R^2$, $R^4$, $R^5$, $R^6$, $L^1$, $L^2$ and X are as previously defined for Scheme (I) and Z is a leaving group as discussed in more detail in connection with Scheme IV, infra. Referring to Scheme (III), 2-amino-4-pyrimidinol 30 is reacted with amine 6 (or optionally protected amine 21) to yield N2-substituted-4-pyrimidinol 32, which is then halogenated as previously described to yield N2-substituted-4-halo-2-pyrimidineamine 34. Optional deprotection (for example if protected amine 21 was used in the first step) followed by reaction with amine 10 affords a 2,4-pyrimidinediamine according to structural formula (I). Alternatively, pyrimidinol 30 can be reacted with acylating agent 31.

Suitable commercially-available 2-amino-4-pyrimidinols 30 that can be used as starting materials in Scheme (III) include, but are not limited to, 2-amino-6-chloro-4-pyrimidinol hydrate (Aldrich #A4702-8; CAS Registry 00000-00-0) and 2-amino-6-hydroxy-4-pyrimidinol (Aldrich #A5040-1; CAS Registry 56-09-7). Other 2-amino-4-pyrimidinols 30 useful as starting materials in Scheme (III) are available from General Intermediates of Canada, Inc., Edmonton, Alberta, Calif. (www.generalintermediates.com) and/or Interchim, France (www.interchim.com), or may be prepared using standard techniques. Myriad textbook references teaching suitable synthetic methods are provided infra.

Alternatively, the 2,4-pyrimidinediamine compounds of the invention may be prepared from substituted or unsubstituted 4-amino-2-pyrimidinols as illustrated in Scheme (IV), below:

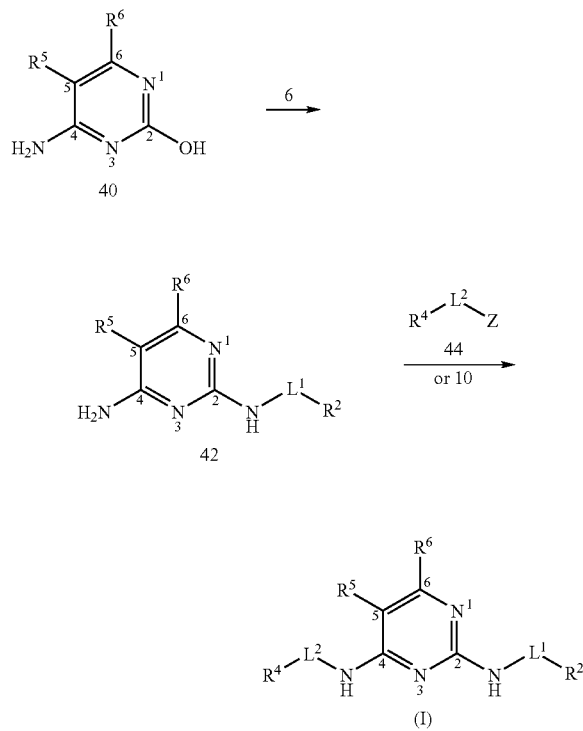

In Scheme (IV), $R^2$, $R^4$, $R^5$, $R^6$, $L^1$ and $L^2$ are as previously defined for Scheme (I) and Z represents a leaving group. Referring to Scheme (IV), the C2-hydroxyl of 4-amino-2-pyrimidinol 40 is more reactive towards nucleophiles than the C4-amino such that reaction with amine 6 yields N2-substituted-2,4-pyrimidinediamine 42. Subsequent reaction with compound 44, which includes a good leaving group Z, or amine 10 yields a 2,4-pyrimidinediamine according to structural formula (I). Compound 44 may include virtually any leaving group that can be displaced by the C4-amino of N2-substituted-2,4-pyrimidinediamine 42. Suitable leaving groups Z include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and metanitro benzene sulfonyloxy ("nosylate"). Other suitable leaving groups will be apparent to those of skill in the art.

Substituted 4-amino-2-pyrimidinol starting materials may be obtained commercially or synthesized using standard techniques. Myriad textbook references teaching suitable synthetic methods are provided infra.

In still another exemplary embodiment, the 2,4-pyrimidinediamine compounds of the invention can be prepared from 2-chloro-4-aminopyrimidines or 2-amino-4-chloropyrimidines as illustrated in Scheme (V), below:

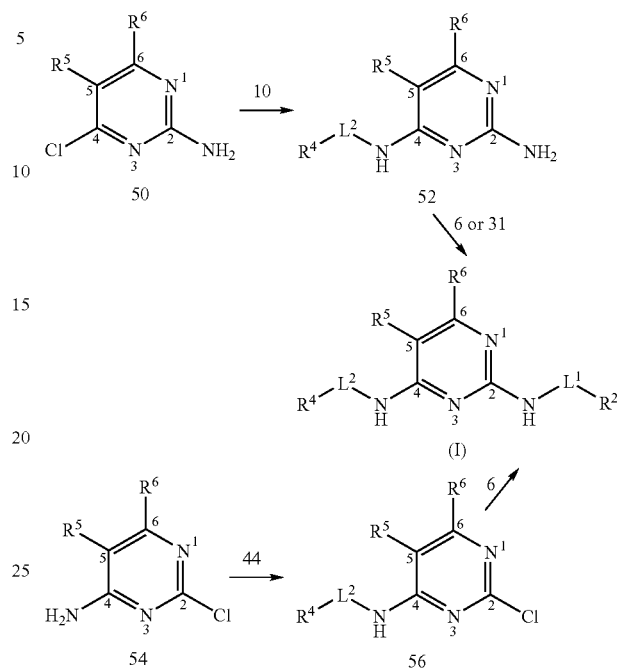

In Scheme (V), $R^2$, $R^4$, $R^5$, $R^6$, $L^1$, $L^2$ and X are as defined for Scheme (I) and Z is as defined for Scheme (IV). Referring to Scheme (V), 2-amino-4-chloropyrimidine 50 is reacted with amino 10 to yield 4N-substituted-2-pyrimidineamine 52 which, following reaction with compound 31 or amine 6, yields a 2,4-pyrimidinediamine according to structural formula (I). Alternatively, 2-chloro-4-amino-pyrimidine 54 may be reacted with compound 44 followed by amine 6 to yield a compound according to structural formula (I).

A variety of pyrimidines 50 and 54 suitable for use as starting materials in Scheme (V) are commercially available, including by way of example and not limitation, 2-amino-4,6-dichloropyrimidine (Aldrich #A4860-1; CAS Registry 56-05-3); 2-amino-4-chloro-6-methoxy-pyrimidine (Aldrich #51,864-6; CAS Registry 5734-64-5); 2-amino-4-chloro-6-methylpyrimidine (Aldrich #12,288-2; CAS Registry 5600-21-5); and 2-amino-4-chloro-6-methylthiopyrimidine (Aldrich #A4600-5; CAS Registry 1005-38-5). Additional pyrimidine starting materials are available from General Intermediates of Canada, Inc., Edmonton, Alberta, Calif. (www.generalintermediates.com) and/or Interchim, France (www.interchim.com), or may be prepared using standard techniques. Myriad textbook references teaching suitable synthetic methods are provided infra.

Alternatively, 4-chloro-2-pyrimidineamines 50 may be prepared as illustrated in Scheme (Va):

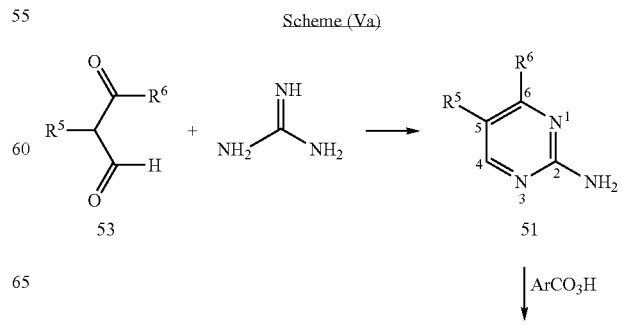

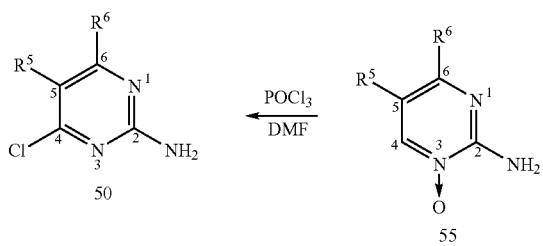

In Scheme (Va), $R^5$ and $R^6$ are as previously defined for structural formula (I). In Scheme (Va), dicarbonyl 53 is reacted with guanidine to yield 2-pyrimidineamine 51. Reaction with peracids like m-chloroperbenzoic acid, trifluoroperacetic acid or urea hydrogen peroxide complex yields N-oxide 55, which is then halogenated to give 4-chloro-2-pyrimidineamine 50. The corresponding 4-halo-2-pyrimidineamines may be obtained by using suitable halogenation reagents.

In yet another exemplary embodiment, the 2,4-pyrimidinediamine compounds of the invention can be prepared from substituted or unsubstituted uridines as illustrated in Scheme (VI), below:

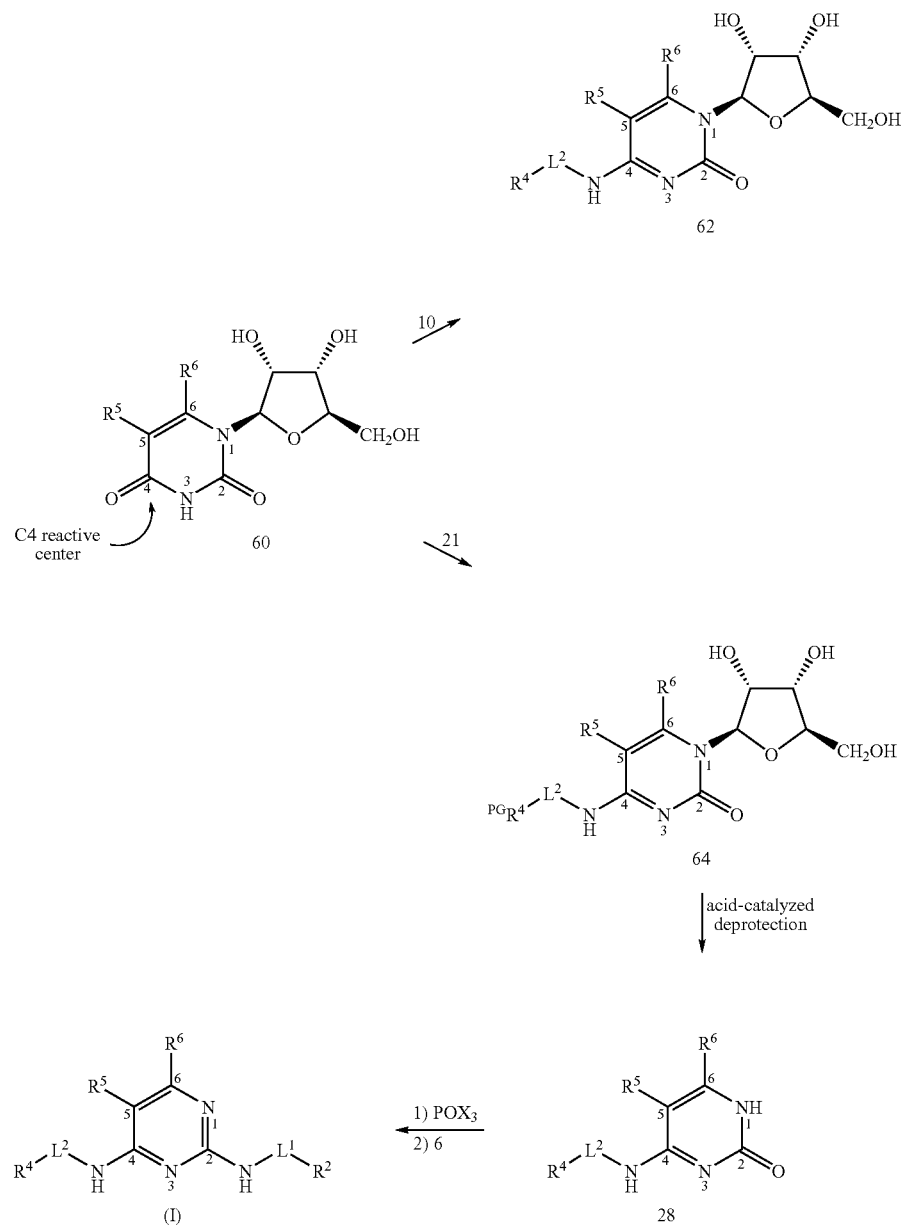

In Scheme (VI), $R^2$, $R^4$, $R^5$, $R^6$, $L^1$, $L^2$ and X are as previously defined for Scheme (I) and the superscript PG represents a protecting group, as discussed in connection with Scheme (IIb). According to Scheme (VI), uridine 60 has a C4 reactive center such that reaction with amine 10 or protected amine 21 yields N4-substituted cytidine 62 or 64, respectively. Acid-catalyzed deprotection of N4-substituted 62 or 64 (when "PG" represents an acid-labile protecting group) yields N4-substituted cytosine 28, which may be subsequently halogenated at the C2-position and reacted with amine 6 to yield a 2,4-pyrimidinediamine according to structural formula (I).

Cytidines may also be used as starting materials in an analogous manner, as illustrated in Scheme (VII), below:

Although Schemes (VI) and (VII) are exemplified with ribosylnucleosides, skilled artisans will appreciate that the corresponding 2'-deoxyribo and 2',3'-dideoxyribo nucleosides, as well as nucleosides including sugars or sugar analogs other than ribose, would also work.

Numerous uridines and cytidines useful as starting materials in Schemes (VI) and (VII) are known in the art, and include, by way of example and not limitation, 5-trifluoromethyl-2'-deoxycytidine (Chem. Sources #ABCR F07669; CAS Registry 66,384-66-5); 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32, 937-1; CAS Registry 316-46-1); 5-iodouridine (Aldrich #85, 259-7; CAS Registry 1024-99-3);

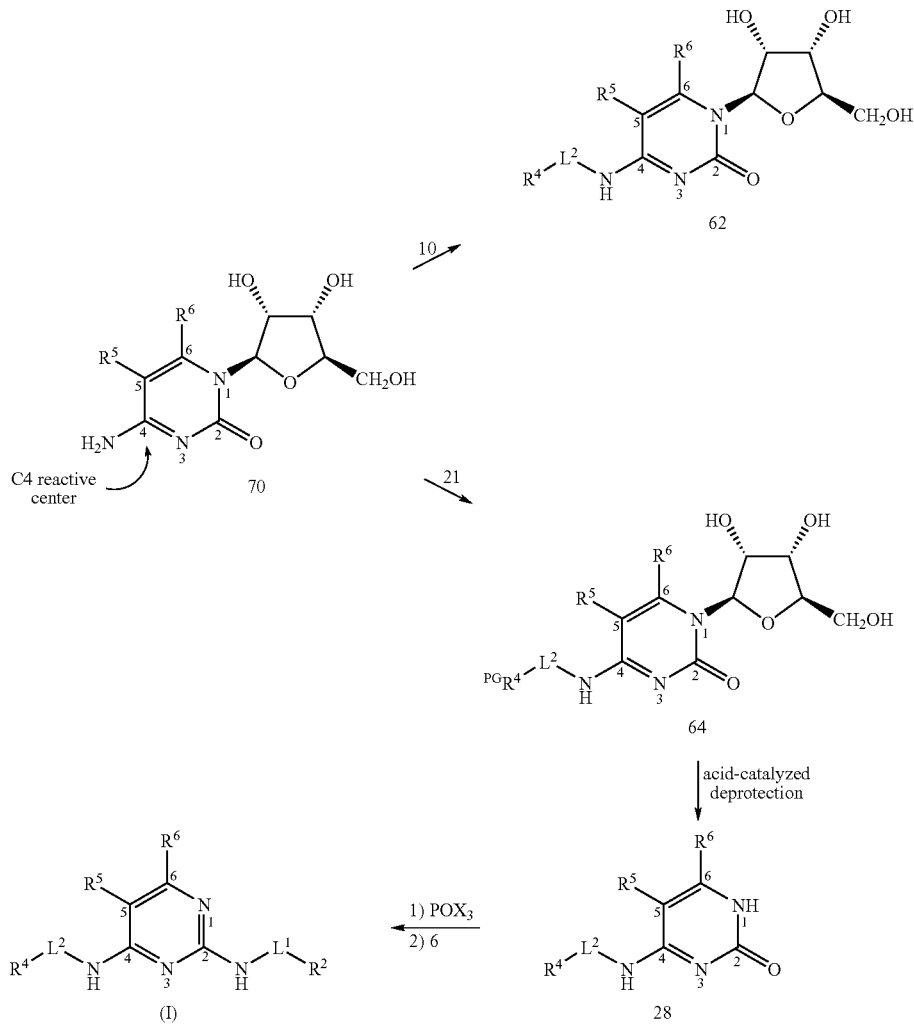

Scheme (VII)

In Scheme (VII), $R^2$, $R^4$, $R^5$, $R^6$, $L^1$, $L^2$ and X are as previously defined in Scheme (I) and the superscript PG represents a protecting group as discussed above. Referring to Scheme (VII), like uridine 60, cytidine 70 has a C4 reactive center such that reaction with amine 10 or protected amine 21 yields N4-substituted cytidine 62 or 64, respectively. These cytidines 62 and 64 are then treated as previously described for Scheme (VI) to yield a 2,4-pyrimidinediamine according to structural formula (I).

5-(trifluoromethyl)uridine (Chem. Sources Int'l 2000; CAS Registry 70-00-8); 5-trifluoromethyl-2'-deoxyuridine (Chem. Sources Int'l 2000; CAS Registry 70-00-8). Additional uridines and cytidines that can be used as starting materials in Schemes (VI) and (VII) are available from General Intermediates of Canada, Inc., Edmonton, Alberta, Calif. (www.generalintermediates.com) and/or Interchim, France (www.interchim.com or may be prepared using standard techniques. Myriad textbook references teaching suitable synthetic methods are provided infra.

The 2,4-pyrimidinediamine compounds of the invention can also be synthesized from substituted pyrimidines, such as chloro-substituted pyrimidines, as illustrated in Schemes (VIII) and (IX), below:
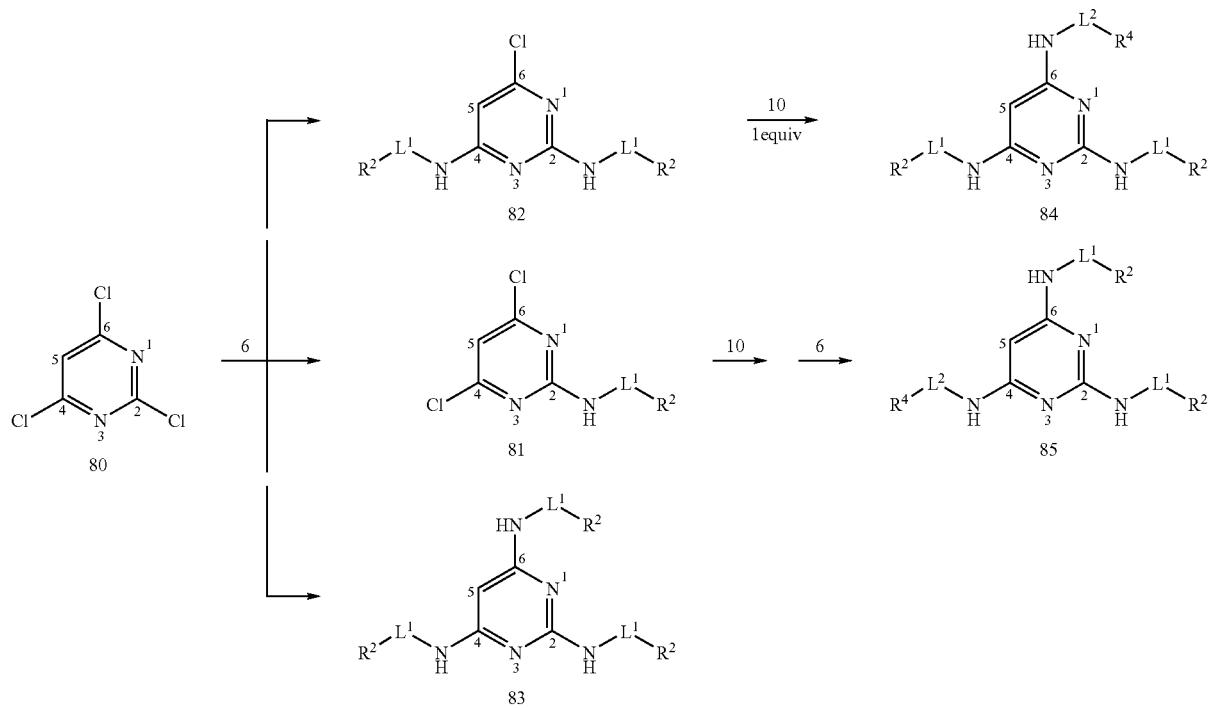
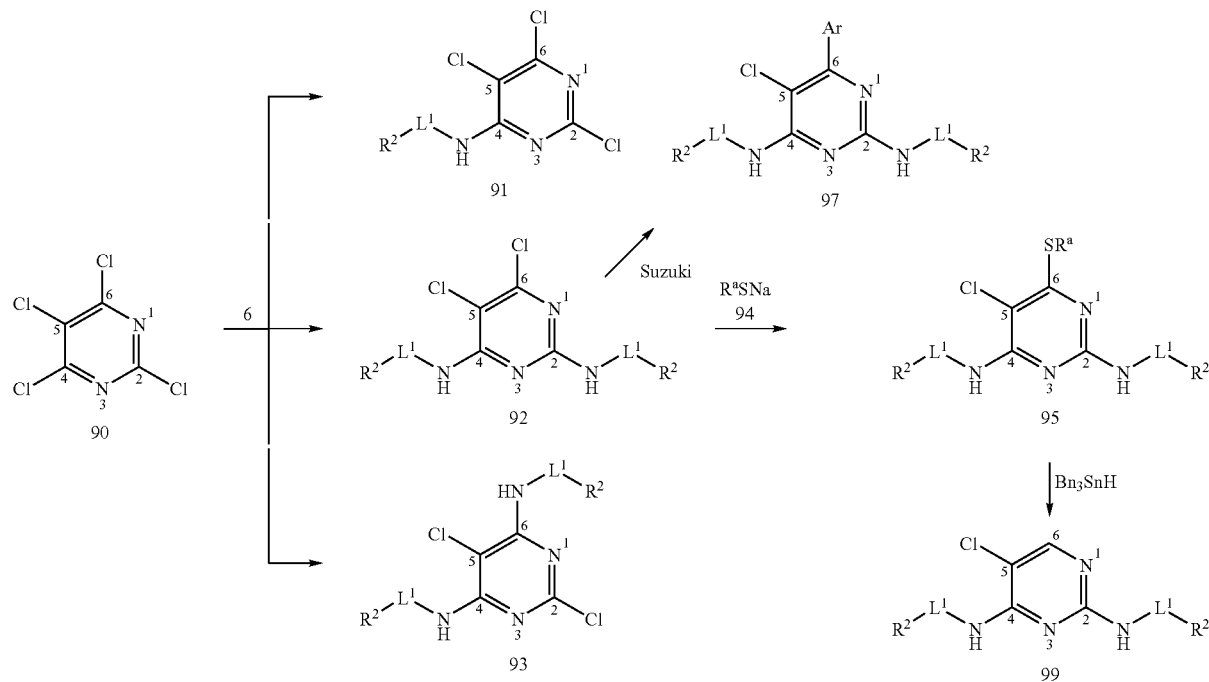

In Schemes (VIII) and (IX), $R^2$, $R^4$, $L^1$, $L^2$ and $R^a$ are as previously defined for structural formula (I) and "Ar" represents an aryl group. Referring to Scheme (VIII), reaction of 2,4,6-trichloropyrimidine 80 (Aldrich #T5, 620-0; CAS#3764-01-0) with amine 6 yields a mixture of three compounds: substituted pyrimidine mono-, di- and triamines 81, 82 and 83, which can be separated and isolated using HPLC or other conventional techniques. Mono- and diamines 81 and 82 may be further reacted with amines 6 and/or 10 to yield N2,N4,N6-trisubstituted-2,4,6-pyrimidinetriamines 84 and 85, respectively.

N2,N4-bis-substituted-2,4-pyrimidinediamines can be prepared in a manner analogous to Scheme (VIII) by employing 2,4-dichloro-5-methylpyrimidine or 2,4-dichloro-pyrimidine as starting materials. In this instance, the mono-substituted pyrimidineamine corresponding to compound 81 is not obtained. Instead, the reaction proceeds to yield the N2,N4-bis-substituted-2,4-pyrimidinediamine directly.

Referring to Scheme (IX), 2,4,5,6-tetrachloropyrimidine 90 (Aldrich #24, 671-9; CAS#1780-40-1) is reacted with excess amine 6 to yield a mixture of three compounds: 91, 92, and 93, which can be separated and isolated using HPLC or other conventional techniques. As illustrated, N2,N4-bis-substituted-5,6,-dichloro-2,4-pyrimidinediamine 92 may be further reacted at the C6 halide with, for example a nucleophilic agent 94 to yield compound 95. Alternatively, compound 92 can be converted into N2,N4-bis-substituted-5-chloro-6-aryl-2,4-pyrimidinediamine 97 via a Suzuki reaction. 2,4-Pyrimidinediamine 95 may be converted to 2,4-pyrimidinediamine 99 by reaction with $Bn_3SnH$.

As will be recognized by skilled artisans, 2,4-pyrimidinediamines according to the invention, synthesized via the exemplary methods described above or by other well-known means, may also be utilized as starting materials and/or intermediates to synthesize additional 2,4-pyrimidinediamine compounds of the invention. A specific example is illustrated in Scheme (X), below:

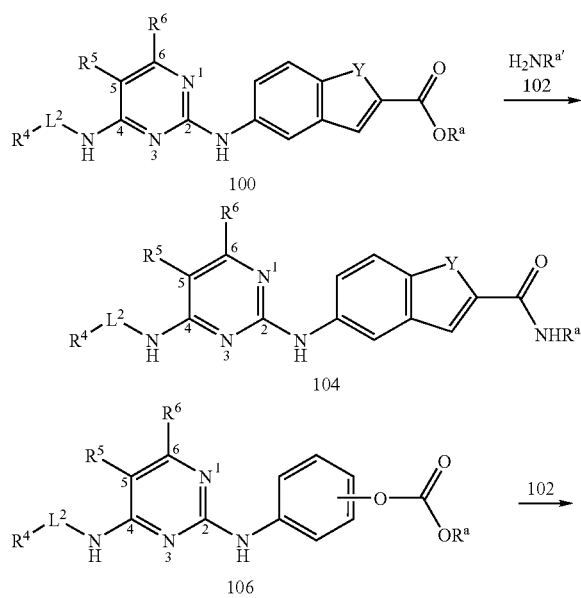

In Scheme (X), $R^4$, $R^5$, $R^6$, $L^2$ and $R^a$ are as previously defined for structural formula (I). Each $R^a$ is independently an $R^a$, and may be the same or different from the illustrated $R^a$. Referring to Scheme (X), carboxylic acid or ester 100 may be converted to amide 104 by reaction with amine 102. In amine 102, $R^a$ may be the same or different than $R^a$ of acid or ester 100. Similarly, carbonate ester 106 may be converted to carbamate 108.

A second specific example is illustrated in Scheme (XI), below:

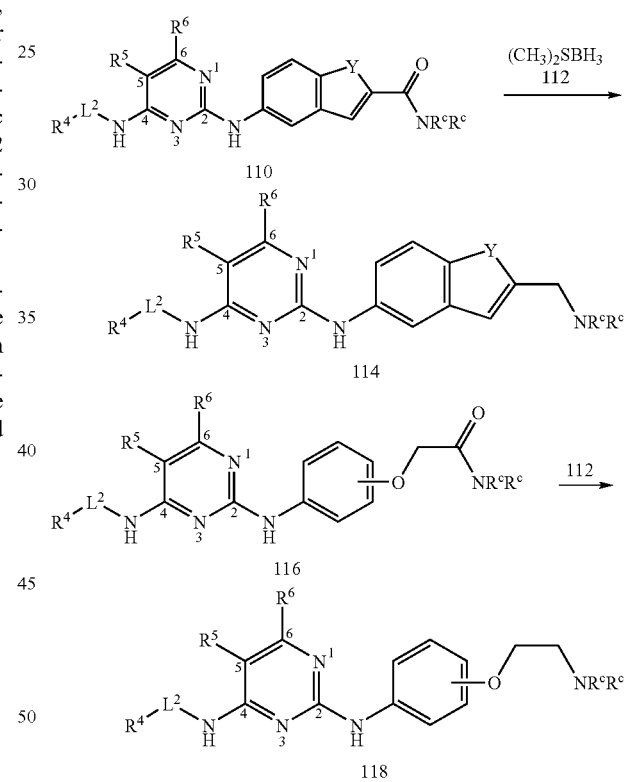

In Scheme (XI), $R^4$, $R^5$, $R^6$, $L^2$ and $R^c$ are as previously defined for structural formula (I). Referring to Scheme (XI), amide 110 or 116 may be converted to amine 114 or 118, respectively, by borane reduction with borane methylsulfide complex 112. Other suitable reactions for synthesizing 2,4-pyrimidinediamine compounds from 2,4-pyrimidinediamine starting materials will be apparent to those of skill in the art.

Although many of the synthetic schemes discussed above do not illustrate the use of protecting groups, skilled artisans will recognize that in some instances substituents $R^2$, $R^4$, $R^5$, $R^6$, $L^1$ and/or $L^2$ may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups and chemistries for their attachment and removal suitable for a particular application can be found, for example, in Greene & Wuts, supra.

Prodrugs according to structural formula (II) may be prepared by routine modification of the above-described methods. Alternatively, such prodrugs may be prepared by reacting a suitably protected 2,4-pyrimidinediamine of structural formula (I) with a suitable progroup. Conditions for carrying out such reactions and for deprotecting the product to yield a prodrug of formula (II) are well-known.

Myriad references teaching methods useful for synthesizing pyrimidines generally, as well as starting materials described in Schemes (I)-(IX), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume 16, Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidine synthesis pp. 313-316; amino pyrimidine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

It should be understood by the skilled artisan that in Schemes I through XI, the N4 nitrogen can be substituted by $R^{4c}$ as described throughout the specification and in the examples provided herein.

6.4 Inhibition of Fc Receptor Signal Cascades

Active 2,4-pyrimidinediamine compounds of the invention inhibit Fc receptor signalling cascades that lead to, among other things, degranulation of cells. As a specific example, the compounds inhibit the FcεRI and/or FcγRI signal cascades that lead to degranulation of immune cells such as neutrophil, eosinophil, mast and/or basophil cells. Both mast and basophil cells play a central role in allergen-induced disorders, including, for example, allergic rhinitis and asthma. Referring to FIG. 1, upon exposure allergens, which may be, among other things, pollen or parasites, allergen-specific IgE antibodies are synthesized by B-cells activated by IL-4 (or IL-13) and other messengers to switch to IgE class specific antibody synthesis. These allergen-specific IgEs bind to the high affinity FcεRI. Upon binding of antigen, the FcεRI-bound IgEs are cross-linked and the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAF) and prostaglandins (e.g., PGD2) and a series of cytokines, including TNF-α, IL-4, IL-13, IL-5, IL-6, IL-8, GMCSF, VEGF and TGF-β. The release and/or synthesis of these mediators from mast and/or basophil cells accounts for the early and late stage responses induced by allergens, and is directly linked to downstream events that lead to a sustained inflammatory state.

The molecular events in the FcεRI signal transduction pathway that lead to release of preformed mediators via degranulation and release and/or synthesis of other chemical mediators are well-known and are illustrated in FIG. 2. Referring to FIG. 2, the FcεRI is a heterotetrameric receptor composed of an IgE-binding alpha-subunit, a beta subunit, and two gamma subunits (gamma homodimer). Cross-linking of FcεRI-bound IgE by multivalent binding agents (including, for example IgE-specific allergens or anti-IgE antibodies or fragments) induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma homodimer. These receptor-associated kinases, which are activated by intra- and intermolecular phosphorylation, phosphorylate other components of the pathway, such as the Btk kinase, LAT, and phospholipase C-gamma PLC-gamma). Activated PLC-gamma initiates pathways that lead to protein kinase C activation and $Ca^{2+}$ mobilization, both of which are required for degranulation. FcεRI cross-linking also activates the three major classes of mitogen activated protein (MAP) kinases, i.e. ERK1/2, JNK1/2, and p38. Activation of these pathways is important in the transcriptional regulation of proinflammatory mediators, such as TNF-α and IL-6, as well as the lipid mediator leukotriene CA (LTC4).

Although not illustrated, the FcγRI signaling cascade is believed to share some common elements with the FcεRI signaling cascade. Importantly, like FcεRI, the FcγRI includes a gamma homodimer that is phosphorylated and recruits Syk, and like FcεRI, activation of the FcγRI signaling cascade leads to, among other things, degranulation. Other Fc receptors that share the gamma homodimer, and which can be regulated by the active 2,4-pyrimidinediamine compounds include, but are not limited to, FcαRI and FcγRIII.

The ability of the 2,4-pyrimidinediamine compounds of the invention to inhibit Fc receptor signaling cascades may be simply determined or confirmed in in vitro assays. Suitable assays for confirming inhibition of FcεRI-mediated degranulation are provided in the Examples section. In one typical assay, cells capable of undergoing FcεRI-mediated degranulation, such as mast or basophil cells, are first grown in the presence of IL-4, Stem Cell Factor (SCF), IL-6 and IgE to increase expression of the FcεRI, exposed to a 2,4-pyrimidinediamine test compound of the invention and stimulated with anti-IgE antibodies (or, alternatively, an IgE-specific allergen). Following incubation, the amount of a chemical mediator or other chemical agent released and/or synthesized as a consequence of activating the FcεRI signaling cascade may be quantified using standard techniques and compared to the amount of the mediator or agent released from control cells (i.e., cells that are stimulated but that are not exposed to test compound). The concentration of test compound that yields a 50% reduction in the quantity of the mediator or agent measured as compared to control cells is the $IC_{50}$ of the test compound. The origin of the mast or basophil cells used in the assay will depend, in part, on the desired use for the compounds and will be apparent to those of skill in the art. For example, if the compounds will be used to treat or prevent a particular disease in humans, a convenient source of mast or basophil cells is a human or other animal which constitutes an accepted or known clinical model for the particular disease. Thus, depending upon the particular application, the mast or basophil cells may be derived from a wide variety of animal sources, ranging from, for example, lower mammals such as mice and rats, to dogs, sheep and other mammals commonly employed in clinical testing, to higher mammals such as monkeys, chimpanzees and apes, to humans. Specific examples of cells suitable for carrying out the in vitro assays include, but are not limited to, rodent or human basophil cells, rat basophil leukemia cell lines, primary mouse mast cells (such as bone marrow-derived mouse mast cells "BMMC") and primary human mast cells isolated from cord blood ("CHMC") or other tissues such as lung. Methods for isolating and culturing these cell types are well-known or are provided in the Examples section (see, e.g., Demo et al., 1999, Cytometry 36(4):340-348 and copending application Ser. No. 10/053,355, filed Nov. 8, 2001, the disclosures of which are incorporated herein by reference). Of course, other types of immune cells that degranulate upon activation of the FcεRI signaling cascade may also be used, including, for example, eosinophils.

As will be recognized by skilled artisans, the mediator or agent quantified is not critical. The only requirement is that it be a mediator or agent released and/or synthesized as a consequence of initiating or activating the Fc receptor signaling cascade. For example, referring to FIG. 1, activation of the FcεRI signaling cascade in mast and/or basophil cells leads to numerous downstream events. For example, activation of the FcεRI signal cascade leads to the immediate release (i.e., within 1-3 min. following receptor activation) of a variety of preformed chemical mediators and agents via degranulation. Thus, in one embodiment, the mediator or agent quantified may be specific to granules (i.e., present in granules but not in the cell cytoplasm generally). Examples of granule-specific mediators or agents that can be quantified to determine and/or confirm the activity of a 2,4-pyrimidinediamine compound of the invention include, but are not limited to, granule-specific enzymes such as hexosaminidase and tryptase and granule-specific components such as histamine and serotonin. Assays for quantifying such factors are well-known, and in many instances are commercially available. For example, tryptase and/or hexosaminidase release may be quantified by incubating the cells with cleavable substrates that fluoresce upon cleavage and quantifying the amount of fluorescence produced using conventional techniques. Such cleavable fluorogenic substrates are commercially available. For example, the fluorogenic substrates Z-Gly-Pro-Arg-AMC (Z=benzyloxycarbonyl; AMC=7-amino-4-methylcoumarin; BIOMOL Research Laboratories, Inc., Plymouth Meeting, Pa. 19462, Catalog No. P-142) and Z-Ala-Lys-Arg-AMC (Enzyme Systems Products, a division of ICN Biomedicals, Inc., Livermore, Calif. 94550, Catalog No. AMC-246) can be used to quantify the amount of tryptase released. The fluorogenic substrate 4-methylumbelliferyl-N-acetyl-β-D-glucosaminide (Sigma, St. Louis, Mo., Catalog #69585) can be used to quantify the amount of hexosaminidase released. Histamine release may be quantified using a commercially available enzyme-linked immunosorbent assay (ELISA) such as Immunotech histamine ELISA assay #IM2015 (Beckman-Coulter, Inc.). Specific methods of quantifying the release of tryptase, hexosaminidase and histamine are provided in the Examples section. Any of these assays may be used to determine or confirm the activity of the 2,4-pyrimidinediamine compounds of the invention.

Referring again to FIG. 1, degranulation is only one of several responses initiated by the FcεRI signaling cascade. In addition, activation of this signaling pathway leads to the de novo synthesis and release of cytokines and chemokines such as IL-4, IL-5, IL-6, TNF-α, IL-13 and MIP1-α), and release of lipid mediators such as leukotrienes (e.g., LTC4), platelet activating factor (PAF) and prostaglandins. Accordingly, the 2,4-pyrimidinediamine compounds of the invention may also be assessed for activity by quantifying the amount of one or more of these mediators released and/or synthesized by activated cells.

Unlike the granule-specific components discussed above, these "late stage" mediators are not released immediately following activation of the FcεRI signaling cascade. Accordingly, when quantifying these late stage mediators, care should be taken to insure that the activated cell culture is incubated for a time sufficient to result in the synthesis (if necessary) and release of the mediator being quantified. Generally, PAF and lipid mediators such as leukotriene C4 are released 3-30 min. following FcεRI activation. The cytokines and other late stage mediators are released approx. 4-8 hrs. following FcεRI activation. Incubation times suitable for a specific mediator will be apparent to those of skill in the art. Specific guidance and assays are provided in the Examples section.

The amount of a particular late stage mediator released may be quantified using any standard technique. In one embodiment, the amount(s) may be quantified using ELISA assays. ELISA assay kits suitable for quantifying the amount of TNFα, IL-4, IL-5, IL-6 and/or IL-13 released are available from, for example, Biosource International, Inc., Camarillo, Calif. 93012 (see, e.g., Catalog Nos. KHC3011, KHC0042, KHC0052, KHC0061 and KHC0132). ELISA assay kits suitable for quantifying the amount of leukotriene C4 (LTC4) released from cells are available from Cayman Chemical Co., Ann Arbor, Mich. 48108 (see, e.g., Catalog No. 520211).

Typically, active 2,4-pyrimidinediamine compounds of the invention will exhibit $IC_{50}$s with respect to FcεRI-mediated degranulation and/or mediator release or synthesis of about 20 μM or lower, as measured in an in vitro assay, such as one of the in vitro assays described above or in the Examples section. Of course, skilled artisans will appreciate that compounds which exhibit lower $IC_{50}$s, for example on the order of 10 μM, 1 μM, 100 nM, 10 nM, 1 nM, or even lower, are particularly useful.

Skilled artisans will also appreciate that the various mediators discussed above may induce different adverse effects or exhibit different potencies with respect to the same adverse effect. For example, the lipid mediator LTC4 is a potent vasoconstrictor—it is approximately 1000-fold more potent at inducing vasoconstriction than histamine. As another example, in addition to mediating atopic or Type I hypersensitivity reactions, cytokines can also cause tissue remodeling and cell proliferation. Thus, although compounds that inhibit release and/or synthesis of any one of the previously discussed chemical mediators are useful, skilled artisans will appreciate that compounds which inhibit the release and/or synthesis of a plurality, or even all, of the previously described mediators find particular use, as such compounds are useful for ameliorating or avoiding altogether a plurality, or even all, of the adverse effects induced by the particular mediators. For example, compounds which inhibit the release of all three types of mediators-granule-specific, lipid and cytokine—are useful for treating or preventing immediate Type I hypersensitivity reactions as well as the chronic symptoms associated therewith.

Compounds of the invention capable of inhibiting the release of more than one type of mediator (e.g., granule-specific or late stage) may be identified by determining the $IC_{50}$ with respect to a mediator representative of each class using the various in vitro assays described above (or other equivalent in vitro assays). Compounds of the invention which are capable of inhibiting the release of more than one mediator type will typically exhibit an $IC_{50}$ for each mediator type tested of less than about 20 µM. For example, a compound which exhibits an $IC_{50}$ of 1 µM with respect to histamine release ($IC_{50}^{histame}$) and an $IC_{50}$ of 1 nM with respect to leukotriene LTC4 synthesis and/or release ($IC_{50}^{LTC4}$) inhibits both immediate (granule-specific) and late stage mediator release. As another specific example, a compound that exhibits an $IC_{50}^{tryptase}$ of 10 µM, an $IC_{50}^{LTC4}$ of 1 µM and an $IC_{50}^{IL-4}$ of 1 µM inhibits immediate (granule-specific), lipid and cytokine mediator release. Although the above specific examples utilize the $IC_{50}$s of one representative mediator of each class, skilled artisans will appreciate that the $IC_{50}$s of a plurality, or even all, mediators comprising one or more of the classes may be obtained. The quantity(ies) and identity(ies) of mediators for which $IC_{50}$ data should be ascertained for a particular compound and application will be apparent to those of skill in the art.

Similar assays may be utilized to confirm inhibition of signal transduction cascades initiated by other Fc receptors, such as FcαRI, FcγRI and/or FcγRIII signaling, with routine modification. For example, the ability of the compounds to inhibit FcγRI signal transduction may be confirmed in assays similar to those described above, with the exception that the FcγRI signaling cascade is activated, for example by incubating the cells with IgG and an IgG-specific allergen or antibody, instead of IgE and an IgE-specific allergen or antibody. Suitable cell types, activating agents and agents to quantify to confirm inhibition of other Fc receptors, such as Fc receptors that comprise a gamma homodimer, will be apparent to those of skill in the art.

One particularly useful class of compounds includes those 2,4-pyrimidinediamine compounds that inhibit the release of immediate granule-specific mediators and late stage mediators with approximately equivalent $IC_{50}$s. By approximately equivalent is meant that the $IC_{50}$s for each mediator type are within about a 10-fold range of one another. Another particularly useful class of compounds includes those 2,4-pyrimidinediamine compounds that inhibit the release of immediate granule-specific mediators, lipid mediators and cytokine mediators with approximately equivalent $IC_{50}$s. In a specific embodiment, such compounds inhibit the release of the following mediators with approximately equivalent $IC_{50}$s: histamine, tryptase, hexosaminidase, IL-4, IL-5, IL-6, IL-13, TNFα and LTC4. Such compounds are particularly useful for, among other things, ameliorating or avoiding altogether both the early and late stage responses associated with atopic or immediate Type I hypersensitivity reactions.

Ideally, the ability to inhibit the release of all desired types of mediators will reside in a single compound. However, mixtures of compounds can also be identified that achieve the same result. For example, a first compound which inhibits the release of granule specific mediators may be used in combination with a second compound which inhibits the release and/or synthesis of cytokine mediators.

In addition to the FcεRI or FcγRI degranulation pathways discussed above, degranulation of mast and/or basophil cells can be induced by other agents. For example, ionomycin, a calcium ionophore that bypasses the early FcεRI or FcγRI signal transduction machinery of the cell, directly induces a calcium flux that triggers degranulation. Referring again to FIG. 2, activated PLCγ initiates pathways that lead to, among other things, calcium ion mobilization and subsequent degranulation. As illustrated, this $Ca^{2+}$ mobilization is triggered late in the FcεRI signal transduction pathway. As mentioned above, and as illustrated in FIG. 3, ionomycin directly induces $Ca^{2+}$ mobilization and a $Ca^{2+}$ flux that leads to degranulation. Other ionophores that induce degranulation in this manner include A23187. The ability of granulation-inducing ionophores such as ionomycin to bypass the early stages of the FcεRI and/or FcγRI signaling cascades may be used as a counter screen to identify active compounds of the invention that specifically exert their degranulation-inhibitory activity by blocking or inhibiting the early FcεRI or FcγRI signaling cascades, as discussed above. Compounds which specifically inhibit such early FcεRI or FcγRI-mediated degranulation inhibit not only degranulation and subsequent rapid release of histamine, tryptase and other granule contents, but also inhibit the pro-inflammatory activation pathways causing the release of TNFα, IL-4, IL-13 and the lipid mediators such as LTC4. Thus, compounds which specifically inhibit such early FcεRI and/or FcγRI-mediated degranulation block or inhibit not only acute atopic or Type I hypersensitivity reactions, but also late responses involving multiple inflammatory mediators.

Compounds of the invention that specifically inhibit early FcεRI and/or FcγRI-mediated degranulation are those compounds that inhibit FcεRI and/or FcγRI-mediated degranulation (for example, have an $IC_{50}$ of less than about 20 µM with respect to the release of a granule-specific mediator or component as measured in an in vitro assay with cells stimulated with an IgE or IgG binding agent) but that do not appreciably inhibit ionophore-induced degranulation. In one embodiment, compounds are considered to not appreciably inhibit ionophore-induced degranulation if they exhibit an $IC_{50}$ of ionophore-induced degranulation of greater than about 20 µM, as measured in an in vitro assay. Of course, active compounds that exhibit even higher $IC_{50}$s of ionophore-induced degranulation, or that do not inhibit ionophore-induced degranulation at all, are particularly useful. In another embodiment, compounds are considered to not appreciably inhibit ionophore-induced degranulation if they exhibit a greater than 10-fold difference in their $IC_{50}$s of FcεRI and/or FcγRI-mediated degranulation and ionophore-induced degranulation, as measured in an in vitro assay. Assays suitable for determining the $IC_{50}$ of ionophore-induced degranulation include any of the previously-described degranulation assays, with the modification that the cells are stimulated or activated with a degranulation-inducing calcium ionophore such as ionomycin or A23187 (A.G. Scientific, San Diego, Calif.) instead of anti-IgE antibodies or an IgE-specific allergen. Specific assays for assessing the ability of a particular 2,4-pyrimidinediamine compound of the invention to inhibit ionophore-induced degranulation are provided in the Examples section.

As will be recognized by skilled artisans, compounds which exhibit a high degree of selectivity of FcεRI-mediated degranulation find particular use, as such compounds selectively target the FcεRI cascade and do not interfere with other degranulation mechanisms. Similarly, compounds which exhibit a high degree of selectivity of FcγRI-mediated degranulation find particular use, as such compounds selectively target the FcγRI cascade and do not interfere with other degranulation mechanisms. Compounds which exhibit a high degree of selectivity are generally 10-fold or more selective for FcεRI- or FcγRI-mediated degranulation over ionophore-induced degranulation, such as ionomycin-induced degranulation.

Accordingly, the activity of the 2,4-pyrimidinediamine compounds of the invention may also be confirmed in biochemical or cellular assays of Syk kinase activity. Referring again to FIG. 2, in the FcεRI signaling cascade in mast and/or basophil cells, Syk kinase phosphorylates LAT and PLC-gamma1, which leads to, among other things, degranulation. Any of these activities may be used to confirm the activity of the 2,4-pyrimidinediamine compounds of the invention. In one embodiment, the activity is confirmed by contacting an isolated Syk kinase, or an active fragment thereof with a 2,4-pyrimidinediamine compound in the presence of a Syk kinase substrate (e.g., a synthetic peptide or a protein that is known to be phosphorylated by Syk in a signaling cascade)

and assessing whether the Syk kinase phosphorylated the substrate. Alternatively, the assay may be carried out with cells that express a Syk kinase. The cells may express the Syk kinase endogenously or they may be engineered to express a recombinant Syk kinase. The cells may optionally also express the Syk kinase substrate. Cells suitable for performing such confirmation assays, as well as methods of engineering suitable cells will be apparent to those of skill in the art. Specific examples of biochemical and cellular assays suitable for confirming the activity of the 2,4-pyrimidinediamine compounds are provided in the Examples section.

Generally, compounds that are Syk kinase inhibitors will exhibit an $IC_{50}$ with respect to a Syk kinase activity, such as the ability of Syk kinase to phosphorylate a synthetic or endogenous substrate, in an in vitro or cellular assay in the range of about 20 µM or less. Skilled artisans will appreciate that compounds that exhibit lower IC50s, such as in the range of 10 µM, 1 µM, 100 nM, 10 nM, 1 nM, or even lower, are particularly useful.

6.5 Uses and Compositions

As previously discussed, the active compounds of the invention inhibit Fc receptor signaling cascades, especially those Fc receptors including a gamma homodimer, such as the FcεRI and/or FcγRI signaling cascades, that lead to, among other things, the release and/or synthesis of chemical mediators from cells, either via degranulation or other processes. As also discussed, the active compounds are also potent inhibitors of Syk kinase. As a consequence of these activities, the active compounds of the invention may be used in a variety of in vitro, in vivo and ex vivo contexts to regulate or inhibit Syk kinase, signaling cascades in which Syk kinase plays a role, Fc receptor signaling cascades, and the biological responses effected by such signaling cascades. For example, in one embodiment, the compounds may be used to inhibit Syk kinase, either in vitro or in vivo, in virtually any cell type expressing Syk kinase. They may also be used to regulate signal transduction cascades in which Syk kinase plays a role. Such Syk-dependent signal transduction cascades include, but are not limited to, the FcεRI, FcγRI, FcγRIII, BCR and integrin signal transduction cascades. The compounds may also be used in vitro or in vivo to regulate, and in particular inhibit, cellular or biological responses effected by such Syk-dependent signal transduction cascades. Such cellular or biological responses include, but are not limited to, respiratory burst, cellular adhesion, cellular degranulation, cell spreading, cell migration, cell aggregation, phagocytosis, cytokine synthesis and release, cell maturation and $Ca^{2+}$ flux. Importantly, the compounds may be used to inhibit Syk kinase in vivo as a therapeutic approach towards the treatment or prevention of diseases mediated, either wholly or in part, by a Syk kinase activity. Non-limiting examples of Syk kinase mediated diseases that may be treated or prevented with the compounds are those discussed in more detail, below.

In another embodiment, the active compounds may be used to regulate or inhibit the Fc receptor signaling cascades and/or FcεRI- and/or FcγRI-mediated degranulation as a therapeutic approach towards the treatment or prevention of diseases characterized by, caused by and/or associated with the release or synthesis of chemical mediators of such Fc receptor signaling cascades or degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

In addition to the myriad diseases discussed above, cellular and animal empirical data confirm that the 2,4-pyrimidinediamine compounds described herein are also useful for the treatment or prevention of autoimmune diseases, as well as the various symptoms associated with such diseases. The types of autoimmune diseases that may be treated or prevented with the 2,4-pyrimidinediamine compounds generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

As discussed previously, Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosus, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the 2,4-pyrimidinediamine compounds of the invention. In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated. Many of these symptoms, as well as their underlying disease states, result as a consequence of activating the FcγR signaling cascade in monocyte cells. As the 2,4-pyrimidinediamine compounds described herein are potent inhibitors of such FcγR signaling in monocytes and other cells, the methods find use in the treatment and/or prevention of myriad adverse symptoms associated with the above-listed autoimmune diseases.

As a specific example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dentritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The methods may be used to treat or ameliorate any one, several or all of these symptoms of RA. Thus, in the context of RA, the methods are considered to provide therapeutic benefit (discussed more generally, infra) when a reduction or amelioration of any of the symptoms commonly associated with RA is achieved, regardless of whether the treatment results in a concomitant treatment of the underlying RA and/or a reduction in the amount of circulating rheumatoid factor ("RF").

As another specific example, systemic lupus erythematosis ("SLE") is typically associated with symptoms such as fever, joint pain (arthralgias), arthritis, and serositis (pleurisy or pericarditis). In the context of SLE, the methods are considered to provide therapeutic benefit when a reduction or amelioration of any of the symptoms commonly associated with SLE are achieved, regardless of whether the treatment results in a concomitant treatment of the underlying SLE.

As another specific example, multiple sclerosis ("MS") cripples the patient by disturbing visual acuity; stimulating double vision; disturbing motor functions affecting walking and use of the hands; producing bowel and bladder incontinence; spasticity; and sensory deficits (touch, pain and temperature sensitivity). In the context of MS, the methods are considered to provide therapeutic benefit when an improvement or a reduction in the progression of any one or more of the crippling effects commonly associated with MS is achieved, regardless of whether the treatment results in a concomitant treatment of the underlying MS.

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The active compounds may be administered per se in the form of prodrugs or as pharmaceutical compositions, comprising an active compound or prodrug.

Pharmaceutical compositions comprising the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

Another specific example of an aqueous suspension suitable for administration of the compounds via inhalation, and in particular for such administration of a compound of the invention, contains 1-20 mg/mL of the compound or prodrug, 0.1-1% (v/v) Polysorbate 80 (TWEEN®80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

6.6 Effective Dosages

The active compound(s) or prodrug(s) of the invention, or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound may be administered to a patient at risk of developing one of the previously described diseases. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al, 2000, Immunopharmacology 48(1):1-7. Suitable animal models of allergic conjunctivitis are described in Carreras et al., 1993, Br. J. Opthalmol. 77(8):509-514; Saiga et al., 1992, Ophthalmic Res. 24(1):45-50; and Kunert et al., 2001, Invest. Opthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-5511. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Ordinarily skilled artisans can routinely adapt such information to determine dosages suitable for human administration. Additional suitable animal models are described in the Examples section.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

The invention having been described, the following examples are offered by way of illustration and not limitation.

7. EXAMPLES

7.1 2,4-Pyrimidinediamine Compounds

A variety of N4-substituted-N2-monosubstituted-4-pyrimidinediamines were prepared based on procedures described herein. Such compounds are depicted in Table 1.

7.2 The 2,4-Pyrimidinediamine Compounds of the Invention Inhibit FcεRI Receptor-Mediated Degranulation The ability of the 2,4-pyrimidinediamine compounds of the invention to inhibit IgE-induced degranulation was demonstrated in a variety of cellular assays with cultured human mast cells (CHMC) and/or mouse bone marrow derived cells (BMMC). Inhibition of degranulation was measured at both low and high cell density by quantifying the release of the granule specific factors tryptase, histamine and hexosaminidase. Inhibition of release and/or synthesis of lipid mediators was assessed by measuring the release of leukotriene LTC4 and inhibition of release and/or synthesis of cytokines was monitored by quantifying TNF-α, IL-6 and IL-13. Tryptase and hexosaminidase were quantified using fluorogenic substrates as described in their respective examples. Histamine, TNFα, IL-6, IL-13 and LTC4 were quantified using the following commercial ELISA kits: histamine (Immunotech #2015, Beckman Coulter), TNFα (Biosource #KHC3011), IL-6 (Biosource #KMC0061), IL-13 (Biosource #KHC0132) and LTC4 (Cayman Chemical #520211). The protocols of the various assays are provided below.

7.2.1 Culturing of Human Mast and Basophil Cells

Human mast and basophil cells were cultured from CD34-negative progenitor cells as described below (see also the methods described in copending U.S. application Ser. No. 10/053,355, filed Nov. 8, 2001, the disclosure of which is incorporated herein by reference).

7.2.1.1 Preparation of STEMPRO-34 Complete Medium

To prepare STEMPRO-34 complete medium ("CM"), 250 mL STEMPRO-34 serum free medium ("SFM"; GibcoBRL, Catalog No. 10640) was added to a filter flask. To this was added 13 mL STEMPRO-34 Nutrient Supplement ("NS"; GibcoBRL, Catalog No. 10641) (prepared as described in more detail, below). The NS container was rinsed with approximately 10 mL SFM and the rinse added to the filter flask. Following addition of 5 mL L-glutamine (200 mM;

Mediatech, Catalog No. MT 25-005-CI and 5 mL 100× penicillin/streptomycin ("pen-strep"; HyClone, Catalog No. SV30010), the volume was brought to 500 mL with SFM and the solution was filtered.

The most variable aspect of preparing the CM is the method by which the NS is thawed and mixed prior to addition to the SFM. The NS should be thawed in a 37° C. water bath and swirled, not vortexed or shaken, until it is completely in solution. While swirling, take note whether there are any lipids that are not yet in solution. If lipids are present and the NS is not uniform in appearance, return it to the water bath and repeat the swirling process until it is uniform in appearance. Sometimes this component goes into solution immediately, sometimes after a couple of swirling cycles, and sometimes not at all. If, after a couple of hours, the NS is still not in solution, discard it and thaw a fresh unit. NS that appears non-uniform after thaw should not be used.

7.2.1.2 Expansion of CD34+ Cells

A starting population of CD34-positive (CD34+) cells of relatively small number ($1$-$5 \times 10^6$ cells) was expanded to a relatively large number of CD34-negative progenitor cells (about $2$-$4 \times 10^9$ cells) using the culture media and methods described below. The CD34+ cells (from a single donor) were obtained from Allcells (Berkeley, Calif.). Because there is a degree of variation in the quality and number of CD34+ cells that Allcells typically provides, the newly delivered cells were transferred to a 15 mL conical tube and brought up to 10 mL in CM prior to use.

On day 0, a cell count was performed on the viable (phase-bright) cells and the cells were spun at 1200 rpm to pellet. The cells were resuspended to a density of 275,000 cells/mL with CM containing 200 ng/mL recombinant human Stem Cell Factor ("SCF"; Peprotech, Catalog No. 300-07) and 20 ng/mL human flt-3 ligand (Peprotech, Catalog No. 300-19) ("CM/SCF/flt-3 medium"). On about day 4 or 5, the density of the culture was checked by performing a cell count and the culture was diluted to a density of 275,000 cells/mL with fresh CM/SCF/flt-3 medium. On about day 7, the culture was transferred to a sterile tube and a cell count was performed. The cells were spun at 1200 rpm and resuspended to a density of 275,000 cells/mL with fresh CM/SCF/flt-3 medium.

This cycle was repeated, starting from day 0, a total of 3-5 times over the expansion period.

When the culture is large and being maintained in multiple flasks and is to be resuspended, the contents of all of the flasks are combined into a single container prior to performing a cell count. This ensures that an accurate cell count is achieved and provides for a degree of uniformity of treatment for the entire population. Each flask is checked separately for contamination under the microscope prior to combining to prevent contamination of the entire population.

Between days 17-24, the culture can begin to go into decline (i.e., approximately 5-10% of the total number of cells die) and fail to expand as rapidly as before. The cells are then monitored on a daily basis during this time, as complete failure of the culture can take place in as little as 24 hours. Once the decline has begun, the cells are counted, spun down at 850 rpm for 15 minutes, and resuspended at a density of 350,000 cells/mL in CM/SCF/flt-3 medium to induce one or two more divisions out of the culture. The cells are monitored daily to avoid failure of the culture.

When greater than 15% cell death is evident in the progenitor cell culture and some debris is present in the culture, the CD34-negative progenitor cells are ready to be differentiated.

7.2.1.3 Differentiation of CD34-Negative Progenitor Cells into Mucosal Mast Cells A second phase is performed to convert the expanded CD34-negative progenitor cells into differentiated mucosal mast cells. These mucosal cultured human mast cells ("CHMC") are derived from CD34+ cells isolated from umbilical cord blood and treated to form a proliferated population of CD34-negative progenitor cells, as described above. To produce the CD43-negative progenitor cells, the resuspension cycle for the culture was the same as that described above, except that the culture was seeded at a density of 425,000 cells/mL and 15% additional media was added on about day four or five without performing a cell count. Also, the cytokine composition of the medium was modified such that it contained SCF (200 ng/mL) and recombinant human IL-6 (200 ng/mL; Peprotech, Catalog No. 200-06 reconstituted to 100 ug/mL in sterile 10 mM acetic acid) ("CM/SCF/IL-6 medium").

Phases I and II together span approximately 5 weeks. Some death and debris in the culture is evident during weeks 1-3 and there is a period during weeks 2-5 during which a small percentage of the culture is no longer in suspension, but is instead attached to the surface of the culture vessel.

As during Phase I, when the culture is to be resuspended on day seven of each cycle, the contents of all flasks are combined into a single container prior to performing a cell count to ensure uniformity of the entire population. Each flask is checked separately for contamination under the microscope prior to combining to prevent contamination of the entire population.

When the flasks are combined, approximately 75% of the volume is transferred to the communal container, leaving behind about 10 mL or so in the flask. The flask containing the remaining volume was rapped sharply and laterally to dislodge the attached cells. The rapping was repeated at a right angle to the first rap to completely dislodge the cells.

The flask was leaned at a 45 degree angle for a couple of minutes before the remaining volume was transferred to the counting vessel. The cells were spun at 950 rpm for 15 min prior to seeding at 35-50 mL per flask (at a density of 425,000 cells/mL).

7.2.1.4 Differentiation of CD34-Negative Progenitor Cells into Connective Tissue-Type Mast Cells A proliferated population of CD34-negative progenitor cells is prepared as above and treated to form a tryptase/chymase positive (connective tissue) phenotype. The methods are performed as described above for mucosal mast cells, but with the substitution of IL-4 for IL-6 in the culture medium. The cells obtained are typical of connective tissue mast cells.

7.2.1.5 Differentiation of CD34-Negative Progenitor Cells into Basophil Cells

A proliferated population of CD34-negative progenitor cells is prepared as described in Section 7.2.1.3, above, and used to form a proliferated population of basophil cells. The CD34-negative cells are treated as described for mucosal mast cells, but with the substitution of IL-3 (at 20-50 ng/mL) for IL-6 in the culture medium.

7.2.2 CHMC Low Cell Density IgE Activation: Tryptase and LTC4 Assays

To duplicate 96-well U-bottom plates (Costar 3799) add 65 ul of compound dilutions or control samples that have been prepared in MT [137 mM NaCl, 2.7 mM KCl, 1.8 mM $CaCl_2$, 1.0 mM $MgCl_2$, 5.6 mM Glucose, 20 mM Hepes (pH 7.4), 0.1% Bovine Serum Albumin, (Sigma A4503)] containing 2% MeOH and 1% DMSO. Pellet CHMC cells (980 rpm, 10 min) and resuspend in pre-warmed MT. Add 65 ul of cells to each 96-well plate. Depending on the degranulation activity for each particular CHMC donor, load 1000-1500 cells/well.

Mix four times followed by a 1 hr incubation at 37° C. During the 1 hr incubation, prepare 6× anti-IgE solution [rabbit anti-human IgE (1 mg/ml, Bethyl Laboratories A80-109A) diluted 1:167 in MT buffer]. Stimulate cells by adding 25 ul of 6× anti-IgE solution to the appropriate plates. Add 25 ul MT to un-stimulated control wells. Mix twice following addition of the anti-IgE. Incubate at 37° C. for 30 minutes. During the 30 minute incubation, dilute the 20 mM tryptase substrate stock solution [(Z-Ala-Lys-Arg-AMC.2TFA; Enzyme Systems Products, #AMC-246)] 1:2000 in tryptase assay buffer [0.1 M Hepes (pH 7.5), 10% w/v Glycerol, 10 uM Heparin (Sigma H-4898) 0.01% $NaN_3$]. Spin plates at 1000 rpm for 10 min to pellet cells. Transfer 25 ul of supernatant to a 96-well black bottom plate and add 100 ul of freshly diluted tryptase substrate solution to each well. Incubate plates at room temperature for 30 min. Read the optical density of the plates at 355 nm/460 nm on a spectrophotometric plate reader.

Leukotriene C4 (LTC4) is also quantified using an ELISA kit on appropriately diluted supernatant samples (determined empirically for each donor cell population so that the sample measurement falls within the standard curve) following the supplier's instructions.

7.2.3 CHMC High Cell Density IgE Activation: Degranulation (Tryptase, Histamine), Leukotriene (LTC4), and Cytokine (TNFalpha, IL-13) Assays Cultured human mast cells (CHMC) are sensitized for 5 days with IL-4 (20 ng/ml), SCF (200 ng/ml), IL-6 (200 ng/ml), and Human IgE (CP 1035K from Cortx Biochem, 100-500 ng/ml depending on generation) in CM medium. After sensitizing, cells are counted, pelleted (1000 rpm, 5-10 minutes), and resuspended at $1-2 \times 10^6$ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× anti-IgE. Mix wells with the cells and allow plates to incubate at 37° C. (5% $CO_2$) for one hour. After 1 hour incubation, pellet cells (10 minutes, 1000 RPM) and collect 200 ul per well of the supernatant, being careful not to disturb pellet. Place the supernatant plate on ice. During the 7-hour step (see next) perform tryptase assay on supernatant that had been diluted 1:500. Resuspend cell pellet in 240 ul of CM media containing 0.5% DMSO and corresponding concentration of compound. Incubate CHMC cells for 7 hours at 37° C. (5% $CO_2$). After incubation, pellet cells (1000 RPM, 10 minutes) and collect 225 ul per well and place in −80° C. until ready to perform ELISAS. ELISAS are performed on appropriately diluted samples (determined empirically for each donor cell population so that the sample measurement falls within the standard curve) following the supplier's instructions.

7.2.4 Results

The results of low density CHMC assays are provided in Table 1. In Table 1, all reported values are $IC_{50}$s (in µM). Most compounds tested had $IC_{50}$s of less than 10 µM, with many exhibiting $IC_{50}$s in the sub-micromolar range. In Table 1, all reported values are $IC_{50}$s (in µM). A value of "−" indicates an $IC_{50}>10$ µM, with no measurable activity at a 10 µM concentration. Most compounds tested had $IC_{50}$s of less than 10 µM, with many exhibiting $IC_{50}$s in the sub-micromolar range. A value of "+" indicates an $IC_{50}<10$ µM. Of the compounds tested, BMMC values are comparable to those noted for the CHMC results.

7.3 The 2,4-Pyrimidinediamine Compounds of the Invention Selectively Inhibit the Upstream IgE Receptor Cascade To confirm that many of the 2,4-pyrimidinediamine compounds of the invention exert their inhibitory activity by blocking or inhibiting the early IgE receptor signal transduction cascade, several of the compounds were tested in cellular assays for ionomycin-induced degranulation, as described below.

7.3.1 CHMC Low Cell Density Ionomycin Activation: Tryptase Assay

Assays for ionomycin-induced mast cell degranulation were carried out as described for the CHMC Low Density IgE Activation assays (Section 7.2.2, supra), with the exception that during the 1 hour incubation, 6× ionomycin solution [5 mM ionomycin (Sigma I-0634) in MeOH (stock) diluted 1:416.7 in MT buffer (2 µM final)] was prepared and cells were stimulated by adding 25 µl of the 6× ionomycin solution to the appropriate plates.

7.3.2 Results

The results of the ionomycin-induced degranulation assays, reported as $IC_{50}$ values (in µM) are provided in Table 1. Of the active compounds tested (i.e., those that inhibit IgE-induced degranulation), the vast majority do not inhibit ionomycin-induced degranulation, confirming that these active compounds selectively inhibit the early (or upstream) IgE receptor signal transduction cascade. In Table 1, all reported values are $IC_{50}$s (in µM). A value of "−" indicates an $IC_{50}>10$ µM, with no measurable activity at a 10 µM concentration. A value of "+" indicates an $IC_{50}<10$ µM.

7.4 2,4-Pyrimidinediamine Compounds Inhibit Syk Kinase in Biochemical Assays Many of the 2,4-pyrimidinediamine compounds were tested for the ability to inhibit Syk kinase catalyzed phosphorylation of a peptide substrate in a biochemical fluorescenced polarization assay with isolated Syk kinase. In this experiment, Compounds were diluted to 1% DMSO in kinase buffer (20 mM HEPES, pH 7.4, 5 mM $MgCl_2$, 2 mM $MnCl_2$, 1 mM DTT, 0.1 mg/mL acetylated Bovine Gamma Globulin). Compound in 1% DMSO (0.2% DMSO final) was mixed with ATP/substrate solution at room temperature. Syk kinase (Upstate, Lake Placid N.Y.) was added to a final reaction volume of 20 uL, and the reaction was incubated for 30 minutes at room temperature. Final enzyme reaction conditions were 20 mM HEPES, pH 7.4, 5 mM $MgCl_2$, 2 mM $MnCl_2$, 1 mM DTT, 0.1 mg/mL acetylated Bovine Gamma Globulin, 0.125 ng Syk, 4 uM ATP, 2.5 uM peptide substrate (biotin-EQEDE-PEGDYEEVLE-CONH2, SynPep Corporation). EDTA (10 mM final)/anti-phosphotyrosine antibody (1× final)/fluorescent phosphopeptide tracer (0.5× final) was added in FP Dilution Buffer to stop the reaction for a total volume of 40 uL according to manufacturer's instructions (PanVera Corporation) The plate was incubated for 30 minutes in the dark at room temperature. Plates were read on a Polarion fluorescence polarization plate reader (Tecan). Data were converted to amount of phosphopeptide present using a calibration curve generated by competition with the phosphopeptide competitor provided in the Tyrosine Kinase Assay Kit, Green (PanVera Corporation).

These data, shown in Table 1, demonstrate that most all of the compounds tested, inhibit Syk kinase phosphorylation with $IC_{50}$s in the submicromolar range. A vast majority of the compounds tested inhibit Syk kinase phosphorylation with $IC_{50}$s in the micromolar range. In Table 1, all reported values are $IC_{50}$s (in µM). A value of "−" indicates an $IC_{50}>10$ µM, with no measurable activity at a 10 µM concentration. A value of "+" indicates an $IC_{50}<10$ µM.

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 200 | (S)-5-Fluoro-N2-(indazol-6-yl)-N4-(2-methyl-3-oxo-2H,4H-benz[1,4]oxazin-6-yl)-2,4-pyrimidinediamine | ¹H NMR (DMSO-d6): δ 8.08 (d, 1H), 7.95 (s, 1H), 7.58 (d, 1H), 7.40 (m, 1H), 7.25 (m, 3H), 6.94 (m, 1H), 4.80 (m, 1H), 1.40 (s, 3H); MS purity: 96%; MS (m/e): 406 (MH+). | | + | | |
| 201 | (S)-5-Fluoro-N2-(1-methylindazol-6-yl)-N4-(2-methyl-3-oxo-2H,4H-benz[1,4]oxazin-6-yl)-2,4-pyrimidinediamine | ¹H NMR (DMSO-d6): δ 8.17 (d, 1H), 8.08 (s, 1H), 7.52 (m, 1H), 7.32 (m, 2H), 7.17 (m, 2H), 6.94 (m, 1H), 4.60 (m, 1H), 3.77 (s, 3H), 1.45 (s, 3H); LCMS: purity: 94%; MS (m/e): 420 (MH+). | | + | | |
| 202 | (S)—N2-(3,5-Dimethylphenyl)-5-fluoro-N4-(2-methyl-3-oxo-2H,4H-benz[1,4]oxazin-6-yl)-2,4-pyrimidinediamine | ¹H NMR (DMSO-d6): δ 8.01 (d, 1H), 7.28 (m, 2H), 7.20 (s, 2H), 6.95 (m, 1H), 6.58 (s, 1H), 4.63 (m, 1H), 3.77 (s, 3H), 2.07 (s, 6H), 1.42 (d, 3H); LCMS: purity: 92%; MS (m/e): 393 (MH+). | | | + | + |
| 203 | N4-(3,4-Dihydro-3,3-dimethyl-2H,4H-benz[1,4]oxazin-6-yl)-N2-(3,5-dimethoxyphenyl)-5-fluoro-2,4-pyrimidinediamine | ¹H NMR (DMSO-d6): δ 8.02 (d, 1H), 6.98 (m, 2H), 6.90 (m, 2H), 6.80 (m, 1H), 6.03 (s, 1H), 3.72 (s, 2H), 3.60 (s, 6H), 1.05 (s, 6H); LCMS: purity: 96%; MS (m/e): 425 (MH+). | | + | | |
| 204 | (R)—N2-(3,5-Dimethylphenyl)-5-fluoro-N4-(2-methyl-3-oxo-2H,4H-benz[1,4]oxazin-6-yl)-2,4-pyrimidinediamine | ¹H NMR (DMSO-d6): δ 8.01 (d, 1H), 7.28 (m, 2H), 7.20 (s, 2H), 6.95 (m, 1H), 6.58 (s, 1H), 4.63 (m, 1H), 3.77 (s, 3H), 2.07 (s, 6H), 1.42 (d, 3H); LCMS: purity: 92%; MS (m/e): 393 (MH+). | | + | | |
| 205 | (R)-5-Fluoro-N2-[6-(2-hydroxyethyl)-2,3-dihydropyrrolo[1,2,3-d,e]benzoxazin-8-yl]-N4-(2-methyl-3-oxo-2H,4H-benz[1,4]oxazin-6-yl)-2,4-pyrimidinediamine | ¹H NMR (MeOD-d4): δ 7.75 (d, 1H), 7.38 (m, 1H), 7.02 (m, 3H), 6.78 (m, 2H), 4.54 (m, 1H), 4.4 (m, 2H), 4.14 (m, 2H), 3.62 (m, 2H), 2.80 (m, 3H), 1.41 (d, 3H); LCMS: purity: 93%; MS (m/e): 491 (MH+). | | + | | |
| 206 | N4-(3,4-Dihydro-3,3-dimethyl-2H,4H-benz[1,4]oxazin-6-yl)-5-fluoro-N2-[6-(2-hydroxyethyl)-2,3-dihydropyrrolo[1,2,3-d,e]benzoxazin-8-yl]-2,4-pyrimidinediamine | ¹H NMR (MeOD-d4): δ 7.62 (d, 1H), 7.04 (s, 1H), 6.98 (m, 2H), 6.75 (m, 1H), 6.59 (m, 2H), 4.47 (m, 1H), 4.4 (m, 2H), 4.14 (m, 2H), 3.62 (m, 4H), 2.80 (m, 2H), 1.07 (s, 6H); LCMS: purity: 98%; MS (m/e): 491 (MH+). | | + | | |
| 207 | (R)—N2-(3-Chloro-4-methoxyphenyl)-5-fluoro-N4-(2-methyl-3-oxo-2H,4H-benz[1,4]oxazin-6-yl)-2,4-pyrimidinediamine Benzene Sulfonic Acid Salt | ¹H NMR (MeOD-d4): δ 7.98 (d, 1H), 7.82 (m, 2H), 7.48 (s, 1H), 7.41 (m, 3H), 7.25 (dd, 1H), 7.15 (m, 3H), 6.94 (d, 1H), 4.62 (q, 1H), 3.82 (s, 3H), 1.50 (d, 3H); LCMS: purity: 97%; MS (m/e): 430 (MH+). | | + | | |
| 208 | (R)—N2-(3-Chloro-4-methoxyphenyl)-5-fluoro-N4-(2-methyl-3-oxo-2H,4H-benz[1,4]oxazin-6-yl)-2,4-pyrimidinediamine Methanesulfonic Acid Salt | ¹H NMR (MeOD-d4): δ 7.98 (d, 1H), 7.48 (s, 1H), 7.25 (dd, 1H), 7.15 (m, 3H), 6.94 (d, 1H), 4.62 (q, 1H), 3.82 (s, 3H), 2.68 (s, 3H), 1.50 (d, 3H); LCMS: purity: 98%; MS (m/e): 430 (MH+). | | + | | |
| 209 | (R)—N2-(3-Chloro-4-methoxyphenyl)-5-fluoro-N4-(2-methyl-3-oxo-2H,4H-benz[1,4]oxazin-6-yl)-2,4-pyrimidinediamine (1S)-(+)-Camphorsulfonic Acid Salt | ¹H NMR (DMSO-d6): δ 8.19 (d, 1H), 7.62 (m, 1H), 7.38 (m, 1H), 7.21 (m, 1H), 7.12 (m, 2H), 6.91 (d, 1H), 4.62 (q, 1H), 3.82 (s, 3H), 3.40 (q, 1H), 2.91 (m, 1H), 2.61 (m, 1H), 2.38 (m, 1H), 2.22 (m, 1H), 1.85 (m, 2H), 1.40 (d, 3H), 1.31 (m, 2H), 1.03 (s, 3H), 0.77 (s, 3H); LCMS: purity: 97%; MS (m/e): 430 (MH+). | | + | | |
| 210 | (R)-5-Fluoro-N2-(1-methylindazol-6-yl)-N4-(2-methyl-3-oxo-2H,4H-benz[1,4]oxazin-6-yl)-2,4-pyrimidinediamine | ¹H NMR (DMSO-d6): δ 8.16 (s, 1H), 8.08 (s, 1H), 7.80 (s, 1H), 7.52 (m, 1H), 7.32 (m, 1H), 7.17 (m, 2H), 6.94 (m, 1H), 4.60 (m, 1H), 3.77 (s, 3H), 1.45 (s, 3H); LCMS: purity: 97%; MS (m/e): 420 (MH+). | | + | | |
| 211 | (R)—N2-(3-Chloro-4-methoxyphenyl)-5-fluoro-N4-(2-methyl-3-oxo-2H,4H-benz[1,4]oxazin-6-yl)-2,4-pyrimidinediamine Hydrogen Chloride Salt | ¹H NMR (DMSO-d6): δ 8.12 (d, 1H), 7.41 (dd, 1H), 7.22 (m, 3H), 6.97 (m, 1H), 4.61 (q, 1H), 3.78 (s, 3H), 1.40 (d, 3H); LCMS: purity: 97%; MS (m/e): 430 (MH+). | + | + | | |
| 212 | (R)—N2-(3-Chloro-4-methoxyphenyl)-5-fluoro-N4-(2-methyl-3-oxo-2H,4H-benz[1,4]oxazin-6-yl)-2,4-pyrimidinediamine (1R)-(-)-Camphorsulfonic Acid Salt | ¹H NMR (DMSO-d6): δ 8.19 (d, 1H), 7.62 (m, 1H), 7.38 (m, 1H), 7.21 (m, 1H), 7.12 (m, 2H), 6.91 (d, 1H), 4.62 (q, 1H), 3.82 (s, 3H), 3.40 (q, 1H), 2.91 (m, 1H), 2.61 (m, 1H), 2.38 (m, 1H), 2.22 (m, 1H), 1.85 (m, 2H), 1.40 (d, 3H), 1.31 (m, 2H), 1.03 (s, 3H), 0.77 (s, 3H); LCMS: purity: 98%; MS (m/e): 430 (MH+). | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 213 | (R)—N2-(3-Chloro-4-methoxy-6-methylphenyl)-5-fluoro-N4-(2-methyl-3-oxo-2H,4H-benz[1,4]oxazin-6-yl)-2,4-pyrimidinediamine | ¹H NMR (DMSO-d6): δ 8.17 (s, 1H), 7.98 (d, 1H), 7.43 (m, 1H), 7.32 (m, 1H), 7.15 (s, 1H), 6.95 (s, 1H), 6.72 (d, 1H), 4.58 (m, 1H), 3.90 (s, 3H), 2.17 (s, 3H), 1.38 (d, 3H); LCMS: purity: 97%; MS (m/e): 444 (MH+). | + | | | |
| 214 | (S)—N2-(3-Chloro-4-methoxy-6-methylphenyl)-5-fluoro-N4-(2-methyl-3-oxo-2H,4H-benz[1,4]oxazin-6-yl)-2,4-pyrimidinediamine | ¹H NMR (DMSO-d6): δ 8.17 (s, 1H), 7.98 (d, 1H), 7.43 (m, 1H), 7.32 (m, 1H), 7.15 (s, 1H), 6.95 (s, 1H), 6.72 (d, 1H), 4.58 (m, 1H), 3.90 (s, 3H), 2.17 (s, 3H), 1.38 (d, 3H); LCMS: purity: 99%; MS (m/e): 444 (MH+). | | + | − | |
| 215 | (S)-3-Chloro-4,6-dimethoxyphenyl)-5-fluoro-N4-(2-methyl-3-oxo-2H,4H-benz[1,4]oxazin-6-yl)-2,4-pyrimidinediamine | ¹H NMR (DMSO-d6): δ 1.38 (d, 3H), 3.82 (s, 3H), 3.90 (s, 3H), 4.58 (q, 1H), 6.85 (m, 2H), 7.19 (m, 1H), 7.37 (m, 1H), 7.43 (m, 1H), 7.59 (s, 1H), 8.17 (m, 2H) purity: 99%; MS (m/e): 460 (MH+). | + | + | − | |
| 216 | N2-(3-Chloro-4-methoxy-6-methylphenyl)-N4-(3,4-dihydro-3,3-dimethyl-2H,4H-benz[1,4]oxazin-6-yl)-5-fluoro-2,4-pyrimidinediamine | ¹H NMR (DMSO-d6): δ 1.38 (s, 6H), 2.17 (s, 3H), 3.64 (s, 3H), 3.81 (s, 3H), 6.48 (m, 1H), 6.77 (m, 1H), 6.93 (m, 1H), 7.41 (s, 1H), 7.82 (d, 1H) purity: 99%; MS (m/e): 444 (MH+). | + | + | − | |
| 217 | N4-(3,4-Dihydro-2H,4H-benz[1,4]oxazin-6-yl)-5-fluoro-N2-[3-(oxazol-2-yl)phenyl]-2,4-pyrimidinediamine | ¹H NMR (DMSO-d6): δ 8.19 (m, 1H), 8.15 (d, 1H), 7.78 (m, 1H), 7.39 (m, 2H), 6.90 (m, 1H), 6.47 (m, 1H), 4.07 (m, 2H), 3.22 (m, 2H); LCMS: purity: 97%; MS (m/e): 405 (MH+). | + | + | − | |
| 218 | N4-(3,4-Dihydro-3,3-dimethyl-2H,4H-benz[1,4]oxazin-6-yl)-5-fluoro-N2-[3-(oxazol-2-yl)phenyl]-2,4-pyrimidinediamine | ¹H NMR (DMSO-d6): δ 1.18 (s, 6H), 3.81 (s, 2H), 6.77 (m, 1H), 6.93 (m, 1H), 6.99 (m, 1H), 7.38 (m, 2H), 7.63 (m, 1H), 7.71 (m, 1H), 8.12 (s, 1H), 8.22 (m, 2H) purity: 99%; MS (m/e): 433 (MH+). | + | + | − | |
| 219 | 5-Fluoro-N2-[3-(oxazol-2-yl)phenyl]-N4-(3-oxo-2H,4H-benz[1,4]oxazin-6-yl)-2,4-pyrimidinediamine | ¹H NMR (DMSO-d6): δ 4.50 (s, 2H), 6.78 (m, 1H), 7.18 (m, 1H), 7.23 (m, 2H), 7.38 (m, 2H), 7.59 (m, 1H), 7.77 (m, 1H), 8.22 (m, 3H) purity: 99%; MS (m/e): 419 (MH+). | + | + | − | |
| 220 | 5-Fluoro-N2-[3-(oxazol-2-yl)phenyl]-N4-(3-oxo-2H,4H-benz[1,4]oxazin-7-yl)-2,4-pyrimidinediamine | ¹H NMR (DMSO-d6): δ 4.50 (s, 2H), 6.78 (m, 1H), 7.18 (m, 1H), 7.23 (m, 1H), 7.41 (m, 2H), 7.59 (m, 1H), 7.78 (m, 1H), 8.22 (m, 3H) purity: 97%; MS (m/e): 419 (MH+). | + | + | − | |
| 221 | 5-Fluoro-N4-[2-(2-hydroxyethyl)-3-oxo-2H,4H-benz[1,4]oxazin-6-yl]-N2-[3-(oxazol-2-yl)phenyl]-2,4-pyrimidinediamine | ¹H NMR (DMSO-d6): δ 1.98 (m, 1H), 3.58 (m, 2H), 6.78 (m, 1H), 7.18 (m, 1H), 7.38 (m, 3H), 7.57 (m, 1H), 7.79 (m, 1H), 8.22 (m, 2H) purity: 99%; MS (m/e): 463 (MH+). | + | + | − | |
| 222 | N4-(3,4-Dihydro-2H,4H-benz[1,4]oxazin-6-yl)-5-fluoro-N2-[4-(oxazol-5-yl)phenyl]-2,4-pyrimidinediamine | ¹H NMR (DMSO-d6): δ 8.29 (m, 1H), 8.17 (d, 1H), 7.76 (m, 1H), 7.59 (m, 3H), 6.90 (m, 1H), 6.77 (m, 1H), 6.62 (m, 1H), 4.07 (m, 2H), 3.22 (m, 2H); LCMS: purity: 90%; MS (m/e): 405 (MH+). | + | + | − | |
| 223 | N4-(3,4-Dihydro-3,3-dimethyl-2H,4H-benz[1,4]oxazin-6-yl)-5-fluoro-N2-[4-(oxazol-5-yl)phenyl]-2,4-pyrimidinediamine | ¹H NMR (DMSO-d6): δ 1.18 (s, 6H), 3.80 (s, 2H), 6.71 (m, 2H), 6.95 (m, 1H), 7.51 (s, 1H), 7.69 (m, 2H), 8.20 (d, 1H), 8.38 (s, 1H) purity: 95%; MS (m/e): 433 (MH+). | + | + | − | |
| 224 | 5-Fluoro-N2-[4-(oxazol-5-yl)phenyl]-N4-(3-oxo-2H,4H-benz[1,4]oxazin-6-yl)-2,4-pyrimidinediamine | ¹H NMR (DMSO-d6): δ 4.68 (s, 2H), 6.98 (m, 2H), 7.22 (m, 1H), 7.51 (s, 1H), 7.57 (m, 2H), 7.78 (m, 2H), 8.28 (d, 1H), 8.38 (s, 1H) purity: 98%; MS (m/e) 419 (MH+). | + | + | − | |
| 225 | (S)-5-Fluoro-N4-(2-methyl-3-oxo-2H,4H-benz[1,4]oxazin-6-yl)-N2-[4-(oxazol-5-yl)phenyl]-2,4-pyrimidinediamine | ¹H NMR (DMSO-d6): δ 8.28 (s, 1H), 8.22 (d, 1H), 7.62 (m, 2H), 7.57 (m, 2H), 7.49 (s, 1H), 7.25 (m, 2H), 6.98 (m, 1H), 4.62 (q, 1H), 1.42 (d, 3H); LCMS: purity: 88%; MS (m/e): 433 (MH+). | + | + | − | |
| 226 | 5-Fluoro-N2-[4-(oxazol-5-yl)phenyl]-N4-(3-oxo-2H,4H-benz[1,4]oxazin-7-yl)-2,4-pyrimidinediamine | ¹H NMR (DMSO-d6): δ 4.66 (s, 2H), 6.98 (m, 2H), 7.22 (m, 1H), 7.51 (s, 1H), 7.57 (m, 2H), 7.76 (m, 2H), 8.28 (d, 1H), 8.38 (s, 1H) purity: 92%; MS (m/e) 419 (MH+). | + | + | − | |
| 227 | 5-Fluoro-N4-[2-(2-hydroxyethyl)-3-oxo-2H,4H-benz[1,4]oxazin-6-yl]-N2-[4-(oxazol-5-yl)phenyl]-2,4-pyrimidinediamine | ¹H NMR (DMSO-d6): δ 1.93 (m, 2H), 3.58 (m, 2H), 4.62 (m, 1H), 6.98 (m, 2H), 7.22 (m, 2H), 7.51 (s, 1H), 7.57 (m, 2H), 7.76 (m, 2H), 8.28 (d, 1H), 8.38 (s, 1H) purity: 95%; MS (m/e): 463 (MH+). | + | + | − | + |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 228 | N4-(3,4-Dihydro-4-methyl-2H-benz[1,4]oxazin-6-yl)-5-fluoro-N2-[4-(oxazol-5-yl)phenyl]-2,4-pyrimidinediamine | $^1$H NMR (DMSO-d6): δ 8.29 (s, 1H), 8.15 (d, 1H), 7.76 (m, 1H), 7.57 (m, 3H), 6.88 (m, 1H), 6.77 (m, 1H), 6.62 (m, 1H), 4.10 (m, 2H), 3.20 (m, 2H), 2.80 (s, 3H); LCMS: purity: 94%; MS (m/e) 419 (MH+). | + | + | − | |
| 229 | N4-(3,4-Dihydro-4-methyl-2H-benz[1,4]oxazin-7-yl)-5-fluoro-N2-[4-(oxazol-5-yl)phenyl]-2,4-pyrimidinediamine | $^1$H NMR (DMSO-d6): δ 8.37 (s, 1H), 8.19 (d, 1H), 7.61 (m, 5H), 7.07 (m, 2H), 6.68 (m, 1H), 4.22 (m, 2H), 3.22 (m, 2H), 2.81 (s, 3H); LCMS: purity: 94%; MS (m/e) 419 (MH+). | + | + | − | |
| 230 | 5-Fluoro-N4(4-methyl-3-oxo-2H-benz[1,4]oxazin-7-yl)-N2-[4-(oxazol-5-yl)phenyl]-2,4-pyrimidinediamine | $^1$H NMR (DMSO-d6): δ 8.36 (s, 1H), 8.20 (m, 1H), 8.19 (d, 1H), 7.77 (m, 2H), 7.54 (m, 2H), 7.37 (s, 1H), 6.97 (m, 1H), 4.58 (s, 2H), 2.97 (s, 3H); LCMS: purity: 98%; MS (m/e) 433 (MH+). | − | − | − | |
| 231 | 5-Fluoro-N4-(4-methyl-3-oxo-2H-benz[1,4]oxazin-6-yl)-N2-[4-(oxazol-5-yl)phenyl]-2,4-pyrimidinediamine | $^1$H NMR (DMSO-d6): δ 8.34 (s, 1H), 8.20 (m, 1H), 8.17 (d, 1H), 7.71 (m, 2H), 7.54 (m, 2H), 7.33 (s, 1H), 7.25 (m, 1H), 6.92 (m, 1H), 4.60 (s, 2H), 2.90 (s, 3H); LCMS: purity: 95%; MS (m/e) 433 (MH+). | − | − | − | |
| 232 | N4-(3,4-Dihydro-2H,4H-benz[1,4]oxazin-6-yl)-5-fluoro-N2-[3-(oxazol-5-yl)phenyl]-2,4-pyrimidinediamine | $^1$H NMR (DMSO-d6): δ 8.39 (m, 1H), 8.22 (d, 1H), 7.86 (m, 1H), 7.59 (m, 4H), 6.87 (m, 2H), 6.52 (m, 1H), 4.09 (m, 2H), 3.23 (m, 2H); LCMS: purity: 90%; MS (m/e) 405 (MH+). | + | + | − | |
| 233 | N4-(3,4-Dihydro-3,3-dimethyl-2H,4H-benz[1,4]oxazin-6-yl)-5-fluoro-N2-[3-(oxazol-5-yl)phenyl]-2,4-pyrimidinediamine | $^1$H NMR (DMSO-d6): δ 8.37 (s, 1H), 8.19 (d, 1H), 7.82 (m, 1H), 7.63 (m, 2H), 7.50 (s, 1H), 7.38 (m, 1H), 6.87 (m, 1H), 6.65 (m, 2H), 3.82 (s, 2H), 1.19 (s, 6H); LCMS: purity: 98%; MS (m/e) 433 (MH+). | + | + | − | |
| 234 | 5-Fluoro-N2-[3-(oxazol-5-yl)phenyl]-N4-(3-oxo-2H,4H-benz[1,4]oxazin-6-yl)-2,4-pyrimidinediamine | 1H NMR (DMSO-d6): δ 4.42 (s, 2H), 6.61 (m, 2H), 6.95 (m, 1H), 7.51 (m, 1H), 7.49 (m, 2H), 7.59 (m, 2H), 8.20 (d, 1H), 8.38 (s, 1H) purity: 90% MS (m/e) 419 (MH+). | + | + | − | |
| 235 | 5-Fluoro-N4-[2-(2-hydroxyethyl)-3-oxo-2H,4H-benz[1,4]oxazin-6-yl]-N2-[3-(oxazol-5-yl)phenyl]-2,4-pyrimidinediamine | 1H NMR (DMSO-d6): δ 1.93 (m, 2H), 3.58 (m, 2H), 4.62 (m, 1H), 6.61 (m, 2H), 6.95 (m, 1H), 7.51 (s, 1H), 7.49 (m, 2H), 7.59 (m, 2H), 8.20 (d, 1H), 8.38 (s, 1H) purity: 90% MS (m/e) 463 (MH+). | + | + | − | |
| 236 | N4-(3,4-Dihydro-4-methyl-2H-benz[1,4]oxazin-6-yl)-5-fluoro-N2-[3-(oxazol-5-yl)phenyl]-2,4-pyrimidinediamine | 1H NMR (DMSO-d6): δ 1.93 (m, 2H), 3.58 (m, 2H), 4.62 (m, 1H), 6.61 (m, 2H), 6.95 (m, 1H), 7.51 (s, 1H), 7.49 (m, 2H), 7.59 (m, 2H), 8.20 (d, 1H), 8.38 (s, 1H) purity: 95% MS (m/e) 419 (MH+). | + | + | − | |
| 237 | N4-(3,4-Dihydro-4-methyl-2H-benz[1,4]oxazin-7-yl)-5-fluoro-N2-[3-(oxazol-5-yl)phenyl]-2,4-pyrimidinediamine | 1H NMR (DMSO-d6): δ 1.93 (m, 2H), 2.82 (s, 3H), 3.58 (m, 2H), 4.62 (m, 1H), 6.61 (m, 2H), 6.95 (m, 1H), 7.51 (s, 1H), 7.49 (m, 2H), 7.59 (m, 2H), 8.20 (d, 1H), 8.38 (s, 1H) purity: 95%; MS (m/e): 419 (MH+). | + | + | − | |
| 238 | N4-(3,4-Dihydro-3,3-dimethyl-2H,4H-benz[1,4]oxazin-6-yl)-5-fluoro-N2-[4-(oxazol-2-yl)phenyl]-2,4-pyrimidinediamine | 1H NMR (DMSO-d6): δ 1.38 (s, 6H), 3.81 (s, 2H), 6.71 (m, 2H), 6.95 (m, 1H), 7.51 (s, 1H), 7.69 (m, 2H), 8.20 (d, 1H), 8.38 (s, 1H) purity: 99%, MS (m/e) 433 (MH+). | + | + | − | |
| 239 | 5-Fluoro-N4-[4-(oxazol-2-yl)phenyl]-N4-(3-oxo-2H,4H-benz[1,4]oxazin-6-yl)-2,4-pyrimidinediamine | 1H NMR (DMSO-d6): δ 8.15 (d 1H), 8.10 (s, 1H), 7.78 (m, 3H), 7.14 (m, 3H), 6.97 (m, 1H), 4.56 (s, 2H); LCMS: purity: 98%; MS (m/e): 419 (MH+) | − | − | − | |
| 240 | (S)-5-Fluoro-N4-(2-methyl-3-oxo-2H,4H-benz[1,4]oxazin-6-yl)-N2-[4-(oxazol-2-yl)phenyl]-2,4-pyrimidinediamine | 1H NMR (DMSO-d6): δ 8.25 (m, 1H), 8.22 (d, 1H), 8.12 (m, 1H), 7.77 (m, 2H), 7.34 (m, 1H), 7.23 (m, 2H), 6.98 (m, 2H), 4.63 (q, 1H), 1.42 (d, 3H); LCMS: purity: 95%; MS (m/e): 433 (MH+). | + | + | − | |
| 241 | 5-Fluoro-N4-[2-(2-hydroxyethyl)-3-oxo-2H,4H-benz[1,4]oxazin-6-yl]-N2-[4-(oxazol-2-yl)phenyl]-2,4-pyrimidinediamine | 1H NMR (DMSO-d6): δ 4.45 (s, 2H), 6.71 (m, 2H), 6.95 (m, 1H), 7.51 (s, 1H), 7.69 (m, 2H), 8.20 (d, 1H), 8.38 (s, 1H) purity: 95%; MS (m/e) 419 (MH+). | − | − | − | |
| 242 | 5-Fluoro-N4-[2-(2-hydroxyethyl)-3-oxo-2H,4H-benz[1,4]oxazin-6-yl]-N2-[4-(oxazol-2-yl)phenyl]-2,4-pyrimidinediamine | 1H NMR (DMSO-d6): δ 8.25 (d 1H), 8.20 (d, 1H), 8.16 (s, 1H), 7.82 (m, 3H), 7.35 (s, 1H), 7.20 (m, 2H), 6.95 (m, 1H), 4.62 (m, 1H), 3.58 (m, 1H), 1.95 (m, 2H); LCMS: purity: 99%, MS (m/e): 463 (MH+). | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 243 | N4-(2,3-Dihydro-4-methyl-2H-benz[1,4]oxazin-6-yl)-5-fluoro-N2-[4-(oxazol-2-yl)phenyl]-2,4-pyrimidinediamine | 1H NMR (DMSO-d6): δ 1.93 (m, 2H), 2.80 (s, 3H), 3.58 (m, 2H), 4.62 (m, 1H), 6.71 (m, 2H), 6.95 (m, 1H), 7.51 (s, 1H), 7.69 (m, 2H), 7.69 (m, 2H), 8.20 (d, 1H), 8.38 (s, 1H) purity: 99%; MS (m/e): 419 (MH+). | + | | | |
| 244 | 5-Fluoro-N4-(4-methyl-3-oxo-2H-benz[1,4]oxazin-7-yl)-N2-[4-(oxazol-2-yl)phenyl]-2,4-pyrimidinediamine | 1H NMR (DMSO-d6): δ 8.18 (d, 1H), 8.14 (s, 1H), 7.82 (d, 2H), 7.56 (m, 2H), 7.40 (m, 2H), 7.30 (s, 1H), 6.95 (m, 1H), 4.62 (s, 2H), 2.78 (s, 3H); LCMS: purity: 99%; MS (m/e): 433 (MH+). | − | + | − | |
| 245 | 5-Fluoro-N4-(4-methyl-3-oxo-2H-benz[1,4]oxazin-6-yl)-N2-[4-(oxazol-2-yl)phenyl]-2,4-pyrimidinediamine | 1H NMR (DMSO-d6): δ 8.20 (d, 1H), 8.12 (s, 1H), 7.82 (d, 2H), 7.55 (m, 2H), 7.40 (m, 2H), 7.33 (s, 1H), 6.88 (m, 1H), 4.59 (s, 2H), 2.77 (s, 3H); LCMS: purity: 98%; MS (m/e): 433 (MH+). | − | | − | |
| 246 | 5-Fluoro-N2-[3-(oxazol-5-yl)phenyl]-N4-[3-oxo-2H,4H-benz[1,4]oxazin-6-yl]-2,4-pyrimidinediamine | 1H NMR (DMSO-d6): δ 4.45 (s, 2H), 6.78 (m, 1H), 7.18 (m, 1H), 7.38 (m, 3H), 7.57 (m, 1H), 7.79 (m, 1H), 8.22 (m, 2H) purity: 93%; MS (m/e): 419 (MH+). | + | + | | |
| 247 | (S)-5-Fluoro-N4-(2-methyl-3-oxo-2H,4H-benz[1,4]oxazin-6-yl)-N2-[3-(oxazol-5-yl)phenyl]-2,4-pyrimidinediamine | 1H NMR (DMSO-d6): δ 1.38 (d, 3H), 4.58 (q, 1H), 6.78 (m, 1H), 7.18 (m, 1H), 7.38 (m, 3H), 7.57 (m, 1H), 7.79 (m, 1H), 8.22 (m, 2H) purity: 90%; MS (m/e): 433 (MH+). | + | + | − | |
| 248 | 5-Fluoro-N4-[2-(2-hydroxyethyl)-3-oxo-2H,4H-benz[1,4]oxazin-7-yl]-N2-[3-(oxazol-2-yl)phenyl]-2,4-pyrimidinediamine | 1H NMR (DMSO-d6): δ 1.93 (m, 2H), 3.58 (m, 2H), 4.62 (m, 1H), 6.88 (m, 2H), 7.22 (m, 3H), 7.57 (m, 2H), 7.79 (m, 2H), 8.22 (m, 2H) purity: 99%; MS (m/e): 463 (MH+). | + | + | | |
| 249 | 5-Fluoro-N4-[2-(2-hydroxyethyl)-3-oxo-2H,4H-benz[1,4]oxazin-7-yl]-N2-[4-(oxazol-5-yl)phenyl]-2,4-pyrimidinediamine | 1H NMR (DMSO-d6): δ 1.93 (m, 2H), 3.58 (m, 2H), 4.62 (m, 1H), 6.71 (m, 2H), 6.95 (m, 1H), 7.51 (s, 1H), 7.69 (m, 2H), 7.69 (m, 2H), 8.20 (d, 1H), 8.38 (s, 1H) purity: 99%; MS (m/e): 463 (MH+). | + | − | + | |
| 250 | (R)-5-Fluoro-N4-(2-methyl-3-oxo-2H,4H-benz[1,4]oxazin-6-yl)-N2-[3-(oxazol-4-yl)phenyl]-2,4-pyrimidinediamine | 1H NMR (DMSO-d6): δ 1.38 (d, 3H), 4.58 (q, 1H), 6.88 (m, 1H), 7.22 (m, 4H), 7.57 (m, 1H), 7.99 (m, 2H), 8.12 (m, 2H) purity: 95%; MS (m/e): 433 (MH+). | + | + | + | |
| 251 | (S)-5-Fluoro-N4-(2-methyl-3-oxo-2H,4H-benz[1,4]oxazin-6-yl)-N2-[3-(oxazol-4-yl)phenyl]-2,4-pyrimidinediamine | 1H NMR (DMSO-d6): δ d 1.38 (d, 3H), 4.58 (q, 1H), 6.88 (m, 1H), 7.22 (m, 4H), 7.57 (m, 1H), 7.99 (m, 2H), 8.12 (m, 2H) purity: 99%; MS (m/e): 433 (MH+). | + | + | − | |
| 252 | (R,S)—N2-(3,5-Dimethylphenyl)-5-fluoro-N4-(tetrahydrofurano[2,3]-2H-benz[1,4]oxazin-6-yl)-2,4-pyrimidinediamine | 1H NMR (DMSO-d6): δ 2.18 (s, 6H), 2.25 (m, 2H), 3.75 (t, 2H) 4.58 (q, 1H), 6.52 (d, 1H), 6.92 (dd, 2H), 7.37 (m, 3H), 8.12 (d, 1H) purity: 90%; MS (m/e): 406 (MH+). | + | + | | |
| 253 | N4-[3,4-Dihydro-2-(2-hydroxyethyl)-2H,4H-benz[1,4]oxazin-6-yl]-N2-(3,5-dimethoxyphenyl)-5-fluoro-2,4-pyrimidinediamine | 1H NMR (DMSO-d6): δ 1.88 (m, 2H), 2.97 (m, 2H), 3.55 (m, 2H), 3.61 (s, 6H), 4.08 (q, 1H), 6.02 (m, 1H), 6.58 (d, 1H), 6.96 (m, 5H), 8.02 (d, 1H) purity: 96%; MS (m/e): 442 (MH+). | + | + | − | |
| 254 | 5-Fluoro-N2-[3-(N-methylamino)carbonylmethyleneoxyphenyl]-N4-(3-oxo-2H,4H-benzo[1,4]thiazin-6-yl)-2,4-pyrimidinediamine | 1H NMR (DMSO-d6): δ 2.62 (d, 3H), 3.32 (s, 2H), 4.37 (s, 2H), 6.60 (m, 1H), 7.22 (m, 3H), 7.37 (m, 4H), 7.43 (m, 1H), 8.02 (m, 1H), 8.22 (d, 1H) purity: 94%; MS (m/e): 455 (MH+). | + | + | + | |
| 266 | 5-Fluoro-N4-(2-methyl-1,1,3-trioxo-2H,4H-benzo[1,4]thiazin-6-yl)-N2-(3,4,5-trimethoxyphenyl)-2,4-pyrimidinediamine | 1H NMR (DMSO-d6): δ 1.42 (d, 3H), 3.66 (s, 9H), 4.70 (q, 1H), 7.04 (m, 2H), 7.72 (s, 2H), 8.22 (d, 1H) purity: 96%; MS (m/e): 504 (MH+). | + | + | − | + |
| 267 | N2-(3,5-Dimethoxyphenyl)-N4-(2,2-dimethyl-1,1,3-trioxo-4H-benzo[1,4]thiazin-6-yl)-5-fluoro-2,4-pyrimidinediamine | LCMS: ret time 12.32 min purity: 100%; MS (m/e): 488 (MH+) | | + | | + |
| 268 | N2-(3,5-Dimethylphenyl)—N4-(2,2-dimethyl-1,1,3-trioxo-4H-benzo[1,4]thiazin-6-yl)-5-fluoro-2,4-pyrimidinediamine | LCMS: ret time 13.35 min purity: 99%; MS (m/e): 456 (MH+) | | + | | + |
| 269 | N4-(2,2-Dimethyl-1,1,3-trioxo-4H-benzo[thiazin-6-yl)-5-fluoro-2-(3,4,5-trimethoxyphenyl)-2,4-pyrimidinediamine | LCMS: ret time 11.28 min purity: 99%; MS (m/e): 518 (MH+) | | + | | + |
| 270 | N2-(3,5-Dimethoxyphenyl)-5-fluoro-N4-(2-methyl-3-oxo-2H,4H-benzo[1,4]thiazin-6-yl)-2,4-pyrimidinediamine | LCMS: ret time 11.69 min purity: 95%; MS (m/e): 442 (MH+) | | + | | + |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 271 | N2-(3,5-Dimethylphenyl)-5-fluoro-N4-(2-methyl-3-oxo-2H,4H-benzo[1,4]thiazin-6-yl)-2,4-pyrimidinediamine | LCMS: ret time 12.12 min purity: 98%; MS (m/e): 410 (MH+) | | | | |
| 272 | 5-Fluoro-N4-(2-methyl-3-oxo-2H,4H-benzo[1,4]thiazin-6-yl)-N2-(3,4,5-trimethoxyphenyl)-2,4-pyrimidinediamine | LCMS: ret time 10.44 min purity: 99%; MS (m/e): 472 (MH+) | | + | | |
| 273 | N4-(2,2-Dimethyl-1,1,3-trioxo-4H-benzo[1,4]thiazin-6-yl)-5-fluoro-N2-(indazol-6-yl)-2,4-pyrimidinediamine | LCMS: ret time 10.49 min purity: 95%; MS (m/e): 468 (MH+) | | + | | |
| 274 | N4-(2,2-Dimethyl-1,1,3-trioxo-4H-benzo[1,4]thiazin-6-yl)-5-fluoro-N2-(indazol-5-yl)-2,4-pyrimidinediamine | LCMS: ret time 8.66 min purity: 96%; MS (m/e): 468 (MH+) | | + | | |
| 275 | N4-(2,2-Dimethyl-1,1,3-trioxo-4H-benzo[1,4]thiazin-6-yl)-5-fluoro-N2-[3-(N-methylamino)carbonylmethyleneoxyphenyl]-2,4-pyrimidinediamine | LCMS: ret time 10.16 min purity: 93%; MS (m/e): 515 (MH+) | | + | | |
| 276 | N2-(3-Chloro-4-methoxyphenyl)-N4-(2,2-dimethyl-1,1,3-trioxo-4H-benzo[thiazin-6-yl)-5-fluoro-2,4-pyrimidinediamine | LCMS: ret time 12.66 min purity: 99%; MS (m/e): 492 (MH+) | | + | | |
| 277 | 5-Fluoro-N2-(indazol-6-yl)-N4-(2-methyl-3-oxo-2H,4H-benzo[1,4]thiazin-6-yl)-2,4-pyrimidinediamine | LCMS: ret time 9.40 min purity: 95%; MS (m/e): 422 (MH+) | | + | | |
| 278 | 5-Fluoro-N2-(indazol-5-yl)-N4-(2-methyl-3-oxo-2H,4H-benzo[1,4]thiazin-6-yl)-2,4-pyrimidinediamine | LCMS: ret time 8.23 min purity: 98%; MS (m/e): 422 (MH+) | | + | | |
| 279 | 5-Fluoro-N2-[3-(N-methylamino)carbonylmethyleneoxyphenyl]-N4-(2-methyl-3-oxo-2H,4H-benzo[1,4]thiazin-6-yl)-2,4-pyrimidinediamine | LCMS: ret time 9.51 min purity: 96%; MS (m/e): 469 (MH+) | | + | | |
| 280 | N2-(3-Chloro-4-methoxyphenyl)-N4-(2-methyl-3-oxo-2H,4H-benzo[1,4]thiazin-6-yl)-5-fluoro-2,4-pyrimidinediamine | LCMS: ret time 11.77 min purity: 97%; MS (m/e): 446 (MH+) | + | + | | |
| 281 | 5-Fluoro-N2-(3-hydroxyphenyl)-N4-(3-oxo-2H,4H-benzo[1,4]thiazin-6-yl)-2,4-pyrimidinediamine | LCMS: ret time 8.18 min purity: 99%; MS (m/e): 384 (MH+) | | + | | |
| 282 | 5-Fluoro-N2-(3-hydroxyphenyl)-N4-(2-methyl-3-oxo-2H,4H-benzo[1,4]thiazin-6-yl)-2,4-pyrimidinediamine | LCMS: ret time 9.11 min purity: 99%; MS (m/e): 398 (MH+) | | + | | |
| 283 | racemic-N4-(2,2-Dimethyl-1,1,3-trioxo-4H-benzo[1,4]thiazin-6-yl)-5-fluoro-N2-[3-hydroxyphenyl]-2,4-pyrimidinediamine | LCMS: ret time 9.89 min purity: 99%; MS (m/e): 444 (MH+) | | + | | |
| 284 | racemic-5-Fluoro-N2-[3-hydroxyphenyl]-N4-(2-methyl-1,1,3-trioxo-2H,4H-benzo[1,4]thiazin-6-yl)-2,4-pyrimidinediamine | LCMS: ret time 9.33 min purity: 97%; MS (m/e): 430 (MH+) | | + | | |
| 285 | racemic-5-Fluoro-N2-[3-(N-methylamino)carbonylmethyleneoxyphenyl]-N4-(2-methyl-1,1,3-trioxo-2H,4H-benzo[1,4]thiazin-6-yl)-2,4-pyrimidinediamine | LCMS: ret time 9.44 min purity: 93%; MS (m/e): 501 (MH+) | | + | | |
| 286 | racemic-N2-(3-Chloro-4-methoxyphenyl)-5-fluoro-N4-(2-methyl-1,1,3-trioxo-2H,4H-benzo[1,4]thiazin-6-yl)-2,4-pyrimidinediamine | LCMS: ret time 11.68 min purity: 95%; MS (m/e): 478 (MH+) | | + | | |
| 287 | 5-Fluoro-N4-(3-oxo-2H,4H-benzo[1,4]thiazin-6-yl)-N2-(3,4,5-trimethoxyphenyl)-2,4-pyrimidinediamine | LCMS: ret time 9.49 min purity: 99%; MS (m/e): 458 (MH+) | | + | | |
| 288 | 5-Fluoro-N2-(indazol-5-yl)-N4-(3-oxo-2H,4H-benzo[1,4]thiazin-6-yl)-2,4-pyrimidinediamine | LCMS: ret time 7.28 min purity: 98%; MS (m/e): 408 (MH+) | | + | | |
| 289 | N2-(3-Chloro-4-methoxyphenyl)-N4-(2,2-dimethyl-3-oxo-4H-benzo[thiazin-6-yl)-5-fluoro-2,4-pyrimidinediamine | LCMS: ret time 12.45 min purity: 97%; MS (m/e): 460 (MH+) | | + | | |
| 290 | N2-(3,5-Dimethoxyphenyl)-N4-(2,2-dimethyl-3-oxo-4H-benzo[1,4]thiazin-6-yl)-5-fluoro-2,4-pyrimidinediamine | LCMS: ret time 12.81 min purity: 99%; MS (m/e): 456 (MH+) | | + | | |
| 291 | N4-(2,2-Dimethyl-3-oxo-4H-benzo[1,4]thiazin-6-yl)-N2-(3,5-dimethylphenyl)-5-fluoro-2,4-pyrimidinediamine | LCMS: ret time 13.44 min purity: 99%; MS (m/e): 424 (MH+) | | + | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 292 | N4-(2,2-dimethyl-3-oxo-4H-benzo[1,4]thiazin-6-yl)-5-fluoro-N2-(3,4,5-trimethoxyphenyl)-2,4-pyrimidinediamine | LCMS: ret time 11.86 min purity: 99%; MS (m/e): 486 (MH+) | | | | |
| 293 | N4-(2,2-Dimethyl-3-oxo-4H-benzo[1,4]thiazin-6-yl)-5-fluoro-N2-(3-hydroxyphenyl)-2,4-pyrimidinediamine | LCMS: ret time 10.39 min purity: 99%; MS (m/e): 412 (MH+) | | + | | |
| 294 | N4-(2,2-Dimethyl-3-oxo-4H-benzo[1,4]thiazin-6-yl)-5-fluoro-N2-[3-(N-methylamino)carbonylmethyleneoxyphenyl]-2,4-pyrimidinediamine | LCMS: ret time 10.04 min purity: 97%; MS (m/e): 483 (MH+) | + | + | | |
| 295 | N4-(2,2-Dimethyl-3-oxo-4H-benzo[1,4]thiazin-6-yl)-5-fluoro-N2-(indazol-6-yl)-2,4-pyrimidinediamine | LCMS: ret time 10.54 min purity: 96%; MS (m/e): 436 (MH+) | + | | | + |
| 296 | racemic-5-Fluoro-N2-(3-fluoro-4-methoxyphenyl)-N4-(2-methyl-1,1,3-trioxo-2H,4H-benzo[1,4]thiazin-6-yl)-2,4-pyrimidinediamine | LCMS: ret time 11.91 min purity: 96%; MS (m/e): 462 (MH+) | + | + | | |
| 297 | N4-(2,2-Dimethyl-1,1,3-trioxo-4H-benzo[1,4]thiazin-6-yl)-5-fluoro-N2-(3-fluoro-4-methoxyphenyl)-2,4-pyrimidinediamine | LCMS: ret time 12.11 min purity: 96%; MS (m/e): 476 (MH+) | + | + | | |
| 298 | racemic-5-Fluoro-N2-(3-fluoro-4-methoxyphenyl)-N4-(2-methyl-3-oxo-2H,4H-benzo[1,4]thiazin-6-yl)-2,4-pyrimidinediamine | LCMS: ret time 11.29 min purity: 98%; MS (m/e): 430 (MH+) | + | + | | |
| 299 | N4-(2,2-Dimethyl-3-oxo-4H-benzofthiazin-6-yl)-5-fluoro-N2-(3-fluoro-4-methoxyphenyl)-2,4-pyrimidinediamine | LCMS: ret time 12.14 min purity: 99%; MS (m/e): 444 (MH+) | + | + | | |
| 300 | 5-Fluoro-N2-(3-fluoro-4-methoxyphenyl)-N4-(3-oxo-2H,4H-benzo[1,4]thiazin-6-yl)-2,4-pyrimidinediamine | LCMS: ret time 10.56 min purity: 97%; MS (m/e): 415 (MH+) | + | + | | |
| 301 | N4-(3,5-Dimethylphenyl)-5-fluoro-N4-(3-oxo-2H,4H-benzo[1,4]thiazin-6-yl)-2,4-pyrimidinediamine | LCMS: ret time 11.76 min purity: 98%; MS (m/e): 396 (MH+) | + | + | | |
| 302 | N2-(3,5-Dimethylphenyl)-5-fluoro-N4-(1,1,3-trioxo-2H,4H-benzo[1,4]thiazin-6-yl)-2,4-pyrimidinediamine | LCMS: ret time 10.72 min purity: 96%; MS (m/e): 428 (MH+) | + | + | | |
| 303 | N2-(3,5-Dimethoxyphenyl)-5-fluoro-N4-(1,1,3-trioxo-2H,4H-benzo[1,4]thiazin-6-yl)-2,4-pyrimidinediamine | LCMS: ret time 10.06 min purity: 95%; MS (m/e): 460 (MH+) | + | + | | |
| 304 | N2-(3-Chloro-4-methoxyphenyl)-5-fluoro-N4-(1,1,3-trioxo-2H,4H-benzo[1,4]thiazin-6-yl)-2,4-pyrimidinediamine | LCMS: ret time 10.13 min purity: 97%; MS (m/e): 464 (MH+) | + | + | | |
| 305 | 5-Fluoro-N2-[3-(N-methylamino)carbonylmethyleneoxyphenyl]-N4-(1,1,3-trioxo-2H,4H-benzo[1,4]thiazin-6-yl)-2,4-pyrimidinediamine | LCMS: ret time 8.40 min purity: 97%; MS (m/e): 487 (MH+) | | + | | |
| 306 | 5-Fluoro-N2-(3,4,5-trimethoxyphenyl)-N4-(1,1,3-trioxo-2H,4H-benzo[1,4]thiazin-6-yl)-2,4-pyrimidinediamine | LCMS: ret time 9.19 min purity: 95%; MS (m/e): 490 (MH+) | | + | | |
| 307 | 5-Fluoro-N2-(indazol-6-yl)-N4-(1,1,3-trioxo-2H,4H-benzo[1,4]thiazin-6-yl)-2,4-pyrimidinediamine | LCMS: ret time 8.33 min purity: 91%; MS (m/e): 440 (MH+) | | + | | |
| 308 | 5-Fluoro-N2-(3-hydroxyphenyl)-N4-(1,1,3-trioxo-2H,4H-benzo[1,4]thiazin-6-yl)-2,4-pyrimidinediamine | LCMS: ret time 8.07 min purity: 96%; MS (m/e): 416 (MH+) | | + | | |
| 309 | 5-Fluoro-N2-(3-fluoro-4-methoxyphenyl)-N4-(1,1,3-trioxo-2H,4H-benzo[1,4]thiazin-6-yl)-2,4-pyrimidinediamine | LCMS: ret time 9.74 min purity: 95%; MS (m/e): 448 (MH+) | | + | | |
| 310 | 5-Fluoro-N2-(indazol-5-yl)-N4-(1,1,3-trioxo-2H,4H-benzo[1,4]thiazin-6-yl)-2,4-pyrimidinediamine | LCMS: ret time 7.40 min purity: 94%; MS (m/e): 440 (MH+) | | + | | |
| 311 | N4-(2,2-Dimethyl-3-oxo-4H-benzo[1,4]thiazin-6-yl)-5-fluoro-N2-(1-methylindazol-6-yl)-2,4-pyrimidinediamine | LCMS: ret time 10.15 min purity: 99%; MS (m/e): 450 (MH+) | + | + | | |
| 312 | N4-(2,2-Dimethyl-3-oxo-4H-benzo[1,4]thiazin-6-yl)-5-fluoro-N2-(indazol-6-yl)-2,4-pyrimidinediamine Trifluoro Acetate Salt | LCMS: ret time 10.54 min purity: 100%; MS (m/e): 436 (MH+) | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 313 | N2-Chloro-5-fluoro-N4-(3-oxo-2H,4H-benzo[1,4]thiazin-6-yl)-4-pyrimidineamine | LCMS: ret time 5.58 min purity: 95%; MS (m/e) 311 (MH+) | + | | | |
| 314 | racemic-N2-Chloro-5-fluoro-N4-(2-methyl-3-oxo-2H,4H-benzo[1,4]thiazin-6-yl)-4-pyrimidineamine | LCMS: ret time 11.18 min purity: 95%; MS (m/e) 325 (MH+) | + | | | |
| 315 | N2-Chloro-5-fluoro-N4-(1,1,3-trioxo-2H,4H-benzo[1,4]thiazin-6-yl)-4-pyrimidineamine | LCMS: ret time 10.03 min purity: 95%; MS (m/e) 343 (MH+) | − | | | |
| 316 | N2-Chloro-N4-(2,2-dimethyl-3-oxo-4H-benzo[1,4]thiazin-6-yl)-5-fluoro-4-pyrimidineamine | LCMS: ret time 12.29 min purity: 95%; MS (m/e) 339 (MH+) | + | | | |
| 317 | racemic-N2-Chloro-5-fluoro-N4-(2-methyl-1,1,3-trioxo-2H,4H-benzo[1,4]thiazin-6-yl)-4-pyrimidineamine | LCMS: ret time 10.16 min purity: 96%; MS (m/e) 357 (MH+) | − | | | |
| 318 | N2-Chloro-N4-(2,2-dimethyl-1,1,3-trioxo-4H-benzo[1,4]thiazin-6-yl)-5-fluoro-4-pyrimidineamine | LCMS: ret time 10.50 min purity: 96%; MS (m/e) 371 (MH+) | + | | | |
| 319 | N4-[benzoxathiazin-3(4H)-one-6-yl]2-chloro-5-fluoro-4-pyrimidineamine | LCMS: ret time 6.40 min purity: 99%; MS (m/e) 296 (MH+) | + | | | |
| 320 | N2-Chloro-N4-(3,3-dimethyl-1,4-benzoxazin-6-yl)-5-fluoro-pyrimidineamine | LCMS: ret time 12.20 min purity 99% MS (m/e) 309 (MH+) | + | | | |
| 324 | N2-(3,5-Dimethoxyphenyl)-5-fluoro-N4-(3-trifluoromethoxyphenyl)-2,4-pyrimidinediamine | 1H NMR (DMSO-d6): δ 9.57 (bs, 1H), 9.21 (bs, 1H), 8.16 (d, J = 3.6 Hz, 1H), 8.01 (d, J = 8.1 Hz, 1H), 7.75 (s, 1H), 7.40 (t, J = 8.1 Hz, 1H), 7.01 (d, J = 8.4 Hz, 1H), 6.91 (d, J = 2.1 Hz, 2H), 6.09-6.06 (m, 1H), 3.65 (s, 6H); 19F NMR (282 MHz, DMSO-d6): −57.17, −163.27; LCMS: purity: 99%; MS (m/e) 425 (MH+) | + | | | |
| 325 | N2-(3,5-Dimethoxyphenyl)-5-fluoro-N4-(3-trifluoromethoxyphenyl)-2,4-pyrimidinediamine | 1H NMR (DMSO-d6): δ 9.54 (bs, 1H), 9.12 (bs, 1H), 8.15 (dd, J = 1.8 and 3.6 Hz, 1H), 7.96 (d, J = 8.1 Hz, 1H), 7.75 (s, 1H), 7.41 (t, J = 8.1 Hz, 1H), 7.01 (d, J = 8.1 Hz, 1H), 6.55 (s, 1H), 2.18 (s, 6H); 19F NMR (282 MHz, DMSO-d6): −57.01, −163.96; LCMS: purity: 99%; MS (m/e): 393 (MH+) | + | | | |
| 326 | 5-Fluoro-N2-(indol-6-yl)-N4-(3-trifluoromethoxyphenyl)-2,4-pyrimidinediamine | 1H NMR (DMSO-d6): δ 10.83 (bs, 1H), 9.49 (s, 1H), 9.11 (s, 1H), 8.13 (dd, J = 1.2 and 3.3 Hz, 1H), 8.05 (d, J = 8.1 Hz, 1H), 7.80 (d, J = 13.2 Hz, 2H), 7.40-7.32 (m, 2H), 7.21-7.16 (m, 2H), 6.99-6.95 (m, 1H), 6.34-6.28 (m, 1H); 19F NMR (282 MHz, DMSO-d6): −57.14, −164.68; LCMS: purity: 99%; MS (m/e): 404 (MH+) | | + | | |
| 327 | 5-Fluoro-N4-[1-(N-methylamino)carbonylindol-6-yl]-N2-[3-(N-methylamino)carbonylmethyleneoxyphenyl]-2,4-pyrimidinediamine | 1H NMR (DMSO-d6): δ 10.87 (bs, 1H), 9.61 (s, 1H), 9.46-9.43 (m, 1H), 8.08 (d, J = 3.6 Hz, 1H), 8.04-7.98 (m, 1H), 7.40-7.25 (m, 4H), 7.02 (dd, J = 1.8 and 8.4 Hz, 1H), 6.95-6.90 (m, 1H), 6.77-6.70 (m, 2H), 6.38-6.35 (m, 1H), 4.39 (s, 2H), 2.62 (d, J = 4.8 Hz, 3H), 2.48 (d, J = 4.6 Hz, 3H); LCMS: purity: 96%; MS (m/e): 464 (MH+) | + | | | |
| 328 | N2-(3,5-Dimethoxyphenyl)-N4-(3,5-dimethylphenyl)-5-fluoro-2,4-pyrimidinediamine | 1H NMR (DMSO-d6): δ 9.15 (bs, 1H), 9.11 (s, 1H), 8.07 (d, J = 3.9 Hz, 1H), 7.37 (s, 2H), 6.89 (d, J = 1.81 Hz, 2H), 6.68 (s, 1H), 6.05 (t, J = 2.1 Hz, 1H), 3.61 (s, 6H), 2.23 (s, 6H); 19F NMR (282 MHz, DMSO-d6): −163.60; LCMS: purity: 99%; MS (m/e): 369 (MH+) | | + | | |
| 329 | N4-(3,5-Dimethylphenyl)-5-fluoro-N2-(3-methoxy-5-trifluoromethylphenyl)-2,4-pyrimidinediamine | 1H NMR (DMSO-d6): δ 9.45 (s, 1H), 9.22 (s, 1H), 8.12 (d, J = 3.9 Hz, 1H), 7.68-7.64 (m, 1H), 7.58-7.54 (m, 1H), 7.33 (s, 2H), 6.71 (s, 2H), 3.69 (s, 3H), 2.23 (s, 6H); LCMS: purity: 99%; MS (m/e): 407 (MH+) | + | | | |
| 330 | N4-(3,5-Dimethylphenyl)-5-fluoro-N4-(3-methyl-5-trifluoromethylphenyl)-2,4-pyrimidinediamine | 1H NMR (DMSO-d6): δ 10.11 (bs, 1H), 9.94 (bs, 1H), 8.25 (d, J = 4.8 Hz, 1H), 7.67 (s, 2H), 7.24 (s, 2H), 7.14 (s, 1H), 6.80 (s, 1H), 2.25 (s, 3H), 2.21 (s, 6H); 19F NMR (282 MHz, DMSO-d6): −61.76, −161.10; LCMS: purity: 99%; MS (m/e): 390 (M+). | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 331 | N2-(3,5-Dimethylphenyl)-5-fluoro-N4-(3-methoxy-5-trifluoromethylphenyl)-2,4-pyrimidinediamine | ¹H NMR (DMSO-d6): δ 9.86 (bs, 1H), 9.42 (bs, 1H), 8.20 (d, J = 4.2 Hz, 1H), 7.80-7.76 (m, 1H), 7.56-7.51 (m, 1H), 7.18 (s, 2H), 6.94 (s, 1H), 6.59 (s, 1H), 3.74 (s, 3H), 2.15 (s, 6H); LCMS: purity: 97%; MS (m/e): 407 (MH+). | + | | | |
| 332 | N2-(3,5-Dimethoxyphenyl)-5-fluoro-N4-(3-methoxy-5-trifluoromethylphenyl)-2,4-pyrimidinediamine | ¹H NMR (DMSO-d6): δ 9.59 (bs, 1H), 9.24 (bs, 1H), 8.18 (d, J = 3.3 Hz, 1H), 7.84-7.68 (m, 1H), 7.61-7.57 (m, 1H), 6.89 (d, J = 2.4 Hz, 3H), 6.06 (t, J = 2.4 Hz, 1H), 3.77 (s, 3H), 3.61 (s, 6H); 19F NMR (282 MHz, DMSO-d6): −61.85, −163.20; LCMS: purity: 97%; MS (m/e): 439 (MH+). | + | | | |
| 333 | 5-Fluoro-N4-(3-methoxy-5-trifluoromethylphenyl)-N2-(3,4,5-trimethoxyphenyl)-2,4-pyrimidinediamine | ¹H NMR (DMSO-d6): δ 9.80 (bs, 1H), 9.24 (bs, 1H), 8.25 (d, J = 3.3 Hz, 1H), 7.77-7.72 (m, 1H), 7.60-7.52 (m, 3H), 6.92 (s, 1H), 6.75 (s, 1H), 3.77 (s, 3H), 3.71 (s, 3H); 19F NMR (282 MHz, DMSO-d6): −61.90, −161.82; LCMS: purity: 97%; MS (m/e): 477 (MH+). | + | | | |
| 334 | 5-Fluoro-N4-(3-methoxy-5-trifluoromethylphenyl)-N2-(3-methyl-5-trifluoromethylphenyl)-2,4-pyrimidinediamine | ¹H NMR (DMSO-d6): δ 9.83 (bs, 1H), 9.72 (s, 1H), 8.25 (d, J = 3.6 Hz, 1H), 7.81-7.68 (m, 3H), 7.57-7.52 (m, 1H), 7.06 (s, 1H), 6.96-6.91 (m, 1H), 3.75 (s, 3H), 2.26 (s, 3H); 19F NMR (282 MHz, DMSO-d6): −61.82, −162.02; LCMS: purity: 91%; MS (m/e): 461 (MH+). | + | | | |
| 335 | 5-Fluoro-N4-(3-methoxy-5-trifluoromethylphenyl)-N2-(3,4,5-trimethoxyphenyl)-2,4-pyrimidinediamine | ¹H NMR (DMSO-d6): δ 9.67 (bs, 1H), 9.24 (bs, 1H), 8.17 (d, J = 3.6 Hz, 1H), 7.84-7.78 (m, 1H), 7.59 (s, 1H), 6.95-6.87 (m, 3H), 3.74 (s, 3H), 3.59 (s, 6H); 19F NMR (282 MHz, DMSO-d6): −61.86, −163.40; LCMS: purity: 96%; MS (m/e): 469 (MH+). | + | + | | |
| 336 | N2-(3-Chloro-4-hydroxy-5-methylphenyl)-5-fluoro-N4-(3-methoxy-5-trifluoromethylphenyl)-2,4-pyrimidinediamine | ¹H NMR (DMSO-d6): δ 9.56 (s, 1H), 9.09 (s, 1H), 8.61 (s, 1H), 8.14 (d, J = 3.6 Hz, 1H), 7.82-7.77 (m, 1H), 7.57-7.53 (m, 1H), 7.52-7.48 (m, 1H), 7.27-7.23 (m, 1H), 6.89 (bs, 1H), 3.76 (s, 3H), 2.10 (s, 3H); 19F NMR (282 MHz, DMSO-d6): −61.80, −164.13; LCMS: purity: 96%; MS (m/e): 444 (MH+). | + | | | |
| 337 | N2-(3,5-Dichlorophenyl)-5-fluoro-N4-(3-methoxy-5-trifluoromethylphenyl)-2,4-pyrimidinediamine | ¹H NMR (DMSO-d6): δ 9.74 (s, 1H), 9.70 (s, 1H), 8.25 (d, J = 3.6 Hz, 1H), 7.77-7.71 (m, 3H), 7.55-7.50 (m, 1H), 7.03-7.01 (m, 1H), 6.95-6.93 (m, 1H), 3.79 (s, 3H); 19F NMR (282 MHz, DMSO-d6): −61.78, −161.76; LCMS: purity: 96%; MS (m/e): 448 (MH+). | + | + | | |
| 338 | N2-[3,5-Bis(hydroxymethyl)phenyl]-5-fluoro-N4-(3-methoxy-5-trifluoromethylphenyl)-2,4-pyrimidinediamine | ¹H NMR (DMSO-d6): δ 10.11 (bs, 1H), 9.82 (bs, 1H), 8.26 (d, J = 4.2 Hz, 1H), 7.83-7.79 (m, 1H), 7.57-7.51 (m, 1H), 7.34 (bs, 2H), 6.99-6.94 (m, 2H), 4.38 (s, 4H), 3.74 (s, 3H); LCMS: purity: 92%; MS (m/e): 439 (MH+). | + | + | | |
| 339 | N2-(4-Chloro-3,5-dimethylphenyl)-5-fluoro-N4-(3-methoxy-5-trifluoromethylphenyl)-2,4-pyrimidinediamine | ¹H NMR (DMSO-d6): δ 9.98 (bs, 1H), 9.66 (bs, 1H), 8.24 (d, J = 4.2 Hz, 1H), 7.76-7.71 (m, 1H), 7.56-7.52 (m, 1H), 7.37 (s, 2H), 6.98-6.95 (m, 1H), 3.75 (s, 3H), 2.20 (s, 6H); LCMS: purity: 98%; MS (m/e): 442 (MH+). | − | | | |
| 340 | N2,N4-Bis(3,5-dimethoxyphenyl)-5-fluoro-2,4-pyrimidinediamine | 1H NMR (DMSO-d6): δ 9.27 (s, 1H), 9.18 (d, 1H, J = 3.9 Hz), 6.99 (d, 2H, J = 2.1 Hz), 6.92 (d, 2H, J = 2.4 Hz), 6.21 (t, 1H, J = 2.1 Hz), 6.05 (t, 1H, J = 2.4 Hz), 3.68 (s, 6H), 3.62 (s, 6H); LCMS: purity: 100%; MS (m/e): 401 (MH+) | + | + | | |
| 341 | N2,N4-Bis(3,5-dimethylphenyl)-5-fluoro-2,4-pyrimidinediamine | ¹H NMR (DMSO-d6): δ 9.11 (s, 1H), 8.98 (s, 1H), 8.05 (d, 1H, J = 3.9 Hz), 7.33 (bs, 2H), 7.24 (bd, 2H), 6.69 (bs, 1H), 6.51 (bs, 1H), 2.25 (bs, 6H), 2.14 (s, 6H); LCMS: purity: 100%; MS (m/e) 336 (M+). | + | | | |
| 342 | N2-[3,5-Bis(hydroxymethyl)phenyl]-N4-(3,4-ethylenedioxyphenyl)-5-fluoro-2,4-pyrimidinediamine | ¹H NMR (DMSO-d6): δ 9.10 (s, 1H), 9.09 (s, 1H), 8.02 (d, 1H, J = 3.9 Hz), 7.44 (s, 2H), 7.28 (d, 1H, J = 3.0 Hz), 7.24 (d, 1H, J = 2.7 Hz), | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 343 | N2-[3,5-Bis(hydroxymethylene)phenyl]-N4-(3,5-dimethoxyphenyl)-5-fluoro-2,4-pyrimidinediamine | 6.86 (s, 1H), 6.79 (d, 1H, J = 8.7 Hz), 5.05 (t, 2H, J = 6 Hz), 4.39 (d, 4H, J = 5.4 Hz), 4.22 (bs, 4H); LCMS: purity: 97%; MS (m/e): 399 (MH+). | + | | | |
| 344 | N2-[3,5-Bis(hydroxymethylene)phenyl]-N4-(2,2-dimethyl-3-oxo-4H-benz[1,4]oxazin-6-yl)-5-fluoro-2,4-pyrimidinediamine | $^1$H NMR (DMSO-d6): δ 9.19 (s, 1H), 9.15 (s, 1H), 8.08 (d, 1H, J = 3.6 Hz), 7.46 (s, 2H), 7.01 (d, 2H, J = 2.1 Hz), 6.86 (s, 1H), 6.21 (t, 1H, J = 1.8 Hz), 5.03 (t, 2H, J = 5.4 Hz), 4.38 (d, 4H, J = 5.4 Hz), 3.68 (s, 6H); LCMS: purity: 86%; MS (m/e): 401 (MH+). | | | | + |
| 345 | N2-[3,5-Bis(hydroxymethylene)phenyl]-N4-(3-chloro-4-methoxyphenyl)-5-fluoro-2,4-pyrimidinediamine | $^1$H NMR (DMSO-d6): δ 10.55 (s, 1H), 9.27 (bd, 1H), 8.97 (s, 1H), 8.04 (d, 1H, 3.6 Hz), 7.44 (d, 2H, J = 1.2 Hz), 7.39 (dd, 1H, J = 2.4 and 8.4 Hz), 7.24 (d, 1H, J = 2.4 Hz), 6.88 (d, 1H, J = 8.7 Hz), 6.85 (bs, 1H), 6.38 (s, 2H), 5.08 (t, 1H, J = 5.6 Hz), 4.93 (t, 1H, J = 5.7 Hz), 4.38 (d, 2H, J = 5.4 Hz), 4.31 (d, 2H, J = 6 Hz), 1.41 (s, 6H); LCMS: purity: 93%; MS (m/e): 440 (MH+). | | | | |
| 346 | N2-[3,5-Bis(hydroxymethylene)phenyl]-N4-(3,4-dichlorophenyl)-5-fluoro-2,4-pyrimidinediamine | $^1$H NMR (DMSO-d6): δ 9.26 (s, 1H), 9.15 (s, 1H), 8.07 (bd, 1H, J = 3.9 Hz), 7.79 (dd, 1H, J = 2.7 and 9 Hz), 7.74 (d, 1H, J = 2.7 Hz), 7.43 (s, 2H), 7.11 (d, 1H, J = 9 Hz), 6.86 (s, 1H), 5.06 (t, 2H, J = 5.4 Hz), 4.38 (d, 4H, J = 5.4 Hz), 3.84 (s, 3H); LCMS: purity: 98%; MS (m/e): 405 (MH+). | | + | | |
| 347 | N4-(2,2-Dimethyl-3-oxo-4H-benz[1,4]oxazin-6-yl)-N2-[1-(N-methylaminocarbonyl)indol-6-yl)-5-fluoro-2,4-pyrimidinediamine | $^1$H NMR (DMSO-d6): δ 9.50 (bs, 1H), 9.28 (s, 1H), 8.16 (d, 1H, J = 3.6 Hz), 8.05 (d, 1H, J = 2.7 Hz), 7.93 (dd, 1H, J = 2.7 and 9.0 Hz), 7.52 (d, 1H, J = 8.7 Hz), 7.44 (s, 2H), 6.87 (s, 1H), 5.09 (t, 2H, J = 5.7 Hz), 4.41 (d, 4H), J = 5.4 Hz); LCMS: purity: 97%; MS (m/e): 409 (M+). | + | + | | |
| 348 | N2-(1-Aminocarbonylindol-6-yl)-N4-(2,2-dimethyl-3-oxo-4H-benz[1,4]oxazin-6-yl)-5-fluoro-2,4-pyrimidinediamine | $^1$H NMR (DMSO-d6): δ 11.02 (s, 1H), 10.49 (s, 1H), 9.69 (d, 1H, J = 4.8 Hz), 9.53 (s, 1H), 8.12 (d, 1H, J = 3.6 Hz), 7.52 (d, 1H, J = 8.4 Hz), 7.38 (t, 1H, J = 2.7 Hz), 7.11 (s, 1H), 6.81 (d, 1H, J = 2.4 Hz), 6.72 (dd, 1H, J = 1.8 and 8.4 Hz), 6.59 (dd, 1H, J = 2.4 and 8.7 Hz), 6.49 (s, 1H), 5.84 (d, 1H, J = 8.4 Hz), 2.74 (d, 3H, J = 4.5 Hz), 1.31 (s, 6H); LCMS: purity: 96%; MS (m/e): 476 (MH+). | − | | | |
| 349 | N2-(4-Chloro-3,5-dimethylphenyl)-N4-(3,5-dimethoxyphenyl)-5-fluoro-2,4-pyrimidinediamine | $^1$H NMR (DMSO-d6): δ 11.01 (s, 1H), 10.44 (s, 1H), 9.50 (s, 1H), 8.16 (d, 1H, J = 3.6 Hz), 8.07 (d, 1H, J = 5.4 Hz), 7.52 (d, 1H, J = 8.4 Hz), 7.38 (t, 1H, J = 2.7 Hz), 6.73 (dd, 1H, J = 1.5 and 8.4 Hz), 6.54 (m, 2H), 5.69 (d, 1H, J = 8.7 Hz), 2.93 (s, 2H), 1.29 (s, 6H); LCMS: purity: 95%; MS (m/e): 462 (MH+) | + | | | |
| 350 | N4-(3,5-Dimethoxyphenyl)-N2-(3,5-dimethylphenyl)-5-fluoro-2,4-pyrimidinediamine | $^1$H NMR (DMSO-d6): δ 9.26 (bs, 1H), 9.20 (s, 1H), 8.10 (d, 1H, J = 3.9 Hz), 7.48 (s, 2H), 6.94 (d, 2H, J = 2.4 Hz), 6.23 (t, 1H, J = 2.4 Hz), 3.68 (s, 6H), 2.20 (s, 6H); LCMS: purity: 92%; MS (m/e): 403 (MH+). | + | + | − | + |
| 351 | N4-(3,5-Dimethoxyphenyl)-N2-(3,4-ethylenedioxyphenyl)-5-fluoro-2,4-pyrimidinediamine | $^1$H NMR (DMSO-d6): δ 9.20 (s, 1H), 9.05 (s, 1H), 8.08 (d, 1H, J = 3.6 Hz), 7.27 (m, 2H), 6.97 (d, 2H, J = 2.1 Hz), 6.51 (s, 1H), 6.21 (t, 1H, J = 1.8 Hz), 3.67 (s, 6H), 2.15 (s, 6H); LCMS: purity: 96%; MS (m/e): 369 (MH+). | + | + | | |
| 352 | N2-(3,5-Dichlorophenyl)-N4-(3,5-dimethoxyphenyl)-5-fluoro-2,4-pyrimidinediamine | $^1$H NMR (DMSO-d6): δ 9.16 (s, 1H), 9.96 (s, 1H), 8.05 (d, 1H, J = 3.3 Hz), 7.22 (d, 1H, J = 2.7 Hz), 7.06 (dd, 1H, J = 2.4 and 8.7 Hz), 6.99 (d, 2H, J = 2.1 Hz), 6.65 (d, 1H, J = 8.7 Hz), 6.20 (t, 1H, J = 2.1 Hz), 4.17 (s, 4H), 3.69 (s, 6H); LCMS: purity: 91%; MS (m/e): 399 (MH+). | + | | | |
| | | $^1$H NMR (DMSO-d6): δ 9.82 (bs, 1H), 9.58 (bs, 1H), 8.21 (d, 1H, J = 3.6 Hz), 7.75 (bs, 2H), 7.04 (t, 1H, J = 1.8 Hz), 6.89 (d, 2H, J = 1.8 Hz), 6.27 (t, 1H, J = 2.1 Hz), 3.67 (s, 6H); LCMS: purity: 95%; MS (m/e): 410 (MH+). | | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 353 | N4-(3,5-Dimethoxyphenyl)-5-fluoro-N2-(3-methyl-5-trifluoromethylphenyl)-2,4-pyrimidinediamine | ¹H NMR (DMSO-d6): δ 9.47 (s, 1H), 9.31 (s, 1H), 8.15 (d, 1H, J = 3.6 Hz), 7.86 (s, 1H), 7.79 (s, 1H), 6.98 (m, 3H), 6.23 (t, 1H, J = 2.4 Hz), 3.68 (s, 6H), 2.27 (s, 3H); LCMS: purity: 96%; MS (m/e): 423 (MH+). | + | | | |
| 354 | N2-(3,5-Dichlorophenyl)-N4-(3,4-ethylenedioxyphenyl)-5-fluoro-2,4-pyrimidinediamine | ¹H NMR (DMSO-d6): δ 9.56 (s, 1H), 9.28 (s, 1H), 8.11 (d, 1H, J = 3.6 Hz), 7.76 (d, 2H, J = 1.8 Hz), 7.18 (d, 1H, J = 2.4 Hz), 7.13 (dd, 1H, J = 3.6 and 9 Hz), 6.98 (t, 1H, J = 1.8 Hz), 6.82 (d, 1H, J = 8.7 Hz), 4.21 (bs, 4H); LCMS: purity: 81%; MS (m/e): 407 (MH+). | | + | | |
| 355 | N2-(3,5-Dimethoxyphenyl)-5-fluoro-N2-(3-methoxy-5-trifluoromethylphenyl)-2,4-pyrimidinediamine | ¹H NMR (DMSO-d6): δ 9.53 (s, 1H), 9.33 (d, 1H, J = 1.5 Hz), 8.16 (d, 1H, J = 3.6 Hz), 7.65 (d, 1H, J = 2.1 Hz), 6.98 (d, 2H, J = 2.1 Hz), 6.72 (bs, 1H), 6.22 (t, 1H, J = 2.4 Hz), 3.72 (s, 3H), 3.69 (s, 6H); LCMS: purity: 96%; MS (m/e): 439 (MH+). | + | | | |
| 356 | N4-(3,4-Ethylenedioxyphenyl)-5-fluoro-N2-(3-methoxy-5-trifluoromethylphenyl)-2,4-pyrimidinediamine | ¹H NMR (DMSO-d6): δ 9.47 (s, 1H), 9.23 (s, 1H), 8.09 (d, 1H, J = 3.9 Hz), 7.67 (s, 1H), 7.59 (s, 1H), 7.27 (d, 1H, J = 2.7 Hz), 7.18 (dd, 1H, J = 2.4 and 8.4 Hz), 6.78 (d, 1H, J = 8.7 Hz), 6.78 (s, 1H), 4.21, bs, 4H), 3.72, (s, 3H); LCMS: purity: 90%; MS (m/e): 437 (MH+). | | + | | |
| 357 | N2-(3,5-Dimethoxyphenyl)-5-fluoro-N4-[3,4-(tetrafluoroethylenedioxy)phenyl]-2,4-pyrimidinediamine | ¹H NMR (DMSO-d6): δ 9.64 (s, 1H), 9.29 (s, 1H), 8.15 (m, 2H), 7.62 (dd, 1H, J = 2.4 and 9 Hz), 7.39 (d, 1H, J = 8.7 Hz), 6.90 (d, 2H, J = 2.4 Hz), 6.09 (t, 1H, J = 1.8 Hz), 3.66 (s, 6H); LCMS: purity: 97%; MS (m/e): 471 (MH+) | + | | | |
| 358 | N2-(4-Chloro-3,5-dimethylphenyl)-5-fluoro-N4-[3,4-(tetrafluoroethylenedioxy)phenyl]-2,4-pyrimidinediamine | ¹H NMR (DMSO-d6): δ 9.90 (bs, 1H), 8.21 (bd, 1H, J = 3.6 Hz), 8.06 (bs, 1H), 7.57 (dd, 1H, J = 2.4 and 9.0 Hz), 7.43 (d, 1H, J = 9.3 Hz), 7.39 (s, 2H), 7.06 (bs, 1H), .25 (s, 6H); LCMS: purity: 97%; MS (m/e):473 (MH+). | − | | | |
| 359 | N2-[3,5-Bis(hydroxymethylene)phenyl]-5-fluoro-N4-[3,4-(tetrafluoroethylenedioxy)phenyl]-2,4-pyrimidinediamine | ¹H NMR (DMSO-d6): δ 9.60 (s, 1H), 9.32 (s, 1H), 8.16 (d, 2H, J = 3.6 Hz), 7.70 (dd, 1H, J = 2.7 and 9 Hz), 7.47 (s, 2H), 7.40 (d, 1H, J = 9.0 Hz), 6.88 (bs, 1H), 5.11 (t, 2H, J = 5.4 Hz), 4.42 (d, 4H, J = 5.4 Hz); LCMS: purity: 98%; MS (m/e): 471 (MH+). | | + | | |
| 360 | N2-(3,5-Dichlorophenyl)-5-fluoro-N4-[3,4-(tetrafluoroethylenedioxy)phenyl]-2,4-pyrimidinediamine | ¹H NMR (DMSO-d6): δ 9.76 (s, 1H), 9.72 (s, 1H), 8.25 (d, 1H, J = 3.6 Hz), 8.00 (d, 1H, J = 2.4 Hz), 7.74 (d, 2H, J = 1.8 Hz), 7.58 (dd, 1H, J = 2.4 and 9.0 Hz), 7.44 (d, 1H, J = 9.0 Hz), 7.04 (t, 1H, J = 1.8 Hz); LCMS: purity: 98%; MS (m/e): 480 (MH+). | − | | | |
| 361 | 5-Fluoro-N2-(3-methoxy-5-trifluoromethylphenyl)-N4-[3,4-(tetrafluoroethylenedioxy)phenyl]-2,4-pyrimidinediamine | ¹H NMR (DMSO-d6): δ 9.72 (s, 1H), 9.64 (s, 1H), 8.23 (d, 1H, J = 3.6 Hz), 8.07 (d, 1H, J = 2.4 Hz), 7.67 (bs, 1H), 7.60 (dd, 1H, J = 2.4 and 9.3 Hz), 7.54 (bs, 1H), 7.39 (d, 1H, J = 9 Hz), 6.75 (bs, 1H), 3.75 (s, 3H); LCMS: purity: 97%; MS (m/e): 509 (MH+) | + | | | |
| 362 | N2-(3,5-Dimethyphenyl)-5-fluoro-N4-[3,4-(tetrafluoroethylenedioxy)phenyl]-2,4-pyrimidinediamine | ¹H NMR (DMSO-d6): δ 9.60 (s, 1H), 9.19 (s, 1H), 8.15 (d, 1H, J = 3.6 Hz), 8.12 (d, 1H, J = 2.4 Hz), 7.60 (dd, 2.4 and 8.7 Hz), 7.40 (d, 1H, J = 9 Hz), 7.22 (s, 2H), 6.56 (s, 1H), 2.18 (s, 6H); LCMS: purity: 100%; MS (m/e):439 (MH+). | + | | | |
| 363 | N4-(3,4-Ethylenedioxyphenyl)-5-fluoro-N2-[3,4-(tetrafluoroethylenedioxy)phenyl]-2,4-pyrimidinediamine | ¹H NMR (DMSO-d6): δ 9.53 (s, 1H), 9.27 (s, 1H), 8.08 (d, 1H, J = 3.6 Hz), 7.93 (d, 1H, J = 2.4 Hz), 7.37 (dd, 1H, J = 2.4 and 9.3 Hz), 7.26 (d, 1H, J = 9 Hz), 7.11 (dd, 1H, J = 2.4 and 8.7 Hz), 6.80 (d, 1H, J = 8.4 Hz), 4.22 (s, 4H); LCMS: purity: 96%; MS (m/e): 469 (MH+). | + | | | |
| 364 | N4-(3,5-Dimethoxyphenyl)-5-fluoro-N2-[3,4-(tetrafluoroethylenedioxy)phenyl]-2,4-pyrimidinediamine | ¹H NMR (DMSO-d6): δ 9.59 (s, 1H), 9.37 (d, 1H, J = 0.9 Hz), 8.14 (d, 1H, J = 2.4 Hz), 7.38 (dd, 1H, J = 2.7 and 9.3 Hz), 7.27 (d, 1H, J = 9.0 Hz), 6.91 (d, 2H, J = 2.4 Hz), 6.26 (t, 1H, J = 2.4 Hz), 3.69 (s, 6H); LCMS: purity: 96%; MS (m/e): 471 (MH+). | + | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 365 | 5-Fluoro-N2-[2-(N-methylamino)carbonylindol-7-yl]-N4-[3,4-(tetrafluoroethylenedioxy)phenyl]-2,4-pyrimidinediamine | ¹H NMR (DMSO-d6): δ 11.59 (s, 1H), 9.66 (s, 1H), 9.34 (s, 1H), 8.46 (d, 1H, J = 4.8 Hz), 8.20 (d, 1H, J = 3.6 Hz), 8.10 (d, 1H, J = 2.4 Hz), 7.91 (d, 1H, J = 7.2 Hz), 7.60 (dd, 1H, J = 2.7 and 9 Hz), 7.39 (d, 1H, J = 9.0 Hz), 7.24 (d, 1H, J = 7.5 Hz), 7.06 (d, 1H, J = 1.8 Hz), 6.94 (t, 1H, J = 7.8 Hz), 2.80 (d, 3H, J = 4.8 Hz); LCMS: purity: 100%; MS (m/e): 507 (MH+). | + | | | |
| 366 | 5-Fluoro-N2-(3-methyl-5-trifluoromethyl)-N4-[3,4-(tetrafluoroethylenedioxy)phenyl]-2,4-pyrimidinediamine | ¹H NMR (DMSO-d6): δ 9.70 (s, 1H), 9.60 (s, 1H), 8.22 (d, 1H, J = 2.4 Hz), 8.07 (d, 1H, J = 2.4 Hz), 7.87 (s, 1H), 7.70 (s, 1H), 7.60 (dd, 1H, J = 2.1 and 9 Hz), 7.41 (d, 1H, J = 9 Hz), 7.04 (s, 1H), 2.31 (s, 3H); LCMS: purity: 100%; MS (m/e): 493 (MH+). | + | | | |
| 367 | N2-(3,4-Ethylenedioxyphenyl)-5-fluoro-N4-[3,4-(tetrafluoroethylenedioxy)phenyl]-2,4-pyrimidinediamine | ¹H NMR (DMSO-d6): δ 9.48 (s, 1H), 9.12 (s, 1H), 8.11 (d, 2H, J = 3.6 Hz), 7.59 (dd, 1H, J = 2.4 and 9 Hz), 7.39 (d, 1H, J = 9.3 Hz), 7.22 (d, 1H, J = 2.4 Hz), 6.99 (dd, 1H, J = 2.4 and 8.7 Hz), 6.70 (d, 1H, J = 9 Hz); LCMS: purity: 96%; MS (m/e): 469 (MH+). | + | + | | + |
| 368 | N4-(3,5-Dimethoxyphenyl)-5-fluoro-N2-[2-(N-methylamino)carbonylindol-7-yl]-2,4-pyrimidinediamine | ¹H NMR (DMSO-d6): δ 11.70 (s, 1H), 9.31 (s, 1H), 9.28 (s, 1H), 8.43 (d, 1H, J = 4.8 Hz), 8.14 (d, 1H, J = 4.8 Hz), 8.04 (dd, 1H, J = 0.9 and 8.4 Hz), 7.19 (d, 1H, J = 7.5 Hz), 7.03 (d, 1H, J = 2.4 Hz), 6.89 (t, 1H, J = 8.4 Hz), 6.24 (t, 1H, J = 2.4 Hz), 3.69 (s, 6H), 2.80 (d, 3H, J = 4.5 Hz); LCMS: purity: 91%; MS (m/e): 437 (MH+). | + | | | |
| 369 | N2-(3-Chloro-5-methoxyphenyl)-N4-(2,2-dimethyl-3-oxo-4H-benz[1,4]oxazin-6-yl)-5-fluoro-2,4-pyrimidinediamine | ¹H NMR (DMSO-d6): δ 10.57 (s, 1H), 9.35 (s, 1H), 9.27 (s, 1H), 8.10 (d, 1H, J = 3.6 Hz), 7.47 (m, 1H), 7.25 (dd, 1H, J = 2.7 and 8.7 Hz), 7.16 (d, 2H, J = 2.1 Hz), 6.87 (d, 1H, J = 8.4 Hz), 6.49 (t, 1H, J = 1.8 Hz), 3.66 (s, 3H), 1.40 (s, 6H); LCMS: purity: 100%; MS (m/e): 445 (MH+). | | + | | |
| 370 | N2-(3-Chloro-5-methoxyphenyl)-N4-(3,4-ethylenedioxyphenyl)-5-fluoro-2,4-pyrimidinediamine | ¹H NMR (DMSO-d6): δ 9.31 (s, 1H), 9.21 (s, 1H), 8.08 (d, 1H, J = 3.9 Hz), 7.48 (t, 1H, J = 1.8 Hz), 7.20 (m, 3H), 6.80 (d, 1H, J = 8.4 Hz), 6.49 (t, 1H, J = 2.4 Hz), 4.21 (s, 4H), 3.67 (s, 3H); LCMS: purity: 95%; MS (m/e): 403 (MH+). | | + | | |
| 371 | 5-Fluoro-N4-(3,4-methylenedioxyphenyl)-N2-[2-(N-methylamino)carbonylindol-7-yl]-2,4-pyrimidinediamine | ¹H NMR (DMSO-d6): δ 11.27 (s, 1H), 9.25 (s, 2H), 8.43 (d, 1H, J = 4.5 Hz), 8.09 (d, 1H, J = 3.9 Hz), 8.01 (d, 1H, J = 7.8 Hz), 7.51 (d, 1H, J = 2.1 Hz), 7.16 (m, 2H), 7.04 (d, 1H, J = 1.8 Hz), 6.92 (t, 1H, J = 7.8 Hz), 6.84 (d, 1H, J = 8.1 Hz), 6.01 (s, 2H), 2.81 (d, 3H, J = 4.8 Hz); LCMS: purity: 100%; MS (m/e): 421 (MH+). | | + | | |
| 372 | N2-(3,5-Dimethoxyphenyl)-5-fluoro-N4-(3,4-methylenedioxyphenyl)-2,4-pyrimidinediamine | ¹H NMR (DMSO-d6): δ 9.20 (s, 1H), 9.10 (s, 1H), 8.05 (d, 1H, J = 3.6 Hz), 7.44 (d, 1H, J = 2.1 Hz), 7.16 (dd, 1H, J = 2.1 and 8.4 Hz), 6.93 (d, 2H, J = 2.4 Hz), 6.84 (d, 1H, J = 8.4 Hz), 6.04 (t, 1H, J = 2.1 Hz), 5.99 (s, 2H), 3.64 (s, 6H); LCMS: purity: 89%; MS (m/e): 385 (MH+). | | + | | |
| 373 | 5-Fluoro-N4-(3,4-methylenedioxyphenyl)-N2-(3-methoxy-5-trifluoromethylphenyl)-2,4-pyrimidinediamine | ¹H NMR (DMSO-d6): δ 9.49 (s, 1H), 9.30 (s, 1H), 8.10 (d, 1H, J = 3.6 Hz), 9.67 (bs, 1H), 7.58 (bs, 1H), 7.40 (d, 1H, J = 1.8 Hz), 7.11 (dd, 1H, J = 1.8 and 8.4 Hz), 6.84 (d, 1H, J = 8.4 Hz), 6.70 (bs, 1H), 6.99 (s, 2H), 3.73 (s, 3H); LCMS: purity: 97%; MS (m/e): 423 (MH+). | + | | | |
| 374 | 5-Fluoro-N4-(3,4-methylenedioxyphenyl)-N2-(3-methyl-5-trifluoromethylphenyl)-2,4-pyrimidinediamine | ¹H NMR (DMSO-d6): δ 9.46 (s, 1H), 9.29 (s, 1H), 8.10 (d, 1H, J = 3.6 Hz), 7.78 (bs, 1H), 7.39 (d, 1H, J = 2.1 Hz), 7.10 (1H, J = 2.4 and 8.4 Hz), 6.99 (bs, 1H), 6.85 (d, 1H, J = 8.4 Hz), 5.99 (s, 2H), 2.28 (s, 3H); LCMS: purity: 99%; MS (m/e): 407 (MH+). | - | | | |
| 375 | N2-(3,5-Dichlorophenyl)-5-fluoro-N4-(3,4-methylenedioxyphenyl)-2,4-pyrimidinediamine | ¹H NMR (DMSO-d6): δ 9.59 (s, 1H), 9.36 (s, 1H), 8.12 (d, 1H, J = 3.9 Hz), 7.74 (d, 2H, J = 2.1 Hz), 7.30 (d, 1H, J = 2.1 Hz), 7.06 (dd, 1H, J = 2.4 | + | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 376 | N2-(3,5-Dimethylphenyl)-5-fluoro-N4-(3,4-methylenedioxyphenyl)-2,4-pyrimidinediamine | and 8.4 Hz), 6.97 (t, 1H, 2.1 Hz), 6.88 (d, 1H, J = 8.4 Hz); 6.00 (s, 2H); LCMS: purity: 94%; MS (m/e): 393 (M+). | | | | |
| 377 | N2-(4-Chloro-2,5-dimethoxyphenyl)-N4-(3-chloro-4-methoxyphenyl)-5-fluoro-2,4-pyrimidinediamine | ¹H NMR (DMSO-d6): δ 9.18 (bs, 1H), 9.03 (s, 1H), 8.04 (d, 1H, J = 3.9 Hz), 7.43 (d, 1H, J = 2.1 Hz), 7.24 (s, 2H), 7.11 (dd, 1H, J = 2.1 and 8.4 Hz), 6.85 (d, 1H, J = 8.4 Hz), 6.50 (bs, 1H), 5.98 (s, 2H), 2.16 (s, 6H); LCMS: purity: 87%; MS (m/e): 353 (MH+). | + | + | | |
| 378 | N2-(3-Chloro-4-methoxyphenyl)-N4-(2,2-dimethyl-3-oxo-4H-benz[1,4]oxazin-6-yl)-5-fluoro-2,4-pyrimidinediamine p-Toluene Sulfonic Acid Salt | LCMS: purity: 100%; MS (m/e): 439 (M+). | | + | | |
| 379 | N2-(4-Chloro-2,5-dimethoxyphenyl)-N4-(3,4-ethylenedioxyphenyl)-5-fluoro-2,4-pyrimidinediamine | ¹H NMR (DMSO-d6): δ 10.63 (s, 1H), 10.05 (s, 1H), 9.62 (s, 1H), 8.15 (d, 1H, J = 4.8 Hz), 7.66 (bs, 1H), 7.44 (dd, 2H, J = 1.8 and 8.7 Hz), 7.35 (bd, 1H, J = 9 Hz), 7.20 (dd, 1H, J = 2.1 and 8.7 Hz), 7.10 (bd, 2H, J = 7.5 Hz), 7.02 (d, 1H, J = 9 Hz), 6.89 (d, 1H, J = 8.4 Hz), 3.78 (s, 3H), 2.28 (s, 3H), 1.39 (s, 6H); LCMS: puerity: 97%; MS (m/e): 444 (M for parent molecule + H). | + | | | |
| 380 | N2-(4-Chloro-2,5-dimethoxyphenyl)-N4-(3,5-dimethoxyphenyl)-5-fluoro-2,4-pyrimidinediamine | ¹H NMR (DMSO-d6): δ 9.24 (s, 1H), 8.05 (d, 1H, J = 3.9 Hz), 7.87 (s, 1H), 7.70 (s, 1H), 7.17 (d, 1H, J = 2.4 Hz), 7.06 (m, 2H), 6.74 (d, 1H, J = 8.7 Hz), 4.21 (s, 4H), 3.79 (s, 3H), 3.54 (s, 3H); LCMS: purity: 100%; MS (m/e): 433 (MH+). | + | | | |
| 381 | N4-(3,5-Dimethoxyphenyl)-5-fluoro-N2-(2-methoxycarbonylbenzofuran-5-yl)-2,4-pyrimidinediamine | ¹H NMR (DMSO-d6): δ 9.36 (s, 1H), 8.25 (d, 1H, J = 1.8 Hz), 8.11 (d, 1H, J = 3.9 Hz), 7.57 (m, 3H), 6.99 (m, 2H), 6.26 (t, 1H, J = 2.1 Hz), 3.88 (s, 3H), 3.69 (s, 6H); LCMS: purity: 92%; MS (m/e): 439 (MH+). | + | + | | |
| 382 | N2-(2-Carboxybenzofuran-5-yl)-N4-(3,5-dimethoxyphenyl)-5-fluoro-2,4-pyrimidinediamine | LCMS: purity: 91%; MS (m/e): 425 (MH+). | – | | – | |
| 383 | N2-(2-Carboxyindol-7-yl)-N4-(3,5-dimethoxyphenyl)-5-fluoro-2,4-pyrimidinediamine | 1H NMR (DMSO-d6): δ 11.85 (s, 1H), 9.31 (s, 1H), 9.26 (s, 1H), 8.16 (d, 1H, J = 3.6 Hz), 8.12 (d, 1H, J = 8.1 Hz), 7.22 (d, 1H, J = 8.1 Hz), 7.02 (d, 2H, J = 2.1 Hz), 6.91 (t, 1H, J = 7.8 Hz), 6.25 (s, 1H)3.70 (bs, 6H); LCMS: purity: 80%; MS: 424 (MH+) | + | | | |
| 384 | N4-(3,5-Dimethoxyphenyl)-5-fluoro-N2-[2-(N-2-hydroxyethyl-N-methylamino)carbonylindol-7-yl]-2,4-pyrimidinediamine | ¹H NMR (DMSO-d6): δ 11.52 (s, 1H), 9.30 (bs, 1H), 9.27 (s, 1H), 8.14 (d, 1H, J = 3.6 Hz), 8.04 (m, 1H), 7.22 (d, 1H, J = 8.4 Hz), 7.03 (m, 2H), 6.90 9m, 2H), 6.23 9bs, 1H), 3.68 (s, 6H), 3.64 (bs, 4H), 3.20 (s, 3H); LCMS: purity: 94%; MS (m/e): 481 (MH+). | + | + | | + |
| 385 | N4-(3,4-Ethylenedioxyphenyl)-5-fluoro-N4-methyl-N2-[3-(N-methylamino)carbonylmethyleneoxyphenyl]-2,4-pyrimidinediamine | 1H NMR (CDCl3): δ 7.50 (bs, 1H), 7.30 (m, 2H), 6.91 (bd, 1H, J = 7.2 Hz), 6.73 (m, 5H), 4.49 (s, 2H), 4.31 (s, 4H), 3.60 (s, 3H), 2.92 (d, 3H, J = 4.5 Hz); CMS: purity: 97%; MS (m/e): 440 (MH+) | + | + | | |
| 386 | N4-(3,4-Ethylenedioxyphenyl)-N2-(3,5-dimethoxyphenyl)-5-fluoro-N4-methyl-2,4-pyrimidinediamine | 1H NMR (CDCl3): δ 7.94 (d, 1H, J = 5.1 Hz), 7.50 (bd, 1H), 6.90 (d, 1H, J = 9 Hz), 6.83 (s, 1H), 6.73 (m, 3H), 6.62 (d. 1H, 2.4 Hz), 4.31 (m, 4H), 3.80 (s, 3H), 3.79 (s, 3H), 3.60 (s, 3H); LCMS: purity: 90%; MS: 413 (MH+). | + | + | – | |
| 387 | N2-(3,5-Dimethylphenyl)-N4-(3,4-ethylenedioxyphenyl)-5-fluoro-N4-methyl-2,4-pyrimidinediamine | 1H NMR (CDCl3): δ 7.40 (s, 1H), 7.27 (m,1H), 6.90 (bdd, 1H), 6.81 (m, 1H), 6.77 (d, 2H, J = 2.4 Hz), 6.70 (dd, 1H, J = 2.7 and 8.7 Hz), 4.30 (s, 4H), 3.50 (s, 3H), 2.32 (s, 6H); LCMS: purity: 94%, MS (m/e): 381 (MH+). | + | + | – | |
| 388 | N2-(3,5-Dimethoxyphenyl)-N4-(2,2-dimethyl-3-oxo-4H-benz[1,4]oxazin-6-yl)-5-fluoro-N4-methyl-2,4- | 1H NMR (DMSO-d6): δ 10.60 (s, 1H), 9.21 (s, 1H), 7.94 (d, 1H, J = 6.0 Hz), 7.01 (d, 2H, J = 1.2 Hz), 6.88 (m, 2H), 6.75 (d, 1H, J = 2.4 Hz), | – | | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| | pyrimidinediamine | 6.05 (t, 1H, J = 2.4 Hz), 3.60 (s, 6H), 3.41 (s, 3H), 1.34 (s, 6H); LCMS: purity: 92%, MS (m/e): 454 (MH+). | | | | |
| 389 | N4-(3,5-Dimethoxyphenyl)-N2-[2-(N-1,1-dimethyl-2-hydroxyethylamino)carbonylindol-7-yl]-5-fluoro-2,4-pyrimidinediamine | ¹H NMR (DMSO-d6): δ 11.63 (s, 1H), 9.25 (d, 1H, J = 7.8 Hz), 8.14 (d, 1H, J = 3.6 Hz), 8.02 (d, 1H, J = 8.1 Hz), 7.53 (s, 1H), 7.19 (d, 1H, J = 7.5 Hz), 7.14 (s, 1H), 7.04 (s, 2H), 6.89 (t, 1H, J = 7.5 Hz), 6.23 (s, 1H), 4.94 (t, 1H, J = 6.3 Hz), 3.69 (s, 6H), 3.53 (d, 2H, J = 5.4 Hz), 1.33 (s, 6H); LCMS: purity: 80%; MS (m/e): 495 (MH+). | + | | – | |
| 390 | 2-Chloro-N4-(3,4-ethylenedioxyphenyl)-5-fluoro-N4-methyl-4-pyrimidineamine | 1H NMR (CDCl3): δ 7.85 (d, 1H, J = 4.8 Hz), 6.86 (d, 1H, J = 8.4 Hz), 6.73 (d, 1H, J = 2.7 Hz), 6.60 (dd, 1H, J = 2.7 and 8.1 Hz); LCMS: purity: 100%, MS (m/e): 296 (M+) | – | | – | |
| 391 | N2-(3,5-Dimethylphenyl)-5-fluoro-N4-methyl-N4-(3-oxo-2,2,4-trimethylbenz[1,4]oxazin-6-yl)-2,4-pyrimidinediamine | 1H NMR (CDCl3): δ 7.95 (d, 1H, J = 6.4 Hz), 7.67 (bs, 1H), 7.21 (s, 2H), 6.96 (s, 1H), 6.87 (dd, 1H, J = 2.4 and 8.7 Hz), 6.78 (d, 1H, J = 2.4 Hz), 6.72 (s, 1H), 3.55 (s, 3H), 3.32 (s, 3H), 2.30 (s, 6H), 1.53 (s, 6H); LCMS: purity: 92%, MS (m/e): 436 (MH+). | + | | + | |
| 392 | N2-(3-Chloro-4-methoxyphenyl)-5-fluoro-N4-methyl-N4-(3-oxo-2,2,4-trimethylbenz[1,4]oxazin-6-yl)-2,4-pyrimidinediamine | 1H NMR (CD3OD): δ 7.77 (d, 1H, J = 2.4 Hz), 7.75 (bd, 1H), 7.34 (dd, 1H, J = 2.7 and 9.3 Hz), 7.05 (d, 1H, J = 1.8 Hz), 6.95 (m, 3H), 4.62 (s, 3H), 3.83 (s, 3H), 3.51 (s, 3H), 1.48 (s, 6H); LCMS: purity: 94%, MS (m/e): 472 (M+). | + | | + | |
| 393 | N2-(3,5-Dimethoxyphenyl)-5-fluoro-N4-methyl-N4-(3-oxo-2,2,4-trimethylbenz[1,4]oxazin-6-yl)-2,4-pyrimidinediamine | 1H NMR (CD3OD): δ 7.78 (d, 1H, J = 8.4 Hz), 7.07 (bs, 1H), 6.96 (bs, 2H), 6.87 (d, 2H, J = 2.4 Hz), 6.10 (t, 1H, J = 2.4 Hz), 3.70 (s, 6H), 3.54 (s, 3H), 3.32 (s, 3H), 1.48 (s, 6H); LCMS: purity: 97%, MS (m/e): 468 (MH+). | + | | + | |
| 394 | N2-(3-Chloro-4-methoxyphenyl)-N4-(2,2-dimethyl-3-oxo-4H-benz[1,4]oxazin-6-yl)-5-fluoro-N4-methyl-2,4-pyrimidinediamine | LCMS: purity: 93%, MS (m/e): 351 (MH+). | + | | + | |
| 395 | N4-(3,4-Ethylenedioxybenzyl)-5-fluoro-N2-(2-methoxycarbonyl-benzofuran-5-yl)-N4-methyl-2,4-pyrimidinediamine | 1H NMR (DMSO-d6): δ 7.95 (s, 1H), 7.76 (bd, 1H), 7.54 (s, 1H), 7.49 (bd, 2H), 6.87 (d, 1H, J = 8.4 Hz), 6.79 (dd, 1H, J = 2.4 and 6.6 Hz), 6.74 (bd, 1H); LCMS: purity: 94%, MS (m/e): 452 (MH+). | + | + | + | |
| 396 | N2-(3,5-Dimethylphenyl)-N4-(3-oxo-2,2,4-trimethylbenz[1,4]oxazin-6-yl)-5-fluoro-2,4-pyrimidinediamine | LCMS: purity: 90%; MS (m/e): 422 (MH+). | + | + | + | |
| 397 | N2-(3,5-Dimethylphenyl)-N4-(3-oxo-2,2,4-trimethylbenz[1,4]oxazin-6-yl)-5-fluoro-2,4-pyrimidinediamine | LCMS: purity: 94%; MS (m/e): 454 (MH+). | + | + | + | |
| 398 | N2-(3,5-Dimethoxyphenyl)-5-fluoro-N4-methyl-N2-[3-(N-methyl)amino)carbonylmethyleneoxyphenyl]-2,4-pyrimidinediamine | LCMS: purity: 94%; MS (m/e): 442 (MH+). | + | | – | |
| 399 | N4-(3,5-Dimethoxyphenyl)-N2-(3,5-dimethylphenyl)-5-fluoro-N4-methyl-2,4-pyrimidinediamine | LCMS: purity: 92%; MS (m/e): 382 (MH+). | + | + | – | |
| 400 | N2,N4-Bis(3,5-dimethylphenyl)-5-fluoro-N4-methyl-2,4-pyrimidinediamine | 1H NMR (DMSO-d6): δ 9.23 (s, 1H), 7.97 (d, 1H, J = 5.1 Hz), 7.01 (d, 2H, J = 1.8 Hz), 6.45 (d, 2H, J = 1.2 Hz), 6.34 (bt, 1H), 6.05 (bt, 1H), 3.72 (s, 6H), 3.68 (6H), 3.45 (s, 3H); LCMS: purity: 95%, MS (m/e): 415 (MH+). | + | | – | + |
| 401 | N4-(3,5-Dimethoxyphenyl)-5-fluoro-N2-(2-methoxycarbonyl-benzofuran-5-yl)-N4-methyl-2,4-pyrimidinediamine | 1H NMR (DMSO): δ 9.70 (s, 1H), 8.13 (s, 1H), 8.04 (d, 1H, J = 3.8 Hz), 7.69 (s, 1H), 7.62 (m, 2H), 6.51 (d, 2H, J = 1.5 Hz), 6.44 (bt, 1H); 3.88 (s, 3H), 3.72 (s, 6H), 3.46 (s, 3H); LCMS: MS (m/e): 453 (MH+), purity: 95%. | + | | + | |
| 402 | N4-[3-Chloro-4-(methoxycarbonyl-1,1-dimethylmethyleneoxyphenyl]-N2-(3,5-dimethylphenyl)-5-fluoro-2,4-pyrimidinediamine | LCMS: purity: 81%, MS (m/e): 459 (MH+) | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 403 | N2-(3,5-Dimethylphenyl)-N4-[4-(methoxycarbonyl-1,1-dimethylmethyleneoxy)phenyl]-5-fluoro-2,4-pyrimidinediamine | LCMS: purity: 80%; MS (m/e): 425 (MH+). | | | | |
| 404 | N2-(3-Chloro-4-methoxyphenyl)-N4-(3,5-dimethoxyphenyl)-5-fluoro-N4-methyl-2,4-pyrimidinediamine | 1H NMR (DMSO-d6): δ 10.00 (s, 1H), 8.08 (d, 1H, J = 6.00 Hz), 7.89 (d, 1H, J = 5.1 Hz), 7.47 (dd, 1H, J = 2.7 and 9.3 Hz), 7.08 (d, 1H, J = 9.0 Hz), 6.53 (d, 2H, J = 1.8 Hz), 6.46 (t, 1H, J = 2.1 Hz); LCMS: purity: 92%, 419 (MH+). | − | + | − | |
| 405 | N2-(4-Chloro-3-methoxyphenyl)-N4-(3,5-dimethoxyphenyl)-5-fluoro-N4-methyl-2,4-pyrimidinediamine | 1H NMR (DMSO-d6): δ 9.30 (s, 1H), 9.03 (s, 1H), 8.07 (d, 1H, J = 4.2 Hz), 7.48 (d, 1H, J = 2.1 Hz), 7.37 (dd, 1H, J = 2.4 and 8.4 Hz), 7.24 (s, 2H); LCMS: purity: 91%, MS (m/e): 419 (M+). | + | | | |
| 406 | N2-(3,5-Dimethoxyphenyl)-5-fluoro-N4-methyl-N2-[2-(N-methylamino)carbonylindol-7-yl]-2,4-pyrimidinediamine | 1H NMR (DMSO-d6): δ 11.71 (s, 1H), 9.39 (s, 1H), 8.44 (bd, 1H, J = 4.8 Hz), 8.02 (m, 2H), 7.20 (d, 1H, J = 7.5 Hz), 7.04 (d, 1H, J = 2.1 Hz), 6.93 (t, 1H, J = 7.8 Hz), 6.47 (d, 2H, J = 2.1 Hz), 6.41 (t, 1H, J = 2.1 Hz), 3.72 (s, 6H), 3.46 (s, 3H), 2.81 (d, 3H, J = 4.5 Hz); LCMS: purity: 95%, MS (m/e):450 (M+). | + | + | − | |
| 407 | 2-Chloro-N4-[3-chloro-4-(ethoxycarbonyl-1,1-dimethylmethyleneoxy)phenyl]-5-fluoro-4-pyrimidineamine | 1H NMR (DMSO-d6): δ 8.07 (d, 1H, J = 2.7 Hz), 7.69 (m, 1H), 7.45 (m, 1H), 6.95 (d, 1H, J = 9 Hz), 6.92 (bs, 1H), 4.28 (q, 2H, J = 6.9 Hz), 1.62 (s, 6H), 1.31 (t, 3H, J = 7.2 Hz); LCMS: purity: 85%; MS (m/e): 388 (M+). | | | | |
| 408 | N4-[3-Chloro-4-(ethoxycarbonyl-1,1-dimethylmethyleneoxy)phenyl]-N2-(3,5-dimethoxyphenyl)-5-fluoro-2,4-pyrimidinediamine | 1H NMR (CD3OD): δ 7.91 (d, 1H, J = 2.7 Hz), 7.74 (d, 1H, J = 2.7 Hz), 7.66 (dd, 1H, J = 2.7 and 8.7 Hz), 6.91 (d, 1H, J = 9 Hz), 6.78 9d, 2H, J = 2.1 Hz), 6.12 (t, 1H, J = 2.1 Hz), 4.26 (q, 2H, J = 6.9 Hz), 3.71 (s, 6H), 1.59 (s, 6H), 1.29 (t, 3H, J = 7.2 Hz); LCMS: purity: 90%; MS (m/e): 505 (MH+). | + | + | | |
| 409 | N4-[3-Chloro-4-(hydroxycarbonyl-1,1-dimethylmethyleneoxy)phenyl]-N2-(3,5-dimethoxyphenyl)-5-fluoro-2,4-pyrimidinediamine | 1H NMR (DMSO-d6): δ 13.15 (bs, 1H), 9.38 (s, 1H), 9.18 (s, 1H), 8.10 (d, 1H, J = 3.9 Hz), 7.93 (s, 1H), 7.84 (dd, 1H, J = 2.7 and 9.3 Hz), 7.77 (d, 1H, J = 2.7 Hz), 6.91 (m, 3H), 6.07 (t, 1H, J = 2.1 Hz), 3.65 (s, 6H), 1.52 (s, 6H); LCMS: purity: 90%; MS (m/e): 477 (MH+). | + | + | + | |
| 410 | N4-[3-Chloro-4-(ethoxycarbonyl-1,1-dimethylmethyleneoxy)phenyl]-N2-(3-chloro-4-methoxyphenyl)-5-fluoro-2,4-pyrimidinediamine | 1H NMR (DMSO-d6): δ 9.36 (s, 1H), 9.17 (s, 1H), 8.08 (d, 1H, J = 3.6 Hz), 7.78 (d, 1H, J = 2.7 Hz), 7.75 (d, 1H, J = 2.1 Hz), 7.70 (dd, 1H, J = 3.0 and 9.3 Hz), 7.44 (dd, 1H, J = 2.7 and 9.0 Hz), 6.99 (d, 1H, J = 9.0 Hz), 6.88 (d, 1H, J = 9.0 Hz), 4.20 (q, 2H, J = 7.2 Hz), 3.78 (s, 3H), 1.52 (s, 6H), 1.20 (t, 3H, J = 6.9 Hz); LCMS: purity: 93%; MS (m/e): 509 (M+). | + | + | + | |
| 411 | N4-(3,4-Ethylenedioxyphenyl)-5-fluoro-N4-methyl-N2-[3-(oxazol-5-yl)phenyl]-2,4-pyrimidinediamine | LCMS: purity: 91%; MS (m/e): 420 (MH+). | + | + | − | |
| 412 | N4-(3,4-Ethylenedioxyphenyl)-5-fluoro-N4-methyl-N2-[3-(oxazol-2-yl)phenyl]-2,4-pyrimidinediamine | 1H NMR (DMSO-d6): δ 9.61 (s, 1H), 8.57 (s, 1H), 8.17 (s, 1H), 9.97 (d, 1H, J = 6.0 Hz), 7.70 (bd, 1H, J = 4.8 Hz), 7.52 (bd, 1H, J = 7.8 Hz), 7.38 (d, 2H, J = 8.1 Hz), 7.33 (m, 1H), 6.79 (m, 3H), 4.24 (s, 4H), 3.44 (s, 3H); LCMS: purity: 92%, MS (m/e): 420 (MH+). | + | + | + | |
| 413 | N4-(3,4-Dimethoxyphenyl)-N2-(3,5-dimethylphenyl)-5-fluoro-2,4-pyrimidinediamine | 1H NMR (DMSO-d6): δ 9.15 (s, 1H), 8.97 (s, 1H), 8.02 (d, 1H, J = 3.9 Hz), 7.24 (m, 4H), 6.88 (d, 1H, J = 8.4 Hz), 6.48 (d, 1H), 3.73 (s, 3H), 3.65 (s, 3H), 2.12 (s, 6H); LCMS: purity: 97%; MS (m/e): 369 (MH+). | + | + | − | |
| 414 | N2-(3,5-Dimethoxyphenyl)-N4-(3,4-dimethoxyphenyl)-5-fluoro-2,4-pyrimidinediamine | 1H NMR (DMSO-d6): δ 9.17 (s, 1H), 9.05 (s, 1H), 8.03 (d, 1H, J = 3.9 Hz), 7.32 (dd, 2.4 and 8.7 Hz), 7.24 (d, 1H, J = 2.4 Hz), 6.92 (d, 2H, J = 2.4 Hz), 6.85 (d, 1H, 8.4 Hz), 6.03 (t, 1H, J = 2.1 Hz), 3.73 (s, 3H), 3.66 (s, 3H), 3.60 (s, 6H); LCMS: purity: 96%, MS (m/e): 401 (MH+). | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 415 | N4-(3,4-Dimethoxyphenyl)-N2-[2-(ethoxycarbonyl)indol-7-yl]-5-fluoro-2,4-pyrimidinediamine | 1H NMR (DMSO-d6): δ 11.89 (s, 1H), 9.25 (s, 1H), 9.21 (s, 1H), 8.10 (d, 1H, J = 3.9 Hz), 8.87 (s, 1H), 8.73 (m, 3H), 7.11 (d, 1H, J = 2.1 Hz), 6.88 (m, 2H), 4.32 (q, 2H, J = 3.9 Hz), 3.76 (s, 3H), 3.66 (s, 3H), 1.34 (q, t, 3H, J = 3.9 Hz); LCMS: purity: 93%, MS (m/e) 452 (M+). | + | | | |
| 416 | N4-(3,4-Ethylenedioxyphenyl)-5-fluoro-N4-methyl-N2-[4-(oxazol-2-yl)phenyl]-2,4-pyrimidinediamine | 1H NMR (DMSO-d6): δ 9.59 (s, 1H), 8.05 (s, 1H), 7.96 (d, 1H, J = 5.7 Hz), 7.80 (bs, 4H), 7.27 (s, 1H), 6.85 (m, 2H), 6.78 (dd, 1H), 4.52 (s, 4H), 3.41 (s, 3H), 3.31 (s, 3H); LCMS: purity: 91%, MS (m/e): 420 (MH+). | + | + | | |
| 417 | 2-Chloro-N4(3,4-dimethoxyphenyl)-5-fluoro-N4-methyl-4-pyrimidineamine | 1H NMR (DMSO-d6): δ 8.09 (d, 1H, J = 5.4 Hz), 7.02 (d, 1H, J = 2.4 Hz), 6.93 (d, 1H, J = 8.4 Hz), 6.84 (dd, 1H, J = 2.1 and 8.4 Hz), 3.75 (s, 3H), 3.71 (s, 3H); LCMS: purity: 87%, MS (m/e): 298 (M+). | – | – | – | – |
| 418 | 2-Chloro-N4-(3,4-ethylenedioxyphenyl)-5-fluoro-N4-(methoxycarbonylmethyl)-4-pyrimidineamine | LCMS: purity: 99%, MS (m/e): 354 (M+). | – | | – | |
| 419 | N4-(3,4-Dimethoxyphenyl)-5-fluoro-N2-[3-(oxazol-5-yl)phenyl]-2,4-pyrimidinediamine | 1H NMR (DMSO-d6): δ 9.29 (s, 1H), 9.21 (s, 1H), 8.33 (s, 1H), 8.07 (d, 1H, J = 3.0 Hz), 8.04 (s, 1H), 7.61 (bd, 1H), 7.39 (s, 1H), 7.29 (bdd, 1H, J = 2.7 and 8.4 Hz), 7.25 (m, 3H), 6.76 (d, 1H, J = 8.7 Hz), 3.70 (s, 3H), 3.64 (s, 3H); LCMS: purity: 98%, MS (m/e): 408 (MH+) | + | + | – | |
| 420 | N4-(3,4-Ethylenedioxyphenyl)-5-fluoro-N2-(indol-6-yl)-N4-(methoxycarbonylmethyl)-2,4-pyrimidinediamine | 1H NMR (DMSO-d6): δ 10.77 (s, 1H), 9.05 (s, 1H), 7.94 (d, 1H, J = 5.7 Hz), 7.70 (s, 1H), 7.32 (d, 1H, J = 2.8 Hz), 7.19 (d, 1H, J = 1.5 Hz), 7.17 (t, 1H, J = 3 Hz), 6.82 (m, 1H), 6.28 (d, 1H, J = 2.1 Hz), 4.60 (s, 2H), 4.24 (s, 4H), 3.33 (s, 3H); LCMS: purity: 99%, MS (m/e): 450 (MH+). | + | – | – | |
| 421 | N4-(3,4-Dimethoxyphenyl)-5-fluoro-N2-[2-(N-methylaminocarbonyl)indol-7-yl]-2,4-pyrimidinediamine | 1H NMR (DMSO-d6): δ 11.66 (s, 1H), 9.27 (s, 1H), 9.22 (s, 1H), 8.41 (bd, 1H, J = 4.8 Hz), 8.09 (d, 1H, J = 3.3 Hz), 7.99 (d, 1H, J = 7.8 Hz), 7.33 (dd, 1H, J = 2.4 and 8.4 Hz), 7.28 (d, 1H, J = 2.7 Hz), 7.18 (d, 1H, J = 7.5 Hz), 7.03 (d, 1H, J = 2.1 Hz), 6.89 (m, 2H0, 3.75 (s, 3H), 3.66 (s, 3H), 2.80 (d, 3H, J = 4.2 Hz); LCMS: purity: 91%, MS (m/e): 437 (MH+). | + | + | – | |
| 422 | N4-(3,4-Dimethoxyphenyl)-5-fluoro-N2-[4-(oxazol-5-yl)phenyl]-2,4-pyrimidinediamine | 1H NMR (DMSO-d6): δ 9.36 (s, 1H), 9.24 (s, 1H), 8.33 (s, 1H), 8.07 (d, 1H, J = 3.9 Hz), 7.75 (d, 2H, J = 6.0 Hz), 7.50 (d, 2H, J = 8.7 Hz), 7.75 (d, 2H, J = 8.7 Hz), 7.47 (s, 1H), 7.26 (m, 2H), 6.92 (d, 1H, J = 9.6 Hz), 3.76 (s, 3H), 3.69 (s, 3H); LCMS: purity: 94%, MS (m/e): 408 (M+). | + | + | – | |
| 423 | N4-(3,4-Dimethoxyphenyl)-5-fluoro-N2-[3-(oxazol-2-yl)phenyl]-2,4-pyrimidinediamine | 1H NMR (DMSO-d6): δ 9.36 (s, 1H), 9.22 (s, 1H), 8.29 (s, 1H), 8.12 (s, 1H), 8.08 (d, 1H, J = 3 Hz), 7.81 (dd, 1H, J = 1.8 and 7.1 Hz), 7.49 (d, 1H, J = 6.9 Hz), 7.31 (m, 4H), 6.79 (d, 1H, J = 8.7 Hz), 3.71 (s, 3H), 3.67 (s, 3H); LCMS: purity: 98%, MS (m/e): 409 (MH+) | + | + | – | + |
| 424 | N4-(3,4-Dimethoxyphenyl)-5-fluoro-N2-[4-(oxazol-2-yl)phenyl]-2,4-pyrimidinediamine | 1H NMR (DMSO-d6): δ 9.50 (s, 1H), 9.28 (s, 1H), 8.09 (s and d, 2H, J = 4.5 Hz), 7.76 (m, 4H), 7.28 (m, 3H), 6.93 (d, 1H, J = 8.4 Hz), 3.76 (s, 3H), 3.70 (s, 3H); LCMS: purity: 89%, MS (m/e): 408 (M+). | + | + | – | |
| 425 | N2-(3-Chloro-4-methoxyphenyl)-N4-(3,4-dimethoxyphenyl)-5-fluoro-2,4-pyrimidinediamine | 1H NMR (DMSO-d6): δ 9.17 (s, 1H), 9.08 (s, 1H), 8.02 (d, 1H, J = 3.9 Hz), 7.84 (s, 1H), 7.41 (dd, 1H, J = 2.7 Hz), 7.27 (dd, 1H, J = 2.4 and 8.7 Hz), 7.21 (d, 1H, J = 2.4 Hz), 6.97 9d, 1H, J = 8.7 Hz), 6.88 (d, 1H, J = 8.7 Hz), 3.77 (s, 3H), 3.73 (s, 3H), 3.68 (s, 3H); LCMS: purity: 95%, MS (m/e): 405 (M+) | + | + | – | |
| 426 | N2-[3-(4-Acetylpiperazino)phenyl]-N4-(3,4-ethylenedioxyphenyl)-5-fluoro-2,4-pyrimidinediamine | 1H NMR (DMSO-d6): δ 9.13 (s, 1H), 8.99 (s, 1H), 8.02 (d, 1H, J = 4.2 Hz), 7.22 (m, 4H), 7.03 (m, 1H), 6.77 (d, 1H, J = 8.7 Hz), 6.50 (bd, 1H, J = 7.2 Hz), 4.21 (bs, 4H), 3.02 (bm, 2H), 2.95 (bm, 2H), 2.02 (s, 3H); LCMS: purity: 97%, MS (m/e): 465 (MH+) | + | + | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 427 | N2-[4-(4-Acetylpiperazinophenyl]-N4-(3,4-ethylenedioxyphenyl)-5-fluoro-2,4-pyrimidinediamine | 1H NMR (DMSO-d6): δ 9.07 (s, 1H), 8.92 (s, 1H), 7.98 (d, 1H, J = 3.9 Hz), 7.48 (d, J = 8.7 Hz), 7.33 (d, 1H, J = 2.4 Hz), 7.18 (dd, 1H, J = 2.1 and 8.7 Hz), 6.83 (d, 1H, J = 9.3 Hz), 6.73 (d, 1H, J = 1H, J = 8.7 Hz), 4.23 (bs, 4H), 3.56 (bs, 4H), 3.03 (t, 2H, J = 5.1 Hz), 2.97 (t, 2H, J = 5.1 Hz), 2.03 (s, 3H); LCMS: purity: 96%, MS (m/e): 465 (MH+). | + | – | – | – |
| 428 | N2-[3-(4-Acetylpiperazinophenyl]-N4-(3,5-dimethoxyphenyl)-5-fluoro-2,4-pyrimidinediamine | 1H NMR (DMSO-d6): δ 9.23 (s, 1H), 9.07 (d, 1H, J = 3 Hz), 7.26 (s, 1H), 7.15 (d, 1H, J = Hz), 7.07 (t, 1H, J = 8.4 Hz), 6.97 (d, 2H, J = 2.4 Hz), 6.50 (bd, 1H, J = 7.5 Hz), 6.18 (d, 1H, J = 2.1 Hz), 5.74 (s, 1H), 3.49 (m, 4H), 3.32 (s, 6H), 2.96 (m, 4H), 2.01 (s, 3H); LCMS: purity: 98%, MS (m/e): 467 (M+) | + | + | – | – |
| 429 | N2-[3-(4-Acetylpiperazinophenyl]-N4-(3,4-dimethoxyphenyl)-5-fluoro-2,4-pyrimidinediamine | 1H NMR (DMSO-d6): δ 9.17 (bs, 1H), 8.99 (s, 1H), 8.02 (d, 1H, J = 3.9 Hz), 7.27 (m, 2H), 7.01 (bd, 1H, J = 8.4 Hz), 7.00 (t, 1H, J = 8.1 Hz), 6.86 (d, 1H, J = 8.4 Hz), 6.48 (bd, 1H, J = 9.9 Hz), 6.13 (bs, 1H), 3.72 (s, 3H), 3.62 (s, 3H), 3.46 (m, 4H), 2.96 (m, 2H), 2.90 (m, 2H), 2.02 (s, 3H); LCMS: MS (m/e): 467 (M+), purity: 99%. | + | – | – | – |
| 430 | N2-[4-(4-Acetylpiperazinophenyl]-N4-(3,4-dimethoxyphenyl)-5-fluoro-2,4-pyrimidinediamine | 1H NMR (DMSO-d6): δ 9.11 (s, 1H), 8.88 (s, 1H), 7.98 (d, 1H, J = 3.9 Hz), 7.46 (d, 2H, J = 9.3 Hz), 7.27 (m, 2H), 6.87 (d, 1H, J = 8.4 Hz), 6.80 (d, 2H, J = 9 Hz), 3.74 (s, 3H), 3.65 (s, 3H), 3.56 (m, 4H), 3.02 (m, 2H), 2.96 (m, 2H), 2.03 (s, 3H); LCMS: purity: 90%, MS (m/e): 467 (M+) | + | – | – | – |
| 431 | N2-[3-(4-Acetylpiperazinophenyl]-5-fluoro-N4-(3,4-(tetrafluoroethylenedioxyphenyl)-2,4-pyrimidinediamine | 1H NMR (DMSO-d6): δ 9.62 (s, 1H), 9.19 (s, 1H), 8.14 (m, 1H), 7.62 (dd, 1H, J = 2.7 and 9.6 Hz), 7.39 (d, 1H, J = 9 Hz), 7.23 (d, 1H, J = 8 Hz), 7.16 (s, 1H), 7.07 (t, 1H, J = 2.6 Hz), 6.55 (d, 1H, J = 2.6 Hz), 6.12 (s, 1H), 3.54 (bs, 4H), 2.02 (s, 3H); LCMS: purity: 91%, MS (m/e): 537 (MH+). | + | + | – | – |
| 432 | N2-[4-(4-Acetylpiperazinophenyl]-5-fluoro-N4-(3,4-(tetrafluoroethylenedioxyphenyl)-2,4-pyrimidinediamine | 1H NMR (DMSO-d6): δ 9.57 (s, 1H), 9.11 (s, 1H), 8.15 (bd, 1H), 8.10 (d, 1H, J = 3.3 Hz), 7.57 (bdd, 1H, J = 9.6 Hz), 7.45 (d, 2H, J = 8.7 Hz), 7.37 (d, 1H, J = 9 Hz), 6.87 (d, 2H, J = 9.3 Hz), 6.69 (d, 1H, J = 8.7 Hz), 6.47 (d, 1H, J = 8.7 Hz), 3.52 (m, 4H), 2.99 (m, 2H), 2.85 (m, 2H), 2.03 (s, 3H); LCMS: purity: 88%, MS (m/e): 537 (MH+). | + | – | – | – |
| 433 | N4-(3,5-Dimethoxyphenyl)-N2-(3,5-dimethylphenyl)-5-fluoro-N4-methyl-2,4-pyrimidinediamine | 1H NMR (DMSO-d6): δ 9.05 (s, 1H), 7.89 (d, 1H, J = 6.0 Hz), 7.31 (s, 2H), 6.93 (d, 1H, J = 2.7 Hz), 6.90 (s, 1H), 6.81 (dd, 1H, J = 2.4 and 8.1 Hz), 6.50 (s, 1H), 3.75 (s, 3H), 3.71 (s, 1H), 3.42 (s, 3H), 2.18 (s, 6H); LCMS: purity: 95%, MS (m/e): 383 (MH+). | + | – | – | – |
| 434 | N2-(3,5-Dimethoxyphenyl)-N4-(3,4-dimethoxyphenyl)-5-fluoro-N4-methyl-2,4-pyrimidinediamine | LCMS: purity: 96%, MS (m/e): 415 (MH+). | + | – | – | – |
| 435 | N4-(3,4-Dimethoxyphenyl)-N2-[2-(ethoxycarbonyl)indol-7-yl]-5-fluoro-N4-methyl-2,4-pyrimidinediamine | 1H NMR (DMSO-d6): δ 11.94 (s, 1H), 9.32 (s, 1H), 8.15 (d, 1H, J = J = 7.5 Hz), 7.97 (d, 1H, J = 6.0 Hz), 7.22 (d, 1H, J = 7.8 Hz), 7.12 (d, 1H, J = 2.1 Hz), 6.96 (m, 3H), 6.82 (m, 1H), 4.33 (q, 2H, J = 4.2 Hz), 3.76 (s, 3H), 3.72 (s, 3H), 3.46 (s, 3H), 1.35 (t, 3H, J = 6.9 Hz); LCMS: purity: 90%, MS (m/e): 466 (MH+). | + | – | – | – |
| 436 | N4-(3,4-Dimethoxyphenyl)-5-fluoro-N2-(indol-6-yl)-N4-methyl-2,4-pyrimidinediamine | 1H NMR (DMSO-d6): δ 10.85 (s, 1H), 9.07 (s, 1H), 8.03 (s, 1H), 7.87 (d, 1H, J = 8.4 Hz), 7.34 (d, 1H, J = 8.7 Hz), 7.16 (m, 2H), 6.93 (m, 2H), 6.90 (s, 1H), 6.80 (m, 1H), 6.28 (s, 1H), 3.75 (s, 3H), 3.73 (s, 3H), 3.44 (s, 3H); LCMS: purity: 94%, MS (m/e): 394 (MH+). | + | – | – | – |
| 437 | N2-[4-(4-Acetylpiperazinophenyl]-N4-(3,5-dimethoxyphenyl)-5-fluoro-2,4-pyrimidinediamine | LCMS: purity: 80%, MS (m/e): 467 (MH+). | + | – | – | – |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 438 | N4-(3,4-Dimethoxyphenyl)-5-fluoro-N4-methyl-N2-[3-(oxazol-5-yl)phenyl]-2,4-pyrimidinediamine | 1H NMR (DMSO-d6): δ 9.42 (s, 1H), 8.40 (s, 1H), 8.28 (bs, 1H), 7.93 (d, 1H, J = 8.7 Hz), 7.58 (bd, 1H, J = 6.8 Hz), 7.55 (s, 1H), 7.27 (m, 2H), 6.96 (d, 1H, J = 2.4 Hz), 6.92 (m, 1H), 6.81 (dd, 1H, J = 2.1 and 8.4 Hz), 3.75 (s, 3H), 3.75 2 (s, 3H), 3.47 (s, 3H); LCMS: purity: 80%, MS (m/e): 422 (MH+). | + | + | − | − |
| 439 | N4-(3,4-Dimethoxyphenyl)-5-fluoro-N4-methyl-N2-[3-(oxazol-2-yl)phenyl]-2,4-pyrimidinediamine | 1H NMR (DMSO-d6): δ 9.50 (s, 1H), 8.62 (d, 1H, J = 3.6 Hz), 8.17 (s, 1H), 7.94 (d, 1H, J = 6.0 Hz), 7.70 (dd, 1H, J = 2.4 Hz), 7.33 (m, 2H), 6.97 (d, 1H, J = 2.4 Hz), 6.92 (d, 1H, J = 8.4 Hz), 6.82 (dd, 1H, J = 2.4 and 8.7 Hz), 3.76 (s, 3H), 3.73 (s, 3H), 3.48 (s, 3H); LCMS: purity: 80%, MS (m/e): 422 (MH+). | + | + | − | |
| 440 | N4-(3,4-Dimethoxyphenyl)-5-fluoro-N4-methyl-N2-[4-(oxazol-2-yl)phenyl]-2,4-pyrimidinediamine | 1H NMR (DMSO-d6): δ 9.59 (s, 1H), 8.10 (s, 1H), 7.98 (m, 2H), 7.62 (dd, 1H, J = 2.1 and 6.6 Hz), 7.27 (s, 1H), 6.96 (m, 2H), 6.92 (s, 1H), 6.81 (dd, 2.4 and 8.4 Hz), 6.61 (dd, 1H, J = 2.1 and 6.6 Hz), 5.67 (bs, 1H), 3.77 (s, 3H), 3.72 (s, 3H), 3.45 (s, 3H). LCMS: purity: 91%, MS 9m/e): 439 (MH+). | + | | − | |
| 441 | N2-(3,5-Dimethylphenyl)-N4-(3,4-ethylenedioxyphenyl)-5-fluoro-N4-(methoxycarbonylmethyl)-2,4-pyrimidinediamine | 1H NMR (DMSO-d6): δ 9.14 (s, 1H), 7.97 (d, 1H, J = 5.7 Hz), 6.84 (m, 5H), 6.07 (m, 1H), 4.62 (s, 2H), 4.24 (s, 3H), 3.68 (bs, 4H), 3.34 (s, 6H); LCMS: purity: 94%, MS: 471 (MH+). | + | | − | |
| 442 | N2-(3,5-Dimethoxyphenyl)-N4-(3,4-ethylenedioxyphenyl)-5-fluoro-N4-(methoxycarbonylmethyl)-2,4-pyrimidinediamine | 1H NMR (DMSO-d6): δ 9.40 (s, 1H), 8.40 (s, 1H), 8.00 (d, 1H, J = J = 4.2 Hz), 7.93 (bs, 1H), 7.60 (m, 1H), 7.57 (s, 1H), 7.27 (m, 2H), 6.83 (m, 3H), 4.63 (s, 2H), 4.23 (s, 4H), 3.51 (s, 3H); LCMS: purity: 95%, MS (m/e):478 (MH+). | + | | − | |
| 443 | N4-(3,4-Ethylenedioxyphenyl)-5-fluoro-N4-(methoxycarbonylmethyl)-N2-[3-(oxazol-5-yl)phenyl]-2,4-pyrimidinediamine | 1H NMR (DMSO-d6): δ 9.49 (s, 1H), 8.24 (s, 1H), 8.17 (s, 1H), 8.00 (d, 1H, J = 5.7 Hz), 7.76 (bd, 1H, J = 9.6 Hz), 7.51 (bd, 1H, J = 8.1 Hz), 7.34 (m, 3H), 6.86 (m, 1H), 6.83 (m, 1H), 4.64 (s, 2H), 4.24 (s, 4H), 3.54 (s, 3H); LCMS: purity: 91%, MS (m/e): 478 (MH+). | + | | − | |
| 444 | N4-(3,4-Ethylenedioxyphenyl)-5-fluoro-N4-(methoxycarbonylmethyl)-N2-[3-(oxazol-2-yl)phenyl]-2,4-pyrimidinediamine | 1H NMR (DMSO-d6): δ 9.61 (s, 1H), 8.10 (s, 1H), 8.05 (d, 1H, J = 8.1 Hz), 7.77 (dd, 2H, J = 8.4 Hz), 7.70 (dd, 2H, J = 8.4 Hz), 7.29 (s, 1H), 6.85 (m, 3H), 4.64 (s, 2H), 4.25 (s, 4H), 3.63 (s, 3H); LCMS: purity: 92%, MS (m/e): 478 (MH+). | + | | − | |
| 445 | N4-(3,4-Ethylenedioxyphenyl)-5-fluoro-N4-(methoxycarbonylmethyl)-N2-[4-(oxazol-2-yl)phenyl]-2,4-pyrimidinediamine | 1H NMR (DMSO-d6): δ 9.24 (s, 1H), 7.97 (d, 1H, J = 5.7 Hz), 7.94 (m, 1H), 7.22 (m, 2H), 7.08 (t, 1H, J = 7.8 Hz), 6.83 (m, 3H), 6.49 (m, 1H), 4.62 (s, 2H), 4.39 (s, 2H), 4.24 (s, 4H), 3.60 (s, 3H), 2.66 (d, 3H, J = 5.1 Hz); LCMS: purity: 97%, MS (498 MH+). | + | | − | |
| 446 | N4-(3,4-Ethylenedioxyphenyl)-5-fluoro-N4-(methoxycarbonylmethyl)-N2-[3-(N-methylamino)carbonylmethyleneoxyphenyl]-2,4-pyrimidinediamine | 1H NMR (DMSO-d6): δ 9.24 (s, 1H), 7.94 (bs, 1H), 7.90 (d, 1H, J = 5.7 Hz), 7.46 (t, 1H, J = 2.1 Hz), 7.27 (bd, 1H, J = 9 Hz), 7.10 (t, 1H, J = 5.1 Hz), 6.93 (m, 1H), 6.79 (dd, 1H, J = 2.7 and 8.7 Hz), 6.45 (dd, 1H, J = 1.8 and 8.1 Hz), 6.12 (m, 1H), 4.38 (s, 2H), 3.75 (s, 3H), 3.72 (s, 3H), 3.42 (s, 3H), 2.4 (bd, 3H); LCMS: purity: 98%, MS: 442 (MH+). | + | | − | |
| 447 | N4-(3,4-Dimethoxyphenyl)-5-fluoro-N4-methyl-N2-[3-(N-methylamino)carbonylmethyleneoxyphenyl]-2,4-pyrimidinediamine | 1H NMR (DMSO-d6): δ 9.37 (s, 1H), 9.18 (s, 1H), 8.21 (d, 1H, J = 4.5 Hz), 8.05 (d, 1H, J = 3.6 Hz), 7.72 (m, 2H), 7.22 (m, 2H), 7.20 (m, 3H), 6.80 (bdd, 1H, J = 2.1 and 9 Hz), 4.11 (bs, 4H), 2.71 (d, 3H, J = 4.5 Hz); LCMS: purity: 95%, MS (m/e): 430 (MH+). | + | + | − | |
| 448 | N2-[4-Chloro-3-(N-methylamino)carbonylphenyl]-N4-(3,4-ethylenedioxyphenyl)-5-fluoro-2,4-pyrimidinediamine | 1H NMR (DMSO-d6): δ 8.20 (d, 1H), 8.05 (d, 1H, J = 3.9 Hz), 7.75 (d, 1H, J = 2.7 Hz), 7.66 (dd, 1H, J = 3.0 and 8.7 Hz), 7.32 (dd, 1H, J = 2.4 and 9.0 Hz), 7.23 (s, 1H), 7.18 (m, 1H), 6.88 (d, 1H, J = 8.7 Hz), | + | | − | |
| 449 | N2-[4-Chloro-3-(N-methylamino)carbonylphenyl]-N4-(3,4-dimethoxyphenyl)-5-fluoro-2,4-pyrimidinediamine | | + | | − | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 450 | N2-[4-Chloro-3-(N-methylamino)carbonylphenyl]-N4-(3,5-dimethoxyphenyl)-5-fluoro-2,4-pyrimidinediamine | 4.00 (s, 4H), 3.76 (s, 3H), 3.71 (s, 3H), 2.69 (d, 3H, J = 3.6 Hz); LCMS: purity: 95%, MS (m/e): 432 (M+). | + | | – | |
| 451 | N4-(3-Chloro-4-methoxyphenyl)-N2-[4-chloro-3-(N-methylamino)carbonylphenyl]-5-fluoro-2,4-pyrimidinediamine | 1H NMR (DMSO-d6): δ 8.15 (d, 1H, J = 4.2 Hz), 7.82 (dd, 1H, J = 2.7 and 9.0 Hz), 7.61 (d, 1H, J = 2.7 Hz), 7.25 (d, 1H, J = 9.0 Hz), 6.96 (t, 2H, J = 2.4 Hz), 6.26 (t, 1H, J = 2.1 Hz), 3.71 (s, 6H), 2.71 (d, 3H, 3.3 Hz); LCMS: purity: 87%, MS (m/e): 432 (M+). | + | | + | |
| 452 | N4-[3-Chloro-4-(ethoxycarbonyl-1,1-dimethylmethyleneoxy)phenyl]-N2-[4-chloro-3-(N-methylamino)carbonylphenyl]-5-fluoro-2,4-pyrimidinediamine | 1H NMR (DMSO-d6): δ 8.16 (d, 1H, J = 3.9 Hz), 7.70 (d, 1H, J = 2.7 Hz), 7.64 (m, 2H), 7.30 (d, 1H, J = 9.3 Hz), 7.10 (d, 1H, J = 9 Hz), 3.87 (s, 3H), 2.69 (s, 3H); LCMS: purity: 91%, MS (m/e): 536 (M+). | + | | + | |
| 453 | N2-[4-Chloro-3-(N-methylamino)carbonylphenyl]-N4-(3,4-ethylenedioxyphenyl)-5-fluoro-N4-methyl-4-pyrimidinediamine | 1H NMR (DMSO-d6): δ 9.65 (bs, 2H), 8.26 (d, 1H, J = 4.8 Hz), 8.17 (s, 1H), 7.80-7.58 (m, 4H), 7.27 (d, 1H, J = 8.7 Hz), 6.89 (d, 1H, J = 9 Hz), 4.20 (q, 2H, J = 6.9 Hz), 2.71 (d, 3H, J = 4.2 Hz), 1.54 (s, 6H), 1.21 (t, 3H, J = 7.2 Hz); LCMS: purity: 91%, MS (m/e): 536 (M+). | + | | – | |
| 454 | N2-[4-Chloro-3-(N-methylamino)carbonylphenyl]-5-fluoro-N4-methyl-4-pyrimidinediamine | 1H NMR (DMSO-d6): δ 9.69 (s, 1H), 8.28 (d, 1H, J = 4.5 Hz), 7.98 (d, 1H, J = 6.0 Hz), 7.83 (d, 1H, J = 2.4 Hz), 7.66 (dd, 1H, J = 2.7 and 8.7 Hz), 7.29 (d, 1H, J = 9 Hz), 6.84 (m, 2H), 6.76 (dd, 1H, 2.7 and 8.7 Hz), 4.24 (s, 4H), 3.38 (s, 1H), 2.72 (d, 3H, J = 4.2 Hz); LCMS: purity: 91%, MS (m/e): 444 (M+). | + | | – | |
| 455 | N4-[2-Chloro-4-(N-methylamino)carbonylphenyl]-N4-(2,2-dimethyl-3-oxo-4H-benz[1,4]oxazin-6-yl)-5-fluoro-2,4-pyrimidinediamine | 1H NMR (DMSO-d6): δ 9.50 (s, 1H), 8.26 (d, 1H, J = 4.5 Hz), 7.93 (d, 1H, 6.0 Hz), 7.87 (d, 1H, J = 2.7 Hz), 7.68 (dd, 1H, J = 2.4 and 5.7 Hz), 7.26 (d, 1H, J = 8.7 Hz), 6.93 (m, 2H), 6.80 (dd, 1H, J = 2.4 and 8.4 Hz), 3.76 (s, 3H), 3.76 (s, 3H), 3.72 (s, 3H), 3.41 (s, 3H), 2.71 (d, 3H, J = 4.5 Hz); LCMS: purity: 90%, MS (m/e): 446 (M+). | + | + | + | |
| 456 | N2-[3-Chloro-4-(N-methylamino)carbonylphenyl]-N4-(2,2-dimethyl-3-oxo-4H-benz[1,4]oxazin-6-yl)-5-fluoro-2,4-pyrimidinediamine | 1H NMR (DMSO-d6): δ 10.71 (s, 1H), 9.87 (s, 1H), 8.26 (d, 1H, J = 4.2 Hz), 8.16 (d, 1H, J = 4.2 Hz), 7.63 (m, 2H), 7.25 (m, 2H), 7.17 (d, 1H, J = 2.1 Hz), 6.90 (d, 1H, J = 8.7 Hz), 2.71 (d, 3H, J = 4.5 Hz), 1.40 (s, 6H); LCMS: purity: 97%, MS (m/e): 471 (M+). | + | + | + | |
| 457 | N2-[4-Chloro-4-(N-methylamino)carbonylphenyl]-N4-(3,5-dimethoxyphenyl)-5-fluoro-N4-methyl-2,4-pyrimidinediamine | 1H NMR (DMSO-d6): δ 10.74 (s, 1H), 10.09 (s, 1H), 8.24 (d, 1H, J = 4.8 Hz), 8.15 (d, 1H, J = 4.5 Hz), 7.83 (d, 1H, J = 1.5 Hz), 7.44 (dd, 1H, J = 1.8 and 8.4 Hz), 7.23 (m, 2H), 6.93 (d, 1H, J = 8.4 Hz), 2.71 (d, 3H, J = 4.2 Hz), 1.40 (s, 6H); LCMS: purity: 94%, MS (m/e): 471 (M+). | + | + | + | |
| 458 | N2-(2,6-Dimethoxypyrid-3-yl)-N4-(3,4-ethylenedioxyphenyl)-5-fluoro-N4-methyl-2,4-pyrimidinediamine | 1H NMR (DMSO-d6): δ 8.02 (d, 1H, J = 8.4 Hz), 7.87 (d, 1H, J = 6.4 Hz), 7.76 (s, 1H), 6.41 (m, 3H), 6.32 (d, 1H, J = 8.4 Hz), 3.89 (s, 3H), 3.82 (s, 3H), 3.71 (s, 3H), 3.34 (s, 3H); LCMS: purity: 95%, MS (m/e): 416 (MH+). | – | | + | |
| 459 | N4-(3,5-Dimethoxyphenyl)-N2-(2,6-dimethoxypyrid-3-yl)-5-fluoro-2,4-pyrimidinediamine | 1H NMR (DMSO-d6); d 8.02 (d, 1H, J = 8.4 Hz), 7.82 (d, 1H, J = 6.6 Hz), 7.68 (s, 1H), 6.79 (m, 2H), 6.72 (dd, 1H, J = 2.1 and 8.1 Hz), 6.30 (d, 1H, J = 8.1 Hz), 4.23 (s, 4H), 3.89 (s, 3H), 3.81 (s, 3H), 3.28 (s, 3H); LCMS: purity: 97%, MS (m/e): 414 (MH+). | + | | – | |
| 460 | N2-(2,6-Dimethoxypyrid-3-yl)-N4-(3,4-ethylenedioxyphenyl)-5-fluoro-2,4-pyrimidinediamine | 1H NMR (DMSO-d6): δ 9.12 (s, 1H), 7.97 (d, 1H, J = 5.1 Hz), 7.89 (s, 1H), 7.82 (d, 1H, J = 7.8 Hz), 6.95 (s, 1H), 6.28 (d, 1H, J = 7.8 Hz), 6.15 (s, 1H), 3.84 (s, 3H), 3.83 (s, 3H), 23.64 (s, 6H); LCMS: purity: 85%, MS (m/e): 402 (MH+). LCMS: purity: 93%, MS (m/e): 400 (MH+). | + | | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 461 | N4-(3,4-Ethylenedioxyphenyl)-5-fluoro-N2-methyl-N4-methyl-2,4-pyrimidinediamine | 1H NMR (DMSO-d6): δ 7.72 (d, 1H, J = 5.1 Hz), 6.79 (d, 1H, J = 9.0 Hz), 6.73 (bs, 1H), 6.66 (bd, 1H), 2.74 (d, 3H, J = 4.5 Hz); LCMS: purity: 93%, MS (m/e): 291 (MH+). | − | | − | |
| 462 | N2-Dimethyl-N4-(3,4-ethylenedioxyphenyl)-5-fluoro-N4-methyl-2,4-pyrimidinediamine | 1H NMR (DMSO-d6): δ 7.78 (d, 1H, J = 6.0 Hz), 6.80 (d, 1H, J = 8.4 Hz), 6.75 (d, 1H, J = 2.7 Hz), 6.66 (dd, 1H, J = 1.8 and 8.4 Hz), 4.22 (s, 4H), 3.31 (s, 3H), 3.30 (s, 3H); LCMS: purity: 95%; MS (m/e): 305 (MH+). | | | | |
| 463 | N2-[3-Chloro-4-(N-methylamino)carbonylphenyl]-N4-(3,4-ethylenedioxyphenyl)-5-fluoro-2,4-pyrimidinediamine | 1H NMR (DMSO-d6): δ 9.45 (s, 1H), 9.24 (s, 1H), 8.11 (m, 2H), 7.89 (d, 1H, J = 2.1 Hz), 7.54 (dd, 1H, J = 2.1 and 8.7 Hz), 7.20 (m, 3H), 6.82 (d, 1H, J = 8.4 Hz), 4.22 (bs, 4H), 2.71 (d, 3H, J = 4.5 Hz); LCMS: purity: 99%; MS (m/e): 430 (MH+). | + | + | | |
| 464 | N2-[3-Chloro-4-(N-methylamino)carbonylphenyl]-N4-(3,4-dimethoxyphenyl)-5-fluoro-2,4-pyrimidinediamine | 1H NMR (DMSO-d6): δ 10.34 (s, 1H), 10.10 (s, 1H), 8.25 (d, 1H, J = 4.5 Hz), 8.18 (d, 1H, J = 4.8 Hz), 7.81 (s, 1H), 7.41 (d, 1H, J = 8.1 Hz), 7.27 (d, 1H, J = 8.4 Hz), 7.18 (m, 2H), 6.95 (d, 1H, J = 8.7 Hz), 3.75 (s, 3H), 3.68 (s, 3H), 2.71 (d, 3H); LCMS: purity: 96%, MS (m/e): 432 (MH+). | + | | − | |
| 465 | N2-[3-Chloro-4-(N-methylamino)carbonylphenyl]-N4-(3,5-dimethoxyphenyl)-5-fluoro-2,4-pyrimidinediamine | LCMS: purity: 100%, MS (m/e): 432 (MH+). | + | + | − | |
| 466 | N4-(3-Chloro-4-methoxyphenyl)-N2-[3-chloro-4-(N-methyl)amino)carbonylphenyl]-5-fluoro-2,4-pyrimidinediamine | LCMS: purity: 100%, MS (m/e): 436 (MH+). | + | + | − | |
| 467 | N4-[3-Chloro-4-(ethoxycarbonyl-1,1-dimethylmethyleneoxy)phenyl]-N2-[3-chloro-4-(N-methylamino)carbonylphenyl]-5-fluoro-2,4-pyrimidinediamine | LCMS: purity: 95%, MS (m/e): 536 (MH+). | + | + | + | |
| 468 | N2-[3-Chloro-4-(N-methylamino)carbonylphenyl]-5-fluoro-N4-(3-hydroxyphenyl)-2,4-pyrimidinediamine | LCMS: purity: 100%, MS (m/e): 388 (MH+). | + | + | − | |
| 469 | N4-(3,4-Ethylenedioxyphenyl)-5-fluoro-N2-(2-hydroxyethyl)-N4-methyl-2,4-pyrimidinediamine | 1H NMR (DMSO-d6): δ 7.70 (d, 1H, J = 5.7 Hz), 6.79 (d, 1H, J = 8.7 Hz), 6.74 (d, 1H, J = 2.4 Hz), 6.66 (dd, 1H, J = 2.4 and 8.4 Hz), 6.50 (t, 1H, J = 5.1 Hz), 4.61 (t, 1H, J = 5.4 Hz), 4.22 (s, 4H), 3.47 (q, 2H, J = 6.3 Hz), 3.29 (t, 2H, J = 5.4 Hz), 3.25 (s, 3H); LCMS: purity: 96%, MS (m/e): 321 (MH+). | − | | − | |
| 470 | 2-Chloro-N4-[3-chloro-4-(ethoxycarbonyl-1,1-dimethylmethyleneoxy)phenyl]-5-fluoro-N4-methyl-4-pyrimidineamine | 1H NMR (CDCl3): δ 7.87 (d, 1H, J = 4.8 Hz), 7.25 (m, 1H), 6.95 (m, 2H), 4.25 (q, 2H, J = 4.8 Hz), 3.46 (s, 3H), 1.65 (s, 6H), 1.29 (t, 3H, J = 4.8 Hz); LCMS: purity: 95%, MS (m/e): 404 (MH+; Cl37). | − | | + | |
| 471 | N4-(3,4-Ethylenedioxyphenyl)-5-fluoro-N2-fluoro-N4-isopropyl-N4-methyl-2,4-pyrimidinediamine | 1H NMR (DMSO-d6): δ 7.70 (d, 1H, J = 5.7 Hz), 6.77 (m, 1H, J = 8.7 Hz), 6.37 (d, 1H, J = 2.4 Hz), 6.68 (dd, 1H, J = 2.4 and 8.7 Hz), 6.44 (d, 1H, J = 8.1 Hz), 4.22 (s, 4H), 3.90 (sept, 1H, J = 7.5 Hz), 3.27 (s, 3H), 1.12 (d, 6H, J = 6.6 Hz); LCMS: purity: 93%, MS (m/e): 319 (MH+). | − | | − | |
| 472 | N2-(2,6-Dimethoxypyrid-3-yl)-5-fluoro-N4-(3-hydroxyphenyl)-2,4-pyrimidinediamine | 1H NMR (DMSO-d6): δ 10.39 (s, 1H), 9.52 (s, 1H), 8.20 (d, 1H, J = 5.7 Hz), 7.77 (m, 1H), 7.08 (m, 1H), 6.59 (m, 1H), 6.45 (d, 1H, J = 8.4 Hz), 6.37 (d, 1H, J = 8.1 Hz), 3.88 (s, 3H), 3.86 (s, 3H); LCMS: purity: 89%, MS (m/e): 358 (MH+). | + | | − | |
| 473 | N2-[3-Chloro-4-(N-methylamino)carbonylphenyl]-N4-(3,4-ethylenedioxyphenyl)-5-fluoro-N4-methyl-2,4-pyrimidinediamine | 1H NMR (DMSO-d6): δ 9.71 (s, 1H), 8.16 (d, 1H, J = 4.5 Hz), 8.00 (d, 1H, J = 5.7 Hz), 7.95 (d, 1H, J = 1.8 Hz), 7.53 (dd, 1H, J = 2.1 and 8.4 Hz), 7.29 (d, 1H, J = 8.4 Hz), 6.85 (m, 2H), 6.77 (dd, 1H, J = 2.1 and 8.4 Hz), 4.24 (s, 4H), 3.40 (s, 3H), 2.71 (d, 3H, J = 3.9 Hz); LCMS: purity: 100%, MS (m/e): 444 (M+). | + | | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 474 | N2-[3-Chloro-4-(N-methylamino)carbonylphenyl]-N4-(3,4-dimethoxyphenyl)-5-fluoro-N4-methyl-2,4-pyrimidinediamine | 1H NMR (DMSO-d6): δ 9.86 (bs, 1H), 8.18 (d, 1H, J = 4.5 Hz), 8.03 (dd, 1H, J = 1.2 and 6.3 Hz), 7.94 (d, 1H, J = 1.8 Hz), 7.52 (dd, 1H, J = 2.1 and 8.4 Hz), 7.30 (d, 1H, J = 8.4 Hz), 6.99 (d, 1H, J = 2.4 Hz), 6.93 (d, 1H, J = 8.4 Hz), 6.86 (dd, 1H, J = 2.4 and 8.4 Hz), 3.76 (s, 3H), 3.72 (s, 3H), 3.45 (s, 3H), 2.71 (d, 3H, J = 4.5 Hz); LCMS: purity: 100%, MS (m/e):446 (M+). | + | | – | |
| 475 | N4-[4-Chloro-3-(N-methylamino)carbonylphenyl]-N2-(3,5-dimethoxyphenyl)-5-fluoro-2,4-pyrimidinediamine | 1H NMR (DMSO-d6): δ 10.11 (s, 1H), 9.83 (s, 1H), 8.30 (d, 1H, J = 4.5 Hz), 8.24 (d, 1H, J = 4.5 Hz), 8.00 (dd, 1H, J = 2.7 and 8.7 Hz), 7.63 (d, 1H, J = 2.4 Hz), 7.36 (d, 1H, J = 8.7 Hz), 6.78 (d, 2H, J = 2.1 Hz), 6.20 (t, 1H, J = 2.1 Hz), 3.67 (s, 6H), 2.73 (d, 3H, J = 5.4 Hz); LCMS: purity: 100%, MS (m/e): 432 (M+). | + | + | – | |
| 476 | N4-[3-Chloro-4-(N-methylamino)carbonylphenyl]-N2-(3,5-dimethylphenyl)-5-fluoro-2,4-pyrimidinediamine | 1H NMR (DMSO-d6): δ 9.91 (s, 1H), 9.52 (s, 1H), 8.29 (d, 1H, J = 4.8 Hz), 8.19 (d, 1H, J = 4.2 Hz), 8.00 (bdd, 1H, J = 8.7 Hz), 7.62 (d, 1H, J = 2.1 Hz), 7.38 (d, 1H, J = 9.0 Hz), 7.17 (s, 2H), 6.63 (s, 1H), 2.72 (d, 3H, J = 4.8 Hz), 2.19 (s, 6H); LCMS: purity: 95%, MS (m/e): 400 (M+). | + | + | – | |
| 477 | N4-[4-Chloro-3-(N-methylamino)carbonylphenyl]-N2-[3-(N-methylamino)carbonyl-methyleneoxyphenyl]-5-fluoro-2,4-pyrimidinediamine | 1H NMR (DMSO-d6): δ 9.55 (s, 1H), 9.32 (s, 1H), 8.31 (bd, 1H), 8.15 (bs, 1H), 7.99 (m, 2H), 7.79 (m, 1H), 7.39 (d, 1H, J = 9 Hz), 7.29 (m, 2H), 7.14 (m, 1H), 6.49 (bd, 1H, J = 7.8 Hz), 4.36 (s, 2H), 2.72 (s, 3H), 2.64 (s, 3H); LCMS: purity: 99%, MS (m/e): 459 (MH+). | + | + | – | |
| 478 | N4-[4-Chloro-3-(N-methylamino)carbonylphenyl]-N2-[4-chloro-3-(N-methylamino)carbonylphenyl]-5-fluoro-2,4-pyrimidinediamine | 1H NMR (DMSO-d6): δ 9.69 (s, 1H), 8.34 (d, 1H, J = 4.5 Hz), 8.22 (d, 1H, J = 3.6 Hz), 8.17 (d, 1H, J = 4.5 Hz), 7.95 (dd, 1H, J = 2.7 and 8.7 Hz), 7.81 (d, 1H, J = 2.1 Hz), 7.71 (d, 1H, J = 7.8 Hz), 7.56 (dd, 1H, J = 2.1 and 8.4 Hz), 7.43 (d, 1H, J = 9.0 Hz), 7.30 (d, 1H, J = 8.4 Hz), 2.73 (d, 6H, J = 4.5 Hz); LCMS: purity: 100%, MS (m/e): 466 (M+). | + | + | – | |
| 479 | N4-[4-Chloro-3-(N-methylamino)carbonylphenyl]-N2-(indol-6-yl)-2,4-pyrimidinediamine | 1H NMR (DMSO-d6): δ 11.98 (s, 1H), 10.28 (s, 1H), 10.05 (s, 1H), 8.35 (d, 1H, J = 4.2 Hz), 8.21 (d, 1H, J = 4.8 Hz), 7.86 (bd, 1H, J = 8.7 Hz), 7.77 (d, 1H, J = 2.7 Hz), 7.54 (s, 1H), 7.47 (d, 1H, J = 8.4 Hz), 7.35 (d, 1H, J = 8.7 Hz), 7.30 (m, 1H), 7.05 (dd, 1H, J = 1.8 and 8.4 Hz), 6.38 (bs, 1H), 2.75 (d, 3H, J = 4.5 Hz); LCMS: purity: 92%, MS (m/e): 411 (M+). | + | + | – | |
| 480 | N4-(3,4-Ethylenedioxyphenyl)-5-fluoro-2-methoxy-N4-methyl-4-pyrimidineamine | LCMS: purity: 97%, MS (m/e): 292 (M+). | – | | – | |
| 481 | N4-[3-Chloro-4-(N-methylamino)carbonylphenyl]-N2-(3,5-dimethoxyphenyl)-5-fluoro-2,4-pyrimidinediamine | 1H NMR (DMSO-d6): δ 9.85 (bs, 1H), 9.50 (bs, 1H), 8.22 (m, 2H), 7.89 (m, 1H), 7.33 (d, 1H, J = 9.0 Hz), 6.85 (d, 2H, J = 1.5 Hz), 6.13 (d, 1H, J = 1.8 Hz), 3.66 (s, 1H), 2.74 (d, 3H, J = 4.5 Hz); LCMS: purity: 98%, MS (m/e):432 (M+). | + | + | – | |
| 482 | N4-[3-Chloro-4-(N-methylamino)carbonylphenyl]-N2-(3,5-dimethoxyphenyl)-5-fluoro-2,4-pyrimidinediamine | 1H NMR (DMSO-d6): δ 10.01 (s, 1H), 9.65 (s, 1H), 8.24 (d, 1H, J = 4.5 Hz), 7.85 (d, 1H, J = 7.35 (d, 1H, J = 8.7 Hz), 7.16 (s, 2H), 6.94 (s, 2H), 6.65 (s, 1H), 2.74 (d, 3H, J = 4.8 Hz), 2.29 (s, 3H), 2.20 (s, 3H); LCMS: purity: 98%, MS (m/e): 400 (M+). | + | + | – | |
| 483 | N4-[3-Chloro-4-(N-methylamino)carbonylphenyl]-N2-[3-(N-methylamino)carbonyl-methyleneoxyphenyl]-5-fluoro-2,4-pyrimidinediamine | 1H NMR (DMSO-d6): δ 9.82 (bs, 1H), 9.56 (bs, 1H), 8.22 (m, 2H), 7.98 (bd, 1H), 7.91 (d, 1H, J = 1.5 Hz), 7.82 (bd, 1H, J = 8.7 Hz), 7.37 (d, 1H, J = 8.7 Hz), 7.22 (m, 3H), 6.56 (m, 1H), 4.38 (s, 2H), 2.74 (d, 3H, J = 4.5 Hz), 2.64 (d, 3H, J = 4.8 Hz); LCMS: purity: 97%, MS (m/e): 459 (M+). | | + | – | |
| 484 | N2-[4-Chloro-3-(N-methylamino)carbonylphenyl]-N4-[3-chloro-4-(N-methylamino)carbonylphenyl]-5-fluoro-2,4-pyrimidinediamine | 1H NMR (DMSO-d6): δ 9.69 (s, 1H), 9.60 (s, 1H), 8.25 (m, 3H), 7.85 (m, 3H), 7.36 (m, 3H), 2.75 (d, 3H, J = 4.8 Hz), 2.70 (d, 3H, J = 4.5 Hz); LCMS: purity: 86%, MS (m/e): 463 (M+). | – | | – | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 485 | N4-[3-Chloro-4-(N-methylamino)carbonylphenyl]-5-fluoro-N2-(indol-6-yl)-2,4-pyrimidinediamine | 1H NMR (DMSO-d6): δ 10.99 (s, 1H), 10.10 (s, 1H), 9.80 (bs, 1H), 8.25 (d, 1H, J = 4.5 Hz), 8.20 (d, 1H, J = 4.2 Hz), 7.93 (d, 1H, J = 1.8 Hz), 7.83 (bd, 1H, J = 9.6 Hz), 7.58 (s, 1H), 7.47 (m, 2H), 7.30 (m, 2H), 7.12 (bd, 1H, J = 8.1 Hz), 6.38 (s, 1H); LCMS: purity: 86%, MS (m/e): 411 (M+). | + | | | |
| 486 | N4-(2-Aminopyrid-6-yl)-2-chloro-5-fluoro-4-pyrimidineamine | 1H NMR (CD3OD): δ 8.16 (d, 1H, J = 3.6 Hz), 7.46 (m, 2H), 6.32 (dd, 1H, J = 3.9 and 5.1 Hz); LCMS: purity: 92%, MS (m/e): 240 (M+). | − | + | − | |
| 487 | N4-(3,4-Ethylenedioxyphenyl)-5-fluoro-N4-methyl-2,4-pyrimidinediamine | 1H NMR (CD3OD): δ 7.43 (d, 1H, J = 7.2 Hz), 6.83 (d, 1H, J = 8.4 Hz), 6.78 (d, 1H, J = 2.4 Hz), 6.72 (dd, 1H, J = 2.7 and 8.4 Hz), 4.25 (s, 4H), 3.40 (s, 3H); LCMS: purity: 100%, MS (m/e): 278 (MH+). | − | | | |
| 488 | 2-Chloro-N4-(3,5-dimethoxyphenyl)-5-fluoro-N4-methyl-4-pyrimidineamine | 1H NMR (CD3OD): δ 7.93 (d, 1H, J = 5.4 Hz), 6.46 (s, 3H), 4.62 (s, 6H), 3.77 (s, 3H); LCMS: purity: 100%, MS (m/e) 298 (MH+). | + | | | |
| 489 | N2-(2-Ethoxycarbonylindol-7-yl)-5-fluoro-N4-(2-hydroxyethyl)-2,4-pyrimidinediamine | 1H NMR (CD3OD): δ 7.73 (m, 2H), 7.34 (dd, 1H, J = 1.2 and 8.1 Hz), 7.17 (s, 1H), 7.04 (t, 2H, J = 7.8 Hz), 4.38 (q, 2H, J = 6.9 Hz), 3.69 (t, 2H, J = 5.1 Hz), 3.58 (t, 2H, J = 6.6 Hz), 1.42 (t, 3H, J = 7.2 Hz); LCMS: purity: 98%, MS (m/e): 360 (MH+). | − | | | |
| 490 | 2-Chloro-N4-(2,6-dimethoxypyrid-5-yl)-5-fluoro-N4-methyl-4-pyrimidineamine | 1H NMR (CD3OD): δ 7.89 (d, 1H, J = 5.7 Hz), 7.57 (d, 1H, J = 8.1 Hz), 6.37 (d, 1H, J = 8.7 Hz), 3.94 (s, 3H), 3.91 (s, 3H), 3.37 (s, 3H); LCMS: purity: 97%, MS (m/e): 299 (MH+). | − | | | |
| 491 | 2-Chloro-N4-(3,5-dichloro-4-methoxyphenyl)-5-fluoro-N4-methyl-4-pyrimidineamine | 1H NMR (CD3OD): δ 8.02 (d, 1H, J = 5.4 Hz), 7.43 (s, 2H), 3.91 (s, 3H), 3.47 (s, 3H); LCMS: purity: 89%, MS (m/e): 366 (MH+). | − | | | |
| 492 | N2-(2-hydroxyethyl)-N4-(3,4-ethylenedioxyphenyl)-5-fluoro-N4-methyl-2,4-pyrimidinediamine | 1H NMR (DMSO-d6): δ 7.76 (d, 1H, J = 4.7 Hz), 6.79 (d, 1H, J = 6.3 Hz), 6.75 (d, 1H, J = 2.4 Hz), 6.67 (dd, 1H, J = 2.7 and 9.3 Hz), 4.71 (bs, 2H), 4.22 (bs, 4H), 3.57 (bs, 4H), 3.31 (bs, 4H), 3.28 (s, 3H); LCMS: purity: 97%, MS (m/e): 416 (MH+). | − | | | |
| 493 | N4-(3,4-Ethylenedioxyphenyl)-5-fluoro-N2-[4-(N-methylaminosulfonyl)phenyl-3-methoxyphenyl]-2,4-pyrimidinediamine | 1H NMR (DMSO-d6): δ 9.58 (s, 1H), 9.29 (s, 1H), 8.11 (d, 1H, J = 3.6 Hz), 7.47 (m, 2H), 7.42 (bdd, 1H), 7.27 (d, 1H, J = 2.1 Hz), 7.13 (dd, 1H, J = 2.1 and 8.4 Hz), 6.79 (d, 1H, J = 8.7 Hz), 6.73 (m, 1H), 4.22 (s, 4H), 3.68 (s, 3H), 2.34 (d, 3H, J = 4.8 Hz); LCMS: purity: 80%, MS (m/e): 462 (MH+). | + | + | − | |
| 494 | N4-(3,4-Dimethoxyphenyl)-5-fluoro-N2-[3-methoxyphenyl-4-(N-methylaminosulfonyl)]-2,4-pyrimidinediamine | 1H NMR (DMSO-d6): δ 9.57 (s, 1H), 9.33 (s, 1H), 8.11 (d, 1H, J = 3.6 Hz), 7.51 (d, 1H, J = 1.8 Hz), 7.45 (d, 1H, J = 8.4 Hz), 7.34 (dd, 1H, J = 1.8 and 8.7 Hz), 7.24 (m, 2H), 6.90 (d, 1H, J = 9.0 Hz), 6.72 (d, 1H, J = 4.8 Hz), 3.75 (s, 3H), 3.67 (s, 3H), 3.63 (s, 3H), 2.33 (d, 3H, J = 4.8 Hz); LCMS: purity: 96%, MS (m/e): 464 (M+). | + | + | − | |
| 495 | N4-(3,5-Dimethoxyphenyl)-5-fluoro-N2-[3-methoxyphenyl-4-(methylaminosulfonyl)]-2,4-pyrimidinediamine | 1H NMR (DMSO-d6): δ 9.64 (s, 1H), 9.37 (s, 1H), 8.16 (bd, 1H), 7.51 (m, 3H), 6.97 (bs, 2H), 6.71 (bd, 1H), 6.24 (bs, 1H), 3.69 (s, 6H), 3.31 (s, 3H), 2.34 (d, 3H, J = 4.8 Hz); LCMS: purity: 94%, MS (m/e): 464 (M+). | + | + | − | |
| 496 | N4-(2,2-Dimethyl-3-oxo-4H-benz[1,4]oxazin-6-yl)-5-fluoro-N2-[3-methoxyphenyl-4-(methylamino)sulfonyl]-2,4-pyrimidinediamine | 1H NMR (DMSO-d6): δ 10.62 (s, 1H), 9.50 (s, 1H), 9.43 (s, 1H), 8.12 (d, 1H, J = 3.9 Hz), 7.46 (s, 1H), 7.44 (s, 1H), 7.26 (dd, 1H, J = 2.4 and 8.7 Hz), 7.14 (d, 1H, J = 2.4 Hz), 6.90 (d, 1H, J = 8.4 Hz), 6.70 (d, 1H, J = 5.4 Hz), 3.69 (s, 3H), 2.32 (d, 3H, J = 5.1 Hz), 1.41 (s, 6H); LCMS: purity: 90%, MS (m/e): 503 (MH+). | + | + | + | |
| 497 | N4-(4-Chloro-3-trifluoromethylphenyl)-5-fluoro-N2-[3-methoxyphenyl-4-(methylamino)sulfonyl]-2,4- | 1H NMR (DMSO-d6): δ 9.88 (s, 1H), 9.72 (s, 1H), 8.26 (m, 2H), 8.18 (d, 1H, J = 4.5 Hz), 7.65 (d, 1H, J = 8.7 Hz), 7.51 (d, 1H, J = 8.7 Hz), | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| | pyrimidinediamine | 7.44 (m, 2H), 6.74 (d, 1H, J = 8.4 Hz), 3.72 (s, 3H), 2.34 (d, 3H, J = 5.1 Hz); LCMS: purity: 97%, MS (m/e): 506 (M+). | | | | |
| 498 | N4-(3-Chloro-4-trifluoromethoxyphenyl)-5-fluoro-N2-[4-(3-methoxyphenyl-N-methylamino)sulfonyl]-2,4-pyrimidinediamine | 1H NMR (DMSO-d6): δ 9.78 (s, 1H), 9.72 (s, 1H), 8.25 (m, 1H), 8.15 (d, 1H, J = 3.6 Hz), 7.84 (dd, 1H, J = 2.4 and 9.0 Hz), 7.52 (m, 2H), 7.43 (m, 4H), 6.74 (m, 1H), 3.74 (s, 3H), 2.33 (d, 3H, J = 2.1 Hz); LCMS: purity: 83%, MS (m/e): 522 (M+). | + | + | – | |
| 499 | 5-Fluoro-N4-(3-hydroxyphenyl)-N2-[3-methoxyphenyl-4-(N-methylamino)sulfonyl]-2,4-pyrimidinediamine | 1H NMR (DMSO-d6): δ 9.57 (s, 1H), 9.38 (s, 1H), 9.31 (s, 1H), 8.13 (d, 1H, J = 3.9 Hz), 7.51 (m, 1H), 7.47 (m, 2H), 7.21 (d, 1H, J = 1.5 Hz), 7.08 (m, 1H), 6.70 (d, 1H, J = 5.4 Hz), 6.51 (bdd, 1H, J = 8.1 Hz), 3.31 (s, 3H), 2.30 (d, 3H, J = 2.4 Hz); LCMS: purity: 91%, MS (m/e): 420 (MH+). | + | + | – | |
| 500 | N4-(2,6-Dimethoxypyrid-3-yl)-N2,N4-dimethyl-5-fluoro-2,4-pyrimidinediamine | 1H NMR (DMSO-d6): δ 7.66 (d, 1H, J = 5.4 Hz), 7.59 (d, 1H, J = 7.5 Hz), 6.54 (bd, 1H), 6.35 (d, 1H, J = 8.4 Hz), 3.85 (s, 3H), 3.83 (s, 3H), 2.71 (d, 3H, J = 3.9 Hz); LCMS: purity: 92%, MS (m/e): 294 (M+). | – | – | – | |
| 501 | N4-(3,5-Dichloro-4-methoxyphenyl)-N2,N4-dimethyl-5-fluoro-2,4-pyrimidinediamine | 1H NMR (DMSO-d6): δ 7.86 (d, 1H, J = 5.4 Hz), 7.42 (s, 2H), 3.80 (s, 3H), 3.38 (s, 3H), 2.73 (d, 3H, J = 4.8 Hz); LCMS: purity: 98%, MS (m/e): 331 (M+). | – | – | – | |
| 502 | 2-Chloro-5-fluoro-N4-[4-(N-methylamino)sulfonyl-3-methoxyphenyl]-2,4-pyrimidineamine | 1H NMR (DMSO-d6): δ 10.28 (s, 1H), 8.42 (d, 1H, J = 3.0 Hz), 7.71 (d, 1H, J = 1.8 Hz), 7.67 (d, 1H, J = 8.4 Hz), 7.46 (dd, 1H, J = 1.5 and 8.4 Hz), 6.95 (d, 1H, J = 5.4 Hz), 3.87 (s, 3H), 2.38 (d, 3H, J = 4.8 Hz); LCMS: purity: 80%, MS (m/e): 349 (M + 2). | – | – | – | |
| 503 | N2-(3,5-Dimethoxyphenyl)-5-fluoro-N4-[2-(2-hydroxyethyleneoxy)pyrid-5-yl]-2,4-pyrimidinediamine | 1H NMR (DMSO-d6): δ 9.34 (s, 1H), 9.14 (s, 1H), 8.57 (d, 1H, J = 2.7 Hz), 8.08 (d, 1H, J = 3.0 Hz), 7.98 (dd, 1H, J = 2.7 and 8.7 Hz), 6.91 (d, 2H, J = 1.8 Hz), 6.77 (d, 1H, J = 8.7 Hz), 6.03 (t, 1H, J = 3.6 Hz), 4.23 (t, 2H, J = 4.5 Hz), 3.69 (m, 2H), 3.65 (s, 3H), 3.62 (s, 3H); LCMS: purity: 96%, MS (m/e): 401 (M+). | + | + | – | |
| 504 | N2-(3,5-Dimethoxyphenyl)-5-fluoro-N4-[2-(2-hydroxyethyleneoxy)pyrid-5-yl]-2,4-pyrimidinediamine | 1H NMR (DMSO-d6): δ 9.30 (s, 1H), 9.06 (s, 1H), 8.54 (d, 1H, J = 2.4 Hz), 8.06 (d, 1H, J = 3.6 Hz), 7.94 (dd, 1H, J = 2.7 and 9.0 Hz), 7.20 (d, 2H, J = 0.9 Hz), 6.79 (d, 1H, J = 9.0 Hz), 6.50 (s, 1H), 4.8 (t, 1H, J = 5.7 Hz), 4.23 (t, 2H, J = 5.7 Hz), 3.70 (q, 2H, J = 4.8 Hz), 2.16 (s, 6H); LCMS: purity: 100%, MS (m/e): 369 (M+). | + | + | – | |
| 505 | N2-(3-Chloro-4-methoxyphenyl)-5-fluoro-N4-[2-(2-hydroxyethyleneoxy)pyrid-5-yl]-2,4-pyrimidinediamine | 1H NMR (DMSO-d6): δ 9.35 (s, 1H), 9.17 (s, 1H), 8.49 (s, 1H), 8.07 (d, 1H, J = 3.6 Hz), 7.98 (dd, 1H, J = 2.7 and 9.0 Hz), 7.81 (s, 1H), 7.40 (bd, 1H, J = 8.7 Hz), 6.98 (d, 1H, J = 8.4 Hz), 6.80 (d, 1H, J = 8.7 Hz), 4.83 (t, 1H, J = 5.7 Hz), 4.24 (t, 1H, J = 4.8 Hz), 3.77 (s, 3H), 3.69 (q, 2H, J = 4.8 Hz); LCMS: purity: 100%, MS (m/e): 406 (MH+). | + | + | – | |
| 506 | N2-Allyl-N4-(3,4-ethylenedioxyphenyl)-5-fluoro-N4-methyl-2,4-pyrimidinediamine | 1H NMR (DMSO-d6): δ 7.70 (d, 1H, J = 4.4 Hz), 7.68 (m, 2H), 7.66 (dd, 1H, J = 1.2 and 7.8 Hz), 5.85 (m, 1H), 5.10 (dd, 1H, J = 1.5 and 16.8 Hz), 5.00 (dd, 1H, J = 1.8 and 12.0 Hz), 4.22 (s, 4H), 3.83 (t, 2H, J = 4.5 Hz), 3.28 (s, 3H); LCMS: purity: 100%, MS (m/e): 317 (MH+). | – | – | – | |
| 507 | N2-(3,5-Dimethoxyphenyl)-5-fluoro-N4-[4-(N-methylamino)sulfonyl-3-methoxyphenyl]-2,4-pyrimidinediamine | | + | + | – | |
| 508 | N2-(3,5-Dimethoxyphenyl)-5-fluoro-N4-(3-methylpyrid-6-yl)-2,4-pyrimidinediamine | 1H NMR (DMSO-d6): δ 9.50 (s, 1H), 9.22 (s, 1H), 8.16 (s, 1H), 8.13 (dd, 1H, J = 0.9 and 6.6 Hz), 8.06 (d, 1H, J = 8.7 Hz), 7.55 (bdd, 1H, J = 5.7 Hz), 6.94 (d, 2H, J = 1.2 Hz), 6.07 (t, 1H, J = 1.2 Hz), 3.68 (s, 3H), 3.66 (s, 6H), 2.49 (s, 6H); LCMS: purity: 96%, MS (m/e): 356 (MH+). | + | + | – | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 509 | N2-(3,5-Dimethylphenyl)-5-fluoro-N4-(3-methylpyrid-6-yl)-2,4-pyrimidinediamine | 1H NMR (DMSO-d6): δ 9.46 (s, 1H), 9.14 (s, 1H), 3.17 (bs, 1H), 8.13 (d, 1H, J = 3.3 Hz), 8.04 (d, 1H, J = 8.4 Hz), 7.55 (dd, 1H, J = 2.1 and 8.4 Hz), 7.24 (s, 2H), 6.24 (s, 1H), 3.33 (s, 3H), 3.32 (s, 3H), 2.18 (s, 3H); LCMS: purity: 93%, MS (m/e): 324 (MH+). | + | + | – | |
| 510 | N4-(5-Chloropyrid-2-yl)-N2-(3,5-dimethoxyphenyl)-5-fluoro-2,4-pyrimidinediamine | LCMS: purity: 93%, MS (m/e): 376 (MH+). | + | + | – | |
| 511 | 5-Fluoro-N4-(3-hydroxyphenyl)-N2-[3-(oxazol-2-yl)phenyl]-2,4-pyrimidinediamine | 1H NMR (DMSO-d6): δ 9.39 (s, 1H), 9.30 (s, 1H), 9.22 (s, 1H), 8.29 (bs, 1H), 8.14 (s, 1H), 8.11 (d, 1H, J = 3.9 Hz), 7.90 (dd, 1H, J = 1.2 and 9.0 Hz), 7.50 (dd, 1H, J = 1.5 and 6.3 Hz), 7.33 (m, 3H), 7.09 (t, 1H, J = 2.1 Hz), 7.01 (t, 1H, J = 8.1 Hz), 6.45 9dd, 1H, J = 1.5 and 7.8 Hz); LCMS: purity: 98%, MS (m/e): 364 (MH+). | + | | – | |
| 512 | N4-(3,4-Ethylenedioxyphenyl)-5-fluoro-N2-[3-(1,2,4-oxadiazol-3-yl)phenyl]-2,4-pyrimidinediamine | 1H NMR (DMSO-d6): δ 9.54 (s, 1H), 9.26 (s, 1H), 8.18 (s, 1H), 8.10 (d, 1H, J = 2.4 Hz), 7.83 (bd, 1H, J = 8.1 Hz), 7.38 (t, 1H, J = 7.8 Hz), 7.27 (m, 2H), 7.13 (bd, 1H, J = 8.7 Hz), 6.82 (d, 1H, j = 9.0 Hz), 4.22 (s, 4H); LCMS: purity: 91%, MS (m/e): 406 (M+). | + | | – | |
| 513 | N4-(3,4-Dimethoxyphenyl)-5-fluoro-N2-[3-(1,2,4-oxadiazol-3-yl)phenyl]-2,4-pyrimidinediamine | 1H NMR (DMSO-d6): δ 9.53 (s, 1H), 9.29 (s, 1H), 8.21 (s, 1H), 8.10 (d, 1H, J = 3.9 Hz), 7.79 (dd, 1H, J = 1.2 and 8.4 Hz), 7.33 (m, 3H), 7.16 (s, 1H), 6.94 (d, 1H, J = 8.7 Hz), 3.75 (s, 3H), 3.70 (s, 3H); LCMS: purity: 95%, MS (m/e): 407 (MH−). | + | | – | |
| 514 | N4-(2,2-Dimethyl-3-oxo-4H-benz[1,4]oxazin-6-yl)-5-fluoro-N2-[3-(1,2,4-oxadiazol-3-yl)phenyl]-2,4-pyrimidinediamine | 1H NMR (DMSO-d6): δ 1.6 (s, 1H), 9.49 (s, 1H), 9.40 (s, 1H), 8.15 (d, 1H, J = 8.1 Hz), 8.11 (d, 1H, J = 3.9 Hz), 7.85 (bd, 1H, J = 8.4 Hz), 7.29 (m, 3H), 7.13 (d, 1H, J = 2.4 Hz), 6.91 (dd, 1H, J = 3.0 and 8.4 Hz), 5.73 (d, 1H, J = 3.6 Hz), 1.40 (s, 3H); LCMS: purity: 91%, MS (m/e): 446 (M−). | + | | – | |
| 515 | N4-(3,4-Dimethoxyphenyl)-5-fluoro-N2-[5-methoxycarbonyl-3-(oxazol-2-yl)phenyl]-2,4-pyrimidinediamine | 1H NMR (DMSO-d6): δ 9.61 (s, 1H), 9.27 (s, 1H), 8.62 (s, 1H), 8.38 (s, 1H), 8.17 (d, 1H, J = 0.9 Hz), 8.12 (d, 1H, J = 3.6 Hz), 8.04 (d, 1H, J = 1.5 Hz), 7.35 (m, 3H), 7.27 (m, 1H), 6.76 (d, 1H, J = 7.8 Hz), 3.82 (s, 3H), 3.70 (s, 3H), 3.65 (s, 3H); LCMS: purity: 99%, MS (m/e): 466 (MH+). | – | | – | |
| 516 | N4-(3,4-Ethylenedioxyphenyl)-5-fluoro-N2-[5-methoxycarbonyl-3-(oxazol-2-yl)phenyl]-2,4-pyrimidinediamine | 1H NMR (DMSO-d6): δ 9.64 (s, 1H), 9.23 (s, 1H), 8.61 (s, 1H), 8.37 (s, 1H), 8.19 (s, 1H), 8.12 (d, 1H, J = 3.3 Hz), 8.05 (s, 1H), 7.38 (m, 2H), 7.22 (dd, 1H, J = 2.7 and 8.7 Hz), 6.70 (d, 1H, J = 8.7 Hz), 5.74 (s, 1H), 4.15 (s, 4H), 3.85 (s, 3H); LCMS: purity: 98%, MS (m/e): 464 (MH+). | – | | – | |
| 517 | N4-(2,2-Dimethyl-3-oxo-4H-benz[1,4]oxazin-6-yl)-5-fluoro-N2-[5-methoxycarbonyl-3-(oxazol-2-yl)phenyl]-2,4-pyrimidinediamine | 1H NMR (DMSO-d6): δ 10.51 (s, 1H), 9.54 (s, 1H), 9.40 (s, 1H), 8.63 (s, 1H), 8.39 (s, 1H), 8.18 (s, 1H), 8.14 (d, 1H, J = 3.9 Hz), 8.04 (s, 1H), 7.44 (dd, 1H, J = 2.1 and 8.7 Hz), 7.37 (s, 1H), 6.77 (d, 1H, J = 8.4 Hz), 3.84 (s, 3H), 1.38 (s, 6H); LCMS: purity: 90%, MS (m/e): 505 (MH+). | – | | – | |
| 518 | 5-Fluoro-N4-(3-hydroxyphenyl)-N2-[5-methoxycarbonyl-3-(oxazol-2-yl)phenyl]-2,4-pyrimidinediamine | 1H NMR (DMSO-d6): δ 9.64 (s, 1H), 9.25 (s, 1H), 8.62 (s, 1H), 8.43 (s, 1H), 8.19 (s, 1H), 8.15 (d, 1H, J = 3.9 Hz), 8.05 (s, 1H), 7.38 (s, 2H), 7.36 (s, 2H), 7.13 (s, 1H), 6.98 (t, 1H, J = 8.7 Hz), 6.42 (dd, 1H, J = 2.4 and 6.6 Hz), 3.83 (s, 3H); LCMS: purity: 98%, MS (m/e): 422 (M+). | + | | – | |
| 519 | N4-(3,4-Ethylenedioxyphenyl)-5-fluoro-N2-[3-(oxazol-2-yl)-5-trifluoromethylphenyl]-2,4-pyrimidinediamine | 1H NMR (DMSO-d6): δ 9.75 (s, 1H), 9.23 (s, 1H), 8.59 (s, 1H), 8.22 (t, 2H, J = 0.9 Hz), 8.14 (d, 1H, J = 3.9 Hz), 7.69 (s, 1H), 7.40 (s, 1H), 7.31 (s, 1H, J = 2.4 Hz), 7.19 (dd, 1H, J = 2.7 and 9.0 Hz), 6.72 (d, 1H, J = 8.4 Hz), 4.17 (s, 4H); LCMS: purity: 92%, MS (m/e): 474 (MH+). | + | | – | |
| 520 | N4-(3,4-Dimethoxyphenyl)-5-fluoro-N2-[3-(oxazol-2-yl)-5-trifluoromethylphenyl]-2,4-pyrimidinediamine | 1H NMR (DMSO-d6): δ 9.73 (s, 1H), 9.31 (s, 1H), 8.57 (s, 1H), 8.24 (s, 1H), 8.20 (bs, 1H), 8.14 (d, 1H, J = 4.2 Hz), 7.68 (s, 1H), 7.40 (s, 1H), | + | | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 521 | N4-(2,2-Dimethyl-3-oxo-4H-benz[1,4]oxazin-6-yl)-5-fluoro-N2-[3-(oxazol-2-yl)-5-trifluoromethylphenyl]-2,4-pyrimidinediamine | 7.33 (bdd, 1H, J = 9.0 Hz), 7.23 (bs, 1H), 6.82 (d, 1H, J = 7.5 Hz), 3.71 (s, 3H), 3.68 (s, 3H); LCMS: purity: 97%; MS (m/e): 476 (MH+). 1H NMR (DMSO-d6): δ 10.54 (s, 1H), 9.70 (s, 1H), 9.42 (s, 1H), 8.54 (s, 1H), 8.27 (s, 1H), 8.21 (s, 1H), 8.16 (d, 1H, J = 2.7 Hz), 7.67 (s, 1H), 7.40 (d, 1H), 7.33 (bdd, 1H, J = 8.4 Hz), 7.17 (d, 1H, J = 2.4 Hz), 6.81 (d, 1H, J = 8.4 Hz), 1.39 (s, 6H); LCMS: purity: 100%, MS (m/e): 515 (MH+). | + | | − | |
| 522 | 5-Fluoro-N4-(3-hydroxyphenyl)-N2-[3-(1,2,4-oxadiazol-3-yl)phenyl]-2,4-pyrimidinediamine | 1H NMR (DMSO-d6): δ 9.55 (s, 1H), 9.36 (s, 1H), 9.30 (s, 1H), 8.13 (m, 2H), 7.88 (bd, 1H, J = 7.8 Hz), 7.38 (t, 1H, J = 7.8 Hz), 7.27 (m, 2H), 7.13 (t, 1H, J = 7.8 Hz), 7.02 (s, 1H), 6.50 (bdd, 1H, J = 5.7 Hz); LCMS: purity: 95%; MS (m/e): 364 (M+) | + | | | |
| 523 | 2-Chloro-5-fluoro-N4-methyl-N4-(3,4,5-trimethoxyphenyl)-4-pyrimidineamine | 1H NMR (DMSO-d6): δ 8.11 (d, 1H, J = 5.4 Hz), 6.79 (s, 2H), 3.74 (s, 3H), 3.72 (s, 3H), 3.65 (s, 3H), 3.38 (s, 3H); LCMS: purity: 94%, MS (m/e): 329 (MH+). | − | | | |
| 524 | 5-Fluoro-N4-(5-methylisoxazol-3-yl)-N2-[3-(oxazol-2-yl)phenyl]-2,4-pyrimidinediamine | 1H NMR (DMSO-d6): δ 10.45 (s, 1H), 9.59 (s, 1H), 8.33 (s, 1H), 8.21 (d, 1H, J = 2.7 Hz), 8.18 (s, 1H), 7.83 (bd, 1H, J = 7.2 Hz), 7.55 (bd, 1H, J = 8.1 Hz), 7.40 (t, 1H, J = 8.1 Hz), 7.35 (s, 1H, J = 6.92 (s, 1H), 2.29 9s, 3H); LCMS: purity: 100%, MS (m/e): 353 (MH+). | + | | | |
| 525 | 5-Fluoro-N4-(5-methyl-3-phenylisoxazol-4-yl)-N2-[3-(oxazol-2-yl)phenyl]-2,4-pyrimidinediamine | 1H NMR (DMSO-d6): δ 9.33 (s, 1H), 9.06 (s, 1H), 8.23 (s, 1H), 8.14 (bs, 1H), 8.09 (d, 1H, J = 3.6 Hz), 7.66 (m, 3H), 7.43 (m, 4H), 7.32 (s, 1H), 7.24 (t, 1H, J = 7.2 Hz), 2.36 (s, 3H); LCMS: purity: 85%, MS (m/e): 429 (MH+). | + | | | |
| 526 | 5-Fluoro-N4-(1-methyl-3-phenylpyrazol-5-yl)-N2-[3-(oxazol-2-yl)phenyl]-2,4-pyrimidinediamine | 1H NMR (DMSO-d6): δ 9.48 (m, 2H), 8.19 (m, 2H), 8.11 (m, 2H), 7.77 (m, 2H), 7.35 (m, 6H), 6.73 (s, 1H), 3.32 (s, 3H); LCMS: purity: 83%, MS (m/e): 428 (MH+). | + | | | |
| 527 | N2,N4-Bis[3-methoxycarbonyl-5-(oxazol-2-yl)phenyl]-5-fluoro-2,4-pyrimidinediamine | 1H NMR (DMSO-d6): δ 9.89 (s, 1H), 9.83 (s, 1H), 8.58 (s, 1H), 8.49 (s, 1H), 8.46 (s, 1H), 8.35 (s, 1H), 8.27 (d, 1H, J = 3.6 Hz), 8.08 (m, 3H), 7.30 (s, 1H), 7.27 (s, 3H), 3.71 (s, 3H), 3.68 (s, 3H); LCMS: purity: 86%, MS (M/e): 531 (MH+). | − | | | |
| 528 | N2,N4-Bis(3,5-dimethylisoxazol-4-yl)-5-fluoro-2,4-pyrimidinediamine | 1H NMR (DMSO-d6): δ 8.76 (s, 1H), 8.13 (s, 1H), 7.83 (d, 1H, J = 3.9 Hz), 2.19 (s, 3H), 2.10 (s, 3H), 2.03 (s, 3H), 1.85 (s, 3H); LCMS: purity: 91%, MS (m/e): 319 (MH+). | + | | | |
| 529 | N2,N4-Bis[3-(oxazol-2-yl)-5-trifluoromethylphenyl]-5-fluoro-2,4-pyrimidinediamine | 1H NMR (DMSO-d6): δ 9.99 (s, 1H), 9.19 (s, 1H), 8.60 (s, 1H), 8.54 (s, 1H), 8.31 (d, 1H, J = 2.7 Hz), 8.11 (d, 1H, J = 5.1 Hz), 8.05 (s, 1H), 7.79 (s, 1H), 7.61 (s, 1H), 7.31 (s, 1H), 7.27 (s, 1H); LCMS: purity: 92%, MS (m/e):551 (MH+). | + | | | |
| 530 | N2-[(2-tert-Butyl-1,3,4-oxadiazol-5-yl)phenyl]-N4-(3,4-dimethoxyphenyl)-5-fluoro-2,4-pyrimidinediamine | 1H NMR (DMSO-d6): δ 9.23 (s, 1H), 9.23 (s, 1H), 8.25 (s, 1H), 8.08 (d, 1H, J = 3.6 Hz), 7.93 (bd, 1H, J = 8.7 Hz), 7.49 9bd, 1H, J = 7.5 Hz), 7.35 (m, 2H), 7.25 (d, 1H, J = 2.4 Hz), 6.75 (d, 1H, J = 8.7 Hz), 3.70 (s, 3H), 3.66 (s, 3H), 1.37 (s, 9H). | + | + | | + |
| 531 | N2-[(2-tert-Butyl-1,3,4-oxadiazol-5-yl)phenyl]-N4-(3,4-ethylenedioxyphenyl)-5-fluoro-2,4-pyrimidinediamine | 1H NMR (DMSO-d6): δ 9.45 (s, 1H), 9.19 (s, 1H), 8.25 (t, 1H, J = 1.8 Hz), 8.07 (d, 1H, J = 3.3 Hz), 7.87 (bd, 1H, J = 2.4 Hz), 7.51 (bd, 1H, J = 7.8 Hz), 7.40 (m, 2H), 7.16 (dd, 1H, J = 2.4 and 8.7 Hz), 6.70 (d, 1H, J = 9 Hz), 4.15 (m, 4H), 1.37 (s, 9H); LCMS: purity: 95%, MS (m/e): 463 (MH+). | + | | | |
| 532 | N2-[(2-tert-Butyl-1,3,4-oxadiazol-5-yl)phenyl]-5-fluoro-N4-(3-hydroxyphenyl)-2,4-pyrimidinediamine | 1H NMR (DMSO-d6): δ 9.45 (s, 1H), 9.28 (s, 1H), 9.23 (s, 1H), 8.24 (s, 1H), 8.11 (d, 1H, J = 3.9 Hz), 8.00 (bd, 1H, J = 8.1 Hz), 7.50 (d, 1H, J = 7.8 Hz), | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 533 | N4-(3,4-Ethylenedioxyphenyl)-5-fluoro-N4-methyl-2-hydrazine-4-pyrimidineamine | 7.39 (t, 1H, J = 8.4 Hz), 7.30 (bd, 1H, J = 8.4 Hz), 7.12 (t, 1H, J = 2.1 Hz), 6.99 (t, 1H, J = 8.4 Hz), 6.43 (dd, 1H, J = 1.8 and 8.4 Hz), 1.38 (s, 9H); LCMS: purity: 93%, MS (m/e): 421 (MH+). | | | | |
| | | 1H NMR (DMSO-d6): δ 7.61 (d, 1H, J = 5.4 Hz), 6.86 (m, 1H), 6.69 (m, 2H), 4.29 (s, 4H), 3.51 (s, 3H); LCMS: purity: 90%, MS (m/e): 292 (MH+). | − | | | |
| 534 | N4-(3,5-Dimethylisoxazol-4-yl)-5-fluoro-N2-[3-(oxazol-2-yl)phenyl]-2,4-pyrimidinediamine | 1H NMR (DMSO-d6): δ 9.35 (s, 1H), 8.88 (s, 1H), 8.31 (s, 1H), 8.14 (s, 1H), 8.10 (d, 1H, J = 3.6 Hz), 7.71 (bd, 1H, J = 7.8 Hz), 7.45 (d, 1H, J = 6.6 Hz), 7.32 (d, 1H, J = 0.9 Hz), 7.29 (t, 1H, J = 8.1 Hz), 2.87 (s, 3H), 2.10 (s, 3H); LCMS: purity: 96%, MS (m/e): 367 (MH+). | + | | | |
| 535 | N4-(3,5-Dimethylisoxazol-4-yl)-5-fluoro-N2-[5-methoxycarbonyl-3-(oxazol-2-yl)phenyl]-2,4-pyrimidinediamine | LCMS: purity: 85%, MS (m/e): 425 (MH+). | + | | | |
| 536 | N2-(3,5-Dimethyl-4-methoxyphenyl)-N4-(2,2-dimethyl-3-oxo-4H-5-pyrid[1,4]oxazin-6-yl)-5-fluoro-2,4-pyrimidinediamine p-Toluene Sulfonic Acid Salt | 1H NMR (DMSO-d6): δ 11.16 (s, 1H), 10.00 (s, 1H), 9.52 (s, 1H), 8.16 (d, 1H, J = 4.2 Hz), 7.46 (m, 2H), 7.35 (d, 1H, J = 8.1 Hz), 7.13 (s, 2H), 7.08 (d, 1H, J = 2.4 Hz), 3.60 (s, 3H), 2.28 (s, 3H), 2.14 (s, 6H), 1.43 (s, 6H); LCMS: purity: 99%, MS (m/e): 439 | | − | | |
| 537 | N2-(3,5-Dimethyl-4-methoxyphenyl)-N4-(2,2-dimethyl-3-oxo-4H-5-pyrid[1,4]oxazin-6-yl)-5-fluoro-2,4-pyrimidinediamine Benzenesulfonic Acid Salt | 1H NMR (DMSO-d6): δ 11.19 (s, 1H), 10.52 (s, 1H), 9.65 (s, 1H), 8.19 (d, 1H, J = 4.5 Hz), 7.56 (m, 2H), 7.44 (d, 1H, J = 8.4 Hz), 7.35 (d, 1H, J = 8.4 Hz), 7.30 (m, 3H), 7.10 (s, 2H), 3.60 (s, 3H), 2.14 (s, 6H), 1.43 (s, 6H); LCMS: purity: 93%, MS (m/e): 439 (MH+, for parent ion). | | − | | |
| 538 | N2-(3,5-Dimethyl-4-methoxyphenyl)-N4-(2,2-dimethyl-3-oxo-4H-5-pyrid[1,4]oxazin-6-yl)-5-fluoro-2,4-pyrimidinediamine Methanesulfonic Acid Salt | 1H NMR (DMSO-d6): δ 11.80 (s, 1H), 10.16 (s, 1H), 9.73 (s, 1H), 8.21 (d, 1H, J = 4.2 Hz), 7.44 (d, 1H, J = 8.4 Hz), 7.36 (d, 1H, J = 8.4 Hz), 7.12 (s, 2H), 3.60 (s, 3H), 2.32 (s, 3H), 2.13 (s, 6H), 1.43 (s, 6H); LCMS: purity: 97%, MS (m/e): 439 (MH+, for parent ion). | | | | |
| 539 | N4-(2,2-Dimethyl-3-oxo-4H-benz[1,4]oxazin-6-yl)-5-fluoro-N2-(2-trifluoromethyl-3H-benzimidazol-5-yl)-2,4-pyrimidinediamine p-Toluenesulfonic Acid Salt | 1H NMR (DMSO-d6): δ 10.67 (s, 1H), 10.60 (s, 1H), 10.05 (s, 1H), 8.20 (d, 1H, J = 4.8 Hz), 7.84 (s, 1H), 7.62 (d, 1H, J = 9 Hz), 7.45 (bd, 2H, J = 7.8 Hz), 7.23 (d, 1H, J = 8.7 Hz), 7.15 (s, 1H), 7.09 (d, 1H, J = 7.8 Hz), 6.85 (d, 1H, J = 8.7 Hz), 2.28 (s, 3H), 1.38 (s, 6H); LCMS: purity: 99%, MS (m/e): 488 (MH+, for parent ion). | | + | | |
| 540 | N4-(2,2-Dimethyl-3-oxo-4H-benz[1,4]oxazin-6-yl)-5-fluoro-N2-(2-trifluoromethyl-3H-benzimidazol-5-yl)-2,4-pyrimidinediamine Benzenesulfonic Acid Salt | 1H NMR (DMSO-d6): δ 10.67 (s, 1H), 10.20 (s, 1H), 9.90 (s, 1H), 8.17 (d, 1H, J = 4.5 Hz), 7.88 (s, 1H), 7.57 (m, 3H), 7.48 (d, 1H, J = 8.4 Hz), 7.29 (m, 4H), 7.15 (s, 1H), 6.85 (d, 1H, J = 8.4 Hz); LCMS: purity: 95%, MS (m/e): MH+, for parent ion. | | + | | |
| 541 | N4-(2,2-Dimethyl-3-oxo-4H-benz[1,4]oxazin-6-yl)-5-fluoro-N2-(2-trifluoromethyl-3H-benzimidazol-5-yl)-2,4-pyrimidinediamine Methanesulfonic Acid Salt | 1H NMR (DMSO-d6): δ 10.67 (s, 1H), 10.45 (s, 1H), 10.19 (s, 1H), 8.23 (d, 1H, J = 5.1 Hz), 7.80 (s, 1H), 7.62 (d, 1H, J = 8.7 Hz), 7.45 (d, 1H, J = 8.4 Hz), 7.11 9s, 1H), 6.85 (d, 1H, J = 8.4 Hz), 2.38 (s, 3H), 1.37 (s, 6H); LCMS: purity: 99%, MS (m/e): 488 (MH+, for parent ion). | | + | | |
| 542 | N4-(2,2-Dimethyl-3-oxo-4H-benz[1,4]oxazin-6-yl)-5-fluoro-N2-(2-trifluoromethyl-3H-benzimidazol-5-yl)-2,4-pyrimidinediamine Hydrogen Chloride Salt | 1H NMR (DMSO-d6): δ 10.64 (s, 1H), 9.90 (s, 1H), 9.80 (s, 1H), 8.15 (d, 1H, J = 4.8 Hz), 7.96 (s, 1H), 7.59 (d, 1H, J = 8.7 Hz), 7.50 (dd, 1H, J = 1.5 and 9.3 Hz), 7.25 (m, 2H), 6.87 (d, 1H, J = 8.4 Hz); LCMS: purity: 99%, MS (m/e): 488 (MH+, for parent ion). | | + | | |
| 543 | N4-(2,2-Dimethyl-3-oxo-4H-benz[1,4]oxazin-6-yl)-5-fluoro-N2-(3,4,5-trimethoxyphenyl)-2,4-pyrimidinediamine | LCMS: purity: 98%; MS (m/e): 470 (MH+); | + | + | | + |
| 544 | N4-(2-Amino-3-methoxy-pyrid-6-yl)-N2-(3,5-dimethoxyphenyl)-5-fluoro-2,4-pyrimidinediamine | LCMS: purity: 92%; MS (m/e): 387 (MH+) | + | | | |
| 545 | N4-(2-Amino-3-methoxypyrid-6-yl)-5-fluoro-N2-(3,4,5-trimethoxyphenyl)-2,4-pyrimidinediamine | LCMS: purity: 94%; MS (m/e): 417 (MH+) | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 546 | N4-(2-Amino-3-methoxypyrid-6-yl)-5-fluoro-N2-(2-methoxycarbonylbenzofuran-5-yl)-2,4-pyrimidinediamine | LCMS: purity: 82%; MS (m/e): 425 (MH+) | + | | | |
| 547 | N4-(2-Amino-3-methoxypyrid-6-yl)-5-fluoro-N2[3-(N-methyl)aminocarbonyl)methyleneoxy)phenyl]-2,4-pyrimidinediamine | LCMS: purity: 89%; MS (m/e): 414 (MH+) | + | | | |
| 548 | N2-(3,5-Dichloro-4-hydroxyphenyl)-N4-(3,5-dichloro-4-methoxyphenyl)-5-fluoro-2,4-pyrimidinediamine | LCMS: purity: 92%; MS (m/e): 465 (MH+) | + | + | | |
| 549 | N4-(4-Acetyl-2,2-dimethyl-3-oxo-pyrid[1,4]oxazin-6-yl)-5-fluoro-N2-(3,4,5-trimethoxyphenyl)-2,4-pyrimidinediamine | LCMS: purity: 97%; MS (m/e): 513 (M+) | | | | |
| 550 | N4-Acetyl-N4-(2,2-dimethyl-3-oxo-4H-pyrid[1,4]oxazin-6-yl)-5-fluoro-N2-(3,4,5-trimethoxyphenyl)-2,4-pyrimidinediamine | LCMS: purity: 96%; MS (m/e): 513 (M+) | | | | |
| 551 | N2-Acetyl-N4-(2,2-dimethyl-3-oxo-4H-pyrid[1,4]oxazin-6-yl)-5-fluoro-N2-(3,4,5-trimethoxyphenyl)-2,4-pyrimidinediamine | LCMS: purity: 95%; MS (m/e): 514 (MH+) | | | | |
| 552 | 2,N4-Bis[3-methyl-4-(4-methylpiperazinyl)phenyl)-5-fluoro-2,4-pyrimidinediamine | LCMS: purity: 99%; MS (m/e): 506 (MH+) | | | | |
| 553 | N4-(3,5-Dimethylphenyl)-5-fluoro-N2-(3,4,5-trimethoxyphenyl)-2,4-pyrimidinediamine | $^1$H NMR (DMSO-d6): δ 9.14 (bs, 1H), 9.04 (s, 1H), 8.06 (d, J = 3.9 Hz, 1H), 7.40-7.36 (m, 2H), 6.95 (s, 2H), 6.67 (s, 1H), 3.58-3.56 (m, 9H), 2.19 (s, 6H); LCMS: purity: 96%; MS (m/e): 399 (MH+). | | + | | |
| 554 | N2-(3-Chloro-4-hydroxy-5-methylphenyl)-N4-(3,5-dimethylphenyl)-2,4-pyrimidinediamine | $^1$H NMR (DMSO-d6): δ 9.21 (bs, 1H), 9.04 (bs, 1H), 8.63 (bs, 1H), 8.05 (d, J = 3.6 Hz, 1H), 7.53-7.49 (m, 2H), 7.34-7.30 (m, 2H), 7.24-7.20 (m, 1H), 6.69 (bs, 1H), 2.22 (s, 6H), 2.09 (s, 3H); LCMS: purity: 93%; MS (m/e): 373 (MH+). | | + | | |
| 555 | N2-[3,5-Bis(hydroxymethylene)phenyl]-N4-(3,5-dimethylphenyl)-5-fluoro-2,4-pyrimidinediamine | $^1$H NMR (DMSO-d6): δ 9.11 (s, 2H), 8.06 (d, J = 3.9 Hz, 1H), 7.45 (s, 2H), 7.38 (s, 2H), 6.85 (s, 1H), 6.68 (s, 1H), 4.38-4.34 (m, 4H), 2.22 (s, 6H); LCMS: purity: 99%; MS (m/e): 369 (MH+). | | + | | |
| 556 | N2-(3,5-Dichlorophenyl)-N4-(3,5-dimethylphenyl)-5-fluoro-2,4-pyrimidinediamine | $^1$H NMR (DMSO-d6): δ 9.76 (bs, 1H), 9.51 (bs, 1H), 8.18 (d, J = 3.9 Hz, 1H), 7.73-7.69 (m, 2H), 7.29-7.25 (m, 2H), 7.04 (t, J = 1.8 Hz, 1H), 6.75 (s, 1H), 2.25 (s, 6H); LCMS: purity: 92%; MS (m/e): 378 (MH+). | + | + | | |
| 557 | N4-(3,5-Dimethylphenyl)-5-fluoro-N2-[2-(N-methylamino)carbonylindol-7-yl]-2,4-pyrimidinediamine | $^1$H NMR (DMSO-d6): δ 11.66 (s, 1H), 9.37 (s, 1H), 9.28 (s, 1H), 8.48-8.40 (m, 1H), 8.13 (d, J = 3.6 Hz, 1H), 7.98-7.88 (m, 1H), 7.33 (s, 2H), 7.22 (d, J = 7.8 Hz, 1H), 7.04 (d, J = 1.8 Hz, 1H), 6.90 (t, J = 8.1 Hz, 1H), 6.71 (s, 1H), 2.80 (d, J = 3.0 Hz, 3H), 2.23 (s, 6H); LCMS: purity: 99%; MS (m/e): 405 (MH+). | | − | | |
| 558 | 5-Fluoro-N4-(3-methoxy-5-trifluoromethylphenyl)-N2-[2-(N-methylamino)carbonylindol-7-yl]-2,4-pyrimidinediamine | $^1$H NMR (DMSO-d6): δ 11.57 (s, 1H), 9.65 (s, 1H), 9.40 (s, 1H), 8.39-8.35 (m, 1H), 8.15 (d, J = 3.9 Hz, 1H), 7.78 (d, J = 7.5 Hz, 1H), 7.73-7.69 (m, 1H), 7.57-7.52 (m, 1H), 7.18 (d, J = 7.8 Hz, 1H), 9.98 (d, J = 1.8 Hz, 1H), 6.87-6.80 (m, 2H), 3.70 (s, 3H), 2.74 (d, J = 4.5 Hz, 3H); 19F NMR (282 MHz, DMSO-d6): −61.70, −162.97; LCMS: purity: 99%; MS (m/e): 475 (MH+). | + | + | | |
| 559 | N2-(3,5-Dichloro-4-hydroxyphenyl)-N4-(3,5-dimethylphenyl)-5-fluoro-2,4-pyrimidinediamine | $^1$H NMR (DMSO-d6): δ 9.49 (s, 1H), 9.21 (s, 1H), 8.08 (d, J = 3.3 Hz, 1H), 7.66 (d, J = 1.5 Hz, 2H), 7.29 (s, 2H), 6.70 (s, 1H), 2.24 (s, 6H); LCMS: purity: 95%; MS (m/e): 394 (MH+). | | + | | |
| 560 | N2-(4-Chloro-3,5-dimethylphenyl)-N4-(3,5-dimethylphenyl)-5-fluoro-2,4-pyrimidinediamine | $^1$H NMR (DMSO-d6): δ 9.17 (s, 1H), 9.13 (s, 1H), 8.07 (d, J = 3.9 Hz, 1H), 7.45 (s, 2H), 7.30 (s, 2H), 6.72 (s, 1H), 2.22 (s, 6H), 2.18 (s, 6H); LCMS: purity: 93%; MS (m/e): 372 (MH+). | − | | | |
| 561 | N4-[3,4-(Difluoromethylenedioxy)phenyl]-5-fluoro-N2-(3,4,5-trimethoxyphenyl)-2,4-pyrimidinediamine | $^1$H NMR (DMSO-d6): δ 9.53 (s, 1H), 9.13 (s, 1H), 7.42 (dd, J = 2.4 and 9.0 Hz, 1H), 8.11 (d, J = 3.9 Hz, 1H), 8.17-8.12 (m, 1H), 7.32 (d, J = 8.4 Hz, | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 562 | N4-[3,4-(Difluoromethylenedioxy)phenyl]-N2-(3,5-dimethoxyphenyl)-5-fluoro-2,4-pyrimidinediamine | 1H), 7.00 (s, 2H), 3.64 (s, 6H); 19F NMR (282 MHz, DMSO-d6): −49.77, −164.19; LCMS: purity: 93%; MS (m/e): 451 (MH+). 1H NMR (DMSO-d6): δ 9.54 (s, 1H), 9.22 (s, 1H), 8.12 (d, J = 3.6 Hz, 1H), 8.11-8.08 (m, 1H), 7.42 (dd, J = 2.1 and 9.0 Hz, 1H), 7.32 (d, J = 8.7 Hz, 1H), 6.90 (d, J = 2.1 Hz, 2H), 6.07 (t, J = 2.4 Hz, 1H), 3.65 (s, 6H); 19F NMR (282 MHz, DMSO-d6): −49.69, −163.86; LCMS: purity: 96%; MS (m/e): 421 (MH+). | + | | | |
| 563 | N4-[3,4-(Difluoromethylenedioxy)phenyl]-N2-(3,5-dimethylphenyl)-5-fluoro-2,4-pyrimidinediamine | 1H NMR (DMSO-d6): δ 9.51 (s, 1H), 9.13 (s, 1H), 8.11 (d, J = 3.6 Hz, 1H), 8.09-8.06 (m, 1H), 7.39 (dd, J = 2.1 and 8.7 Hz, 1H), 7.34 (d, J = 9.0 Hz, 1H), 7.22 (s, 2H), 6.53 (s, 1H), 2.16 (s, 6H); 19F NMR (282 MHz, DMSO-d6): −49.67, −164.51; LCMS: purity: 98%; MS (m/e): 389 (MH+). | + | + | | |
| 564 | N2-(3,5-Dichloro-4-hydroxyphenyl)-N4-[3,4-(difluoromethylenedioxy)phenyl]-5-fluoro-2,4-pyrimidinediamine | 1H NMR (DMSO-d6): δ 9.59 (s, 1H), 9.45 (bs, 1H), 9.31 (s, 1H), 8.08 (d, J = 3.6 Hz, 1H), 7.85-7.79 (m, 1H), 7.55 (s, 1H), 7.29 (s, 1H); 19F NMR (282 MHz, DMSO-d6): −49.50, −163.68; LCMS: purity: 96%; MS (m/e): 446 (MH+). | + | + | | |
| 565 | N2-(3,5-Dichlorophenyl)-N4-[3,4-(difluoromethylenedioxy)phenyl]-5-fluoro-2,4-pyrimidinediamine | 1H NMR (DMSO-d6): δ 9.62-9.68 (m, 2H), 8.19 (d, J = 3.6 Hz, 1H), 7.92-7.88 (m, 1H), 7.71 (s, 1H), 7.52 (s, 1H), 7.38-7.33 (m, 2H), 7.00 (t, J = 1.8 Hz, 1H); 19F NMR (282 MHz, DMSO-d6): −49.51, −162.64; LCMS: purity: 99%; MS (m/e): 430 (MH+). | + | | | |
| 566 | N2-(4-Chloro-3,5-dimethylphenyl)-N4-[3,4-(difluoromethylenedioxy)phenyl]-5-fluoro-2,4-pyrimidinediamine | 1H NMR (DMSO-d6): δ 9.84 (s, 1H), 9.51 (s, 1H), 8.18 (s, J = 2.7 Hz, 1H), 7.99 (bs, 1H), 7.41-7.35 (m, 4H), 2.22 (s, 6H); LCMS: purity: 94%; MS (m/e): 424 (MH+). | − | + | | |
| 567 | N2-(3-Chloro-4-hydroxy-5-methylphenyl)-N4-[3,4-(difluoromethylenedioxy)phenyl]-5-fluoro-2,4-pyrimidinediamine | 1H NMR (DMSO-d6): δ 9.57 (s, 1H), 9.14 (s, 1H), 8.58 (bs, 1H), 8.05 (d, J = 3.9 Hz, 1H), 7.90 (s, 1H), 7.44 (d, J = 1.8 Hz, 1H), 7.31 (dd, J = 1.8 and 8.7 Hz, 1H), 7.26 (d, J = 8.4 Hz, 1H), 7.14-7.09 (m, 1H), 2.06 (s, 3H); 19F NMR (282 MHz, DMSO-d6): −49.60, −164.34; LCMS: purity: 97%; MS (m/e): 425 (MH+). | − | + | | |
| 568 | N4-[3,4-(Difluoromethylenedioxy)phenyl]-5-fluoro-N2-(3-methoxy-5-trifluoromethylphenyl)-2,4-pyrimidinediamine | 1H NMR (DMSO-d6): δ 9.60 (s, 1H), 9.56 (s, 1H), 8.17 (d, J = 3.3 Hz, 1H), 8.00 (s, 1H), 7.66 (s, 1H), 7.52 (s, 1H), 7.41-7.31 (m, 2H), 6.72 (s, 1H), 3.74 (s, 3H); 19F NMR (282 MHz, DMSO-d6): −49.75, −61.96, −162.93; LCMS: purity: 93%; MS (m/e): 459 (MH+). | + | | | |
| 569 | N4-[3,4-Difluoromethylenedioxy)phenyl]-5-fluoro-N2-(3-methyl-5-trifluoromethylphenyl)-2,4-pyrimidinediamine | 1H NMR (DMSO-d6): δ 9.66 (s, 1H), 9.59 (s, 1H), 8.19 (d, J = 3.6 Hz, 1H), 8.04-7.97 (m, 1H), 7.84 (bs, 1H), 7.68 (bs, 2H), 7.36 (bs, 2H), 7.03 (s, 1H), 2.29 (s, 3H); 19F NMR (282 MHz, DMSO-d6): −49.63, −61.86, −61.86, −163.10; LCMS: purity: 98%; MS (m/e): 443 (MH+). | + | + | | |
| 570 | N4-[3,4-(Difluoromethylenedioxy)phenyl]-5-fluoro-N2-[2-(N-methylamino)carbonylindol-7-yl]-2,4-pyrimidinediamine | 1H NMR (DMSO-d6): δ 11.56 (s, 1H), 9.63 (s, 1H), 9.34 (s, 1H), 8.44-8.38 (m, 1H), 8.12 (d, J = 3.6 Hz, 1H), 7.97 (bs, 1H), 7.84-7.78 (m, 1H), 7.38-7.32 (m, 1H), 7.26 (d, J = 9.0 Hz, 1H), 7.20 (d, J = 8.1 Hz, 1H), 7.00 (s, 1H), 6.87 (t, J = 7.8 Hz, 1H), 2.74 (d, J = 3.6 Hz, 3H); 19F NMR (282 MHz, DMSO-d6): −49.66, −163.58; LCMS: purity: 99%; MS (m/e): 457 (MH+). | + | | | |
| 571 | N4-(3-Chloro-4-methoxyphenyl)-N2-[3,5-dimethyl-4-(N-methylamino)carbonylmethyleneoxyphenyl]-5-fluoro-2,4-pyrimidinediamine | 1H NMR (DMSO-d6): δ 9.28 (s, 1H), 9.03 (s, 1H), 8.15-8.07 (m, 1H), 8.05 (d, J = 3.3 Hz, 1H), 7.76-7.72 (m, 2H), 7.68-7.60 (m, 1H), 7.23 (s, 2H), 7.09 (d, J = 9.0 Hz, 1H), 4.10 (s, 2H), 3.83 (s, 3H), 2.69 (d, J = 4.2 Hz, 3H), 2.11 (s, 6H); LCMS: purity: 99%; MS (m/e): 461 (MH+). | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 572 | N2-[3,5-dimethyl-4-(N-methylamino)carbonylmethyleneoxyphenyl]-N4-(3,4-ethylenedioxyphenyl)-5-fluoro-2,4-pyrimidinediamine | 1H NMR (DMSO-d6): δ 9.08 (s, 1H), 8.95 (s, 1H), 8.14-8.06 (m, 1H), 8.00 (d, J = 3.6 Hz, 1H), 7.23-7.25 (m, 3H), 7.20-7.14 (m, 1H), 6.78 (d, J = 8.7 Hz, 1H), 4.21 (s, 4H), 4.11 (s, 2H), 2.69 (d, J = 4.5 Hz, 3H), 2.13 (s, 6H); LCMS: purity: 99%; MS (m/e): 454 (MH+). | + | | | |
| 573 | N4-(3,5-Dimethoxyphenyl)-N2-[3,5-dimethyl-4-(N-methylamino)carbonylmethyleneoxyphenyl]-5-fluoro-2,4-pyrimidinediamine | 1H NMR (DMSO-d6): δ 9.20 (s, 1H), 9.01 (s, 1H), 8.14-8.05 (m, 2H), 7.29 (s, 2H), 7.00-6.96 (m, 2H), 6.24-6.19 (m, 1H), 4.11 (s, 2H), 3.67 (s, 6H), 2.70 (d, J = 4.8 Hz, 3H), 2.12 (s, 6H); LCMS: purity: 99%; MS (m/e): 456 (MH+). | + | + | | |
| 574 | N2-[3,5-dimethyl-4-(N-methylamino)carbonylmethyleneoxyphenyl]-N4-(2,2-dimethyl-3-oxo-4H-benz[1,4]oxazin-6-yl)-5-fluoro-2,4-pyrimidinediamine | 1H NMR (DMSO-d6): δ 10.59 (s, 1H), 9.32 (s, 1H), 8.95 (s, 1H), 8.11-8.06 (m, 1H), 8.04 (d, J = 3.9 Hz, 1H), 7.34-7.23 (m, 3H), 7.21-7.18 (m, 1H), 6.87 (d, J = 9.0 Hz, 1H), 4.10 (s, 2H), 2.69 (d, J = 4.8 Hz, 3H), 2.11 (s, 6H), 1.40 (s, 6H); LCMS: purity: 95%; MS (m/e): 495 (MH+). | + | + | | |
| 575 | N2-[3,5-dimethyl-4-(N-methylamino)carbonylmethyleneoxyphenyl]-5-fluoro-N4-(3,4-methylenedioxyphenyl)-2,4-pyrimidinediamine | 1H NMR (DMSO-d6): δ 9.15 (s, 1H), 8.96 (s, 1H), 8.12-8.05 (m, 1H), 8.01 (d, J = 3.9 Hz, 1H), 7.44-7.40 (m, 1H), 7.25 (s, 2H), 7.15-7.07 (m, 1H), 6.84 (d, J = 8.1 Hz, 1H), 5.98 (s, 2H), 4.11 (s, 2H), 2.69 (d, J = 4.8 Hz, 3H), 2.13 (s, 6H); LCMS: purity: 99%; MS (m/e): 440 (MH+). | + | + | | |
| 576 | 2-Chloro-5-fluoro-N4-(2-isopropoxypyrid-5-yl)-N4-methyl-4-pyrimidineamine | 1H NMR (DMSO-d6): δ 8.17 (d, J = 2.7 Hz, 1H), 8.14 (d, J = 5.4 Hz, 1H), 7.74 (dd, J = 2.7 and 8.7 Hz, 1H), 6.77 (dd, J = 0.6 and 8.7 Hz, 1H), 5.21 (quintet, J = 6.3 Hz, 1H), 3.38 (s, 3H), 1.29 (d, J = 6.3 Hz, 6H); LCMS: purity: 95%; MS (m/e): 298 (MH+). | − | | | |
| 577 | N4-(3-Chloro-4-methoxyphenyl)-N2-(3,5-dimethoxyphenyl)-5-fluoro-N4-methyl-2,4-pyrimidinediamine | 1H NMR (DMSO-d6): δ 7.95 (d, J = 5.7 Hz, 1H), 7.46 (d, J = 2.7 Hz, 1H), 7.28 (dd, J = 2.4 and 9.0 Hz, 1H), 7.13 (d, J = 9.0 Hz, 1H), 6.98 (s, 1H), 6.09-6.06 (m, 1H), 3.86 (s, 3H), 3.69 (s, 6H), 3.44 (s, 3H); LCMS: purity: 96%; MS (m/e): 419 (MH+). | + | | | |
| 578 | N2-(3-Chloro-4-methoxy-5-methylphenyl)-N4-(3-chloro-4-methoxyphenyl)-5-fluoro-N4-methyl-2,4-pyrimidinediamine | 1H NMR (DMSO-d6): δ 9.41 (s, 1H), 7.99 (d, J = 6.3 Hz, 1H), 7.69 (d, J = 2.7 Hz, 1H), 7.47 (d, J = 2.4 Hz, 1H), 7.36 (d, J = 1.8 Hz, 1H), 7.28 (dd, J = 2.7 and 8.7 Hz, 1H), 7.14 (d, J = 8.7 Hz, 1H), 3.87 (s, 3H), 3.68 (s, 3H), 3.42 (s, 3H), 2.19 (s, 3H); LCMS: purity: 86%; MS (m/e): 438 (MH+). | + | | | |
| 579 | N4-(3-Chloro-4-methoxyphenyl)-N2-[3,5-dimethyl-4-(N-methylamino)carbonylmethyleneoxyphenyl]-5-fluoro-N4-methyl-2,4-pyrimidinediamine | 1H NMR (DMSO-d6): δ 9.24 (s, 1H), 8.16-8.04 (m, 1H), 7.96 (d, J = 6.0 Hz, 1H), 7.47 (d, J = 2.4 Hz, 1H), 7.31-7.24 (m, 3H), 7.15 (d, J = 8.7 Hz, 1H), 4.12 (s, 2H), 3.87 (s, 3H), 3.42 (s, 3H), 2.69 (d, J = 4.8 Hz, 3H), 2.15 (s, 6H); LCMS: purity: 92%; MS (m/e): 475 (MH+). | + | | | |
| 580 | N4-(3-Chloro-4-methoxyphenyl)-N2-[3-(N-methylamino)carbonylmethyleneoxyphenyl]-5-fluoro-N4-methyl-2,4-pyrimidinediamine | 1H NMR (DMSO-d6): δ 9.63 (bs, 1H), 8.02 (d, J = 6.3 Hz, 1H), 8.00-7.97 (m, 1H), 7.50 (d, J = 2.7 Hz, 1H), 7.36-7.34 (m, 2H), 7.33-7.20 (m, 3H), 7.16 (d, J = 9.0 Hz, 2H), 6.57-6.52 (m, 1H), 4.41 (s, 2H), 3.87 (s, 3H), 3.44 (s, 3H), 2.64 (d, J = 4.8 Hz, 3H); LCMS: purity: 94%; MS (m/e): 447 (MH+). | + | | | |
| 581 | N2-(3,5-Dimethoxyphenyl)-5-fluoro-N4-(2-isopropoxypyrid-5-yl)-N4-methyl-2,4-pyrimidinediamine | 1H NMR (DMSO-d6): δ 9.47 (bs, 1H), 8.14 (d, J = 2.7 Hz, 1H), 7.99 (d, J = 6.0 Hz, 1H), 7.71 (dd, J = 3.0 and 8.7 Hz, 1H), 6.96-6.93 (m, 2H), 6.77 (dd, J = 0.6 and 8.7 Hz, 1H), 6.12 (t, J = 2.1 Hz, 1H), 5.21 (quintet, J = 6.3 Hz, 1H), 3.70 (s, 6H), 3.45 (s, 3H), 1.29 (d, J = 6.3 Hz, 6H); LCMS: purity: 93%; MS (m/e): 414 (MH+). | + | | | |
| 582 | 5-Fluoro-N4-(2-isopropoxypyrid-5-yl)-N4-methyl-N2-[3-(N-methylamino)carbonylmethyleneoxyphenyl]-2,4-pyrimidinediamine | 1H NMR (DMSO-d6): δ 9.53 (s, 1H), 8.14 (d, J = 3.0 Hz, 1H), 8.02-7.93 (m, 2H), 7.70 (dd, J = 2.7 and 8.7 Hz, 1H), 7.37 (t, J = 2.1 Hz, 1H), 7.26-7.20 (m, 1H), 7.13 (t, J = 8.1 Hz, 1H), 6.78 (d, J = 8.7 Hz, 1H), 6.56-6.50 (m, 1H), 5.22 (quintet, J = 6.0 Hz, 1H), 4.40 (s, 2H), 3.44 (s, | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 583 | N2-(3,5-Dimethylphenyl)-5-fluoro-N4-(2-isopropoxypyrid-5-yl)-N4-methyl-2,4-pyrimidinediamine | 3H), 2.64 (d, J = 4.8 Hz, 3H), 1.30 (d, J = 6.0 Hz, 6H); LCMS: purity: 95%; MS (m/e): 441 (MH+). | + | | – | |
| 584 | N4-(3-Chloro-4-methoxyphenyl)-N2-(3,5-dimethylphenyl)-5-fluoro-N4-methyl-2,4-pyrimidinediamine | 1H NMR (DMSO-d6): δ 9.42 (s, 1H), 8.14 (d, J = 2.7 Hz, 1H), 8.01 (d, J = 6.6 Hz, 1H), 3.45 (s, 3H), 2.19 (s, 6H), 1.29 (d, J = 6.3 Hz, 6H), 7.70 (dd, J = 2.7 and 8.7 Hz, 1H), 7.24 (s, 2H), 6.77 (d, J = 8.4 Hz, 1H), 6.57 (s, 1H), 5.22 (quintet, J = 6.3 Hz, 1H); LCMS: purity: 96%; MS (m/e): 382 (MH+). | + | | – | |
| 585 | N4-(3-Chloro-4-methoxyphenyl)-N2-(2-methoxycarbonylbenzofuran-5-yl)-N4-methyl-2,4-pyrimidinediamine | 1H NMR (DMSO-d6): δ 9.09 (s, 1H), 7.94 (d, J = 6.0 Hz, 1H), 7.45 (d, J = 2.1 Hz, 1H), 7.31-7.23 (m, 3H), 7.13 (d, J = 9.0 Hz, 1H), 6.51 (s, 1H), 3.86 (s, 3H), 3.42 (s, 3H), 2.18 (s, 6H); LCMS: purity: 88%; MS (m/e) 387 (MH+). | – | | – | |
| 586 | 5-Fluoro-N4-(2-isopropoxypyrid-5-yl)-N2-(2-methoxycarbonylbenzofuran-5-yl)-N4-methyl-2,4-pyrimidinediamine | 1H NMR (DMSO-d6): δ 9.45 (s, 1H), 8.16 (d, J = 1.8 Hz, 1H), 8.05 (d, J = 6.0 Hz, 1H), 7.68 (dd, J = 2.1 and 9.0 Hz, 1H), 7.65 (d, J = 0.9 Hz, 1H), 7.63-7.57 (m, 1H), 7.54 (d, J = 2.7 Hz, 1H), 7.35 (dd, J = 2.7 and 8.7 Hz, 1H), 7.23 (d, J = 8.7 Hz, 1H), 3.95 (s, 3H), 3.94 (s, 3H), 3.51 (d, J = 1.2 Hz, 3H); LCMS: purity: 91%; MS (m/e): 457 (MH+). | + | | + | |
| 587 | N4-(4-Chloro-3-methoxyphenyl)-N2-(3,5-dimethoxyphenyl)-5-fluoro-N4-methyl-2,4-pyrimidinediamine | 1H NMR (DMSO-d6): δ; 9.39 (s, 1H), 8.13 (d, J = 2.4 Hz, 1H), 8.09 (d, J = 1.8 Hz, 1H), 7.98 (d, J = 6.3 Hz, 1H), 7.70 (dd, J = 3.0 and 8.7 Hz, 1H), 7.64-7.57 (m, 2H), 7.54 (d, J = 8.7 Hz, 1H), 3.87 (s, 3H), 3.45 (s, 3H), 1.31 (d, J = 6.3 Hz, 6H); LCMS: purity: 93%; MS (m/e): 452 (MH+). | + | + | – | |
| 588 | N4-(4-Chloro-3-methoxyphenyl)-N2-(3,5-dimethoxyphenyl)-5-fluoro-N4-methyl-2,4-pyrimidinediamine | 1H NMR (DMSO-d6): δ 9.44 (bs, 1H), 8.03 (d, J = 6.0 Hz, 1H), 7.40 (d, J = 8.1 Hz, 1H), 7.15 (d, J = 2.1 Hz, 1H), 6.95 (d, J = 1.2 Hz, 2H), 6.90 (dd, J = 2.1 and 8.4 Hz, 1H), 6.12-6.08 (m, 1H), 3.82 (s, 3H), 3.69 (s, 6H), 3.49 (s, 3H); LCMS: purity: 96%; MS (m/e): 420 (MH+). | + | + | – | |
| 589 | N4-(4-Chloro-3-methoxyphenyl)-5-fluoro-N4-methyl-N2-[3-(N-methylamino)carbonylmethyleneoxyphenyl]-2,4-pyrimidinediamine | 1H NMR (DMSO-d6): δ 9.35 (bs, 1H), 8.03 (d, J = 6.0, 1H), 7.41 (d, J = 8.4, 1H), 7.26-7.23 (m, 2H), 7.16 (d, J = 2.4 Hz, 1H), 6.90 (dd, J = 2.1 and 8.7 Hz, 1H), 6.58-6.55 (m, 2H), 3.82 (s, 3H), 3.49 (s, 3H), 2.19 (s, 6H); LCMS: purity: 91%; MS (m/e): 387 (MH+). | + | + | – | |
|  |  | 1H NMR (DMSO-d6): δ 9.34 (s, 1H), 8.00 (d, J = 5.4, 1H), 7.93-8.00 (m, 1H), 7.44 (t, J = 1.8 Hz, 2H), 7.39 (d, J = 8.4 Hz, 1H), 7.26 (dd, J = 1.2 and 8.4 Hz, 1H), 7.15-7.12 (m, 1H), 7.09 (d, J = 8.4 Hz, 1H), 6.87 (dd, J = 2.1 and 9.0 Hz, 1H), 6.47 (dd, J = 2.7 and 7.2 Hz, 1H), 4.39 (s, 2H), 3.82 (s, 3H), 3.48 (s, 3H), 2.64 (d, J = 4.5 Hz, 3H); LCMS: purity: 98%; MS (m/e): 447 (MH+). |  |  |  |  |
| 590 | N4-(4-Chloro-3-methoxyphenyl)-5-fluoro-N2-(indol-5-yl)-N4-methyl-2,4-pyrimidinediamine | 1H NMR (DMSO-d6): δ 10.84 (s, 1H), 9.010 (s, 1H), 7.96 (d, J = 5.4 Hz, 1H), 7.87-7.84 (m, 1H), 7.39 (d, J = 8.1 Hz, 1H), 7.27-7.19 (m, 3H), 7.12 (d, J = 2.1 Hz, 1H), 6.87 (dd, J = 2.4 and 8.7 Hz, 1H), 6.29-6.25 (m, 1H), 3.82 (s, 3H), 3.47 (s, 3H); LCMS: purity: 97%; MS (m/e): 399 (MH+). | + | + | – | |
| 591 | N4-(4-Chloro-3,5-dimethoxyphenyl)-N2-(3,5-dimethoxyphenyl)-5-fluoro-N4-methyl-2,4-pyrimidinediamine | 1H NMR (DMSO-d6): δ 9.51 (bs, 1H), 8.03 (d, J = 6.0 Hz, 1H), 7.19 (s, 2H), 6.93 (d, J = 1.8 Hz, 2H), 6.12 (t, J = 2.4 Hz, 1H), 3.70 (s, 6H), 3.46 (s, 3H), 2.32 (s, 6H); LCMS: purity: 98%; MS (m/e): 418 (MH+). | + | + | – | |
| 592 | N4-(4-Chloro-3,5-dimethylphenyl)-N2-(3,5-dimethylphenyl)-5-fluoro-N4-methyl-2,4-pyrimidinediamine | 1H NMR (DMSO-d6): δ 9.49 (bs, 1H), 8.04 (d, J = 6.0 Hz, 1H), 7.24 (s, 2H), 7.20 (s, 2H), 6.60 (s, 1H), 3.45 (s, 3H), 2.32 (s, 6H), 2.19 (s, 6H); LCMS: purity: 98%; MS (m/e): 386 (MH+). | – | + | – | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 593 | N4-(4-Chloro-3,5-dimethylphenyl)-5-fluoro-N4-methyl-N2-[3-(N-methylamino)carbonylmethyleneoxyphenyl]-2,4-pyrimidinediamine | 1H NMR (DMSO-d6): δ 9.32 (s, 1H), 7.98 (d, J = 5.7 Hz, 1H), 8.00-7.92 (m, 1H), 7.44 (t, J = 2.1 Hz, 1H), 7.29-7.23 (m, 1H), 7.16 (s, 2H), 7.10 (t, J = 8.1 Hz, 1H), 6.47 (dd, J = 2.4 and 7.8 Hz, 1H), 4.39 (s, 2H), 3.44 (s, 3H), 2.64 (d, J = 4.5 Hz, 3H), 2.32 (s, 6H); LCMS: purity: 98%; MS (m/e): 445 (MH+). | + | + | – | – |
| 594 | N4-(4-Chloro-3,5-dimethylphenyl)-5-fluoro-N2-(indol-5-yl)-N4-methyl-2,4-pyrimidinediamine | 1H NMR (DMSO-d6): δ 10.84 (s, 1H), 8.98 (s, 1H), 7.94 (d, J = 5.7 Hz, 1H), 7.84 (s, 1H), 7.29-7.19 (m, 3H), 7.15 (s, 2H), 6.26 (t, J = 2.1 Hz, 1H), 3.42 (s, 3H), 2.32 (s, 6H); LCMS: purity: 94%; MS (m/e): 397 (MH+). | + | + | + | – |
| 595 | N4-(4-Chloro-3,5-dimethylphenyl)-5-fluoro-N2-(2-methoxycarbonyl-benzofuran-5-yl)-N4-methyl-2,4-pyrimidinediamine | 1H NMR (DMSO-d6): δ 9.43 (s, 1H), 8.17 (d, J = 1.8 Hz, 1H), 8.01 (d, J = 5.4 Hz, 1H), 7.68-7.61 (m, 2H), 7.55 (d, J = 9.3 Hz, 1H), 7.17 (s, 2H), 3.87 (s, 3H), 3.45 (s, 3H), 2.32 (s, 6H); LCMS: purity: 97%; MS (m/e): 457 (MH+). | – | – | – | – |
| 596 | N4-(4-Chloro-3,5-dimethylphenyl)-5-fluoro-N4-methyl-N2-[4-(oxazol-2-yl)phenyl]-2,4-pyrimidinediamine | 1H NMR (DMSO-d6): δ 9.66 (s, 1H), 8.11 (d, J = 0.90 Hz, 1H), 8.04 (d, J = 5.4 Hz, 1H), 7.81 (s, 4H), 7.28 (d, J = 0.6 Hz, 1H), 7.18 (s, 2H), 3.46 (s, 3H), 2.33 (s, 6H); LCMS: purity: 89%; MS (m/e): 425 (MH+). | – | – | – | – |
| 597 | N4-(4-Chloro-3,5-dimethylphenyl)-5-fluoro-N4-methyl-N2-[3-(oxazol-5-yl)phenyl]-2,4-pyrimidinediamine | 1H NMR (DMSO-d6): δ 9.71 (s, 1H), 8.40 (s, 1H), 8.24-8.18 (m, 1H), 8.06 (d, J = 6.0 Hz, 1H), 7.59-7.53 (m, 2H), 7.34-7.29 (m, 2H), 7.20 (s, 2H), 3.49 (s, 3H), 2.32 (s, 6H); LCMS: purity: 96%; MS (m/e): 425 (MH+). | + | + | + | – |
| 598 | N4-(4-Chloro-3,5-dimethylphenyl)-5-fluoro-N4-methyl-N2-[4-(oxazol-5-yl)phenyl]-2,4-pyrimidinediamine | 1H NMR (DMSO-d6): δ 9.64 (s, 1H), 8.35 (s, 1H), 8.04 (d, J = 5.7 Hz, 1H), 7.76 (d, J = 8.7 Hz, 2H), 7.57 (d, J = 8.7 Hz, 2H), 7.49 (s, 1H), 7.19 (s, 2H), 3.46 (s, 3H), 2.32 (s, 6H); LCMS: purity: 96%; MS (m/e): 425 (MH+). | + | + | – | – |
| 599 | N4-(4-Chloro-3,5-dimethylphenyl)-5-fluoro-N2-(indol-6-yl)-N4-methyl-2,4-pyrimidinediamine | 1H NMR (DMSO-d6): δ 11.00 (s, 1H), 9.58 (bs, 1H), 8.00 (d, J = 6.0 Hz, 1H), 7.89 (s, 1H), 7.41 (d, J = 8.4 Hz, 1H), 7.24-7.18 (m, 3H), 7.11 (dd, J = 1.8 and 8.4 Hz, 1H), 6.35-6.31 (m, 1H), 3.47 (s, 3H), 2.33 (s, 6H); LCMS: purity: 95%; MS (m/e): 397 (MH+). | + | + | – | – |
| 600 | N4-[3-Chloro-4-(N-methylamino)carbonylmethyleneoxyphenyl]-N2-(3,5-dimethylphenyl)-5-fluoro-2,4-pyrimidinediamine | 1H NMR (DMSO-d6): δ 9.94 (bs, 1H), 9.65 (bs, 1H), 8.18 (d, J = 4.2 Hz, 1H), 7.93-7.84 (m, 1H), 7.74 (d, J = 2.4 Hz, 1H), 7.66 (dd, J = 2.7 and 9.0 Hz, 1H), 7.12 (s, 2H), 6.99 (d, J = 9.0 Hz, 1H), 6.64 (s, 1H), 4.55 (s, 2H), 2.66 (d, J = 4.8 Hz, 3H), 2.18 (s, 6H); LCMS: purity: 91%; MS (m/e): 431 (MH+). | + | + | – | – |
| 601 | N4-[3-Chloro-4-(N-methylamino)carbonylmethyleneoxyphenyl]-N2-(3,5-dimethoxyphenyl)-5-fluoro-2,4-pyrimidinediamine | 1H NMR (DMSO-d6): δ 9.52 (bs, 1H), 9.30 (bs, 1H), 8.11 (d, J = 3.9 Hz, 1H), 7.92-7.85 (m, 1H), 7.79 (d, J = 2.4 Hz, 1H), 7.74 (dd, J = 2.7 and 8.7 Hz, 1H), 6.96 (d, J = 9.0 Hz, 1H), 6.85 (d, J = 1.8 Hz, 2H), 6.10 (t, J = 2.4 Hz, 1H), 4.54 (s, 2H), 3.64 (s, 6H), 2.67 (d, J = 4.5 Hz, 3H); LCMS: purity: 93%; MS (m/e): 463 (MH+). | + | + | – | – |
| 602 | N2-(3-Chloro-4-methoxyphenyl)-N4-[3-chloro-4-(N-methylamino)carbonylmethyleneoxyphenyl]-5-fluoro-2,4-pyrimidinediamine | 1H NMR (DMSO-d6): δ 9.45 (bs, 1H), 9.25 (bs, 1H), 8.03 (d, J = 3.3 Hz, 1H), 7.86-7.78 (m, 1H), 7.70 (d, J = 2.4 Hz, 1H), 7.64 (d, J = 2.4 Hz, 1H), 7.58 (dd, J = 2.7 and 9.3 Hz, 1H), 6.96 (d, J = 9.3 Hz, 1H), 6.93 (d, J = 9.3 Hz, 1H), 4.48 (s, 2H), 3.73 (s, 3H), 2.60 (d, J = 4.5 Hz, 3H); LCMS: purity: 95%; MS (m/e): 467 (MH+). | + | + | – | – |
| 603 | N2-(4-Chloro-3,5-dimethylphenyl)-N4-[3-chloro-4-(N-methylamino)carbonylmethyleneoxyphenyl]-5-fluoro-2,4-pyrimidinediamine | 1H NMR (DMSO-d6): δ 9.45 (bs, 1H), 9.2 = 8 (bs, 1H), 8.11 (d, J = 3.9 Hz, 1H), 7.92-7.87 (m, 1H), 7.75 (d, J = 2.4, 1H), 7.68 (dd, J = 2.7 and 9.3 Hz, 1H), 7.40 (s, 2H), 6.99 (d, J = 8.7 Hz, 1H), 4.54 (s, 2H), 2.67 (d, | + | – | – | – |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 604 | N4-(4-Chloro-3,5-dimethylphenyl)-5-fluoro-N4-methyl-N2-[4-(oxazol-4-yl)phenyl]-2,4-pyrimidinediamine | J = 4.2 Hz, 3H), 2.22 (s, 6H); LCMS: purity: 95%; MS (m/e): 464 (MH+). 1H NMR (DMSO-d6): δ 9.42 (s, 1H), 8.46-8.43 (m, 1H), 8.39-8.37 (m, 1H), 8.00 (d, J = 5.4 Hz, 1H), 7.73 (d, J = 9.0 Hz, 2H), 7.62 (d, J = 9.0 Hz, 2H), 7.17 (s, 2H), 3.45 (s, 3H), 2.32 (s, 6H); LCMS: purity: 96%; MS (m/e): 424 (MH+). | + | | − | |
| 605 | N4-[3-Chloro-4-(N-methylamino)carbonylmethyleneoxyphenyl]-5-fluoro-N2-(indol-6-yl)-2,4-pyrimidinediamine | 1H NMR (DMSO-d6): δ 10.80 (s, 1H), 9.26 (s, 1H), 9.07 (s, 1H), 8.06 (s, J = 3.9 Hz, 1H), 7.93-7.75 (m, 4H), 7.36 (d, J = 8.4 Hz, 1H), 7.22-7.15 (m, 2H), 6.95 (d, J = 8.7 Hz, 1H), 6.33-6.27 (m, 1H), 4.54 (s, 2H), 2.67 (d, J = 4.2 Hz, 3H); LCMS: purity: 96%; MS (m/e): 441 (MH+). | + | + | | |
| 606 | N4-(4-Chloro-3-methoxyphenyl)-5-fluoro-N4-methyl-N2-[4-(oxazol-4-yl)phenyl]-2,4-pyrimidinediamine | 1H NMR (DMSO-d6): δ 9.44 (s, 1H), 8.44 (d, J = 0.90 Hz, 1H), 8.38 (d, J = 0.90 Hz, 1H), 8.02 (d, J = 5.7 Hz, 1H), 7.73 (d, J = 8.7 Hz, 2H), 7.63 (d, J = 8.7 Hz, 2H), 7.41 (d, J = 8.4 Hz, 1H), 7.14 (d, J = 2.4 Hz, 1H), 6.92-6.86 (m, 1H), 3.83 (s, 3H), 3.49 (s, 3H); LCMS: purity: 97%; MS (m/e) 426 (MH+). | + | + | + | |
| 607 | N4-(4-Chloro-3-methoxyphenyl)-N2-[4-chloro-3-(N-methylamino)carbonylphenyl]-5-fluoro-2,4-pyrimidinediamine | 1H NMR (DMSO-d6): δ 9.70 (bs, 2H), 8.23-8.18 (m, 1H), 8.15 (d, J = 4.2 Hz, 1H), 7.71 (d, J = 2.7 Hz, 1H), 7.54 (dd, J = 2.7 and 9.0 Hz, 1H), 7.45 (dd, J = 2.4 and 8.7 Hz, 1H), 7.35 (d, J = 2.7 Hz, 1H), 7.28 (d, J = 8.7 Hz, 1H), 7.24 (d, J = 9.0 Hz, 1H), 3.73 (s, 3H), 2.65 (d, J = 4.5 Hz, 3H); LCMS: purity: 92%; MS (m/e): 436 (M+). | + | + | − | |
| 608 | N4-[3-Chloro-4-(N-methylamino)carbonylmethyleneoxyphenyl]-N2-[4-chloro-3-(N-methylamino)carbonylphenyl]-5-fluoro-2,4-pyrimidinediamine | 1H NMR (DMSO-d6): δ 8.13 (d, J = 3.9 Hz, 1H), 9.49 (bs, 1H), 8.28-8.21 (m, 1H), 8.13 (d, J = 3.9 Hz, 1H), 7.93-7.87 (m, 1H), 7.77-7.64 (m, 4H), 7.28 (d, J = 8.7 Hz, 1H), 6.98 (d, J = 9.0 Hz, 1H), 4.59 (s, 2H), 2.70 (d, J = 4.8 Hz, 3H), 2.67 (d, J = 4.5 Hz, 3H); LCMS: purity: 94%; MS (m/e): 494 (MH+). | + | + | − | |
| 609 | N2-[4-Chloro-3-(N-methylamino)carbonylphenyl]-N4-(4-chloro-3-trifluoromethylphenyl)-5-fluoro-2,4-pyrimidinediamine | 1H NMR (DMSO-d6): δ 9.84 (s, 1H), 9.59 (s, 1H), 8.35-8.27 (m, 2H), 8.23 (d, J = 3.9 Hz, 1H), 8.06 (d, J = 2.7 Hz, 1H), 7.75 (d, J = 2.4 Hz, 1H), 7.67-7.60 (m, 2H), 7.29 (d, J = 9.0 Hz, 1H), 2.71 (d, J = 4.5 Hz, 3H); LCMS: purity: 92%; MS (m/e): 475 (MH+). | + | + | − | |
| 610 | N4-(4-Chloro-3,5-dimethylphenyl)-N2-[4-chloro-3-(N-methylamino)carbonylphenyl]-5-fluoro-N4-methyl-2,4-pyrimidinediamine | 1H NMR (DMSO-d6): δ 9.55 (s, 1H), 8.30-8.24 (m, 1H), 8.01 (d, J = 6.6 Hz, 1H), 7.86 (d, J = 2.7 Hz, 1H), 7.68 (dd, J = 2.7 and 9.0 Hz, 1H), 7.27 (d, J = 8.7 Hz, 1H), 7.16 (s, 2H), 3.42 (s, 3H), 2.72 (d, J = 4.5 Hz, 3H), 2.32 (s, 6H); LCMS: purity: 98%; MS (m/e): 448 (M+). | − | + | − | |
| 611 | N4-(3-Chloro-4-methoxyphenyl)-N2-[4-chloro-3-(N-methylamino)carbonylphenyl]-5-fluoro-2,4-pyrimidinediamine | 1H NMR (DMSO-d6): δ 9.57 (s, 1H), 9.54 (s, 1H), 8.19 (d, J = 3.6 Hz, 1H), 8.15-8.08 (m, 1H), 7.93 (d, J = 2.1 Hz, 1H), 7.51 (dd, J = 2.4 and 8.7 Hz, 1H), 7.47 (dd, J = 2.45 and 8.7 Hz, 1H), 7.43 (d, J = 2.1 Hz, 1H), 7.34 (d, J = 8.7 Hz, 1H), 7.27 (d, J = 8.4 Hz, 1H), 3.80 (s, 3H), 2.72 (d, J = 4.5 Hz, 3H); LCMS: purity: 99%; MS (m/e): 436 (M+). | + | + | − | |
| 612 | N2-[3-Chloro-4-(N-methylamino)carbonylphenyl]-N4-(4-chloro-3-trifluoromethylphenyl)-5-fluoro-2,4-pyrimidinediamine | 1H NMR (DMSO-d6): δ 9.83 (s, 1H), 9.65 (s, 1H), 8.33-8.26 (m, 1H), 8.25 (d, J = 3.6 Hz, 1H), 8.16-8.11 (m, 1H), 8.06 (d, J = 2.7 Hz, 1H), 7.87 (d, J = 1.8 Hz, 1H), 7.66 (d, J = 8.7 Hz, 1H), 7.52 (dd, J = 1.8 and 8.4 Hz, 1H), 7.28 (d, J = 8.4 Hz, 1H), 2.72 (d, J = 4.5 Hz, 3H); LCMS: purity: 97%; MS (m/e): 474 (M+). | + | + | − | |
| 613 | N4-(4-Chloro-3,5-dimethylphenyl)-N2-[3-chloro-4-(N-methylamino)carbonylphenyl]-5-fluoro-N4-methyl-2,4-pyrimidinediamine | 1H NMR (DMSO-d6): δ 9.66 (s, 1H), 8.17-8.09 (m, 1H), 8.05 (d, J = 5.4 Hz, 1H), 7.94 (d, J = 2.1 Hz, 1H), 7.54 (dd, J = 2.1 and 8.4 Hz, 1H), 7.18 (s, 2H), 3.44 (s, 3H), 2.71 (d, J = 4.5 Hz, 3H), 2.32 (s, 6H); LCMS: purity: 99%; MS (m/e): 448 (M+). | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 614 | N4-[3-Chloro-4-(methoxycarbonyl)methyleneoxyphenyl]-N2-(3,5-dimethylphenyl)-5-fluoro-2,4-pyrimidinediamine | 1H NMR (DMSO-d6): δ 10.28 (s, 1H), 10.05 (s, 1H), 8.26 (d, J = 4.8 Hz, 1H), 7.74 (d, J = 2.7 Hz, 1H), 7.57 (dd, J = 2.7 and 8.7 Hz, 1H), 7.10-7.01 (m, 3H), 6.69 (s, 1H), 4.93 (s, 2H), 3.70 (s, 3H), 2.17 (s, 6H); LCMS: purity: 98%; MS (m/e): 431 (MH+). | + | + | + | |
| 615 | N4-[3-Chloro-4-(methoxycarbonyl)methyleneoxyphenyl]-N2-(3,5-dimethoxyphenyl)-5-fluoro-2,4-pyrimidinediamine | 1H NMR (DMSO-d6): δ 9.75 (s, 1H), 8.15 (d, J = 4.5 Hz, 1H), 7.80 (d, J = 2.7 Hz, 1H), 7.66 (dd, J = 2.7 and 9.0 Hz, 1H), 7.00 (d, J = 9.0 Hz, 1H), 6.81 (d, J = 2.4 Hz, 1H), 6.14 (t, J = 2.1 Hz, 1H), 4.90 (s, 2H), 3.71 (s, 3H), 3.64 (s, 6H); LCMS: purity: 98%; MS (m/e): 463 (MH+). | + | + | + | |
| 616 | N4-[3-Chloro-4-(methoxycarbonyl)methyleneoxyphenyl]-N2-(3-chloro-4-methoxyphenyl)-5-fluoro-2,4-pyrimidinediamine | 1H NMR (DMSO-d6): δ 9.63 (s, 1H), 9.41 (s, 1H), 8.12 (d, J = 4.2 Hz, 1H), 7.76 (d, J = 2.7 Hz, 1H), 7.69 (d, J = 2.4 Hz, 1H), 7.60 (dd, J = 2.4 and 9.0 Hz, 1H), 7.44 (dd, J = 2.7 and 8.7 Hz, 1H), 7.04 (d, J = 8.7 Hz, 1H), 7.02 (d, J = 9.0 Hz, 1H), 4.90 (s, 2H), 3.80 (s, 3H), 3.70 (s, 3H); LCMS: purity: 92%; MS (m/e): 467 (M+). | + | + | + | |
| 617 | N4-[3-Chloro-3,5-dimethylphenyl)-N4-[3-chloro-4-(methoxycarbonyl)methyleneoxyphenyl]-5-fluoro-2,4-pyrimidinediamine | 1H NMR (DMSO-d6): δ 9.64 (s, 1H), 9.45 (s, 1H), 8.14 (d, J = 4.2 Hz, 1H), 7.75 (d, J = 2.4 Hz, 1H), 7.61 (dd, J = 2.4 and 9.0 Hz, 1H), 7.38 (s, 2H), 7.02 (d, J = 9.0 Hz, 1H), 4.91 (s, 2H), 3.70 (s, 3H), 2.21 (s, 6H); LCMS: purity: 95%; MS (m/e): 465 (M+). | + | + | + | |
| 618 | N4-[3-Chloro-4-(methoxycarbonyl)methyleneoxyphenyl]-5-fluoro-N2-(indol-5-yl)-2,4-pyrimidinediamine | 1H NMR (DMSO-d6): δ 10.86 (s, 1H), 9.23 (s, 1H), 8.94 (s, 1H), 8.03 (d, J = 3.9 Hz, 1H), 7.83 (d, J = 2.4 Hz, 1H), 7.79 (s, 1H), 7.68 (dd, J = 2.4 and 9.0 Hz, 1H), 7.25-7.21 (m, 3H), 6.93 (d, J = 9.0 Hz, 1H), 6.27 (t, J = 2.4 Hz, 1H), 4.89 (s, 2H), 3.71 (s, 3H); LCMS: purity: 95%; MS (m/e):442 (MH+). | + | + | − | |
| 619 | N4-[3-Chloro-4-(2-hydroxyethyleneoxyphenyl]-N2-(3,5-dimethylphenyl)-5-fluoro-2,4-pyrimidinediamine | 1H NMR (DMSO-d6): δ 9.63 (bs, 1H), 9.34 (bs, 1H), 8.11 (d, J = 4.2 Hz, 1H), 7.72 (d, J = 2.7 Hz, 1H), 7.64 (dd, J = 2.7 and 9.0 Hz, 1H), 7.12 (d, J = 8.7 Hz, 1H), 6.58 (s, 1H), 4.05 (t, J = 5.1 Hz, 2H), 3.73 (t, J = 5.1 Hz, 2H), 2.16 (s, 6H); LCMS: purity: 91%; MS (m/e): 403 (MH+). | + | + | + | |
| 620 | N4-[3-Chloro-4-(2-hydroxyethyleneoxyphenyl]-N2-(3,5-dimethoxyphenyl)-5-fluoro-2,4-pyrimidinediamine | 1H NMR (DMSO-d6): δ 9.29 (s, 1H), 9.13 (s, 1H), 8.08 (d, J = 3.6 Hz, 1H), 7.75 (d, J = 2.7 Hz, 1H), 7.71 (dd, J = 2.7 and 8.7 Hz, 1H), 7.08 (d, J = 9.0 Hz, 1H), 6.90 (d, J = 2.1 Hz, 2H), 6.05 (t, J = 2.1 Hz, 1H), 4.89 (t, J = 5.1 Hz, 1H), 4.05 (t, J = 5.1 Hz, 2H), 3.73 (q, J = 5.1 Hz, 2H), 3.63 (s, 6H); LCMS: purity: 99%; MS (m/e): 435 (MH+). | + | + | + | |
| 621 | N4-[3-Chloro-4-(2-hydroxyethyleneoxyphenyl]-N2-(3-chloro-4-methoxyphenyl)-5-fluoro-2,4-pyrimidinediamine | 1H NMR (DMSO-d6): δ 9.29 (s, 1H), 9.15 (s, 1H), 8.06 (d, J = 3.6 Hz, 1H), 7.74 (d, J = 2.1 Hz, 2H), 7.63 (dd, J = 2.7 and 9.0 Hz, 1H), 7.46 (dd, J = 2.7 and 9.0 Hz, 1H), 7.10 (d, J = 9.0 Hz, 1H), 7.00 (d, J = 9.0 Hz, 1H), 4.87 (t, J = 5.4 Hz, 1H), 4.05 (t, J = 5.1 Hz, 2H), 3.78 (s, 3H), 3.74 (q, J = 4.8 Hz, 2H); LCMS: purity: 100%; MS (m/e): 441 (MH+). | + | + | + | |
| 622 | N2-(4-Chloro-3,5-dimethylphenyl)-N4-[3-chloro-4-(2-hydroxyethyleneoxyphenyl]-5-fluoro-2,4-pyrimidinediamine | 1H NMR (DMSO-d6): δ 9.31 (s, 1H), 9.18 (s, 1H), 8.08 (d, J = 3.9 Hz, 1H), 7.72 (d, J = 2.7 Hz, 1H), 7.63 (dd, J = 2.4 and 9.0 Hz, 1H), 7.42 (s, 2H), 7.12 (d, J = 9.0 Hz, 1H), 4.87 (t, J = 5.7 Hz, 1H), 4.04 (t, J = 5.1 Hz, 2H), 3.73 (q, J = 5.1 Hz, 2H), 2.20 (s, 6H); LCMS: purity: 99%; MS (m/e): 438 (MH+). | + | + | − | |
| 623 | N4-[3-Chloro-4-(2-hydroxyethyleneoxyphenyl]-5-fluoro-N2-(indol-5-yl)-2,4-pyrimidinediamine | 1H NMR (DMSO-d6): δ 10.84 (s, 1H), 9.17 (s, 1H), 8.90 (s, 1H), 8.01 (d, J = 3.9 Hz, 1H), 7.82-7.76 (m, 2H), 7.67 (dd, J = 3.0 and 9.3 Hz, 1H), 7.25-7.21 (m, 3H), 7.03 (d, J = 9.0 Hz, 1H), 6.28-6.25 (m, 1H), 4.87 (t, J = 5.4 Hz, 1H), 4.04 (t, J = 5.1 Hz, 2H), 3.73 (q, J = 5.1 Hz, 2H); LCMS: purity: 100%; MS (m/e): 414 (MH+). | + | + | + | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 624 | N4-[3-Chloro-4-(2-hydroxyethyleneoxyphenyl]-N2-(4-chloro-3-methoxyphenyl)-5-fluoro-2,4-pyrimidinediamine | 1H NMR (DMSO-d6): δ 9.49 (s, 1H), 9.42 (s, 1H), 8.12 (d, J = 3.9 Hz, 1H), 7.80 (d, J = 2.4 Hz, 1H), 7.59 (dd, J = 2.7 and 9.0 Hz, 1H), 7.40-7.36 (m, 1H), 7.30 (dd, J = 2.7 and 8.4 Hz, 1H), 7.20 (d, J = 8.7 Hz, 1H), 7.12 (d, J = 8.7 Hz, 1H), 4.06 (t, J = 4.8 Hz, 2H), 3.77-3.71 (m, 2H), 3.66 (s, 3H); LCMS: purity: 93%; MS (m/e): 440 (MH+). | + | | − | |
| 625 | N4-[3-Chloro-4-(N-methylamino)carbonylmethyleneoxyphenyl]-5-fluoro-N2-(indol-5-yl)-2,4-pyrimidinediamine | 1H NMR (DMSO-d6): δ 10.84 (s, 1H), 9.20 (s, 1H), 8.91 (s, 1H), 8.02 (d, J = 3.9 Hz, 1H), 7.90-7.82 (m, 2H), 7.73 (dd, J = 2.4 and 9.0 Hz, 1H), 7.26-7.19 (m, 3H), 6.93 (d, J = 8.7 Hz, 1H), 6.28 (t, J = 2.4 Hz, 1H), 4.52 (s, 2H), 2.67 (d, J = 4.5 Hz, 3H); LCMS: purity: 98%; MS (m/e): 441 (MH+). | + | + | + | |
| 626 | 2-Chloro-N4(4-chloro-3,5-dimethylphenyl)-5-fluoro-N4-methyl-4-pyrimidineamine | 1H NMR (DMSO-d6): δ 8.17 (d, J = 5.1 Hz, 1H), 7.23 (s, 2H), 3.38 (s, 3H), 2.32 (s, 6H); LCMS: purity: 98%; MS (m/e): 301 (MH+). | − | + | + | |
| 627 | 2-Chloro-5-fluoro-N4-methyl-N4-[3,4-(tetrafluoroethylenedioxy)phenyl]-4-pyrimidineamine | 1H NMR (DMSO-d6): δ 7.94 (d, J = 4.8 Hz, 1H), 7.17 (d, J = 9.6 Hz, 1H), 7.17 (d, J = 9.6 Hz, 1H), 7.05-7.00 (m, 2H), 3.50 (s, 3H); LCMS: purity: 92%; MS (m/e): 368 (MH+). | − | + | − | |
| 628 | 2-Chloro-N4-[3,4-(difluoromethylenedioxy)phenyl]-5-fluoro-N4-methyl-4-pyrimidineamine | 1H NMR (DMSO-d6): δ 7.82 (d, J = 4.5 Hz, 1H), 6.98 (d, J = 8.4 Hz, 1H), 6.90-6.83 (m, 2H), 3.40 (s, 3H); LCMS: purity: 100%; MS (m/e): 318 (MH+). | + | + | − | |
| 629 | N4(4-Chloro-3-trifluoromethylphenyl)-5-fluoro-N2-(indol-6-yl)-2,4-pyrimidinediamine | 1H NMR (DMSO-d6): δ 10.86 (s, 1H), 9.67 (s, 1H), 9.14 (s, 1H), 8.44 (dd, J = 2.4 and 9.0 Hz, 1H), 8.15 (d, J = 3.9 Hz, 1H), 8.12 (d, J = 2.7 Hz, 1H), 7.77 (s, 1H), 7.51 (d, J = 9.3 Hz, 1H), 7.37 (d, J = 8.4 Hz, 1H), 7.19 (t, J = 2.1 Hz, 1H), 7.14 (dd, J = 1.8 and 8.4 Hz, 1H), 6.34-6.30 (m, 1H); LCMS: purity: 100%; MS (m/e): 422 (MH+). | + | + | − | |
| 630 | N4(4-Chloro-3-methoxyphenyl)-5-fluoro-N2-(indol-6-yl)-2,4-pyrimidinediamine | 1H NMR (DMSO-d6): δ 10.85 (s, 1H), 9.35 (s, 1H), 9.04 (s, 1H), 8.10 (d, J = 3.6 Hz, 1H), 7.79 (s, 1H), 7.62-7.57 (m, 2H), 7.36 (d, J = 8.4 Hz, 1H), 7.24 (d, J = 9.0 Hz, 1H), 7.19 (t, J = 2.7 Hz, 1H), 7.15 (dd, J = 1.8 and 8.4 Hz, 1H), 6.34-6.30 (m, 1H), 3.67 (s, 3H); LCMS: purity: 99%; MS (m/e): 384 (MH+). | + | + | − | |
| 631 | N4-(3-Chloro-4-methoxycarbonylmethyleneoxyphenyl)-5-fluoro-N2-(indol-6-yl)-2,4-pyrimidinediamine | 1H NMR (DMSO-d6): δ 10.78 (s, 1H), 9.23 (s, 1H), 9.03 (s, 1H), 8.05 (d, J = 3.6 Hz, 1H), 7.85 (d, J = 2.7 Hz, 1H), 7.79-7.73 (m, 2H), 7.36 (d, J = 8.4 Hz, 1H), 7.19 (dd, J = 2.1 and 8.7 Hz, 1H), 7.16 (t, J = 3.0 Hz, 1H), 6.95 (d, J = 9.0 Hz, 1H), 6.32-6.28 (m, 1H), 4.88 (s, 2H), 3.71 (s, 3H); LCMS: purity: 98%; MS (m/e): 442 (MH+). | + | + | − | |
| 632 | N4-[3-Chloro-4-(2-hydroxyethyleneoxyphenyl]-5-fluoro-N2-(indol-6-yl)-2,4-pyrimidinediamine | 1H NMR (DMSO-d6): δ 10.79 (s, 1H), 9.19 (d, J = 1.2 Hz, 1H), 9.01 (s, 1H), 8.04 (d, J = 3.6 Hz, 1H), 7.84 (d, J = 2.7, 1H), 7.79-7.73 (m, 2H), 7.36 (d, J = 8.4 Hz, 1H), 7.19 (dd, J = 1.8 and 8.4 Hz, 1H), 7.16 (t, J = 2.4 Hz, 1H), 7.05 (d, J = 9.3 Hz, 1H), 6.32-6.28 (m, 1H), 4.86 (t, J = 5.1 Hz, 1H), 4.04 (t, J = 5.4 Hz, 2H), 3.73 (q, J = 5.1 Hz, 2H); LCMS: purity: 99%; MS (m/e): 414 (MH+). | + | + | − | |
| 633 | 5-Fluoro-N2-[3-(oxazol-2-yl)phenyl]-N4-[3,4-(tetrafluoroethylenedioxy)phenyl]-2,4-pyrimidinediamine | 1H NMR (DMSO-d6): δ 9.76 (s, 1H), 9.63 (s, 1H), 8.33-8.29 (m, 1H), 8.22 (d, J = 3.6 Hz, 1H), 8.16-8.13 (m, 1H), 7.78-7.74 (m, 1H), 7.62 (dd, J = 2.4 and 9.0 Hz, 1H), 7.58-7.53 (m, 1H), 7.42-7.31 (m, 3H); LCMS: purity: 92%; MS (m/e): 478 (MH+). | − | + | − | |
| 634 | 5-Fluoro-N4-methyl-N2-[3-(oxazol-2-yl)phenyl]-N4-[3,4-(tetrafluoroethylenedioxy)phenyl]-2,4-pyrimidinediamine | 1H NMR (DMSO-d6): δ 9.67 (s, 1H), 8.57 (t, J = 1.8 Hz, 1H), 8.18-8.16 (m, 1H), 8.09 (d, J = 5.7 Hz, 1H), 7.72-7.66 (m, 1H), 7.60 (d, J = 1.8 Hz, 1H), 7.54-7.47 (m, 2H), 7.39-7.32 (m, 3H), 3.53 (s, 3H); LCMS: purity: 96%; MS (m/e): 492 (MH+). | | + | − | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 635 | N2-[3,5-Dimethyl-4-(N-methylamino)carbonylmethyleneoxyphenyl]-N4-(3,4-ethylenedioxyphenyl)-5-fluoro-N4-methyl-2,4-pyrimidinediamine | 1H NMR (DMSO-d6): δ 9.02 (s, 1H), 8.12-8.06 (m, 1H), 7.88 (d, J = 5.7 Hz, 1H), 7.34 (s, 2H), 6.83 (d, J = 6.9 Hz, 1H), 6.82 (s, 1H), 6.73 (dd, J = 3.0 and 9.0 Hz, 1H), 4.24 (s, 4H), 4.11 (s, 2H), 3.38 (s, 3H), 2.69 (d, J = 4.8 Hz, 3H), 2.16 (s, 6H); LCMS: purity: 99%; MS (m/e): 468 (MH+). | + | + | + | + |
| 636 | N2-[3,5-Dimethyl-4-(N-methylamino)carbonylmethyleneoxyphenyl]-5-fluoro-N4-methyl-N4-[3,4-(tetrafluoroethylenedioxy)phenyl]-2,4-pyrimidinediamine | 1H NMR (DMSO-d6): δ 9.15 (s, 1H), 8.12-8.05 (m, 1H), 8.02 (d, J = 5.7 Hz, 1H), 8.02 (d, J = 5.7 Hz, 1H), 7.55 (dd, J = 0.9 and 2.7 Hz, 1H), 7.48 (d, J = 9.3 Hz, 1H), 7.31 (s, 2H), 7.27 (dd, J = 0.9 and 2.1 Hz, 1H), 4.11 (s, 2H), 3.46 (s, 3H), 2.69 (d, J = 4.8 Hz, 3H), 2.14 (s, 6H); LCMS: purity: 99%; MS (m/e): 540 (MH+). | + | + | + | + |
| 637 | N2-[3,5-Dimethyl-4-(N-methylamino)carbonylmethyleneoxyphenyl]-5-fluoro-N4-[3,4-(tetrafluoroethylenedioxy)phenyl]-2,4-pyrimidinediamine | 1H NMR (DMSO-d6): δ 9.59 (s, 1H), 9.14 (s, 1H), 8.16-8.08 (m, 3H), 7.61 (dd, J = 2.7 and 9.0 Hz, 1H), 7.40 (d, J = 9.0 Hz, 1H), 7.25 (s, 2H), 4.12 (s, 2H), 2.69 (d, J = 4.8 Hz, 3H), 2.15 (s, 6H); LCMS: purity: 99%; MS (m/e): 526 (MH+). | + | + | – | |
| 638 | N2-[3,5-Dimethyl-4-(N-methylamino)carbonylmethyleneoxyphenyl]-5-fluoro-N4-(3,5-dimethoxyphenyl)-5-fluoro-N4-methyl-2,4-pyrimidinediamine | 1H NMR (DMSO-d6): δ 9.07 (s, 1H), 8.13-8.05 (m, 1H), 7.94 (d, J = 5.7 Hz, 1H), 7.35 (s, 2H), 6.44 (dd, J = 0.6 and 2.4 Hz, 2H), 6.39 (t, J = 2.4 Hz, 1H), 4.16 (s, 2H), 3.72 (s, 6H), 3.43 (s, 6H), 2.69 (d, J = 4.8 Hz, 3H), 2.16 (s, 6H); LCMS: purity: 99%; MS (m/e): 470 (MH+). | + | + | + | |
| 639 | N4-(2,2-Dimethyl-3-oxo-4H-benz[1,4]oxazin-6-yl)-5-fluoro-N2-[1-(methoxycarbonylmethylene)indol-6-yl]-2,4-pyrimidinediamine | 1H NMR (DMSO-d6): δ 10.60 (s, 1H), 9.45 (s, 1H), 9.09 (s, 1H), 8.04 (d, J = 3.6 Hz, 1H), 7.57 (s, 1H), 7.40-7.33 (m, 2H), 7.31-7.24 (m, 2H), 7.20 (d, J = 3.3 Hz, 1H), 6.81 (d, J = 8.7 Hz, 1H), 3.35 (d, J = 2.4 Hz 1H), 4.91 (s, 2H), 3.63 (s, 3H), 1.40 (s, 6H); LCMS: purity: 97%; MS (m/e): 491 (MH+). | + | + | – | |
| 640 | N4-[3-Chloro-4-(N-methylamino)carbonylmethylene)indol-6-yl]-5-fluoro-N2-[1-(methoxycarbonylmethylene)indol-6-yl]-2,4-pyrimidinediamine | 1H NMR (DMSO-d6): δ 9.42 (s, 1H), 9.24 (s, 1H), 8.07 (d, J = 3.9 Hz, 1H), 7.92-7.84 (m, 2H), 7.71 (dd, J = 2.7 and 9.3 Hz, 1H), 7.55 (s, 1H), 7.41 (d, J = 8.4 Hz, 1H), 7.29 (dd, J = 1.5 and 8.4 Hz, 1H), 7.20 (d, J = 3.3 Hz, 1H), 6.94 (d, J = 9.0 Hz, 1H), 6.36 (d, J = 3.3 Hz, 1H), 4.92 (s, 2H), 4.53 (s, 2H), 3.63 (s, 3H), 2.67 (d, J = 4.5 Hz, 1H); LCMS: purity: 99%; MS (m/e): 514 (MH+). | + | + | + | |
| 641 | N4-(4-Chloro-3-methoxyphenyl)-5-fluoro-N2-[1-(methoxycarbonylmethylene)indol-6-yl]-2,4-pyrimidinediamine | 1H NMR (DMSO-d6): δ 9.34 (s, 1H), 9.10 (s, 1H), 8.09 (d, J = 3.6 Hz, 1H), 7.62-7.59 (m, 1H), 7.54 (d, J = 2.4 Hz, 1H), 7.49 (dd, J = 2.4 and 8.4 Hz, 1H), 7.38 (d, J = 8.7 Hz, 1H), 7.27-7.22 (m, 2H), 7.20 (d, J = 3.3 Hz, 1H), 6.36 (dd, J = 0.6 and 3.0 Hz, 1H), 4.88 (s, 2H), 3.62 (s, 3H), 3.60 (s, 3H); LCMS: purity: 98%; MS (m/e): 457 (MH+). | + | + | – | |
| 642 | N4-(3,4-Ethylenedioxyphenyl)-5-fluoro-N2-[1-(methoxycarbonylmethylene)indol-6-yl]-2,4-pyrimidinediamine | 1H NMR (DMSO-d6): δ 9.19 (s, 1H), 9.14 (s, 1H), 8.02 (d, J = 3.9 Hz, 1H), 7.63 (s, 1H), 7.40-7.31 (m, 2H), 7.30-7.17 (m, 3H), 6.74 (d, J = 9.0 Hz, 1H), 6.35 (d, J = 2.7 Hz, 1H), 4.90 (s, 2H), 4.21 (s, 4H), 3.63 (s, 3H); LCMS: purity: 93%; MS (m/e): 450 (MH+). | + | + | + | |
| 643 | N4-(2,2-Dimethyl-3-oxo-4H-benz[1,4]oxazin-6-yl)-5-fluoro-N2-[1-(methoxycarbonylmethylene)indol-5-yl]-2,4-pyrimidinediamine | 1H NMR (DMSO-d6): δ 10.56 (s, 1H), 9.20 (s, 1H), 8.79 (s, 1H), 8.00 (d, J = 3.6 Hz, 1H), 7.86 (s, 1H), 7.33 (dd, J = 2.1 and 8.7 Hz, 1H), 7.27-7.16 (m, 4H), 6.83 (d, J = 8.7 Hz, 1H), 6.27 (d, J = 3.0 Hz, 1H), 5.05 (s, 2H), 3.66 (s, 3H), 1.40 (s, 6H); LCMS: purity: 96%; MS (m/e): 491 (MH+). | + | + | – | |
| 644 | N4-[3-Chloro-4-(N-methylamino)carbonylmethyleneoxyphenyl]-5-fluoro-N2-[1-(methoxycarbonylmethylene)indol-5-yl]-2,4-pyrimidinediamine | 1H NMR (DMSO-d6): δ 9.22 (s, 1H), 8.96 (s, 1H), 8.03 (d, J = 3.9 Hz, 1H), 7.90-7.72 (m, 4H), 7.28-7.23 (m, 3H), 6.94 (d, J = 8.7 Hz, 1H), 6.32 (d, J = 3.0 Hz, 1H), 5.07 (s, 2H), 4.53 (s, 2H), 3.67 (s, 3H), 2.67 (d, J = 4.5 Hz, 3H); LCMS: purity: 90%; MS (m/e): 514 (MH+). | + | + | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 645 | N4-(4-Chloro-3-methoxyphenyl)-5-fluoro-N2-[1-(methoxycarbonylmethylene)indol-5-yl]-2,4-pyrimidinediamine | 1H NMR (DMSO-d6): δ 9.32 (s, 1H), 8.96 (s, 1H), 8.07 (d, J = 3.6 Hz, 1H), 7.84 (s, 1H), 7.55-7.47 (m, 2H), 7.28-7.17 (m, 4H), 6.29 (d, J = 3.0 Hz, 1H), 5.08 (s, 2H), 3.67 (s, 3H), 3.64 (s, 3H); LCMS: purity: 96%; MS (m/e): 457 (MH+). | + | + | − | |
| 646 | N4-(3-Chloro-4-methoxyphenyl)-5-fluoro-N2-[1-(methoxycarbonylmethylene)indol-5-yl]-2,4-pyrimidinediamine | 1H NMR (DMSO-d6): δ 9.18 (s, 1H), 8.94 (s, 1H), 8.02 (d, J = 3.0 Hz, 1H), 7.82-7.76 (m, 2H), 7.70 (dd, J = 2.1 and 9.0 Hz, 1H), 7.27-7.21 (m, 3H), 7.03 (d, J = 9.0 Hz, 1H), 6.30 (d, J = 2.7 Hz, 1H), 5.06 (s, 2H), 3.83 (s, 3H), 3.66 (s, 3H); LCMS: purity: 98%; MS (m/e): 456 (MH+). | + | + | − | |
| 647 | N4-(3,4-Ethylenedioxyphenyl)-5-fluoro-N2-[1-(methoxycarbonylmethylene)indol-5-yl]-2,4-pyrimidinediamine | 1H NMR(DMSO-D6): δ 10.18 (s, 1H), 9.99 (s, 1H), 8.16 (d, J = 4.5 Hz,) 1H), 7.74 (s, 1H), 7.46-7.18 (m, 3H), 7.34-7.18 (m, 3H), 6.83 (d, J = 8.1 Hz, 1H), 6.46 (d, J = 3.0 Hz, 1H), 5.20 (s, 2H), 4.29 (s, 4H), 3.74 (s, 3H); LCMS: purity: 92%; MS (m/e): 450 (MH+). | + | + | − | |
| 648 | N4-[3-Chloro-4-(N-methylamino)carbonylmethyleneoxyphenyl]-5-fluoro-N2-[1-(N-methylamino)carbonylmethyleneindol-6-yl]-2,4-pyrimidinediamine | 1H NMR (DMSO-d6): δ 9.25 (s, 1H), 9.07 (s, 1H), 8.04 (d, J = 3.6 Hz, 1H), 7.90-7.83 (m, 3H), 7.77-7.73 (m, 1H), 7.55-7.52 (m, 1H), 7.39 (d, J = 9.0 Hz, 1H), 7.32-7.26 (m, 1H), 7.16 (d, J = 3.3 Hz, 1H), 6.91 (d, J = 9.3 Hz, 1H), 6.33 (d, J = 3.0 Hz, 1H), 4.62 (s, 4H), 4.52 (s, 2H), 2.67 (d, J = 4.2 Hz, 3H), 2.58 (d, J = 4.5 Hz, 3H); LCMS: purity: 94%; MS (m/e): 513 (MH+). | + | + | − | + |
| 649 | N4-[3-Chloro-4-(N-methylamino)carbonylmethyleneoxyphenyl]-5-fluoro-N2-[1-(N-methylamino)carbonylmethyleneindol-6-yl]-2,4-pyrimidinediamine | 1H NMR (DMSO-d6): δ 9.06 (s, 1H), 9.02 (s, 1H), 7.99 (d, J = 3.9 Hz, 1H), 7.88-7.82 (m, 1H), 7.58 (s, 1H), 7.39-7.33 (m, 2H), 7.32-7.25 (m, 2H), 7.16 (d, J = 3.3 Hz, 1H), 6.71 (d, J = 8.7 Hz, 1H), 6.33 (d, J = 3.3 Hz, 1H), 4.63 (s, 2H), 4.19 (s, 4H), 2.58 (d, J = 4.2 Hz, 3H); LCMS: purity: 97%; MS (m/e): 449 (MH+). | + | + | | |
| 650 | 5-Fluoro-N4-[2-(2-hydroxyethyleneoxy)pyrid-5-yl]-N2-[1-(N-methylamino)carbonylmethyleneindol-5-yl]-2,4-pyrimidinediamine | 1H NMR (DMSO-d6): δ 9.26 (s, 1H), 8.98 (s, 1H), 8.51 (s, 1H), 8.07 (dd, J = 2.4 and 9.0 Hz, 1H), 8.03 (d, J = 3.9 Hz, 1H), 7.98-7.92 (m, 1H), 7.87 (s, 1H), 7.24-7.14 (m, 3H), 6.76 (d, J = 9.0 Hz, 1H), 6.27 (d, J = 3.0 Hz, 1H), 4.84 (t, J = 5.4 Hz, 1H), 4.72 (s, 2H), 4.25 (t, J = 5.7 Hz, 2H), 3.71 (q, J = 5.7 Hz, 2H), 2.60 (d, J = 4.5 Hz, 3H); LCMS: purity: 90%; MS (m/e): 452 (MH+). | | + | | |
| 651 | N4-(3-Chloro-4-trifluoromethoxyphenyl)-5-fluoro-N2-[1-(N-methylamino)carbonylmethyleneindol-5-yl]-2,4-pyrimidinediamine | 1H NMR (DMSO-d6): δ 9.55 (s, 1H), 9.09 (s, 1H), 8.15-7.99 (m, 2H), 8.02-7.95 (m, 1H), 7.89 (dd, J = 1.5 and 9.6 Hz, 1H), 7.75 (s, 1H), 7.40 (d, J = 9.0 Hz, 1H), 7.27-7.21 (m, 3H), 6.30 (d, J = 2.7 Hz, 1H), 4.73 (s, 2H), 2.61 (d, J = 4.5 Hz, 3H); LCMS: purity: 99%; MS (m/e): 510 (MH+). | | + | − | |
| 652 | N4-(3-Chloro-4-(N-methylamino)carbonylmethyleneoxyphenyl)-5-fluoro-N2-[1-(N-methylamino)carbonylmethyleneindol-5-yl]-2,4-pyrimidinediamine | 1H NMR (DMSO-d6): δ 9.88 (s, 1H), 9.70 (s, 1H), 8.12-8.03 (m, 2H), 7.94-7.87 (m, 1H), 7.81 (d, J = 2.4 Hz, 1H), 7.69-7.63 (m, 2H), 7.35-7.27 (m, 2H), 7.17 (d, J = 8.7 Hz, 1H), 6.94 (d, J = 9.0 Hz, 1H), 6.35 (d, J = 3.0 Hz, 1H), 4.77 (s, 2H), 4.55 (s, 2H), 2.66 (d, J = 4.8 Hz, 3H), 2.61 (d, J = 4.8 Hz, 3H); LCMS: purity: 97%; MS (m/e): 513 (MH+). | | + | | + |
| 653 | N4-(4-Chloro-3-methoxyphenyl)-5-fluoro-N2-[1-(N-methylamino)carbonylmethyleneindol-5-yl]-2,4-pyrimidinediamine | 1H NMR (DMSO-d6): δ 10.22 (s, 1H), 9.91 (s, 1H), 8.16 (d, J = 4.8 Hz, 1H), 8.12-8.05 (m, 1H), 7.70-7.66 (m, 1H), 7.52-7.48 (m, 1H), 7.42 (d, J = 7.8 Hz, 1H), 7.37-7.28 (m, 3H), 7.16-7.10 (m, 1H), 6.35 (d, J = 2.7 Hz, 1H), 4.79 (s, 2H), 3.63 (s, 3H), 2.62 (d, J = 4.5 Hz, 3H); LCMS: purity: 97%; MS (m/e): 456 (MH+). | | + | − | |
| 654 | N4-(3-Chloro-4-methoxyphenyl)-5-fluoro-N2-[1-(N-methylamino)carbonylmethyleneindol-5-yl]-2,4-pyrimidinediamine | 1H NMR (DMSO-d6): δ 10.21 (s, 1H), 9.94 (s, 1H), 8.16-8.03 (m, 2H), 7.79-7.74 (m, 1H), 7.65-7.58 (m, 2H), 7.37-7.30 (m, 2H), 7.14 (d, J = 8.4 Hz, 1H), 7.05 (d, J = 8.7 Hz, 1H), 6.37 (d, J = 3.0 Hz, 1H), 4.78 (s, | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 655 | N4-(3,4-Ethylenedioxyphenyl)-5-fluoro-N2-[1-(N-methylamino)carbonylmethyleneindol-5-yl]-2,4-pyrimidinediamine | 2H), 3.84 (s, 3H), 2.61 (d, J = 4.5 Hz, 3H); LCMS: purity: 97%; MS (m/e):456 (MH+). | | | | |
| 656 | N4-[3-Chloro-4-(N-methylamino)carbonylphenyl]-5-fluoro-N2-[1-(N-methylamino)carbonylmethyleneindol-5-yl]-2,4-pyrimidinediamine | 1H NMR (DMSO-d6): δ 10.19 (bs, 1H), 10.04 (bs, 1H), 8.12-8.03 (m, 2H), 7.66-7.61 (m, 1H), 7.36-7.30 (m, 2H), 7.27-7.09 (m, 3H), 6.78 (d, J = 8.4 Hz, 1H), 6.38 (d, J = 2.7 Hz, 1H), 4.79 (s, 2H), 4.23 (s, 4H), 2.61 (d, J = 4.2 Hz, 3H); LCMS: purity: 99%; MS (m/e): 449 (MH+). | | + | | |
| 657 | 2-Chloro-5-fluoro-N4-(2-methoxypyrid-5-yl)-N4-methyl-4-pyrimidineamine | 1H NMR (DMSO-d6): δ 9.46 (s, 1H), 9.07 (s, 1H), 8.24-8.17 (m, 1H), 8.11 (d, J = 3.0 Hz, 1H), 8.00-7.94 (m, 1H), 7.94-7.86 (m, 2H), 7.77 (s, 1H), 7.31-7.22 (m, 4H), 6.33 (d, J = 3.3 Hz, 1H), 4.73 (s, 2H), 2.73 (d, J = 4.8 Hz, 3H), 2.60 (d, J = 4.8 Hz, 3H); LCMS: purity: 99%; MS (m/e): 482 (MH+). | | + | | |
| 658 | 2-Chloro-N4-(4-chloro-3-trifluoromethylphenyl)-5-fluoro-N4-methyl-4-pyrimidineamine | 1H NMR (DMSO-d6): δ 8.21 (d, J = 3.0 Hz, 1H), 8.15 (d, J = 5.7 Hz, 1H), 7.78 (dd, J = 2.7 and 8.7 Hz, 1H), 6.87 (d, J = 8.7 Hz, 1H), 3.86 (s, 3H), 3.38 (s, 3H); LCMS: purity: 95%; MS (m/e): 269 (MH+). | – | | | |
| 659 | 2-Chloro-N4-(4-chloro-3-methoxyphenyl)-5-fluoro-N4-methyl-4-pyrimidineamine | 1H NMR (DMSO-d6): δ 8.25 (d, J = 5.4 Hz, 1H), 7.97-7.94 (m, 1H), 7.78-7.72 (m, 2H), 3.45 (s, 3H); LCMS: purity: 96%; MS (m/e): 341 (MH+). | – | | | |
| 660 | 2-Chloro-N4-(3-chloro-4-methoxyphenyl)-5-fluoro-N4-methyl-4-pyrimidineamine | 1H NMR (DMSO-d6): δ 8.18 (d, J = 5.1 Hz, 1H), 7.42 (d, J = 8.7 Hz, 1H), 7.24 (s, 1H), 6.96 (d, J = 8.7 Hz, 1H), 3.82 (s, 1H), 3.31 (s, 3H); LCMS: purity: 99%; MS (m/e): 303 (MH+). | – | | | |
| 661 | 2-Chloro-N4-[3-chloro-4-(N-methylamino)carbonylmethyleneoxyphenyl]-5-fluoro-N4-methyl-4-pyrimidineamine | 1H NMR (DMSO-d6): δ 8.14 (d, J = 5.4 Hz, 1H), 7.56 (d, J = 2.7 Hz, 1H), 7.34 (dd, J = 2.4 and 8.7 Hz, 1H), 7.15 (d, J = 8.4 Hz, 1H), 3.87 (s, 3H), 3.36 (s, 3H); LCMS: purity: 96%; MS (m/e): 303 (MH+). | – | | | |
| 662 | N4-(3-Chloro-4-trifluoromethoxyphenyl)-5-fluoro-N2-[1-(N-methylamino)carbonylmethyleneindol-6-yl]-2,4-pyrimidinediamine | 1H NMR (DMSO-d6): δ 8.15 (d, J = 5.4 Hz, 1H), 7.94-7.87 (m, 1H), 7.58 (d, J = 2.4 Hz, 1H), 7.32 (dd, J = 2.4 and 8.7 Hz, 1H), 7.02 (d, J = 9.0 Hz, 1H), 4.60 (s, 2H), 3.36 (s, 3H), 2.66 (d, J = 4.8 Hz, 3H); LCMS: purity: 90%; MS (m/e): 360 (MH+). | + | + | | |
| 663 | N4-(4-Chloro-3-methoxyphenyl)-5-fluoro-N2-[1-(N-methylamino)carbonylmethyleneindol-6-yl]-2,4-pyrimidinediamine | 1H NMR (DMSO-d6): δ 10.22 (s, 1H), 9.88 (s, 1H), 8.22 (d, J = 3.9 Hz, 1H), 8.14 (d, J = 2.7 Hz, 1H), 8.02-7.95 (m, 1H), 7.84-7.78 (m, 1H), 7.49 (d, J = 8.1 Hz, 1H), 7.45-7.37 (m, 2H), 7.27 (d, J = 2.7 Hz, 1H), 7.27 (d, J = 2.7 Hz, 1H), 7.18 (d, J = 8.4 Hz, 1H), 6.41 (d, J = 3.3 Hz, 1H), 4.70 (s, 2H), 2.58 (d, J = 4.5 Hz, 3H); LCMS: purity: 91%; MS (m/e) 509 (MH+). | + | | | |
| 664 | N4-(3-Chloro-4-methoxyphenyl)-5-fluoro-N2-[1-(N-methylamino)carbonylmethyleneindol-6-yl]-2,4-pyrimidinediamine | 1H NMR (DMSO-d6): δ 10.13 (s, 1H), 9.90 (s, 1H), 8.10 (d, J = 4.5 Hz, 1H), 7.91 (d, J = 3.9 Hz, 1H), 7.49-7.34 (m, 4H), 7.23 (d, J = 3.3 Hz, 1H), 7.17 (d, J = 8.4 Hz, 1H), 7.07 (d, J = 8.4 Hz, 1H), 6.37 (d, J = 3.0 Hz, 1H), 4.62 (s, 2H), 3.52 (s, 3H), 2.51 (d, J = 4.5 Hz, 3H); LCMS: purity: 97%; MS (m/e): 456 (MH+) | + | + | | |
| 665 | N4-[3-Chloro-4-(N-methylamino)carbonylphenyl]-5-fluoro-N2-[1-(N-methylamino)carbonylmethyleneindol-6-yl]-2,4-pyrimidinediamine | 1H NMR (DMSO-d6): δ 10.21 (s, 1H), 10.04 (s, 1H), 8.14 (d, J = 5.1 Hz, 1H), 7.98-7.92 (m, 1H), 7.84 (d, J = 2.7 Hz, 1H), 7.60 (dd, J = 2.4 and 8.7 Hz, 1H), 7.51 (d, J = 8.7 Hz, 1H), 7.39 (s, 1H), 7.30 (d, J = 3.3 Hz, 1H), 7.15 (d, J = 7.8 Hz, 1H), 7.01 (d, J = 9.0 Hz, 1H), 6.43 (d, J = 3.0 Hz, 1H), 4.70 (s, 2H), 3.82 (s, 3H), 2.58 (d, J = 4.5 Hz, 3H); LCMS: purity: 96%; MS (m/e): 455 (MH+). | + | | | |
| | | 1H NMR (DMSO-d6): δ 9.50 (s, 1H), 9.19 (s, 1H), 8.28-8.20 (m, 1H), 8.12 (d, J = 3.3 Hz, 1H), 7.97-7.84 (m, 3H), 7.53 (s, 1H), 7.42 (d, J = 8.7 Hz, 1H), 7.32-7.25 (d, J = 3.3 Hz, 1H), 6.35 (d, J = 3.0 Hz, 1H), 4.63 (s, | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 666 | 2-Chloro-N4-(3-chloro-4-methoxyphenyl)-5-fluoro-4-pyrimidineamine | 2H), 2.74 (d, J = 4.5 Hz, 3H), 2.58 (d, J = 4.5 Hz, 3H); LCMS: purity: 96%; MS (m/e): 482 (MH+). | – | | – | |
| 667 | 5-Fluoro-N2-[3-(oxazol-2-yl)phenyl]-N4-(3,4,5-trimethoxyphenyl)-2,4-pyrimidinediamine | 1H NMR (DMSO-d6): δ 9.94 (s, 1H), 8.28 (dd, J = 0.6 and 3.6 Hz, 1H), 7.75 (d, J = 2.1 Hz, 1H), 7.58 (dd, J = 2.4 and 8.7 Hz, 1H), 7.16 (d, J = 8.7 Hz, 1H), 3.84 (s, 3H); LCMS: purity: 96%; MS (m/e): 288 (M+). | + | | | |
| 668 | N4-(3,4-Ethylenedioxyphenyl)-5-fluoro-N2-(2,3,4-trimethoxyphenyl)-2,4-pyrimidinediamine | 1H NMR (DMSO-d6): δ 9.38 (s, 1H), 9.28 (s, 1H), 8.28 (s, 1H), 8.14-8.10 (m, 2H), 7.87 (d, J = 7.2 Hz, 1H), 7.50 (d, J = 7.5 Hz, 1H), 7.34-7.27 (m, 2H), 7.06 (s, 2H), 3.70 (s, 6H), 3.63 (s, 3H); LCMS: purity: 98%; MS (m/e): 438 (MH+). | + | | | |
| 669 | N4-(3-Chloro-4-methoxyphenyl)-5-fluoro-N2-(2,3,4-trimethoxyphenyl)-2,4-pyrimidinediamine | 1H NMR (DMSO-d6): δ 9.10 (s, 1H), 7.96 (d, J = 3.9 Hz, 1H), 7.75 (s, 1H), 7.50 (d, J = 8.7 Hz, 1H), 7.26 (d, J = 2.4 Hz, 1H), 7.10 (dd, J = 2.4 Hz, 1H), 6.74-6.64 (m, 2H), 4.25-4.18 (m, 4H), 3.77 (s, 3H), 3.75 (s, 3H), 3.74 (s, 3H); LCMS: purity: 99%; MS (m/e): 429 (MH+). | – | | | |
| 670 | N4-(4-Chloro-3-methoxyphenyl)-5-fluoro-N2-(2,3,4-trimethoxyphenyl)-2,4-pyrimidinediamine | 1H NMR (DMSO-d6): δ 9.26 (s, 1H), 8.01 (d, J = 3.6 Hz, 1H), 7.86 (s, 1H), 7.81 (d, J = 2.7 Hz, 1H), 7.54 (dd, J = 2.4 and 9.0 Hz, 1H), 7.43 (d, J = 9.0 Hz, 1H), 7.03 (d, J = 9.0 Hz, 1H), 6.70 (d, J = 9.3 Hz, 1H), 3.81 (s, 3H), 3.76 (s, 3H), 3.74 (s, 3H), 3.73 (s, 3H); LCMS: purity: 96%; MS (m/e): 435 (MH+). | – | | | |
| 671 | N4-(3-Chloro-4-trifluoromethoxyphenyl)-5-fluoro-N2-(2,3,4-trimethoxyphenyl)-2,4-pyrimidinediamine | 1H NMR (DMSO-d6): δ 816 (d, J = 4.8 Hz, 1H), 7.56-7.51 (m, 1H), 7.36-7.24 (m, 4H), 6.74 (d, J = 9.3 Hz, 1H), 3.80 (s, 3H), 3.74 (s, 3H), 3.73 (s, 3H), 3.68 (s, 3H); LCMS: purity: 95%; MS (m/e) 436 (MH+). | + | | | |
| 672 | N4-(2,2-Dimethyl-3-oxo-4H-benz[1,4]oxazin-6-yl)-5-fluoro-N2-(2,3,4-trimethoxyphenyl)-2,4-pyrimidinediamine | 1H NMR (DMSO-d6): δ 8.20 (d, J = 4.5 Hz, 1H), 8.05 (d, J = 2.7 Hz, 1H), 7.73-7.66 (m, 1H), 7.45 (d, J = 9.6 Hz, 1H), 7.24 (d, J = 8.7 Hz, 1H), 6.75 (d, J = 9.0 Hz, 1H), 3.78 (s, 3H), 3.74 (s, 3H), 3.73 (s, 3H); LCMS: purity: 95%; MS (m/e): 490 (MH+). | + | | | |
| 673 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine Benzenesulfonic Acid Salt | 1H NMR (DMSO-d6): δ 10.73 (s, 1H), 10.44 (s, 1H), 8.21 (d, J = 4.8 Hz, 1H), 7.43-7.32 (m, 1H), 7.27-7.13 (m, 2H), 6.89 (d, J = 8.4 Hz, 1H), 6.65 (d, J = 9.6 Hz, 1H), 3.77 (s, 3H), 3.76 (s, 3H), 3.74 (s, 3H), 1.41 (s, 6H); LCMS: purity: 98%; MS (m/e): 470 (MH+). | + | + | | |
| 674 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine Methanesulfonic Acid Salt | 1H NMR (DMSO-d6): δ 11.14 (s, 1H), 9.98 (s, 1H), 9.63 (s, 1H), 8.17 (d, J = 3.9 Hz, 1H), 7.62-7.52 (m, 3H), 7.36-7.25 (m, 4H), 6.87 (s, 2H), 3.66 (s, 6H), 3.61 (s, 3H), 1.43 (s, 6H). | + | + | | |
| 675 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine p-Toluene Sulfonic Acid Salt | 1H NMR (DMSO-d6): δ 11.13 (s, 1H), 9.95 (s, 1H), 9.62 (s, 1H), 8.18 (d, J = 3.9 Hz, 1H), 7.56 (d, J = 9.0 Hz, 1H), 7.31 (d, J = 8.4 Hz, 1H), 6.88 (s, 2H), 3.66 (s, 6H), 3.61 (s, 3H), 2.33 (s, 3H), 1.43 (s, 6H). 1H NMR (DMSO-d6): δ 11.12 (s, 1H), 9.89 (s, 1H), 9.57 (s, 1H), 8.17 (d, J = 3.9 Hz, 1H), 7.57 (d, J = 8.4 Hz, 1H), 7.45 (d, J = 7.8 Hz, 2H), 7.31 (d, J = 8.4 Hz, 1H), 7.09 (d, J = 7.8 Hz, 2H), 6.89 (s, 2H), 3.66 (s, 6H), 3.61 (s, 3H), 2.28 (s, 3H), 1.43 (s, 6H). | + | + | | |
| 676 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine 4-Hydroxybenzenesulfonic Acid Salt | 1H NMR (DMSO-d6): δ 11.12 (s, 1H), 9.81 (s, 1H), 9.53 (s, 1H), 8.16 (d, J = 4.2 Hz, 1H), 7.58 (d, J = 8.1 Hz, 2H), 7.37 (d, J = 8.1 Hz, 2H), 7.31 (d, J = 8.7 Hz, 1H), 6.90 (s, 2H), 6.64 (d, J = 8.7 Hz, 2H), 3.66 (s, 6H), 3.61 (s, 3H), 1.43 (s, 6H). | + | + | | |
| 677 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine 2,4,6-Trimethylbenzenesulfonic Acid Salt | 1H NMR (DMSO-d6): δ 11.10 (s, 1H), 9.72 (s, 1H), 9.47 (s, 1H), 8.15 (d, J = 4.2 Hz, 1H), 7.62-7.56 (m, 1H), 7.31 (d, J = 8.1 Hz, 1H), 6.91 (s, 2H), 6.72 (s, 2H), 3.66 (s, 6H), 3.61 (s, 3H), 2.48 (s, 6H), 2.16 (s, 3H), 1.43 (s, 6H). | + | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 678 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine 0.5 Pyridine-3-sulfonic Acid Salt | 1H NMR (DMSO-d6): δ 11.08 (s, 2H), 9.46 (s, 2H), 9.30 (s, 2H), 8.91 (s, 1H), 8.70 (d, J = 5.4 Hz, 1H), 8.37 (dd, J = 1.5 and 7.8 Hz, 1H), 8.13 (d, J = 3.6 Hz, 2H), 7.80-7.74 (m, 1H), 7.62 (d, J = 8.1 Hz, 2H), 7.31 (d, J = 8.1 Hz, 2H), 6.97 (s, 4H), 3.66 (s, 6H), 1.43 (s, 12H). | + | | | |
| 679 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine p-Ethylbenzenesulfonic Acid Salt | 1H NMR (DMSO-d6): δ 11.08 (s, 1H), 9.44 (s, 1H), 9.26 (s, 1H), 8.13 (d, J = 3.3 Hz, 1H), 7.63 (d, J = 8.4 Hz, 1H), 7.47 (d, J = 8.1 Hz, 2H), 7.31 (d, J = 8.1 Hz, 1H), 7.12 (d, J = 7.8 Hz, 2H), 6.97 (s, 2H), 3.65 (s, 6H), 3.59 (s, 3H), 2.57 (q, J = 7.8 Hz, 2H), 1.42 (s, 6H), 1.15 (t, J = 7.8 Hz, 3H). | + | + | | |
| 680 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine 0.5 1,2-Ethanedisulfonic Acid Salt | R932125 1H NMR (DMSO-d6): δ 11.08 (s, 2H), 9.54 (s, 2H), 9.35 (s, 2H), 8.14 (d, J = 3.9 Hz, 2H), 7.60 (d, J = 8.4 Hz, 2H), 7.31 (d, J = 8.4 Hz, 2H), 6.95 (s, 4H), 3.66 (s, 12H), 3.60 (s, 6H), 2.62 (s, 4H), 1.43 (s, 12H). | + | | | |
| 681 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine (1R)-10-Camphorsulfonic Acid Salt | 1H NMR (DMSO-d6): δ 11.11 (s, 1H), 9.83 (s, 1H), 9.54 (s, 1H), 8.17 (d, J = 3.9 Hz, 1H), 7.57 (d, J = 8.7 Hz, 1H), 7.30 (d, J = 8.4 Hz, 1H), 6.99 (s, 2H), 3.66 (s, 6H), 3.61 (s, 3H), 2.86 (d, J = 14.7 Hz, 1H), 2.67 (t, J = 9.9 Hz, 1H), 2.38 (d, J = 14.7 Hz, 1H), 2.22 (dt, J = 3.6 and 18.0 Hz, 1H), 1.93 (t, J = 4.5 Hz, 1H), 1.89-1.75 (m, 2H), 1.43 (s, 6H), 1.30-1.23 (m, 2H), 1.08 (t, J = 6.9 Hz, 1H), 1.04 (s, 3H), 0.74 (s, 3H). | + | + | | |
| 682 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine (1S)-10-Camphorsulfonic Acid Salt | 1H NMR (DMSO-d6): δ 11.08 (s, 1H), 9.55 (s, 1H), 9.36 (s, 1H), 8.14 (d, J = 3.9 Hz, 1H), 7.60 (d, J = 8.7 Hz, 1H), 7.31 (d, J = 8.4 Hz, 1H), 6.94 (s, 2H), 3.66 (s, 6H), 3.60 (s, 3H), 2.85 (d, J = 14.7 Hz, 1H), 2.68 (t, 11.4 Hz, 1H), 2.36 (d, J = 14.7 Hz, 1H), 2.28-2.17 (m, 1H), 1.92 (t, J = 4.8 Hz, 1H), 1.89-1.74 (m, 2H), 1.43 (s, 6H), 1.26 (q, J = 10.8 Hz, 2H), 1.05 (s, 3H), 0.74 (s, 3H). | + | + | | |
| 683 | N4-(2,2-Dimethyl-3-oxo-4H-5-pyrid[1,4]oxazin-6-yl)-5-fluoro-N2-[1-(N-methylamino)carbonylmethyleneindol-5-yl]-2,4-pyrimidinediamine | 1H NMR (DMSO-d6): δ 11.04 (s, 1H), 9.08-8.90 (m, 2H), 8.07 (d, J = 3.3 Hz, 1H), 7.99-7.89 (m, 1H), 7.81-7.96 (m, 1H), 7.70-7.64 (m, 1H), 7.29-7.20 (m, 4H), 6.29 (d, J = 3.0 Hz, 1H), 4.73 (s, 2H), 2.61 (d, J = 4.5 Hz, 3H), 1.42 (s, 6H); LCMS: purity: 99%; MS (m/e): 491 (MH+). | + | + | | |
| 684 | N4-(4-Chloro-3,5-dimethylphenyl)-N4-(2,2-dimethyl-3-oxo-4H-5-pyrid[1,4]oxazin-6-yl)-5-fluoro-2,4-pyrimidinediamine p-Toluenesulfonic Acid Salt | 1H NMR (DMSO-d6): δ 11.13 (s, 1H), 9.68 (s, 1H), 9.46 (s, 1H), 8.17 (d, J = 3.6 Hz, 1H), 7.51-7.35 (m, 6H), 7.09 (d, J = 8.4 Hz, 2H), 2.28 (s, 3H), 2.22 (s, 6H), 1.43 (s, 6H). | + | | | |
| 685 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine Hydrogen Chloride Salt | 1H NMR (DMSO-d6): δ 11.31 (s, 1H), 9.89 (s, 1H), 9.66 (s, 1H), 8.18 (d, J = 4.5 Hz, 1H), 7.55 (d, J = 8.4 Hz, 1H), 7.30 (d, J = 8.7 Hz, 1H), 6.89 (s, 2H), 3.65 (s, 6H), 3.61 (s, 3H), 1.43 (s, 6H). | + | + | | |
| 686 | N4-(2,2-Dimethyl-3-oxo-4H-5-pyrid[1,4]oxazin-6-yl)-N2-(3,5-dichloro-4-hydroxyphenyl)-5-fluoro-2,4-pyrimidinediamine | 1H NMR (DMSO-d6): δ 11.07 (s, 1H), 9.32 (s, 1H), 9.27 (s, 1H), 8.13 (d, J = 3.3 Hz, 1H), 7.63 (s, 2H), 7.45 (d, J = 8.7 Hz, 1H), 7.35 (d, J = 8.7 Hz, 1H), 1.43 (s, 6H); LCMS: purity: 92%; MS (m/e): 467 (MH+). | + | + | | |
| 687 | N2,N4-Bis(3-oxo-2,2,4-trimethyl-5-pyrid[1,4]oxazin-6-yl)-5-fluoro-2,4-pyrimidinediamine | 1H NMR (DMSO-d6): δ 9.49 (bs, 2H), 8.18 (d, J = 3.3 Hz, 1H), 7.93 (d, J = 8.7 Hz, 1H), 7.74 (d, J = 8.4 Hz, 1H), 7.37 (d, J = 8.7 Hz, 1H), 7.28 (d, J = 8.4 Hz, 1H), 3.34 (s, 3H), 3.33 (s, 3H), 1.44 (s, 6H), 1.41 (s, 6H); LCMS: purity: 98%; MS (m/e): 509 (MH+). | + | + | | |
| 688 | N2,N4-Bis(2,2-dimethyl-4-carbomethoxymethyl-3-oxo-5-pyrid[1,4]oxazin-6-yl)-2,4-pyrimidinediamine | 1H NMR (DMSO-d6): δ 9.55 (s, 1H), 9.49 (s, 1H), 8.19 (s, 1H), 7.97 (d, J = 8.7 Hz, 1H), 7.79 (d, J = 8.7 Hz, 1H), 7.45 (d, J = 8.7 Hz, 1H), 7.38 (d, J = 8.7 Hz, 1H), 4.81 (s, 2H), 4.80 (s, 2H), 3.67 (s, 3H), 3.66 (s, 3H), 1.48 (s, 6H), 1.45 (s, 6H); LCMS: purity: 97%; MS (m/e): 625 (MH+). | - | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 689 | 5-Fluoro-N4-(3-oxo-2,2,4-trimethyl-5-pyrid[1,4]oxazin-6-yl)-N2-(3,4,5-trimethoxyphenyl)-2,4-pyrimidinediamine | 1H NMR (DMSO-d6): δ 9.42 (s, 1H), 9.13 (s, 1H), 8.14 (d, J = 3.6 Hz, 1H), 7.80 (d, J = 8.4 Hz, 1H), 7.32 (d, J = 8.4 Hz, 1H), 7.03 (s, 2H), 3.66 (s, 6H), 3.60 (s, 3H), 1.44 (s, 6H); LCMS: purity: 97%; MS (m/e): 485 (MH+). | | | | |
| 690 | N4-(2,2-Dimethyl-4-carbomethoxymethyl-3-oxo-5-pyrid[1,4]oxazin-6-yl)-5-fluoro-N2-(3,4,5-trimethoxyphenyl)-2,4-pyrimidinediamine | 1H NMR (DMSO-d6): δ 9.46 (s, 1H), 9.15 (s, 1H), 8.15 (d, J = 3.6 Hz, 1H), 7.86 (d, J = 8.7 Hz, 1H), 7.37 (d, J = 8.7 Hz, 1H), 7.04 (s, 2H), 4.80 (s, 2H), 3.67 (s, 6H), 3.66 (s, 3H), 3.60 (s, 3H), 1.47 (s, 6H); LCMS: purity: 96%; MS (m/e): 543 (MH+). | | + | | |
| 691 | N4-(2,2-Dimethyl-4-carbomethoxymethyl-3-oxo-5-pyrid[1,4]oxazin-6-yl)-5-fluoro-N4-carbomethoxymethyl-N2-(3,4,5-trimethoxyphenyl)-2,4-pyrimidinediamine | 1H NMR (DMSO-d6): δ 9.27 (s, 1H), 8.22 (d, J = 4.8 Hz, 1H), 7.42 (d, J = 8.4 Hz, 1H), 6.98 (s, 2H), 6.81 (dd, J = 3.3 and 8.4 Hz, 1H), 4.83 (s, 2H), 4.63 (s, 2H), 3.72 (s, 6H), 3.63 (s, 3H), 3.59 (s, 3H), 3.57 (s, 3H), 1.47 (s, 6H); LCMS: purity: 99%; MS (m/e): 615 (MH+). | + | | | |
| 692 | N2-[3,5-Dimethoxy-4-(2-(N-morpholino)ethyl)oxo)phenyl]-N4-(2,2-dimethyl-3-oxo-4H-5-pyrid[1,4]oxazin-6-yl)-5-fluoro-2,4-pyrimidinediamine | 1H NMR (DMSO-d6): δ 11.04 (s, 1H), 9.14 (s, 1H), 9.09 (s, 1H), 8.11 (d, J = 3.6 Hz, 1H), 7.65 (d, J = 8.4 Hz, 1H), 7.31 (d, J = 8.4 Hz, 1H), 7.02 (s, 2H), 3.87 (t, J = 6.0 Hz, 2H), 3.65 (s, 6H), 3.58-3.53 (m, 4H), 2.58 (t, J = 6.0 Hz, 2H), 2.47-2.42 (m, 4H), 1.42 (s, 6H); LCMS: purity: 96%; MS (m/e): 570 (MH+). | + | + | | |
| 693 | N2,N4-Bis(2,2-dimethyl-3-oxo-4H-5-pyrid[1,4]oxazin-6-yl)-5-fluoro-2,4-pyrimidinediamine | 1H NMR (DMSO-d6): δ 11.07 (s, 1H), 10.91 (s, 1H), 9.27 (s, 1H), 9.12 (s, 1H), 8.13 (d, J = 3.3 Hz, 1H), 7.69 (d, J = 8.4 Hz, 1H), 7.60 (d, J = 9.0 Hz, 1H), 7.32 (d, J = 8.4 Hz, 1H), 7.22 (d, J = 9.0 Hz, 1H), 1.43 (s, gH), 1.39 (s, 6H); LCMS: purity: 99%; MS (m/e): 481 (MH+). | + | + | | |
| 694 | N4-(3-Chloro-4-methoxyphenyl)-N2-(1-ethylindazol-5-yl)-5-fluoro-2,4-pyrimidinediamine | 1H NMR (DMSO-d6): δ 10.36 (s, 1H), 10.21 (s, 1H), 8.24 (d, 1H, J = 4.9 Hz), 7.92 (s, 1H), 7.83 (s, 1H), 7.74 (d, 1H, J = 2.6 Hz), 7.65 (d, 1H, J = 9.1 Hz), 7.54 (app dd, 1H, J = 2.3 and 9.1 Hz), 7.38 (dd, 1H, J = 1.8 and 9.1 Hz), 7.09 (d, 1H, J = 9.1 Hz), 4.40 (qt, 2H, J = 7.0 Hz), 3.83 (s, 3H), 1.38 (t, 3H, J = 7.0 Hz). LCMS: ret. time: 9.30 min.; purity: 97%; MS (m/e): 414 (MH+) | + | + | − | |
| 695 | N4-(3,4-Dichlorophenyl)-N2-(1-ethylindazol-5-yl)-5-fluoro-2,4-pyrimidinediamine | ¹H NMR (DMSO-d6): δ 10.28 (s, 1H), 10.02 (s, 1H), 8.28 (d, 1H, J = 4.7 Hz), 8.02 (d, 1H, J = 2.3 Hz), 7.94 (s, 1H), 7.87 (s, 1H), 7.70 (s, 1H), 7.66 (d, 1H, J = 9.1 Hz), 7.52 (d, 1H, J = 8.8 Hz), 7.42 (dd, 1H, J = 2.3 and 8.8 Hz), 4.41 (qt, 2H, J = 7.0 Hz), 1.38 (t, 3H, J = 7.0 Hz). LCMS: ret. time: 12.41 min.; purity: 99%; MS (m/e): 418 (MH+). | − | + | − | |
| 696 | N4-(2,2-Dimethyl-3-oxo-4H-benz[1,4]oxazin-6-yl)-N2-(1-ethylindazol-5-yl)-5-fluoro-2,4-pyrimidinediamine | ¹H NMR (DMSO-d6): δ 10.77 (s, 1H), 10.39 (s, 1H), 10.21 (s, 1H), 8.22 (d, 1H, J = 5.3 Hz), 7.89 (s, 1H), 7.61 (d, 1H, J = 8.8 Hz), 7.37 (d, 1H, J = 8.8 Hz), 7.20 (dd, 2H, J = 2.3 and 8.2 Hz), 6.81 (d, 1H, J = 8.2 Hz), 4.39 (qt, 2H, J = 7.0 Hz), 1.37 (s, 6H), 1.36 (t, 3H, J = 7.0 Hz). LCMS: ret. time: 8.77 min.; purity: 97%; MS (m/e): 448 (MH+). | + | + | + | + |
| 697 | N2-(1-Ethylindazol-5-yl)-5-fluoro-N4-(4-fluoro-3-methoxyphenyl)-2,4-pyrimidinediamine | ¹H NMR (DMSO-d6): δ 10.42 (s, 1H), 10.29 (s, 1H), 8.26 (d, 1H, J = 4.9 Hz), 7.89 (s, 2H), 7.63 (d, 1H, J = 8.8 Hz), 7.44 (d, 1H, J = 8.2 Hz), 7.37 (d, 1H, J = 9.0 Hz), 7.31-7.23 (m, 1H), 7.19 (dd, 1H, J = 8.8 and 11.8 Hz), 4.41 (qt, 2H, J = 7.0 Hz), 3.60 (s, 3H), 1.37 (t, 3H, J = 7.0 Hz). LCMS: ret. time: 9.09 min.; purity: 98%; MS (m/e): 398 (MH+) | + | + | − | |
| 698 | N4-(3-Chloro-4-methoxyphenyl)-N2-(1-ethylindazol-6-yl)-5-fluoro-2,4-pyrimidinediamine | ¹H NMR (DMSO-d6): δ 10.44 (s, 1H), 10.40 (s, 1H), 8.32 (d, 1H, J = 4.9 Hz), 7.92 (s, 1H), 7.78 (app t, 2H, J = 2.6 Hz), 7.67 (d, 1H, J = 8.5 Hz), 7.58-7.52 (dt, 1H, J = 2.6 and 9.1 Hz), 4.11 (qt, 2H, J = 7.0 Hz), 3.83 (s, 3H), 1.25 (t, | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 699 | N4-(3,4-Dichlorophenyl)-N2-(1-ethylindazol-6-yl)-5-fluoro-2,4-pyrimidinediamine | 3H, J = 7.0 Hz). LCMS: ret. time: 10.83 min.; purity: 96%; MS (m/e): 414 (MH+)<br>¹H NMR (DMSO-d6): δ 9.92 (s, 1H), 9.78 (s, 1H), 8.27 (d, 1H, J = 4.1 Hz0, 8.08 (app d, 1H, J = 2.6 Hz), 7.93 (s, 1H), 7.91 (s, 1H), 7.76 (dt, 1H, J = 2.6 and 8.1 Hz), 7.62 (d, 1H, J = 8.5 Hz), 7.54 (d, 1H, J = 8.8 Hz), 7.23 (d, 1H, J = 8.5 Hz), 4.14 (qt, 2H, J = 7.0 Hz), 1.29 (t, 3H, J = 7.0 Hz). LCMS: ret. time: 14.02 min.; purity: 98%; MS (m/e): 418 (MH+). | + | + |  |  |
| 700 | N4-(2,2-Dimethyl-3-oxo-4H-benz[1,4]oxazin-6-yl)-N2-(1-ethylindazol-6-yl)-5-fluoro-2,4-pyrimidinediamine | ¹H NMR (DMSO-d6): δ 10.75 (s, 1H), 10.18 (s, 2H), 8.25 (d, 1H, J = 4.7 Hz), 7.94 (s, 1H), 7.84 (s, 1H), 7.63 (d, 1H, J = 8.5 Hz) 7.27-7.17 (m, 3H), 6.86 (d, 1H, J = 8.5 Hz), 4.14 (qt, 2H, J = 7.0 Hz), 1.38 (s, 6H), 1.28 (t, 3H, J = 7.0 Hz). LCMS: ret. time: 9.07 min.; purity: 98%; MS (m/e): 448 (MH+) | + | + | + |  |
| 701 | N2-(1-Ethylindazol-6-yl)-5-fluoro-N4-(4-fluoro-3-methoxyphenyl)-2,4-pyrimidinediamine | ¹H NMR (DMSO-d6): δ 10.18 (s, 2H), 8.26 (d, 1H, J = 4.7 Hz), 7.93 (s, 1H), 7.90 (s, 1H), 7.62 (d, 1H, J = 8.5 Hz) 7.50-7.46 (m, 1H), 7.30-7.27 (m, 1H), 7.19-7.13 (m, 2H), 4.09 (qt, 2H, J = 7.0 Hz), 3.60 (s, 3H), 1.27 (t, 3H, J = 7.0 Hz). LCMS: ret. time: 10.82 min.; purity: 99%; MS (m/e): 397 (MH+) | + |  | + |  |
| 702 | N4-(3-Chloro-4-methoxyphenyl)-5-fluoro-N2-(1-n-propylindazol-5-yl)-2,4-pyrimidinediamine | ¹H NMR (DMSO-d6): δ 10.39 (s, 1H), 8.26 (s, 1H), 8.26 (d, 1H, J = 4.7 Hz), 7.92 (s, 1H), 7.82 (s, 1H), 7.75 (d, 1H, J = 2.7 Hz), 6.66 (d, 1H, J = 9.1 Hz), 7.54 (dt, 1H, J = 2.3 and 9.1 Hz), 7.08 (d, 1H, J = 9.1 Hz), 4.33 (t, 2H, J = 7.0 Hz), 3.83 (s, 3H), 1.82 (q, 2H, J = 7.03 Hz), 0.81 (t, 3H, J = 7.0 Hz). LCMS: ret. time: 10.32 min.; purity: 98%; MS (m/e) 427 (MH+) |  | + |  |  |
| 703 | N4-(3,4-Dichlorophenyl)-5-fluoro-N2-(1-n-propylindazol-5-yl)-2,4-pyrimidinediamine | ¹H NMR (DMSO-d6): δ 10.21 (s, 1H), 9.93 (s, 1H), 8.26 (d, 1H, J = 4.4 Hz), 8.01 (d, 1H, J = 2.6 Hz), 7.94 (s, 1H), 7.87 (s, 1H), 7.69 (dd, 1H, J = 1.8 and 8.8 Hz), 7.65 (d, 1H, J = 9.1 Hz), 7.49 (d, 1H, J = 8.8 Hz), 7.41 (dd, 1H, J = 9.1 Hz), 4.34 (t, 2H, J = 7.0 Hz), 1.83 (qt, 2H, J = 7.0 Hz), 0.82 (t, 3H, J = 7.0 Hz). LCMS: ret. time: 13.49 min.; purity: 98%; MS (m/e): 432 (MH+) |  |  |  | + |
| 704 | N4-(2,2-Dimethyl-3-oxo-4H-benz[1,4]oxazin-6-yl)-5-fluoro-N2-(1-n-propylindazol-5-yl)-2,4-pyrimidinediamine | ¹H NMR (DMSO-d6): δ 10.75 (s, 1H), 10.21 (s, 2H), 8.26 (d, 1H, J = 4.9 Hz), 7.94 (s, 1H), 7.83 (s, 1H), 7.63 (d, 1H, J = 8.8 Hz), 7.27-7.17 (m, 3H), 6.86 (d, 1H, J = 8.8 Hz), 4.06 (t, 2H, J = 7.0 Hz), 1.72 (qt, 2H, J = 7.0 Hz), 1.38 (s, 6H), 0.71 (t, 3H, J = 7.0 Hz). LCMS: ret. time: 8.27 min.; purity: 96%; MS (m/e): 462 (MH+) |  | + |  |  |
| 705 | 5-Fluoro-N4-(4-fluoro-3-methoxyphenyl)-N2-(1-n-propylindazol-5-yl)-2,4-pyrimidinediamine | ¹H NMR (DMSO-d6): δ 10.46 (s, 1H), 10.35 (s, 1H), 8.28 (d, 1H, J = 4.9 Hz), 7.90 (s, 1H), 7.87 (s, 1H), 7.63 (d, 1H, J = 9.1 Hz), 7.43 (dd, 1H, J = 2.3 and 8.8 Hz), 7.27-7.22 (m, 1H), 7.14 (dd, 1H, J = 1.8 and 11.1 Hz), 4.34 (t, 2H, J = 7.0 Hz), 3.60 (s, 3H), 1.82 (qt, 2H, J = 7.0 Hz), 0.81 (t, 3H, J = 7.0 Hz). LCMS: ret. time: 10.03 min.; purity: 99%; MS (m/e): 411 (MH+) |  | + |  |  |
| 706 | N4-(3-Chloro-4-methoxyphenyl)-5-fluoro-N2-(1-n-propylindazol-6-yl)-2,4-pyrimidinediamine | ¹H NMR (DMSO-d6): δ 10.51 (s, 1H), 10.44 (s, 1H), 8.33 (d, 1H, J = 4.9 Hz), 7.96 (s, 1H), 7.77 (d, 1H, J = 2.6 Hz), 7.67 (d, 1H, J = 8.8 Hz), 7.55 (dd, 1H, J = 2.6 and 8.8 Hz), 7.16 (dd, 1H, J = 2.6 and 8.8 Hz), 4.03 (t, 2H, J = 7.0 Hz), 3.83 (s, 3H), 1.68 (qt, 2H, J = 7.0 Hz), 0.68 (t, 3H, J = 7.0 Hz). LCMS: ret. time: 11.82 min.; purity: 99%; MS (m/e): 427 (MH+) |  | + | + |  |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 707 | N4-(3,4-Dichlorophenyl)-5-fluoro-N2-(1-n-propylindazol-6-yl)-2,4-pyrimidinediamine | ¹H NMR (DMSO-d6): δ 10.15 (s, 1H), 10.02 (s, 1H), 8.30 (d, 1H, J = 4.4 Hz), 8.06 (d, 1H, J = 2.6 Hz), 7.93 (s, 1H), 7.89 (s, 1H), 7.73 (dd, 1H, J = 2.6 and 8.5 Hz), 7.65 (d, 1H, J = 8.5 Hz), 7.55 (d, 1H, J = 8.8 Hz), 7.21 (d, 1H, J = 8.8 Hz), 4.07 (t, 2H, J = 7.0 Hz), 1.71 (qt, 2H, J = 7.0 Hz), 0.72 (t, 3H, J = 7.0 Hz). LCMS: ret. time: 14.82 min.; purity: 98%; MS (m/e): 433 (MH+) | + | | | |
| 708 | N4-(2,2-Dimethyl-3-oxo-4H-benz[1,4]oxazin-6-yl)-5-fluoro-N2-(1-n-propylindazol-6-yl)-2,4-pyrimidinediamine | ¹H NMR (DMSO-d6): δ 10.77 (s, 1H), 10.37 (s, 1H), 10.16 (s, 1H), 8.21 (d, 1H, J = 5.3 Hz), 7.89 (s, 1H), 7.87 (s, 1H), 7.61 (d, 1H, J = 8.8 Hz), 7.37 (dd, 1H, J = 1.8 and 8.8 Hz), 7.20 (d, 1H, J = 8.8 Hz), 8.87 (d, 1H, J = 8.8 Hz), 4.31 (t, 2H, J = 7.0 Hz), 1.81 (qt, 2H, J = 7.0 Hz), 1.36 (s, 6H), 0.79 (t, 2H, J = 7.0 Hz). LCMS: ret. time: 9.97 min.; purity: 99%; MS (m/e): 462 (MH+) | | | | + |
| 709 | 5-Fluoro-N4-(4-fluoro-3-methoxyphenyl)-N2-(1-n-propylindazol-6-yl)-2,4-pyrimidinediamine | ¹H NMR (DMSO-d6): δ 10.40 (s, 1H), 10.37 (s, 1H), 8.33 (d, 1H, J = 5.0 Hz), 7.96 (s, 1H), 7.84 (s, 1H), 7.64 (d, 1H, J = 8.5 Hz), 7.47 (dt, 1H, J = 1.8 and 8.5 Hz), 7.26-7.22 (m, 2H), 7.15 (dd, 1H, J = 11.8 and 8.8 Hz), 4.02 (t, 2H, J = 7.0 Hz), 3.55 (s, 3H), 1.68 (qt, 2H, J = 7.0 Hz), 0.69 (t, 3H, J = 7.0 Hz). LCMS: ret. time: 11.72 min.; purity: 100%; MS (m/e): 411 (MH+) | | | | |
| 710 | N2-(1-n-Butylindazol-5-yl)-N4-(3-chloro-4-methoxyphenyl)-5-fluoro-2,4-pyrimidinediamine | ¹H NMR (DMSO-d6): δ 10.40 (s, 1H), 7.92 (s, 1H), 7.82 (s, 1H), 7.75 (d, 1H, J = 2.3 Hz), 7.65 (d, 1H, J = 9.1 Hz), 7.54 (dd, 1H, J = 2.3 and 9.1 Hz), 7.39 (d, 1H, J = 9.1 Hz), 7.09 (d, 1H, J = 9.1 Hz), 4.36 (t, 2H, J = 7.3 Hz), 3.83 (s, 3H), 1.78 (q, 2H, J = 7.3 Hz), 1.22 (app hex, 2H, J = 7.3 Hz), 0.86 (t, 3H, J = 7.3 Hz). LCMS: ret. time: 12.69 min.; purity: 99%; MS (m/e): 442 (MH+) | + | | | |
| 711 | N2-(1-n-Butylindazol-5-yl)-N4-(3,4-dichlorophenyl)-5-fluoro-2,4-pyrimidinediamine | ¹H NMR (DMSO-d6): δ 10.43 (s, 1H), 10.20 (s, 1H), 8.32 (d, 1H, J = 4.7 Hz), 8.00 (d, 1H, J = 2.3 Hz), 7.95 (s, 1H), 7.83 (s, 1H), 7.67 (d, 2H, J = 8.8 Hz), 7.49 (d, 1H, J = 8.8 Hz), 7.41 (dd, 1H, J = 2.3 and 8.8 Hz), 4.38 (t, 2H, J = 7.3 Hz), 1.79 (q, 2H, J = 7.3 Hz), 1.23 (app hex, 2H, J = 7.3 Hz), 0.87 (t, 3H, J = 7.3 Hz). LCMS: ret. time: 15.87 min.; purity: 98%; MS (m/e): 446 (MH+) | + | | | |
| 712 | N2-(1-n-Butylindazol-5-yl)-N4-(2,2-dimethyl-3-oxo-4H-benz[1,4]oxazin-6-yl)-5-fluoro-2,4-pyrimidinediamine | ¹H NMR (DMSO-d6): δ 10.75 (s, 1H), 10.28 (s, 1H), 10.05 (s, 1H), 8.19 (d, 1H, J = 4.9 Hz), 7.89 (s, 2H), 7.60 (d, 1H, J = 9.1 Hz), 7.38 (d, 1H, J = 9.1 Hz), 7.20 (dd, 1H, J = 1.8 and 9.1 Hz), 7.16 (s, 1H), 6.86 (d, 1H, J = 9.1 Hz), 4.35 (t, 2H, J = 7.3 Hz), 1.77 (q, 2H, J = 7.3 Hz), 1.36 (s, 6H), 1.20 (app hex, 2H, J = 7.3 Hz), 0.86 (t, 3H, J = 7.3 Hz). LCMS: ret. time: 11.06 min.; purity: 97%; MS (m/e): 476 (MH+) | | + | | |
| 713 | N2-(1-n-Butylindazol-5-yl)-5-fluoro-N4-(4-fluoro-3-methoxyphenyl)-2,4-pyrimidinediamine | ¹H NMR (DMSO-d6): δ 10.42 (s, 1H), 10.29 (s, 1H), 8.27 (d, 1H, J = 4.9 Hz), 7.89 (s, 1H), 7.87 (s, 1H), 7.63 (d, 1H, J = 8.8 Hz), 7.43 (dd, 1H, J = 2.3 and 8.8 Hz), 7.36 (dd, 1H, J = 1.8 and 9.1 Hz), 7.28-7.23 (m, 1H), 7.13 (dd, 1H, J = 11.3 and 9.1 Hz0, 4.37 (t, 2H, J = 7.3 Hz), 3.60 (s, 3H), 1.78 (q, 2H, J = 7.3 Hz), 1.22 (app hex, 2H, J = 7.3 Hz), 0.86 (t, 3H, J = 7.3 Hz). LCMS: ret. time: 12.60 min.; purity: 99%; MS (m/e): 426 (MH+) | | + | | |
| 714 | N2-(1-n-Butylindazol-6-yl)-N4-(3-chloro-4-methoxyphenyl)-5-fluoro-2,4-pyrimidinediamine | ¹H NMR (DMSO-d6): δ 10.27 (s, 2H), 8.30 (d, 1H, J = 4.7 Hz), 7.94 (s, 1H), 7.82 (s, 1H), 7.77 (d, 1H, J = 2.6 Hz), 7.65 (d, 1H, J = 8.8 Hz), 7.56 (dd, 1H, J = 2.6 and 8.8 Hz), 7.16 (d, 1H, J = 8.8 Hz0, 7.11 (d, 1H, J = 8.8 Hz), 4.06 (t, 2H, J = 7.3 Hz), 3.83 (s, 3H), 1.64 (q, 2H, J = 7.3 Hz), | | | + | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 715 | N2-(1-n-Butylindazol-6-yl)-N4-(3,4-dichlorophenyl)-5-fluoro-2,4-pyrimidinediamine | 1.08 (app hex, 2H, J = 7.3 Hz), 0.78 (t, 3H, J = 7.3 Hz). LCMS: ret. time: 14.10 min.; purity: 96%; MS (m/e): 442 (MH+) $^1$H NMR (DMSO-d6): δ 10.21 (s, 1H), 10.09 (s, 1H), 8.32 (d, 1H, J = 4.4 Hz), 8.05 (d, 1H, J = 2.3 Hz), 7.94 (s, 1H), 7.86 (s, 1H0, 7.72 (d, 1H, J = 8.8 Hz), 7.66 (d, 1H, J = 8.8 Hz), 7.55 (d, 1H, J = 8.8 Hz), 7.20 (d, 1H, J = 8.8 Hz), 4.11 (t, 2H, J = 7.3 Hz), 1.66 (q, 2H, J = 7.3 Hz), 1.12 (app hex, 2H, J = 7.3 Hz), 0.79 (t, 3H, J = 7.3 Hz). LCMS ret. time: 16.86 min.; purity: 96%; MS (m/e): 446 (MH+) | + | | | |
| 716 | N2-(1-n-Butylindazol-6-yl)-N4-(2,2-dimethyl-3-oxo-4H-benz[1,4]oxazin-6-yl)-5-fluoro-2,4-pyrimidinediamine | $^1$H NMR (DMSO-d6): δ 11.77 (s, 1H), 10.40 (s, 1H), 10.36 (s, 1H), 8.29 (d, 1H, J = 4.9 Hz), 7.94 (s, 1H), 7.81 (s, 1H), 7.62 (d, 1H, J = 8.8 Hz), 7.23 (s, 2H), 7.18 (d, 1H, J = 8.8 Hz), 6.85 (d, 1H, J = 8.8 Hz), 4.10 (t, 2H, J = 7.3 Hz), 1.67 (q, 2H, J = 7.3 Hz), 1.38 (s, 6H), 1.09 (app hex, J = 2H, J = 7.3 Hz), 0.78 (t, 3H, J = 7.3 Hz). LCMS ret. time: 12.49 min.; purity: 96%; MS (m/e): 476 (MH+) | | | | + |
| 717 | N2-(1-n-Butylindazol-6-yl)-5-fluoro-N4-(4-fluoro-3-methoxyphenyl)-2,4-pyrimidinediamine | $^1$H NMR (DMSO-d6): δ 10.42 (s, 1H), 10.37 (s, 1H), 8.33 (d, 1H, J = 4.7 Hz), 7.96 (s, 1H), 7.84 (s, 1H), 7.64 (d, 1H, J = 8.8 Hz), 7.50-7.46 (m, 1H), 7.27-7.22 (m, 1H), 7.16 (app t, 1H, J = 11.8 and 8.8 Hz), 4.06 (t, 2H, J = 7.3 Hz), 3.54 (s, 3H), 1.65 (q, 2H, J = 7.3 Hz), 1.08 (app hex, 2H, J = 7.3 Hz), 0.78 (t, 3H, J = 7.3 Hz). LCMS: ret. time: 14.23 min.; purity: 97%; MS (m/e): 425 (MH+) | + | | | |
| 718 | N4-(3-Chloro-4-methoxyphenyl)-N2-[1-(cyclohexylmethyl)indazol-5-yl]-5-fluoro-2,4-pyrimidinediamine | $^1$H NMR (DMSO-d6): δ 10.19 (s, 1H), 10.03 (s, 1H), 8.22 (d, 1H, J = 4.9 Hz), 7.90 (s, 1H), 7.84 (s, 1H), 7.76 (d, 1H, J = 2.6 Hz), 7.62 (d, 1H, J = 9.1 Hz), 7.56 (dd, 1H, J = 2.6 and 9.1 Hz), 7.39 (dd, 1H, J = 1.8 and 9.1 Hz), 7.09 (d, 1H, J = 9.1 Hz), 4.20 (d, 2H, J = 7.0 Hz), 3.83 (s, 3H), 1.89-1.86 (m, 3H), 1.60 (br s, 3H), 1.48-1.44 (br s, 2H), 1.13-0.96 (m, 5H). LCMS ret. time: 13.78 min.; purity: 98%; MS (m/e): 481 (MH+) | + | + | | |
| 719 | N2-[1-(Cyclohexylmethyl)indazol-5-yl]-N4-(3,4-dichlorophenyl)-5-fluoro-2,4-pyrimidinediamine | $^1$H NMR (DMSO-d6): δ 9.69 (s, 1H), 9.38 (s, 1H), 8.17 (d, 1H, J = 3.8 Hz), 8.07 (app d, 1H, J = 2.6 Hz), 7.92 (s, 1H), 7.88 (s, 1H0, 7.78 (d, 1H, J = 8.8 Hz), 7.58 (d, 1H, J = 9.1 Hz0, 7.49-7.44 (m, 2H), 4.19 (d, 2H, J = 7.3 Hz), 1.91-1.84 (m, 1H), 1.62 (m, 3H), 1.49-1.45 (m, 2H), 1.15-0.96 (m, 5H). LCMS ret. time: 17.23 min.; purity: 96%; MS (m/e): 485 (MH+) | + | | | |
| 720 | N2-[1-(Cyclohexylmethyl)indazol-5-yl]-N4-(2,2-dimethyl-3-oxo-4H-benz[1,4]oxazin-6-yl)-5-fluoro-2,4-pyrimidinediamine | $^1$H 7.90 (s, 1H), 7.84 (s, 1H), 7.62 (d, 1H, J = 9.1 Hz), 7.37 (dd, 1H, J = 2.3 and 8.8 Hz), 7.23 (dd, 1H, J = 2.3 and 9.1 Hz), 7.17 (s, 1H), 6.84 (d, 1H, J = 9.1 Hz), 4.19 (d, 2H, J = 7.3 Hz), 1.91-1.84 (m, 1H), 1.62 (br s, 3H), 1.47-1.38 (m, 2H), 1.36 (s, 6H), 1.13-0.96 (m, 5H). LCMS: ret. time: 11.95 min.; purity: 96%; MS (m/e): 516 (MH+) | + | + | | |
| 721 | N2-[1-(Cyclohexylmethyl)indazol-5-yl]-5-fluoro-N4-(4-fluoro-3-methoxyphenyl)-2,4-pyrimidinediamine | $^1$H NMR (DMSO-d6): δ 10.31 (s, 1H), 10.13 (s, 1H), 8.25 (d, 1H, J = 4.9 Hz), 7.89 (s, 1H), 7.87 (s, 1H), 7.62 (d, 1H, J = 8.8 Hz), 7.43 (dd, 1H, J = 2.6 and 8.8 Hz), 7.36 (dd, 1H, J = 1.8 and 9.1 Hz), 7.29-7.25 (s, 1H), 7.12 (dd, 1H, J = 8.8 and 11.4 Hz), 4.21 (d, 2H, J = 7.3 Hz), 3.61 (s, 3H), 1.91-1.84 (m, 1H), 1.62 (br s, 3H), 1.48-1.44 (m, 2H), 1.16-0.96 (m, 5H). LCMS ret. time: 13.82 min.; purity: 98%; MS (m/e): 465 (MH+) | + | | | |
| 722 | N4-(3-Chloro-4-methoxyphenyl)-N2-[1-(cyclohexylmethyl)indazol-6-yl]-5-fluoro-2,4-pyrimidinediamine | $^1$H NMR (DMSO-d6): δ 10.12 (s, 2H), 8.26 (d, 1H, J = 4.7 Hz), 7.93 (s, 1H), 7.85 (s, 1H), 7.78 (d, 1H, J = 2.6 Hz), 7.63 (d, 1H, J = 8.8 Hz), | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 723 | N2-[1-(Cyclohexylmethyl)indazol-6-yl]-N4-(3,4-dichlorophenyl)-5-fluoro-2,4-pyrimidinediamine | 7.58 (dd, 1H, J = 2.6 and 8.8 Hz), 7.19 (d, 1H, J = 8.8 Hz), 7.11 (d, 1H, J = 8.8 Hz), 3.90 (d, 2H, J = 7.3 Hz), 3.82 (s, 3H0, 1.74-1.71 (m, 1H), 1.53 (br s, 3H), 1.37-1.33 (m, 2H), 1.08-1.02 (m, 3H), 0.82-0.78 (m, 2H). LCMS: ret. time: 15.24 min.; purity: 91%; MS (m/e): 481 (MH+) | − | | | |
| 724 | N2-[1-(Cyclohexylmethyl)indazol-6-yl]-N4-(2,2-dimethyl-3-oxo-4H-benz[1,4]oxazin-6-yl)-5-fluoro-2,4-pyrimidinediamine | 1H NMR (DMSO-d6): δ 10.05 (s, 1H), 9.91 (s, 1H), 8.29 (d, 1H, J = 4.1 Hz0, 8.05 (d, 1H, J = 2.3 Hz), 7.92 (s, 1H), 7.90 (s, 1H), 7.73 (dd, 1H, J = 2.3 and 8.8 Hz), 7.63 (d, 1H, J = 8.8 Hz), 7.54 (d, 1H, J = 8.8 Hz), 7.21 (d, 1H, J = 8.8 Hz), 3.93 (d, 2H, J = 7.3 Hz), 1.78-1.74 (m, 1H), 1.54 (br s, 3H), 1.40-1.35 (m, 2H), 1.13-1.03 (m, 3H), 0.88-0.81 (m, 2H). LCMS: ret. time: 17.78 min.; purity: 91%; MS (m/e): 485 (MH+) | | + | | |
| 725 | N2-[1-(Cyclohexylmethyl)indazol-6-yl]-5-fluoro-N4-(4-fluoro-3-methoxyphenyl)-2,4-pyrimidinediamine | 1H NMR (DMSO-d6): δ 10.73 (s, 1H), 10.07 (s, 1H), 10.01 (s, 1H), 8.22 (d, 1H, J = 4.7 Hz), 7.91 (s, 1H), 7.86 (s, 1H), 7.60 (d, 1H, J = 8.8 Hz0, 7.26 (dd, 1H, J = 2.3 and 8.5 Hz), 7.22-7.19 (app m, 2H), 6.85 (d, 1H, J = 8.5 Hz), 3.93 (d, 2H, J = 7.3 Hz), 1.78-175 (m, 1H), 1.52 (br s, 3H), 1.38 (s, 6H), 1.36-1.32 (m, 2H), 1.09-1.03 (m, 3H), 0.88-0.82 (m, 2H). LCMS: ret. time: 13.52 min.; purity: 95%; MS (m/e): 516 (MH+) | + | | | |
| 726 | N4-(3-Chloro-4-methoxyphenyl)-N2-[1-(cyclobutylmethyl)indazol-5-yl]-5-fluoro-2,4-pyrimidinediamine | 1H NMR (DMSO-d6): δ 10.24 (s, 2H), 8.29 (d, 1H, J = 4.7 Hz), 7.95 (s, 1H), 7.86 (s, 1H), 7.63 (d, 1H, J = 8.8 Hz), 7.49 (dd, 1H, J = 2.3 and 8.8 Hz), 7.28-7.24 (m, 1H), 7.19-7.12 (m, 2H), 3.91 (d, 2H, J = 7.3 Hz), 3.55 (s, 3H), 1.75-1.73 (m, 1H), 1.54 (br s, 3H), 1.37-1.33 (m, 2H), 1.09-1.03 (m, 3H), 0.84-0.79 (m, 2H). LCMS: ret. time: 15.18 min.; purity: 96%; MS (m/e): 465 (MH+) | + | | | |
| 727 | N2-[1-(Cyclobutylmethyl)indazol-5-yl]-N4-(3,4-dichlorophenyl)-5-fluoro-2,4-pyrimidinediamine | 1H NMR (DMSO-d6): δ 10.40 (s, 1H), 10.26 (s, 1H), 8.26 (d, 1H, J = 5.3 Hz), 7.91 (s, 1H), 7.81 (s, 1H), 7.75 (dd, 1H, J = 2.6 Hz), 7.68 (d, 1H, J = 8.8 Hz), 7.55 (dd, 1H, J = 2.6 and 2.6 and 8.8 Hz), 7.38 (d, 1H, J = 8.8 Hz), 7.09 (d, 1H, J = 9.1 Hz), 4.39 (d, 2H, J = 7.0 Hz), 3.83 (s, 3H), 2.80 (m, 1H), 1.94-1.74 (m, 6H). LCMS: ret. time: 12.08 min.; purity: 99%; MS (m/e): 455 (MH+) | + | | | |
| 728 | N2-[1-(Cyclobutylmethyl)indazol-5-yl]-N4-(2,2-dimethyl-3-oxo-4H-benz[1,4]oxazin-6-yl)-5-fluoro-2,4-pyrimidinediamine | 1H NMR (DMSO-d6): δ 10.32 (s, 1H), 10.06 (s, 1H), 8.29 (d, 1H, J = 4.7 Hz), 8.00 (s, 1H), 7.93 (s, 1H), 7.84 (s, 1H), 7.68 (d, 2H, J = 8.8 Hz), 7.49 (d, 1H, J = 8.8 Hz), 7.41 (d, 1H, J = 8.8 Hz), 4.40 (d, 2H), 2.86-2.76 (m, 1H), 1.96-1.75 (m, 6H). LCMS: ret. time: 15.32 min.; purity: 98%; MS (m/e): 458 (MH+) | | + | | |
| 729 | N2-[1-(Cyclobutylmethyl)indazol-5-yl]-5-fluoro-N4-(4-fluoro-3-methoxyphenyl)-2,4-pyrimidinediamine | 1H NMR (DMSO-d6): δ 10.48 (s, 1H), 10.36 (s, 1H), 8.29 (d, 1H, J = 5.3 Hz), 7.88 (s, 1H), 7.86 (s, 1H0, 7.67 (d, 1H, J = 8.0 Hz), 7.43 (dd, 1H, J = 2.3 and 8.0 Hz), 7.35 (dd, 1H, J = 1.8 and 8.8 Hz), 7.26-7.23 (m, 1H), 7.14 (dd, 1H, J = 9.1 and 11.8 Hz), 4.40 (d, 2H, J = 7.0 Hz), 3.60 (s, 3H), 1.95-1.71 (m, 6H). LCMS: ret. time: 12.16 min.; purity: 99%; MS (m/e): 437 (MH+) | | + | | |
| 730 | N4-(3-Chloro-4-methoxyphenyl)-N2-[1-(cyclobutylmethyl)indazol-6-yl]-5-fluoro-2,4-pyrimidinediamine | 1H NMR (DMSO-d6): δ 10.35 (s, 2H), 8.31 (d, 1H, J = 4.7 Hz), 7.94 (s, 1H0, 7.86 (s, 1H), 7.78 (d, 1H, J = 2.3 Hz), 7.66 (d, 1H, J = 8.8 Hz), | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 731 | N2-[1-(Cyclobutylmethyl)indazol-6-yl]-N4-(3,4-dichlorophenyl)-5-fluoro-2,4-pyrimidinediamine | 7.57 (dd, 1H, J = 2.3 and 8.8 Hz0, 7.16 (d, 1H, J = 8.8 Hz), 7.12 (d, 1H, J = 8.8 Hz), 4.09 (d, 2H, J = 7.3 Hz), 3.83 (s, 3H), 2.69-2.59 (m, 1H), 1.86-1.56 (m, 6H). LCMS: ret. time: 13.56 min.; purity: 97%; MS (m/e): 454 (MH+) | | | | |
| 732 | N2-[1-(Cyclobutylmethyl)indazol-6-yl]-N4-(2,2-dimethyl-3-oxo-4H-benz[1,4]oxazin-6-yl)-5-fluoro-2,4-pyrimidinediamine | $^1$H NMR (DMSO-d6): δ 10.27 (s, 1H), 10.16 (s, 1H), 8.30 (d, 1H, J = 4.4 Hz), 7.99 (d, 1H, J = 2.3 Hz), 7.88 (s, 1H), 7.85 (s, 1H), 7.67 (dd, 1H, J = 2.3 and 8.8 Hz), 7.60 (d, 1H, J = 8.8 Hz), 7.51 (d, 1H, J = 8.8 Hz), 7.13 (d, 1H, J = 8.8 Hz), 4.07 (d, 2H, J = 7.0 Hz), 2.66-2.56 (m, 1H), 1.83-1.56 (m, 6H). LCMS: ret. time: 16.25 min.; purity: 96%; MS (m/e):458 (MH+) | + | | | |
| 733 | N2-[1-(Cyclobutylmethyl)indazol-6-yl]-5-fluoro-N4-(4-fluoro-3-methoxyphenyl)-2,4-pyrimidinediamine | $^1$H NMR (DMSO-d6): δ 10.81 (s, 1H), 10.63 (s, 1H), 8.33 (d, 1H, J = 5.3 Hz), 7.94 (s, 1H), 7.81 (s, 1H), 7.64 (d, 1H, J = 8.8 Hz), 7.24-7.21 (m, 2H), 7.17 (d, 1H, J = 8.5 Hz), 6.86 (d, 1H, J = 8.5 Hz), 4.12 (d, 2H, J = 7.0 Hz), 2.71-2.61 (m, 1H), 1.85-1.59 (m, 6H), 1.38 (s, 6H). LCMS: ret. time: 12.01 min.; purity: 97%; MS (m/e): 488 (MH+) | + | | | |
| 734 | N4-(3-Chloro-4-methoxyphenyl)-N2-[1-(cyclopropylmethyl)indazol-5-yl]-5-fluoro-2,4-pyrimidinediamine | $^1$H NMR (DMSO-d6): δ 10.67 (s, 1H), 10.58 (s, 1H), 8.38 (d, 1H, J = 5.3 Hz), 7.96 (s, 1H), 7.85 (s, 1H), 7.66 (d, 1H, J = 8.5 Hz), 7.48 (dd, 1H, J = 2.3 and 8.5 Hz), 7.23-7.11 (m, 3H), 4.07 (d, 2H, J = 7.0 Hz), 3.51 (s, 3H), 2.67-2.57 (m, 6H). LCMS: ret. time: 13.67 min.; purity: 98%; MS (m/e): 439 (MH+) | | + | | |
| 735 | N2-[1-(Cyclopropylmethyl)indazol-5-yl]-N4-(3,4-dichlorophenyl)-5-fluoro-2,4-pyrimidinediamine | $^1$H NMR (DMSO-d6): δ 10.05 (s, 1H), 9.91 (s, 1H), 8.31 (d, 1H, J = 5.2 Hz), 7.96 (s, 1H), 7.87 (s, 1H), 7.80 (s, 1H), 7.72 (d, 1H, J = 8.8 Hz), 7.60 (d, 1H, J = 8.8 Hz), 7.43 (d, 1H, J = 9.1 Hz), 7.14 (d, 1H, J = 8.8 Hz), 4.31 (d, 2H, J = 7.0 Hz), 3.48 (s, 3H), 1.33 (m, 1H), 0.58-0.40 (m, 4H). LCMS: ret. time: 13.98 min.; purity: 98%; MS (m/e): 439 (MH+) | + | + | | |
| 736 | N2-[1-(Cyclopropylmethyl)indazol-5-yl]-N4-(2,2-dimethyl-3-oxo-4H-benz[1,4]oxazin-6-yl)-5-fluoro-2,4-pyrimidinediamine | $^1$H NMR (DMSO-d6): δ 10.39 (s, 1H), 10.14 (s, 1H), 8.31 (d, 1H, J = 4.7 Hz), 8.05 (d, 1H, J = 2.3 Hz), 7.98 (s, 1H), 7.89 (s, 1H), 7.73 (d, 1H, J = 9.1 Hz), 7.54 (d, 1H, J = 8.8 Hz), 7.45 (dd, 1H, J = 2.3 and 8.8 Hz), 4.32 (d, 2H, J = 7.0 Hz), 1.34-1.24 (m, 1H), 0.54-0.44 (m, 4H). LCMS: ret. time: 13.89 min.; purity: 96%; MS (m/e): 444 (MH+) | | + | | + |
| 737 | N2-[1-(Cyclopropylmethyl)indazol-5-yl]-5-fluoro-N4-(4-fluoro-3-methoxyphenyl)-2,4-pyrimidinediamine | $^1$H NMR (DMSO-d6): δ 10.85 (s, 1H), 10.46 (s, 1H), 10.29 (s, 1H), 8.23 (d, 1H, J = 5.3 Hz), 7.95 (s, 1H), 7.94 (s, 1H0, 7.71 (d, 1H, J = 9.1 Hz), 7.42 (dd, 1H, J = 2.3 and 9.1 Hz), 7.27 (d, 1H, J = 8.5 Hz), 7.25 (s, 1H), 6.95 (d, 1H, J = 8.5 Hz), 4.32 (d, 2H, J = 7.0 Hz), 1.38 (s, 6H), 1.34-1.24 (m, 1H), 0.54-0.44 (m, 4H). LCMS: ret. time: 9.65 min.; purity: 96%; MS (m/e): 474 (MH+) | | + | | |
| 738 | N4-(3-Chloro-4-methoxyphenyl)-N2-[1-(cyclopropylmethyl)indazol-6-yl]-5-fluoro-2,4-pyrimidinediamine | $^1$H NMR (DMSO-d6): δ 10.28 (s, 2H), 8.31 (d, 1H, J = 4.3 Hz), 7.95 (s, 1H), 7.96 (s, 2H), 7.87 (s, 1H), 7.79 (d, 1H, J = 2.6 Hz), 7.69 (d, 1H, J = 8.8 Hz), 7.58 (dd, 1H, J = 2.6 and 9.1 Hz), 7.19 (dd, 1H, J = 1.8 and 8.8 Hz), 7.11 (d, 1H, J = 9.1 Hz), 4.32 (d, 2H, J = 6.7 Hz), 3.84 (s, 3H), | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 739 | N2-[1-(Cyclopropylmethyl)indazol-6-yl]-N4-(3,4-dichlorophenyl)-5-fluoro-2,4-pyrimidinediamine | 1.33-1.17 (m, 1H), 0.55-0.46 (m, 4H). LCMS: ret. time: 12.54 min.; purity: 98%; MS (m/e): 440 (MH+) ¹H NMR (DMSO-d6): δ 10.21 (s, 1H), 10.10 (s, 1H), 8.32 (d, 1H, J = 4.3 Hz), 8.04 (d, 1H, J = 2.6 Hz), 7.93 (s, 1H), 7.91 (s, 1H), 7.71 (dd, 1H, J = 2.6 and 8.8 Hz), 7.65 (d, 1H, J = 8.8 Hz), 7.54 (d, 1H, J = 8.8 Hz), 7.20 (d, 1H, J = 8.8 Hz), 4.32 (d, 2H, J = 6.7 Hz), 1.33-1.17 (m, 1H), 0.55-0.46 (m, 4H). LCMS: ret. time: 15.18 min.; purity: 95%; MS (m/e): 444 (MH+) | + | | | |
| 740 | N2-[1-(Cyclopropylmethyl)indazol-6-yl]-N4-(2,2-dimethyl-3-oxo-4H-benz[1,4]oxazin-6-yl)-5-fluoro-2,4-pyrimidinediamine | ¹H NMR (DMSO-d6): δ 10.82 (s, 1H), 10.22 (s, 1H), 10.16 (s, 1H), 8.31 (d, 1H, J = 4.7 Hz), 8.00 (d, 1H, J = 0.8 Hz), 7.97 (s, 1H), 7.34 (d, 1H, J = 8.8 Hz), 7.35-7.27 (m, 3H), 6.92 (d, 1H, J = 8.5 Hz), 4.32 (d, 2H, J = 7.0 Hz), 1.36 (s, 6H), 1.33-1.17 (m, 1H), 0.55-0.45 (m, 2H), 0.35-0.30 (m, 2H). LCMS: ret. time: 10.93 min.; purity: 96%; MS (m/e): 474 (MH+) | | | | + |
| 741 | N2-[1-(Cyclopropylmethyl)indazol-6-yl]-5-fluoro-N4-(4-fluoro-3-methoxyphenyl)-2,4-pyrimidinediamine | ¹H NMR (DMSO-d6): δ 10.23 (s, 2H), 8.31 (d, 1H, J = 4.9 Hz), 7.95 (s, 1H), 7.91 (s, 1H), 7.65 (d, 1H, J = 8.8 Hz), 7.48 (dd, 1H, J = 2.3 and 8.8 Hz), 7.29-7.24 (m, 1H), 7.20-7.13 (m, 3H), 4.09 (d, 2H, J = 6.7 Hz), 3.65 (s, 3H), 1.33-1.17 (m, 1H), 0.55-0.46 (m, 2H), 0.35-0.30 (m, 2H). LCMS: ret. time: 12.54 min.; purity: 98%; MS (m/e): 423 (MH+) | | | | |
| 742 | N4-(3-Chloro-4-methoxyphenyl)-N2-(1-cyclohexylindazol-5-yl)-5-fluoro-2,4-pyrimidinediamine | ¹H NMR (DMSO-d6): δ 10.35 (s, 1H), 10.20 (s, 1H), 8.24 (d, 1H, J = 5.3 Hz), 7.92 (s, 1H), 7.81 (s, 1H), 7.74 (d, 1H, J = 2.6 Hz), 7.71 (d, 1H, J = 8.1 Hz), 7.55 (dd, 1H, J = 2.6 and 8.8 Hz), 7.36 (dd, 1H, J = 1.8 and 8.8 Hz), 7.09 (d, 1H, J = 8.1 Hz), 4.56-4.53 (m, 1H), 3.82 (s, 3H), 1.91-1.82 (m, 6H), 1.72-1.68 (m, 1H), 1.51-1.46 (m, 2H), 1.31-1.23 (m, 1H). LCMS: ret. time: 13.04 min.; purity: 98%; MS (m/e): 467 (MH+) | + | + | | |
| 743 | N2-(1-Cyclohexylindazol-5-yl)-N4-(3,4-dichlorophenyl)-5-fluoro-2,4-pyrimidinediamine | ¹H NMR (DMSO-d6): δ 10.26 (s, 1H), 9.99 (s, 1H), 8.23 (d, 1H, J = 4.9 Hz), 7.96 (s, 1H), 7.89 (s, 1H), 7.80 (s, 1H), 7.66 (d, 1H, J = 8.1 Hz), 7.61 (app s, 1H), 7.45 (d, 1H, J = 9.1 Hz), 7.34 (d, 1H, J = 9.1 Hz), 4.53-4.49 (m, 1H), 1.87-1.78 (m, 6H), 1.67-1.63 (m, 1H), 1.46-1.42 (m, 2H), 1.27-1.18 (m, 1H). LCMS: ret. time: 16.43 min.; purity: 97%; MS (m/e): 472 (MH+) | + | + | | |
| 744 | N2-(1-Cyclohexylindazol-5-yl)-N4-(2,2-dimethyl-3-oxo-4H-benz[1,4]oxazin-6-yl)-5-fluoro-2,4-pyrimidinediamine | ¹H NMR (DMSO-d6): δ 10.80 (s, 1H), 10.36 (s, 1H), 10.15 (s, 1H), 8.21 (d, 1H, J = 4.9 Hz), 7.89 (s, 1H), 7.86 (s, 1H), 7.64 (d, 1H, J = 9.4 Hz), 7.36 (dd, 1H, J = 2.3 and 8.8 Hz), 7.18 (d, 1H, J = 2.3 Hz), 6.86 (d, 1H, J = 9.4 Hz), 4.53-4.49 (m, 1H), 1.89-1.82 (m, 6H), 1.72-1.68 (m, 1H), 1.52-1.43 (m, 2H), 1.36 (s, 6H), 1.29-1.23 (m, 1H). LCMS: ret. time: 11.44 min.; purity: 96%; MS (m/e): 502 (MH+) | | + | | + |
| 745 | N2-(1-Cyclohexylindazol-5-yl)-5-fluoro-N4-(4-fluoro-3-methoxyphenyl)-2,4-pyrimidinediamine | ¹H NMR (DMSO-d6): δ 10.26 (s, 1H), 10.07 (s, 1H), 8.22 (d, 1H, J = 5.0 Hz), 7.90 (s, 1H), 7.89 (s, 1H), 7.67 (d, 1H, J = 8.8 Hz), 7.44 (dd, 1H, J = 8.5 Hz), 7.34 (dd, 1H, J = 1.8 and 8.8 Hz), 7.28-7.24 (m, 1H), 7.15 (dd, 1H, J = 8.8 and 11.1 Hz), 4.53-4.49 (m, 1H), 3.59 (s, 3H), 1.91-1.84 (m, 6H), 1.72-1.68 (m, 1H), 1.52-1.43 (m, 2H), 1.31-1.23 (m, 1H). LCMS: ret. time: 13.11 min.; purity: 98%; MS (m/e): 451 (MH+) | + | | | |
| 746 | N4-(3-Chloro-4-methoxyphenyl)-N2-(1-cyclohexylindazol-6-yl)-5-fluoro-2,4-pyrimidinediamine | ¹H NMR (DMSO-d6): δ 10.21 (s, 1H), 10.19 (s, 1H), 8.28 (d, 1H, J = 4.9 Hz), 7.95 (s, 1H), 7.86 (d, 1H, J = 2.6 Hz), 7.84 (s, 1H), 7.66 (d, 1H, J = 8.5 Hz), 7.59 (dd, 1H, J = 2.6 and 9.1 Hz), 7.21 (dd, 1H, J = 1.8 and 8.5 Hz), 7.06 (d, 1H, J = 9.1 Hz), 4.19-4.06 (m, 1H), 3.80 (s, 3H), | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 747 | N2-(1-Cyclohexylindazol-6-yl)-N4-(3,4-dichlorophenyl)-5-fluoro-2,4-pyrimidinediamine | 1.83-1.74 (m, 6H), 1.65-1.62 (m, 1H), 1.29-1.15 (m, 3H). LCMS: ret. time: 14.39 min.; purity: 97%; MS (m/e): 465 (MH+) ¹H NMR (DMSO-d6): δ 10.05 (s, 1H), 9.88 (s, 1H), 8.29 (d, 1H, J = 4.9 Hz), 8.11 (d, 1H, J = 2.6 Hz), 7.93 (s, 1H), 7.92 (s, 1H), 7.78 (dd, 1H, J = 2.6 and 8.8 Hz), 7.64 (d, 1H, J = 8.5 Hz), 7.51 (d, 1H, J = 8.8 Hz), 7.22 (dd, 1H, J = 1.7 and 8.5 Hz), 4.19-4.06 (m, 1H), 1.85-1.77 (m, 6H), 1.65-1.62 (m, 1H), 1.29-1.13 (m, 3H). LCMS: ret. time: 17.10 min.; purity: 94%; MS (m/e): 472 (MH+) | + | | | |
| 748 | N2-(1-Cyclohexylindazol-6-yl)-N4-(2,2-dimethyl-3-oxo-4H-benz[1,4]oxazin-6-yl)-5-fluoro-2,4-pyrimidinediamine | ¹H NMR (DMSO-d6): δ 10.76 (s, 1H), 10.25 (s, 1H), 10.18 (s, 1H), 8.24 (d, 1H, J = 4.9 Hz), 7.94 (s, 1H), 7.83 (s, 1H), 7.63 (d, 1H, J = 8.5 Hz), 7.31-7.22 (m, 3H), 6.80 (d, 1H, J = 8.5 Hz), 4.23-4.12 (m, 1H), 1.85-1.77 (m, 6H), 1.65-1.62 (m, 1H), 1.38 (s, 6H), 1.29-1.13 (m, 3H). LCMS: ret. time: 12.78 min.; purity: 94%; MS (m/e): 502 (MH+) | + | + | | |
| 749 | N2-(1-Cyclohexylindazol-6-yl)-5-fluoro-N4-(4-fluoro-3-methoxyphenyl)-2,4-pyrimidinediamine | ¹H NMR (DMSO-d6): δ 10.02 (s, 1H), 9.95 (s, 1H), 8.26 (d, 1H, J = 4.3 Hz), 7.93 (s, 2H), 7.83 (s, 1H), 7.63 (d, 1H, J = 8.8 Hz), 7.55 (dd, 1H, J = 2.6 and 8.8 Hz0, 7.31-7.28 (m, 1H), 7.18 (d, 1H, J = 8.8 Hz), 7.12 (dd, 1H, J = 8.8 and 11.4 Hz), 4.11-4.00 (m, 1H), 3.49 (s, 3H), 1.82-1.75 (m, 6H), 1.65-1.62 (m, 1H), 1.29-1.13 (m, 3H). LCMS: ret. time: 14.35 min.; purity: 94%; MS (m/e): 452 (MH+) | + | + | | |
| 750 | N4-(3,4-Dichlorophenyl)-5-fluoro-N2-(3-methylindazol-6-yl)-2,4-pyrimidinediamine | ¹H NMR (DMSO-d6): δ 12.23 (s, 1H), 9.53 (s, 1H), 9.36 (s, 1H), 8.14 (d, 1H, J = 3.5 Hz), 8.10 (d, 1H, J = 2.7 Hz), 7.88 (s, 1H), 7.86 (dd, 1H, J = 2.7 and 8.8 Hz), 7.47 (d, 2H, J = 8.8 Hz), 7.16 (dd, 1H, J = 1.8 and 8.8 Hz), 2.36 (s, 3H). LCMS: ret. time: 12.62 min.; purity: 94%; MS (m/e): 404 (MH+) | + | + | | |
| 751 | N4-(2,2-Dimethyl-1-3-oxo-4H-benz[1,4]oxazin-6-yl)-5-fluoro-N2-(3-methylindazol-6-yl)-2,4-pyrimidinediamine | ¹H NMR (DMSO-d6): δ 10.62 (s, 1H), 9.63 (s, 1H), 9.44 (s, 1H), 8.13 (d, 1H, J = 41 Hz), 7.84 (s, 1H), 7.50 (d, 1H, J = 8.8 Hz), 7.36 (dd, 1H, J = 2.3 and 8.5 Hz), 7.31 (d, 1H, J = 8.5 Hz), 7.24 (dd, 1H, J = 1.8 and 8.8 Hz), 6.89 (d, 1H, J = 8.5 Hz), 2.41 (s, 3H), 1.39 (s, 6H). LCMS: ret. time: 8.78 min.; purity: 92%; MS (m/e): 434 (MH+) | + | + | | |
| 752 | N4-(3-Chloro-4-methoxyphenyl)-N2-(1,3-dimethylindazol-6-yl)-5-fluoro-2,4-pyrimidinediamine | ¹H NMR (DMSO-d6): δ 10.49 (s, 1H), 10.43 (s, 1H), 8.33 (d, 1H, J = 5.3 Hz), 7.77 (d, 1H, J = 2.6 Hz), 7.67 (d, 1H, J = 1.2 Hz), 7.62 (d, 1H, J = 8.8 Hz), 7.55 (dd, 1H, J = 2.6 and 8.8 Hz), 7.10 (d, 1H, J = 8.8 Hz), 7.09 (d, 1H, J = 8.8 Hz), 3.83 (s, 3H), 3.67 (s, 3H), 2.41 (s, 3H). LCMS: ret. time: 11.19 min.; purity: 94%; MS (m/e): 413 (MH+) | + | + | | |
| 753 | N4-(3,4-Dichlorophenyl)-N2-(1,3-dimethylindazol-6-yl)-5-fluoro-2,4-pyrimidinediamine | ¹H NMR (DMSO-d6): δ 9.65 (s, 1H), 9.50 (s, 1H), 8.22 (d, 1H, J = 3.5H), 8.12 (d, 1H, J = 2.3 Hz), 7.91 (d, 1H, J = 1.8 Hz), 7.79 (dd, 1H, J = 2.3 and 8.8 Hz), 7.52 (dd, 2H, J = 2.3 and 8.8 Hz), 7.18 (dd, 1H, J = 1.8 and 8.8 Hz), 3.69 (s, 3H), 2.39 (s, 3H). LCMS: ret. time: 13.96 min.; purity: 97%; MS (m/e): 418 (MH+) | + | + | | |
| 754 | N2-(1,3-Dimethylindazol-6-yl)-N4-(2,2-dimethyl-3-oxo-4H-benz[1,4]oxazin-6-yl)-5-fluoro-2,4-pyrimidinediamine | ¹H NMR (DMSO-d6): δ 10.72 (s, 1H), 10.25 (s, 2H), 8.26 (d, 1H, J = 4.9 Hz), 7.72 (s, 1H), 7.57 (d, 1H, J = 8.5 Hz), 7.25 (dd, 1H, J = 2.3 and 8.5 Hz), 7.22 (app s, 1H), 7.14 (dd, 1H, J = 2.3 and 8.5 Hz), 6.87 (d, 1H, J = 8.5 Hz), 3.37 (s, 3H), 2.40 (s, 3H), 1.38 (s, 6H). LCMS: ret. time: 9.77 min.; purity: 94%; MS (m/e): 448 (MH+) | + | + | | + |
| 755 | N2-(1,3-Dimethylindazol-6-yl)-5-fluoro-N4-(4-fluoro-3-methoxyphenyl)-2,4-pyrimidinediamine | ¹H NMR (DMSO-d6): δ 10.14 (s, 2H), 8.28 (d, 1H, J = 3.7 Hz), 7.79 (d, 1H, J = 1.8 Hz), 7.57 (d, 1H, J = 8.5 Hz), 7.48 (dd, 1H, J = 2.3 and 8.5 Hz), 7.31-7.26 (m, 1H), 7.17 (dd, 1H, J = 8.8 and 11.4 Hz), 7.10 (dd, | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 756 | N4-(3-Chloro-4-methoxyphenyl)-N2-(1,6-dimethylindazol-5-yl)-5-fluoro-2,4-pyrimidinediamine | 1H, J = 1.8 and 8.8 Hz), 3.66 (s, 3H), 3.60 (s, 3H), 2.41 (s, 3H). LCMS: ret. time: 11.36 min.; purity: 99%; MS (m/e): 397 (MH+) | + | | | |
| 757 | N4-(3,4-Dichlorophenyl)-N2-(1,6-dimethylindazol-5-yl)-5-fluoro-2,4-pyrimidinediamine | $^1$H NMR (DMSO-d6): δ 10.44 (s, 1H), 9.89 (s, 1H), 8.21 (d, 1H, J = 5.6 Hz), 7.97 (s, 1H), 7.70 (s, 1H), 7.62 (s, 1H), 7.58 (s, 1H), 7.46 (d, 1H, J = 8.5 Hz), 6.91 (d, 1H, J = 8.5 Hz), 4.00 (s, 3H), 3.75 (s, 3H), 2.32 (s, 3H). LCMS: ret. time: 9.25 min.; purity: 93%; MS (m/e): 413 (MH+) | + | | | |
| 758 | N2-(1,6-Dimethylindazol-5-yl)-N4-(2,2-dimethyl-3-oxo-4H-benz[1,4]oxazin-6-yl)-5-fluoro-2,4-pyrimidinediamine | $^1$H NMR (DMSO-d6): δ 10.34 (s, 1H), 9.70 (s, 1H), 8.24 (d, 1H, J = 4.7 Hz), 7.97 (s, 1H), 7.87 (s, 1H), 7.68 (s, 1H), 7.58 (s, 1H), 7.55 (d, 1H, J = 8.5 Hz), 7.37 (d, 1H, J = 8.5 Hz), 4.01 (s, 3H), 2.32 (s, 3H). LCMS: ret. time: 11.58 min.; purity: 91%; MS (m/e): 417 (MH+) | + | + | | |
| 759 | N2-(1,6-Dimethylindazol-5-yl)-5-fluoro-N4-(4-fluoro-3-methoxyphenyl)-2,4-pyrimidinediamine | $^1$H NMR (DMSO-d6): δ 10.70 (s, 1H), 10.51 (s, 1H), 8.16 (d, 1H, J = 4.9 Hz), 7.95 (s, 1H), 7.74 (s, 1H), 7.55 (s, 1H), 7.17 (d, 1H, J = 8.5 Hz), 6.69 (d, 1H, J = 8.5 Hz), 4.00 (s, 3H), 2.34 (s, 3H), 1.31 (s, 6H). LCMS: ret. time: 8.24 min.; purity: 96%; MS (m/e): 448 (MH+) | + | + | | |
| 760 | N4-(3,4-Dichlorophenyl)-N2-(2-ethylindazol-6-yl)-5-fluoro-2,4-pyrimidinediamine | $^1$H NMR (DMSO-d6): δ 10.42 (s, 1H), 9.84 (s, 1H), 8.18 (d, 1H, J = 3.9 Hz), 7.96 (s, 1H), 7.74 (s, 1H), 7.57 (s, 1H), 7.45 (d, 1H, J = 8.5 Hz), 7.20 (m, 1H), 6.97 (m, 1H), 4.02 (s, 3H), 3.55 (s, 3H), 2.33 (s, 3H). LCMS: ret. time: 9.33 min.; purity: 96%; MS (m/e): 397 (MH+) | + | + | | |
| 761 | N4-(2,2-Dimethyl-3-oxo-4H-benz[1,4]oxazin-6-yl)-N2-(2-ethylindazol-6-yl)-5-fluoro-2,4-pyrimidinediamine | $^1$H NMR (DMSO-d6): δ 10.25 (s, 1H), 10.06 (s, 1H), 8.36 (d, 1H, J = 1.8 Hz), 8.30 (d, 1H, J = 4.4 Hz), 8.03 (d, 1H, J = 2.3 Hz), 7.86 (s, 1H), 7.82 (dd, 1H, J = 2.6 and 8.8 Hz), 7.66 (d, 1H, J = 8.8 Hz), 7.53 (d, 1H, J = 8.8 Hz), 7.14 (dd, 1H, J = 1.8 and 8.8 Hz), 4.42 (qt, 2H, J = 7.3 Hz), 1.50 (t, 3H, J = 7.3 Hz). LCMS: ret. time: 12.85 min.; purity: 94%; MS (m/e): 418 (MH+) | + | + | − | |
| 762 | N4-(2,2-Dimethyl-3-oxo-4H-benz[1,4]oxazin-6-yl)-5-fluoro-N2-(2-n-propylindazol-5-yl)-2,4-pyrimidinediamine | $^1$H NMR (DMSO-d6): δ 10.57 (s, 1H), 9.51 (s, 1H), 9.30 (s, 1H), 8.21 (s, 1H), 8.12 (d, 1H, J = 4.1 Hz), 8.07 (s, 1H), 7.51 (d, 1H, J = 9.1 Hz), 7.40 (d, 1H, J = 2.3 Hz), 7.27 (dd, 1H, J = 2.3 and 8.8 Hz), 7.11 (dd, 1H, J = 1.8 and 9.1 Hz), 6.89 (d, 1H, J = 8.8 Hz), 4.39 (qt, 2H, J = 7.3 Hz), 1.45 (t, 3H, J = 7.3 Hz), 1.40 (s, 6H). LCMS: ret. time: 9.58 min.; purity: 93%; MS (m/e): 448 (MH+) | + | + | | |
| 763 | N4-(2,2-Dimethyl-3-oxo-4H-benz[1,4]oxazin-6-yl)-5-fluoro-N2-(2-n-propylindazol-5-yl)-2,4-pyrimidinediamine | $^1$H NMR (DMSO-d6): δ 10.14 (s, 1H), 9.82 (s, 1H), 8.25 (d, 1H, J = 4.4 Hz), 8.22 (s, 1H), 8.06 (d, 1H, J = 2.3 Hz), 7.83 (s, 1H), 7.74 (dd, 1H, J = 2.3 and 9.1 Hz), 7.57 (d, 1H, J = 9.1 Hz), 7.50 (d, 1H, J = 9.1 Hz), 7.27 (dd, 1H, J = 2.3 and 9.1 Hz), 4.34 (t, 2H, J = 7.3 Hz), 1.91 (sextet, 2H, J = 7.3 Hz), 0.83 (t, 3H, J = 7.3 Hz). LCMS: ret. time: 12.80 min.; purity: 92%; MS (m/e): 432 (MH+) | + | + | | |
| 764 | N4-(2,2-Dimethyl-3-oxo-4H-benz[1,4]oxazin-6-yl)-5-fluoro-N2-(2-n-propylindazol-6-yl)-2,4-pyrimidinediamine | $^1$H NMR (DMSO-d6): δ 10.77 (s, 1H), 10.33 (s, 1H), 10.07 (s, 1H), 8.20 (d, 1H, J = 5.3 Hz), 8.15 (s, 1H), 7.81 (s, 1H), 7.54 (d, 1H, J = 9.1 Hz), 7.23–7.18 (m, 3H), 6.86 (d, 1H, J = 9.1 Hz), 4.32 (t, 2H, J = 7.3 Hz), 1.90 (sextet, 2H, J = 7.3 Hz), 1.36 (s, 6H), 0.82 (t, 3H, J = 7.3 Hz). LCMS: ret. time: 9.08 min.; purity: 98%; MS (m/e): 462 (MH+) | + | + | | |
| | | $^1$H NMR (DMSO-d6): δ 10.56 (s, 1H), 9.29 (s, 1H), 9.09 (s, 1H), 8.17 (d, 1H, J = 0.8 Hz), 8.13 (d, 1H, J = 0.8 Hz), 8.09 (d, 1H, J = 3.8 Hz), 7.48 (d, 1H, J = 9.1 Hz), 7.41 (d, 1H, J = 2.3 Hz), 7.29 (dd, 1H, J = 2.3 and 9.1 Hz), 7.12 (dd, 1H, J = 2.3 and 8.8 Hz), 6.88 (d, 1H, J = 8.8 Hz), 4.30 (t, 2H, J = 7.3 Hz), 1.87 (sextet, 2H, J = 7.3 Hz), 1.40 (s, 6H), | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 765 | N4-(3,4-Dichlorophenyl)-5-fluoro-N2-(2-n-propylindazol-6-yl)-2,4-pyrimidinediamine | 0.82 (t, 3H, J = 7.3 Hz). LCMS: ret. time: 10.48 min.; purity: 97%; MS (m/e):462 (MH+) $^1$H NMR (DMSO-d6): δ 9.93 (s, 1H), 9.67 (s, 1H), 8.28 (s, 1H), 8.24 (d, 1H, J = 4.1 Hz), 8.05 (d, 1H, J = 2.3 Hz), 7.91 (s, 1H), 7.88 (dd, 1H, J = 2.6 and 8.8 Hz), 7.61 (d, 1H, J = 8.8 Hz), 7.51 (d, 1H, J = 8.8 Hz), 7.15 (d, 1H, J = 8.8 Hz), 4.28 (t, 2H, J = 7.3 Hz), 1.90 (sextet, 2H, J = 7.3 Hz), 0.86 (t, 3H, J = 7.3 Hz). LCMS: ret. time: 13.66 min.; purity: 91%; MS (m/e): 432 (MH+) | + | | | |
| 766 | N4-(2,2-Dimethyl-3-oxo-4H-benz[1,4]oxazin-6-yl)-5-fluoro-N2-(1-methylindazol-6-yl)-2,4-pyrimidinediamine DL-Camphor-1-sulfonic Acid Salt | $^1$H NMR (DMSO-d6): δ 10.69 (s, 1H), 10.09 (s, 1H), 9.88 (s, 1H), 8.21 (d, 1H, J = 4.7 Hz), 7.91 (d, 1H, J = 0.8 Hz), 7.83 (s, 1H), 7.61 (d, 1H, J = 8.5 Hz), 7.29 (dd, 1H, J = 2.3 and 8.5 Hz), 7.17 (dd, 1H, J = 2.3 and 8.5 Hz), 7.13 (d, 1H, J = 2.3 Hz), 6.85 (d, 1H, J = 8.5 Hz), 3.80 (s, 3H), 2.87 (d, 1H, AB qt, J = 14.6 Hz), 2.26-2.18 (m, 1H), 1.92 (brt, 1H, J = 4.7 Hz), 1.88-1.83 (m, 2H), 1.38 (s, 6H), 1.32-1.21 (, 2H), 1.03 (s, 3H), 0.73 (s, 3H). LCMS: ret. time: 9.53 min.; purity: 94%; MS (m/e): 434 (MH+) | + | + | — | |
| 767 | N4-(2,2-Dimethyl-3-oxo-4H-benz[1,4]oxazin-6-yl)-5-fluoro-N2-(1-methylindazol-6-yl)-2,4-pyrimidinediamine Ethanesulfonic Acid Salt | $^1$H NMR (DMSO-d6): δ 10.70 (s, 1H), 10.22 (s, 1H), 10.00 (s, 1H), 8.24 (d, 1H, J = 4.9 Hz), 7.92 (d, 1H, J = 0.8 Hz), 7.80 (s, 1H), 7.63 (d, 1H, J = 8.8 Hz), 7.28 (dd, 1H, J = 2.3 and 8.8 Hz), 7.16 (d, 1H, J = 1.8 and 8.5 Hz), 7.11 (d, 1H, J = 2.3 Hz), 6.84 (d, 1H, J = 8.5 Hz), 3.80 (s, 3H), 2.46 (qt, 1H, J = 7.3 Hz), 1.38 (s, 6H), 1.06 (t, 3H, J = 7.3 Hz). LCMS: ret. time: 9.52 min.; purity: 97%; MS (m/e): 434 (MH+) | + | + | — | |
| 768 | N4-(2,2-Dimethyl-3-oxo-4H-benz[1,4]oxazin-6-yl)-5-fluoro-N2-(1-methylindazol-6-yl)-2,4-pyrimidinediamine p-Hydroxybenzenesulfonic Acid Salt | $^1$H NMR (DMSO-d6): δ 10.69 (s, 1H), 10.17 (s, 1H), 9.92 (s, 1H), 8.21 (d, 1H, J = 4.7 Hz), 7.92 (d, 1H, J = 0.8 Hz), 7.81 (s, 1H), 7.62 (d, 1H, J = 8.5 Hz), 7.38 (td, 2H, J = 2.6 and 8.8 Hz), J = 7.28 (dd, 1H, J = 2.3 and 8.5 Hz), 7.16 (d, 1H, J = 1.8 and 8.5 Hz), 7.11 (d, 1H, J = 2.3 Hz), 6.84 (d, 1H, J = 8.5 Hz), 6.64 (td, 2H, J = 2.6 and 8.8 Hz), 3.81 (s, 3H), 1.37 (s, 6H). LCMS: ret. time: 9.51 min.; purity: 97%; MS (m/e): 434 (MH+) | + | + | | |
| 769 | N4-(2,2-Dimethyl-3-oxo-4H-benz[1,4]oxazin-6-yl)-5-fluoro-N2-(1-methylindazol-6-yl)-2,4-pyrimidinediamine Benzenesulfonic Acid Salt | $^1$H NMR (DMSO-d6): δ 10.70 (s, 1H), 10.28 (s, 1H), 10.00 (s, 1H), 8.22 (d, 1H, J = 4.9 Hz), 7.94 (d, 1H, J = 0.8 Hz), 7.78 (d, 1H), 7.64 (d, 1H, J = 8.8 Hz), 7.60-7.56 (m, 2H), 7.33-7.26 (m, 4H), 7.15 (d, 1H, J = 1.8 and 8.5 Hz), 7.10 (d, 1H, J = 2.3 Hz), 6.84 (d, 1H, J = 8.5 Hz), 3.82 (s, 3H), 1.37 (s, 6H). LCMS: ret. time: 9.51 min.; purity: 97%; MS (m/e): 434 (MH+) | + | + | — | |
| 770 | N4-(2,2-Dimethyl-3-oxo-4H-benz[1,4]oxazin-6-yl)-5-fluoro-N2-(1-methylindazol-6-yl)-2,4-pyrimidinediamine Hydrochloric Acid Salt | $^1$H NMR (DMSO-d6): δ 10.74 (s, 1H), 10.21 (s, 2H), 8.26 (d, 1H, J = 4.9 Hz), 7.92 (d, 1H, J = 0.8 Hz), 7.82 (s, 1H), 7.62 (d, 1H, J = 8.8 Hz), 7.27 (dd, 1H, J = 2.3 and 8.5 Hz), 7.21 (d, 1H, J = 2.3 Hz), 7.18 (dd, 1H, J = 1.8 and 8.5 Hz), 6.86 (d, 1H, J = 8.8 Hz), 3.79 (s, 3H), 1.38 (s, 6H). LCMS: ret. time: 9.52 min.; purity: 98%; MS (m/e): 434 (MH+) | + | + | — | |
| 771 | N4-(3,4-Dichlorophenyl)-5-fluoro-N2-[1-(2-methoxyethyl)indazol-5-yl]-2,4-pyrimidinediamine | $^1$H NMR (DMSO-d6): δ 10.18 (s, 1H), 9.91 (s, 1H), 8.21 (d, 1H, J = 4.7 Hz), 7.98 (d, 1H, J = 2.3 Hz), 7.90 (s, 1H), 7.81 (s, 1H), 7.66 (app d, 1H, J = 8.8 Hz), 7.60 (d, 1H, J = 9.1 Hz), 7.46 (d, 1H, J = 9.1 Hz), 7.37 (dd, 1H, J = 2.3 and 8.8 Hz), 4.48 (t, 2H, J = 5.2 Hz), 3.69 (t, 2H, J = 5.2 Hz), 3.12 (s, 3H). LCMS: ret. time: 12.23 min.; purity: 91%; MS (m/e): 448 (MH+) | + | + | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 772 | N4-(3-Chloro-4-methoxyphenyl)-5-fluoro-N2-[1-(2-methoxyethyl)indazol-5-yl]-2,4-pyrimidinediamine | 1H NMR (DMSO-d6): δ 10.45 (s, 1H), 10.33 (s, 1H), 8.27 (d, 1H, J = 4.9 Hz), 7.93 (s, 1H), 7.81 (d, 1H, J = 1.5 Hz), 7.74 (d, 1H, J = 2.3 Hz), 7.65 (d, 1H, J = 8.8 Hz), 7.54 (dd, 1H, J = 2.3 and 9.1 Hz), 7.37 (dd, 1H, J = 2.6 and 9.1 Hz), 7.10 (d, 1H, J = 8.8 Hz), 4.52 (t, 2H, J = 5.2 Hz), 3.83 (s, 3H), 3.73 (t, 2H, J = 5.2 Hz), 3.16 (s, 3H). LCMS: ret. time: 12.23 min.; purity: 91%; MS (m/e): 448 (MH+) | + | + | − | |
| 773 | N4-(2,2-Dimethyl-3-oxo-4H-benz[1,4]oxazin-6-yl)-5-fluoro-N2-[1-(2-methoxyethyl)indazol-5-yl]-2,4-pyrimidinediamine | 1H NMR (DMSO-d6): δ 10.78 (s, 1H), 10.19 (s, 1H), 8.21 (d, 1H, J = 4.9 Hz), 7.90 (s, 1H), 7.87 (s, 1H), 7.60 (d, 1H, J = 8.8 Hz), 7.36 (dd, 1H, J = 1.8 and 8.8 Hz), 7.21 (dd, 1H, J = 1.8 and 8.5 Hz), 7.17 (s, 1H), 6.87 (d, 1H, J = 8.5 Hz), 4.51 (t, 2H, J = 5.3 Hz), 3.71 (t, 3H, J = 5.3 Hz), 3.16 (s, 3H), 1.36 (s, 6H). LCMS: ret. time: 8.53 min.; purity: 91%; MS (m/e): 478 (MH+) | + | + | − | |
| 774 | 5-Fluoro-N4-(4-fluoro-3-methoxyphenyl)-N2-[1-(2-methoxyethyl)indazol-5-yl]-2,4-pyrimidinediamine | 1H NMR (DMSO-d6): δ 10.19 (s, 1H), 9.93 (s, 1H), 8.20 (d, 1H, J = 4.7 Hz), 7.90 (s, 2H), 7.61 (d, 1H, J = 8.8 Hz), 7.44 (dd, 1H, J = 2.6 and 8.8 Hz), 7.37 (dd, 1H, J = 2.0 and 8.8 Hz), 7.29-7.26 (m, 1H), 7.13 (dd, 1H, J = 8.8 and 11.1 Hz), 4.53 (t, 2H, J = 5.3 Hz), 3.73 (t, 3H, J = 5.3 Hz), 3.62 (s, 3H), 3.17 (s, 3H). LCMS: ret. time: 9.60 min.; purity: 95%; MS (m/e): 427 (MH+) | + | + | − | |
| 775 | N4-(3,4-Dichlorophenyl)-5-fluoro-N2-[1-(2-methoxyethyl)indazol-6-yl]-2,4-pyrimidinediamine | 1H NMR (DMSO-d6): δ 10.08 (s, 1H), 9.96 (s, 1H), 8.26 (d, 1H, J = 4.4 Hz), 8.03 (d, 1H, J = 2.3 Hz), 7.91 (d, 1H, J = 0.8 Hz), 7.82 (s, 1H), 7.70 (dd, 1H, J = 2.3 and 8.8 Hz), 7.60 (d, 1H, J = 8.8 Hz), 7.49 (d, 1H, J = 8.8 Hz), 7.19 (dd, 1H, J = 1.8 and 8.8 Hz), 4.24 (t, 2H, J = 5.3 Hz), 3.61 (t, 3H, J = 5.3 Hz), 3.06 (s, 3H). LCMS: ret. time: 13.66 min.; purity: 93%; MS (m/e): 448 (MH+) | + | + | − | |
| 776 | N4-(3-Chloro-4-methoxyphenyl)-5-fluoro-N2-[1-(2-methoxyethyl)indazol-6-yl]-2,4-pyrimidinediamine | 1H NMR (DMSO-d6): δ 10.02 (br s, 2H), 8.24 (d, 1H, J = 4.7 Hz), 7.95 (d, 1H, J = 0.8 Hz), 7.83 (s, 1H), 7.79 (d, 1H, J = 2.6 Hz), 7.63 (d, 1H, J = 8.8 Hz), 6.59 (dd, 1H, J = 2.6 and 9.1 Hz), 7.21 (dd, 1H, J = 1.8 and 8.8 Hz), 7.09 (d, 1H, J = 9.1 Hz), 4.25 (t, 2H, J = 5.3 Hz), 3.82 (s, 3H), 3.63 (t, 3H, J = 5.3 Hz), 3.09 (s, 3H). LCMS: ret. time: 10.93 min.; purity: 96%; MS (m/e): 443 (MH+) | + | + | − | |
| 777 | N4-(2,2-Dimethyl-3-oxo-4H-benz[1,4]oxazin-6-yl)-5-fluoro-N2-[1-(2-methoxyethyl)indazol-6-yl]-2,4-pyrimidinediamine | 1H NMR (DMSO-d6): δ 10.71 (s, 1H), 10.18 (br s, 2H), 8.20 (d, 1H, J = 4.9 Hz), 7.91 (d, 1H, J = 0.8 Hz), 7.75 (s, 1H), 7.57 (d, 1H, J = 8.5 Hz), 7.23-7.15 (m, 3H), 6.81 (d, 1H, J = 8.8 Hz), 4.24 (t, 2H, J = 5.3 Hz), 3.61 (t, 3H, J = 5.3 Hz), 3.06 (s, 3H), 1.33 (s, 6H). LCMS: ret. time: 9.59 min.; purity: 96%; MS (m/e): 479 (MH+) | + | + | − | |
| 778 | 5-Fluoro-N4-(4-fluoro-3-methoxyphenyl)-N2-[1-(2-methoxyethyl)indazol-6-yl]-2,4-pyrimidinediamine | 1H NMR (DMSO-d6): δ 9.92 (br s, 2H), 8.23 (d, 1H, J = 4.4 Hz), 7.94 (d, 1H, J = 0.8 Hz), 7.91 (s, 1H), 7.59 (d, 1H, J = 8.5 Hz), 7.48 (dd, 1H, J = 2.6 and 8.8 Hz), 7.34-7.30 (m, 1H), 7.21 (dd, 1H, J = 1.8 and 8.8 Hz), 7.15 (dd, 1H, J = 8.8 and 11.1 Hz), 4.24 (t, 2H, J = 5.3 Hz), 3.64 (t, 3H, J = 5.3 Hz), 3.61 (s, 3H), 3.06 (s, 3H). LCMS: ret. time: 10.93 min.; purity: 96%; MS (m/e): 427 (MH+) | + | | − | |
| 779 | N4-(3-Chloro-4-methoxyphenyl)-5-fluoro-N2-[1-(1-methylethyl)indazol-5-yl]-2,4-pyrimidinediamine | 1H NMR (DMSO-d6): δ 10.39 (s, 1H), 10.27 (s, 1H), 8.26 (d, 1H, J = 4.9 Hz), 7.93 (s, 1H), 7.81 (d, 1H, J = 1.4 Hz), 7.74 (d, 1H, J = 2.3 Hz), 6.67 (d, 1H, J = 9.1 Hz), 7.54 (dd, 1H, J = 2.3 and 9.1 Hz), 7.37 (dd, 1H, J = 1.8 and 8.8 Hz), 7.09 (d, 1H, J = 9.1 Hz), 4.94 (q, 1H, J = 6.7 Hz), 3.83 (s, 3H), 1.476 (d, 6H, J = 6.7 Hz). LCMS: ret. time: 10.94 min.; purity: 97%; MS (m/e): 427 (MH+) | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 780 | N4-(3,4-Dichorophenyl)-5-fluoro-N2-[1-(1-methylethyl)indazol-5-yl]-2,4-pyrimidinediamine | $^1$H NMR (DMSO-d6): δ 10.20 (s, 1H), 9.91 (s, 1H), 8.26 (d, 1H, J = 4.7 Hz), 8.02 (d, 1H, J = 2.3 Hz), 7.94 (s, 1H), 7.86 (s, 1H), 7.68 (d, 1H, J = 8.8 Hz), 7.66 (d, 1H, J = 9.1 Hz), 7.50 (d, 1H, J = 8.8 Hz), 7.41 (dd, 1H, J = 1.8 and 9.1 Hz), 4.95 (q, 1H, J = 6.7 Hz), 1.47 (d, 6H, J = 6.7 Hz). LCMS: ret. time: 13.92 min.; purity: 97%; MS (m/e): 432 (MH+) | | + | | |
| 781 | N4-(2,2-Dimethyl-1-oxo-4H-benz[1,4]oxazin-6-yl)-5-fluoro-N2-[1-(1-methylethyl)indazol-5-yl]-2,4-pyrimidinediamine | $^1$H NMR (DMSO-d6): δ 10.76 (s, 1H), 10.32 (s, 1H), 10.11 (s, 1H), 8.19 (d, 1H, J = 5.3 Hz), 7.90 (s, 1H), 7.89 (s, 1H), 7.62 (d, 1H, J = 8.8 Hz), 7.36 (dd, 1H, J = 1.8 and 8.8 Hz), 7.19 (d, 2H, J = 8.9 Hz), 6.87 (d, 1H, J = 8.8 Hz), 4.91 (q, 1H, J = 6.4 Hz), 1.44 (d, 6H, J = 6.4 Hz), 1.36 (s, 6H). LCMS: ret. time: 9.60 min.; purity: 96%; MS (m/e): 462 (MH+) | | + | | |
| 782 | 5-Fluoro-N4-(4-fluoro-3-methoxyphenyl)-N2-[1-(1-methylethyl)indazol-5-yl]-2,4-pyrimidinediamine | $^1$H NMR (DMSO-d6): δ 10.35 (s, 1H), 10.21 (s, 1H), 8.25 (d, 1H, J = 4.9 Hz), 7.90 (s, 1H), 7.88 (s, 1H), 7.65 (d, 1H, J = 8.1 Hz), 7.43 (dd, 1H, j = 2.3 and 8.8 Hz), 7.35 (dd, 1H, J = 1.8 and 8.8 Hz), 7.26-7.22 (m, 1H), 7.14 (dd, 1H, J = 8.8 and 11.1 Hz), 4.95 (q, 1H, J = 6.4 Hz), 3.59 (s, 3H), 1.46 (d, 6H, J = 6.4 Hz). LCMS: ret. time: 10.96 min.; purity: 96%; MS (m/e): 411 (MH+) | | + | | |
| 783 | N4-(3-Chloro-4-methoxyphenyl)-5-fluoro-N2-[1-(1-methylethyl)indazol-6-yl]-2,4-pyrimidinediamine | $^1$H NMR (DMSO-d6): δ 10.10 (s, 2H), 8.25 (d, 1H, J = 4.7 Hz), 7.93 (s, 1H), 7.86 (s, 1H), 7.78 (d, 1H, J = 2.3 Hz), 7.64 (d, 1H, J = 8.8 Hz), 7.56 (dd, 1H, J = 2.3 and 8.8 Hz), 7.18 (d, 1H, J = 8.8 Hz), 7.10 (d, 1H, J = 8.9 Hz), 4.45 (q, 1H, J = 6.4 Hz), 3.82 (s, 3H), 1.35 (d, 6H, J = 6.4 Hz). LCMS: ret. time: 12.26 min.; purity: 97%; MS (m/e): 427 (MH+) | | + | | |
| 784 | N4-(3,4-Dichlorophenyl)-5-fluoro-N2-[1-(1-methylethyl)indazol-6-yl]-2,4-pyrimidinediamine | $^1$H NMR (DMSO-d6): δ 10.06 (s, 1H), 9.93 (s, 1H), 8.30 (d, 1H, J = 4.3 Hz), 8.06 (d, 1H, J = 2.3 Hz), 7.93 (s, 2H), 7.76 (dd, 1H, J = 2.3 and 8.8 Hz), 7.64 (d, 1H, J = 8.8 Hz), 7.54 (d, 1H, J = 8.8 Hz), 7.21 (dd, 1H, J = 1.8 and 8.8 Hz), 4.55 (q, 1H, J = 6.4 Hz), 1.38 (d, 6H, J = 6.4 Hz). LCMS: ret. time: 15.20 min.; purity: 97%; MS (m/e): 432 (MH+) | | + | | |
| 785 | N4-(2,2-Dimethyl-3-oxo-4H-benz[1,4]oxazin-6-yl)-5-fluoro-N2-[1-(1-methylethyl)indazol-6-yl]-2,4-pyrimidinediamine | $^1$H NMR (DMSO-d6): δ 10.76 (s, 1H), 10.14 (s, 2H), 8.24 (d, 1H, J = 4.9 Hz), 7.93 (s, 1H), 7.88 (s, 1H), 7.61 (d, 1H, J = 8.8 Hz), 7.27-7.16 (m, 3H), 6.88 (d, 1H, J = 8.8 Hz), 4.50 (q, 1H, J = 6.4 Hz), 1.37 (d, 6H, J = 6.4 Hz), 1.35 (s, 6H). LCMS: ret. time: 10.91 min.; purity: 97%; MS (m/e): 462 (MH+) | | + | | |
| 786 | (S)—N4-[2-Methyl-3-oxo-2H,4H-benz[1,4]oxazin-6-yl]-5-fluoro-N2-[1-(1-methylethyl)indazol-6-yl]-2,4-pyrimidinediamine | $^1$H NMR (DMSO-d6): δ 10.77 (s, 1H), 10.14 (s, 1H), 9.93 (s, 1H), 8.22 (d, 1H, J = 4.7 hz), 7.93 (s, 1H), 7.92 (s, 1H), 7.60 (d, 1H, J = 8.5 Hz), 7.27 (dd, 1H, J = 2.3 and 8.5 Hz0, 7.21-7.16 (m, 2H), 6.90 (d, 1H, J = 8.5 Hz), 4.65 (qt, 1H, J = 6.7 Hz), 4.49 (q, 1H, J = 6.4 Hz), 1.41 (d, 3H, J = 6.7 Hz), 1.36 (d, 6H, J = 6.4 Hz). LCMS: ret. time: 10.30 min.; purity: 95%; MS (m/e): 448 (MH+) | | + | | |
| 787 | N2-[1-(3-Acetyloxypropyl)indazol-5-yl]-N4-(3,4-dichlorophenyl)-5-fluoro-2,4-pyrimidinediamine | $^1$H NMR (DMSO-d6): δ 10.17 (s, 1H), 9.90 (s, 1H), 8.21 (d, 1H, J = 4.7 Hz), 7.97 (d, 1H, J = 2.3 Hz), 7.90 (dd, 1H, J = 2.3 and 8.8 Hz), 7.59 (d, 1H, J = 8.8 Hz), 7.47 (d, 1H, J = 8.8 Hz), 7.38 (dd, 1H, J = 2.0 and 8.8 Hz), 4.41 (d, 2H, J = 6.7 Hz), 3.88 (t, 2H, J = 6.4 Hz), 2.07 (q, 2H, J = 6.7 Hz), 1.89 (s, 3H). | + | + | − | |
| 788 | N2-[1-(3-Acetyloxypropyl)indazol-5-yl]-N4-(3-chloro-4-methoxyphenyl)-5-fluoro-2,4-pyrimidinediamine | 1H NMR (DMSO-d6): δ 10.32 (s, 1H), 10.19 (s, 1H), 8.24 (d, 1H, J = 5.3 Hz), 7.93 (s, 1H), 7.85 (s, 1H), 7.74 (d, 1H, J = 2.3 Hz), 7.63 (d, 1H, J = 8.8 Hz), 7.54 (dd, 1H, J = 2.3 and 9.1 Hz), 7.40 (dd, 1H, J = 2.3 | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | Tryptase, fp_syk, 11 pt |
|---|---|---|---|---|---|---|
| 789 | N2-[1-(3-Acetyloxypropyl)indazol-5-yl]-5-fluoro-N4-(4-fluoro-3-methoxyphenyl)-2,4-pyrimidinediamine | and 8.8 Hz), 7.09 (d, 1H, J = 9.1 Hz), 4.45 (t, 2H, J 6.7 Hz), 3.93 (t, 2H, J = 6.4 Hz), 3.83 (s, 3H), 2.11 (q, 2H, J = 6.7 Hz), 1.93 (s, 3H). 1H NMR (DMSO-d6): δ 10.31 (s, 1H), 10.15 (s, 1H), 8.24 (d, 1H, J = 4.7 Hz), 7.91 (s, 2H), 7.61 (d, 1H, J = 8.8 Hz), 7.44 (dd, 1H, J = 2.3 and 8.8 Hz), 7.38 (dd, 1H, J = 1.8 and 9.1 Hz), 7.27-7.25 (m, 1H), 7.15 (dd, 1H, J = 8.8 and 11.1 Hz), 4.45 (t, 2H, J = 6.7 Hz), 3.92 (t, 2H, J = 6.4 Hz), 3.62 (s, 3H), 2.11 (app q, 2H, J = 6.4 Hz), 1.93 (s, 3H). | + | + | − | |
| 790 | N2-[1-(3-Acetyloxypropyl)indazol-6-yl]-N4-(3,4-dichlorophenyl)-5-fluoro-2,4-pyrimidinediamine | 1H NMR (DMSO-d6): δ 9.96 (s, 1H), 9.83 (s, 1H), 8.27 (d, 1H, J = 4.1 Hz), 8.09 (d, 1H, J = 2.3 Hz), 7.94 (s, 1H), 7.92 (s, 1H), 7.75 (dd, 1H, J = 2.3 and 8.8 Hz), 7.63 (d, 1H, J = 8.8 Hz), 7.53 (d, 1H, J = 8.8 Hz), 7.23 (dd, 1H, J = 1.8 and 8.8 Hz), 4.20 (t, 2H, J = 6.7 Hz), 3.83 (t, 2H, J = 6.4 Hz), 2.02 (app q, 2H, J = 6.4 Hz), 1.89 (s, 3H). | + | + | − | |
| 791 | N4-(2,2-Dimethyl-3-oxo-4H-benz[1,4]oxazin-6-yl)-5-fluoro-N2-[1-(3-hydroxypropyl)indazol-6-yl]-2,4-pyrimidinediamine | 1H NMR (DMSO-d6): δ 10.68 (s, 1H), 9.84 (s, 1H), 9.74 (s, 1H), 8.18 (d, 1H, J = 4.4 Hz), 7.90 (s, 1H), 7.56 (s, 1H), 7.58 (d, 1H, J = 8.8 Hz), 7.32-7.24 (m, 3H), 6.85 (d, 1H, J = 8.8 Hz), 4.20 (t, 2H, J = 6.7 Hz), 3.29 (t, 2H, J = 6.4 Hz), 1.87 (app q, 2H, J = 6.7 Hz), 1.38 (s, 6H). | + | + | − | |
| 792 | N4-(3-Chloro-4-methoxyphenyl)-5-fluoro-N2-[1-(3-methoxypropyl)indazol-5-yl]-2,4-pyrimidinediamine | 1H NMR (DMSO-d6): δ 10.42 (s, 1H), 10.30 (s, 1H), 8.26 (d, 1H, J = 5.2 Hz), 7.93 (s, 1H), 7.82 (d, 1H, J = 1.8 Hz), 7.74 (d, 1H, J = 2.3 Hz), 7.60 (d, 1H, J = 9.1 Hz), 7.53 (dd, 1H, J = 2.3 and 9.1 Hz), 7.38 (dd, 1H, J = 1.8 and 9.1 Hz), 7.09 (d, 1H, J = 9.1 Hz), 4.40 (t, 2H, J = 6.7 Hz), 3.83 (s, 3H), 3.23 (t, 2H, J = 6.4 Hz), 3.17 (s, 3H), 2.02 (app q, 2H, J = 6.7 Hz). | + | + | − | + |
| 793 | N4-(2,2-Dimethyl-3-oxo-4H-benz[1,4]oxazin-6-yl)-5-fluoro-N2-[1-(3-methoxypropyl)indazol-5-yl]-2,4-pyrimidinediamine | 1H NMR (DMSO-d6): δ 10.36 (s, 1H), 10.13 (s, 1H), 8.30 (d, 1H, J = 5.0 Hz), 8.01 (d, 1H, J = 2.3 Hz), 7.95 (s, 1H), 7.86 (s, 1H), 7.68 (dd, 1H, J = 2.3 and 8.8 Hz), 7.61 (d, 1H, J = 9.1 Hz), 7.51 (d, 1H, J = 8.8 Hz), 7.41 (dd, 1H, J = 1.8 and 9.1 Hz), 4.41 (t, 2H, J = 6.7 Hz), 3.19 (s, 3H), 3.24 (t, 2H, J = 6.4 Hz), 2.03 (q, 2H, J = 6.7 Hz). | + | + | − | |
| 794 | N4-(2,2-Dimethyl-3-oxo-4H-benz[1,4]oxazin-6-yl)-5-fluoro-N2-[1-(3-methoxypropyl)indazol-5-yl]-2,4-pyrimidinediamine | 1H NMR (DMSO-d6): δ 10.77 (s, 1H), 10.42 (s, 1H), 10.27 (s, 1H), 8.23 (d, 1H, J = 4.3 Hz), 7.90 (s, 1H), 7.88 (s, 1H), 7.56 (d, 1H, J = 8.8 Hz), 7.37 (dd, 1H, J = 1.8 and 8.8 Hz), 7.21 (app d, 2H, J = 9.1 Hz), 6.87 (d, 1H, J = 9.1 Hz), 4.39 (t, 2H, J = 6.7 Hz), 3.21 (t, 2H, J = 6.4 Hz), 3.17 (s, 3H), 2.00 (app q, 2H, J = 6.7 Hz), 1.36 (s, 6H). | + | + | − | |
| 795 | (S)-5-Fluoro-N2-[1-(3-methoxypropyl)indazol-5-yl]-N4-(2-methyl-3-oxo-2H,4H-benz[1,4]oxazin-6-yl)-2,4-pyrimidinediamine | 1H NMR (DMSO-d6): δ 10.73 (s, 1H), 10.32 (s, 1H), 10.15 (s, 1H), 8.17 (d, 1H, J = 4.9 Hz), 7.85 (s, 1H), 7.83 (s, 1H), 7.51 (d, 1H, J = 8.8 Hz), 7.33 (dd, 1H, J = 2.1 and 9.1 Hz), 7.16 (dd, 2H, J = 2.3 and 9.1 Hz), 6.84 (d, 1H, J = 8.8 Hz), 4.60 (qt, 1H, J = 6.7 Hz), 4.34 (t, 2H, J = 6.7 Hz), 3.17 (t, 2H, J = 6.4 Hz), 3.12 (s, 3H), 1.95 (q, 2H, J = 6.7 Hz), 1.36 (d, 3H, J = 6.7 Hz). | + | + | − | |
| 796 | N4-(3-Chloro-4-methoxyphenyl)-5-fluoro-N2-[1-(3-methoxypropyl)indazol-6-yl]-2,4-pyrimidinediamine | 1H NMR (DMSO-d6): δ 10.16 (s, 2H), 8.27 (d, 1H, J = 4.7 Hz), 7.95 (d, 1H, J = 0.8 Hz), 7.80 (s, 1H), 7.78 (d, 1H, J = 8.8 Hz), 7.65 (d, 1H, J = 2.3 and 9.1 Hz), 7.58 (dd, 1H, J = 2.3 and 9.1 Hz), 7.20 (dd, 1H, J = 1.8 an 8.8 Hz), 7.09 (d, 1H, J = 9.1 Hz), 4.15 (t, 2H, J = 6.7 Hz), 3.82 (s, 3H), 3.13 (t, 2H, J = 6.7 Hz), 3.12 (s, 3H), 1.89 (app qt, 2H, J = 6.7 Hz). | + | + | − | |
| 797 | N4-(3,4-Dichlorophenyl)-5-fluoro-N2-[1-(3-methoxypropyl)indazol-6-yl]-2,4-pyrimidinediamine | 1H NMR (DMSO-d6): δ 10.13 (s, 1H), 10.02 (s, 1H), 8.31 (d, 1H, J = 4.1 Hz), 8.06 (d, 1H, J = 2.3 Hz), 7.95 (s, 1H), 7.87 (s, 1H), 7.74 (dd, 1H, J = 2.3 and 8.8 Hz), 7.65 (d, 1H, J = 8.5 Hz), 7.54 (d, 1H, J = 8.8 Hz), | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 798 | N4-(2,2-Dimethyl-3-oxo-4H-benz[1,4]oxazin-6-yl)-5-fluoro-N2-[1-(3-methoxypropyl)indazol-6-yl]-2,4-pyrimidinediamine | 7.22 (d, 1H, J = 8.5 Hz), 4.17 (t, 2H, J = 6.7 Hz), 3.17 (t, 2H, J = 6.7 Hz), 3.12 (s, 3H), 1.91 (app q, 2H, J = 6.7 Hz). | | | | |
| 799 | (S)-5-Fluoro-N2-[1-(3-methoxypropyl)indazol-6-yl]-N4-(2-methyl-3-oxo-2H,4H-benz[1,4]oxazin-6-yl)-2,4-pyrimidinediamine | 1H NMR (DMSO-d6): δ 10.73 (s, 1H), 9.92 (s, 2H), 8.21 (d, 1H, J = 4.7 Hz), 7.92 (s, 1H), 7.89 (s, 1H), 7.58 (d, 1H, J = 8.8 Hz), 7.29-7.24 (m, 3H), 6.85 (d, 1H, J = 8.5 Hz), 4.17 (t, 2H, J = 6.7 Hz), 3.14 (app qt, 2H, J = 6.4 Hz), 3.13 (s, 3H), 1.92 (app q, 2H, J = 6.4 Hz), 1.38 (s, 6H). | + | + | + | + |
| 800 | N4-(3-Chloro-4-methoxyphenyl)-5-fluoro-N2-(2-trifluoromethyl-1H-benzimidazol-5-yl)-2,4-pyrimidinediamine | 1H NMR (DMSO-d6): δ 10.76 (s, 1H), 10.11 (s, 2H), 8.23 (d, 1H, J = 4.7 Hz), 7.94 (s, 1H), 7.86 (s, 1H), 7.62 (d, 1H, J = 8.5 Hz), 7.28-7.19 (m, 3H), 6.88 (d, 1H, J = 8.5 Hz), 4.64 (qt, 1H, J = 6.7 Hz), 4.17 (t, 2H, J = 6.7 Hz), 3.16 (app qt, 2H, J = 6.7 Hz), 3.13 (s, 3H), 1.91 (app q, 2H, J = 6.7 Hz), 1.41 (d, 3H, J = 6.7 Hz). | + | + | − | + |
| 801 | N4-(3,4-Dichlorophenyl)-5-fluoro-N2-(2-trifluoromethyl-1H-benzimidazol-5-yl)-2,4-pyrimidinediamine | 1H NMR (DMSO-d6): δ 10.17 (s, 1H), 8.20 (d, 1H, J = 4.9 Hz), 7.85 (s, 1H), 7.69 (d, 1H, J = 2.3 Hz), 7.61 (d, 1H, J = 8.8 Hz), 7.59 (dd, 1H, J = 2.3 and 8.8 Hz), 7.39 (dd, 1H, J = 2.0 and 8.8 Hz), 7.04 (d, 1H, J = 9.1 Hz), 3.76 (s, 3H). | + | + | + | + |
| 802 | N4-(2,2-Dimethyl-3-oxo-4H-benz[1,4]oxazin-6-yl)-5-fluoro-N2-(2-trifluoromethyl-1H-benzimidazol-5-yl)-2,4-pyrimidinediamine | 1H NMR (DMSO-d6): δ 9.84 (s, 1H), 9.70 (s, 1H), 8.19 (d, 1H, J = 4.1 Hz), 8.05 (d, 1H, J = 2.3 Hz), 7.96 (s, 1H), 7.75 (dd, 1H, J = 2.3 and 8.8 Hz), 7.60 (d, 1H, J = 9.1 Hz), 7.47-7.43 (m, 2H). | + | + | + | + |
| 803 | (S)-5-Fluoro-N4-(2-methyl-3-oxo-2H,4H-benz[1,4]oxazin-6-yl)-N2-(2-trifluoromethyl-1H-benzimidazol-5-yl)-2,4-pyrimidinediamine | 1H NMR (DMSO-d6): δ 10.71 (s, 1H), 10.26 (s, 1H), 10.21 (s, 1H), 8.22 (d, 1H, J = 4.9 Hz), 7.88 (s, 1H), 7.61 (d, 1H, J = 8.8 Hz), 7.49 (dd, 1H, J = 2.3 and 8.8 Hz), 7.24 (s, 1H), 7.22 (s, 1H), 6.86 (d, 1H, J = 8.8 Hz), 1.36 (s, 6H). | + | + | − | |
| 804 | N2-(3-Amino-1-methylindazol-5-yl)-N4-(3-chloro-4-methoxyphenyl)-5-fluoro-2,4-pyrimidinediamine | 1H NMR (DMSO-d6): δ 10.71 (s, 1H), 10.22 (s, 1H), 8.22 (d, 1H, J = 4.9 Hz), 7.93 (s, 1H), 7.62 (d, 1H, J = 8.8 Hz), 7.46 (dd, 1H, J = 2.3 and 8.8 Hz), 7.24 (s, 1H), 7.21 (s, 1H), 6.89 (d, 1H, J = 8.8 Hz), 4.66 (qt, 1H, J = 6.7 Hz), 1.40 (d, 3H, J = 6.7 Hz). | + | + | − | |
| 805 | N2-(3-Amino-1-methylindazol-5-yl)-N4-(3,4-dichlorophenyl)-5-fluoro-2,4-pyrimidinediamine | 1H NMR (DMSO-d6): δ 10.13 (s, 1H), 9.94 (s, 1H), 8.17 (d, 1H, J = 4.9 Hz), 7.76 (s, 1H), 7.75 (d, 1H, J = 2.3 Hz), 7.61 (dd, 1H, J = 2.3 and 9.1 Hz), 7.44 (s, 2H), 7.05 (d, 1H, J = 9.1 Hz), 3.80 (s, 3H), 3.79 (s, 3H). | + | + | | + |
| 806 | N2-(3-Amino-1-methylindazol-5-yl)-N4-(2,2-dimethyl-3-oxo-4H-benz[1,4]oxazin-6-yl)-5-fluoro-2,4-pyrimidinediamine | 1H NMR (DMSO-d6): δ 10.17 (s, 1H), 9.90 (s, 1H), 8.21 (d, 1H, J = 4.7 Hz), 7.97 (d, 1H, J = 2.3 Hz), 7.90 (dd, 1H, J = 2.3 and 8.8 Hz), 7.59 (d, 1H, J = 8.8 Hz), 7.47 (d, 1H, J = 9.1 Hz), 7.28 (app br s, 1H), 7.22 (dd, 1H, J = 2.3 and 8.8 Hz), 4.41 (d, 2H, J = 6.7 Hz), 3.88 (t, 2H, J = 6.4 Hz), 2.07 (q, 2H, J = 6.7 Hz), 1.89 (s, 3H). | + | + | | + |
| 807 | (S)-N2-(3-Amino-1-methylindazol-5-yl)-5-fluoro-N4-(2-methyl-3-oxo-4H-benz[1,4]oxazin-6-yl)-2,4-pyrimidinediamine | 1H NMR (DMSO-d6): δ 10.75 (s, 1H), 10.46 (s, 1H), 10.40 (s, 1H), 8.22 (d, 1H, J = 4.9 Hz), 7.79 (s, 1H), 7.54 (dd, 1H, J = 2.3 and 8.8 Hz), 7.48 (d, 1H, J = 9.1 Hz), 7.28 (app br s, 1H), 7.22 (dd, 1H, J = 2.3 and 9.1 Hz), 6.54 (d, 1H, J = 8.8 Hz), 3.84 (s, 3H), 1.34 (s, 6H). | + | + | | + |
| 808 | N4-(3-Chloro-4-methoxyphenyl)-5-fluoro-N2-(2-methyl-3H-benzimidazol-5-yl)-2,4-pyrimidinediamine | 1H NMR (DMSO-d6): δ 10.76 (s, 1H), 10.38 (s, 1H), 10.28 (s, 1H), 8.20 (d, 1H, J = 5.3 Hz), 7.80 (s, 1H), 7.53 (d, 1H, J = 9.1 Hz), 7.48 (d, 1H, J = 9.1 Hz), 7.27 (s, 1H), 7.25 (s, 1H), 6.87 (d, 1H, J = 9.1 Hz), 4.63 (qt, 1H, J = 6.7 Hz), 3.83 (s, 3H), 1.38 (d, 3H, J = 6.7 Hz). 1H NMR (DMSO-d6): δ 9.53 (s, 1H), 9.40 (s, 1H), 8.14 (d, 1H, J = 3.8 Hz), 8.13 (s, 1H), 7.86 (d, 1H, J = 2.6 Hz), 7.72-7.67 (m, 2H), 7.59 (d, 1H, J = 8.8 Hz), 7.11 (d, 1H, J = 9.1 Hz), 3.83 (s, 3H), 2.72 (s, 3H). | + | + | − | + |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 809 | N4-(3,4-Dichlorophenyl)-5-fluoro-N2-(2-methyl-3H-benzimidazol-5-yl)-2,4-pyrimidinediamine | 1H NMR (DMSO-d6): δ 9.93 (s, 2H), 8.28 (d, 1H, J = 4.8 Hz), 8.12 (d, 1H, J = 2.6 Hz), 8.07 (s, 1H), 7.81 (dd, 1H, J = 2.3 and 9.1 Hz), 7.66 (s, 2H), 7.56 (d, 1H, J = 8.8 Hz), 2.75 (s, 3H). | + | + | − | + |
| 810 | N4-(2,2-Dimethyl-3-oxo-4H-benz[1,4]oxazin-6-yl)-5-fluoro-N2-(2-methyl-3H-benzimidazol-5-yl)-2,4-pyrimidinediamine | 1H NMR (DMSO-d6): δ 10.70 (s, 1H), 9.56 (s, 1H), 9.40 (s, 1H), 8.21 (s, 1H), 8.12 (d, 1H, J = 3.8 Hz), 7.79 (dd, 1H, J = 2.3 and 9.1 Hz), 7.55 (d, 1H, J = 8.8 Hz), 7.52 (s, 1H), 7.31 (dd, 1H, J = 2.3 and 8.8 Hz), 6.88 (d, 1H, J = 8.8 Hz), 2.72 (s, 3H), 1.39 (s, 6H). | + | + | − | + |
| 811 | (S)-5-Fluoro-N2-(2-methyl-3H-benzimidazol-5-yl)-N4-(2-methyl-3-oxo-2H,4H-benz[1,4]oxazin-6-yl)-2,4-pyrimidinediamine | 1H NMR (DMSO-d6): δ 10.69 (s, 1H), 9.58 (s, 1H), 9.42 (s, 1H), 8.23 (s, 1H), 8.12 (d, 1H, J = 3.5 Hz), 7.74 (dd, 1H, J = 2.3 and 8.8 Hz), 7.57 (d, 1H, J = 9.1 Hz), 7.53 (d, 1H, J = 2.3 Hz), 7.29 (dd, 1H, J = 2.3 and 8.8 Hz), 6.91 (d, 1H, J = 8.8 Hz), 4.64 (qt, 1H, J = 6.7 Hz), 2.71 (s, 3H), 1.42 (d, 3H, J = 6.7 Hz). | + | + | − | + |
| 812 | N2-(1,3-Dimethylindazol-6-yl)-N4-(2,2-dimethyl-3-oxo-4H-5-pyrid[1,4]oxazin-6-yl)-5-fluoro-2,4-pyrimidinediamine | 1H NMR (DMSO-d6): δ 11.06 (s, 1H), 9.53 (s, 1H), 9.44 (s, 1H), 8.16 (d, 1H, J = 3.5 Hz), 7.83 (s, 1H), 7.53 (d, 1H, J = 8.5 Hz), 7.45 (d, 1H, J = 8.8 Hz), 7.30 (d, 1H, J = 8.5 Hz), 2.33 (s, 3H), 2.15 (dd, 1H, J = 2.3 and 8.8 Hz), 3.67 (s, 3H), 2.33 (s, 3H), 1.36 (s, 6H). | | + | | |
| 813 | N4-(2,2-Dimethyl-3-oxo-4H-5-pyrid[1,4]oxazin-6-yl)-5-fluoro-N2-(3-methyl-1H-indazol-6-yl)-2,4-pyrimidinediamine | 1H NMR (DMSO-d6): δ 12.21 (s, 1H), 11.02 (s, 1H), 9.30 (s, 1H), 9.12 (s, 1H), 8.11 (d, 1H, J = 3.5 Hz), 7.90 (s, 1H), 7.69 (d, 1H, J = 8.5 Hz), 7.43 (d, 1H, J = 8.5 Hz), 7.33 (d, 1H, J = 8.8 Hz), 7.19 (d, 1H, J = 8.8 Hz), 2.34 (s, 3H), 1.36 (s, 6H). | | + | | |
| 814 | N4-(2,2-Dimethyl-3-oxo-4H-5-pyrid[1,4]oxazin-6-yl)-5-fluoro-N2-[1-(3-methoxypropyl)indazol-5-yl]-2,4-pyrimidinediamine | 1H NMR (DMSO-d6): δ 11.10 (s, 1H), 9.22 (s, 1H), 9.19 (s, 1H), 8.12 (d, 1H, J = 3.5 Hz), 8.05 (s, 1H), 7.84 (s, 1H), 7.57 (d, 1H, J = 8.5 Hz), 7.50 (d, 1H, J = 8.8 Hz), 7.46 (d, 1H, J = 2.3 Hz), 7.35 (d, 1H, J = 8.8 Hz), 4.37 (t, 2H, J = 6.4 Hz), 3.22 (t, 2H, J = 6.4 Hz), 3.19 (s, 3H), 2.00 (app q, 2H, J = 6.4 Hz), 1.42 (s, 6H). | | + | | |
| 815 | N4-(3-Chloro-4-methoxyphenyl)-5-fluoro-N2-[1-[3-(N-phthalimidopropyl)]indazol-5-yl]-2,4-pyrimidinediamine | 1H NMR (DMSO-d6): δ 10.36 (s, 1H), 10.25 (s, 1H), 8.21 (d, 1H, J = 4.9 Hz), 7.85 (s, 1H), 7.79-7.75 (m, 5H), 7.67 (d, 1H, J = 2.3 Hz), 7.63 (d, 1H, J = 8.8 Hz), 7.49 (dd, 1H, J = 2.3 and 8.8 Hz), 7.32 (dd, 1H, J = 1.8 and 9.1 Hz), 7.03 (d, 1H, J = 8.8 Hz), 4.39 (t, 2H, J = 6.7 Hz), 3.75 (s, 3H), 3.57 (t, 2H, J = 6.7 Hz), 2.12 (app q, 2H, J = 6.7 Hz). | | + | | |
| 816 | N4-(2,2-Dimethyl-3-oxo-4H-benz[1,4]oxazin-6-yl)-5-fluoro-N2-[1-[3-(N-phthalimidopropyl)]indazol-5-yl]-2,4-pyrimidinediamine | 1H NMR (DMSO-d6): δ 10.24 (s, 1H), 9.99 (s, 1H), 8.23 (d, 1H, J = 4.7 Hz), 7.95 (d, 1H, J = 2.0 Hz), 7.87 (s, 1H), 7.80 (s, 1H), 7.78-7.73 (m, 4H), 7.64 (d, 1H, J = 9.1 Hz), 7.45 (d, 1H, J = 8.8 Hz), 7.36 (dd, 1H, J = 1.8 and 9.1 Hz), 4.41 (t, 2H, J = 6.7 Hz), 3.57 (t, 2H, J = 6.7 Hz), 2.12 (app q, 2H, J = 6.7 Hz). | | − | | |
| 817 | N4-(2,2-Dimethyl-3-oxo-4H-benz[1,4]oxazin-6-yl)-5-fluoro-N2-[1-[3-(N-phthalimidopropyl)]indazol-5-yl]-2,4-pyrimidinediamine | 1H NMR (DMSO-d6): δ 10.78 (s, 1H), 10.45 (s, 1H), 10.32 (s, 1H), 8.24 (d, 1H, J = 4.9 Hz), 7.88 (s, 1H), 7.87 (s, 1H), 7.84-7.77 (m, 4H), 7.65 (dd, 1H, J = 8.8 Hz), 7.37 (dd, 1H, J = 1.8 and 9.1 Hz), 7.20 (d, 1H, J = 8.8 Hz), 6.86 (d, 1H, J = 9.1 Hz), 4.43 (t, 2H, J = 6.7 Hz), 3.60 (t, 2H, J = 6.7 Hz), 2.16 (app q, 2H, J = 6.7 Hz), 1.32 (s, 6H). | | + | | |
| 818 | (S)-5-Fluoro-N4-(2-methyl-3-oxo-2H,4H-benz[1,4]oxazin-6-yl)-N2-[1-[3-(N-phthalimidopropyl)]indazol-5-yl]-2,4-pyrimidinediamine | 1H NMR (DMSO-d6): δ 10.80 (s, 1H), 10.44 (s, 1H), 10.30 (s, 1H), 8.24 (d, 1H, J = 5.3 Hz), 7.89 (s, 1H), 7.87 (s, 1H), 7.82-7.77 (m, 4H), 7.67 (d, 1H, J = 8.8 Hz), 7.37 (dd, 1H, J = 1.8 and 9.1 Hz), 7.22 (dd, 1H, J = 1.8 and 8.8 Hz), 7.18 (s, 1H), 6.89 (d, 1H, J = 8.8 Hz), 4.59 (qt, 1H, J = 6.7 Hz), 4.44 (t, 2H, J = 6.7 Hz), 3.60 (t, 2H, J = 6.7 Hz), 2.16 (app q, 2H, J = 6.7 Hz), 1.35 (d, 3H, J = 6.7 Hz). | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 819 | N2-[1-[3-(N-Acetylamino)propyl]indazol-5-yl]-N4-(3-chloro-4-methoxyphenyl)-5-fluoro-2,4-pyrimidinediamine | 1H NMR (DMSO-d6): δ 10.22 (s, 1H), 10.05 (s, 1H), 8.21 (d, 1H, J = 4.9 Hz), 7.92 (s, 1H), 7.90 (m, 1H), 7.86 (s, 1H), 7.75 (d, 1H, J = 2.3 Hz), 7.64 (d, 1H, J = 9.1 Hz), 7.57 (dd, 1H, J = 2.3 and 8.8 Hz), 7.39 (dd, 1H, J = 1.8 and 8.8 Hz), 7.09 (d, 1H, J = 8.8 Hz), 4.37 (t, 2H, J = 7.0 Hz), 3.83 (s, 3H), 3.02 (qt, 2H, J = 7.0 Hz), 1.92 (app q, 2H, J = 7.0 Hz), 1.78 (s, 3H). | | | | + |
| 820 | N2-[1-[3-(N-Acetylamino)propyl]indazol-5-yl]-N4-(3,4-dichlorophenyl)-5-fluoro-2,4-pyrimidinediamine | 1H NMR (DMSO-d6): δ 9.51 (s, 1H), 9.23 (s, 1), 8.10 (d, 1H, J = 3.8 Hz), 8.04 (d, 1H, J = 2.3 Hz), 7.95 (s, 1H), 7.82 (m, 2H), 7.74 (dd, 1H, J = 2.0 and 9.1 Hz), 7.51 (d, 1H, J = 9.1 Hz), 7.44 (d, 1H, J = 9.1 Hz), 7.43 (dd, 1H, J = 1.8 and 9.1 Hz), 4.30 (t, 2H, J = 6.7 Hz), 2.95 (qt, 2H, J = 6.7 Hz), 1.87 (app q, 2H, J = 7.0 Hz), 1.73 (s, 3H). | | + | | |
| 821 | N2-[1-[3-(N-Acetylamino)propyl]indazol-5-yl]-N4-(2,2-dimethyl-3-oxo-4H-benz[1,4]oxazin-6-yl)-5-fluoro-2,4-pyrimidinediamine | 1H NMR (DMSO-d6): δ 10.77 (s, 1H), 10.38 (s, 1H), 10.18 (s, 1H), 8.21 (d, 1H, J = 4.9 Hz), 7.90 (s, 3H), 7.61 (d, 1H, J = 8.8 Hz), 7.36 (dd, 1H, J = 2.0 and 9.1 Hz), 7.21 (d, 1H, J = 8.5 Hz), 7.18 (s, 1H), 6.89 (d, 1H, J = 8.5 Hz), 4.36 (t, 2H, J = 7.0 Hz), 2.99 (app qt, 2H, J = 6.7 Hz), 1.92 (app q, 2H, J = 6.7 Hz), 1.78 (s, 3H), 1.36 (s, 6H). | | + | | |
| 822 | N2-[1-[3-(N-Acetylamino)propyl]indazol-5-yl]-N4-(2,2-dimethyl-3-oxo-4H-pyrid[1,4]oxazin-6-yl)-5-fluoro-2,4-pyrimidinediamine | 1H NMR (DMSO-d6): δ 11.05 (s, 1H), 9.18 (s, 1H), 9.15 (s, 1H), 8.07 (d, 1H, 3.5 Hz), 8.01 (s, 1H), 7.80 (d, 1H, J = 6.3 Hz), 7.79 (s, 1H), 7.52 (d, 1H, J = 8.5 Hz), 7.48-7.40 (m, 2H), 7.31 (d, 1H, J = 8.5 Hz), 4.29 (t, 2H, J = 7.0 Hz), 2.94 (qt, 2H, J = 6.4 Hz), 1.86 (app q, 2H, J = 7.0 Hz), 1.72 (s, 3H), 1.37 (s, 6H). | | | | + |
| 823 | N2-[1-(3-Aminopropyl)indazol-5-yl]-N4-(3-chloro-4-methoxyphenyl)-5-fluoro-2,4-pyrimidinediamine | 1H NMR (DMSO-d6): δ 10.25 (s, 1H), 10.21 (s, 1H), 8.21 (d, 1H, J = 4.8 Hz), 7.97 (brs, 2H), 7.88 (s, 1H), 7.84-7.78 (m, 2H), 7.70 (d, 1H, J = 2.6 Hz), 9.08 (d, 1H, J = 9.1 Hz), 7.49 (dd, 1H, J = 2.6 and 8.8 Hz), 7.36 (dd, 1H, J = 1.8 and 8.8 Hz), 7.06 (d, 1H, J = 8.8 Hz), 4.43 (t, 2H, J = 6.7 Hz), 3.79 (s, 3H), 2.76-2.70 (m, 2H), 2.05 (app q, 2H, J = 6.7 Hz). | | + | | |
| 824 | N2-[1-(3-Aminopropyl)indazol-5-yl]-N4-(3,4-dichlorophenyl)-5-fluoro-2,4-pyrimidinediamine | 1H NMR (DMSO-d6): δ 10.01 (s, 1H), 9.77 (s, 1H), 8.24 (d, 1H, J = 3.1 Hz), 8.06 (d, 1H, J = 2.6 Hz), 7.96 (s, 1H), 7.95 (s, 1H), 7.90-7.85 (m, 2H), 7.75 (d, 1H, J = 8.5 Hz), 7.67 (d, 1H, J = 8.8 Hz), 7.53 (d, 1H, J = 8.8 Hz), 7.47 (d, 1H, J = 2.0 and 9.1 Hz), 4.43 (t, 2H, J = 6.7 Hz), 2.81-2.77 (m, 2H), 2.14-2.04 (app q, 2H, J = 6.7 Hz). | | + | | |
| 825 | N2-[1-(3-Aminopropyl)indazol-5-yl]-N4-(2,2-dimethyl-3-oxo-4H-benz[1,4]oxazin-6-yl)-5-fluoro-2,4-pyrimidinediamine | 1H NMR (DMSO-d6): δ 10.77 (s, 1H), 10.35 (s, 2H), 8.20 (d, 1H, J = 5.0 Hz), 7.94 (br s, 2H), 7.94 (s, 1H), 7.86 (s, 1H), 7.82-7.79 (m, 1H), 7.62 (d, 1H, J = 9.1 Hz), 7.34 (dd, 1H, J = 1.8 and 9.1 Hz), 7.21 (br s, 1H), 7.15 (dd, 1H, J = 1.8 and 8.8 Hz), 6.86 (d, 1H, J = 8.8 Hz), 4.42 (t, 2H, J = 6.7 Hz), 2.76-2.67 (m, 2H), 2.03 (app q, 2H, J = 6.7 Hz). | | + | | |
| 826 | (S)—N2-[1-(3-Aminopropyl)indazol-5-yl]-5-fluoro-N4-(2-methyl-3-oxo-2H,4H-benz[1,4]oxazin-6-yl)-2,4-pyrimidinediamine | 1H NMR (DMSO-d6): δ 10.78 (s, 1H), 10.30 (s, 2H), 8.18 (d, 1H, J = 4.9 Hz), 7.93 (br s, 2H), 7.91 (s, 1H), 7.87 (s, 1H), 7.83-7.80 (m, 1H), 7.63 (d, 1H, J = 8.8 Hz), 7.36 (dd, 1H, J = 1.8 and 8.8 Hz), 7.21 (br s, 1H), 7.17 (dd, 1H, J = 2.3 and 8.5 Hz), 6.88 (d, 1H, J = 8.5 Hz), 4.61 (qt, 1H, J = 6.7 Hz), 4.42 (t, 2H, J = 6.7 Hz), 2.76-2.67 (m, 2H), 2.03 (app q, 2H, J = 6.7 Hz), 1.36 (d, 3H, J = 6.7 Hz). | | + | | |
| 827 | N4-(3-Chloro-4-methoxyphenyl)indazol-5-yl]-5-fluoro-N2-[1-(3-hydroxypropyl)indazol-5-yl]-2,4-pyrimidinediamine p-Toluenesulfonic Acid Salt | 1H NMR (DMSO-d6): δ 10.39 (s, 1H), 10.03 (s, 1H), 8.20 (d, 1H, J = 5.3 Hz), 7.95 (s, 1H), 7.80 (d, 1H, J = 1.8 Hz), 7.74 (d, 1H, J = 2.6 Hz), 7.64 (d, 1H, J = 8.8 Hz), 7.54 (dd, 1H, J = 2.6 and 9.1 Hz), 7.46 (d, 2H, J = 8.1 Hz), 7.38 (dd, 1H, J = 2.1 and 9.1 Hz), 7.10 (d, 2H, J = 8.1 Hz), | | | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 828 | N4-(3-Chloro-4-methoxyphenyl)-5-fluoro-N2-[1-(3-hydroxypropyl)indazol-5-yl]-2,4-pyrimidinediamine Bis p-Toluenesulfonic Acid Salt | 7.07 (d, 1H, J = 8.8 Hz), 4.42 (t, 2H, J = 6.7 Hz), 3.82 (s, 3H), 3.37 (t, 2H, J = 6.7 Hz), 2.27 (s, 3H), 1.94 (app q, 2H, J = 6.7 Hz). 1H NMR (DMSO-d6): δ 10.63 (s, 1H), 10.23 (s, 1H), 8.24 (d, 1H, J = 5.5 Hz), 7.97 (s, 1H), 7.76 (d, 1H, J = 1.8 Hz), 7.52 (d, 1H, J = 2.4 Hz), 7.66 (d, 1H, J = 9.1 Hz), 7.52 (dd, 1H, J = 2.6 and 8.8 Hz), 7.47 (d, 4H, J = 8.1 Hz), 7.35 (dd, 1H, J = 1.8 and 8.8 Hz), 7.10 (d, 4H, J = 8.1 Hz), 7.07 (d, 1H, J = 9.1 Hz), 4.43 (t, 2H, J = 6.7 Hz), 3.82 (s, 3H), 3.38 (t, 2H, J = 6.4 Hz), 2.27 (s, 6H), 1.95 (app q, 2H, J = 6.7 Hz). | + | + | – | |
| 829 | N4-(3-Chloro-4-methoxyphenyl)-5-fluoro-N2-[1-(3-hydroxypropyl)indazol-5-yl]-2,4-pyrimidinediamine Benzenesulfonic Acid Salt | 1H NMR (DMSO-d6): δ 10.38 (s, 1H), 10.02 (s, 1H), 8.19 (d, 1H, J = 4.7 Hz), 7.95 (s, 1H), 7.80 (s, 1H), 7.74 (s, 1H), 7.65-7.58 (m, 4H), 7.38 (d, 1H, J = 9.1 Hz), 7.29 (s, 3H), 7.07 (d, 1H, J = 8.8 Hz), 4.42 (t, 2H, J = 6.7 Hz), 3.82 (s, 3H), 3.37 (t, 2H, J = 6.4 Hz), 1.95 (app q, 2H, J = 6.7 Hz). | + | + | + | |
| 830 | N4-(3-Chloro-4-methoxyphenyl)-5-fluoro-N2-[1-(3-hydroxypropyl)indazol-5-yl]-2,4-pyrimidinediamine Bis Benzenesulfonic Acid Salt | 1H NMR (DMSO-d6): δ 10.29 (s, 1H), 9.95 (s, 1H), 8.19 (d, 1H, J = 5.1 Hz), 7.94 (s, 1H), 7.81 (d, 1H, J = 1.8 Hz), 7.75 (d, 1H, J = 2.6 Hz), 7.65-7.53 (m, 7H), 7.39 (dd, 1H, J = 2.0 and 8.8 Hz), 7.31-7.26 (m, 5H), 7.07 (d, 1H, J = 8.8 Hz), 4.42 (t, 2H, J = 6.7 Hz), 3.82 (s, 3H), 3.37 (t, 2H, J = 6.4 Hz), 1.95 (app q, 2H, J = 6.7 Hz). | + | + | – | |
| 831 | N4-(3-Chloro-4-methoxyphenyl)-5-fluoro-N2-[1-(3-hydroxypropyl)indazol-5-yl]-2,4-pyrimidinediamine Hydrogen Chloride Salt | 1H NMR (DMSO-d6): δ 10.36 (s, 1H), 10.25 (s, 1H), 8.21 (d, 1H, J = 5.3 Hz), 7.87 (s, 1H), 7.77 (d, 1H, J = 1.5 Hz), 7.69 (d, 1H, J = 2.1 Hz), 7.57 (d, 1H, J = 9.1 Hz), 7.49 (dd, 1H, J = 2.3 and 8.8 Hz), 7.33 (dd, 1H, J = 2.0 and 9.1 Hz), 7.03 (d, 1H, J = 8.8 Hz), 4.36 (t, 2H, J = 6.7 Hz), 3.78 (s, 3H), 3.32 (t, 2H, J = 6.7 Hz), 1.89 (app q, 2H, J = 6.7 Hz). | + | + | – | |
| 832 | N4-(3-Chloro-4-methoxyphenyl)-5-fluoro-N2-[1-[3-(N-methylsulfonylamino)propyl]indazol-5-yl]-2,4-pyrimidinediamine | 1H NMR (DMSO-d6): δ 10.60 (s, 1H), 10.52 (s, 1H), 8.30 (d, 1H, J = 5.6 Hz), 7.95 (s, 1H), 7.81 (d, 1H, J = 1.8 Hz), 7.73 (s, 1H), 7.69 (dd, 1H, J = 2.3 and 8.8 Hz), 7.52 (dd, 1H, J = 2.3 and 8.8 Hz), 7.37 (dd, 1H, J = 2.0 and 8.8 Hz), 7.10 (br s, 1H), 7.09 (d, 1H, J = 9.1 Hz), 4.42 (t, 2H, J = 6.7 Hz), 3.83 (s, 3H), 2.95 (app m, 2H), 2.86 (s, 3H), 2.00 (app q, 2H, J = 6.7 Hz). | + | + | – | |
| 833 | N4-(3,4-Dichlorophenyl)-5-fluoro-N2-[1-[3-(N-methylsulfonylamino)propyl]indazol-5-yl]-2,4-pyrimidinediamine | 1H NMR (DMSO-d6): δ 9.53 (s, 1H), 9.25 (s, 1H), 8.11 (d, 1H, J = 3.8 Hz), 8.04 (d, 1H, J = 2.3 Hz), 7.97 (br s, 1H), 7.83 (s, 1H), 7.73 (d, 1H, J = 2.3 and 8.8 Hz), 7.53 (d, 1H, J = 8.8 Hz), 7.44 (d, 1H, J = 8.8 Hz), 7.43 (dd, 1H, J = 2.3 and 8.8 Hz), 7.02 (t, 1H, J = 5.3 Hz), 4.34 (t, 2H, J = 7.0 Hz), 2.89 (qt, 2H, J = 6.4 Hz), 1.96 (app q, 2H, J = 7.0 and 6.7 Hz), 2.86 (s, 3H). | – | + | – | |
| 834 | N4-(2,2-Dimethyl-3-oxo-4H-benz[1,4]oxazin-6-yl)-5-fluoro-N2-[1-[3-(N-methylsulfonylamino)propyl]indazol-5-yl]-2,4-pyrimidinediamine | 1H NMR (DMSO-d6): δ 10.74 (s, 1H), 10.24 (s, 1H), 9.98 (s, 1H), 8.21 (d, 1H, J = 4.3 Hz), 7.93 (s, 1H), 7.90 (s, 1H), 7.61 (d, 1H, J = 8.8 Hz), 7.38 (dd, 1H, J = 1.8 and 9.1 Hz), 7.22 (dd, 1H, J = 1.8 and 8.8 Hz), 7.17 (s, 1H), 7.09 (app t, 1H, J = 5.3 Hz), 6.89 (d, 1H, J = 8.8 Hz), 4.40 (t, 2H, J = 7.0 Hz), 2.91 (app qt, 2H, J = 6.7 Hz), 2.86 (s, 3H), 1.98 (app q, 2H, J = 6.7 Hz), 1.37 (s, 6H). | + | + | – | |
| 835 | (S)-5-Fluoro-N4-(2-methyl-3-oxo-2H,4H-benz[1,4]oxazin-6-yl)-N2-[1-(3-(N-methylsulfonylamino)propyl)indazol-5-yl]-2,4-pyrimidinediamine | 1H NMR (DMSO-d6): δ 10.80 (s, 1H), 10.42 (s, 1H), 10.25 (s, 1H), 9.98 (s, 1H), 8.22 (d, 1H, J = 4.9 Hz), 7.92 (s, 1H), 7.90 (d, 1H, J = 1.5 Hz), 7.64 (d, 1H, J = 8.8 Hz), 7.38 (dd, 1H, J = 2.0 and 9.1 Hz), 7.24-7.19 (m, 3H), 7.09 (t, 1H, J = 5.3 Hz), 6.91 (d, 1H, J = 8.8 Hz), 4.65 (qt, H, J = 6.7 Hz), 4.41 (t, 2H, J = 7.0 Hz), 2.92 (app qt, 2H, J = 6.7 Hz), 2.86 (s, 3H), 2.00 (app q, 2H, J = 6.7 Hz), 1.40 (d, 3H, J = 6.7 Hz). | + | + | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 836 | N4-(2,2-Dimethyl-3-oxo-4H-5-pyrid[1,4]oxazin-6-yl)-5-fluoro-N2-[1-[3-(N-methylsulfonylamino)propyl]indazol-5-yl]-2,4-pyrimidinediamine | 1H NMR (DMSO-d6): δ 11.11 (s, 1H), 9.25 (s, 1H), 9.24 (s, 1H), 8.11 (d, 1H, J = 3.0 Hz), 8.07 (s, 1H), 7.85 (s, 1H), 7.58 (d, 1H, J = 8.5 Hz), 7.54 (d, 1H, J = 9.1 Hz), 7.48 (d, 1H, J = 9.1 Hz), 7.36 (d, 1H, J = 8.5 Hz), 7.06 (t, 1H, J = 6.7 Hz), 4.39 (t, 2H, J = 6.7 Hz), 2.93 (qt, 2H, J = 6.7 Hz), 2.85 (s, 3H), 1.98 (app q, 2H, J = 6.7 Hz), 1.42 (s, 6H). | + | + | − | |
| 837 | N2-(3-Amino-1-methylindazol-5-yl)-N4-(2,2-dimethyl-3-oxo-4H-5-pyrid[1,4]oxazin-6-yl)-5-fluoro-2,4-pyrimidinediamine | 1H NMR (DMSO-d6): δ 11.17 (s, 1H), 10.22 (s, 1H), 8.25 (d, 1H, J = 4.4 Hz), 7.92 (s, 1H), 7.58 (d, 1H, J = 9.1 Hz), 7.50 (d, 1H, J = 9.1 Hz), 7.34 (d, 1H, J = 8.5 Hz), 3.86 (s, 3H), 1.39 (s, 3H). | + | + | | |
| 838 | N4-(2,2-Dimethyl-3-oxo-4H-5-pyrid[1,4]oxazin-6-yl)-5-fluoro-N2-[1-(3-hydroxypropyl)indazol-5-yl]-2,4-pyrimidinediamine | 1H NMR (DMSO-d6): δ 11.22 (s, 1H), 10.22 (s, 1H), 10.09 (s, 1H), 8.25 (d, 1H, J = 4.4 Hz), 7.90 (s, 2H), 7.57 (d, 1H, J = 9.3 Hz), 7.41-7.35 (m, 3H), 4.40 (t, 2H, J = 6.7 Hz), 3.35 (t, 2H, J = 6.4 Hz), 1.93 (app q, 2H, J = 6.7 Hz), 1.40 (s, 6H). | + | + | | |
| 839 | N4-(2,2-Dimethyl-3-oxo-4H-5-pyrid[1,4]oxazin-6-yl)-5-fluoro-N2-[1-(3-methoxypropyl)indazol-6-yl]-2,4-pyrimidinediamine | 1H NMR (DMSO-d6): δ 11.10 (s, 1H), 9.46 (s, 1H), 9.27 (s, 1H), 8.19 (d, 1H, J = 3.5 Hz), 8.01 (s, 1H), 7.87 (s, 1H), 7.65 (d, 1H, J = 8.5 Hz), 7.54 (d, 1H, J = 8.8 Hz), 7.35 (d, 1H, J = 8.5 Hz), 7.29 (d, 1H, J = 8.8 Hz), 4.19 (t, 2H, J = 6.7 Hz), 3.16 (t, 2H, J = 6.4 Hz), 3.13 (s, 3H), 1.94 (app q, 2H, J = 6.7 Hz), 1.42 (s, 3H). | + | + | | |
| 840 | N4-(3-Chloro-4-methoxyphenyl)-5-fluoro-N2-[1-[3-(N-trifluoromethylsulfonylamino)propyl]indazol-5-yl]-2,4-pyrimidinediamine | 1H NMR (DMSO-d6): δ 9.47 (br s, 1H), 9.28 (s, 1H), 9.17 (s, 1H), 8.07 (d, 1H, J = 3.8 Hz), 8.04 (s, 1H), 7.84 (s, 1H), 7.79 (d, 1H, J = 2.6 Hz), 7.64 (dd, 1H, J = 2.3 and 9.1 Hz), 7.52 (d, 1H, J = 8.8 Hz), 7.49 (d, 1H, J = 9.1 Hz), 7.07 (d, 1H, J = 8.8 Hz), 4.45 (t, 2H, J = 7.0 Hz), 3.82 (s, 3H), 3.19 (t, 2H, J = 7.0 Hz), 2.06 (app q, 2H, J = 7.0 Hz). | | + | | |
| 841 | N4-(3,4-Dichlorophenyl)-5-fluoro-N2-[1-(N-trifluoromethylsulfonylamino)propyl]indazol-5-yl]-2,4-pyrimidinediamine | 1H NMR (DMSO-d6): δ 10.48 (s, 1H), 10.28 (s, 1H), 9.55 (t, 1H, J = 5.2 Hz), 8.32 (d, 1H, J = 4.9 Hz), 8.00 (d, 1H, J = 2.0 Hz), 7.98 (s, 1H), 7.85-7.81 (m, 1H), 7.70-7.65 (m, 2H), 7.52 (d, 1H, J = 8.8 Hz), 7.42 (dd, 1H, J = 2.0 and 9.1 Hz), 4.45 (t, 2H, J = 6.7 Hz), 3.19 (app qt, 2H, J = 6.7 Hz), 2.06 (app q, 2H, J = 6.7 Hz). | | + | | |
| 842 | N4-(2,2-Dimethyl-3-oxo-4H-benz[1,4]oxazin-6-yl)-5-fluoro-N2-[1-[3-(N-trifluoromethylsulfonylamino)propyl]indazol-5-yl]-2,4-pyrimidinediamine | 1H NMR (DMSO-d6): δ 10.63 (s, 1H), 9.46 (br s, 1H), 9.28 (s, 1H), 9.06 (s, 1H), 8.12 (s, 1H), 8.05 (d, 1H, J = 3.8 Hz), 7.80 (s, 1H), 7.47 (app d, 2H, J = 9.1 Hz), 7.29 (dd, 1H, J = 2.0 and 8.8 Hz), 7.20 (d, 1H, J = 2.0 Hz), 6.89 (d, 1H, J = 8.8 Hz), 4.37 (t, 2H, J = 6.7 Hz), 3.15 (m, 2H), 2.02 (app q, 2H, J = 6.7 Hz), 1.39 (s, 6H). | | + | | |
| 843 | (S)-5-Fluoro-N4-(2-methyl-3-oxo-2H,4H-benz[1,4]oxazin-6-yl)-N2-[1-[3-(N-trifluoromethylsulfonylamino)propyl]indazol-5-yl]-2,4-pyrimidinediamine | 1H NMR (DMSO-d6): δ 10.74 (s, 1H), 9.88 (s, 1H), 9.68 (s, 1H), 9.49 (t, 1H, J = 6.7 Hz), 8.13 (d, 1H, J = 4.7 Hz), 8.01 (s, 1H), 7.87 (s, 1H), 7.56 (d, 1H, J = 9.1 Hz), 7.43 (d, 1H, J = 9.1 Hz), 7.26 (d, 1H, J = 8.5 Hz), 7.21 (s, 1H), 6.90 (d, 1H, J = 8.5 Hz), 4.64 (qt, 1H, J = 6.7 Hz), 4.40 (t, 2H, J = 6.7 Hz), 3.17 (qt, 2H, J = 6.77 Hz), 2.03 (app q, 2H, J = 6.7 Hz), 1.43 (d, 3H, J = 6.7 Hz). | | + | | |
| 844 | N4-(2,2-Dimethyl-3-oxo-4H-5-pyrid[1,4]oxazin-6-yl)-5-fluoro-N2-[1-[3-(N-trifluoromethylsulfonylamino)propyl]indazol-5-yl]-2,4-pyrimidinediamine | 1H NMR (DMSO-d6): δ 11.10 (s, 1H), 9.46 (br s, 1H), 9.23 (s, 1H), 9.19 (s, 1H), 8.11 (dd, 1H, J = 0.9 and 3.5 Hz), 8.07 (s, 1H), 7.86 (s, 1H), 7.59 (d, 1H, J = 8.5 Hz), 7.53 (d, 1H, J = 9.1 Hz), 7.49 (d, 1H, J = 8.8 Hz), 7.35 (d, 1H, J = 8.5 Hz), 4.39 (t, 2H, J = 7.0 Hz), 3.17 (app qt, 2H, J = 7.0 Hz), 2.03 (app q, 2H, J = 7.0 Hz), 1.42 (s, 6H). | | − | | |
| 845 | N4-(2,2-Dimethyl-3-oxo-4H-5-pyrid[1,4]oxazin-6-yl)-5-fluoro-N2-(2-methyl-3H-benzimidazol-5-yl)-2,4-pyrimidinediamine | 1H NMR (DMSO-d6): δ 11.11 (s, 1H), 9.68 (s, 1H), 9.42 (s, 1H), 8.20 (d, 1H, J = 3.5 Hz), 8.13 (s, 1H), 7.73 (dd, 1H, J = 1.8 and 9.1 Hz), 7.63 (d, 1H, J = 8.5 Hz), 7.57 (d, 1H, J = 9.1 Hz), 7.39 (d, 1H, J = 8.5 Hz), 2.73 (s, 3H), 1.42 (s, 6H). | | + | + | + |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 846 | N4-(2,2-Dimethyl-3-oxo-4H-pyrido[1,4]oxazin-6-yl)-5-fluoro-N2-(2-trifluoromethyl-1H-benzimidazol-5-yl)-2,4-pyrimidinediamine | 1H NMR (DMSO-d6): δ 13.56 (br s 1H), 11.07 (s, 1H), 9.43 (s, 1H), 9.20 (s, 1H), 8.16 (d, 1H, J = 3.5 Hz), 8.13 (s, 1H), 7.73 (dd, 1H, J = 1.8 and 9.1 Hz), 7.61 (d, 1H, J = 8.5 Hz), 7.55 (d, 1H, J = 9.1 Hz), 7.36 (d, 1H, J = 8.5 Hz), 1.42 (s, 6H). | | | + | + |
| 847 | N4-(3-Chloro-4-methoxyphenyl)-N2-[1-(3-(diethylphosphonamido)propyl)indazol-5-yl]-5-fluoro-2,4-pyrimidinediamine | 1H NMR (DMSO-d6): δ 9.27 (s, 1H), 9.16 (s, 1H), 8.07 (d, 1H, J = 3.5 Hz), 8.03 (s, 1H), 7.82 (s, 1H), 7.79 (d, 1H, J = 2.3 Hz), 7.65 (dd, 1H, J = 2.3 and 8.5 Hz), 7.53 (d, 1H, J = 8.5 Hz), 7.47 (d, 1H, J = 9.1 Hz), 7.08 (d, 1H, J = 9.1 Hz), 4.91 (dt, 1H, JHH = 6.7 and J2PH = 11.0 Hz), 4.35 (t, 2H, J = 6.7 Hz), 3.84 (app qt, 4H, JHH = 6.7 and J3PH = 11.0 Hz), 3.84 (s, 3H), 2.73 (m, 2H), 1.92 (app q, 2H, J = 6.7 Hz), 1.15 (t, 6H, J = 7.0 Hz). | | + | | |
| 848 | N4-(3-Chloro-4-methoxyphenyl)-5-fluoro-N2-[1-(3-pivalamidopropyl)indazol-5-yl]-2,4-pyrimidinediamine | 1H NMR (DMSO-d6): δ 10.42 (s, 1H), 10.29 (s, 1H), 8.26 (d, 1H, J = 4.9 Hz), 7.93 (s, 1H), 7.83 (s, 1H), 7.74 (s, 1H), 7.62 (d, 1H, J = 8.8 Hz), 7.55-7.47 (m, 2H), 7.39 (d, 1H, J = 9.1 Hz), 7.09 (d, 1H, J = 8.8 Hz), 4.35 (t, 2H, J = 7.0 Hz), 3.82 (s, 3H), 3.06 (app qt, 2H, J = 6.4 Hz), 1.94 (app q, 2H, J = 6.7 Hz), 1.06 (s, 9H). | | + | | |
| 849 | N4-(3,4-Dichlorophenyl)-5-fluoro-N2-[1-(3-pivalamidopropyl)indazol-5-yl]-2,4-pyrimidinediamine | 1H NMR (DMSO-d6): δ 9.55 (s, 1H), 9.28 (s, 1H), 8.15 (dd, 1H, J = 1.2 and 3.7 Hz), 8.09 (d, 1H, J = 1.5 Hz), 8.00 (s, 1H), 7.87 (s, 1H), 7.79 (dd, 1H, J = 1.8 and 9.1 Hz), 7.54-7.44 (m, 4H), 4.33 (t, 2H, J = 6.7 Hz), 3.04 (qt, 2H, J = 6.4 Hz), 1.94 (app q, 2H, J = 6.7 Hz). | | + | | |
| 850 | N4-(2,2-Dimethyl-3-oxo-4H-benz[1,4]oxazin-6-yl)-5-fluoro-N2-[1-(3-pivalamidopropyl)indazol-5-yl]-2,4-pyrimidinediamine | 1H NMR (DMSO-d6): δ 10.74 (s, 1H), 10.21 (s, 1H), 9.89 (s, 1H), 8.18 (d, 1H, J = 4.4 Hz), 7.93 (s, 1H), 7.88 (s, 1H), 7.56 (d, 1H, J = 8.5 Hz), 7.46 (t, 1H, J = 5.6 Hz), 7.37 (d, 1H, J = 9.1 Hz), 7.23 (d, 1H, J = 9.1 Hz), 7.17 (s, 1H), 6.88 (d, 1H, J = 8.8 Hz), 4.33 (t, 2H, J = 6.4 Hz), 3.02 (qt, 2H, J = 6.7 Hz), 1.92 (app q, 2H, J = 6.7 Hz), 1.37 (s, 6H), 1.05 (s, 9H). | | + | | |
| 851 | 5-Fluoro-(S)—N4-(2-methyl-3-oxo-4H-benz[1,4]oxazin-6-yl)-N2-[1-(3-pivalamidopropyl)indazol-5-yl]-2,4-pyrimidinediamine | 1H NMR (DMSO-d6): δ 10.80 (s, 1H), 10.42 (s, 1H), 10.28 (s, 1H), 8.22 (d, 1H, J = 4.4 Hz), 7.90 (s, 2H), 7.59 (d, 1H, J = 8.8 Hz), 7.47 (m, 1H), 7.38 (d, 1H, J = 8.8 Hz), 7.22 (app d, 2H, J = 8.8 Hz), 6.91 (d, 1H, J = 8.8 Hz), 4.64 (qt, 1H, J = 6.7 Hz), 4.34 (t, 2H, J = 6.7 Hz), 3.03 (qt, 2H, J = 6.7 Hz), 1.95 (app q, 2H, J = 7.0 Hz), 1.40 (d, 3H, J = 6.7 Hz), 1.05 (s, 9H). | | + | | |
| 852 | N4-(2,2-Dimethyl-3-oxo-4H-5-pyrido[1,4]oxazin-6-yl)-5-fluoro-N2-[1-(3-pivalamidopropyl)indazol-5-yl]-2,4-pyrimidinediamine | 1H NMR (DMSO-d6): δ 11.10 (s, 1H), 9.22 (s, 1H), 9.18 (s, 1H), 8.12 (d, 1H, J = 3.5 Hz), 7.84 (s, 1H), 7.82 (s, 1H), 7.59 (d, 1H, J = 8.8 Hz), 7.48-7.43 (m, 3H), 7.36 (d, 1H, J = 8.5 Hz), 4.32 (t, 2H, J = 6.7 Hz), 3.02 (qt, 2H, J = 6.7 Hz), 1.92 (app q, 2H, J = 6.7 Hz), 1.42 (s, 6H), 1.05 (s, 9H). | | + | | |
| 853 | N4-(3-Chloro-4-methoxyphenyl)-5-fluoro-N2-[1-[3-(N-succinimidopropyl)]indazol-5-yl]-2,4-pyrimidinediamine | 1H NMR (DMSO-d6): δ 9.28 (s, 1H), 9.17 (d, 1H, J = 3.5 Hz), 7.82 (s, 1H), 7.78 (d, 1H, J = 2.0 Hz), 7.66 (dd, 1H, J = 2.0 and 8.5 Hz), 7.52 (d, 1H, J = 9.1 Hz), 7.46 (d, 1H, J = 9.1 Hz), 7.09 (d, 1H, J = 8.5 Hz), 4.33 (t, 2H, J = 6.3 Hz), 3.84 (s, 3H), 3.38 (t, 2H, J = 6.3 Hz), 2.54 (s, 2H), 2.48 (s, 2H), 2.02 (q, 2H, J = 6.3 Hz). | + | + | | |
| 854 | N4-(3,4-Dichlorophenyl)-5-fluoro-N2-[1-[3-(N-succinimidopropyl)]indazol-5-yl]-2,4-pyrimidinediamine | 1H NMR (DMSO-d6): δ 9.55 (s, 1H), 9.28 (s, 1H), 8.16 (d, 1H, J = 3.5 Hz), 8.08 (d, 1H, J = 2.3 Hz), 8.01 (s, 1H), 7.88 (s, 1H), 7.80 (dd, 1H, J = 2.3 and 8.8 Hz), 7.56 (d, 1H, J = 8.8 Hz), 7.51-7.46 (m, 2H), 4.35 (t, | + | − | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 855 | N4-(2,2-Dimethyl-3-oxo-4H-benz[1,4]oxazin-6-yl)-5-fluoro-N2-[1-[3-(N-succinimidopropyl)]indazol-5-yl]-2,4-pyrimidinediamine | 2H, J = 6.7 Hz), 3.40 (t, 2H, J = 7.0 Hz), 2.55 (s, 2H), 2.48 (s, 2H), 2.03 (app q, 2H, J = 7.0 Hz). | + | | | |
| 856 | (S)-5-Fluoro-N4-(2-methyl-3-oxo-2H,4H-benz[1,4]oxazin-6-yl)-N2-[1-[3-(N-succinimidopropyl)]indazol-5-yl]-2,4-pyrimidinediamine | 1H NMR (DMSO-d6): δ 10.73 (s, 1H), 10.38 (s, 1H), 10.25 (s, 1H), 8.18 (d, 1H, J = 3.9 Hz), 7.85 (s, 1H), 7.83 (s, 1H), 7.56 (d, 1H, J = 9.1 Hz), 7.32 (d, 1H, J = 8.8 Hz), 7.14 (d, 2H, J = 9.1 Hz), 6.84 (d, 1H, J = 8.8 Hz), 4.30 (t, 2H, J = 7.0 Hz), 3.34 (t, 2H, J = 6.7 Hz), 2.50 (s, 2H), 2.42 (s, 2H), 1.98 (app q, 2H, J = 7.0 Hz), 1.31 (s, 6H). | + | + | | |
| 857 | N4-(2,2-Dimethyl-3-oxo-4H-5-pyrid[1,4]oxazin-6-yl)-N2-[1-[3-(N-succinimidopropyl)]indazol-5-yl]-2,4-pyrimidinediamine | 1H NMR (DMSO-d6): δ 10.82 (s, 1H), 10.52 (s, 1H), 10.42 (s, 1H), 8.24 (d, 1H, J = 4.9 Hz), 7.92 (s, 1H), 7.87 (s, 1H), 7.63 (d, 1H, J = 8.8 Hz), 7.37 (dd, 1H, J = 1.0 and 8.8 Hz), 7.20 (d, 2H, J = 8.8 Hz), 6.91 (d, 1H, J = 9.1 Hz), 4.65 (qt, 1H, J = 6.7 Hz), 4.36 (t, 2H, J = 6.7 Hz), 3.39 (t, 2H, J = 6.7 Hz), 2.55 (s, 2H), 2.48 (s, 2H), 2.01 (app q, 2H, J = 6.7 Hz), 1.39 (d, 3H, J = 6.7 Hz). | + | + | | |
| 858 | N4-(3-Chloro-4-methoxyphenyl)-N2-[1-[3-(2,6-dioxopiperidino)propyl]indazol-5-yl]-5-fluoro-2,4-pyrimidinediamine | 1H NMR (DMSO-d6): δ 11.10 (s, 1H), 9.23 (s, 1H), 9.19 (s, 1H), 8.12 (d, 1H, J = 3.5 Hz), 8.06 (s, 1H), 7.57 (d, 1H, J = 8.8 Hz), 7.53-7.46 (m, 2H), 7.36 (d, 1H, J = 8.8 Hz), 4.33 (t, 2H, J = 7.0 Hz), 3.39 (t, 2H, J = 6.7 Hz), 2.54 (s, 2H), 2.48 (s, 2H), 2.02 (app q, 2H, J = 7.0 Hz), 1.42 (s, 6H). | + | + | | |
| 859 | N4-(3,4-Dichlorophenyl)-N2-[1-[3-(2,6-dioxopiperidino)propyl]indazol-5-yl]-5-fluoro-2,4-pyrimidinediamine | 1H NMR (DMSO-d6): δ 10.26 (s, 1H), 10.08 (s, 1H), 8.22 (d, 1H, J = 4.3 Hz), 7.92 (s, 1H), 7.85 (s, 1H), 7.74 (d, 1H, J = 2.0 Hz), 7.62 (d, 1H, J = 8.8 Hz), 7.57 (dd, 1H, J = 2.3 and 8.8 Hz), 7.39 (dd, 1H, J = 2.0 and 8.3 Hz), 7.09 (d, 1H, J = 8.8 Hz), 4.35 (t, 2H, J = 7.0 Hz), 3.83 (s, 3H), 3.67 (t, 2H, J = 7.0 Hz), 2.53 (t, 4H, J = 6.7 Hz), 1.96 (app q, 2H, J = 7.0 Hz), 1.76 (q, 2H, J = 6.7 Hz). | + | + | | |
| 860 | N4-(2,2-Dimethyl-3-oxo-4H-benz[1,4]oxazin-6-yl)-N2-[1-[3-(2,6-dioxopiperidino)propyl]indazol-5-yl]-5-fluoro-2,4-pyrimidinediamine | 1H NMR (DMSO-d6): δ 10.05 (s, 1H), 9.77 (s, 1h), 8.23 (d, 1H, J = 5.1 Hz), 8.03 (s, 1H), 7.92 (s, 1H), 7.91 (s, 1H), 7.73 (d, 1H, J = 8.8 Hz), 7.61 (d, 1H, J = 8.8 Hz), 7.51 (d, 1H, J = 8.8 Hz), 7.44 (d, 1H, J = 8.8 Hz), 4.35 (t, 2H, J = 6.7 Hz), 3.67 (t, 2H, J = 6.7 Hz), 2.53 (t, 4H, J = 6.4 Hz), 1.97 (q, 2H, J = 6.4 Hz), 1.75 (app q, 2H, J = 6.7 Hz). | + | + | | |
| 861 | (S)—N2-[1-[3-(2,6-Dioxopiperidino)propyl]indazol-5-yl]-5-fluoro-N4-(2-methyl-3-oxo-2H,4H-benz[1,4]oxazin-6-yl)-2,4-pyrimidinediamine | 1H NMR (DMSO-d6): δ 10.76 (s, 1H), 10.34 (s, 1H), 10.16 (s, 1H), 8.21 (d, 1H, J = 4.3 Hz), 7.89 (s, 2H), 7.59 (d, 1H, J = 8.5 Hz), 7.37 (dd, 1H, J = 1.5 and 8.5 Hz), 7.21 (d, 1H, J = 8.8 Hz), 7.19 (s, 1H), 6.88 (d, 1H, J = 8.8 Hz), 4.35 (t, 2H, J = 7.0 Hz), 3.66 (t, 2H, J = 7.0 Hz), 2.53 (t, 4H, J = 7.0 Hz), 1.95 (q, 2H, J = 7.0 Hz), 1.76 (app q, 2H, J = 7.0 Hz), 1.36 (s, 6H). | + | + | | |
| 862 | N4-(2,2-Dimethyl-3-oxo-4H-5-pyrid[1,4]oxazin-6-yl)-N2-[1-[3-(2,6-dioxopiperidino)propyl]indazol-5-yl]-5-fluoro-2,4-pyrimidinediamine | 1H NMR (DMSO-d6): δ 10.78 (s, 1H), 10.49 (s, 1H), 10.44 (s, 1H), 8.21 (d, 1H, J = 4.9 Hz), 7.85 (s, 1H), 7.82 (s, 1H), 7.56 (d, 1H, J = 8.8 Hz), 7.31 (d, 1H, J = 8.8 Hz), 7.17 (s, 1H), 7.16 (d, 1H, J = 8.8 Hz), 6.86 (d, 1H, J = 8.8 Hz), 4.59 (qt, 1H, J = 6.7 Hz), 4.29 (t, 2H, J = 6.7 Hz), 3.61 (t, 2H, J = 7.0 Hz), 2.47 (t, 4H, J = 7.0 Hz), 1.90 (q, 2H, J = 7.0 Hz), 1.71 (app q, 2H, J = 6.7 Hz), 1.35 (d, 3H, J = 6.7 Hz). | + | + | | |
| | N4-(2,2-Dimethyl-3-oxo-4H-5-pyrid[1,4]oxazin-6-yl)-N2-[1-[3-(2,6-dioxopiperidino)propyl]indazol-5-yl]-5-fluoro-2,4-pyrimidinediamine | 1H NMR (DMSO-d6): δ 11.10 (s, 1H), 9.22 (s, 1H), 9.18 (s, 1H), 8.12 (d, 1H, J = 3.2 Hz), 8.05 (s, 1H), 7.84 (s, 1H), 7.58 (d, 1H, J = 8.2 Hz), 7.48 (s, 2H), 7.36 (d, 1H, J = 8.2 Hz), 4.32 (t, 2H, J = 7.3 Hz), 3.66 (t, 2H, J = 7.3 Hz), 2.45 (t, 2H, J = 7.3 Hz), 1.95 (app q, 2H, J = 7.3 Hz), 1.75 (app q, 2H, J = 7.3 Hz), 1.42 (s, 6H). | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 863 | N4-(3,4-Dichlorophenyl)-5-fluoro-N2-(2-trifluoromethyl-1H-benzimidazol-5-yl)-2,4-pyrimidinediamine Hydrogen Chloride Salt | 1H NMR (DMSO-d6): δ 10.33 (s, 1H), 10.23 (s, 1H), 8.32 (d, 1H, J = 4.7 Hz), 8.03 (d, 1H, J = 2.0 Hz), 7.90 (s, 1H), 7.74 (d, 1H, J = 2.0 Hz), 7.69 (d, 1H, J = 8.8 Hz), 7.51 (d, 1H, J = 8.8 Hz), 7.45 (dd, 1H, J = 2.0 and 8.8 Hz). | + | + | | |
| 864 | N4-(3,4-Dichlorophenyl)-5-fluoro-N2-(2-trifluoromethyl-1H-benzimidazol-5-yl)-2,4-pyrimidinediamine Ethanesulfonic Acid Salt | 1H NMR (DMSO-d6): δ 10.11 (s, 1H), 9.92 (s, 1H), 8.27 (d, 1H, J = 4.4 Hz), 8.06 (d, 1H, J = 2.0 Hz), 7.94 (s, 1H), 7.76 (d, 1H, J = 2.0 Hz), 7.67 (d, 1H, J = 8.8 Hz), 7.51 (d, 1H, J = 8.8 Hz), 7.41 (dd, 1H, J = 2.0 and 8.8 Hz), 2.42 (qt, 2H, J = 7.3 Hz), 1.05 (t, 3H, J = 7.3 Hz). | − | + | | |
| 865 | N4-(3,4-Dichlorophenyl)-5-fluoro-N2-(2-trifluoromethyl-1H-benzimidazol-5-yl)-2,4-pyrimidinediamine Benzenesulfonic Acid Salt | 1H NMR (DMSO-d6): δ 10.25 (s, 1H), 10.04 (s, 1H), 8.29 (d, 1H, J = 4.4 Hz), 8.03 (s, 1H), 7.91 (s, 1H), 7.73-7.26 (m, 2H), 7.58-7.43 (m, 4H), 7.29-7.27 (m, 3H). | − | + | | |
| 866 | N4-(3,4-Dichlorophenyl)-5-fluoro-N2-(2-trifluoromethyl-1H-benzimidazol-5-yl)-2,4-pyrimidinediamine p-Toluenesulfonic Acid Salt | 1H NMR (DMSO-d6): δ 10.30 (s, 1H), 10.08 (s, 1H), 8.30 (d, 1H, J = 4.7 Hz), 8.03 (d, 1H, J = 2.0 Hz), 7.90 (s, 1H), 7.71 (d, 2H, J = 8.8 Hz), 7.51 (d, 1H, J = 8.8 Hz), 7.47-7.43 (m, 3H), 7.10 (d, 2H, J = 8.8 Hz), 2.26 (s, 3H). | − | + | | |
| 867 | N4-(3,4-Dichlorophenyl)-5-fluoro-N2-(2-methyl-3H-benzimidazol-5-yl)-2,4-pyrimidinediamine Benzenesulfonic Acid Salt | 1H NMR (DMSO-d6): δ 9.77 (s, 1H), 9.74 (s, 1H), 8.25 (d, 1H, J = 3.8 Hz), 8.14 (d, 1H, J = 2.3 Hz), 8.12 (s, 1H), 7.81 (dd, 1H, J = 2.3 and 8.8 Hz), 7.66 (d, 2H, J = 9.1 Hz), 7.59-7.52 (m, 3H), 7.33-7.27 (m, 3H), 2.74 (s, 3H). | + | + | | |
| 868 | N4-(3,4-Dichlorophenyl)-5-fluoro-N2-(2-methyl-3H-benzimidazol-5-yl)-2,4-pyrimidinediamine p-Toluenesulfonic Acid Salt | 1H NMR (DMSO-d6): δ 9.78 (s, 1H), 9.74 (s, 1H), 8.25 (d, 1H, J = 3.8 Hz), 8.14 (d, 1H, J = 2.3 Hz), 8.12 (s, 1H), 7.81 (dd, 1H, J = 2.3 and 8.8 Hz), 7.66 (d, 2H, J = 9.1 Hz), 7.54 (d, 1H, J = 8.8 Hz), 7.46 (d, 2H, J = 8.2 Hz), 7.10 (d, 2H, J = 8.2 Hz), 2.74 (s, 3H), 2.26 (s, 3H). | + | + | | |
| 869 | N4-(3,4-Dichlorophenyl)-5-fluoro-N2-(2-methyl-3H-benzimidazol-5-yl)-2,4-pyrimidinediamine Hydrogen Chloride Salt | 1H NMR (DMSO-d6): δ 9.93 (s, 2H), 8.28 (d, 1H, J = 3.8 Hz), 8.12 (d, 1H, J = 2.3 Hz), 8.07 (s, 1H), 7.81 (dd, 1H, J = 1.8 and 8.8 Hz), 7.66 (d, 2H, J = 8.8 Hz), 7.56 (d, 1H, J = 8.8 Hz), 2.75 (s, 3H). | + | + | | |
| 870 | N4-(3,4-Dichlorophenyl)-5-fluoro-N2-(2-methyl-3H-benzimidazol-5-yl)-2,4-pyrimidinediamine Ethanesulfonic Acid Salt | 1H NMR (DMSO-d6): δ 9.75 (s, 2H), 9.72 (s, 1H), 8.24 (d, 1H, J = 3.8 Hz), 8.14 (d, 1H, J = 2.0 Hz), 8.12 (s, 1H), 7.82 (d, 1H, J = 8.8 Hz), 7.66 (d, 2H, J = 8.5 Hz), 7.53 (d, 1H, J = 8.8 Hz), 2.74 (s, 3H), 2.40 (qt, 2H, J = 7.3 Hz), 1.05 (t, 3H, J = 7.3 Hz). | + | + | | |
| 871 | N4-(3-Chloro-4-methoxyphenyl)-N2-[1-(3-ethoxypropyl)indazol-5-yl]-5-fluoro-2,4-pyrimidinediamine | 1H NMR (DMSO-d6): δ 10.37 (s, 1H), 10.23 (s, 1H), 8.25 (d, 1H, J = 5.3 Hz), 7.92 (s, 1H), 7.83 (s, 1H), 7.74 (d, 1H, J = 2.6 Hz), 7.59 (d, H, J = 8.8 Hz), 7.53 (dd, 1H, J = 2.3 and 8.5 Hz), 7.38 (dd, 1H, J = 1.8 and 8.8 Hz), 7.09 (d, 1H, J = 9.1 Hz), 4.40 (t, 2H, J = 6.7 Hz), 3.83 (s, 3H), 3.31 (qt, 2H, J = 6.7 Hz), 3.26 (t, 2H, J = 6.7 Hz), 2.01 (app q, 2H, J = 6.7 Hz), 1.06 (t, 3H, J = 6.7 Hz). | + | + | | |
| 872 | N4-(3,4-Dichlorophenyl)-N2-[1-(3-ethoxypropyl)indazol-5-yl]-5-fluoro-2,4-pyrimidinediamine | 1H NMR (DMSO-d6): δ 10.27 (s, 1H), 10.02 (s, 1H), 8.28 (d, 1H, J = 4.7 Hz), 8.02 (d, 1H, J = 2.3 Hz), 7.95 (s, 1H), 7.87 (s, 1H), 7.68 (d, 1H, J = 8.8 Hz), 7.60 (d, 1H, J = 8.8 Hz), 7.51 (d, 1H, J = 8.8 Hz), 7.42 (dd, 1H, J = 2.3 and 8.8 Hz), 4.41 (t, 2H, J = 6.4 Hz), 3.32 (qt, 2H, J = 6.7 Hz), 3.27 (t, 2H, J = 6.4 Hz), 2.02 (q, 2H, J = 6.4 Hz), 1.07 (t, 3H, J = 6.7 Hz). | + | + | | |
| 873 | N4-(2,2-Dimethyl-3-oxo-4H-benz[1,4]oxazin-6-yl)-N2-[1-(3-ethoxypropyl)indazol-5-yl]-5-fluoro-2,4-pyrimidinediamine | 1H NMR (DMSO-d6): δ 10.76 (s, 1H), 10.36 (s, 1H), 10.19 (s, 1H), 8.22 (d, 1H, J = 5.3 Hz), 7.90 (s, 2H), 7.55 (d, 1H, J = 9.1 Hz), 7.37 (dd, 1H, J = 1.8 and 8.8 Hz), 7.20 (d, 1H, J = 8.8 Hz), 7.18 (s, 1H), 6.87 (d, 1H, J = 8.8 Hz), 4.39 (t, 2H, J = 6.7 Hz), 3.31 (qt, 2H, J = 7.0 Hz), 3.25 (t, 2H, J = 6.7 Hz), 1.99 (app q, 2H, J = 6.7 Hz), 1.36 (s, 6H), 1.07 (t, 3H, J = 7.0 Hz). | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 874 | (S)—N2-[1-(3-Ethoxypropyl)indazol-5-yl]-5-fluoro-N4-(2-methyl-3-oxo-2H,4H-benz[1,4]oxazin-6-yl)-2,4-pyrimidinediamine | 1H NMR (DMSO-d6): δ 10.79 (s, 1H), 10.40 (s, 1H), 8.22 (d, 1H, J = 5.3 Hz), 7.90 (d, 1H, J = 1.8 Hz), 7.88 (s, 1H), 7.57 (d, 1H, J = 9.1 Hz), 7.37 (dd, 1H, J = 1.8 and 9.1 Hz), 7.22 (dd, 2H, J = 1.8 and 8.5 Hz), 6.89 (d, 1H, J = 8.5 Hz), 4.65 (qt, 1H, J = 7.0 Hz), 4.40 (t, 2H, J = 6.7 Hz), 3.29 (qt, 2H, J = 7.0 Hz), 3.25 (t, 2H, J = 6.7 Hz), 2.00 (app q, 2H, J = 6.7 Hz), 1.40 (d, 3H, J = 7.0 Hz), 1.07 (t, 3H, J = 7.0 Hz). | + | | | |
| 875 | N4-(2,2-Dimethyl-3-oxo-4H-5-pyrid[1,4]oxazin-6-yl)-N2-[1-(3-ethoxypropyl)indazol-5-yl]-5-fluoro-2,4-pyrimidinediamine | 1H NMR (DMSO-d6): δ 11.10 (s, 1H), 9.22 (s, 1H), 9.19 (s, 1H), 8.11 (d, 1H, J = 3.5 Hz), 8.05 (s, 1H), 7.84 (s, 1H), 7.58 (d, 1H, J = 8.5 Hz), 7.42 (d, 2H, J = 8.8 Hz), 7.35 (d, 1H, J = 8.5 Hz), 4.37 (t, 2H, J = 6.7 Hz), 3.32 (qt, 2H, J = 7.0 Hz), 3.28 (t, 2H, J = 6.7 Hz), 2.02 (app q, 2H, J = 6.7 Hz), 1.42 (s, 6H), 1.07 (t, 3H, J = 7.0 Hz). | + | + | | |
| 876 | N4-(2-Chloro-3-methoxypyrid-6-yl)-5-fluoro-N2-(3,4,5-trimethoxyphenyl)-2,4-pyrimidinediamine | 1H NMR (DMSO-d6): δ 10.32 (s, 1H), 9.63 (s, 1H), 8.19 (d, 1H, J = 4.1 Hz), 8.06 (dd, 1H, J = 8.5 Hz), 7.52 (d, 1H, J = 8.5 Hz), 6.91 (s, 2H), 3.88 (s, 3H), 3.64 (s, 6H), 3.61 (s, 3H). | + | + | | |
| 877 | N4-(2-Chloro-3-methoxypyrid-6-yl)-N2-(3,4-dimethoxyphenyl)-5-fluoro-2,4-pyrimidinediamine | 1H NMR (DMSO-d6): δ 9.84 (s, 1H), 9.23 (s, 1H), 8.15 (d, 1H, J = 8.8 Hz), 8.14 (d, 1H, J = 3.5 Hz), 7.55 (d, 1H, J = 9.1 Hz), 6.90 (d, 1H, J = 2.3 Hz), 6.08 (d, 2H, J = 2.3 Hz), 3.88 (s, 3H), 3.65 (s, 3H). | + | | | |
| 878 | N2-(3-Chloro-4-methoxyphenyl)-N4-(2-chloro-3-methoxypyrid-6-yl)-5-fluoro-2,4-pyrimidinediamine | 1H NMR (DMSO-d6): δ 9.83 (s, 1H), 9.26 (s, 1H), 8.14 (d, 1H, J = 3.5 Hz), 8.01 (d, 1H, J = 9.1 Hz), 7.80 (d, 1H, J = 2.6 Hz), 7.59 (d, 1H, J = 9.1 Hz), 7.43 (dd, 1H, J = 2.6 and 9.1 Hz), 7.03 (d, 1H, J = 9.1 Hz), 3.88 (s, 3H), 3.78 (s, 3H). | − | | | |
| 879 | N4-(2-Chloro-3-methoxypyrid-6-yl)-N2-(3,5-dimethylphenyl)-5-fluoro-2,4-pyrimidinediamine | 1H NMR (DMSO-d6): δ 9.79 (s, 1H), 9.15 (s, 1H), 8.13 (d, 1H, J = 3.5 Hz), 8.08 (dd, 1H, J = 2.3 and 8.8 Hz), 7.57 (d, 1H, J = 8.8 Hz), 7.22 (s, 2H), 6.53 (s, 1H), 3.82 (s, 3H), 2.19 (s, 6H), H+). | + | + | | |
| 880 | N4-(2-Chloro-3-methoxypyrid-6-yl)-5-fluoro-N2-[3-(N-methylamino)carbonylmethyleneoxyphenyl]-2,4-pyrimidinediamine | 1H NMR (DMSO-d6): δ 9.84 (s, 1H), 9.32 (s, 1H), 8.14 (d, 1H, J = 3.5 Hz), 8.12 (d, 1H, J = 8.8 Hz), 7.96 (qt, 1H, J = 4.7 Hz), 7.60 (d, 1H, J = 8.8 Hz), 7.37 (app s, 1H), 7.23 (d, 1H, J = 8.2 Hz), 7.13 (t, 1H, J = 8.2 Hz), 6.48 (dd, 1H, J = 2.3 and 8.2 Hz), 4.37 (s, 2H), 3.87 (s, 3H), 2.61 (d, 3H, J = 4.7 Hz). | + | + | | |
| 881 | 2-Chloro-N4-(2-chloro-3-methoxypyrid-6-yl)-5-fluoro-4-pyrimidineamine | 1H NMR (DMSO-d6): δ 8.33 (d, 1H, J = 8.8 Hz), 8.12 (d, 1H, J = 2.3 Hz), 7.65 (br s, 1H), 7.38 (d, 1H, J = 8.8 Hz), 3.94 (s, 3H). | | | | |
| 882 | N4-(2-Chloro-3-methoxypyrid-6-yl)-5-fluoro-N2-(indazol-6-yl)-2,4-pyrimidinediamine | LCMS: ret. time: 10.99 min.; purity: 93%; MS (m/e) 386 (MH+). | + | | | |
| 883 | N4-(2-Chloro-3-methoxypyrid-6-yl)-5-fluoro-N2-(2-trifluoromethyl-1H-benzimidazol-5-yl)-2,4-pyrimidinediamine | LCMS: ret. time: 11.74 min.; purity: 97%; MS (m/e): 454 (MH+). | + | | | |
| 884 | N4-(2-Chloro-3-methoxypyrid-6-yl)-5-fluoro-N2-(2-methyl-3H-benzimidazol-5-yl)-2,4-pyrimidinediamine | LCMS: ret. time: 7.71 min.; purity: 93%; MS (m/e): 400 (MH+). | + | | | |
| 885 | N4-(2-Chloro-3-methoxypyrid-6-yl)-5-fluoro-N2-(1-methylindazol-6-yl)-2,4-pyrimidinediamine | LCMS: ret. time: 12.20 min.; purity: 93%; MS (m/e): 400 (MH+). | + | | | |
| 886 | N4-(2-Chloro-3-methoxypyrid-6-yl)-5-fluoro-N2-(1-methylindazol-5-yl)-2,4-pyrimidinediamine | LCMS: ret. time: 10.79 min.; purity: 94%; MS (m/e): 400 (MH+). | − | | | |
| 887 | N4-(2-Chloro-3-methoxypyrid-6-yl)-5-fluoro-N2-(1-ethylindazol-6-yl)-2,4-pyrimidinediamine | LCMS: ret. time: 12.97 min.; purity: 95%; MS (m/e): 414 (MH+). | + | | | |
| 888 | N4-(2-Chloro-3-methoxypyrid-6-yl)-5-fluoro-N2-(1-isopropylindazol-6-yl)-2,4-pyrimidinediamine | LCMS: ret. time: 13.86 min.; purity: 92%; MS (m/e): 428 (MH+). | + | | | |
| 889 | N4-(2-Chloro-3-methoxypyrid-6-yl)-N2-(2,2-dimethyl-3-oxo-4H-benz[1,4]oxazin-6-yl)-5-fluoro-2,4-pyrimidinediamine | LCMS: ret. time: 11.84 min.; purity: 94%; MS (m/e): 445 (MH+). | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 890 | N2-[1-[3-(N-Acetylamino)propyl]indazol-5-yl]-N4-(2-chloro-3-methoxypyrid-6-yl)-5-fluoro-2,4-pyrimidinediamine | LCMS: ret. time: 9.42 min.; purity: 95%; MS (m/e): 485 (MH+). | + | | | |
| 891 | N4-(2-Chloro-3-methoxypyrid-6-yl)-N2-[1-[3-(N-cyclopropanecarbonylamino)propyl]indazol-5-yl]-5-fluoro-2,4-pyrimidinediamine | LCMS: ret. time: 10.30 min.; purity: 95%; MS (m/e): 511 (MH+). | + | | | |
| 892 | N4-(2-Chloro-3-methoxypyrid-6-yl)-5-fluoro-N2-[1-(3-pivalamidopropyl)indazol-5-yl]-2,4-pyrimidinediamine | LCMS: ret. time: 11.73 min.; purity: 99%; MS (m/e): 527 (MH+). | + | | | |
| 893 | N4-(2-Chloro-3-methoxypyrid-6-yl)-5-fluoro-N2-[1-[3-(N-isobutyrylamino)propyl]indazol-5-yl]-2,4-pyrimidinediamine | LCMS: ret. time: 10.71 min.; purity: 97%; MS (m/e): 514 (MH+). | + | | | |
| 894 | N4-(3,4-Dichlorophenyl)-N2-(1,2-dimethylbenzimidazol-5-yl)-5-fluoro-2,4-pyrimidinediamine | LCMS: ret. time: 9.44 min.; purity: 100%; MS (m/e): 418 (MH+). | + | | | |
| 895 | N4-(3-Chloro-4-methoxyphenyl)-N2-(1,2-dimethylbenzimidazol-5-yl)-5-fluoro-2,4-pyrimidinediamine | LCMS: ret. time: 7.66 min.; purity: 96%; MS (m/e): 413 (MH+). | + | | | |
| 896 | N2-(1,2-Dimethylbenzimidazol-5-yl)-N4-(2,2-dimethyl-3-oxo-4H-benz[1,4]oxazin-6-yl)-5-fluoro-2,4-pyrimidinediamine | LCMS: ret. time: 7.09 min.; purity: 99%; MS (m/e): 448 (MH+). | + | + | | |
| 897 | (S)—N2-(1,2-Dimethylbenzimidazol-5-yl)-5-fluoro-N4-(2-methyl-3-oxo-2H,4H-benz[1,4]oxazin-6-yl)-2,4-pyrimidinediamine | LCMS: ret. time: 6.52 min.; purity: 97%; MS (m/e): 434 (MH+). | + | + | | + |
| 898 | N2-(1,2-Dimethylbenzimidazol-5-yl)-N4-(2,2-dimethyl-3-oxo-4H-5-pyrid[1,4]oxazin-6-yl)-5-Fluoro-2,4-pyrimidinediamine | LCMS: ret. time: 7.85 min.; purity: 91%; MS (m/e): 449 (MH+). | + | + | | + |
| 899 | N4-(3,4-Dichlorophenyl)-5-fluoro-N2-[1-(2-hydroxyethyl)-2-methylbenzimidazol-5-yl)-2,4-pyrimidinediamine | LCMS: ret. time: 8.77 min.; purity: 97%; MS (m/e): 448 (MH+). | + | + | | |
| 900 | N4-(3-Chloro-4-methoxyphenyl)-5-fluoro-N2-[1-(2-hydroxyethyl)-2-methylbenzimidazol-5-yl]-2,4-pyrimidinediamine | LCMS: ret. time: 7.06 min.; purity: 93%; MS (m/e): 443 (MH+). | + | | | |
| 901 | N4-(2,2-Dimethyl-3-oxo-4H-benz[1,4]oxazin-6-yl)-5-fluoro-N2-[1-(2-hydroxyethyl)-2-methylbenzimidazol-5-yl]-2,4-pyrimidinediamine | LCMS: ret. time: 6.50 min.; purity: 97%; MS (m/e): 478 (MH+). | + | + | + | + |
| 902 | (S)-5-Fluoro-N2-[1-(2-hydroxyethyl)-2-methylbenzimidazol-5-yl]-N4-(2-methyl-3-oxo-2H,4H-benz[1,4]oxazin-6-yl)-2,4-pyrimidinediamine | LCMS: ret. time: 5.99 min.; purity: 94%; MS (m/e): 464 (MH+). | + | + | | |
| 903 | N4-(2,2-Dimethyl-3-oxo-4H-5-pyrid[1,4]oxazin-6-yl)-5-fluoro-N2-[1-(2-hydroxyethyl)-2-methylbenzimidazol-5-yl]-2,4-pyrimidinediamine | LCMS: ret. time: 6.89 min.; purity: 97%; MS (m/e): 479 (MH+). | + | + | | + |
| 904 | N4-(3,4-Dichlorophenyl)-N2-(2,3-dihydro-1-methyl-2-oxo-benzimidazol-5-yl)-5-fluoro-2,4-pyrimidinediamine | LCMS: ret. time: 10.32 min.; purity: 100%; MS (m/e): 420 (MH+). | − | − | | |
| 905 | N4-(3-Chloro-4-methoxyphenyl)-N2-(2,3-dihydro-1-methyl-2-oxo-benzimidazol-5-yl)-5-fluoro-2,4-pyrimidinediamine | LCMS: ret. time: 8.24 min.; purity: 96%; MS (m/e): 415 (MH+). | + | + | | |
| 906 | N4-(2,2-Dimethyl-3-oxo-4H-benz[1,4]oxazin-6-yl)-N2-(2,3-dihydro-1-methyl-2-oxo-benzimidazol-5-yl)-5-fluoro-2,4-pyrimidinediamine | LCMS: ret. time: 7.53 min.; purity: 97%; MS (m/e): 450 (MH+). | + | + | | |
| 907 | (S)—N2-(2,3-Dihydro-1-methyl-2-oxo-benzimidazol-5-yl)-5-fluoro-N4-(2-methyl-3-oxo-2H,4H-benz[1,4]oxazin-6-yl)-2,4-pyrimidinediamine | LCMS: ret. time: 7.00 min.; purity: 98%; MS (m/e): 436 (MH+). | + | + | | |
| 908 | N4-(2,2-Dimethyl-3-oxo-4H-5-pyrid[1,4]oxazin-6-yl)-N2-(2,3-dihydro-1-methyl-2-oxo-benzimidazol-5-yl)-5-fluoro-2,4-pyrimidinediamine | LCMS: ret. time: 8.19 min.; purity: 94%; MS (m/e): 451 (MH+). | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 909 | 5-Fluoro-N2-(2-methyl-3H-benzimidazol-5-yl)-N4-(2-methyl-1,1,3-trioxo-2H,4H-benzo[1,4]thiazin-6-yl)-2,4-pyrimidinediamine | LCMS: ret. time: 7.11 min.; purity: 94%; MS (m/e): 468 (MH+). | + | | | + |
| 910 | 5-Fluoro-N4-(2-methyl-1,1,3-trioxo-2H,4H-benzo[1,4]thiazin-6-yl)-N2-(2-trifluoromethyl-1H-benzimidazol-5-yl)-2,4-pyrimidinediamine | LCMS: ret. time: 10.29 min.; purity: 98%; MS (m/e): 521 (MH+). | + | | | + |
| 911 | N4-(3,4-Dichlorophenyl)-5-fluoro-N2-(1-methyl-2-trifluoromethylbenzimidazol-5-yl)-2,4-pyrimidinediamine | LCMS: ret. time: 14.28 min.; purity: 97%; MS (m/e): 472 (MH+). | | + | | |
| 912 | N4-(3-Chloro-4-methoxyphenyl)-5-fluoro-N2-(1-methyl-2-trifluoromethylbenzimidazol-5-yl)-2,4-pyrimidinediamine | LCMS: ret. time: 11.38 min.; purity: 91%; MS (m/e): 467 (MH+). | | + | | |
| 913 | N4-(2,2-Dimethyl-3-oxo-4H-benz[1,4]oxazin-6-yl)-N2-(1-methyl-2-trifluoromethylbenzimidazol-5-yl)-2,4-pyrimidinediamine | LCMS: ret. time: 10.21 min.; purity: 94%; MS (m/e): 502 (MH+). | | + | | |
| 914 | (S)-5-Fluoro-N4-(2-methyl-3-oxo-2H,4H-benz[1,4]oxazin-6-yl)-N2-(1-methyl-2-trifluoromethylbenzimidazol-5-yl)-2,4-pyrimidinediamine | LCMS: ret. time: 9.66 min.; purity: 93%; MS (m/e): 488 (MH+). | | + | | |
| 915 | N4-(2,2-Dimethyl-3-oxo-4H-5-pyrid[1,4]oxazin-6-yl)-N2-(1-methyl-2-trifluoromethylbenzimidazol-5-yl)-2,4-pyrimidinediamine | LCMS: ret. time: 11.48 min.; purity: 91%; MS (m/e): 503 (MH+). | | + | | |
| 916 | N4-(3,4-Dichlorophenyl)-5-fluoro-N2-[1-(2-hydroxyethyl)-2-trifluoromethylbenzimidazol-5-yl]-2,4-pyrimidinediamine | LCMS: ret. time: 12.15 min.; purity: 96%; MS (m/e): 502 (MH+). | | + | | |
| 917 | N4-(3-Chloro-4-methoxyphenyl)-5-fluoro-[1-(2-hydroxyethyl)-2-trifluoromethylbenzimidazol-5-yl]-2,4-pyrimidinediamine | LCMS: ret. time: 9.90 min.; purity: 94%; MS (m/e): 497 (MH+). | | + | | |
| 918 | N4-(2,2-Dimethyl-3-oxo-4H-benz[1,4]oxazin-6-yl)-5-fluoro-[1-(2-hydroxyethyl)-2-trifluoromethylbenzimidazol-5-yl]-2,4-pyrimidinediamine | LCMS: ret. time: 9.08 min.; purity: 96%; MS (m/e): 532 (MH+). | + | + | | |
| 919 | (S)-5-Fluoro-[1-(2-hydroxyethyl)-2-trifluoromethylbenzimidazol-5-yl]-N4-(2-methyl-3-oxo-2H,4H-benz[1,4]oxazin-6-yl)-2,4-pyrimidinediamine | LCMS: ret. time: 8.67 min.; purity: 92%; MS (m/e): 518 (MH+). | + | + | | |
| 920 | N4-(3,4-Dichlorophenyl)-5-fluoro-[1-(2-hydroxymethyl)-2-trifluoromethylbenzimidazol-5-yl]-2,4-pyrimidinediamine | LCMS: ret. time: 14.96 min.; purity: 97%; MS (m/e): 486 (MH+). | + | + | | |
| 921 | N4-(3-Chloro-4-methoxyphenyl)-5-fluoro-[1-(2-hydroxymethyl)-2-trifluoromethylbenzimidazol-5-yl]-2,4-pyrimidinediamine | LCMS: ret. time: 12.21 min.; purity: 98%; MS (m/e): 481 (MH+). | + | + | | |
| 922 | N4-(2,2-Dimethyl-3-oxo-4H-benz[1,4]oxazin-6-yl)-5-fluoro-[1-(2-hydroxymethyl)-2-trifluoromethylbenzimidazol-5-yl]-2,4-pyrimidinediamine | LCMS: ret. time: 10.93 min.; purity: 96%; MS (m/e): 516 (MH+). | | + | | |
| 923 | (S)-5-Fluoro-[1-(2-hydroxymethyl)-2-trifluoromethylbenzimidazol-5-yl]-N4-(2-methyl-3-oxo-2H,4H-benz[1,4]oxazin-6-yl)-2,4-pyrimidinediamine | LCMS: ret. time: 10.43 min.; purity: 92%; MS (m/e): 502 (MH+). | | + | | |
| 924 | N4-(2,2-Dimethyl-3-oxo-4H-5-pyrid[1,4]oxazin-6-yl)-5-fluoro-[1-(2-hydroxymethyl)-2-trifluoromethylbenzimidazol-5-yl]-2,4-pyrimidinediamine | LCMS: ret. time: 12.25 min.; purity: 98%; MS (m/e): 517 (MH+). | | + | | |
| 925 | N2-(1,2-Benzisoxazol-5-yl)-N4-(3-chloro-4-methoxyphenyl)-5-fluoro-2,4-pyrimidinediamine | LCMS: ret. time: 9.63 min.; purity: 100%; MS (m/e): 386 (MH+). | + | | | |
| 926 | N2-(1,2-Benzisoxazol-5-yl)-N4-(2,2-dimethyl-3-oxo-4H-benz[1,4]oxazin-6-yl)-5-fluoro-2,4-pyrimidinediamine | LCMS: ret. time: 8.48 min.; purity: 100%; MS (m/e): 421 (MH+). | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 927 | (S)—N2-(1,2-Benzisoxazol-5-yl)-5-fluoro-N4-(2-methyl-3-oxo-2H,4H-benz[1,4]oxazin-6-yl)-2,4-pyrimidinediamine | LCMS: ret. time: 8.11 min.; purity: 100%; MS (m/e): 407 (MH+). | | + | | |
| 928 | N2-(1,2-Benzisoxazol-5-yl)-N4-(2,2-dimethyl-3-oxo-4H-5-pyrido[1,4]oxazin-6-yl)-5-fluoro-2,4-pyrimidinediamine | LCMS: ret. time: 9.57 min.; purity: 100%; MS (m/e): 422 (MH+). | | + | | |
| 929 | racemic-N2-(1,2-Benzisoxazol-5-yl)-5-fluoro-N4-(2-methyl-1,1,3-trioxo-2H,4H-benzo[1,4]thiazin-6-yl)-2,4-pyrimidinediamine | LCMS: ret. time: 9.69 min.; purity: 95%; MS (m/e): 455 (MH+). | + | | | |
| 930 | N2-(1,2-Benzisoxazol-5-yl)-N4-(2,2-dimethyl-1,1,3-trioxo-4H-benzol[1,4]thiazin-6-yl)-5-fluoro-2,4-pyrimidinediamine | LCMS: ret. time: 10.13 min.; purity: 97%; MS (m/e): 470 (MH+). | + | | | |
| 931 | racemic-N2-(1,2-Benzisoxazol-5-yl)-5-fluoro-N4-(2-methyl-3-oxo-2H,4H-benz[1,4]thiazin-6-yl)-2,4-pyrimidinediamine | LCMS: ret. time: 9.21 min.; purity: 96%; MS (m/e): 423 (MH+). | + | + | | |
| 932 | N4-(3,4-Dichlorophenyl)-N2-(1-ethyl-2-methylbenzimidazol-5-yl)-5-fluoro-2,4-pyrimidinediamine | LCMS: ret. time: 10.09 min.; purity: 99%; MS (m/e): 432 (MH+). | − | | | |
| 933 | N4-(3-Chloro-4-methoxyphenyl)-N2-(1-ethyl-2-methylbenzimidazol-5-yl)-5-fluoro-2,4-pyrimidinediamine | LCMS: ret. time: 8.64 min.; purity: 92%; MS (m/e): 427 (MH+). | + | | | |
| 934 | N4-(2,2-Dimethyl-3-oxo-4H-benz[1,4]oxazin-6-yl)-N2-(1-ethyl-2-methylbenzimidazol-5-yl)-5-fluoro-2,4-pyrimidinediamine | LCMS: ret. time: 7.91 min.; purity: 99%; MS (m/e): 462 (MH+). | + | | | |
| 935 | (S)—N2-(1-Ethyl-2-methylbenzimidazol-5-yl)-5-fluoro-N4-(2-methyl-3-oxo-2H,4H-benz[1,4]oxazin-6-yl)-2,4-pyrimidinediamine | LCMS: ret. time: 7.72 min.; purity: 95%; MS (m/e): 448 (MH+). | + | + | | |
| 936 | N4-(2,2-Dimethyl-3-oxo-4H-5-pyrido[1,4]oxazin-6-yl)-N2-(1-ethyl-2-methylbenzimidazol-5-yl)-5-fluoro-2,4-pyrimidinediamine | LCMS: ret. time: 8.48 min.; purity: 96%; MS (m/e): 463 (MH+). | + | | | |
| 937 | N4-(3,4-Dichlorophenyl)-5-fluoro-N2-[1-(3-hydroxypropyl)-2-trifluoromethylbenzimidazol-5-yl]-2,4-pyrimidinediamine | LCMS: ret. time: 12.33 min.; purity: 97%; MS (m/e): 516 (MH+). | + | + | | |
| 938 | N4-(3-Chloro-4-methoxyphenyl)-5-fluoro-N2-[1-(3-hydroxypropyl)-2-trifluoromethylbenzimidazol-5-yl]-2,4-pyrimidinediamine | LCMS: ret. time: 9.85 min.; purity: 94%; MS (m/e): 511 (MH+). | + | | | |
| 939 | N4-(2,2-Dimethyl-3-oxo-4H-benz[1,4]oxazin-6-yl)-5-fluoro-N2-[1-(3-hydroxypropyl)-2-trifluoromethylbenzimidazol-5-yl]-2,4-pyrimidinediamine | LCMS: ret. time: 9.04 min.; purity: 96%; MS (m/e): 546 (MH+). | + | + | | |
| 940 | (S)-5-Fluoro-N2-[1-(3-hydroxypropyl)-2-trifluoromethylbenzimidazol-5-yl]-N4-(2-methyl-3-oxo-2H,4H-benz[1,4]oxazin-6-yl)-2,4-pyrimidinediamine | LCMS: ret. time: 8.49 min.; purity: 95%; MS (m/e): 532 (MH+). | + | + | | |
| 941 | N4-(2,2-Dimethyl-3-oxo-4H-5-pyrido[1,4]oxazin-6-yl)-5-fluoro-N2-[1-(3-hydroxypropyl)-2-trifluoromethylbenzimidazol-5-yl]-2,4-pyrimidinediamine | LCMS: ret. time: 9.85 min.; purity: 93%; MS (m/e): 547 (MH+). | + | + | | |
| 942 | N4-(3,4-Dichlorophenyl)-5-fluoro-N2-[1-methyl-2-(4-morpholino)benzimidazol-5-yl]-2,4-pyrimidinediamine | LCMS: ret. time: 9.49 min.; purity: 97%; MS (m/e): 489 (MH+). | + | | | + |
| 943 | N4-(3-Chloro-4-methoxyphenyl)-5-fluoro-N2-[1-methyl-2-(4-morpholino)benzimidazol-5-yl]-2,4-pyrimidinediamine | LCMS: ret. time: 7.79 min.; purity: 93%; MS (m/e): 484 (MH+). | + | + | | + |
| 944 | N4-(2,2-Dimethyl-3-oxo-4H-benz[1,4]oxazin-6-yl)-5-fluoro-N2-[1-methyl-2-(4-morpholino)benzimidazol-5-yl]-2,4-pyrimidinediamine | LCMS: ret. time: 7.20 min.; purity: 99%; MS (m/e): 519 (MH+). | + | + | | |
| 945 | (S)-5-Fluoro-N2-[1-methyl-2-(4-morpholino)benzimidazol-5-yl]-N4-(2-methyl-3-oxo-2H,4H-benz[1,4]oxazin-6-yl)-2,4-pyrimidinediamine | LCMS: ret. time: 6.78 min.; purity: 90%; MS (m/e): 505 (MH+). | + | + | | + |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 946 | N4-(2,2-Dimethyl-3-oxo-4H-5-pyrido[1,4]oxazin-6-yl)-5-fluoro-N2-[1-methyl-2-(4-morpholino)benzimidazol-5-yl]-2,4-pyrimidinediamine | LCMS: ret. time: 7.86 min.; purity: 96%; MS (m/e): 520 (MH$^+$). | + | | | |
| 947 | N4-(3,4-Dichlorophenyl)-5-fluoro-N2-[1-(3-hydroxypropyl)-2-methylbenzimidazol-5-yl]-2,4-pyrimidinediamine | LCMS: ret. time: 9.65 min.; purity: 95%; MS (m/e): 462 (MH$^+$). | | + | | |
| 948 | N4-(3-Chloro-4-methoxyphenyl)-5-fluoro-N2-[1-(3-hydroxypropyl)-2-methylbenzimidazol-5-yl]-2,4-pyrimidinediamine | LCMS: ret. time: 8.28 min.; purity: 90%; MS (m/e): 457 (MH$^+$). | | + | | |
| 949 | N4-(2,2-Dimethyl-3-oxo-4H-benz[1,4]oxazin-6-yl)-5-fluoro-N2-[1-(3-hydroxypropyl)-2-methylbenzimidazol-5-yl]-2,4-pyrimidinediamine | LCMS: ret. time: 7.70 min.; purity: 96%; MS (m/e): 492 (MH$^+$). | | + | | |
| 950 | (S)-5-Fluoro-N2-[1-(3-hydroxypropyl)-2-methylbenzimidazol-5-yl]-N4-(2-methyl-3-oxo-2H,4H-benz[1,4]oxazin-6-yl)-2,4-pyrimidinediamine | LCMS: ret. time: 7.22 min.; purity: 90%; MS (m/e): 478 (MH$^+$). | | + | | |
| 951 | N4-(2,2-Dimethyl-3-oxo-4H-5-pyrido[1,4]oxazin-6-yl)-5-fluoro-N2-[1-(3-hydroxypropyl)-2-methylbenzimidazol-5-yl]-2,4-pyrimidinediamine | LCMS: ret. time: 7.97 min.; purity: 94%; MS (m/e): 493 (MH$^+$). | + | + | | |
| 952 | N2-[1-[3-(N-Acetylamino)propyl]-2-methylbenzimidazol-5-yl]-N4-(2,2-dimethyl-3-oxo-4H-benz[1,4]oxazin-6-yl)-5-fluoro-2,4-pyrimidinediamine | LCMS: ret. time: 7.89 min.; purity: 97%; MS (m/e): 533 (MH$^+$). | + | + | | |
| 953 | N2-[1-[3-(N-Acetylamino)propyl]-2-methylbenzimidazol-5-yl]-N4-(2,2-Dimethyl-3-oxo-4H-5-pyrido[1,4]oxazin-6-yl)-5-fluoro-2,4-pyrimidinediamine | LCMS: ret. time: 8.09 min.; purity: 97%; MS (m/e): 534 (MH$^+$). | + | + | | |
| 954 | N4-(3,4-Dichlorophenyl)-5-fluoro-N2-[1-methyl-2-(4-morpholinomethyl)benzimidazol-5-yl]-2,4-pyrimidinediamine | LCMS: ret. time: 10.04 min.; purity: 96%; MS (m/e): 503 (MH$^+$). | + | + | | |
| 955 | N4-(3-Chloro-4-methoxyphenyl)-5-fluoro-N2-[1-methyl-2-(4-morpholinomethyl)benzimidazol-5-yl]-2,4-pyrimidinediamine | LCMS: ret. time: 9.29 min.; purity: 93%; MS (m/e): 498 (MH$^+$). | | + | | |
| 956 | N4-(2,2-Dimethyl-3-oxo-4H-benz[1,4]oxazin-6-yl)-5-fluoro-N2-[1-methyl-2-(4-morpholinomethyl)benzimidazol-5-yl]-2,4-pyrimidinediamine | LCMS: ret. time: 8.09 min.; purity: 94%; MS (m/e): 533 (MH$^+$). | | + | | |
| 957 | (S)-5-Fluoro-N2-[1-methyl-2-(4-morpholinomethyl)benzimidazol-5-yl]-N4-(2-methyl-3-oxo-2H,4H-benz[1,4]oxazin-6-yl)-2,4-pyrimidinediamine | LCMS: ret. time: 7.55 min.; purity: 98%; MS (m/e): 519 (MH$^+$). | + | + | | |
| 958 | N4-(2,2-Dimethyl-3-oxo-4H-5-pyrido[1,4]oxazin-6-yl)-5-fluoro-N2-[1-methyl-2-(4-morpholinomethyl)benzimidazol-5-yl]-2,4-pyrimidinediamine | LCMS: ret. time: 8.34 min.; purity: 98%; MS (m/e): 534 (MH$^+$). | | + | | |
| 959 | N4-(3,4-Dichlorophenyl)-5-fluoro-N2-[2-(4-morpholinomethyl)-1H-benzimidazol-5-yl]-2,4-pyrimidinediamine | LCMS: ret. time: 9.12 min.; purity: 95%; MS (m/e): 489 (MH$^+$). | | + | | |
| 960 | N4-(3-Chloro-4-methoxyphenyl)-5-fluoro-N2-[2-(4-morpholinomethyl)-1H-benzimidazol-5-yl]-2,4-pyrimidinediamine | LCMS: ret. time: 8.10 min.; purity: 97%; MS (m/e): 484 (MH$^+$). | | + | | |
| 961 | N4-(2,2-Dimethyl-3-oxo-4H-benz[1,4]oxazin-6-yl)-5-fluoro-N2-[2-(4-morpholinomethyl)-1H-benzimidazol-5-yl]-2,4-pyrimidinediamine | LCMS: ret. time: 7.70 min.; purity: 93%; MS (m/e): 519 (MH$^+$). | | + | | + |
| 962 | N4-(2,2-Dimethyl-3-oxo-4H-5-pyrido[1,4]oxazin-6-yl)-5-fluoro-N2-[2-(4-morpholinomethyl)-1H-benzimidazol-5-yl]-2,4-pyrimidinediamine | LCMS: ret. time: 7.93 min.; purity: 95%; MS (m/e): 520 (MH$^+$). | | + | | + |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 963 | N4-(2,2-Dimethyl-3-oxo-4H-benz[1,4]oxazin-6-yl)-5-fluoro-N2-[2-methyl-1-[3-(N-methylsulfonylamino)propyl]benzimidazol-5-yl]-2,4-pyrimidinediamine | LCMS: ret. time: 8.01 min.; purity: 95%; MS (m/e): 569 (MH$^+$). | | | | |
| 964 | N4-(2,2-Dimethyl-3-oxo-4H-5-pyrido[1,4]oxazin-6-yl)-5-fluoro-N2-[2-methyl-1-[3-(N-methylsulfonylamino)propyl]benzimidazol-5-yl]-2,4-pyrimidinediamine | LCMS: ret. time: 8.36 min.; purity: 95%; MS (m/e): 570 (MH$^+$). | | + | | |
| 965 | N4-(3,4-Dichlorophenyl)-5-fluoro-N2-{1-methyl-2-[(methylsulfonyl)methyl]benzimidazol-5-yl}-2,4-pyrimidinediamine | LCMS: ret. time: 10.63 min.; purity: 94%; MS (m/e): 496 (MH$^+$). | + | + | | |
| 966 | N4-(3-Chloro-4-methoxyphenyl)-5-fluoro-N2-{1-methyl-2-[(methylsulfonyl)methyl]benzimidazol-5-yl}-2,4-pyrimidinediamine | LCMS: ret. time: 9.10 min.; purity: 95%; MS (m/e): 491 (MH$^+$). | + | | | |
| 967 | N4-(2,2-Dimethyl-3-oxo-4H-benz[1,4]oxazin-6-yl)-5-fluoro-N2-{1-methyl-2-[(methylsulfonyl)methyl]benzimidazol-5-yl}-2,4-pyrimidinediamine | LCMS: ret. time: 9.22 min.; purity: 91%; MS (m/e): 525 (MH$^+$). | + | + | | |
| 968 | (S)-5-Fluoro-N2-{1-methyl-2-[(methylsulfonyl)methyl]benzimidazol-5-yl}-N4-(2-methyl-3-oxo-2H,4H-benz[1,4]oxazin-6-yl)-2,4-pyrimidinediamine | LCMS: ret. time: 8.62 min.; purity: 91%; MS (m/e): 512 (MH$^+$). | + | + | | |
| 969 | N4-(2,2-Dimethyl-3-oxo-4H-5-pyrido[1,4]oxazin-6-yl)-5-fluoro-N2-{1-methyl-2-[(methylsulfonyl)methyl]benzimidazol-5-yl}-2,4-pyrimidinediamine | LCMS: ret. time: 9.14 min.; purity: 94%; MS (m/e): 527 (MH$^+$). | + | + | | |
| 970 | N4-(3,4-Dichlorophenyl)-N2-[2-(N,N-diethylaminomethyl)-1-methylbenzimidazol-5-yl]-5-fluoro-2,4-pyrimidinediamine | LCMS: ret. time: 9.42 min.; purity: 91%; MS (m/e): 489 (MH$^+$). | + | + | | |
| 971 | N4-(3-Chloro-4-methoxyphenyl)-N2-[2-(N,N-diethylaminomethyl)-1-methylbenzimidazol-5-yl]-5-fluoro-2,4-pyrimidinediamine | LCMS: ret. time: 7.76 min.; purity: 94%; MS (m/e): 485 (MH$^+$). | + | + | | |
| 972 | N2-[2-(N,N-Diethylaminomethyl)-1-methylbenzimidazol-5-yl]-N4-(2,2-dimethyl-3-oxo-4H-benz[1,4]oxazin-6-yl)-5-fluoro-2,4-pyrimidinediamine | LCMS: ret. time: 7.56 min.; purity: 94%; MS (m/e): 519 (MH$^+$). | + | + | | |
| 973 | (S)—N2-[2-(N,N-Diethylaminomethyl)-1-methylbenzimidazol-5-yl]-5-fluoro-N4-(2-methyl-3-oxo-2H,4H-benz[1,4]oxazin-6-yl)-2,4-pyrimidinediamine | LCMS: ret. time: 7.21 min.; purity: 97%; MS (m/e): 505 (MH$^+$). | + | + | | |
| 974 | N2-[2-(N,N-Diethylaminomethyl)-1-methylbenzimidazol-5-yl]-N4-(2,2-dimethyl-3-oxo-4H-5-pyrido[1,4]oxazin-6-yl)-5-fluoro-2,4-pyrimidinediamine | LCMS: ret. time: 7.51 min.; purity: 97%; MS (m/e): 520 (MH$^+$). | + | + | | |
| 975 | N4-(3,4-Dichlorophenyl)-5-fluoro-N2-[2-(4-morpholino)-1H-benzimidazol-5-yl]-2,4-pyrimidinediamine | LCMS: ret. time: 8.89 min.; purity: 90%; MS (m/e): 475 (MH$^+$). | + | + | | + |
| 976 | N4-(2,2-Dimethyl-3-oxo-4H-benz[1,4]oxazin-6-yl)-5-fluoro-N2-[2-(4-morpholino)-1H-benzimidazol-5-yl]-2,4-pyrimidinediamine | LCMS: ret. time: 7.76 min.; purity: 96%; MS (m/e): 505 (MH$^+$). | + | + | | + |
| 977 | N4-(2,2-Dimethyl-3-oxo-4H-5-pyrido[1,4]oxazin-6-yl)-5-fluoro-N2-[2-(4-morpholino)-1H-benzimidazol-5-yl]-2,4-pyrimidinediamine | LCMS: ret. time: 8.05 min.; purity: 92%; MS (m/e): 506 (MH$^+$). | + | + | | |
| 978 | N4-(3-Chloro-4-methoxyphenyl)-5-fluoro-N2-[2-(4-morpholino)-1H-benzimidazol-5-yl]-2,4-pyrimidinediamine | LCMS: ret. time: 8.03 min.; purity: 92%; MS (m/e): 470 (MH$^+$). | | + | | |
| 979 | N4-(3,4-Dichlorophenyl)-5-fluoro-N2-[1-methyl-2-(4-methyl-1-piperazino)-1H-benzimidazol-5-yl]-2,4-pyrimidinediamine | LCMS: ret. time: 8.12 min.; purity: 98%; MS (m/e): 502 (MH$^+$). | | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 980 | N4-(3-Chloro-4-methoxyphenyl)-5-fluoro-N2-[1-methyl-2-(4-methyl-1-piperazino)-1H-benzimidazol-5-yl]-2,4-pyrimidinediamine | LCMS: ret. time: 7.34 min.; purity: 96%; MS (m/e): 497 (MH+). | | | | |
| 981 | N4-(2,2-Dimethyl-3-oxo-4H-benz[1,4]oxazin-6-yl)-5-fluoro-N2-[1-methyl-2-(4-methyl-1-piperazino)-1H-benzimidazol-5-yl]-2,4-pyrimidinediamine | LCMS: ret. time: 6.99 min.; purity: 97%; MS (m/e): 532 (MH+). | | | | |
| 982 | (S)-5-Fluoro-N2-[1-methyl-2-(4-methyl-1-piperazino)-1H-benzimidazol-5-yl]-N4-(2-methyl-3-oxo-2H,4H-benz[1,4]oxazin-6-yl)-2,4-pyrimidinediamine | LCMS: ret. time: 6.62 min.; purity: 97%; MS (m/e): 518 (MH+). | | | | |
| 983 | N4-(2,2-Dimethyl-3-oxo-4H-5-pyrido[1,4]oxazin-6-yl)-5-fluoro-N2-[1-methyl-2-(4-methyl-1-piperazino)-1H-benzimidazol-5-yl]-2,4-pyrimidinediamine | LCMS: ret. time: 7.05 min.; purity: 96%; MS (m/e): 533 (MH+). | | | | |
| 984 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine Benzensulfonic Acid Salt | $^1$H NMR (DMSO-d6): δ 11.22 (1H, s), 9.79 (1H, s), 9.62 (1H, s), 8.27 (1H, d, J = 3.9 Hz), 8.08 (1H, d, J = 4.5 Hz), 7.68-7.64 (3H, m), 7.47 (1H, d, J = 8.7 Hz), 7.42-7.31 (5H, m), 7.22 (1H, t, J = 8.1 Hz), 6.63 (1H, dd, J = 8.1 Hz, J = 2.4 Hz), 4.47 (2H, s), 2.74 (3H, d, J = 4.5 Hz), 1.52 (6H, s); purity: 100%; MS (m/e): 468 (MH+). | + | + | | + |
| 985 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine p-Toluenesulfonic Acid Salt | $^1$H NMR (DMSO-d6): δ 11.23 (1H, s), 9.91 (1H, s), 9.70 (1H, s), 8.29 (1H, d, J = 3.9 Hz), 8.06 (1H, m), 7.65-7.61 (1H, m), 7.55 (1H, d, J = 8.1 Hz), 7.48 (1H, d, J = 8.1 Hz), 7.33-7.18 (5H, m), 6.66 (1H, d, J = 7.5 Hz), 4.48 (2H, s), 2.75 (3H, d, J = 3.6 Hz), 2.38 (3H, s), 1.53 (6H, s); purity: 100%; MS (m/e): 468 (MH+). | + | + | + | + |
| 986 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine Hydrogen Chloride Salt | $^1$H NMR (DMSO-d6): δ 11.18 (1H, s), 9.54 (2H, broad s), 8.26 (1H, s), 8.05 (1H, broad s), 7.70-7.66 (1H, m), 7.47 (1H, d, J = 8.4 Hz), 7.40 (1H, s), 7.34 (1H, d, J = 9 Hz), 7.20 (1H, t, J = 7.9 Hz), 6.61 (1H, d J = 7.5 Hz), 4.47 (2H, s), 2.75 (3H, d, J = 3.3 Hz), 1.53 (6H, s); purity: 100%; MS (m/e): 468 (MH+). | + | + | | |
| 987 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine Bis-Hydrogen Chloride Salt | $^1$H NMR (DMSO-d6): δ 11.18 (1H, s), 9.50 (2H, broad s), 8.25 (1H, d, J = 3.3 Hz), 8.06 (1H, m), 7.74-7.67 (1H, m), 7.47 (1H, d, J = 8.4 Hz), 7.41 (1H, s), 7.37 (1H, d, J = 8.1 Hz), 7.20 (1H, t, J = 7.9 Hz), 6.59 (1H, d, J = 8.1 Hz), 4.47 (2H, s), 2.74 (3H, d, J = 3.6 Hz), 1.53 (6H, s); purity: 100%; MS (m/e): 468 (MH+). | + | + | | + |
| 988 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine Nitric Acid Salt | $^1$H NMR (DMSO-d6): δ 11.19 (1H, s), 9.58 (1H, broad s), 9.52 (1H, s), 8.25 (1H, d, J = 3.6 Hz), 8.06 (1H, m), 7.70-7.66 (1H, m), 7.47 (1H, d, J = 8.7 Hz), 7.40 (1H, s), 7.34 (1H, d, J = 8.1 Hz), 7.21 (1H, t, J = 8.1 Hz), 6.61 (1H, d, J = 7.5 Hz), 4.47 (2H, s), 2.74 (3H, d, J = 3.6 Hz), 1.53 (6H, s); purity: 95%; MS (m/e): 468 (MH+). | + | + | | |
| 989 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine Bis-Nitric Acid Salt | $^1$H NMR (DMSO-d6): δ 11.21 (1H, s), 9.64 (1H, broad s), 9.54 (1H, s), 8.26 (1H, d, J = 3.6 Hz), 8.07 (1H, m), 7.67 (1H, d, J = 8.4 Hz), 7.47 (1H, d, J = 8.7 Hz), 7.39 (1H, s), 7.34 (1H, d, J = 7.8 Hz), 7.21 (1H, t, J = 8.2 Hz), 6.62 (1H, d, J = 8.4 Hz), 4.47 (2H, s), 2.74 (3H, d, J = 4.5 Hz), 1.53 (6H, s); purity: 100%; MS (m/e): 468 (MH+). | + | + | | |
| 990 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine Methanesulfonic Acid Salt | $^1$H NMR (DMSO-d6): δ 11.24 (1H, s), 9.79 (1H, broad s), 9.63 (1H, s), 8.27 (1H, d, J = 3.9 Hz), 8.07 (1H, m), 7.64 (1H, d, J = 8.4 Hz), 7.48 (1H, d, J = 8.4 Hz), 7.36 (1H, s), 7.32 (1H, d, J = 7.5 Hz), 7.22 (1H, t, J = 7.9 Hz), 6.64 (1H, d, J = 8.7 Hz), 4.47 (2H, s), 2.74 (3H, d, J = 4.5 Hz), 2.42 (3H, s), 1.53 (6H, s); purity: 100%; MS (m/e): 468 (MH+). | + | + | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 991 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine (1S)-(+)-Camphorsulfonic Acid Salt | ¹H NMR (DMSO-d6): δ 11.25 (1H, s), 9.72 (1H, brad s), 9.59 (1H, s), 8.27 (1H, d, J = 3.6 Hz), 8.07 (1H, m), 7.65 (1H, d, J = 8.4 Hz), 7.47 (1H, d, J = 8.7 Hz), 7.37 (1H, s), 7.33 (1H, d, J = 8.7 Hz), 7.21 (1H, t, J = 8.1 Hz), 6.62 (1H, dd, J = 8.1 Hz, J = 2.4 Hz), 4.47 (2H, s), 2.96 (1H, d, J = 14.7 Hz), 2.78 (1H, m), 2.74 (3H, d, J = 4.5 Hz), 2.47 (1H, d, J = 14.7 Hz), 2.33 (2H, dt, J = 18.9 Hz, J = 3.75 Hz), 2.03 (1H, t, J = 4.5 Hz), 1.98-1.90 (1H, m), 1.98 (1H, d, J = 17.7 Hz), 1.53 (6H, s), 1.40 (1H, d, J = 11.1 Hz), 1.33 (1H, d, J = 10.2 Hz), 1.14 (3H, s), 0.84 (3H, s); purity: 100%; MS (m/e): 468 (MH+). | + | | | |
| 992 | N4-(2,2-Dimethyl-3-oxo-4H-5-pyrid[1,4]oxazin-6-yl)-5-fluoro-N2-[3-(N-methylamino)carbonylmethyleneoxyphenyl]-2,4-pyrimidinediamine (+)-Camphorsulfonic Acid Salt | ¹H NMR (DMSO-d6): δ 11.21 (1H, s), 9.63 (1H, brad s), 9.54 (1H, s), 8.26 (1H, d, J = 3.6 Hz), 8.07 (1H, m), 7.67 (1H, d, J = 8.4 Hz), 7.47 (1H, d, J = 8.7 Hz), 7.39 (1H, s), 7.34 (1H, d, J = 8.1 Hz), 7.21 (1H, t, J = 8.1 Hz), 6.61 (1H, dd, J = 8.1 Hz, J = 1.8 Hz), 4.47 (2H, s), 2.95 (1H, d, J = 14.4 Hz), 2.78 (1H, m), 2.74 (3H, d, J = 4.5 Hz), 2.45 (1H, d, J = 14.4 Hz), 2.36 (1H, t, J = 3.6 Hz), 2.30 (1H, t, J = 4 Hz), 2.03 (1H, t, J = 4.5 Hz), 2.00-1.94 (1H, m), 1.92 (1H, d, J = 18 Hz), 1.53 (6H, s), 1.39 (1H, d, J = 9.9 Hz), 1.33 (1H, d, J = 10.2 Hz), 1.14 (3H, s), 0.84 (3H, s); purity: 100%; MS (m/e): 468 (MH+). | + | + | − | |
| 993 | N4-(2,2-Dimethyl-3-oxo-4H-benz[1,4]oxazin-6-yl)-5-fluoro-N2-(1-methylindazol-6-yl)-2,4-pyrimidinediamine p-Toluenesulfonic Acid Salt | ¹H NMR (DMSO-d6): δ 10.78 (1H, s), 10.11 (1H, broad s), 9.89 (1H, broad s), 8.29 (1H, d, J = 4.8 Hz), 8.01 (1H, s), 7.95 (1H, s), 7.70 (1H, d, J = 8.7 Hz), 7.55 (2H, d, J = 8.1 Hz), 7.40 (1H, d, J = 8.4 Hz), 7.29-7.18 (4H, m), 6.95 (1H, d, J = 8.7 Hz), 3.91 (3H, s), 2.38 (3H, s), 1.49 (6H, s); purity: 100%; MS (m/e): 434 (MH+); Anal. Calcd. for C29H28FN7O5S: C, 57.51; H, 4.66; N, 16.19; S, 5.29. Found: C, 57.63; H, 4.65; N, 16.07; S, 4.95. | + | + | + | |
| 994 | N2-(3-Chloro-4-methoxy-5-methylphenyl)-N4-(2,2-dimethyl-3-oxo-4H-benz[1,4]oxazin-6-yl)-5-fluoro-2,4-pyrimidinediamine p-Toluenesulfonic Acid Salt | ¹H NMR (DMSO-d6): δ 10.73 (1H, s), 9.65 (1H, s), 9.41 (1H, s), 8.20 (1H, d, J = 4.2 Hz), 7.71 (1H, s), 7.54 (2H, d, J = 8.1 Hz), 7.43 (1H, s), 7.35 (1H, dd, J = 8.4 Hz, J = 2.4 Hz), 7.23-7.17 (3H, m), 7.00 (1H, d, J = 8.4 Hz), 3.76 (3H, s), 2.38 (3H, s), 2.25 (3H, s), 1.50 (6H, s); purity: 100%; MS (m/e): 458 (MH+); Anal. Calcd. for C29H29ClFN5O6S: C, 55.28; H, 4.64; N, 11.11; S, 5.09. Found: C, 55.37; H, 4.74; N, 11.11; S, 4.59. | + | + | + | + |
| 995 | N2-(3-Chloro-4-hydroxy-5-methylphenyl)-N4-(2,2-dimethyl-3-oxo-4H-pyrid[1,4]oxazin-6-yl)-5-fluoro-2,4-pyrimidinediamine | ¹H NMR (DMSO-d6): δ 9.19 (1H, s), 9.05 (1H, s), 8.64 (1H, s), 8.10 (1H, d, J = 3.9 Hz), 7.62 (1H, d, J = 2.7 Hz), 7.36 (1H, d, J = 1.8 Hz), 7.31 (1H, m), 7.27 (1H, d, J = 2.7 Hz), 6.87 (1H, d, J = 8.4 Hz), 4.31 (4H, s), 2.22 (3H, s); LCMS: purity: 96.98%; MS (m/e): 403 (MH+) | + | + | + | |
| 996 | N2-(3-Chloro-4-hydroxy-5-methylphenyl)-N4-(2,2-dimethyl-3-oxo-4H-pyrid[1,4]oxazin-6-yl)-5-fluoro-2,4-pyrimidinediamine | ¹H NMR (DMSO-d6): δ 11.16 (1H, s), 9.27 (1H, s), 9.15 (1H, s), 8.67 (1H, s), 8.19 (1H, d, J = 3.6 Hz), 7.64 (2H, m), 7.42 (1H, d, J = 8.4 Hz), 7.29 (1H, d, J = 2.7 Hz), 2.22 (3H, s), 1.53 (6H, s); LCMS: purity: 97.69%; MS (m/e): 444 (M+). | + | + | − | |
| 997 | N2-(3,5-Dimethyl-4-methoxyphenyl)-N4-(2,2-dimethyl-3-oxo-4H-pyrid[1,4]oxazin-6-yl)-5-fluoro-2,4-pyrimidinediamine | ¹H NMR (DMSO-d6): δ 11.16 (1H, s), 9.23 (1H, s), 9.11 (1H, s), 8.19 (1H, d, J = 3.6 Hz), 7.69 (1H, d, J = 8.1 Hz), 7.44 (1H, d, J = 8.4 Hz), 7.33 (2H, s), 3.68 (3H, s), 2.23 (6H, s), 1.53 (6H, s); LCMS: purity: 99%; MS (m/e): 439 (MH+). | + | + | − | + |
| 998 | N2-(3,5-Dimethyl-4-methoxyphenyl)-N4-(3,4-ethylenedioxyphenyl)-5-fluoro-2,4-pyrimidinediamine | ¹H NMR (DMSO-d6): δ 10.06 (1H, s), 9.85 (1H, s), 8.25 (1H, d, J = 4.8 Hz), 7.33 (1H, d, J = 2.4 Hz), 7.24 (2H, s), 7.20 (1H, d, J = 2.7 Hz), | + | + | − | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 999 | N2-(3-Chloro-4-methoxy-5-methylphenyl)-N4-(3,4-ethylenedioxyphenyl)-5-fluoro-2,4-pyrimidinediamine | 6.91 (1H, d, J = 8.4 Hz), 4.32 (4H, s), 3.71 (3H, s), 2.25 (6H, s); LCMS: purity: 96.69%; MS (m/e): 397 (MH+). | + | | | |
| 1000 | N4-(3,4-Dihydro-2,2-dimethyl-4H-benz[1,4]oxazin-6-yl)-5-fluoro-N2-[3-(N-methylamino)carbonylmethyleneoxyphenyl]-2,4-pyrimidinediamine | ¹H NMR (DMSO-d6): δ 9.88 (2H, broad s), 8.26 (1H, d, J = 4.2 Hz), 7.64 (1H, s), 7.41 (1H, s), 7.30-7.28 (1H, m), 7.25-7.20 (1H, m), 6.92 (1H, d, J = 10.2 Hz), 4.32 (4H, s), 3.79 (3H, s), 2.29 (3H, s); LCMS: purity: 94.81%; MS (m/e): 417 (MH+). | | + | + | |
| 1001 | N2-(3-Chloro-4-methoxy-5-methylphenyl)-N4-(3,4-dihydro-2,2-dimethyl-4H-benz[1,4]oxazin-6-yl)-5-fluoro-2,4-pyrimidinediamine | ¹H NMR (DMSO-d6): δ 9.15 (1H, s), 9.08 (1H, s), 8.09 (1H, d, J = 3.6 Hz), 8.04 (1H, d, J = 4.5 Hz), 7.45-7.42 (2H, m), 7.17 (1H, t, J = 8.4 Hz), 7.01 (1H, d, J = 2.4 Hz), 6.95 (1H, d, J = 8.4 Hz), 6.65 (1H, d, J = 8.7 Hz), 6.53 (1H, d, J = 9.3 Hz), 5.88 (1H, s), 4.44 (2H, s), 3.07 (2H, s), 2.74 (3H, d, J = 4.2 Hz), 1.34 (6H, s); purity: 96.6%; MS (m/e): 453 (M). | | | | |
| | | ¹H NMR (DMSO-d6): δ 9.59 (1H, broad s), 8.17 (1H, d, J = 4.2 Hz), 7.65 (1H, s), 7.46 (1H, s), 6.94-6.86 (2H, m), 6.68 (1H, d, J = 8.7 Hz), 3.77 (3H, s), 3.08 (2H, s), 2.27 (3H, s), 1.34 (6H, s); purity: 94.5%; MS (m/e): 444 (M). | | | | |
| 1002 | N4-(3,4-Dihydro-2,2-dimethyl-4H-benz[1,4]oxazin-6-yl)-N2-(3,5-dimethoxyphenyl)-5-fluoro-2,4-pyrimidinediamine | ¹H NMR (DMSO-d6): δ 9.06 (2H, s), 8.09 (1H, d, J = 3.6 Hz), 7.03 (1H, dd, J = 1.8 Hz), 6.95 (1H, d, J = 8.1 Hz), 3.71 (6H, s), 3.07 (2H, s), 1.34 (6H, s); purity 95.9%; MS (m/e): 426 (M). | + | + | | |
| 1003 | N4-(2,2-Dimethyl-3-oxo-4H-5-pyrid[1,4]oxazin-6-yl)-5-fluoro-N2-(3-isopropylphenyl)-2,4-pyrimidinediamine | ¹H NMR (DMSO-d6): δ 11.17 (1H, s), 9.27 (1H, s), 9.24 (1H, s), 8.21 (1H, d, J = 3.6 Hz), 7.67 (1H, m), 7.61 (1H, d, J = 9 Hz), 7.52 (1H, s), 7.44 (1H, d, J = 8.7 Hz), 7.19 (1H, t, J = 7.65 Hz), 6.85 (1H, d, J = 7.8 Hz), 2.82 (1H, m), 1.53 (6H, s), 1.25 (6H, d, J = 6.9 Hz); purity 97.7%; MS (m/e): 423 (MH+). | + | + | − | |
| 1004 | N4-(2,2-Dimethyl-3-oxo-4H-5-pyrid[1,4]oxazin-6-yl)-5-fluoro-N2-(2-methylphenyl)-2,4-pyrimidinediamine | ¹H NMR (DMSO-d6): δ 11.23 (1H, s), 10.12 (1H, s), 9.39 (1H, s), 8.27 (1H, d, J = 4.8 Hz), 7.52 (1H, d, J = 6.9 Hz), 7.43 (1H, d, J = 8.7 Hz), 7.34-7.16 (4H, m), 2.30 (3H, s), 1.50 (6H, s); purity 97.9%; MS (m/e): 395 (MH+). | + | + | − | |
| 1005 | 2-Chloro-5-fluoro-N4-methyl-N4-(3-oxo-2,2,4-trimethyl-5-pyrid[1,4]oxazin-6-yl)-4-pyrimidineamine | ¹H NMR (DMSO-d6): δ 8.43 (1H, d, J = 5.1 Hz), 7.57 (1H, d, J = 8.4 Hz), 7.15 (1H, dd, J = 8.1 Hz, J = 0.9 Hz), 3.59 (3H, s), 3.30 (3H, s), 1.55 (6H, s); purity 97.2%; MS (m/e): 352 (MH+). | + | | − | |
| 1006 | 2-Chloro-5-fluoro-N4-(3-oxo-2,2,4-trimethyl-5-pyrid[1,4]oxazin-6-yl)-4-pyrimidineamine | ¹H NMR (DMSO-d6): δ 10.35 (1H, s), 8.47 (1H, d, J = 3.3 Hz), 7.62 (1H, d, J = 8.7 Hz), 7.58 (1H, d, J = 8.4 Hz), 3.45 (3H, s), 1.55 (6H, s); purity 96%; MS (m/e): 338 (MH+). | − | | | |
| 1007 | N4-(2,2-Dimethyl-3-oxo-4H-5-pyrid[1,4]oxazin-6-yl)-5-fluoro-N2-(3,4,5-trimethoxyphenyl)-2,4-pyrimidinediamine | ¹H NMR (DMSO-d6): δ 11.14 (1H, s), 9.24 (1H, s), 9.19 (1H, s), 8.21 (1H, d, J = 3.3 Hz), 7.76 (1H, d, J = 8.7 Hz), 7.41 (1H, d, J = 8.7 Hz), 7.12 (2H, s), 3.75 (6H, s), 3.69 (6H, s), 1.52 (6H, s); purity 96%; MS (m/e): 471 (MH+). | + | + | | + |
| 1008 | N2-(3-Chloro-4-ethoxy-5-methylphenyl)-N4-(2,2-dimethyl-3-oxo-4H-benz[1,4]oxazin-6-yl)-5-fluoro-2,4-pyrimidinediamine | ¹H NMR (DMSO-d6): δ 10.67 (1H, s), 9.40 (1H, s), 9.20 (1H, s), 8.16 (1H, d, J = 3.9 Hz), 7.74 (1H, d, J = 3 Hz), 7.45 (1H, d, J = 2.7 Hz), 7.36 (1H, dd, J = 8.7 Hz, J = 2.4 Hz), 7.25 (1H, d, J = 2.4 Hz), 6.98 (1H, d, J = 8.7 Hz), 3.94 (2H, q, J = 7.2 Hz), 2.24 (3H, s), 1.50 (6H, s), 1.41 (3H, t, J = 6.9 Hz); purity 97%; MS (m/e): 472 (MH+). | + | + | + | + |
| 1009 | N2-(3-Chloro-4-methoxy-5-methylphenyl)-5-fluoro-N4-(3-oxo-2,2,4-trimethyl-5-pyrid[1,4]oxazin-6-yl)-2,4-pyrimidinediamine | ¹H NMR (DMSO-d6): δ 9.62 (1H, s), 9.41 (1H, s), 8.27 (1H, s), 7.80 (1H, s), 7.73 (1H, d, J = 8.7 Hz), 7.48 (1H, s), 7.43 (1H, s), | + | + | − | |

| Com- pound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1010 | N2-(3-Chloro-4-ethoxy-5-methylphenyl)-N4-(2,2-dimethyl-3-oxo-4H-5-pyrid[1,4]oxazin-6-yl)-5-fluoro-2,4-pyrimidinediamine | 3.78 (3H, d, J = 2.4 Hz), 2.92 (3H, s), 1.55 (6H, d, J = 2.4 Hz); purity 97%; MS (m/e): 473 (MH+). | + | | − | |
| 1011 | N4-(2,2-Dimethyl-3-oxo-4H-benz[1,4]oxazin-6-yl)-N2-[4-(oxazol-2-yl)phenyl]-5-fluoro-N2-2,4-pyrimidinediamine | 1H NMR (DMSO-d6): δ 11.18 (1H, s), 9.41 (1H, s), 9.38 (1H, s), 8.23 (1H, d, J = 3.6 Hz), 7.74 (1H, d, J = 2.7 Hz), 7.61 (1H, d, J = 8.4 Hz), 7.46 (1H, d, J = 8.1 Hz), 7.41 (1H, d, J = 2.1 Hz), 3.95 (2H, q, J = 7.2 Hz), 2.27 (3H, s), 1.53 (6H, s), 1.42 (3H, t, J = 6.9 Hz); purity 99%; MS (m/e): 473 (MH+). | + | + | − | + |
| 1012 | 5-Fluoro-N2-[3-(oxazol-2-yl)phenyl]-N4-[3-oxo-2,2,4-trimethyl-5-pyrid[1,4]oxazin-6-yl]-2,4-pyrimidinediamine | 1H NMR (DMSO-d6): δ 10.74 (1H, s), 9.56 (1H, s), 9.49 (1H, s), 8.21-8.19 (2H, m), 7.89 (2H, d, J = 9 Hz), 7.84 (2H, d, J = 9 Hz), 7.37 (1H, d, J = 0.6 Hz), 7.33 (1H, dd, J = 8.1 Hz, J = 2.4 Hz), 7.26 (1H, d, J = 2.7 Hz), 7.02 (1H, d, J = 8.7 Hz), 1.53 (6H, s); purity 96%; MS (m/e): 447 (MH+). | + | + | − | |
| 1013 | 5-Fluoro-N2-[4-(oxazol-2-yl)phenyl]-N4-[3-oxo-2,2,4-trimethyl-5-pyrid[1,4]oxazin-6-yl]-2,4-pyrimidinediamine | 1H NMR (DMSO-d6): δ 9.76 (1H, s), 9.74 (1H, s), 8.41 (1H, s), 8.32 (1H, d, J = 3.6 Hz), 8.25 (1H, s), 7.89-7.83 (2H, m), 7.64 (1H, d, J = 7.8 Hz), 7.48 (1H, d, J = 7.8 Hz), 7.44 (1H, s), 7.36 (1H, d, J = 7.2 Hz), 3.42 (3H, s), 1.54 (6H, s); purity 96%. | + | + | − | |
| 1014 | N2-[3-Chloro-4-ethoxycarbonylmethyleneoxy-5-methylphenyl]-N4-(2,2-dimethyl-3-oxo-4H-benz[1,4]oxazin-6-yl)-5-fluoro-2,4-pyrimidinediamine | 1H NMR (DMSO-d6): δ 9.76 (1H, s), 9.73 (1H, s), 8.31 (1H, s), 8.21 (1H, d, J = 3.6 Hz), 8.21 (1H, d, J = 0.9 Hz), 7.92 (2H, d, J = 9.3 Hz), 7.88 (2H, d, J = 9.6 Hz), 7.76 (1H, d, J = 8.4 Hz), 7.54 (1H, d, J = 8.4 Hz), 7.38 (1H, d, J = 0.9 Hz), 3.44 (3H, s), 1.57 (6H, s); purity 96%; MS (m/e): 462 (MH+). | + | + | + | |
| 1015 | 5-Fluoro-N2-[3-(N-methylamino)carbonylmethyleneoxyphenyl]-N4-[3-oxo-2,2,4-trimethyl-5-pyrid[1,4]oxazin-6-yl]-2,4-pyrimidinediamine | 1H NMR (DMSO-d6): δ 10.69 (1H, s), 9.43 (1H, s), 9.27 (1H, s), 8.17 (1H, d, J = 3.6 Hz), 7.76 (1H, d, J = 2.7 Hz), 7.46 (1H, d, J = 2.4 Hz), 7.36 (1H, dd, J = 9 Hz, J = 2.7 Hz), 7.24 (1H, d, J = 2.4 Hz), 6.99 (1H, d, J = 8.4 Hz), 4.58 (2H, s), 4.28 (2H, q, J = 7.2 Hz), 2.27 (3H, s), 1.50 (6H, s), 1.33 (3H, t, J = 6.9 Hz); purity 95.6%; MS (m/e): 530 (MH+). | + | + | − | |
| 1016 | N4-(2,2-Dimethyl-3-oxo-4H-benz[1,4]oxazin-6-yl)-5-fluoro-N2-[3-(oxazol-5-yl)phenyl]-2,4-pyrimidinediamine | 1H NMR (DMSO-d6): δ 9.58 (1H, s), 9.42 (1H, s), 8.25 (1H, d, J = 3.3 Hz), 8.06 (1H, broad s), 7.88 (1H, d, J = 8.4 Hz), 7.49 (2H, m), 7.36 (1H, d, J = 7.5 Hz), 7.20 (1H, t, J = 8.1 Hz), 6.56 (1H, dd, J = 8.4 Hz, J = 2.4 Hz), 4.46 (2H, s), 3.44 (2H, s), 2.74 (3H, d, J = 4.8 Hz), 1.55 (6H, s); purity 97.2%; MS (m/e): 482 (MH+). | + | + | − | + |
| 1017 | 5-Fluoro-N2-[3-(oxazol-5-yl)phenyl]-N4-[3-oxo-2,2,4-trimethyl-5-pyrid[1,4]oxazin-6-yl]-2,4-pyrimidinediamine | 1H NMR (DMSO-d6): δ 10.67 (1H, s), 9.53 (1H, s), 9.38 (1H, s), 8.47 (1H, s), 8.20 (1H, d, J = 3.6 Hz), 8.04 (1H, s), 7.78 (1H, m), 7.58 (1H, s), 7.41 (1H, dd, J = 8.7 Hz, J = 2.4 Hz), 7.35 (2H, d, J = 4.8 Hz), 7.29 (1H, d, J = 2.4 Hz), 6.89 (1H, d, J = 8.7 Hz), 1.49 (6H, s); purity 96%; MS (m/e): 447 (MH+). | + | + | − | |
| 1018 | N2-[3-Chloro-4-cyclopentyloxy-5-methylphenyl]-N4-(2,2-dimethyl-3-oxo-4H-benz[1,4]oxazin-6-yl)-5-fluoro-2,4-pyrimidinediamine | 1H NMR (DMSO-d6): δ 9.65 (1H, s), 9.57 (1H, s), 9.20 (1H, s), 8.29 (1H, d, J = 3.6 Hz), 8.12 (1H, s), 8.84 (1H, d, J = 8.1 Hz), 7.74 (1H, m), 7.62 (1H, s), 7.43-7.32 (3H, m), 3.42 (3H, s), 1.54 (6H, s); purity 96.4%; MS (m/e): 462 (MH+). | + | + | − | |
| 1019 | N4-(2,2-Dimethyl-3-oxo-4H-benz[1,4]oxazin-6-yl)-5-fluoro-N4-methyl-N2-[3-(oxazol-2-yl)phenyl]-2,4-pyrimidinediamine | 1H NMR (DMSO-d6): δ 10.68 (1H, s), 9.41 (1H, s), 9.20 (1H, s), 8.16 (1H, d, J = 3.6 Hz), 7.73 (1H, d, J = 2.7 Hz), 7.45 (1H, d, J = 2.4 Hz), 7.36 (1H, dd, J = 9 Hz, J = 2.7 Hz), 7.24 (1H, d, J = 2.4 Hz), 6.98 (1H, d, J = 8.7 Hz), 4.65 (1H, m), 2.23 (3H, s), 2.0-1.6 (8H, m), 1.50 (6H, s); purity 98.3%; MS (m/e): 512 (MH+). 1H NMR (DMSO-d6): δ 10.72 (1H, s), 9.65 (1H, s), 8.71 (1H, s), 8.27 (1H, t, J = 1.2 Hz), 8.09 (1H, dd, J = 5.4 Hz, J = 0.9 Hz), 7.82 (1H, dd, | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1020 | N4-(2,2-Dimethyl-3-oxo-4H-benz[1,4]oxazin-6-yl)-5-fluoro-N2-[4-(oxazol-5-yl)phenyl]-2,4-pyrimidinediamine | J = 8.1 Hz, J = 0.9 Hz), 7.60 (1H, d, J = 8.4 Hz), 7.48-7.43 (2H, m), 7.05-6.97 (2H, m), 6.87 (1H, d, J = 2.1 Hz), 3.56 (3H, s), 1.51 (6H, s); purity 97.3%; MS (m/e): 461 (MH+). | + | | – | |
| 1021 | N4-(2,2-Dimethyl-3-oxo-4H-benz[1,4]oxazin-6-yl)-5-fluoro-N2-methyl-N2-[4-(oxazol-2-yl)phenyl]-2,4-pyrimidinediamine | 1H NMR (DMSO-d6): δ 10.75 (1H, s), 9.56 (1H, s), 9.49 (1H, s), 8.43 (1H, s), 8.20 (1H, d, J = 3.9 Hz), 7.83 (2H, d, J = 8.7 Hz), 7.59 (2H, d, J = 8.7 Hz), 7.53 (1H, s), 7.33-7.28 (2H, m), 7.02 (1H, d, J = 8.4 Hz), 1.52 (6H, s); purity 97.4%; MS (m/e): 447 (MH+). | + | + | + | |
| 1022 | N4-(2,2-Dimethyl-3-oxo-4H-benz[1,4]oxazin-6-yl)-5-fluoro-N4-methyl-N2-[4-(oxazol-2-yl)phenyl]-2,4-pyrimidinediamine | 1H NMR (DMSO-d6): δ 10.72 (1H, s), 9.72 (1H, s), 8.20 (1H, d, J = 0.9 Hz), 8.11 (1H, d, J = 5.7 Hz), 7.89 (4H, s), 7.38 (1H, d, J = 0.9 Hz), 7.07-6.97 (2H, m), 6.87 (1H, d, J = 2.7 Hz), 3.54 (3H, s), 1.52 (6H, s); purity 97.1%, MS (m/e): 461 (MH+). | + | + | – | |
| 1023 | N4-(2,2-Dimethyl-3-oxo-4H-benz[1,4]oxazin-6-yl)-5-fluoro-N4-methyl-N2-[3-(N-methylamino)carbonylmethyleneoxyphenyl]-2,4-pyrimidinediamine | 1H NMR (DMSO-d6): δ 10.70 (1H, s), 9.38 (1H, s), 8.05 (2H, d, J = 5.4 Hz), 7.55 (1H, m), 7.37 (1H, d, J = 8.4 Hz), 7.20 (1H, t, J = 7.8 Hz), 7.03 (1H, s), 6.97 (1H, dd, J = 8.4 Hz, J = 2.1 Hz), 6.85 (1H, d, J = 2.1 Hz), 6.57 (1H, dd, J = 7.8 Hz, J = 2.1 Hz), 4.49 (2H, s), 3.51 (3H, s), 2.774 (3H, d, J = 4.5 Hz), 1.50 (6H, s); purity 96.8%; MS (m/e) 481 (MH+). | + | + | – | |
| 1024 | N4-(2,2-Dimethyl-3-oxo-4H-benz[1,4]oxazin-6-yl)-5-fluoro-N4-methyl-N2-[3-(oxazol-5-yl)phenyl]-2,4-pyrimidinediamine | 1H NMR (DMSO-d6): δ 10.71 (1H, s), 9.55 (1H, s), 8.50 (1H, s), 8.37 (1H, s), 8.08 (1H, d, J = 5.7 Hz), 7.68 (1H, d, J = 8.1 Hz), 7.66 (1H, s), 7.43-7.34 (2H, m), 7.05-6.97 (2H, m), 6.87 (1H, d, J = 2.4 Hz), 3.55 (3H, s), 1.51 (6H, s); purity 95.6%; MS (m/e): 461 (MH+). | + | + | + | |
| 1025 | 5-Fluoro-N4-methyl-N2-[4-(oxazol-2-yl)phenyl]-N4-(3-oxo-2,2,4-trimethylbenz[1,4]oxazin-6-yl)-2,4-pyrimidinediamine | 1H NMR (DMSO-d6): δ 9.71 (1H, s), 8.20 (1H, d, J = 0.9 Hz), 8.10 (1H, d, J = 6 Hz), 7.90 (4H, s), 7.38 (1H, d, J = 0.6 Hz), 7.27 (1H, s), 7.09 (2H, s), 3.59 (3H, s), 3.34 (3H, s), 1.52 (6H, s); purity 97.4%; MS (m/e) 475 (MH+). | + | | + | |
| 1026 | 5-Fluoro-N4-methyl-N2-[3-(oxazol-2-yl)phenyl]-N4-(3-oxo-2,2,4-trimethylbenz[1,4]oxazin-6-yl)-2,4-pyrimidinediamine | 1H NMR (DMSO-d6): δ 9.65 (1H, s), 8.72 (1H, d, J = 1.8 Hz), 8.27 (1H, d, J = 0.6 Hz), 8.08 (1H, d, J = 6 Hz), 7.83-7.79 (1H, m), 7.60 (1H, d, J = 7.2 Hz), 7.47 (1H, d, J = 7.8 Hz), 7.43 (1H, d, J = 0.9 Hz), 7.28 (1H, s), 7.07 (2H, s), 3.62 (3H, s), 3.35 (3H, s), 1.51 (6H, s); purity 97.3%; MS (m/e): 475 (MH+). | + | | + | |
| 1027 | 5-Fluoro-N4-methyl-N2-[4-(oxazol-5-yl)phenyl]-N4-(2,2,4-trimethyl-3-oxo-benz[1,4]oxazin-6-yl)-2,4-pyrimidinediamine | 1H NMR (DMSO-d6): δ 9.60 (1H, s), 8.44 (1H, s), 8.07 (1H, d, J = 6 Hz), 7.88 (2H, d, J = 8.4 Hz), 7.65 (2H, d, J = 8.7 Hz), 7.57 (1H, s), 7.27 (1H, s), 7.08 (2H, s), 3.58 (3H, s), 3.34 (3H, s), 1.52 (6H, s); purity 98.61%; MS (m/e): 475 (MH+). | + | + | – | |
| 1028 | N2-(3-Chloro-4-cyclopentyloxy-5-methylphenyl)-N4-(2,2-dimethyl-3-oxo-4H-5-pyrid[1,4]oxazin-6-yl)-5-fluoro-2,4-pyrimidinediamine | 1H NMR (DMSO-d6): δ 11.18 (1H, s), 9.38 (1H, s), 8.22 (1H, d, J = 3.6 Hz), 7.74 (1H, s), 7.61 (1H, d, J = 8.7 Hz), 7.46 (1H, d, J = 8.4 Hz), 7.41 (1H, d, J = 2.7 Hz), 4.67 (1H, m), 2.26 (3H, s), 2.00-1.60 (8H, m), 1.53 (6H, s); purity 94.95%; MS (m/e): 513 (MH+). | + | + | – | |
| 1029 | N4-(2,2-Dimethyl-3-oxo-4H-5-pyrid[1,4]oxazin-6-yl)-5-fluoro-N2-[3-(oxazol-2-yl)phenyl]-2,4-pyrimidinediamine | 1H NMR (DMSO-d6): δ 11.18 (1H, s), 9.60 (1H, s), 9.37 (1H, s), 8.38 (2H, s), 8.27 (2H, m), 7.93 (1H, d, J = 8.4 Hz), 7.71 (1H, d, J = 8.7 Hz), 7.60 (1H, d, J = 8.1 Hz), 7.44-7.34 (3H, m), 1.53 (6H, s); purity 95%; MS (m/e): 448 (MH+). | + | + | – | |
| 1029 | N4-(2,2-Dimethyl-3-oxo-4H-5-pyrid[1,4]oxazin-6-yl)-5-fluoro-N2-[3-(oxazol-4-yl)phenyl]-2,4-pyrimidinediamine | 1H NMR (DMSO-d6): δ 11.17 (1H, s), 9.45 (1H, s), 9.31 (1H, s), 8.54 (2H, dd, J = 9.9 Hz, J = 0.9 Hz), 8.24 (1H, d, J = 3.6 Hz), 8.10 (1H, s), | + | + | – | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1030 | 5-Fluoro-N4-methyl-N2-[3-(oxazol-4-yl)phenyl]-N4-(3-oxo-2,2,4-trimethylbenz[1,4]oxazin-6-yl)-2,4-pyrimidinediamine | 7.78-7.72 (2H, m), 7.42-7.29 (3H, m), 1.52 (6H, s); purity 96.4%; MS (m/e): 448 (MH+). | + | | + | |
| 1031 | N2-(3,5-Dimethyl-4-methoxyphenyl)-5-fluoro-N4-methyl-N4-(3-oxo-2,2,4-trimethyl-benz[1,4]oxazin-6-yl)-2,4-pyrimidinediamine | 1H NMR (DMSO-d6): δ 9.47 (1H, s), 8.59 (1H, s), 8.51 (1H, s), 8.41 (1H, s), 8.05 (1H, d, J = 5.4 Hz), 7.66 (1H, d, J = 7.5 Hz), 7.41-7.32 (2H, m), 7.27 (1H, s), 7.07 (2H, s), 3.60 (3H, s), 3.35 (3H, s), 1.51 (6H, s); purity 97.4%; MS (m/e): 475 (MH+). | + | | − | |
| 1032 | N2-(3-Chloro-4-cyclopentyloxy-5-methylphenyl)-5-fluoro-N4-methyl-N4-(3-oxo-2,2,4-trimethyl-benz[1,4]oxazin-6-yl)-2,4-pyrimidinediamine | 1H NMR (DMSO-d6): δ 9.11 (1H, s), 8.00 (1H, J = 5.7 Hz), 7.42 (2H, s), 7.24 (1H, s), 7.05 (2H, s), 3.68 (3H, s), 3.55 (3H, s), 3.33 (3H, s), 2.25 (6H, s), 1.51 (6H, s); purity 97.84%; MS (m/e): 466 (M). | − | | − | |
| 1033 | N2-(3,5-Dimethyl-4-methoxyphenyl)-5-fluoro-N4-(3-oxo-2,2,4-trimethyl-benz[1,4]oxazin-6-yl)-2,4-pyrimidinediamine | 1H NMR (DMSO-d6): δ 9.49 (1H, s), 8.07 (1H, dd, J = 6 Hz, J = 1.5 Hz), 7.81 (1H, d, J = 2.7 Hz), 7.47 (1H, d, J = 2.4 Hz), 7.27 (1H, s), 7.07 (2H, s), 4.69 (1H, m), 3.61 (3H, s), 3.33 (3H, s), 2.29 (3H, s), 2.0-1.6 (8H, m), 1.51 (6H, s); purity 96.15%; MS (m/e): 540 (M). | + | + | + | |
| 1034 | N2-(3-Chloro-4-cyclopentyloxy-5-methylphenyl)-5-fluoro-N4-(3-oxo-2,2,4-trimethyl-benz[1,4]oxazin-6-yl)-2,4-pyrimidinediamine | 1H NMR (DMSO-d6): δ 9.49 (1H, s), 8.21 (1H, d, J = 3.6 Hz), 7.81 (1H, d, J = 8.7 Hz), 7.45 (1H, d, J = 8.4 Hz), 7.35 (2H, s), 3.69 (3H, s), 3.43 (3H, s), 2.23 (6H, s), 1.54 (6H, s); purity 98.82%; MS (m/e): 453 (M). | + | | − | |
| 1035 | N4-(2,2-Dimethyl-3-oxo-4H-5-pyrid[1,4]oxazin-6-yl)-5-fluoro-N2-[4-(oxazol-2-yl)phenyl]-2,4-pyrimidinediamine | 1H NMR (DMSO-d6): δ 9.63 (1H, s), 9.40 (1H, s), 8.26 (1H, d, J = 3.6 Hz), 7.78 (1H, d, J = 2.4 Hz), 7.72 (1H, d, J = 8.4 Hz), 7.48 (1H, d, J = 8.4 Hz), 7.41 (1H, d, J = 2.4 Hz), 4.68 (1H, m), 3.41 (3H, s), 2.26 (3H, s), 1.95-1.60 (8H, m), 1.54 (6H, s); purity 96%; MS (m/e): 527 (MH+). | + | − | + | |
| 1036 | N4-(2,2-Dimethyl-3-oxo-4H-benz[1,4]oxazin-6-yl)-5-fluoro-N2-[3-(oxazol-4-yl)phenyl]-2,4-pyrimidinediamine | 1H NMR (DMSO-d6): δ 11.23 (1H, s), 9.70 (1H, s), 9.53 (1H, s), 8.27 (1H, d, J = 3.6 Hz), 8.20 (1H, d, J = 0.9 Hz), 7.90 (2H, d, J = 9.3 Hz), 8.86 (2H, d, J = 9.5 Hz), 7.55 (1H, d, J = 8.4 Hz), 7.51 (1H, d, J = 8.4 Hz), 7.37 (1H, J = 0.9 Hz), 1.56 (6H, s); purity 96%; MS (m/e): 448 (MH+). | + | | + | |
| 1037 | N2-[3-Chloro-5-methyl-4-(N-methylamino)carbonylmethyleneoxyphenyl]-N4-(2,2-dimethyl-3-oxo-4H-5-pyrid[1,4]oxazin-6-yl)-5-fluoro-2,4-pyrimidinediamine | 1H NMR (DMSO-d6): δ 10.65 (1H, s), 9.41 (1H, s), 9.32 (1H, s), 8.50 (1H, d, J = 0.6 Hz), 8.47 (1H, s), 8.17 (1H, d, J = 3.9 Hz), 8.08 (1H, s), 7.78 (1H, d, J = 8.7 Hz), 7.43 (1H, dd, J = 8.7 Hz, J = 2.4 Hz), 7.39-7.27 (3H, m), 6.88 (1H, d, J = 8.7 Hz), 1.49 (6H, s); purity 98.9%; MS (m/e): 447 (MH+). | + | + | + | |
| 1038 | N2-(3,5-Dimethyl-4-ethoxycarbonylmethyleneoxyphenyl)-N4-(2,2-dimethyl-3-oxo-4H-benz[1,4]oxazin-6-yl)-5-fluoro-2,4-pyrimidinediamine | 1H NMR (DMSO-d6): δ 11.19 (1H, s), 9.43 (2H, s), 8.24 (1H, d, J = 7.8 Hz), 8.18 (1H, d, J = 4.5 Hz), 7.78 (1H, d, J = 2.4 Hz), 7.60 (1H, d, J = 8.4 Hz), 7.47 (1H, d, J = 8.4 Hz), 7.43 (1H, d, J = 2.4 Hz), 4.32 (2H, s), 2.79 (3H, d, J = 4.8 Hz), 2.29 (3H, s), 1.53 (6H, s); purity 97.6%; MS (m/e): 516 (MH+). | + | + | + | |
| 1039 | N2-(3-Chloro-4-isopropoxy-5-methylphenyl)-3-oxo-4H-benz[1,4]oxazin-6-yl)-5-fluoro-2,4-pyrimidinediamine | 1H NMR (DMSO-d6): δ 11.18 (1H, s), 9.26 (1H, s), 9.16 (1H, s), 8.19 (1H, d, J = 3.3 Hz), 7.68 (1H, d, J = 8.4 Hz), 7.46 (1H, d, J = 8.4 Hz), 7.33 (2H, s), 4.49 (2H, s), 4.28 (2H, q, J = 7.2 Hz), 2.23 (6H, s), 1.52 (6H, s), 1.33 (3H, t, J = 7.2 Hz); purity 97.9%; MS (m/e): 511 (MH+). | + | + | − | |
| 1040 | N2-(3-Chloro-4-isopropoxy-5-methylphenyl)-N4-(2,2-dimethyl-3-oxo-4H-5-pyrid[1,4]oxazin-6-yl)-5-fluoro-2,4- | 1H NMR (DMSO-d6): δ 10.72 (1H, s), 9.68 (1H, s), 9.44 (1H, s), 8.20 (1H, d, J = 3.6 Hz), 7.70 (1H, d, J = 2.1 Hz), 7.42 (1H, d, J = 2.4 Hz), 7.35 (1H, dd, J = 8.7 Hz, J = 2.4 Hz), 7.24 (1H, J = 2.4 Hz), 6.98 (1H, d, J = 8.4 Hz), 4.36 (1H, quint, J = 6.0 Hz), 2.23 (3H, s), 1.50 (6H, s), 1.32 (6H, d, J = 6.3 Hz); purity 96.9%; MS (m/e): 486 (MH+). 1H NMR (DMSO-d6): δ 11.17 (1H, s), 9.35 (1H, s), 8.22 (1H, d, J = 3.0 Hz), 7.74 (1H, d, J = 2.7 Hz), 7.61 (1H, d, J = 8.7 Hz), | + | − | + | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| | pyrimidinediamine | 7.45 (1H, d, J = 8.7 Hz), 7.41 (1H, d, J = 2.7 Hz), 4.36 (1H, quint, J = 6.0 Hz), 2.25 (3H, s), 1.52 (6H, s), 1.33 (6H, d, J = 6.3 Hz); purity 97.3%; MS (m/e): 487 (MH+). | | | | |
| 1041 | N2-[3,5-Dimethyl-4-(N-methylamino)carbonylmethyleneoxyphenyl]-N4-(2,2-dimethyl-3-oxo-4H-5-pyrid[1,4]oxazin-6-yl)-5-fluoro-2,4-pyrimidinediamine | 1H NMR (DMSO-d6): δ 11.18 (1H, s), 9.28 (1H, s), 9.18 (1H, s), 8.19 (2H, d, J = 3.6 Hz), 7.68 (1H, d, J = 8.4 Hz), 7.45 (1H, d, J = 8.7 Hz), 7.34 (2H, s), 4.22 (2H, s), 2.79 (3H, d, J = 4.5 Hz), 2.23 (6H, s), 1.52 (6H, s); purity 98%; MS (m/e): 496 (MH+). | + | + | + | |
| 1042 | N2-(3-Chloro-4-ethoxycarbonylmethyleneoxy-5-methylphenyl)-N4-(2,2-dimethyl-3-oxo-4H-5-pyrid[1,4]oxazin-6-yl)-5-fluoro-2,4-pyrimidinediamine | 1H NMR (DMSO-d6): δ 11.19 (1H, s), 9.42 (2H, s), 8.23 (1H, d, J = 3.6 Hz), 7.76 (1H, d, J = 2.4 Hz), 7.60 (1H, d, J = 8.4 Hz), 7.47 (1H, d, J = 8.4 Hz), 7.42 (1H, d, J = 2.1 Hz), 4.60 (2H, s), 4.27 (2H, q, J = 7.2 Hz), 2.29 (3H, s), 1.52 (6H, s), 1.33 (3H, t, J = 7.2 Hz); purity 98.4%; MS (m/e): 531 (MH+). | − | − | − | |
| 1043 | N2-[3-Chloro-4-[N-(2,3-dihydroxypropyl)amino]carbonylmethyleneoxy-5-methylphenyl]-N4-(2,2-dimethyl-3-oxo-4H-5-pyrid[1,4]oxazin-6-yl)-5-fluoro-2,4-pyrimidinediamine | 1H NMR (DMSO-d6): δ 11.17 (1H, s), 9.42 (1H, s), 9.40 (1H, s), 8.23 (1H, d, J = 3.6 Hz), 7.98 (1H, t, J = 5.7 Hz), 7.78 (1H, d, J = 2.7 Hz), 7.61 (1H, d, J = 8.7 Hz), 7.47 (1H, d, J = 8.4 Hz), 7.34 (1H, d, J = 1.8 Hz), 4.94 (1H, broad s), 4.67 (1H, broad s), 4.36 (2H, s), 3.67 (1H, t, J = 6.3 Hz), 3.26-3.17 (1H, m), 2.3 (3H, s), 1.53 (6H, s); purity 97.3%; MS (m/e): 576 (MH+). | + | − | − | |
| 1044 | N2-[3,5-Dimethyl-4-(N-cyclopentylamino)carbonylmethyleneoxyphenyl]-N4-(2,2-dimethyl-3-oxo-4H-5-pyrid[1,4]oxazin-6-yl)-5-fluoro-2,4-pyrimidinediamine | 1H NMR (DMSO-d6): δ 11.18 (1H, s), 9.27 (1H, s), 9.17 (1H, s), 8.19 (1H, d, J = 3.6 Hz), 8.03 (1H, d, J = 7.8 Hz), 7.67 (1H, d, J = 8.7 Hz), 7.45 (1H, d, J = 8.7 Hz), 7.34 (2H, s), 4.23 (1H, m), 4.21 (2H, s), 2.23 (6H, s), 1.91 (2H, m), 1.76 (2H, m), 1.60 (4H, m), 1.52 (6H, s); purity 98%; MS (m/e): 550 (MH+). | − | − | − | |
| 1045 | N4-(2,2-Difluoro-3-oxo-4H-benz[1,4]oxazin-6-yl)-5-fluoro-N2-[3-(N-methylamino)carbonylmethyleneoxyphenyl]-2,4-pyrimidinediamine Hydrogen Chloride Salt | 1H NMR (DMSO-d6): δ 12.12 (1H, s), 9.95 (1H, s), 9.58 (1H, s), 8.26 (1H, d, J = 3.6 Hz), 8.06 (1H, d, J = 4.2 Hz), 7.65 (1H, d, J = 2.1 Hz), 7.61 (1H, d, J = 2.4 Hz), 7.41 (1H, d, J = 8.7 Hz), 7.35 (1H, d, J = 8.7 Hz), 7.30 (1H, d, J = 9.0 Hz), 7.21 (1H, t, J = 7.8 Hz), 6.61 (1H, d, J = 8.1 Hz), 4.43 (2H, s), 2.73 (3H, d, J = 4.5 Hz); purity 100%; MS (m/e): 475 (MH+). | + | + | − | |
| 1046 | N4-(2,2-Difluoro-3-oxo-4H-benz[1,4]oxazin-6-yl)-5-fluoro-N2-[3-(N-methylamino)carbonylmethyleneoxyphenyl]-2,4-pyrimidinediamine Methanesulfonic Acid Salt | 1H NMR (DMSO-d6): δ 12.05 (1H, s), 9.81 (1H, s), 9.38 (1H, s), 8.24 (1H, d, J = 3.6 Hz), 8.04 (1H, d, J = 4.2 Hz), 7.66 (1H, dd, J = 10.5 Hz, J = 1.5 Hz), 7.51 (1H, d, J = 1.8 Hz), 7.43 (1H, s), 7.36-7.29 (2H, m), 7.19 (1H, t, J = 7.8 Hz), 6.59 (1H, d, J = 10.5 Hz), 4.42 (2H, s), 2.73 (3H, d, J = 4.5 Hz), 2.39 (3H, d, J = 0.6 Hz); purity 100%; MS (m/e): 475 (MH+). | + | + | − | |
| 1047 | N4-(2,2-Dimethyl-3-oxo-4H-benz[1,4]oxazin-6-yl)-5-fluoro-N2-(indazol-6-yl)-2,4-pyrimidinediamine Methanesulfonic Acid Salt | 1H NMR (DMSO-d6): δ 10.74 (1H, s), 10.11 (1H, s), 9.82 (1H, s), 8.26 (1H, d, J = 4.5 Hz), 8.05 (1H, s), 7.88 (1H, s), 7.71 (1H, d, J = 8.4 Hz), 7.45 (1H, dd, J = 9.0 Hz, J = 2.7 Hz), 7.31 (1H, d, J = 8.7 Hz), J = 1.5 Hz), 7.24 (1H, d, J = 2.4 Hz), 6.97 (1H, d, J = 8.7 Hz), 2.43 (3H, s), 1.48 (6H, s); purity 100%; MS (m/e): 420 (MH+). | − | + | − | |
| 1048 | N4-(2,2-Dimethyl-3-oxo-4H-benz[1,4]oxazin-6-yl)-5-fluoro-N2-(indazol-6-yl)-2,4-pyrimidinediamine Hydrogen Chloride Salt | 1H NMR (DMSO-d6): δ 10.73 (1H, s), 9.282 (1H, s), 9.60 (1H, s), 8.24 (1H, d, J = 4.2 Hz), 8.02 (2H, s), 7.67 (1H, d, J = 8.4 Hz), 7.47 (1H, d, J = 8.7 Hz), 7.36-7.33 (2H, m), 6.98 (1H, d, J = 8.7 Hz), 1.49 (6H, s); purity 99.3%; MS (m/e): 420 (MH+). | + | + | − | |
| 1049 | N4-(2,2-Dimethyl-3-oxo-4H-5-pyrid[1,4]oxazin-6-yl)-N2-(1-ethylindazol-6-yl)-5-fluoro-2,4-pyrimidinediamine | 1H NMR (DMSO-d6): δ 11.21 (1H, s), 9.56 (1H, s), 9.40 (1H, s), 8.29 (1H, d, J = 3.6 Hz), 8.11 (1H, s), 7.96 (1H, s), 7.71 (1H, d, J = 7.2 Hz), 7.64 (1H, d, J = 9.0 Hz), 7.46 (1H, d, J = 8.4 Hz), 7.36 (1H, dd, J = 8.7 Hz, | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1050 | N4-(2,2-Dimethyl-3-oxo-4H-5-pyrid[1,4]oxazin-6-yl)-N2-(1-isopropylindazol-6-yl)-5-fluoro-2,4-pyrimidinediamine | J = 1.5 Hz), 4.25 (2H, q, J = 7.2 Hz), 1.53 (6H, s), 1.41 (3H, t, J = 7.2 Hz); purity 100%; MS (m/e): 449 (MH+). | + | + | – | |
| 1051 | 2-Chloro-N4-(3,4-dihydro-2,2-dimethyl-4H-5-pyrid[1,4]oxazin-6-yl)-5-fluoro-4-pyrimidineamine | 8.29 (1H, d, J = 3.3 Hz), 8.15 (1H, s), 7.96 (1H, s), 7.70 (1H, d, J = 8.4 Hz), 7.63 (1H, d, J = 8.4 Hz), 7.46 (1H, d, J = 8.7 Hz), 7.35 (1H, dd, J = 8.7 Hz, J = 1.2 Hz), 4.63 (1H, quint, J = 6.6 Hz), 1.53 (6H, s), 1.49 (6H, d, J = 6.3 Hz); purity 97.67%; MS (m/e) 463 (MH+). 1H NMR (DMSO-d6): δ 9.84 (1H, s), 8.35 (1H, d, J = 3.3 Hz), 7.09 (1H, d, J = 8.1 Hz), 7.06 (1H, d, J = 8.1 Hz), 6.79 (1H, s), 3.23 (2H, s), 1.36 (6H, s); purity 96.73%; MS (m/e): 310 (MH+). | – | – | – | |
| 1052 | N4-(3,4-Dihydro-2,2-dimethyl-4H-5-pyrid[1,4]oxazin-6-yl)-5-fluoro-N2-(1-methylindazol-6-yl)-2,4-pyrimidinediamine | 1H NMR (DMSO-d6): δ 9.50 (1H, s), 8.94 (1H, s), 8.21 (1H, d, J = 3.6 Hz), 8.17 (1H, s), 7.93 (1H, s), 7.63 (1H, d, J = 8.7 Hz), 7.35 (1H, d, J = 1.5 Hz), 7.30 (1H, d, J = 7.8 Hz), 7.01 (1H, d, J = 8.4 Hz), 6.72 (1H, s), 3.92 (3H, s), 3.24 (2H, d, J = 2.4 Hz), 1.37 (6H, s); purity 98.07%; MS (m/e): 421 (M2H+). | + | + | + | |
| 1053 | N4-(3,4-Dihydro-2,2-dimethyl-4H-5-pyrid[1,4]oxazin-6-yl)-5-fluoro-N2-[3-(N-methylamino)carbonylmethyleneoxyphenyl]-2,4-pyrimidinediamine | 1H NMR (DMSO-d6): δ 9.29 (1H, s), 8.83 (1H, s), 8.15 (1H, d, J = 3.6 Hz), 8.03 (1H, m), 7.47 (1H, t, J = 2.1 Hz), 7.40 (1H, d, J = 7.5 Hz), 7.34 (1H, d, J = 6.9 Hz), 7.20 (1H, t, J = 8.4 Hz), 7.02 (1H, d, J = 8.1 Hz), 6.67 (1H, s), 6.56 (1H, dd, J = 7.8 Hz, J = 2.1 Hz), 4.46 (2H, s), 3.23 (2H, d, J = 2.1 Hz), 2.75 (3H, d, J = 4.5 Hz), 1.36 (6H, s); purity 96.2%; MS (m/e): 454 (MH+). | + | + | – | |
| 1054 | N2-[3-Chloro-4-(N-methylamino)carbonylphenyl]-N4-(2,2-dimethyl-3-oxo-4H-5-pyrid[1,4]oxazin-6-yl)-5-fluoro-2,4-pyrimidinediamine | 1H NMR (DMSO-d6): δ 11.19 (1H, s), 9.70 (1H, s), 9.52 (1H, s), 8.28 (1H, d, J = 2.4 Hz), 8.21 (1H, d, J = 5.1 Hz), 7.97 (1H, s), 7.62-7.57 (2H, m), 7.50 (1H, d, J = 9.0 Hz), 7.34 (1H, d, J = 8.4 Hz), 2.81 (3H, d, J = 3.6 Hz), 1.53 (6H, s); purity 99.5%; MS (m/e): 472 (MH+). | + | + | – | |
| 1055 | N4-(2,2-Dimethyl-3-oxo-4H-5-pyrid[1,4]oxazin-6-yl)-N2-(3,4-ethylenedioxyphenyl)-5-fluoro-2,4-pyrimidinediamine | 1H NMR (DMSO-d6): δ 11.12 (1H, s), 9.25 (1H, s), 9.12 (1H, s), 8.17 (1H, d, J = 3.3 Hz), 7.64 (1H, d, J = 8.4 Hz), 7.43 (1H, d, J = 8.4 Hz), 7.35 (1H, d, J = 2.4 Hz), 7.10 (1H, dd, J = 9.0 Hz, J = 2.4 Hz), 6.76 (1H, d, J = 9.0 Hz), 4.26 (4H, m), 1.53 (6H, s); purity 96.9%; MS (m/e): 439 (MH+). | + | + | – | |
| 1056 | N4-(2,2-Dimethyl-3-oxo-4H-5-pyrid[1,4]oxazin-6-yl)-5-fluoro-N2-[1-methylindazol-6-yl]-2,4-pyrimidinediamine Hydrogen Chloride Salt | 1H NMR (DMSO-d6): δ 11.23 (1H, s), 9.88 (1H, s), 9.28 (1H, s), 8.33 (1H, d, J = 3.6 Hz), 8.02 (1H, s), 7.98 (1H, s), 7.66 (2H, t, J = 8.4 Hz), 7.45 (1H, d, J = 8.4 Hz), 7.31 (1H, d, J = 8.4 Hz, J = 1.5 Hz), 3.93 (3H, s), 1.53 (6H, s); purity 100%; MS (m/e): 435 (MH+). | + | + | – | |
| 1057 | N4-(2,2-Dimethyl-3-oxo-4H-5-pyrid[1,4]oxazin-6-yl)-5-fluoro-N2-[1-methylindazol-6-yl]-2,4-pyrimidinediamine p-Toluenesulfonic Acid Salt | 1H NMR (DMSO-d6): δ 11.23 (1H, s), 9.81 (2H, s), 8.32 (1H, d, J = 3.9 Hz), 8.02 (1H, s), 7.98 (1H, s), 7.67 (2H, t, J = 8.7 Hz), 7.55 (2H, d, J = 7.8 Hz), 7.44 (1H, d, J = 8.4 Hz), 7.31 (1H, dd, J = 8.4 Hz, J = 0.9 Hz), 7.19 (2H, d, J = 9.0 Hz), 3.94 (3H, s), 2.38 (3H, s), 1.52 (6H, s); purity 98.8%; MS (m/e): 435 (MH+). | + | + | – | |
| 1058 | N4-(2,2-Dimethyl-3-oxo-4H-5-pyrid[1,4]oxazin-6-yl)-5-fluoro-N2-[1-methylindazol-6-yl]-2,4-pyrimidinediamine Methanesulfonic Acid Salt | 1H NMR (DMSO-d6): δ 11.22 (1H, s), 9.76 (1H, s), 9.72 (1H, s), 8.31 (1H, d, J = 3.3 Hz), 8.04 (1H, s), 7.97 (1H, s), 7.67 (2H, d, J = 8.4 Hz), 7.45 (1H, d, J = 8.1 Hz), 3.32 (1H, d, J = 8.4 Hz), 3.93 (3H, s), 2.41 (3H, s), 1.53 (6H, s); purity 99%; MS (m/e): 435 (MH+). | + | + | – | |
| 1059 | N2-(3,5-Dimethyl-4-methoxyphenyl)-5-fluoro-N4-(3-oxo-2H,4H-5-pyrid[1,4]oxazin-6-yl)-2,4-pyrimidinediamine | 1H NMR (DMSO-d6): δ 2.13 (s, 6H), 3.58 (s, 3H), 4.62 (s, 2H), 7.22 (s, 2H), 7.33 (d, J = 9.0 Hz, 1H), 7.57 (d, J = 8.4 Hz, 1H), 8.08 (d, J = 3.6 Hz, 1H), 9.01 (s, 1H), 9.15 (s, 1H), 11.13 (s, 1H); 19F NMR (282 MHz, | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1060 | N4-(2,2-Dimethyl-3-oxo-4H-benz[1,4]oxazin-6-yl)-5-fluoro-N2-(3-hydroxy-2-methylphenyl)-2,4-pyrimidinediamine | DMSO-d6): δ −163.82; LCMS: ret. time: 10.29 min.; purity: 97.75%; MS (m/e): 411.18 (MH+) | | | | |
| 1061 | 5-Fluoro-N2-(3-methoxy-2-methylphenyl)-N4-(3-oxo-2H,4H-5-pyrid[1,4]oxazin-6-yl)-2,4-pyrimidinediamine | 1H NMR (CDCl3): δ 1.45 (s, 6H), 2.13 (s, 3H), 6.78 (m, 3H), 6.90 (d, J = 7.5 Hz, 1H), 7.04 (t, J = 8.1 Hz, 1H), 7.27 (s, 1H), 7.74 (d, J = 5.1 Hz, 1H), 7.91 (s, 1H), 9.09 (s, 1H), 10.86 (s, 1H); 19F NMR (282 MHz, CDCl3): δ −162.90; LCMS: ret. time: 8.06 min.; purity: 97.47%; MS (m/e): 410.21 (MH+). | | + | | |
| 1062 | N4-(2,2-Dimethyl-3-oxo-4H-benz[1,4]oxazin-6-yl)-5-fluoro-N2-(3-methoxy-2-methylphenyl)-2,4-pyrimidinediamine | 1H NMR (DMSO-d6): δ 1.99 (s, 3H), 3.79 (s, 3H), 4.60 (s, 2H), 6.54 (d, J = 7.8 Hz, 1H), 6.78 (d, J = 8.1 Hz, 1H), 6.98 (dd, J = 2.4 and 8.1 Hz, 1H), 7.12 (t, J = 8.4 Hz, 1H), 7.44 (d, J = 8.7 Hz, 1H), 8.03 (d, J = 3.9 Hz, 1H), 8.73 (s, 1H), 9.23 (s, 1H), 11.08 (s, 1H); 19F NMR (282 MHz DMSO-d6): δ −164.15; LCMS: ret. time: 8.97 min.; purity: 99.74%; MS (m/e): 397.13 (MH+). | + | | | |
| 1063 | 5-Fluoro-N2-(3-hydroxy-2-methylphenyl)-N4-(3-oxo-2H,4H-5-pyrid[1,4]oxazin-6-yl)-2,4-pyrimidinediamine | 1H NMR (CDCl3): δ 1.49 (s, 6H), 2.12 (s, 3H), 3.95 (s, 3H), 6.71 (dd, J = 2.1 and 8.4 Hz, 1H), 6.79 (d, J = 8.4 Hz, 1H), 6.89 (d, J = 7.8 Hz, 1H), 6.98 (d, J = 8.4 Hz, 1H), 7.26 (m, 3H), 7.66 (d, J = 4.2 Hz, 1H), 7.93 (s, 1H), 11.04 (s, 1H); 19F NMR (282 MHz, CDCl3): δ −163.27; LCMS: ret. time: 9.36 min.; purity: 99.94%; MS (m/e): 424.18 (MH+). | | + | | |
| 1064 | N4-(2,2-Dimethyl-3-oxo-4H-benz[1,4]oxazin-6-yl)-5-fluoro-N2-(3-hydroxy-2-methylphenyl)-2,4-pyrimidinediamine | 1H NMR (CDCl3): δ 2.02 (s, 3H), 4.48 (s, 2H), 6.72 (m, 2H), 6.82 (m, 1H), 6.96 (t, J = 8.1 Hz, 1H), 7.25 (m, 1H), 7.79 (d, J = 4.8 Hz, 1H); LCMS: ret. time: 7.10 min.; purity: 77.55%; MS (m/e) 383.14 (MH+). | | + | | |
| 1065 | N4-(2,2-Dimethyl-3-oxo-4H-5-pyrid[1,4]oxazin-6-yl)-5-fluoro-N2-(3-methoxy-2-methylphenyl)-2,4-pyrimidinediamine | 1H NMR (CDCl3): δ 1.41 (s, 6H), 2.04 (s, 3H), 6.61 (t, J = 4.5 Hz, 1H), 6.94 (m, 3H), 7.58 (d, J = 8.7 Hz, 1H), 7.77 (d, J = 3.9 Hz, 1H); 19F NMR (282 MHz, CDCl3): δ −165.40; LCMS: ret. time: 7.83 min.; purity: 99.01%; MS (m/e): 411.19 (MH+). | + | | | |
| 1066 | N4-(2,2-Dimethyl-3-oxo-4H-benz[1,4]oxazin-6-yl)-5-fluoro-N2-[3-methoxycarbonylmethyleneoxy-2-methylphenyl]-2,4-pyrimidinediamine | 1H NMR (CDCl3): δ 1.57 (s, 6H), 2.19 (s, 3H), 3.88 (s, 3H), 6.79 (dd, J = 2.1 and 7.2 Hz, 1H), 7.05 (d, J = 8.7 Hz, 1H), 7.17 (m, 2H), 7.70 (d, J = 8.7 Hz, 1H), 7.85 (d, J = 3.6 Hz, 1H); 19F NMR (282 MHz, CDCl3): δ −161.49; LCMS: ret. time: 10.92 min.; purity: 85.56%; MS (m/e): 425.17 (MH+). | + | | | |
| 1067 | N4-(2,2-Dimethyl-3-oxo-4H-benz[1,4]oxazin-6-yl)-5-fluoro-N2-[2-methyl-3-(N-methylamino)carbonylmethyleneoxyphenyl]-2,4-pyrimidinediamine | 1H NMR (CDCl3): δ 1.49 (s, 6H), 2.26 (s, 3H), 3.80 (s, 3H), 4.84 (s, 2H), 6.69 (dd, J = 2.4 and 8.4 Hz, 1H), 6.82 (d, J = 8.7 Hz, 1H), 6.86 (d, J = 8.1 Hz, 1H), 6.98 (d, J = 8.1 Hz, 1H), 7.19 (t, J = 8.1 Hz, 1H), 7.26 (s, 1H), 7.46 (s, 1H), 7.72 (s, 1H), 7.79 (d, J = 4.8 Hz, 1H), 11.04 (s, 1H); 19F NMR (282 MHz, CDCl3): δ −162.94; LCMS: ret. time: 9.21 min.; purity: 99.68%; MS (m/e): 482.20 (MH+). | | + | | |
| 1068 | 5-Fluoro-N2-[2-methyl-3-(N-methylamino)carbonylmethyleneoxyphenyl]-N4-(3-oxo-2H,4H-5-pyrid[1,4]oxazin-6-yl)-2,4-pyrimidinediamine | 1H NMR (CDCl3): δ 1.50 (s, 6H), 2.25 (s, 3H), 2.93 (d, J = 4.8 Hz, 3H), 4.57 (s, 2H), 6.82 (m, 4H), 6.97 (t, J = 8.1 Hz, 1H), 7.19 (m, 2H), 7.40 (d, J = 8.7 Hz, 1H), 7.54 (s, 1H), 7.81 (d, J = 4.2 Hz, 1H); LCMS: ret. time: 8.08 min.; purity: 99.78%; MS (m/e): 481.21 (MH+). 1H NMR (DMSO-d6): δ 2.08 (s, 3H), 2.66 (d, J = 4.5 Hz, 3H), 4.46 (s, 2H), 4.58 (s, 2H), 6.65 (dd, J = 1.8 and 8.1 Hz, 1H), 7.04 (m, 2H), 7.15 (d, J = 8.7 Hz, 1H), 7.47 (d, J = 8.7 Hz, 1H), 7.84 (d, J = 4.2 Hz, 1H), 8.01 (d, J = 3.6 Hz, 1H), 8.54 (s, 1H), 8.96 (s, 1H), 11.05 (s, 1H); 19F NMR (282 MHz, DMSO-d6): δ −164.59; LCMS: ret. time: 7.60 min.; purity: 76.95%; MS (m/e): 454.14 (MH+). | | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1069 | N2-(3,5-Dimethyl-4-hydroxyphenyl)-5-fluoro-N4-(3-oxo-2H,4H-5-pyrid[1,4]oxazin-6-yl)-2,4-pyrimidinediamine | ¹H NMR (DMSO-d6): δ 2.09 (s, 6H), 4.62 (s, 2H), 7.05 (s, 2H), 7.28 (d, J = 8.4 Hz, 1H), 7.55 (d, J = 8.1 Hz, 1H), 7.89 (br, 1H), 8.07 (d, J = 3.6 Hz, 1H), 9.03 (s, 1H), 9.36 (s, 1H), 11.15 (s, 1H); 19F NMR (282 MHz, DMSO-d6): δ −163.98; LCMS: ret. time: 7.97 min.; purity: 77.84%; MS (m/e): 397.17 (MH+). | | + | | |
| 1070 | N2-[3-(4-Ethoxycarbonylpiperazinophenyl]-5-fluoro-N4-(3-oxo-2H,4H-5-pyrid[1,4]oxazin-6-yl)-2,4-pyrimidinediamine | ¹H NMR (CDCl3): δ 1.14 (t, J = 7.2 Hz, 3H), 3.00 (t, J = 5.1 Hz, 4H), 3.46 (t, J = 5.1 Hz, 4H), 4.00 (q, J = 7.2 Hz, 2H), 4.47 (s, 2H), 6.55 (dd, J = 1.8 and 8.4 Hz, 1H), 6.90 (dd, J = 1.2 and 7.8 Hz, 1H), 6.98 (t, J = 2.1 Hz, 1H), 7.04 (d, J = 8.7 Hz, 1H), 7.08 (t, J = 8.4 Hz, 1H), 7.73 (d, J = 8.7 Hz, 1H), 7.79 (d, J = 3.9 Hz, 1H); 19F NMR (282 MHz, CDCl3): δ −164.67; LCMS: ret. time: 11.64 min.; purity: 96.15%; MS (m/e): 509.21 (MH+). | | + | | |
| 1071 | N2-[3-(4-Acetylpiperazinophenyl]-5-fluoro-N4-(3-oxo-2H,4H-5-pyrid[1,4]oxazin-6-yl)-2,4-pyrimidinediamine | ¹H NMR (CDCl3): δ 2.01 (s, 3H), 3.02 (t, J = 5.1 Hz, 2H), 3.08 (t, J = 5.1 Hz, 2H), 3.50 (t, J = 5.1 Hz, 2H), 3.58 (t, J = 5.4 Hz, 2H), 4.50 (s, 2H), 6.66 (dd, J = 2.4 and 8.4 Hz, 1H), 6.87 (t, J = 2.4 Hz, 1H), 6.92 (ddd, J = 0.9, 2.1 and 7.8 Hz, 1H), 6.98 (d, J = 8.7 Hz, 1H), 7.14 (t, J = 8.1 Hz, 1H), 7.60 (d, J = 8.7 Hz, 1H), 7.80 (d, J = 4.8 Hz, 1H); 19F NMR (282 MHz, CDCl3): δ −161.72; LCMS: ret. time: 9.23 min.; purity: 73.82%; MS (m/e): 479.27 (MH+). | | + | | |
| 1072 | N2-[4-(4-Ethoxycarbonylpiperazinophenyl]-5-fluoro-N4-(3-oxo-2H,4H-5-pyrid[1,4]oxazin-6-yl)-2,4-pyrimidinediamine | ¹H NMR (DMSO-d6): δ 1.20 (t, J = 7.2 Hz, 3H), 2.99 (t, J = 5.1 Hz, 4H), 3.49 (t, J = 5.1 Hz, 4H), 4.05 (q, J = 7.2 Hz, 2H), 4.63 (s, 2H), 6.83 (d, J = 9.3 Hz, 2H), 7.36 (t, J = 8.4 Hz, 1H), 7.47 (d, J = 9.0 Hz, 2H), 7.56 (d, J = 8.4 Hz, 2H), 8.06 (d, J = 3.6 Hz, 1H), 9.01 (s, 1H), 9.14 (s, 1H), 11.13 (s, 1H); 19F NMR (282 MHz, DMSO-d6): δ −164.19; LCMS: ret. time: 10.49 min.; purity: 92.43%; MS (m/e): 509.27 (MH+). | | + | | |
| 1073 | 5-Fluoro-N2-(3-morpholinophenyl)-N4-(3-oxo-2H,4H-5-pyrid[1,4]oxazin-6-yl)-2,4-pyrimidinediamine | ¹H NMR (DMSO-d6): δ 2.98 (t, J = 5.1 Hz, 4H), 3.69 (t, J = 5.1 Hz, 4H), 4.62 (s, 2H), 6.50 (d, J = 7.2 Hz, 1H), 7.04 (t, J = 7.5 Hz, 1H), 7.17 (d, J = 7.2 Hz, 1H), 7.18 (s, 1H), 7.33 (d, J = 8.4 Hz, 1H), 7.58 (d, J = 8.7 Hz, 1H), 8.11 (d, J = 3.6 Hz, 1H), 9.09 (s, 1H), 9.21 (s, 1H), 11.13 (s, 1H); 19F NMR (282 MHz, DMSO-d6): δ −163.12; LCMS: ret. time: 9.27 min.; purity: 94.96%; MS (m/e): 438.23 (MH+). | | + | | |
| 1074 | 5-Fluoro-N2-[3-(4-methylpiperazinophenyl]-N4-(3-oxo-2H,4H-5-pyrid[1,4]oxazin-6-yl)-2,4-pyrimidinediamine | ¹H NMR (DMSO-d6): δ 2.85 (s, 3H), 2.90 (m, 2H), 3.23 (m, 4H), 3.67 (m, 2H), 4.63 (s, 2H), 6.57 (dd, J = 2.1 and 8.4 Hz, 1H), 7.08 (t, J = 8.1 Hz, 1H), 7.20 (s, 1H), 7.28 (m, 1H), 7.35 (d, J = 8.4 Hz, 1H), 7.59 (d, J = 8.4 Hz, 1H), 8.11 (d, J = 3.3 Hz, 1H), 9.13 (s, 1H), 9.26 (s, 1H), 11.15 (s, 1H); 19F NMR (282 MHz, DMSO-d6): δ −162.86; LCMS: ret. time: 6.70 min.; purity: 85.78%; MS (m/e): 451 (MH+). | | + | | |
| 1075 | N4-(2,2-Dimethyl-3-oxo-4H-5-pyrid[1,4]oxazin-6-yl)-N2-[3-(4-ethoxycarbonylpiperazinophenyl]-5-fluoro-2,4-pyrimidinediamine | ¹H NMR (DMSO-d6): δ 1.19 (t, J = 7.2 Hz, 3H), 1.42 (s, 6H), 3.00 (t, J = 4.8 Hz, 4H), 3.45 (t, J = 4.8 Hz, 4H), 4.04 (q, J = 7.2 Hz, 2H), 6.51 (d, J = 9.3 Hz, 1H), 7.03 (t, J = 8.1 Hz, 1H), 7.18 (s, 1H), 7.20 (d, J = 6.6 Hz, 1H), 7.34 (d, J = 8.4 Hz, 1H), 7.59 (d, J = 8.7 Hz, 1H), 8.11 (d, J = 3.3 Hz, 1H), 9.14 (s, 1H), 9.25 (s, 1H), 11.09 (s, 1H); 19F NMR (282 MHz, DMSO-d6): δ −163.08; LCMS: ret. time: 12.30 min.; purity: 87.49%; MS (m/e): 537.33 (MH+). | | + | | |
| 1076 | N2-[3-(4-Acetylpiperazinophenyl]-N4-(2,2-dimethyl-3-oxo-4H-5-pyrid[1,4]oxazin-6-yl)-5-fluoro-2,4-pyrimidinediamine | ¹H NMR (CDCl3): δ 1.46 (s, 6H), 2.06 (s, 3H), 3.08 (t, J = 5.1 Hz, 2H), 3.13 (t, J = 5.1 Hz, 2H), 3.54 (t, J = 5.1 Hz, 2H), 3.65 (t, J = 5.1 Hz, 2H), 6.67 (dd, J = 2.4 and 8.4 Hz, 1H), 6.94 (t, J = 2.1 Hz, 1H), 7.01 (ddd, J = 0.9, | | + | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1077 | N4-(2,2-Dimethyl-3-oxo-4H-5-pyrid[1,4]oxazin-6-yl)-N2-[4-(4-ethoxycarbonylpiperazino)phenyl]-5-fluoro-2,4-pyrimidinediamine | 1.8 and 7.8 Hz, 1H), 7.05 (d, J = 8.7 Hz, 1H), 7.18 (t, J = 8.1 Hz, 1H), 7.73 (d, J = 8.7 Hz, 1H), 7.84 (d, J = 4.5 Hz, 1H); 19F NMR (282 MHz, CDCl3): δ −162.20; LCMS: ret. time: 9.92 min.; purity: 92.80%; MS (m/e): 507.31 (MH+). | | + | | |
| 1078 | N4-(2,2-Dimethyl-3-oxo-4H-5-pyrid[1,4]oxazin-6-yl)-5-fluoro-N2-(3-morpholinophenyl)-2,4-pyrimidinediamine | 1H NMR (DMSO-d6): δ 1.20 (t, J = 7.2 Hz, 3H), 1.43 (s, 6H), 3.03 (t, 4H), 3.50 (t, 4H), 4.05 (q, J = 7.2 Hz, 2H), 6.88 (d, J = 9.3 Hz, 2H), 7.38 (d, J = 8.4 Hz, 1H), 7.45 (d, J = 9.9 Hz, 2H), 7.51 (d, J = 8.7 Hz, 1H), 8.09 (d, J = 3.9 Hz, 1H), 9.24 (s, 1H), 9.44 (s, 1H), 11.12 (s, 1H); LCMS: ret. time: 10.90 min.; purity: 91.64%; MS (m/e): 537.30 (MH+). | | + | | |
| 1079 | N4-(2,2-Dimethyl-3-oxo-4H-5-pyrid[1,4]oxazin-6-yl)-5-fluoro-N2-[2-methyl-3-(N-methylamino)carbonylmethyleneoxyphenyl]-2,4-pyrimidinediamine | 1H NMR (DMSO-d6): δ 1.42 (s, 6H), 3.00 (t, J = 4.8 Hz, 4H), 3.69 (t, J = 4.8 Hz, 4H), 6.51 (dd, J = 7.5 Hz, 1H), 7.04 (t, J = 7.8 Hz, 1H), 7.16 (s, 1H), 7.17 (d, J = 8.4 Hz, 1H), 7.34 (d, J = 8.4 Hz, 1H), 7.59 (d, J = 8.4 Hz, 1H), 8.12 (d, J = 3.6 Hz, 1H), 9.17 (s, 1H), 9.31 (s, 1H), 11.09 (s, 1H); 19F NMR (282 MHz, DMSO-d6): δ −162.98; LCMS: ret. time: 10.81 min.; purity: 98.57%; MS (m/e): 466.27 (MH+). | | + | | |
| 1080 | N4-(2,2-Dimethyl-3-oxo-4H-5-pyrid[1,4]oxazin-6-yl)-5-fluoro-N2-[3-(4-methylpiperazino)phenyl]-2,4-pyrimidinediamine | 1H NMR (DMSO-d6): δ 1.39 (s, 6H), 2.08 (s, 3H), 2.65 (d, J = 4.8 Hz, 3H), 4.45 (s, 2H), 6.64 (dd, J = 2.7 and 6.6 Hz, 1H), 7.04 (m, 2H), 7.15 (d, J = 8.4 Hz, 1H), 7.48 (d, J = 8.4 Hz, 1H), 7.84 (d, J = 3.9 Hz, 1H), 8.01 (d, J = 3.6 Hz, 1H), 8.56 (s, 1H), 8.98 (s, 1H), 11.01 (s, 1H); 19F NMR (282 MHz, DMSO-d6): δ −164.69; LCMS: ret. time: 8.73 min.; purity: 96.88%; MS (m/e): 482.26 (MH+). | + | + | | |
| 1081 | (S)—N2-(3-Chloro-4-methoxyphenyl)-5-fluoro-N4-(2-methyl-3-oxo-2H,4H-5-pyrid[1,4]oxazin-6-yl)-2,4-pyrimidinediamine | 1H NMR (CDCl3): δ 1.42 (s, 6H), 2.77 (s, 3H), 3.20 (m, 4H), 3.30 (m, 4H), 6.61 (d, J = 6.9 Hz, 1H), 6.92 (t, J = 2.4 Hz, 1H), 7.04 (d, J = 8.4 Hz, 1H), 7.13 (m, 2H), 7.70 (d, J = 8.7 Hz, 1H), 7.81 (d, J = 4.2 Hz, 1H); 19F NMR (282 MHz, CDCl3): δ −162.81; LCMS: ret. time: 8.54 min.; purity: 83.90%; MS (m/e): 479.38 (MH+). | + | + | | |
| 1082 | (S)-5-fluoro-N4-(2-methyl-3-oxo-2H,4H-5-pyrid[1,4]oxazin-6-yl)-N2-(3,4,5-trimethoxyphenyl)-2,4-pyrimidinediamine | 1H NMR (DMSO-d6): δ 1.45 (d, J = 6.6 Hz, 3H), 3.77 (s, 3H), 4.73 (q, J = 6.6 Hz, 1H), 6.99 (d, J = 9.0 Hz, 1H), 7.38 (d, J = 8.4 Hz, 1H), 7.48 (m, 2H), 7.80 (d, J = 2.1 Hz, 1H), 8.11 (d, J = 3.6 Hz, 1H), 9.21 (s, 1H), 9.26 (s, 1H), 11.09 (s, 1H); 19F NMR (282 MHz, DMSO-d6): δ −163.36; LCMS: ret. time: 11.59 min.; purity: 97.70%; MS (m/e): 431.16 (MH+). | + | + | | |
| 1083 | N2,N4-Bis(3-oxo-2H,4H-benz[1,4]oxazin-6-yl)-5-fluoro-2,4-pyrimidinediamine | 1H NMR (DMSO-d6): δ 1.45 (d, J = 6.9 Hz, 3H), 3.59 (s, 3H), 3.65 (s, 6H), 4.72 (q, J = 6.6 Hz, 1H), 7.02 (s, 2H), 7.32 (d, J = 8.7 Hz, 1H), 7.65 (d, J = 8.4 Hz, 1H), 8.11 (d, J = 3.3 Hz, 1H), 9.10 (s, 1H), 9.17 (s, 1H), 11.07 (s, 1H); 19F NMR (282 MHz, DMSO-d6): δ −162.83; LCMS: ret. time: 10.07 min.; purity: 90.75%; MS (m/e): 457.22 (MH+). | + | + | | |
| 1084 | (S)—N2-(3,5-Dimethylphenyl)-5-fluoro-N4-(2-methyl-3-oxo-2H,4H-5-pyrid[1,4]oxazin-6-yl)-2,4-pyrimidinediamine | 1H NMR (DMSO-d6): δ 4.46 (s, 2H), 4.52 (s, 2H), 6.76 (d, J = 9.3 Hz, 1H), 6.86 (d, J = 8.7 Hz, 1H), 7.18 (m, 2H), 7.23 (d, J = 2.4 Hz, 2H), 7.33 (dd, J = 2.4 and 8.7 Hz, 1H), 8.00 (d, J = 3.6 Hz, 1H), 8.94 (s, 1H), 9.29 (s, 1H), 10.58 (s, 1H), 10.63 (s, 1H); 19F NMR (282 MHz, DMSO-d6): δ −164.54; LCMS: ret. time: 7.32 min.; purity: 85.68%; MS (m/e): 423.13 (MH+). | − | + | | |
|  |  | 1H NMR (DMSO-d6): δ 1.44 (d, J = 6.9 Hz, 3H), 2.17 (s, 6H), 4.72 (q, J = 6.9 Hz, 1H), 6.52 (s, 1H), 7.22 (s, 2H), 7.35 (d, J = 8.7 Hz, 1H), 7.89 (d, J = 8.4 Hz, 1H), 8.11 (d, J = 3.6 Hz, 1H), 9.09 (d, J = 3.6 Hz, 1H), 9.16 (s, 1H), | | | | + |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1085 | N2-[3-(4-Acetylpiperazinophenyl]-N4-cyclobutyl-5-fluoro-2,4-pyrimidinediamine | 11.08 (s, 1H); 19F NMR (282 MHz, DMSO-d6): δ –163.48; LCMS: ret. time: 12.47 min.; purity: 96.01%; MS (m/e): 395.14 (MH+). | + | | – | |
| 1086 | N2-(5-tert-Butylpyrazol-3-yl)-5-fluoro-N4-(3-oxo-2H,4H-5-pyrid[1,4]oxazin-6-yl)-2,4-pyrimidinediamine | 1H NMR (CDCl3): δ 1.82 (m, 2H), 2.03 (m, 2H), 2.15 (s, 3H), 2.46 (m, 2H), 3.20 (m, 4H), 3.63 (t, J = 5.1 Hz, 2H), 3.78 (t, J = 5.1 Hz, 2H), 4.58 (m, J = 8.1 Hz, 1H), 5.26 (d, J = 6.6 Hz, 1H), 6.58 (dd, J = 1.8 and 8.1 Hz, 1H), 7.01 (dd, J = 1.5 and 7.8 Hz, 1H), 7.19 (t, J = 8.1 Hz, 1H), 7.28 (br, 1H), 7.34 (t, J = 2.1 Hz, 1H), 7.74 (d, J = 3.3 Hz, 1H); 19F NMR (282 MHz, CDCl3): δ –168.12; LCMS: ret. time: 8.93 min.; purity: 84.56%; MS (m/e): 385.77 (MH+). 1H NMR (DMSO-d6): δ 1.29 (s, 9H), 4.64 (s, 2H), 5.59 (s, 1H), 7.10 (d, 1H), 7.47 (d, J = 6.6 Hz, 1H), 8.24 (d, 1H), 10.02 (s, 1H), 10.40 (s, 1H); 19F NMR (282 MHz, DMSO-d6): δ –162.59; LCMS: ret. time: 10.51 min.; purity: 78.44%; MS (m/e): 399.24 (MH+). | + | + | – | |
| 1087 | N4-Cyclobutyl-N2-(3,5-dimethylphenyl)-5-fluoro-2,4-pyrimidinediamine | 1H NMR (CDCl3): δ 1.78-1.87 (m, 2H), 1.96-2.03 (m, 2H), 2.32 (s, 6H), 2.44-2.53 (m, 2H), 4.56 (m, J = 7.8 Hz, 1H), 5.26 (d, J = 7.8 Hz, 1H), 6.67 (s, 1H), 7.23 (s, 2H), 7.34 (br, NH, 1H), 7.72 (d, J = 2.7 Hz, 1H); 19F NMR (282 MHz, CDCl3): δ –168.35; LCMS: ret. time: 13.76 min.; purity: 80.20%; MS (m/e): 287.35 (MH+). | + | + | – | |
| 1088 | N4-Cyclobutyl-N2-(3,5-dimethoxyphenyl)-5-fluoro-2,4-pyrimidinediamine | 1H NMR (CDCl3): δ 1.71-1.86 (m, 2H), 1.93-2.06 (m, 2H), 2.43-2.53 (m, 2H), 3.81 (s, 6H), 4.60 (m, J = 7.8 Hz, 1H), 5.31 (d, 1H), 6.16 (t, J = 2.1 Hz, 1H), 6.84 (d, J = 2.1 Hz, 2H), 7.57 (br, NH, 1H), 7.72 (d, J = 3.6 Hz, 1H); 19F NMR (282 MHz, CDCl3): δ –167.56; LCMS: ret. time: 12.44 min.; purity: 87.82%; MS (m/e): 319.32 (MH+). | + | + | – | |
| 1089 | N4-Cyclobutyl-5-fluoro-N2-(3-methoxy-5-trifluoromethylphenyl)-2,4-pyrimidinediamine | 1H NMR (CDCl3): δ 1.75-2.04 (m, 4H), 2.43-2.53 (m, 2H), 3.85 (s, 3H), 4.58 (m, J = 7.8 Hz, 1H), 5.32 (d, J = 6.6 Hz, 1H), 6.76 (s, 1H), 7.18 (t, J = 2.1 Hz, 1H), 7.52 (br, NH, 1H), 7.76 (s, 2H); 19F NMR (282 MHz, CDCl3): δ –167.20, –63.67; LCMS: ret. time: 13.22 min.; purity: 82.74%; MS (m/e): 357.19 (MH+). | + | + | – | |
| 1090 | N4-(5-tert-Butyl-1H-pyrazol-3-yl)-5-fluoro-N2-(3-morpholinophenyl)-2,4-pyrimidinediamine | LCMS: ret. time: 11.58 min.; purity: 90.45%; MS (m/e): 412.33 (MH+). | + | + | – | |
| 1091 | N2-[3-(4-Acetylpiperazinophenyl]-N4-(5-tert-butyl-1H-pyrazol-3-yl)-5-fluoro-2,4-pyrimidinediamine | 1H NMR (CDCl3): δ 1.20 (s, 9H), 2.04 (s, 3H), 3.06 (t, J = 5.4 Hz, 2H), 3.11 (t, J = 5.1 Hz, 2H), 3.53 (t, J = 5.1 Hz, 2H), 3.63 (t, J = 5.1 Hz, 2H), 6.10 (s, 1H), 6.57 (m, 1H), 6.96 (s, 1H), 7.13 (m, 2H), 7.82 (d, J = 3.9 Hz, 1H); LCMS: ret. time: 8.84 min.; purity: 90.18%; MS (m/e): 453.27 (MH+). | + | + | – | |
| 1092 | (S)—N2-(5-tert-Butyl-1H-pyrazol-3-yl)-5-fluoro-N4-(2-methyl-3-oxo-2H,4H-5-pyrid[1,4]oxazin-6-yl)-2,4-pyrimidinediamine | 1H NMR (DMSO-d6): δ 1.30 (s, 9H), 1.47 (d, J = 6.6 Hz, 3H), 4.74 (q, J = 6.3 Hz, 1H), 5.60 (s, 1H), 7.09 (d, J = 9.0 Hz, 1H), 7.49 (d, J = 8.4 Hz, 1H), 8.23 (d, J = 3.9 Hz, 1H), 10.02 (s, 1H), 10.39 (s, 1H); 19F NMR (282 MHz, DMSO-d6): δ –162.62; LCMS: ret. time: 11.61 min.; purity: 88.68%; MS (m/e): 413.17 (MH+). | + | + | – | |
| 1093 | N2-(3,5-Dimethyl-4-methoxyphenyl)-5-fluoro-[3-(N-2-imidazolin-2-yl)aminophenyl]-2,4-pyrimidinediamine | 1H NMR (DMSO-d6): δ 2.16 (s, 6H), 3.61 (s, 4H), 3.64 (s, 3H), 6.98 (d, J = 11 Hz, 1H), 7.00 (s, 1H), 7.23 (s, 1H), 7.35 (t, J = 8.1 Hz, 1H), 7.75 (d, J = 6.6 Hz, 1H), 8.19 (d, J = 4.5 Hz, 1H), 8.29 (s, 2H), 9.57 (s, 1H), 9.89 (s, 1H), 10.82 (s, 1H); 19F NMR (282 MHz, DMSO-d6): δ –162.53; LCMS: ret. time: 7.49 min.; purity: 83.77%; MS (m/e): 422 (MH+). | + | + | – | + |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1094 | 5-Fluoro-N2-(3-fluoro-4-methoxyphenyl)-N4-[3-(N-2-imidazolin-2-yl)aminophenyl]-2,4-pyrimidinediamine | 1H NMR (DMSO-d6): δ 3.63 (s, 4H), 3.79 (s, 3H), 6.96 (d, J = 9.3 Hz, 1H), 7.04 (t, J = 9.3 Hz, 1H), 7.28 (m, 1H), 7.36 (t, J = 8.1 Hz, 1H), 7.63 (dd, J = 2.1, 13.8 Hz, 1H), 7.68 (d, J = 9.6 Hz, 1H), 7.80 (s, 1H), 8.18 (d, J = 4.2 Hz, 1H), 8.27 (s, 1H), 9.56 (s, 1H), 9.75 (s, 1H), 10.72 (s, 1H); 19F NMR (282 MHz, DMSO-d6): δ −162.96, −134.40; LCMS: ret. time: 6.99 min.; purity: 81.44%; MS (m/e): 412 (MH+). | + | | − | |
| 1095 | N2-(3,5-Dimethylphenyl)-5-fluoro-N4-[3-(N-2-imidazolin-2-yl)aminophenyl]-2,4-pyrimidinediamine | 1H NMR (DMSO-d6): δ 2.20 (s, 6H), 3.60 (s, 4H), 6.92 (s, 1H), 6.98 (m, 1H), 7.22 (s, 1H), 7.35 (t, J = 8.1 Hz, 1H), 7.73 (d, J = 7.8 Hz, 1H), 7.80 (s, 1H), 8.21 (d, J = 4.2 Hz, 1H), 8.26 (s, 2H), 9.60 (s, 1H), 9.86 (s, 1H), 10.80 (s, 1H); 19F NMR (282 MHz, DMSO-d6): δ −162.49; LCMS: ret. time: 7.91 min.; purity: 81.26%; MS (m/e): 392 (MH+). | + | | − | |
| 1096 | N2-(3,5-Dimethoxyphenyl)-5-fluoro-N4-[3-(N-2-imidazolin-2-yl)aminophenyl]-2,4-pyrimidinediamine | 1H NMR (DMSO-d6): δ 3.62 (s, 4H), 3.66 (s, 6H), 6.13 (t, J = 2.1 Hz, 1H), 6.92 (d, J = 2.1 Hz, 1H), 6.95 (dd, J = 1.5, 8.4 Hz, 1H), 7.34 (t, J = 8.4 Hz, 1H), 7.71 (d, J = 8.1 Hz, 1H), 7.93 (s, 1H), 8.20 (d, J = 3.9 Hz, 1H), 8.26 (s, 2H), 9.61 (s, 1H), 9.81 (s, 1H), 10.86 (s, 1H); 19F NMR (282 MHz, DMSO-d6): δ −162.22; LCMS: ret. time: 7.49 min.; purity: 80.65%; MS (m/e): 424 (MH+). | + | | − | |
| 1097 | 5-Fluoro-N4-[3-(N-2-imidazolin-2-yl)aminophenyl]-N2-(3-morpholinophenyl)-2,4-pyrimidinediamine | 1H NMR (DMSO-d6): δ 3.01 (t, J = 4.5 Hz, 4H), 3.60 (s, 4H), 3.70 (t, J = 4.5 Hz, 4H), 6.51 (dd, J = 2.1, 8.4 Hz, 1H), 6.90 (dd, J = 1.5, 7.8 Hz, 1H), 7.05 (t, J = 8.1 Hz, 1H), 7.29 (m, 3H), 7.64 (d, J = 7.8 Hz, 1H), 8.01 (s, 1H), 8.12 (d, J = 3.6 Hz, 1H), 9.20 (s, 1H), 9.48 (s, 1H); 19F NMR (282 MHz, DMSO-d6): δ −163.75; LCMS: ret. time: 6.28 min.; purity: 87.59%; MS (m/e): 449 (MH+). | − | | − | |
| 1098 | N2-[3-(4-Ethoxycarbonylpiperazinophenyl)-5-fluoro-N4-[3-(N-2-imidazolin-2-yl)aminophenyl]-2,4-pyrimidinediamine | 1H NMR (DMSO-d6): δ 1.20 (t, J = 7.2 Hz, 3H), 3.02 (t, J = 5.4 Hz, 4H), 3.47 (t, J = 5.4 Hz, 4H), 3.60 (s, 4H), 4.05 (q, J = 7.2 Hz, 2H), 6.53 (dd, J = 1.5, 8.4 Hz, 1H), 6.90 (d, J = 8.1 Hz, 1H), 7.06 (t, J = 8.1 Hz, 1H), 7.30 (m, 3H), 7.66 (d, J = 8.7 Hz, 1H), 7.99 (s, 1H), 8.12 (d, J = 3.6 Hz, 1H), 9.19 (s, 1H), 9.48 (s, 1H); 19F NMR (282 MHz, DMSO-d6): δ −163.72; LCMS: ret. time: 9.11 min.; purity: 94.51%; MS (m/e): 520.34 (MH+). | − | | − | |
| 1099 | 5-Fluoro-N4-[3-(N-2-imidazolin-2-yl)aminophenyl]-N2-[4-(4-methylpiperazino)phenyl]-2,4-pyrimidinediamine | 1H NMR (DMSO-d6): δ 3.30 (m, 4H), 3.62 (s, 4H), 6.84 (d, J = 9.0 Hz, 2H), 6.91 (d, J = 8.1 Hz, 1H), 7.35 (t, J = 8.1 Hz, 1H), 7.49 (d, J = 8.4 Hz, 2H), 7.73 (d, J = 8.4 Hz, 1H), 7.80 (s, 1H), 8.09 (d, J = 3.3 Hz, 1H), 8.27 (s, 1H), 9.06 (s, 1H), 9.44 (s, 1H); 19F NMR (282 MHz, DMSO-d6): δ −163.72; LCMS: ret. time: 2.86 min.; purity: 84.74%; MS (m/e): 462.37 (MH+). | − | | − | |
| 1100 | 5-Fluoro-N4-[3-(N-2-imidazolin-2-yl)aminophenyl]-N2-[4-(4-methoxycarbonylpiperazino)phenyl]-2,4-pyrimidinediamine | 1H NMR (DMSO-d6): δ 3.00 (t, J = 5.1 Hz, 4H), 3.50 (t, J = 4.5 Hz, 4H), 3.61 (s, 7H), 6.84 (d, J = 9.0 Hz, 2H), 6.91 (dd, J = 1.5, 7.5 Hz, 1H), 7.34 (t, J = 7.8 Hz, 1H), 7.52 (d, J = 8.7 Hz, 2H), 7.66 (d, J = 8.1 Hz, 1H), 7.94 (s, 1H), 8.08 (d, J = 3.6 Hz, 1H), 9.11 (s, 1H), 9.44 (s, 1H); 19F NMR (282 MHz, DMSO-d6): δ −164.62; LCMS: ret. time: 6.94 min.; purity: 86.06%; MS (m/e): 506 (MH+). | − | | − | |
| 1101 | N4-(5-tert-Butyl-1H-pyrazol-3-yl)-N2-[3-(4-ethoxycarbonylpiperazino)phenyl]-5-fluoro-2,4-pyrimidinediamine | 1H NMR (CDCl3): δ 1.28 (t, J = 7.2 Hz, 3H), 1.31 (s, 9H), 3.13 (t, J = 5.1 Hz, 4H), 3.60 (t, J = 5.4 Hz, 4H), 4.15 (q, J = 7.2 Hz, 2H), 6.35 (s, 1H), 6.61 (m, 1H), 7.03 (s, 1H), 7.18 (m, 2H), 7.73 (br, 1H), 7.90 (d, J = 3.3 Hz, 1H), 8.20 (br, 1H); 19F NMR (282 MHz, CDCl3): δ −166.45; LCMS: ret. time: 12.52 min.; purity: 86.92%; MS (m/e): 483.37 (MH+). | + | | − | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1102 | N2-[4-(4-Acetylpiperazinophenyl]-N4-(5-tert-butyl-1H-pyrazol-3-yl)-5-fluoro-2,4-pyrimidinediamine | LCMS: ret. time: 8.02 min.; purity: 94.49%; MS (m/e): 453.29 (MH+). | + | + | − | |
| 1103 | N4-(5-tert-Butyl-1H-pyrazol-3-yl)-5-fluoro-N2-[4-(4-methoxycarbonylpiperazinophenyl]-2,4-pyrimidinediamine | LCMS: ret. time: 10.38 min.; purity: 97.48%; MS (m/e): 469.35 (MH+). | + | + | − | |
| 1104 | N4-(5-tert-Butyl-1H-pyrazol-3-yl)-5-fluoro-N2-[4-(4-methylpiperazinophenyl]-2,4-pyrimidinediamine | 1H NMR (DMSO-d6): δ 1.26 (s, 9H), 2.61 (m, 7H), 3.00 (m, 4H), 6.30 (br, 1H), 6.86 (d, J = 8.4 Hz, 2H), 7.48 (d, J = 9.3 Hz, 2H), 7.97 (s, 1H); 19F NMR (282 MHz, DMSO-d6): δ −165.34; LCMS: ret. time: 6.04 min.; purity: 90.75%; MS (m/e): 425 (MH+). | + | | | |
| 1105 | N2-[4-(4-Acetylpiperazinophenyl]-5-fluoro-N4-[3-(N-2-imidazolin-2-yl)aminophenyl]-2,4-pyrimidinediamine | 1H NMR (DMSO-d6): δ 2.04 (s, 3H), 2.97 (t, J = 4.8 Hz, 2H), 3.04 (t, J = 4.8 Hz, 2H), 3.57 (m, 4H), 3.61 (s, 4H), 6.84 (d, J = 9.0 Hz, 2H), 6.90 (d, J = 9.3 Hz, 1H), 7.33 (t, J = 7.8 Hz, 1H), 7.50 (d, J = 8.7 Hz, 2H), 7.69 (d, J = 8.7 Hz, 1H), 7.79 (s, 1H), 8.08 (d, J = 3.6 Hz, 1H), 9.04 (s, 1H), 9.40 (s, 1H); 19F NMR (282 MHz, DMSO-d6): δ −164.70; LCMS: ret. time: 7.00 min.; purity: 93%; MS (m/e): 490.32 (MH+). | − | | | |
| 1106 | N2-[3-(4-Acetylpiperazinophenyl]-5-fluoro-N4-[N-2-imidazolin-2-yl)aminophenyl]-2,4-pyrimidinediamine | LCMS: ret. time: 7.31 min.; purity: 84.11%; MS (m/e): 490.34 (MH+). | − | | | |
| 1107 | N4-Cyclobutyl-N2-[2-(ethoxycarbonyl)indol-7-yl]-5-fluoro-2,4-pyrimidinediamine | 1H NMR (CDCl3): δ 1.42 (t, J = 7.2 Hz, 3H), 1.63–2.06 (m, 4H), 2.27–2.36 (m, 2H), 4.41 (q, J = 7.2 Hz, 2H), 5.17 (d, J = 6.0 Hz, 1H), 7.06 (t, J = 7.8 Hz, 1H), 7.14 (d, 1H), 7.22 (m, 2H), 7.28 (br, 1H), 7.44 (d, J = 7.8 Hz, 1H), 7.76 (d, J = 3.6 Hz, 1H), 10.68 (br, 1H); 19F NMR (282 MHz, CDCl3): δ −168.82; LCMS: ret. time: 10.65 min.; purity: 82.48%; MS (m/e): 370.20 (MH+). | + | + | | |
| 1108 | N4-Cyclobutyl-5-fluoro-N2-(3-morpholinophenyl)-2,4-pyrimidinediamine | 1H NMR (CDCl3): δ 1.73–2.05 (m, 4H), 2.40–2.50 (m, 2H), 3.20 (t, J = 4.8 Hz, 4H), 3.88 (t, J = 4.8 Hz, 4H), 4.60 (m, J = 7.8 Hz, 1H), 5.14 (d, J = 6.3 Hz, 1H), 6.57 (dd, J = 2.4, 8.1 Hz, 1H), 6.97 (dd, J = 1.8, 7.5 Hz, 1H), 7.06 (br, NH, 1H), 7.19 (t, J = 8.1 Hz, 1H), 7.35 (t, J = 2.4 Hz, 1H), 7.75 (d, J = 3.0 Hz, 1H); 19F NMR (282 MHz, CDCl3): δ −168.59; LCMS: ret. time: 10.09 min.; purity: 92.98%; MS (m/e): 344.32 (MH+). | + | | | |
| 1109 | N4-Cyclobutyl-N2-[3-(4-ethoxycarbonylpiperazino)phenyl]-5-fluoro-2,4-pyrimidinediamine | 1H NMR (CDCl3): δ 1.29 (t, J = 6.9 Hz, 3H), 1.71–2.02 (m, 4H), 2.41–2.51 (m, 2H), 3.18 (t, J = 5.1 Hz, 4H), 3.64 (t, J = 5.1 Hz, 4H), 4.17 (q, J = 6.9 Hz, 2H), 4.59 (m, J = 8.1 Hz, 1H), 5.16 (d, J = 7.8 Hz, 1H), 6.58 (dd, J = 2.4, 8.1 Hz, 1H), 6.97 (dd, J = 1.8, 8.1 Hz, 1H), 7.09 (br, NH, 1H), 7.18 (t, J = 8.1 Hz, 1H), 7.37 (t, J = 2.1 Hz, 1H), 7.74 (d, J = 2.7 Hz, 1H); 19F NMR (282 MHz, CDCl3): δ −168.46; LCMS: ret. time: 10.05 min.; purity: 89.70%; MS (m/e): 415.32 (MH+). | + | | − | |
| 1110 | N4-Cyclobutyl-5-fluoro-N2-[4-(4-methylpiperazino)phenyl]-2,4-pyrimidinediamine | 1H NMR (CDCl3): δ 1.65–1.74 (m, 2H), 1.85–1.95 (m, 2H), 2.19–2.33 (m, 2H), 2.71 (s, 3H), 3.15 (t, J = 4.8 Hz, 4H), 3.32 (t, J = 4.8 Hz, 4H), 4.36 (m, J = 8.1 Hz, 1H), 6.80 (d, J = 9.0 Hz, 2H), 7.36 (d, J = 9.3 Hz, 2H), 7.55 (d, J = 4.2 Hz, 1H); 19F NMR (282 MHz, CDCl3): δ −167.73; LCMS: ret. time: 6.03 min.; purity: 90.91%; MS (m/e): 357.33 (MH+). | + | | − | |
| 1111 | N4-Cyclobutyl-N2-[4-(4-ethoxycarbonylpiperazinophenyl]-5-fluoro-2,4-pyrimidinediamine | 1H NMR (CDCl3): δ 1.31 (t, 3H), 1.50–2.04 (m, 4H), 2.41–2.50 (m, 2H), 3.08 (t, J = 4.8 Hz, 4H), 3.64 (t, J = 5.1 Hz, 4H), 4.17 (q, 2H), 4.52 (m, J = 7.8 Hz, 1H), 5.18 (d, J = 6.6 Hz, 1H), 6.90 (d, J = 9.0 Hz, 2H), 7.07 (br, 1H), 7.45 (d, J = 9.0 Hz, 2H), 7.70 (d, J = 3.3 Hz, 1H); 19F NMR (282 MHz, CDCl3): δ −168.95; LCMS: ret. time: 10.73 min.; purity: 83.62%; MS (m/e): 415.34 (MH+). | + | | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1112 | N2-[3-(4-Acetylpiperazinophenyl]-N4-(3-cyclopropyl-1H-pyrazol-5-yl)-5-fluoro-2,4-pyrimidinediamine | LCMS: ret. time: 9.04 min.; purity: 87.21%; MS (m/e): 437.32 (MH+). | + | + | + | |
| 1113 | N4-(3-Cyclopropyl-1H-pyrazol-5-yl)-5-fluoro-N2-[4-(4-methylpiperazinophenyl]-2,4-pyrimidinediamine | 1H NMR (CDCl3): δ 0.54-0.64 (m, 2H), 0.76-0.86 (m, 1H), 2.42 (s, 3H), 2.76 (br, 4H), 3.17 (t, J = 4.8 Hz, 4H), 5.90 (br, 1H), 6.82 (d, J = 8.7 Hz, 2H), 7.29 (d, J = 8.7 Hz, 2H), 7.71 (d, J = 3.6 Hz, 1H); 19F NMR (282 MHz, CDCl3): δ –167.69; LCMS: ret. time: 5.97 min.; purity: 76.80%; MS (m/e): 409.22 (MH+). | + | + | – | |
| 1114 | N4-(3-Cyclopropyl-1H-pyrazol-5-yl)-5-fluoro-N2-(3-morpholinophenyl)-2,4-pyrimidinediamine | LCMS: ret. time: 8.57 min.; purity: 88.76%; MS (m/e): 396.24 (MH+). | | + | | |
| 1115 | N4-(3-Cyclopropyl-1H-pyrazol-5-yl)-N2-[3-(4-ethoxycarbonylpiperazinophenyl]-5-fluoro-2,4-pyrimidinediamine | 1H NMR (DMSO-d6): δ 0.67 (m, 2H), 0.88 (m, 2H), 1.19 (t, J = 7.1 Hz, 3H), 1.85 (m, 1H), 3.06 (m, 4H), 3.48 (m, 4H), 4.05 (q, J = 7.1 Hz, 2H), 6.52 (d, J = 8.1 Hz, 1H), 7.07 (m, 1H), 7.20 (m, 2H); LCMS: ret. time: 11.80 min.; purity: 79.43%; MS (m/e): 467.30 (MH+). | + | | + | |
| 1116 | N4-(3-Cyclopropyl-1H-pyrazol-5-yl)-N2-[4-(4-ethoxycarbonylpiperazinophenyl]-5-fluoro-2,4-pyrimidinediamine | 1H NMR (DMSO-d6): δ 0.62 (m, 2H), 0.90 (m, 2H), 1.20 (t, J = 7.2 Hz, 3H), 1.84 (m, J = 3.9 Hz, 1H), 3.08 (br, 4H), 3.44 (br, 4H), 4.05 (q, J = 6.9 Hz, 2H), 6.12 (br, 1H), 6.93 (d, J = 8.7 Hz, 2H), 7.40 (d, J = 8.4 Hz, 2H), 8.02 (d, J = 4.2 Hz, 1H), 9.37 (br, 1H), 10.71 (br, 1H), 11.49 (br, 1H); 19F NMR (282 MHz, DMSO-d6): δ –171.17; LCMS: ret. time: 9.23 min.; purity: 94.89%; MS (m/e): 467.29 (MH+). | + | + | + | |
| 1117 | 2-Chloro-5-fluoro-N4-(3,4-dihydro-2H,4H-5-pyrid[1,4]oxazin-6-yl)-4-pyrimidineamine | 1H NMR (DMSO-d6): δ 3.40 (t, J = 4.5 Hz, 2H), 4.10 (t, J = 4.5 Hz, 2H), 6.92 (d, J = 8.4 Hz, 1H), 7.04 (d, J = 8.1 Hz, 1H), 8.27 (d, J = 3.6 Hz, 1H), 9.80 (br, 1H); 19F NMR (282 MHz, DMSO-d6): δ –152.34; LCMS: ret. time: 9.69 min.; purity: 93.93%; MS (m/e): 282.12 (MH+). | – | | – | |
| 1118 | N4-(1-tert-Butoxycarbonylazetidin-3-yl)-5-fluoro-N2-(4-morpholinophenyl)-2,4-pyrimidinediamine | 1H NMR (CDCl3): δ 1.45 (s, 9H), 3.18 (t, J = 4.8 Hz, 4H), 3.89 (m, 4H), 3.96 (m, 2H), 4.28 (m, 2H), 4.69 (m, 1H), 6.93 (d, J = 9.0 Hz, 2H), 7.36 (d, J = 9.3 Hz, 2H), 7.66 (d, J = 3.6 Hz, 1H); 19F NMR (282 MHz, CDCl3): δ –163.92; LCMS: ret. time: 9.28 min.; purity: 100%; MS (m/e): 445.25 (MH+). | + | | + | |
| 1119 | N2-[4-(4-Acetylpiperazinophenyl]-N4-(1-tert-butoxycarbonylazetidin-3-yl)-5-fluoro-2,4-pyrimidinediamine | 1H NMR (CDCl3): δ 1.46 (s, 9H), 2.16 (s, 3H), 3.15 (p, J = 5.1 Hz, 4H), 3.64 (t, J = 5.1 Hz, 2H), 3.78 (t, J = 5.1 Hz, 2H), 3.91 (dd, J = 5.4, 9.9 Hz, 2H), 4.30 (dd, J = 7.8, 9.6 Hz, 2H), 4.70 (m, 1H), 6.91 (d, J = 9.3 Hz, 2H), 7.38 (d, J = 9.3 Hz, 2H), 7.72 (d, J = 3.6 Hz, 1H); 19F NMR (282 MHz, CDCl3): δ –166.44; LCMS: ret. time: 8.48 min.; purity: 91.50%; MS (m/e): 486.32 (MH+). | – | | – | |
| 1120 | N2-[3-(4-Acetylpiperazinophenyl]-N4-(1-tert-butoxycarbonylazetidin-3-yl)-5-fluoro-2,4-pyrimidinediamine | 1H NMR (CDCl3): δ 1.45 (s, 9H), 2.16 (s, 3H), 3.21 (m, 4H), 3.64 (m, 2H), 3.78 (m, 2H), 3.99 (dd, J = 4.8, 9.0 Hz, 2H), 4.30 (dd, J = 7.8, 9.3 Hz, 2H), 4.74 (m, 1H), 6.75 (d, J = 5.1 Hz, 1H), 6.90 (d, J = 8.7 Hz, 1H), 7.19 (d, J = 9.3 Hz, 2H), 7.26 (m, 1H), 7.69 (d, J = 4.2 Hz, 1H); 19F NMR (282 MHz, CDCl3): δ –162.80; LCMS: ret. time: 11.04 min.; purity: 93.28%; MS (m/e): 486.31 (MH+). | – | | – | |
| 1121 | N4-(3-Cyclopropyl-1H-pyrazol-5-yl)-5-fluoro-N2-(4-morpholinophenyl)-2,4-pyrimidinediamine | LCMS: ret. time: 7.80 min.; purity: 96.17%; MS (m/e): 396.22 (MH+). | + | + | | |
| 1122 | N4-(1-tert-Butoxycarbonylazetidin-3-yl)-N2-(4-ethoxycarbonylpiperazinophenyl]-5-fluoro-2,4-pyrimidinediamine | LCMS: ret. time: 10.44 min.; purity: 82.19%; MS (m/e): 516.26 (MH+). | + | | – | |
| 1123 | N4-(Azetidin-3-yl)-5-fluoro-N2-(4-morpholinophenyl)-2,4-pyrimidinediamine | LCMS: ret. time: 2.12 min.; purity: 88.18%; MS (m/e): 345.21 (MH+). | – | | – | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1124 | N2-[4-(4-Acetylpiperazinophenyl]-N4-(azetidin-3-yl)-5-fluoro-2,4-pyrimidinediamine | LCMS: ret. time: 2.33 min.; purity: 92.29%; MS (m/e): 386.25 (MH+). | − | | − | |
| 1125 | N4-(Azetidin-3-yl)-N2-[4-(4-ethoxycarbonylpiperazino)phenyl]-5-fluoro-2,4-pyrimidinediamine | LCMS: ret. time: 7.44 min.; purity: 85.69%; MS (m/e): 416 (MH+). | − | | − | |
| 1126 | N4-(Azetidin-3-yl)-5-fluoro-N2-(3-morpholinophenyl)-2,4-pyrimidinediamine | LCMS: ret. time: 2.85 min.; purity: 100%; MS (m/e): 345.24 (MH+). | + | | + | |
| 1127 | N2-[3-(4-Acetylpiperazinophenyl]-N4-(azetidin-3-yl)-5-fluoro-2,4-pyrimidinediamine | LCMS: ret. time: 3.10 min.; purity: 88.30%; MS (m/e): 386.28 (MH+). | | | | |
| 1128 | N4-(3,4-Dihydro-2H,4H-5-pyrid[1,4]oxazin-6-yl)-5-fluoro-N2-(4-morpholinophenyl)-2,4-pyrimidinediamine | 1H NMR (DMSO-d6): δ 3.00 (t, J = 4.8 Hz, 4H), 3.38 (t, J = 4.8 Hz, 4H), 4.08 (t, J = 4.2 Hz, 2H), 6.50 (br, 1H), 6.82 (d, J = 9.0 Hz, 2H), 6.93 (d, J = 8.1 Hz, 1H), 7.20 (d, J = 8.1 Hz, 1H), 7.48 (d, J = 9.3 Hz, 2H), 7.99 (d, J = 3.6 Hz, 1H), 8.65 (br, 1H), 8.92 (br, 1H); 19F NMR (282 MHz, DMSO-d6): δ −164.78; LCMS: ret. time: 8.12 min.; purity: 99.30%; MS (m/e): 424.25 (MH+). | | + | − | |
| 1129 | N4-(1-tert-Butoxycarbonylazetidin-3-yl)-N2-[3-(4-ethoxycarbonylpiperazino)phenyl]-5-fluoro-2,4-pyrimidinediamine | LCMS: ret. time: 11.35 min.; purity: 86.05%; MS (m/e): 516.32 (MH+). | − | | | |
| 1130 | N4-(Azetidin-3-yl)-N2-[3-(4-ethoxycarbonylpiperazino)phenyl]-5-fluoro-2,4-pyrimidinediamine | LCMS: ret. time: 8.39 min.; purity: 96.94%; MS (m/e): 416 (MH+). | − | | | |
| 1131 | N4-(Azetidin-3-yl)-5-fluoro-N2-[4-(4-methylpiperazino)phenyl]-2,4-pyrimidinediamine | LCMS: ret. time: 1.20 min.; purity: 96.44%; MS (m/e): 358.24 (MH+). | | | | |
| 1132 | N4-(3,4-Dihydro-2H,4H-5-pyrid[1,4]oxazin-6-yl)-5-fluoro-N2-[3-(oxazol-5-yl)phenyl]-2,4-pyrimidinediamine | 1H NMR (DMSO-d6): δ 3.38 (t, J = 4.5 Hz, 2H), 4.08 (t, J = 4.5 Hz, 2H), 6.52 (br, 1H), 6.78 (d, J = 8.1 Hz, 1H), 7.27 (m, 3H), 7.50 (s, 1H), 7.67 (d, J = 8.1 Hz, 1H), 8.01 (s, 1H), 8.08 (d, J = 3.6 Hz, 1H), 8.38 (s, 1H), 8.82 (s, 1H), 9.35 (s, 1H); 19F NMR (282 MHz, DMSO-d6): δ −162.94; LCMS: ret. time: 9.32 min.; purity: 100%; MS (m/e): 406.18 (MH+). | | + | | |
| 1133 | 2-Chloro-N4-cyclobutyl-5-fluoro-N4-methyl-4-pyrimidineamine | 1H NMR (CDCl3): δ 1.68-1.76 (m, 2H), 2.17-2.25 (m, 4H), 3.14 (d, J = 3.0 Hz, 3H), 4.79 (m, J = 8.4 Hz, 1H), 7.85 (d, J = 6.0 Hz, 1H); 19F NMR (282 MHz, CDCl3): δ −150.50; LCMS: ret. time: 13.83 min.; purity: 96.47%; MS (m/e): 216.10 (MH+). | − | | | |
| 1134 | N2-[4-(4-Acetylpiperazinophenyl]-N4-(3,4-dihydro-2H,4H-5-pyrid[1,4]oxazin-6-yl)-5-fluoro-2,4-pyrimidinediamine | 1H NMR (DMSO-d6): δ 2.03 (s, 3H), 2.97 (t, J = 5.1 Hz, 2H), 3.03 (t, J = 5.1 Hz, 2H), 3.39 (t, 2H), 3.56 (t, 4H), 4.08 (t, J = 4.2 Hz, 2H), 6.51 (s, 1H), 6.84 (d, J = 9.0 Hz, 2H), 6.93 (d, J = 8.4 Hz, 1H), 7.19 (d, J = 8.1 Hz, 1H), 7.49 (d, J = 9.0 Hz, 2H), 7.99 (d, J = 3.6 Hz, 1H), 8.67 (br, 1H), 8.95 (br, 1H); 19F NMR (282 MHz, DMSO-d6): δ −164.68; LCMS: ret. time: 7.60 min.; purity: 99.34%; MS (m/e): 465.30 (MH+). | + | + | | |
| 1135 | N4-(3,4-Dihydro-2H,4H-5-pyrid[1,4]oxazin-6-yl)-N2-[4-(4-ethoxycarbonylpiperazino)phenyl]-5-fluoro-2,4-pyrimidinediamine | 1H NMR (DMSO-d6): δ 1.19 (t, J = 7.2 Hz, 3H), 2.99 (t, J = 5.4 Hz, 4H), 3.39 (t, 2H), 3.49 (t, 4H), 4.04 (q, J = 7.2 Hz, 2H), 4.08 (t, J = 4.8 Hz, 2H), 6.51 (s, 1H), 6.84 (d, J = 9.3 Hz, 2H), 6.93 (d, J = 8.4 Hz, 1H), 7.19 (d, J = 8.4 Hz, 1H), 7.49 (d, J = 9.0 Hz, 2H), 7.99 (d, J = 3.6 Hz, 1H), 8.68 (br, 1H), 8.95 (br, 1H); 19F NMR (282 MHz, DMSO-d6): δ −164.66; LCMS: ret. time: 9.61 min.; purity: 94.88%; MS (m/e): 495.31 (MH+). | + | + | | |
| 1136 | N4-(3,4-Dihydro-2H,4H-5-pyrid[1,4]oxazin-6-yl)-5-fluoro-N2-(3-morpholinophenyl)-2,4-pyrimidinediamine | 1H NMR (DMSO-d6): δ 2.99 (t, J = 5.1 Hz, 4H), 3.39 (t, 2H), 3.69 (t, J = 4.8 Hz, 4H), 4.08 (t, J = 4.2 Hz, 2H), 6.50 (m, 2H), 6.91 (d, J = 8.4 Hz, 1H), 7.04 (t, J = 8.1 Hz, 1H), 7.19 (m, 3H), 8.04 (d, J = 3.6 Hz, 1H), | + | + | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1137 | N2-[3-(4-Acetylpiperazinophenyl]-N4-(3,4-dihydro-2H,4H-5-pyrid[1,4]oxazin-6-yl)-5-fluoro-2,4-pyrimidinediamine | 8.74 (s, 1H), 9.02 (s, 1H); 19F NMR (282 MHz, DMSO-d6): δ −163.64; LCMS: ret. time: 9.03 min.; purity: 98.67%; MS (m/e): 424.26 (MH+). 1H NMR (DMSO-d6): δ 2.03 (s, 3H), 2.98 (t, J = 4.8 Hz, 2H), 3.05 (t, J = 4.8 Hz, 2H), 3.39 (t, 2H), 3.53 (t, J = 5.4 Hz, 4H), 4.08 (t, 2H), 6.50 (m, 2H), 6.91 (d, J = 8.4 Hz, 1H), 7.04 (t, J = 8.4 Hz, 1H), 7.21 (m, 3H), 8.04 (d, J = 3.6 Hz, 1H), 8.75 (s, 1H), 9.03 (s, 1H); 19F NMR (282 MHz, DMSO-d6): δ −163.60; LCMS: ret. time: 8.22 min.; purity: 100%; MS (m/e):465.25 (MH+). | + | + |  |  |
| 1138 | N4-(3,4-Dihydro-2H,4H-5-pyrid[1,4]oxazin-6-yl)-N2-[3-(4-ethoxycarbonylpiperazinophenyl)-5-fluoro-2,4-pyrimidinediamine | 1H NMR (DMSO-d6): δ 1.20 (t, J = 7.2 Hz, 3H), 3.01 (t, J = 4.8 Hz, 4H), 3.41 (t, 2H), 3.46 (t, J = 4.8 Hz, 4H), 4.08 (t, 4H), 6.50 (m, 2H), 6.91 (d, J = 8.4 Hz, 1H), 7.04 (t, J = 8.4 Hz, 1H), 7.19 (d, J = 8.1 Hz, 2H), 7.25 (t, 1H), 8.04 (d, J = 3.6 Hz, 1H), 8.73 (s, 1H), 9.02 (s, 1H); 19F NMR (282 MHz, DMSO-d6): δ −163.61; LCMS: ret. time: 10.46 min.; purity: 98.68%; MS (m/e): 495.25 (MH+). | + | + |  |  |
| 1139 | N4-Cyclobutyl-5-fluoro-N4-methyl-N2-(4-morpholinophenyl)-2,4-pyrimidinediamine | 1H NMR (DMSO-d6): δ 1.56-1.69 (m, 2H), 2.07-2.27 (m, 4H), 3.07 (t, J = 4.5 Hz, 4H), 3.12 (d, J = 3.0 Hz, 3H), 3.73 (t, J = 4.5 Hz, 4H), 4.76 (m, J = 8.4 Hz, 1H), 6.92 (d, J = 9.0 Hz, 2H), 7.42 (d, J = 8.7 Hz, 2H), 7.97 (d, J = 7.2 Hz, 1H), 9.36 (br, 1H); 19F NMR (282 MHz, DMSO-d6): δ −157.25; LCMS: ret. time: 9.50 min.; purity: 100%; MS (m/e): 358.23 (MH+). | + | + | − |  |
| 1140 | N2-[4-(4-Acetylpiperazinophenyl)-N4-cyclobutyl-5-fluoro-N4-methyl-2,4-pyrimidinediamine | 1H NMR (DMSO-d6): δ 1.59-1.69 (m, 2H), 2.03 (s, 3H), 2.10-2.27 (m, 4H), 3.03 (t, J = 4.5 Hz, 2H), 3.11 (d, J = 3.0 Hz, 5H), 3.56 (t, 4H), 4.76 (m, J = 7.5 Hz, 1H), 6.93 (d, J = 9.0 Hz, 2H), 7.45 (d, J = 9.0 Hz, 2H), 7.96 (d, J = 7.2 Hz, 1H), 9.26 (br, 1H); LCMS: ret. time: 8.75 min.; purity: 100%; MS (m/e): 399.28 (MH+). | + | + | − |  |
| 1141 | N4-(3,4-Dihydro-2H,4H-5-pyrid[1,4]oxazin-6-yl)-5-fluoro-N2-[4-(4-methylpiperazinophenyl)]-2,4-pyrimidinediamine | 1H NMR (DMSO-d6): δ 2.23 (s, 3H), 3.03 (t, 4H), 3.29 (m 4H), 3.38 (t, 2H), 4.08 (t, J = 4.5 Hz, 2H), 6.50 (br, 1H), 6.81 (d, J = 8.7 Hz, 2H), 6.92 (d, J = 8.4 Hz, 2H), 7.20 (d, J = 8.1 Hz, 1H), 7.46 (d, J = 9.0 Hz, 2H), 7.98 (d, J = 3.6 Hz, 1H), 8.64 (br, 1H), 8.90 (br, 1H); 19F NMR (282 MHz, DMSO-d6): δ −164.86; LCMS: ret. time: 5.58 min.; purity: 100%; MS (m/e): 437 (MH+). | + | + | − |  |
| 1142 | N4-(3,4-Dihydro-2H,4H-5-pyrid[1,4]oxazin-6-yl)-5-fluoro-N2-[3-(4-methylpiperazinophenyl)]-2,4-pyrimidinediamine | 1H NMR (DMSO-d6): δ 2.20 (s, 3H), 2.41 (t, 4H), 3.03 (t, 4H), 3.38 (t, 2H), 4.08 (t, J = 4.8 Hz, 2H), 6.50 (m, 2H), 6.91 (d, J = 7.8 Hz, 1H), 7.02 (t, J = 7.8 Hz, 1H), 7.20 (m, 3H), 8.03 (d, J = 3.6 Hz, 1H), 8.72 (s, 1H), 8.99 (s, 1H); 19F NMR (282 MHz, DMSO-d6): δ −163.72; LCMS: ret. time: 6.32 min.; purity: 99.99%; MS (m/e): 437 (MH+). | + | + | − |  |
| 1143 | N4-(3,4-Dihydro-2H,4H-5-pyrid[1,4]oxazin-6-yl)-5-fluoro-N2-[3-(oxazol-2-yl)phenyl]-2,4-pyrimidinediamine | 1H NMR (DMSO-d6): δ 3.53 (t, J = 4.2 Hz, 2H), 4.16 (t, J = 4.2 Hz, 2H), 6.84 (d, J = 8.7 Hz, 1H), 7.24 (d, J = 1.2, 8.1 Hz, 1H), 7.35 (s, 1H), 7.40 (t, J = 7.8 Hz, 1H), 7.56 (dt, J = 3.3 Hz, 1H), 8.18 (s, 1H), 8.32 (d, J = 3.3 Hz, 1H), 8.44 (s, 1H), 10.35 (br, 2H); 19F NMR (282 MHz, DMSO-d6): δ −161.96; LCMS: ret. time: 9.54 min.; purity: 98.01%; MS (m/e): 406.18 (MH+). | + | + | − |  |
| 1144 | N4-(3-Cyclopropyl-1H-pyrazol-5-yl)-5-fluoro-N2-[3-(oxazol-2-yl)phenyl]-2,4-pyrimidinediamine | 1H NMR (DMSO-d6): δ 0.61-0.66 (m, 2H), 0.86 (m, 2H), 1.81 (m, 1H), 6.41 (br, 1H), 7.35 (m, 2H), 7.52 (d, J = 7.5 Hz, 1H), 7.86 (s, 1H), 8.04 (s, 1H), 8.19 (m, 2H), 9.34 (s, 1H), 9.60 (s, 1H); 19F NMR (282 MHz, DMSO-d6): δ −163.42; LCMS: ret. time: 9.50 min.; purity: 98.57%; MS (m/e): 378.20 (MH+). | + | + | − | + |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1145 | N4-(3,4-Dihydro-2H,4H-5-pyrid[1,4]oxazin-6-yl)-5-fluoro-N2-(3,4,5-trimethoxyphenyl)-2,4-pyrimidinediamine | 1H NMR (DMSO-d6): δ 3.49 (t, 2H), 3.61 (s, 3H), 3.69 (s, 6H), 4.14 (t, J = 4.5 Hz, 2H), 6.94 (d, J = 7.8 Hz, 1H), 7.07 (s, 2H), 7.14 (d, 1H), 8.20 (d, J = 3.6 Hz, 1H), 9.75 (s, 1H); LCMS: ret. time: 8.80 min.; purity: 100%; MS (m/e): 429.45 (MH+). | + | | − | + |
| 1146 | N2-(3-Chloro-4-methoxyphenyl)-N4-(3,4-dihydro-2H,4H-5-pyrid[1,4]oxazin-6-yl)-5-fluoro-2,4-pyrimidinediamine | 1H NMR (DMSO-d6): δ 3.39 (s, 2H), 3.78 (s, 3H), 4.08 (t, J = 3.9 Hz, 2H), 6.54 (br, 1H), 6.95 (d, J = 8.4 Hz, 1H), 7.00 (d, J = 8.7 Hz, 1H), 7.13 (d, J = 8.4 Hz, 1H), 7.46 (dd, J = 2.4, 9.0 Hz, 1H), 7.84 (d, J = 2.4 Hz, 1H), 8.04 (d, J = 3.3 Hz, 1H), 8.80 (s, 1H), 9.16 (s, 1H); 19F NMR (282 MHz, DMSO-d6): δ −163.72; LCMS: ret. time: 10.31 min.; purity: 99.90%; MS (m/e): 403.06 (MH+). | + | + | − | + |
| 1147 | N4-Cyclobutyl-5-fluoro-N4-methyl-N2-[4-(4-methylpiperazino)phenyl]-2,4-pyrimidinediamine | 1H NMR (DMSO-d6): δ 1.56-1.68 (m, 2H), 2.10-2.26 (m, 4H), 2.21 (s, 3H), 2.44 (t, 4H), 3.02 (t, J = 4.8 Hz, 4H), 3.05 (d, J = 2.7 Hz, 3H), 4.74 (m, J = 7.8 Hz, 1H), 6.82 (d, J = 9.0 Hz, 2H), 7.49 (d, J = 8.7 Hz, 2H), 7.88 (d, J = 6.6 Hz, 1H), 8.79 (br, 1H); 19F NMR (282 MHz, DMSO-d6): δ −159.83; LCMS: ret. time: 6.35 min.; purity: 95.87%; MS (m/e): 371.21 (MH+). | + | + | − | |
| 1148 | N4-Cyclobutyl-N2-[4-(4-ethoxycarbonylpiperazino)phenyl]-5-fluoro-N4-methyl-2,4-pyrimidinediamine | 1H NMR (DMSO-d6): δ 1.19 (t, J = 7.2 Hz, 3H), 1.56-1.69 (m, 2H), 2.07-2.27 (m, 4H), 3.06 (m, J = 4.8 Hz, 4H), 3.11 (s, 3H), 3.50 (t, 4H), 4.05 (q, J = 7.2 Hz, 2H), 4.76 (m, J = 8.4 Hz, 1H), 6.93 (d, J = 9.0 Hz, 2H), 7.43 (d, J = 8.7 Hz, 2H), 7.97 (d, J = 7.5 Hz, 1H), 9.33 (br, 1H); LCMS: ret. time: 11.06 min.; purity: 96.72%; MS (m/e): 429.45 (MH+). | + | + | − | |
| 1149 | N4-Cyclobutyl-5-fluoro-N4-methyl-N2-(3-morpholinophenyl)-2,4-pyrimidinediamine | 1H NMR (DMSO-d6): δ 1.57-1.70 (m, 2H), 2.13-2.24 (m, 4H), 3.07 (t, J = 4.8 Hz, 4H), 3.11 (d, J = 3.3 Hz, 3H), 3.73 (t, J = 4.5 Hz, 4H), 4.78 (m, J = 8.7 Hz, 1H), 6.57 (m, 1H), 7.08 (m, 2H), 7.24 (m, 1H), 7.98 (d, J = 6.9 Hz, 1H), 9.19 (br, 1H); LCMS: ret. time: 10.46 min.; purity: 97.98%; MS (m/e): 358.34 (MH+). | + | + | − | |
| 1150 | N2-[3-(4-Acetylpiperazino)phenyl]-N4-cyclobutyl-5-fluoro-N4-methyl-2,4-pyrimidinediamine | 1H NMR (CDCl3): δ 1.66-1.78 (m, 2H), 2.15 (s, 3H), 2.22 (m, 4H), 3.17 (d, J = 2.7 Hz, 3H), 3.22 (m, 4H), 3.62 (t, J = 4.8 Hz, 2H), 3.77 (t, J = 5.1 Hz, 2H), 4.85 (m, J = 8.4 Hz, 1H), 6.58 (dd, J = 2.4, 8.1 Hz, 1H), 7.04 (d, J = 8.4 Hz, 1H), 7.19 (t, J = 8.1 Hz, 1H), 7.24 (d, J = 8.1 Hz, 1H), 7.53 (br, 1H), 7.75 (d, J = 6.9 Hz, 1H); 19F NMR (282 MHz, CDCl3): −157.20; LCMS: ret. time: 9.37 min.; purity: 87.43%; MS (m/e): 399.56 (MH+). | + | + | − | |
| 1151 | N4-Cyclobutyl-5-fluoro-N4-methyl-N2-[3-(4-methylpiperazino)phenyl]-2,4-pyrimidinediamine | 1H NMR (CDCl3): δ 1.63-1.77 (m, 2H), 2.21 (m, 4H), 2.45 (s, 3H), 2.72 (t, J = 4.8 Hz, 4H), 3.13 (d, J = 3.9 Hz, 3H), 3.32 (t, J = 4.8 Hz, 4H), 4.84 (m, J = 8.7 Hz, 1H), 6.56 (dd, J = 2.4, 8.1 Hz, 1H), 6.82 (br, 1H), 7.00 (d, J = 8.1 Hz, 1H), 7.17 (t, J = 7.8 Hz, 1H), 7.25 (d, J = 1.5 Hz, 1H), 7.80 (d, J = 6.6 Hz, 1H); 19F NMR (282 MHz, CDCl3): −158.30; LCMS: ret. time: 7.27 min.; purity: 87.72%; MS (m/e): 371.20 (MH+). | + | + | − | |
| 1152 | N4-Cyclobutyl-N2-[3-(4-ethoxycarbonylpiperazino)phenyl]-5-fluoro-N4-methyl-2,4-pyrimidinediamine | 1H NMR (DMSO-d6): δ 1.19 (t, J = 7.2 Hz, 3H), 1.60-1.70 (m, 2H), 2.13-2.28 (m, 4H), 3.08 (t, J = 5.1 Hz, 4H), 3.12 (d, J = 3.3 Hz, 3H), 3.50 (t, 4H), 4.05 (q, J = 7.2 Hz, 2H), 4.79 (m, J = 9.0 Hz, 1H), 6.59 (d, J = 6.9 Hz, 1H), 7.09 (m, 2H), 7.27 (s, 1H), 7.99 (d, J = 6.9 Hz, 1H), 9.27 (br, 1H); LCMS: ret. time: 11.92 min.; purity: 99.18%; MS (m/e): 429.22 (MH+). | + | + | − | |
| 1153 | N2-(2-Aminocarbonyl-5-benzoxy-4-methoxyphenyl)-N4-cyclobutyl-5-fluoro-N4-methyl-2,4-pyrimidinediamine | 1H NMR (DMSO-d6): δ 1.69-1.78 (m, 2H), 2.28 (m, 4H), 3.36 (d, J = 3.3 Hz, 3H), 3.90 (s, 3H), 4.94 (m, 1H), 5.30 (s, 2H), 7.12 (s, 1H), | − | | − | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1154 | N2-(4-Benzamidophenyl)-N4-cyclobutyl-5-fluoro-2,4-pyrimidinediamine | 7.35-7.48 (m, 6H), 9.04 (d, J = 9.0 Hz, 1H); LCMS: ret. time: 11.25 min.; purity: 98.01%; MS (m/e): 435.22 (M − 16). | + | — | — | — |
| 1155 | N4-Cyclopentyl-5-fluoro-N2-(4-morpholinophenyl)-2,4-pyrimidinediamine | 1H NMR (DMSO-d6): δ 1.62-1.74 (m, 2H), 2.02-2.15 (m, 2H), 2.23-2.31 (m, 2H), 4.50 (m, J = 8.1 Hz, 1H), 7.46-7.68 (m, 8H), 7.84 (d, J = 3.6 Hz, 1H), 7.92 (td, J = 1.2, 6.6 Hz, 2H), 8.99 (s, 1H), 10.07 (s, 1H); 19F NMR (282 MHz, DMSO-d6): δ −167.01; LCMS: ret. time: 9.59 min.; purity: 94.19%; MS (m/e): 378.50 (MH+). | + | — | — | — |
| 1156 | N2-[4-(4-Acetylpiperazinophenyl]-N4-cyclopentyl-5-fluoro-2,4-pyrimidinediamine | 1H NMR (DMSO-d6): δ 1.54 (m, 4H), 1.70 (m, 2H), 1.94 (m, 2H), 2.98 (t, J = 4.8 Hz, 4H), 3.70 (t, J = 4.8 Hz, 4H), 4.30 (q, J = 6.9 Hz, 1H), 6.80 (d, J = 9.0 Hz, 2H), 7.22 (d, J = 6.9 Hz, 1H), 7.55 (d, J = 9.3 Hz, 2H), 7.76 (d, J = 3.6 Hz, 1H), 8.74 (br, 1H); 19F NMR (282 MHz, DMSO-d6): δ −167.62; LCMS: ret. time: 8.98 min.; purity: 99.38%; MS (m/e): 358.18 (MH+). | + | — | — | — |
| 1157 | N4-Cyclopentyl-5-fluoro-N2-[4-(4-methylpiperazino)phenyl]-2,4-pyrimidinediamine | 1H NMR (DMSO-d6): δ 1.54 (m, 4H), 1.70 (m, 2H), 1.93 (m, 2H), 2.02 (s, 3H), 2.94 (t, J = 4.8 Hz, 2H), 3.01 (t, J = 5.1 Hz, 2H), 3.54 (t, 4H), 4.30 (q, J = 6.9 Hz, 1H), 6.83 (d, J = 8.7 Hz, 2H), 7.24 (d, J = 7.2 Hz, 1H), 7.56 (d, J = 9.0 Hz, 2H), 7.76 (d, J = 3.9 Hz, 1H), 8.76 (br, 1H); 19F NMR (282 MHz, DMSO-d6): δ −167.53; LCMS: ret. time: 8.28 min.; purity: 98.08%; MS (m/e): 399.20 (MH+). | + | — | — | — |
| 1158 | N4-Cyclopentyl-5-fluoro-N2-(3-morpholinophenyl)-2,4-pyrimidinediamine | 1H NMR (DMSO-d6): δ 1.54 (m, 4H), 1.70 (m, 2H), 1.93 (m, 2H), 2.21 (s, 3H), 2.44 (t, 4H), 3.01 (t, 4H), 4.30 (q, J = 6.3 Hz, 1H), 6.79 (d, J = 8.7 Hz, 2H), 7.22 (d, J = 6.3 Hz, 1H), 7.53 (d, J = 9.0 Hz, 2H), 7.76 (d, J = 3.0 Hz, 1H), 8.72 (br, 1H); 19F NMR (282 MHz, DMSO-d6): δ −167.68; LCMS: ret. time: 5.53 min.; purity: 83.38%; MS (m/e): 371.08 (MH+). | + | — | — | — |
| 1159 | N2-[3-(4-Acetylpiperazinophenyl]-N4-cyclopentyl-5-fluoro-2,4-pyrimidinediamine | 1H NMR (DMSO-d6): δ 1.52 (m, 4H), 1.71 (m, 2H), 1.93 (m, 2H), 3.03 (t, J = 4.8 Hz, 4H), 3.72 (t, J = 4.8 Hz, 4H), 4.36 (m, 1H), 6.45 (d, J = 9.6 Hz, 1H), 7.02 (t, J = 7.8 Hz, 1H), 7.13 (d, J = 8.1 Hz, 1H), 7.31 (d, J = 7.2 Hz, 1H), 7.42 (s, 1H), 7.80 (d, J = 3.6 Hz, 1H), 8.84 (br, 1H); 19F NMR (282 MHz, DMSO-d6): δ −166.77; LCMS: ret. time: 9.54 min.; purity: 90.50%; MS (m/e): 358.20 (MH+). | + | — | — | — |
| 1160 | N4-Cyclopentyl-5-fluoro-N2-[3-(4-methylpiperazino)phenyl]-2,4-pyrimidinediamine | 1H NMR (DMSO-d6): δ 1.53 (m, 4H), 1.71 (m, 2H), 1.94 (m, 2H), 2.03 (s, 3H), 3.02 (t, J = 5.1 Hz, 2H), 3.08 (t, J = 4.8 Hz, 2H), 3.55 (t, 4H), 4.36 (q, J = 6.6 Hz, 1H), 6.47 (d, J = 7.8 Hz, 1H), 7.03 (t, J = 8.1 Hz, 1H), 7.14 (d, J = 7.8 Hz, 1H), 7.30 (d, J = 7.2 Hz, 1H), 7.44 (s, 1H), 7.80 (d, J = 3.6 Hz, 1H), 8.84 (br, 1H); 19F NMR (282 MHz, DMSO-d6): δ −166.76; LCMS: ret. time: 8.60 min.; purity: 97.49%; MS (m/e): 399.48 (MH+). | + | — | — | — |
| 1161 | N4-Cyclopentyl-N2-[3-(4-ethoxycarbonyl)piperazinophenyl]-5-fluoro-2,4-pyrimidinediamine | LCMS: ret. time: 6.49 min.; purity: 79.17%; MS (m/e): 371.23 (MH+). | + | — | — | — |
| 1162 | N4-Cyclohexyl-5-fluoro-N2-(4-morpholinophenyl)-2,4-pyrimidinediamine | LCMS: ret. time: 10.76 min.; purity: 77.07%; MS (m/e): 429.50 (MH+). | + | — | — | — |
| | | 1H NMR (DMSO-d6): δ 1.14 (m, 1H), 1.31 (m, 4H), 1.64 (d, 1H), 1.75 (m, 2H), 1.90 (m, 2H), 2.98 (t, J = 4.8 Hz, 4H), 3.71 (t, J = 4.8 Hz, 4H), 3.86 (m, 1H), 6.80 (d, J = 9.3 Hz, 2H), 7.14 (d, J = 8.4 Hz, 1H), 7.55 (d, J = 9.0 Hz, 2H), 7.76 (d, J = 3.9 Hz, 1H), 8.74 (br, 1H); 19F NMR (282 MHz, | | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1163 | N2-[4-(4-Acetylpiperazinophenyl]-N4-cyclohexyl-5-fluoro-2,4-pyrimidinediamine | DMSO-d6): δ -167.70; LCMS: ret. time: 9.48 min.; purity: 100%; MS (m/e): 372.45 (MH+). | + | - | - | |
| 1164 | N4-Cyclohexyl-5-fluoro-N2-[4-(4-methylpiperazino)phenyl]-2,4-pyrimidinediamine | 1H NMR (DMSO-d6): δ 1.31 (m, 5H), 1.64 (d, 1H), 1.75 (m, 2H), 1.90 (m, 2H), 2.02 (s, 3H), 2.94 (t, J = 4.8 Hz, 2H), 3.01 (t, J = 5.1 Hz, 2H), 3.55 (m, 4H), 3.86 (m, 1H), 6.82 (d, J = 9.0 Hz, 2H), 7.12 (d, J = 7.5 Hz, 1H), 7.55 (d, J = 8.7 Hz, 2H), 7.76 (d, J = 3.9 Hz, 1H), 8.75 (br, 1H), 19F NMR (282 MHz, DMSO-d6): δ -167.64; LCMS: ret. time: 8.62 min.; purity: 99.89%; MS (m/e): 413.44 (MH+). | + | | | + |
| 1165 | N4-Cyclohexyl-N2-[4-(4-ethoxycarbonyl)piperazino)phenyl]-5-fluoro-2,4-pyrimidinediamine | 1H NMR (DMSO-d6): δ 1.31 (m, 5H), 1.64 (d, 1H), 1.75 (m, 2H), 1.90 (m, 2H), 2.21 (s, 3H), 2.46 (t, J = 4.8 Hz, 4H), 3.01 (t, J = 4.8 Hz, 4H), 3.85 (m, 1H), 6.79 (d, J = 9.0 Hz, 2H), 7.12 (d, J = 8.4 Hz, 1H), 7.52 (d, J = 9.0 Hz, 2H), 7.76 (d, J = 3.9 Hz, 1H), 8.72 (br, 1H); 19F NMR (282 MHz, DMSO-d6): δ -167.78; LCMS: ret. time: 6.09 min.; purity: 99.06%; MS (m/e): 385.20 (MH+). | + | | + | |
| 1166 | N4-Cyclohexyl-5-fluoro-N2-(3-morpholinophenyl)-2,4-pyrimidinediamine | 1H NMR (DMSO-d6): δ 1.19 (t, J = 7.2 Hz, 3H), 1.31 (m, 5H), 1.64 (d, 1H), 1.76 (m, 2H), 1.90 (m, 2H), 2.97 (t, J = 4.8 Hz, 4H), 3.48 (t, 4H), 3.86 (m, 1H), 4.04 (q, J = 7.2 Hz, 2H), 6.82 (d, J = 9.0 Hz, 2H), 7.12 (d, J = 6.9 Hz, 1H), 7.55 (m, 2H), 7.76 (d, J = 9.3 Hz, 2H), 7.76 (d, J = 3.9 Hz, 1H), 8.75 (br, 1H); 19F NMR (282 MHz, DMSO-d6): δ -167.63; LCMS: ret. time: 10.75 min.; purity: 98.19%; MS (m/e): 443.19 (MH+). | + | | - | |
| 1167 | N2-[3-(4-Acetylpiperazino)phenyl]-N4-cyclohexyl-5-fluoro-2,4-pyrimidinediamine | 1H NMR (DMSO-d6): δ 1.27 (m, 5H), 1.63 (d, 1H), 1.76 (m, 2H), 1.87 (m, 2H), 3.04 (t, J = 4.8 Hz, 4H), 3.72 (t, J = 4.8 Hz, 4H), 3.90 (m, 1H), 6.46 (dd, J = 2.1, 7.8 Hz, 1H), 7.03 (t, J = 8.4 Hz, 1H), 7.16 (d, J = 7.8 Hz, 1H), 7.24 (m, 2H), 7.80 (d, J = 3.9 Hz, 1H), 8.78 (br, 1H); 19F NMR (282 MHz, DMSO-d6): δ -166.81; LCMS: ret. time: 10.22 min.; purity: 99.24%; MS (m/e): 372.15 (MH+). | + | | - | |
| 1168 | N4-Cyclohexyl-5-fluoro-N2-[3-(4-methylpiperazino)phenyl]-2,4-pyrimidinediamine | 1H NMR (DMSO-d6): δ 1.31 (m, 5H), 1.61 (m, 1H), 1.76 (m, 2H), 1.87 (m, 2H), 2.03 (s, 3H), 3.04 (t, 2H), 3.09 (t, 2H), 3.56 (t, 4H), 3.90 (m, 1H), 6.48 (d, J = 9.0 Hz, 1H), 7.04 (t, J = 8.4 Hz, 1H), 7.17 (d, J = 8.4 Hz, 1H), 7.25 (m, 2H), 7.80 (d, J = 3.6 Hz, 1H), 8.80 (br, 1H); 19F NMR (282 MHz, DMSO-d6): δ -166.78; LCMS: ret. time: 9.31 min.; purity: 93.22%; MS (m/e): 413.19 (MH+). | + | | - | |
| 1169 | N4-Cyclohexyl-N2-[3-(4-ethoxycarbonyl)piperazino)phenyl]-5-fluoro-2,4-pyrimidinediamine | 1H NMR (DMSO-d6): δ 1.14 (m, 1H), 1.31 (m, 4H), 1.63 (d, 1H), 1.76 (m, 2H), 1.86 (m, 2H), 2.26 (s, 3H), 3.09 (t, 4H), 3.32 (t, 4H), 3.88 (m, 1H), 6.45 (d, J = 6.9 Hz, 1H), 7.01 (t, J = 8.1 Hz, 1H), 7.16 (d, J = 7.2 Hz, 1H), 7.24 (m, 2H), 7.80 (d, J = 3.9 Hz, 1H), 8.76 (br, 1H); 19F NMR (282 MHz, DMSO-d6): δ -166.84; LCMS: ret. time: 7.16 min.; purity: 96.05%; MS (m/e): 385.27 (MH+). | + | | - | |
| 1170 | N2-(4-Benzamidophenyl)-N4-cyclopentyl-5-fluoro-2,4-pyrimidinediamine | 1H NMR (DMSO-d6): δ 1.19 (t, J = 6.9 Hz, 3H), 1.31 (m, 5H), 1.62 (d, 1H), 1.76 (m, 2H), 1.87 (m, 2H), 3.05 (t, J = 4.8 Hz, 4H), 3.49 (t, 4H), 3.90 (m, 1H), 4.05 (q, J = 7.2 Hz, 2H), 6.48 (d, J = 4.5 Hz, 1H), 7.03 (t, J = 8.1 Hz, 1H), 7.16 (d, J = 6.6 Hz, 1H), 7.24 (d, J = 8.7 Hz, 1H), 7.28 (s, 1H), 7.80 (d, J = 3.9 Hz, 1H); 19F NMR (282 MHz, DMSO-d6): δ -166.76; LCMS: ret. time: 11.50 min.; purity: 85.32%; MS (m/e): 442.95 (MH+). | + | | - | |
| | | 1H NMR (DMSO-d6): δ 1.57 (m, 4H), 1.72 (m, 2H), 1.96 (m, 2H), 4.32 (q, J = 7.5 Hz, 1H), 7.29 (d, J = 6.3 Hz, 1H), 7.46-7.69 (m, 7H), 7.81 (d, | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1171 | N2-(2-Aminocarbonyl-5-benzoxy-4-methoxyphenyl)-N4-cyclopentyl-5-fluoro-2,4-pyrimidinediamine | J = 3.9 Hz, 1H), 7.92 (d, J = 9.6 Hz, 2H), 8.97 (s, 1H), 10.05 (s, 1H); 19F NMR (282 MHz, DMSO-d6): δ -166.85; LCMS: ret. time: 10.15 min.; purity: 97.75%; MS (m/e): 392.16 (MH+). | + | | | |
| 1172 | N2-[4-(N-Acetyl-N-methylamino)phenyl]-N4-cyclopentyl-5-fluoro-2,4-pyrimidinediamine | 1H NMR (DMSO-d6): δ 1.60 (m, 4H), 1.74 (m, 2H), 1.96 (m, 2H), 3.85 (s, 3H), 4.43 (q, J = 6.9 Hz, 1H), 5.24 (s, 2H), 7.06 (s, 1H), 7.31-7.50 (m, 6H), 8.53 (d, J = 7.2 Hz, 1H), 8.70 (d, J = 6.9 Hz, 1H); 19F NMR (282 MHz, DMSO-d6): δ -155.92; LCMS: ret. time: 11.18 min.; purity: 96.52%; MS (m/e): 435.16 (M − 16). | + | | | |
| 1173 | N4-Cyclopentyl-5-fluoro-N2-[3-(N-2-imidazolin-2-yl)aminophenyl]-2,4-pyrimidinediamine | 1H NMR (DMSO-d6): δ 1.55 (m, 4H), 1.71 (m, 2H), 1.94 (m, 2H), 3.09 (s, 3H), 3.31 (s, 3H), 4.32 (q, J = 7.2 Hz, 1H), 7.13 (d, J = 9.0 Hz, 2H), 7.34 (d, J = 7.2 Hz, 1H), 7.77 (d, J = 8.7 Hz, 2H), 7.83 (d, J = 3.9 Hz, 1H), 9.14 (s, 1H); 19F NMR (282 MHz, DMSO-d6): δ -166.12; LCMS: ret. time: 8.34 min.; purity: 97.77%; MS (m/e): 344.13 (MH+). | − | | − | |
| 1174 | N2-(4-Benzamidophenyl)-N4-cyclohexyl-5-fluoro-2,4-pyrimidinediamine | 1H NMR (DMSO-d6): δ 1.55 (m, 4H), 1.71 (m, 2H), 1.93 (m, 2H), 3.62 (s, 4H), 4.31 (q, J = 6.6 Hz, 1H), 6.71 (d, J = 7.8 Hz, 1H), 7.25 (t, J = 7.8 Hz, 1H), 7.40 (d, J = 7.2 Hz, 1H), 7.53 (d, J = 7.5 Hz, 1H), 7.84 (s, 2H), 8.22 (s, 1H), 9.23 (s, 1H), 10.54 (br, 1H); 19F NMR (282 MHz, DMSO-d6): δ -165.78; LCMS: ret. time: 5.71 min.; purity: 92.06%; MS (m/e): 356.17 (MH+). | − | + | − | + |
| 1175 | N2-(2-Aminocarbonyl-5-benzoxy-4-methoxyphenyl)-N4-cyclohexyl-5-fluoro-2,4-pyrimidinediamine | 1H NMR (DMSO-d6): δ 1.33 (m, 5H), 1.65 (d, 1H), 1.78 (m, 2H), 1.92 (m, 2H), 3.88 (m, 1H), 7.22 (d, J = 8.1 Hz, 1H), 7.46-7.69 (m, 7H), 7.81 (d, J = 3.9 Hz, 1H), 7.92 (d, J = 6.6 Hz, 2H), 8.99 (s, 1H), 10.05 (s, 1H); 19F NMR (282 MHz, DMSO-d6): δ -166.98; LCMS: ret. time: 10.79 min.; purity: 94.61%; MS (m/e): 406.43 (MH+). | + | + | − | |
| 1176 | N2-[4-(N-Acetyl-N-methylamino)phenyl]-N4-cyclohexyl-5-fluoro-2,4-pyrimidinediamine | 1H NMR (DMSO-d6): δ 1.36 (m, 5H), 1.65 (d, 1H), 1.79 (m, 2H), 1.88 (m, 2H), 3.85 (s, 3H), 4.05 (m, 1H), 5.24 (s, 2H), 7.06 (s, 1H), 7.31-7.50 (m, 6H), 8.44 (d, J = 7.5 Hz, 1H), 8.70 (d, J = 6.9 Hz, 1H); 19F NMR (282 MHz, DMSO-d6): δ -156.00; LCMS: ret. time: 11.66 min.; purity: 98.19%; MS (m/e): 449.43 (M − 16). | + | | − | |
| 1177 | N4-Cyclohexyl-5-fluoro-N2-[3-(N-2-imidazolin-2-yl)aminophenyl]-2,4-pyrimidinediamine | 1H NMR (DMSO-d6): δ 1.32 (m, 5H), 1.64 (d, 1H), 1.74 (m, 2H), 1.90 (m, 2H), 3.09 (s, 3H), 3.32 (s, 3H), 3.88 (m, 1H), 7.13 (d, J = 8.4 Hz, 2H), 7.26 (d, J = 7.5 Hz, 1H), 7.75 (d, J = 8.7 Hz, 2H), 7.83 (d, J = 3.9 Hz, 1H), 9.15 (s, 1H); 19F NMR (282 MHz, DMSO-d6): δ -166.21; LCMS: ret. time: 8.97 min.; purity: 100%; MS (m/e): 358.18 (MH+). | − | | − | |
| 1178 | N2,N4-Bis[3-(oxazol-2-yl)phenyl]-5-fluoro-2,4-pyrimidinediamine | LCMS: ret. time: 6.42 min.; purity: 86.49%; MS (m/e): 370.47 (MH+). | − | | − | |
| 1179 | N4-Cyclobutyl-5-fluoro-N4-methyl-N2-[3-(oxazol-2-yl)phenyl]-2,4-pyrimidinediamine | 1H NMR (DMSO-d6): δ 1.53-1.71 (m, 2H), 2.11-2.32 (m, 4H), 3.16 (d, J = 3.6 Hz, 3H), 4.89 (m, J = 8.4 Hz, 1H), 7.36 (d, J = 0.9 Hz, 1H), 7.40 (t, J = 7.8 Hz, 1H), 7.57 (m, 2H), 8.06 (d, J = 7.2 Hz, 1H), 8.20 (d, J = 0.9 Hz, 1H), 8.57 (t, J = 1.8 Hz, 1H), 9.68 (s, 1H); 19F NMR (282 MHz, DMSO-d6): δ 1.53-1.71 (m, 2H); 11.53 min.; purity: 95.22%; MS (m/e): 415.02 (MH+). | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1180 | (S)—N4-(1-Benzylpyrrolidin-3-yl)-5-fluoro-N2-(4-morpholinophenyl)-2,4-pyrimidinediamine | DMSO-d6): δ −156.69; LCMS: ret. time: 11.99 min.; purity: 95.24%; MS (m/e): 340.18 (MH+). | + | – | – | |
| 1181 | (S)—N2-[4-(4-Acetylpiperazinophenyl]-N4-(1-benzylpyrrolidin-3-yl)-5-fluoro-2,4-pyrimidinediamine | 1H NMR (DMSO-d6): δ 1.83 (m, 1H), 2.16 (m, 1H), 2.40 (dd, J = 5.1, 9.3 Hz, 1H), 2.58 (m, 2H), 2.89 (dd, J = 7.2, 9.3 Hz, 1H), 2.99 (t, J = 4.8 Hz, 4H), 3.58 (d, J = 1.8 Hz, 2H), 3.72 (t, J = 4.8 Hz, 4H), 4.41 (m, 1H), 6.78 (d, J = 9.0 Hz, 2H), 7.22 (m, 1H), 7.29 (d, 4H), 7.35 (d, J = 6.6 Hz, 1H), 7.50 (d, J = 8.7 Hz, 2H), 7.77 (d, J = 3.9 Hz, 1H), 8.73 (br, 1H); 19F NMR (282 MHz, DMSO-d6): δ −167.51; LCMS: ret. time: 5.99 min.; purity: 99.07%; MS (m/e): 449 (MH+). | + | – | – | |
| 1182 | (S)—N4-(1-Benzylpyrrolidin-3-yl)-5-fluoro-N2-[4-(4-methylpiperazinophenyl]-2,4-pyrimidinediamine | 1H NMR (DMSO-d6): δ 1.81-1.87 (m, 1H), 2.03 (s, 3H), 2.14-2.23 (m, 1H), 2.40 (dd, J = 5.7, 9.6 Hz, 1H), 2.56 (m, 2H), 2.89 (dd, J = 7.2, 9.3 Hz, 1H), 2.95 (t, J = 5.1 Hz, 2H), 3.02 (t, J = 5.1 Hz, 2H), 3.55 (m, 4H), 3.58 (s, 2H), 4.41 (m, 1H), 6.81 (d, J = 9.0 Hz, 2H), 7.22 (m, 1H), 7.29 (d, 4H), 7.35 (d, J = 6.3 Hz, 1H), 7.51 (d, J = 9.3 Hz, 2H), 7.78 (d, J = 3.9 Hz, 1H), 8.75 (br, 1H); 19F NMR (282 MHz, DMSO-d6): δ −167.42; LCMS: ret. time: 5.81 min.; purity: 97.77%; MS (m/e): 490.27 (MH+). | – | – | – | |
| 1183 | (S)—N4-(1-Benzylpyrrolidin-3-yl)-N2-[4-(4-ethoxycarbonylpiperazinophenyl]-5-fluoro-2,4-pyrimidinediamine | LCMS: ret. time: 1.17 min.; purity: 95.41%; MS (m/e): 462.15 (MH+). <br> 1H NMR (DMSO-d6): δ 1.19 (t, J = 7.2 Hz, 3H), 1.83 (m, 1H), 2.17 (m, 1H), 2.40 (dd, J = 5.1, 9.0 Hz, 1H), 2.56 (m, 2H), 2.89 (dd, J = 7.2, 9.0 Hz, 1H), 2.98 (t, J = 5.1 Hz, 4H), 3.49 (t, J = 5.1 Hz, 4H), 3.58 (d, J = 1.8 Hz, 2H), 4.05 (q, J = 7.2 Hz, 2H), 4.44 (m, 1H), 6.80 (d, J = 9.0 Hz, 2H), 7.22 (m, 1H), 7.28 (d, 4H), 7.35 (d, J = 6.6 Hz, 1H), 7.50 (d, J = 9.3 Hz, 2H), 7.77 (d, J = 3.9 Hz, 1H), 8.75 (br, 1H); 19F NMR (282 MHz, DMSO-d6): δ −167.41; LCMS: ret. time: 7.42 min.; purity: 95.27%; MS (m/e): 520.22 (MH+). | + | – | – | |
| 1184 | (S)—N4-(1-Benzylpyrrolidin-3-yl)-5-fluoro-N2-(3-morpholinophenyl)-2,4-pyrimidinediamine | LCMS: ret. time: 6.81 min.; purity: 100%; MS (m/e): 449 (MH+). | + | – | – | |
| 1185 | (S)—N2-[3-(4-Acetylpiperazinophenyl]-N4-(benzylpyrrolidin-3-yl)-5-fluoro-2,4-pyrimidinediamine | 1H NMR (DMSO-d6): δ 1.82-1.88 (m, 1H), 2.02 (s, 3H), 2.16-2.26 (m, 1H), 2.37 (dd, J = 5.7, 9.0 Hz, 1H), 2.56 (m, 2H), 2.92 (dd, J = 6.9, 9.0 Hz, 1H), 3.03 (t, J = 5.1 Hz, 2H), 3.10 (t, J = 5.1 Hz, 2H), 3.56 (m, 4H), 3.58 (s, 2H), 4.53 (m, 1H), 6.47 (d, J = 8.4 Hz, 1H), 7.02 (t, J = 8.1 Hz, 1H), 7.10 (d, J = 8.4 Hz, 1H), 7.21 (m, 1H), 7.28 (d, 4H), 7.46 (m, 2H), 7.82 (d, J = 3.9 Hz, 1H), 8.87 (br, 1H); 19F NMR (282 MHz, DMSO-d6): δ −166.63; LCMS: ret. time: 6.43 min.; purity: 94.97%; MS (m/e): 490.40 (MH+). | + | – | – | |
| 1186 | (S)—N4-(1-Benzylpyrrolidin-3-yl)-5-fluoro-N2-[3-(4-methylpiperazinophenyl]-2,4-pyrimidinediamine | LCMS: ret. time: 2.79 min.; purity: 97.87%; MS (m/e): 462 (MH+). | + | – | – | |
| 1187 | (S)—N4-(1-Benzylpyrrolidin-3-yl)-N2-[3-(4-ethoxycarbonylpiperazinophenyl]-5-fluoro-2,4-pyrimidinediamine | 1H NMR (DMSO-d6): δ 1.18 (t, J = 7.2 Hz, 3H), 1.82 (m, J = 6.5 Hz, 1H), 2.19 (m, 1H), 2.37 (dd, J = 5.7, 9.0 Hz, 1H), 2.56 (m, 2H), 2.91 (dd, J = 7.2, 9.0 Hz, 1H), 3.06 (t, J = 5.1 Hz, 4H), 3.51 (t, J = 5.1 Hz, 4H), 3.58 (s, 2H), 4.04 (q, J = 7.2 Hz, 2H), 4.55 (m, 1H), 6.46 (d, J = 7.2 Hz, 1H), 7.02 (t, J = 7.8 Hz, 1H), 7.07 (d, J = 7.5 Hz, 1H), 7.22 (m, 1H), 7.27 (m, 4H), 7.47 (m, 2H), 7.82 (d, J = 3.9 Hz, 1H), 8.86 (br, 1H); 19F NMR (282 MHz, DMSO-d6): δ −166.66; LCMS: ret. time: 8.25 min.; purity: 97.24%; MS (m/e): 520.41 (MH+). | + | – | – | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1188 | N4-Cyclobutyl-5-fluoro-N2-[3-chloro-4-(4-methylpiperazinophenyl]-2,4-pyrimidinediamine | 1H NMR (DMSO-d6); δ 1.61-1.73 (m, 2H), 2.01-2.14 (m, 2H), 2.25-2.33 (m, 2H), 2.29 (s, 3H), 2.55 (m, 4H), 2.91 (t, 4H), 4.47 (m, J = 8.1 Hz, 1H), 7.03 (d, J = 8.7 Hz, 1H), 7.43 (dd, J = 2.7, 9.0 Hz, 1H), 7.69 (d, J = 7.2 Hz, 1H), 7.84 (d, J = 3.6 Hz, 1H), 8.07 (d, J = 2.4 Hz, 1H), 9.08 (br, 1H); 19F NMR (282 MHz, DMSO-d6): δ −166.50; LCMS: ret. time: 11.07 min.; purity: 93.70%; MS (m/e): 391.10 (MH+). | + | | | |
| 1189 | N4-(3,4-Dihydro-2H,4H-5-pyrid[1,4]oxazin-6-yl)-5-fluoro-N2-[3-(4-methylpiperazinophenyl]-2,4-pyrimidinediamine Bis p-Toluenesulfonic Acid Salt | 1H NMR (DMSO-d6); δ 2.28 (s, 6H), 2.86 (d, J = 4.8 Hz, 3H), 2.92 (m, 2H), 3.13 (q, J = 10.8 Hz, 2H), 3.49 (m, 4H), 3.74 (d, J = 13.2 Hz, 2H), 4.15 (d, J = 4.2 Hz, 2H), 6.66 (d, J = 7.8 Hz, 1H), 6.96 (d, J = 8.7 Hz, 1H), 7.08 (d, J = 8.4 Hz, 2H), 7.17 (m, 4H), 7.45 (d, J = 8.1 Hz, 4H), 8.19 (d, J = 3.6 Hz, 1H), 9.42 (br, 1H), 9.51 (br, 1H), 9.95 (br, 1H); 19F NMR (282 MHz, DMSO-d6): δ −162.24; LCMS: ret. time: 1.60 min.; purity: 98.21%; MS (m/e): 436.77 (MH+). | + | | | |
| 1190 | N4-(3,4-Dihydro-2H,4H-5-pyrid[1,4]oxazin-6-yl)-5-fluoro-N2-[3-(4-methylpiperazinophenyl]-2,4-pyrimidinediamine Bis Hydrogen Chloride Salt | 1H NMR (DMSO-d6); δ 2.81 (d, J = 4.5 Hz, 3H), 3.08 (m, 4H), 3.48 (d, J = 11.7 Hz, 2H), 3.55 (t, 2H), 3.72 (d, J = 11.7 Hz, 2H), 4.18 (t, J = 4.2 Hz, 2H), 6.65 (d, J = 9.0 Hz, 1H), 6.74 (d, J = 8.1 Hz, 1H), 7.15 (t, J = 8.1 Hz, 1H), 7.36 (d, J = 8.1 Hz, 1H), 7.41 (m, 2H), 8.30 (d, J = 3.3 Hz, 1H), 10.45 (br, 1H), 10.59 (br, 1H), 10.72 (br, 1H); 19F NMR (282 MHz, DMSO-d6): δ −162.32; LCMS: ret. time: 1.51 min.; purity: 100%; MS (m/e): 437.08 (MH+). | + | + | | |
| 1191 | N2-[3-Chloro-4-(4-methylpiperazino)phenyl]-N4-cyclohexyl-5-fluoro-2,4-pyrimidinediamine | 1H NMR (DMSO-d6); δ 1.14 (m, 1H), 1.33 (m, 4H), 1.63 (d, 1H), 1.74 (m, 2H), 1.90 (m, 2H), 2.21 (s, 3H), 2.45 (m, 4H), 2.88 (t, 4H), 3.89 (m, 1H), 7.01 (d, J = 8.7 Hz, 1H), 7.24 (d, J = 7.8 Hz, 1H), 7.39 (dd, J = 2.4, 8.4 Hz, 1H), 7.81 (d, J = 3.9 Hz, 1H), 8.03 (d, J = 2.1 Hz, 1H), 9.05 (br, 1H); 19F NMR (282 MHz, DMSO-d6): δ −166.45; LCMS: ret. time: 1.57 min.; purity: 96.83%; MS (m/e): 419.15 (MH+). | + | + | | |
| 1192 | N2-[4-(4-Acetylpiperazino)phenyl]-N4-cyclobutyl-5-fluoro-2,4-pyrimidinediamine Bis Hydrogen Chloride Salt | 1H NMR (DMSO-d6); δ 1.65-1.76 (m, 2H), 2.04 (s, 3H), 2.08-2.26 (m, 4H), 3.10 (t, 2H), 3.17 (t, 2H), 3.58 (t, 4H), 4.43 (m, J = 7.8 Hz, 1H), 7.02 (d, J = 8.1 Hz, 2H), 7.37 (d, J = 8.4 Hz, 2H), 8.00 (d, J = 5.1 Hz, 1H), 9.10 (br, 1H), 10.02 (br, 1H); 19F NMR (282 MHz, DMSO-d6): δ −162.88; LCMS: ret. time: 15.12 min.; purity: 97.62%; MS (m/e): 385.16 (MH+). | + | | | |
| 1193 | N4-Cyclohexyl-5-fluoro-N2-[4-(4-methylpiperazino)phenyl]-2,4-pyrimidinediamine Bis p-Toluenesulfonic Acid Salt | 1H NMR (DMSO-d6); δ 1.24 (m, 4H), 1.37 (q, 1H), 1.62 (d, 1H), 1.76 (d, 2H), 1.85 (d, 2H), 2.28 (s, 6H), 2.86 (d, J = 3.9 Hz, 3H), 2.92 (d, 2H), 3.15 (m, 2H), 3.52 (d, 2H), 3.80 (d, 3H), 7.00 (d, J = 9.3 Hz, 2H), 7.09 (d, J = 7.8 Hz, 4H), 7.36 (d, J = 9.3 Hz, 2H), 7.45 (d, J = 8.1 Hz, 4H), 8.01 (d, J = 6.0 Hz, 1H), 8.94 (br, 1H), 9.53 (br, 1H), 9.92 (br, 1H); 19F NMR (282 MHz, DMSO-d6): δ −162.18; LCMS: ret. time: 1.52 min.; purity: 99.98%; MS (m/e): 384.89 (MH+). | + | | | |
| 1194 | N4-Cyclohexyl-5-fluoro-N2-[4-(4-methylpiperazino)phenyl]-2,4-pyrimidinediamine Bis Hydrogen Chloride Salt | 1H NMR (DMSO-d6); δ 1.33 (m, 5H), 1.61 (d, 1H), 1.77 (d, 2H), 1.87 (d, 2H), 2.79 (d, J = 4.8 Hz, 3H), 3.09 (m, 4H), 3.47 (d, 2H), 3.78 (d, 2H), 3.83 (m, 1H), 7.01 (d, J = 9.0 Hz, 2H), 7.39 (d, J = 9.0 Hz, 2H), 8.10 (d, J = 5.4 Hz, 1H), 9.08 (d, J = 8.1 Hz, 1H), 10.46 (br, 1H), 10.91 (br, 1H); 19F NMR (282 MHz, DMSO-d6): δ −161.93; LCMS: ret. time: 1.55 min.; purity: 99.46%; MS (m/e): 385.20 (MH+). | + | | | |
| 1195 | N2-[3-Chloro-4-(4-methylpiperazino)phenyl]-N4-cyclopentyl-5-fluoro-2,4-pyrimidinediamine | 1H NMR (DMSO-d6); δ 1.55 (m, 4H), 1.71 (m, 2H), 1.98 (m, 2H), 2.31 (s, 3H), 2.57 (m, 4H), 2.91 (t, 4H), 4.30 (q, J = 6.9 Hz, 1H), 7.03 (d, J = 8.7 Hz, | + | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| | | 1H), 7.36 (d, J = 6.9 Hz, 1H), 7.43 (dd, J = 2.7, 9.0 Hz, 1H), 7.82 (d, J = 3.9 Hz, 1H), 8.07 (d, J = 2.4 Hz, 1H), 9.08 (br, 1H); 19F NMR (282 MHz, DMSO-d6): δ −166.32; LCMS: ret. time: 13.47 min.; purity: 87.25%; MS (m/e): 405.47 (MH+). | | | | |
| 1196 | N2-[3-Chloro-4-(4-methylpiperazino)phenyl]-N4-(3-cyclopropyl-1H-pyrazol-5-yl)-5-fluoro-2,4-pyrimidinediamine | 1H NMR (DMSO-d6): δ 0.69 (m, 2H), 0.91 (m, 2H), 1.87 (m, 1H), 2.22 (s, 3H), 2.46 (m, 4H), 2.90 (t, 4H), 6.31 (br, 1H), 7.04 (d, J = 9.0 Hz, 1H), 7.51 (br, 1H), 7.79 (s, 1H), 8.02 (s, 1H), 9.14 (br, 1H), 9.52 (br, 1H), 12.07 (br, 1H); 19F NMR (282 MHz, DMSO-d6): δ −164.15; LCMS: ret. time: 1.65 min.; purity: 92.40%; MS (m/e): 443.15 (MH+). | + | | | |
| 1197 | N2-[3-Chloro-4-(4-methylpiperazino)phenyl]-N4-(3,4-dihydro-2H,4H-5-pyrid[1,4]oxazin-6-yl)-5-fluoro-2,4-pyrimidinediamine | 1H NMR (DMSO-d6): δ 2.21 (s, 3H), 2.45 (t, 4H), 2.88 (t, 4H), 3.39 (m, 2H), 4.09 (t, J = 4.2 Hz, 2H), 6.53 (s, 1H), 6.94 (d, J = 8.7 Hz, 1H), 7.01 (d, J = 8.7 Hz, 1H), 7.12 (d, J = 8.4 Hz, 1H), 7.46 (dd, J = 2.7, 8.7 Hz, 1H), 7.84 (d, J = 2.7 Hz, 1H), 8.04 (d, J = 3.6 Hz, 1H), 8.80 (s, 1H), 9.20 (s, 1H); 19F NMR (282 MHz, DMSO-d6): δ −163.49; LCMS: ret. time: 1.60 min.; purity: 98.82%; MS (m/e): 471.12 (MH+). | + | + | | |
| 1198 | N2-[3-Chloro-4-(4-methylpiperazino)phenyl]-N4-cyclobutyl-5-fluoro-2,4-pyrimidinediamine Bis Hydrogen Chloride Salt | 1H NMR (DMSO-d6): δ 1.67-1.76 (m, 2H), 2.11-2.18 (m, 2H), 2.25-2.31 (m, 2H), 2.82 (d, J = 4.5 Hz, 3H), 3.02-3.20 (m, 4H), 3.35 (m, 2H), 3.48 (m, 2H), 4.44 (m, J = 7.5 Hz, 1H), 7.18 (d, J = 8.7 Hz, 1H), 7.40 (dd, J = 2.4, 8.7 Hz, 1H), 7.97 (d, J = 2.1 Hz, 1H), 8.05 (d, J = 4.8 Hz, 1H), 8.79 (br, 1H), 10.09 (br, 1H), 10.60 (br, 1H); 19F NMR (282 MHz, DMSO-d6): δ −163.03; LCMS: ret. time: 10.61 min.; purity: 93.48%; MS (m/e): 391 (MH+). | + | | | |
| 1199 | N2-[3-Chloro-4-(4-methylpiperazino)phenyl]-N4-cyclohexyl-5-fluoro-2,4-pyrimidinediamine Bis Hydrogen Chloride Salt | 1H NMR (DMSO-d6): δ 1.17 (m, 1H), 1.36 (m, 4H), 1.63 (d, 1H), 1.78 (m, 2H), 1.86 (m, 2H), 2.83 (d, J = 4.8 Hz, 3H), 3.00-3.20 (m, 4H), 3.34 (m, 2H), 3.48 (m, 2H), 3.87 (m, 1H), 7.16 (d, J = 8.7 Hz, 1H), 7.36 (dd, J = 2.4, 9.0 Hz, 1H), 7.96 (d, J = 2.4 Hz, 1H), 8.03 (d, J = 5.1 Hz, 1H), 8.41 (br, 1H), 10.05 (br, 1H), 10.50 (br, 1H); LCMS: ret. time: 14.78 min.; purity: 90.99%; MS (m/e): 419.39 (MH+). | + | + | | |
| 1200 | N4-Cyclopentyl-5-fluoro-N2-[3-methyl-4-(4-methylpiperazino)phenyl]-2,4-pyrimidinediamine | LCMS: ret. time: 9.70 min.; purity: 89.34%; MS (m/e): 385 (MH+). | + | | | |
| 1201 | N4-Cyclohexyl-5-fluoro-N2-[3-methyl-4-(4-methylpiperazino)phenyl]-2,4-pyrimidinediamine | LCMS: ret. time: 11.34 min.; purity: 94.34%; MS (m/e): 399.24 (MH+). | + | + | | |
| 1202 | N4-(3-Cyclopropyl-1H-pyrazol-5-yl)-5-fluoro-N2-[3-methyl-4-(4-methylpiperazino)phenyl]-2,4-pyrimidinediamine | LCMS: ret. time: 10.35 min.; purity: 96.72%; MS (m/e): 423 (MH+). | + | + | | |
| 1203 | N4-(3,4-Dihydro-2H,4H-5-pyrid[1,4]oxazin-6-yl)-5-fluoro-N2-[3-methyl-4-(4-methylpiperazino)phenyl]-2,4-pyrimidinediamine | LCMS: ret. time: 10.77 min.; purity: 93.79%; MS (m/e): 451 (MH+). | + | + | | |
| 1204 | 5-Fluoro-N4-isopropyl-N2-[4-(4-methylpiperazino)phenyl]-2,4-pyrimidinediamine | LCMS: ret. time: 3.64 min.; purity: 95.29%; MS (m/e): 345 (MH+). | + | | | |
| 1205 | N2-[3-Chloro-4-(4-methylpiperazino)phenyl]-5-fluoro-N4-isopropyl-2,4-pyrimidinediamine | LCMS: ret. time: 5.14 min.; purity: 92.47%; MS (m/e): 379 (MH+). | + | | | |
| 1206 | 5-Fluoro-N4-isopropyl-N2-[3-methyl-4-(4-methylpiperazino)phenyl]-2,4-pyrimidinediamine | LCMS: ret. time: 1.99 min.; purity: 93.17%; MS (m/e): 359 (MH+). | + | | | |
| 1207 | N4-Cyclobutyl-5-fluoro-N2-[4-(4-methylpiperazino)-3-trifluoromethylphenyl]-2,4-pyrimidinediamine | LCMS: ret. time: 15.09 min.; purity: 94.19%; MS (m/e): 425 (MH+). | + | − | | |
| 1208 | N4-Cyclopentyl-5-fluoro-N2-[4-(4-methylpiperazino)-3-trifluoromethylphenyl]-2,4-pyrimidinediamine | LCMS: ret. time: 15.32 min.; purity: 92.83%; MS (m/e): 439.30 (MH+). | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1209 | N4-Cyclohexyl-5-fluoro-N2-[4-(4-methylpiperazino)-3-trifluoromethylphenyl]-2,4-pyrimidinediamine | LCMS: ret. time: 15.74 min.; purity: 95.26%; MS (m/e): 453 (MH+). | + | | | |
| 1210 | 5-Fluoro-N4-isopropyl-N2-[4-(4-methylpiperazino)-3-trifluoromethylphenyl]-2,4-pyrimidinediamine | LCMS: ret. time: 7.29 min.; purity: 88.24%; MS (m/e): 413.05 (MH+). | + | | | |
| 1211 | N4-(3-Cyclopropyl-1H-pyrazol-5-yl)-5-fluoro-N2-[(4-methylpiperazino)-3-trifluoromethylphenyl]-2,4-pyrimidinediamine | LCMS: ret. time: 8.27 min.; purity: 94.19%; MS (m/e): 477 (MH+). | + | | | |
| 1212 | 2-chloro-5-fluoro-N4-(1,2,2,6,6-pentamethylpiperidin-4-yl)-4-pyrimidineamine | LCMS: ret. time: 9.57 min.; purity: 90.78%; MS (m/e): 301.19 (MH+). | − | | | |
| 1213 | 2-chloro-N4-(1-ethoxycarbonylpiperidin-4-yl)-5-fluoro-4-pyrimidineamine | LCMS: ret. time: 10.29 min.; purity: 94%; MS (m/e): 303.04 (MH+). | − | | | |
| 1214 | 5-Fluoro-N4-isopropyl-N2-[3-(4-methylpiperazino)phenyl]-2,4-pyrimidinediamine | LCMS: ret. time: 4.63 min.; purity: 97.16%; MS (m/e): 345.41 (MH+). | − | | | |
| 1215 | N4-tert-Butyl-5-fluoro-N2-[4-(4-methylpiperazino)phenyl]-2,4-pyrimidinediamine | LCMS: ret. time: 2.80 min.; purity: 97.03%; MS (m/e): 359 (MH+). | − | | | |
| 1216 | N4-tert-Butyl-5-fluoro-N2-[3-(4-methylpiperazino)phenyl]-2,4-pyrimidinediamine | LCMS: ret. time: 7.81 min.; purity: 94.56%; MS (m/e): 359.23 (MH+). | + | | | |
| 1217 | N4-tert-Butyl-N2-[3-chloro-4-(4-methylpiperazino)phenyl]-5-fluoro-2,4-pyrimidinediamine | LCMS: ret. time: 10.53 min.; purity: 93.25%; MS (m/e): 393 (MH+). | | | | |
| 1218 | N4-tert-Butyl-5-fluoro-N2-[3-methyl-4-(4-methylpiperazino)phenyl]-2,4-pyrimidinediamine | LCMS: ret. time: 4.35 min.; purity: 87.23%; MS (m/e): 373.26 (MH+). | | + | | |
| 1219 | 5-Fluoro-N2-[4-(4-methylpiperazino)phenyl]-N4-(1,2,2,6,6-pentamethylpiperidin-4-yl)-2,4-pyrimidinediamine | LCMS: ret. time: 1.30 min.; purity: 95.14%; MS (m/e): 456.63 (MH+). | − | | | |
| 1220 | N4-Cyclobutyl-5-fluoro-N2-[3-methyl-4-(4-methylpiperazino)phenyl]-2,4-pyrimidinediamine | LCMS: ret. time: 9.16 min.; purity: 93.00%; MS (m/e): 371.26 (MH+). | | + | | |
| 1221 | 5-Fluoro-N2-[3-(4-methylpiperazino)phenyl]-N4-(1,2,2,6,6-pentamethylpiperidin-4-yl)-2,4-pyrimidinediamine | LCMS: ret. time: 1.40, 1.71 min.; purity: 95%; MS (m/e): 456.30 (MH+). | | | | |
| 1222 | N2-[3-Chloro-4-(4-methylpiperazino)phenyl]-5-fluoro-N4-(1,2,2,6,6-pentamethylpiperidin-4-yl)-2,4-pyrimidinediamine | LCMS: ret. time: 1.44, 1.74 min.; purity: 97%; MS (m/e): 490.11 (MH+). | − | | | |
| 1223 | 5-Fluoro-N2-[3-methyl-4-(4-methylpiperazino)phenyl]-N4-(1,2,2,6,6-pentamethylpiperidin-4-yl)-2,4-pyrimidinediamine | LCMS: ret. time: 1.46, 2.03 min.; purity: 100%; MS (m/e): 470.29 (MH+). | + | | | |
| 1224 | 5-Fluoro-N4-(1,2,2,6,6-pentamethylpiperidin-4-yl)-N2-[3-trifluoromethyl-4-(4-methylpiperazino)phenyl]-2,4-pyrimidinediamine | LCMS: ret. time: 1.46, 2.70 min.; purity: 97%; MS (m/e): 524.23 (MH+). | − | | | |
| 1225 | N4-(1-Ethoxycarbonylpiperidin-4-yl)-5-fluoro-N2-[4-(4-methylpiperazino)phenyl]-2,4-pyrimidinediamine | LCMS: ret. time: 6.13 min.; purity: 95.45%; MS (m/e): 458 (MH+). | + | | | |
| 1226 | N4-(1-Ethoxycarbonylpiperidin-4-yl)-5-fluoro-N2-[3-(4-methylpiperazino)phenyl]-2,4-pyrimidinediamine | LCMS: ret. time: 9.94 min.; purity: 97%; MS (m/e): 458.27 (MH+). | + | | | |
| 1227 | N2-[3-Chloro-4-(4-methylpiperazino)phenyl]-N4-(1-ethoxycarbonylpiperidin-4-yl)-5-fluoro-2,4-pyrimidinediamine | LCMS: ret. time: 14.71 min.; purity: 98.79%; MS (m/e): 492 (MH+). | + | | | |
| 1228 | N4-(1-Ethoxycarbonylpiperidin-4-yl)-5-fluoro-N2-[3-methyl-4-(4-methylpiperazino)phenyl]-2,4-pyrimidinediamine | LCMS: ret. time: 9.26 min.; purity: 97.16%; MS (m/e): 472 (MH+). | + | | | |
| 1229 | N4-(1-Ethoxycarbonylpiperidin-4-yl)-5-fluoro-N2-[4-(4-methylpiperazino)-3-trifluoromethylphenyl]-2,4-pyrimidinediamine | LCMS: ret. time: 15.48 min.; purity: 97.96%; MS (m/e): 526 (MH+). | + | | | |
| 1230 | N4-Cyclobutyl-N2-[2-(4-ethylpiperazino)pyrid-5-yl]-5-fluoro-2,4-pyrimidinediamine | LCMS: ret. time: 5.52 min.; purity: 94.98%; MS (m/e): 372 (MH+). | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1231 | N4-Cyclopentyl-N2-[2-(4-ethylpiperazino)pyrid-5-yl]-5-fluoro-2,4-pyrimidinediamine | LCMS: ret. time: 6.27 min.; purity: 90.61%; MS (m/e): 386.36 (MH+). | + | | | |
| 1232 | N4-Cyclohexyl-N2-[2-(4-ethylpiperazino)pyrid-5-yl]-5-fluoro-2,4-pyrimidinediamine | LCMS: ret. time: 6.83 min.; purity: 97.62%; MS (m/e): 400 (MH+). | + | | | |
| 1233 | N4-tert-Butyl-5-fluoro-N2-[4-(4-methylpiperazino)-3-trifluoromethylphenyl]-2,4-pyrimidinediamine | LCMS: ret. time: 15.37 min.; purity: 96.00%; MS (m/e): 427 (MH+). | + | | | |
| 1234 | N2-[2-(4-Ethylpiperazino)pyrid-5-yl]-5-fluoro-N4-isopropyl-2,4-pyrimidinediamine | LCMS: ret. time: 1.44, 1.80 min.; purity: 96%; MS (m/e): 360.28 (MH+). | | | | |
| 1235 | N4-Cyclobutyl-5-fluoro-N2-[3-hydroxymethyl-4-(4-methylpiperazino)phenyl]-2,4-pyrimidinediamine | LCMS: ret. time: 1.82 min.; purity: 90%; MS (m/e): 387.14 (MH+). | | − | | |
| 1236 | N4-tert-Butyl-N2-[2-(4-ethylpiperazino)pyrid-5-yl]-5-fluoro-2,4-pyrimidinediamine | LCMS: ret. time: 4.27 min.; purity: 100%; MS (m/e): 374.18 (MH+). | − | | | |
| 1237 | N2-[2-(4-Ethylpiperazino)pyrid-5-yl]-5-fluoro-N4-(1,2,2,6,6-pentamethylpiperidin-4-yl)-2,4-pyrimidinediamine | LCMS: ret. time: 1.27 min.; purity: 99.58%; MS (m/e): 471.73 (MH+). | − | | | |
| 1238 | N4-(1-Ethoxycarbonylpiperidin-4-yl)-N2-[2-(4-ethylpiperazino)pyrid-5-yl]-5-fluoro-2,4-pyrimidinediamine | LCMS: ret. time: 7.03 min.; purity: 94.74%; MS (m/e): 473 (MH+). | − | | | |
| 1239 | N4-Cyclobutyl-5-fluoro-N2-[2-(4-methylpiperazino)-3-methylpyrid-5-yl]-2,4-pyrimidinediamine | LCMS: ret. time: 9.65 min.; purity: 97.08%; MS (m/e): 372.11 (MH+). | + | | | |
| 1240 | N4-Cyclopentyl-5-fluoro-N2-[2-(4-methylpiperazino)-3-methylpyrid-5-yl]-2,4-pyrimidinediamine | LCMS: ret. time: 10.50 min.; purity: 91.36%; MS (m/e): 385.85 (MH+). | + | | | |
| 1241 | N4-Cyclohexyl-5-fluoro-N2-[2-(4-methylpiperazino)-3-methylpyrid-5-yl]-2,4-pyrimidinediamine | LCMS: ret. time: 9.22 min.; purity: 93.96%; MS (m/e): 400.11 (MH+). | + | | | |
| 1242 | 5-Fluoro-N4-isopropyl-N2-[2-(4-methylpiperazino)-3-methylpyrid-5-yl]-2,4-pyrimidinediamine | LCMS: ret. time: 4.21 min.; purity: 91.67%; MS (m/e): 360.15 (MH+). | + | | | |
| 1243 | N4-Cyclobutyl-5-fluoro-N2-[3-hydroxymethyl-4-(4-methylpiperazino)phenyl]-2,4-pyrimidinediamine Bishydrogen chloride salt | LCMS: ret. time: 1.43, 1.85 min.; purity: 94%; MS (m/e): 387.05 (MH+). | − | | | |
| 1244 | 5-Fluoro-N2-[2-(4-methylpiperazino)-3-methylpyrid-5-yl]-N4-(1,2,2,6,6-pentamethylpiperidin-4-yl)-2,4-pyrimidinediamine | LCMS: ret. time: 7.05 min.; purity: 95.56%; MS (m/e): 471.26 (MH+). | − | | | |
| 1245 | N4-Cyclobutyl-5-fluoro-N2-[2-(4-methylpiperazino)-4-methylpyrid-5-yl]-2,4-pyrimidinediamine | LCMS: ret. time: 9.37 min.; purity: 92.45%; MS (m/e): 371.99 (MH+). | − | | | |
| 1246 | N4-Cyclopentyl-5-fluoro-N2-[2-(4-methylpiperazino)-4-methylpyrid-5-yl]-2,4-pyrimidinediamine | LCMS: ret. time: 10.12 min.; purity: 95.69%; MS (m/e): 386.09 (MH+). | − | | | |
| 1247 | N4-Cyclohexyl-5-fluoro-N2-[2-(4-methylpiperazino)-4-methylpyrid-5-yl]-2,4-pyrimidinediamine | LCMS: ret. time: 10.35 min.; purity: 92.30%; MS (m/e): 400.13 (MH+). | + | | | |
| 1248 | 5-Fluoro-N4-isopropyl-N2-[2-(4-methylpiperazino)-4-methylpyrid-5-yl]-2,4-pyrimidinediamine | LCMS: ret. time: 6.77 min.; purity: 84.20%; MS (m/e): 359.97 (MH+). | − | | | |
| 1249 | 5-Fluoro-N2-[2-(4-methylpiperazino)-4-methylpyrid-5-yl]-N4-(1,2,2,6,6-pentamethylpiperidin-4-yl)-2,4-pyrimidinediamine | LCMS: ret. time: 1.48, 2.77 min.; purity: 98%; MS (m/e): 471.22 (MH+). | + | | | |
| 1250 | 5-Fluoro-N4-(1-hydroxymethylcyclopent-1-yl)-N2-[3-methyl-4-(4-methylpiperazino)phenyl]-2,4-pyrimidinediamine | LCMS: ret. time: 11.16 min.; purity: 99.47%; MS (m/e): 415.57 (MH+). | + | | | |
| 1251 | N4-(5-Amino-1,2,4-triazol-3-yl)-5-fluoro-N2-[3-(N-methyl)aminocarbonylmethyleneoxyphenyl]-2,4-pyrimidinediamine | LCMS: purity: 93.2%; MS (m/e): 374.52 (MH+, 100). | | + | | |
| 1252 | N4-(3-Amino-1,2,4-triazol-5-yl)-N2-(3,5-dimethylphenyl)-5-fluoro-2,4-pyrimidinediamine | 1H NMR (DMSO): δ 8.71 (d, 1H, J = 4.5 Hz), 7.75 (s, 1H), 7.53 (s, 2H), 7.21 (s, 1H), 6.61-6.74 (m, 2H), 5.83 (bs, 2H), 2.43 (s, 6H); LCMS: purity: 88.8%; MS (m/e): 315.24 (MH+, 100). | | − | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1253 | N4-(5-Amino-1,2,4-triazol-3-yl)-N2-(3-chloro-4-methoxyphenyl)-5-fluoro-2,4-pyrimidinediamine | LCMS: purity: 92.8%; MS (m/e): 351.09 (MH+, 100). | | – | | |
| 1254 | N4-(5-Amino-1,2,4-triazol-3-yl)-N2-(3,4-dichlorophenyl)-5-fluoro-2,4-pyrimidinediamine | LCMS: purity: 93.2%; MS (m/e): 355.23 (MH+, 100). | | – | | + |
| 1255 | N4-(5-Amino-1,2,4-triazol-3-yl)-5-fluoro-N2-(indazol-6-yl)-2,4-pyrimidinediamine | LCMS: purity: 94.3%; MS (m/e): 327.14 (MH+, 100). | | + | | |
| 1256 | N4-[(2,3-Dihydro-1,4-benzodioxan-2-yl)methyl]-N2-(3,5-dimethylphenyl)-5-fluoro-2,4-pyrimidinediamine | 1H NMR (DMSO): δ 10.09 (bs, 1H), 9.12 (bs, 1H), 8.13 (d, 1H, J = 5.1 Hz), 7.17 (s, 2H), 6.74-6.87 (m, 5H), 4.29-4.50 (m, 2H), 3.98 (dd, 1H, 6.3, 11.4 Hz), 3.59-3.80 (m, 2H), 2.23 (s, 6H); LCMS: purity: 97.8%; MS (m/e): 379.14 (M–, 100). | + | | | |
| 1257 | N4-[(2,3-Dihydro-1,4-benzodioxan-2-yl)methyl]-5-fluoro-N2-[3-(N-methylaminocarbonylmethyleneoxyphenyl]-2,4-pyrimidinediamine | LCMS: purity: 97.4%; MS (m/e): 438.13 (M–, 100). | | + | | |
| 1258 | N4-[(2,3-Dihydro-1,4-benzodioxan-2-yl)methyl]-N2-(3,5-dimethoxyphenyl)-5-fluoro-2,4-pyrimidinediamine | 1H NMR (DMSO): δ 10.13 (s, 1H), 9.05 (bs, 1H), 8.19 (d, 1H, J = 4.8 Hz), 6.79-6.86 (m, 6H), 6.24 (m, 1H), 4.29-4.49 (m, 2H), 4.00 (dd, 1H, 6.9, 11.4 Hz), 3.62-3.79 (m, 8H); LCMS: purity: 96.7%; MS (m/e): 411.10 (M–, 100). | + | | | |
| 1259 | N2-(3-Chloro-4-methoxyphenyl)-N4-[(2,3-dihydro-1,4-benzodioxan-2-yl)methyl]-5-fluoro-2,4-pyrimidinediamine | 1H NMR (DMSO): δ 10.22 (s, 1H), 9.11 (bs, 1H), 8.12 (d, 1H, J = 5.1 Hz), 7.70 (d, 1H, J = 2.4 Hz), 7.35 (dd, 1H, J = 2.7, 9.0 Hz), 7.08 (d, 1H, J = 9.0 Hz), 6.78-6.87 (m, 4H), 4.28-4.49 (m, 2H), 3.99 (dd, 1H, 6.9, 11.7 Hz), 3.59-3.84 (m, 5H); LCMS: purity: 96.4%; MS (m/e): 415.07 (M–, 100). | + | | | |
| 1260 | N4-[(2,3-Dihydro-1,4-benzodioxan-2-yl)methyl]-5-fluoro-N2-(indazol-6-yl)-2,4-pyrimidinediamine | LCMS: purity: 95.0%; MS (m/e): 391.10 (M–, 100). | | + | | |
| 1261 | N4-(3,4-Dichlorophenyl)-5-fluoro-N2-(4-methoxycarbonylphenyl)-2,4-pyrimidinediamine | LCMS: purity: 100%; MS (m/e): 405.09 (M–, 100). | – | | | |
| 1262 | N2-[4-(N-Carboxymethyleneamino)carbonylphenyl]-N4-(3,4-dichlorophenyl)-5-fluoro-2,4-pyrimidinediamine | LCMS: purity: 100%; MS (m/e): 450.11 (M–) | – | | | |
| 1263 | (S)-5-Fluoro-N2-(4-methoxycarbonylphenyl)-N4-(2-methyl-3-oxo-2H,4H-benz[1,4]oxazin-6-yl)-2,4-pyrimidinediamine | 1H NMR (DMSO): δ 10.74 (s, 1H), 9.95 (s, 1H), 9.80 (s, 1H), 8.18 (d, 1H, J = 4.2 Hz), 7.20-7.79 (m, 6H), 6.96 (d, 1H, J = 9.3 Hz), 4.66 (q, 1H, J = 6.6 Hz), 3.78 (s, 3H), 1.45 (d, 3H, J = 6.6 Hz); LCMS: purity: 96.8%; MS (m/e): 422.12 (M–, 100). | | + | | |
| 1264 | (S)—N2-[4-(N-Carboxymethyleneamino)carbonylphenyl]-5-fluoro-N4-(2-methyl-3-oxo-2H,4H-benz[1,4]oxazin-6-yl)-2,4-pyrimidinediamine | 1H NMR (DMSO): δ 10.75 (s, 1H), 9.88 (s, 1H), 9.63 (m, 1H), 8.19 (d, 1H, J = 4.5 Hz), 7.19-7.75 (m, 6H), 6.98 (d, 1H, J = 8.7 Hz), 4.67 (q, 1H, J = 6.9 Hz), 3.89 (d, 1H, 5.7 Hz), 1.44 (d, 3H, J = 6.9 Hz); LCMS: purity: 91.2%; MS (m/e): 465.21 (M–, 100). | – | | | |
| 1265 | (R)—N2-(4-Aminocarbonylphenyl)-5-fluoro-N4-(2-methyl-3-oxo-2H,4H-benz[1,4]oxazin-6-yl)-2,4-pyrimidinediamine | LCMS: purity: 95.5%; MS (m/e): 407.17 (M–, 100). | | + | | |
| 1266 | (R)-5-Fluoro-N2-(4-methoxycarbonylphenyl)-N4-(2-methyl-3-oxo-2H,4H-benz[1,4]oxazin-6-yl)-2,4-pyrimidinediamine | 1H NMR (DMSO): δ 10.74 (s, 1H), 9.95 (s, 1H), 9.80 (s, 1H), 8.18 (d, 1H, J = 4.2 Hz), 7.20-7.79 (m, 6H), 6.96 (d, 1H, J = 9.3 Hz), 4.66 (q, 1H, J = 6.6 Hz), 3.78 (s, 3H), 1.45 (d, 3H, J = 6.6 Hz); LCMS: purity: 98.5%; MS (m/e): 422.17 (M–, 100). | | + | | |
| 1267 | (R)—N2-[4-(N-Carboxymethyleneamino)carbonylphenyl]-5-fluoro-N4-(2-methyl-3-oxo-2H,4H-benz[1,4]oxazin-6-yl)-2,4-pyrimidinediamine | 1H NMR (DMSO): δ 10.75 (s, 1H), 9.88 (s, 1H), 9.63 (m, 1H), 8.19 (d, 1H, J = 4.5 Hz), 7.19-7.75 (m, 6H), 6.98 (d, 1H, J = 8.7 Hz), 4.67 (q, 1H, J = 6.9 Hz), 3.89 (d, 1H, 5.7 Hz), 1.44 (d, 3H, J = 6.9 Hz); LCMS: purity: 87.5%; MS (m/e): 465.21 (M–, 100). | – | | | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | Tryptase, fp_syk, 11 pt |
|---|---|---|---|---|---|---|
| 1268 | N2,N4-Bis[4-(N-tert-butoxycarbonylamino)methylenephenyl]-5-fluoro-2,4-pyrimidinediamine | LCMS: purity: 100%; MS (m/e): 537.34 (M−, 100). | + | | | |
| 1269 | N2,N4-Bis(4-aminomethylenephenyl)-5-fluoro-2,4-pyrimidinediamine | 1H NMR (DMSO): δ 9.25 (bs, 1H), 9.09 (bs, 1H), 8.05 (d, 1H, J = 2.4 Hz), 7.69 (d, 2H, J = 8.7 Hz), 7.56 (d, 2H, J = 8.7 Hz), 7.04-7.40 (m, 4H), 3.67 (s, 3H), 3.61 (s, 3H), 3.35 (bs, 4H); LCMS: purity: 95.5%; MS (m/e): 337.18 (M−, 100) | + | + | + | + |
| 1270 | N4-(3,4-Dichlorophenyl)-5-fluoro-N2-[4-(N-methoxycarbonylmethyleneamino)carbonylphenyl]-2,4-pyrimidinediamine | 1H NMR (DMSO): δ 10.21 (s, 2H), 8.33 (m, 1H), 8.33 (d, 1H, J = 4.5 Hz), 8.10 (d, 1H, J = 2.4 Hz), 7.59-7.83 (m, 6H), 3.99 (m, 2H), 3.65 (s, 3H); LCMS: purity: 100%; MS (m/e): 462.11 (M−, 100). | + | + | | |
| 1271 | (S)-5-Fluoro-N2-[4-(N-methoxycarbonylmethyleneamino)carbonylphenyl]-N4-(2-methyl-3-oxo-2H,4H-benz[1,4]oxazin-6-yl)-2,4-pyrimidinediamine | 1H NMR (DMSO): δ 10.77 (s, 1H), 9.93 (bs, 1H), 8.77 (m, 1H), 8.20 (d, 1H, J = 4.5 Hz), 7.21-7.75 (m, 6H), 6.97 (d, 1H, J = 8.4 Hz), 4.66 (q, 1H, J = 6.6 Hz), 3.97 (m, 2H), 3.64 (s, 3H), 1.44 (d, 3H, J = 6.6 Hz); LCMS: purity: 96.7%; MS (m/e): 481.16 (MH+, 100). | + | + | − | |
| 1272 | (R)-5-Fluoro-N2-[4-(N-methoxycarbonylmethyleneamino)carbonylphenyl]-N4-(2-methyl-3-oxo-2H,4H-benz[1,4]oxazin-6-yl)-2,4-pyrimidinediamine | 1H NMR (DMSO): δ 10.77 (s, 1H), 9.93 (bs, 1H), 8.77 (m, 1H), 8.20 (d, 1H, J = 4.5 Hz), 7.21-7.75 (m, 6H), 6.97 (d, 1H, J = 8.4 Hz), 4.66 (q, 1H, J = 6.6 Hz), 3.97 (m, 2H), 3.64 (s, 3H), 1.44 (d, 3H, J = 6.6 Hz); LCMS: purity: 100%; MS (m/e): 481.39 (MH+, 100). | + | + | − | |
| 1273 | N2,N4-Bis[3-(N-tert-butoxycarbonylamino)methylenephenyl]-5-fluoro-2,4-pyrimidinediamine | 1H NMR (DMSO): δ 9.43 (s, 1H), 9.22 (s, 1H), 9.08 (d, 1H, J = 3.6 Hz), 7.24-7.72 (m, 7H), 7.15 (t, 1H, J = 7.8 Hz), 6.94 (d, 1H, J = 7.5 Hz), 6.78 (d, 1H, J = 7.5 Hz), 4.08 (m, 4H), 1.39 (s, 18H); LCMS: purity: 95.8%; MS (m/e): 537.16 (M−, 100). | + | + | | + |
| 1274 | N2,N4-Bis(3-aminomethylenephenyl)-5-fluoro-2,4-pyrimidinediamine | 1H NMR (DMSO): δ 9.24 (s, 1H), 8.35 (s, 1H), 8.01-8.07 (m, 2H), 6.73-7.71 (m, 7H), 3.69 (s, 2H), 3.61 (s, 2H); LCMS: purity: 100%; MS (m/e): 337.21 (M−, 100). | + | + | | |
| 1275 | N2-[3-(N-tert-Butoxycarbonylamino)methylenephenyl]-N4-(3,4-dichlorophenyl)-5-fluoro-2,4-pyrimidinediamine | LCMS: purity: 93.5%; MS (m/e): 476.19 (M−, 100) | + | + | | |
| 1276 | (S)—N2-[3-(N-tert-Butoxycarbonylamino)methylenephenyl]-5-fluoro-N4-(2-methyl-3-oxo-2H,4H-benz[1,4]oxazin-6-yl)-2,4-pyrimidinediamine | 1H NMR (DMSO): δ 10.61 (s, 1H), 9.30 (s, 1H), 9.04 (s, 1H), 8.03 (d, 1H, J = 3.9 Hz), 7.22-7.54 (m, 5H), 7.10 (t, 1H, J = 7.5 Hz), 6.92 (d, 1H, J = 7.5 Hz), 4.64 (q, 1H, J = 6.6 Hz), 4.01 (m, 2H), 1.44 (d, 3H, J = 6.6 Hz), 1.39 (s, 9H); LCMS: purity: 95.1%; MS (m/e): 493.28 (M−, 100). | + | + | | |
| 1277 | (R)—N2-[3-(N-tert-Butoxycarbonylamino)methylenephenyl]-5-fluoro-N4-(2-methyl-3-oxo-2H,4H-benz[1,4]oxazin-6-yl)-2,4-pyrimidinediamine | 1H NMR (DMSO): δ 10.61 (s, 1H), 9.30 (s, 1H), 9.04 (s, 1H), 8.03 (d, 1H, J = 3.9 Hz), 7.22-7.54 (m, 5H), 7.10 (t, 1H, J = 7.5 Hz), 6.92 (d, 1H, J = 7.5 Hz), 4.64 (q, 1H, J = 6.6 Hz), 4.01 (m, 2H), 1.44 (d, 3H, J = 6.6 Hz), 1.39 (s, 9H); LCMS: purity: 92.2%; MS (m/e): 493.28 (M−, 100). | + | + | | |
| 1278 | N2-(3-Aminomethylenephenyl)-N4-(3,4-dichlorophenyl)-5-fluoro-2,4-pyrimidinediamine | 1H NMR (DMSO): δ 9.60 (bs, 1H), 9.31 (s, 1H), 8.16 (d, 1H, J = 3.6 Hz), 8.12 (d, 1H, J = 2.7 Hz), 6.81-7.88 (m, 6H), 3.70 (s, 2H); LCMS: purity: 96.4%; MS (m/e): 376.11 (M−, 100). | + | + | | |
| 1279 | (S)—N2-(3-Aminomethylenephenyl)-5-fluoro-N4-(2-methyl-3-oxo-2H,4H-benz[1,4]oxazin-6-yl)-2,4-pyrimidinediamine | 1H NMR (DMSO): δ 9.30 (s, 1H), 9.08 (s, 1H), 4.63 (q, 1H, J = 6.9 Hz), 3.64 (s, 2H), 1.43 (d, 3H, J = 6.9 Hz); 6.76-7.60 (m, 8H), LCMS: purity: 100%; MS (m/e): 393.20 (M−, 100). | + | + | | |
| 1280 | (R)—N2-(3-Aminomethylenephenyl)-5-fluoro-N4-(2-methyl-3-oxo-2H,4H-benz[1,4]oxazin-6-yl)-2,4-pyrimidinediamine | 1H NMR (DMSO): δ 9.30 (s, 1H), 9.08 (s, 1H), 4.63 (q, 1H, J = 6.9 Hz), 3.64 (s, 2H), 1.43 (d, 3H, J = 6.9 Hz); 6.76-7.60 (m, 8H), LCMS: purity: 98.5%; MS (m/e): 393.20 (M−, 100). | + | + | | |
| 1281 | N4-(2,2-Dimethyl-3-oxo-4H-benz[1,4]oxazin-6-yl)-5-fluoro-N2-[3-(oxazol-2-yl)phenyl]-2,4-pyrimidinediamine | 1H NMR (DMSO): δ 10.69 (s, 1H), 10.18 (bs, 1H), 8.25 (d, 1H, J = 4.5 Hz), 8.12-8.17 (m, 2H), 7.73 (d, 1H, J = 8.1 Hz), 7.62 (d, 1H, J = 7.5 Hz), | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| | | 7.21-7.39 (m, m, 4H), 6.76 (d, 1H, J = 8.4 Hz), 1.38 (s, 6H); LCMS: purity: 100%; MS (m/e): 445.14 (M−, 100). | | | | |
| 1282 | (S)-5-Fluoro-N4-(2-methyl-3-oxo-2H,4H-benz[1,4]oxazin-6-yl)-N2-[3-(oxazol-2-yl)phenyl]-2,4-pyrimidinediamine | ¹H NMR (DMSO): δ 10.69 (s, 1H), 9.98 (bs, 2H), 8.22 (d, 1H, J = 2.4 Hz), 8.16 (m, 1H), 7.21-7.75 (m, 6H), 6.78 (d, 1H, J = 8.4 Hz), 4.62 (q, 1H, J = 6.9 Hz), 1.42 (d, 3H, J = 6.9 Hz); LCMS: purity: 97.3%; MS (m/e):431.15 (M−, 100). | + | + | − | |
| 1283 | (R)-5-Fluoro-N4-(2-methyl-3-oxo-2H,4H-benz[1,4]oxazin-6-yl)-N2-[3-(oxazol-2-yl)phenyl]-2,4-pyrimidinediamine | ¹H NMR (DMSO): δ 10.69 (s, 1H), 9.98 (bs, 2H), 8.22 (d, 1H, J = 2.4 Hz), 8.16 (m, 1H), 7.21-7.75 (m, 6H), 6.78 (d, 1H, J = 8.4 Hz), 4.62 (q, 1H, J = 6.9 Hz), 1.42 (d, 3H, J = 6.9 Hz); LCMS: purity: 94.9%; MS (m/e):431.15 (M−, 100). | + | + | − | |
| 1284 | N4-(2,2-Difluoro-3-oxo-4H-benz[1,4]oxazin-6-yl)-5-fluoro-N2-[3-(oxazol-2-yl)phenyl]-2,4-pyrimidinediamine | ¹H NMR (DMSO): δ 12.05 (s, 1H), 10.05 (s, 1H), 9.95 (s, 1H), 8.27 (m, 1H), 8.25 (d, 1H, J = 4.5 Hz), 8.14 (s, 1H), 7.32-7.75 (m, 6H), 7.13 (d, 1H, J = 9.0 Hz); LCMS: purity: 98.0%; MS (m/e): 453.12 (M−, 100). | + | + | − | |
| 1285 | N4-(4-Amino-3,4-dihydro-2H-1-benzopyran-6-yl)-5-fluoro-N2-[3-(oxazol-2-yl)phenyl]-2,4-pyrimidinediamine | LCMS: purity: 87.8%; MS (m/e): 417.18 (M−, 100). | + | + | − | |
| 1286 | N4-(2,2-Dimethyl-3-oxo-4H-benz[1,4]oxazin-6-yl)-5-fluoro-N2-[4-(N-methoxycarbonylmethyleneamino)carbonylphenyl]-2,4-pyrimidinediamine | ¹H NMR (DMSO): δ 10.71 (s, 1H), 9.91 (bs, 1H), 8.73 (m, 1H), 1.19 (d, 1H, J = 4.5 Hz), 7.19-7.74 (m, 6H), 6.94 (d, 1H, J = 8.4 Hz), 3.97 (m, 2H), 3.64 (s, 3H), 1.38 (s, 6H); LCMS: purity: 97.5%; MS (m/e): 493.22 (M−, 100). | + | + | + | |
| 1287 | N4-(4-N-tert-Butoxycarbonylamino-3,4-dihydro-2H-1-benzopyran-6-yl)-5-fluoro-N2-[3-(oxazol-5-yl)phenyl]-2,4-pyrimidinediamine | LCMS: purity: 89.3%; MS (m/e): 517.26 (M−, 100). | + | + | − | |
| 1288 | N4-(4-N-tert-Butoxycarbonylamino-3,4-dihydro-2H-1-benzopyran-6-yl)-5-fluoro-N2-[4-(oxazol-5-yl)phenyl]-2,4-pyrimidinediamine | LCMS: purity: 96.6%; MS (m/e): 516.90 (M−, 100). | + | + | + | |
| 1289 | N4-(4-N-tert-Butoxycarbonylamino-3,4-dihydro-2H-1-benzopyran-6-yl)-5-fluoro-N2-[4-(oxazol-2-yl)phenyl]-2,4-pyrimidinediamine | LCMS: purity: 87.2%; MS (m/e): 517.54 (M−, 100). | + | + | + | |
| 1290 | 5-Fluoro-N4-(4-hydroxy-3,4-dihydro-2H-1-benzopyran-6-yl)-N2-[4-(oxazol-5-yl)phenyl]-2,4-pyrimidinediamine | LCMS: purity: 100%; MS (m/e): 518.16 (M−, 100). | + | + | − | |
| 1291 | 5-Fluoro-N4-(4-hydroxy-3,4-dihydro-2H-1-benzopyran-6-yl)-N2-[4-(oxazol-2-yl)phenyl]-2,4-pyrimidinediamine | ¹H NMR (DMSO): δ 10.40 (s, 1H), 10.25 (s, 1H), 8.26 (d, 1H, J = 4.8 Hz), 8.15 (s, 1H), 7.65-7.83 (m, 4H), 7.50 (d, 1H, J = 2.7 Hz), 7.40 (dd, 1H, J 2.7, 8.4 Hz), 7.32 (s, 1H), 6.81 (d, 1H, J = 8.7 Hz), 4.59 (t, 1H, J = 5.1 Hz), 4.20-4.24 (m, 2H), 1.70-2.10 (m, 2H); LCMS: purity: 94.0%; MS (m/e): 418.03 (M−, 100). | + | + | − | |
| 1292 | (R,S)—N4-[4-Amino-3,4-dihydro-2H-1-benzopyran-6-yl)-5-fluoro-N2-[3-(oxazol-5-yl)phenyl]-2,4-pyrimidinediamine | ¹H NMR (DMSO-d6): δ 9.25 (s, 1H), 9.19 (s, 1H), 8.35 (s, 1H), 8.05 (d, J = 3.6 Hz, 1H), 7.99 (m, 1H), 7.20-7.63 (m, 5H), 6.62 (d, J = 8.7 Hz, 1H), 3.86-4.20 (m, 3H), 1.75-2.0 (m, 2H); LCMS: purity: 91.8%; MS (m/e): 419.3 (MH+). | + | + | | |
| 1293 | (R,S)—N4-[4-Amino-3,4-dihydro-2H-1-benzopyran-6-yl)-5-fluoro-N2-[4-(oxazol-5-yl)phenyl]-2,4-pyrimidinediamine | LCMS: purity: 98.0%; MS (m/e): 419.2 (MH+). | | + | | |
| 1294 | (R,S)—N4-[4-Amino-3,4-dihydro-2H-1-benzopyran-6-yl)-5-fluoro-N2-[4-(oxazol-2-yl)phenyl]-2,4-pyrimidinediamine | LCMS: purity: 93.5%; MS (m/e): 419.3 (MH+). | | + | | |
| 1295 | N4-(2,2-Dimethyl-3-oxo-4H-benz[1,4]oxazin-6-yl)-5-fluoro-N2-[4-[N-(N-methylamino)carbonylmethylene]aminocarbonylphenyl]-2,4-pyrimidinediamine | ¹H NMR (DMSO-d6): δ 10.73 (s, 1H), 9.97 (s, 1H), 9.87 (s, 1H), 8.53 (m, 1H), 8.19 (d, J = 4.2 Hz, 1H), 7.66-7.83 (m, 5H), 7.24-7.27 (m, 2H), 6.94 (d, J = 8.4 Hz, 1H), 3.78 (d, J = 5.7 Hz, 2H), 2.58 (d, J = 4.5 Hz, 3H), 1.41 (s, 6H); purity 98.2%; MS (m/e): 494.3 (MH+). | + | + | − | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1296 | (S)-5-Fluoro-N2-[4-[N-(N-methylamino)carbonylmethylene]aminocarbonyl phenyl]-N4-(2-methyl-3-oxo-2H,4H-benz[1,4]oxazin-6-yl)-2,4-pyrimidinediamine | 1H NMR (DMSO-d6): δ 10.85 (s, 1H), 10.21 (s, 1H), 9.98 (s, 1H), 8.58 (m, 1H), 8.22 (d, J = 4.5 Hz, 1H), 7.68-7.79 (m, 6H), 7.43 (m, 1H), 7.23 (m, 1H), 6.95 (d, J = 9.0 Hz, 1H), 4.65 (q, J = 6.3 Hz, 1H), 3.79 (m, 2H), 2.58 (d, J = 4.5 Hz, 3H), 1.43 (d, J = 6.3 Hz, 3H); LCMS: purity: 100%; MS (m/e): 480.3 (MH+). | + | + | − | |
| 1297 | N4-(2,2-Difluoro-3-oxo-4H-benz[1,4]oxazin-6-yl)-5-fluoro-N2-[4-[N-(N-methylamino)carbonylmethylene]aminocarbonyl phenyl]-2,4-pyrimidinediamine | 1H NMR (DMSO-d6): δ 12.11 (s, 1H), 9.87 (s, 1H), 9.81 (s, 1H), 8.53 (m, 1H), 8.20 (d, J = 3.9 Hz, 1H), 7.67-7.78 (m, 6H), 7.54 (dd, J = 2.4, 8.7 Hz, 1H), 7.29 (d, J = 9.0 Hz, 1H), 3.79 (d, J = 6.0 Hz, 2H), 2.58 (d, J = 4.2 Hz, 1H); LCMS: purity: 97.8%; MS (m/e): 502.3 (MH+). | + | | − | |
| 1298 | (R,S)—N4-[4-(N-tert-Butoxycarbonyl)amino-3,4-dihydro-2H-1-benzopyran-6-yl]-5-fluoro-N2-[4-[N-(N-methylamino)carbonylmethylene]aminocarbonyl phenyl]-2,4-pyrimidinediamine | LCMS: purity 97%; MS (m/e): 566.4 (MH+). | + | | − | |
| 1299 | (R,S)—N4-[4-Amino-3,4-dihydro-2H-1-benzopyran-6-yl]-5-fluoro-N2-[4-[N-(N-methylamino)carbonylmethylene]aminocarbonyl phenyl]-2,4-pyrimidinediamine | LCMS: purity: 93.5%; MS (m/e): 466.3 (MH+). | | | | + |
| 1300 | N4-(3,4-Dichlorophenyl)-5-fluoro-N2-[4-[N-(N-methylamino)carbonylmethylene]aminocarbonyl phenyl]-2,4-pyrimidinediamine | 1H NMR (DMSO-d6): δ 9.84 (s, 1H), 9.81 (s, 1H), 8.54 (m, 1H), 8.24 (d, J = 3.9 Hz, 1H), 8.10 (d, J = 2.4 Hz, 1H), 7.68-7.81 (m, 6H), 7.56 (d, J = 9.0 Hz, 1H), 3.79 (d, J = 6.0 Hz, 2H), 2.58 (d, J = 3.9 Hz, 3H); LCMS: purity: 100%; MS (m/e): 463.2 (MH+). | + | + | − | |
| 1301 | N4-(3,4-Dichlorophenyl)-5-fluoro-N4-methyl-N2-[4-[N-(N-methylamino)carbonylmethylene]aminocarbonyl phenyl]-2,4-pyrimidinediamine | 1H NMR (DMSO-d6): δ 9.75 (s, 1H), 8.50 (m, 1H), 8.12 (d, J = 4.8 Hz, 1H), 7.63-7.79 (m, 7H), 7.34 (dd, J = 2.4, 9.6 Hz, 1H), 3.78 (d, J = 4.8 Hz, 2H), 3.09 (s, 3H), 2.58 (d, J = 4.5 Hz, 3H); LCMS: purity: 94.1%; MS (m/e): 477.2 (MH+). | + | + | − | |
| 1302 | N4-(2,2-Dimethyl-3-oxo-4H-benz[1,4]oxazin-6-yl)-5-fluoro-N2-[4-[N-(2-methoxycarbonylethyl)aminocarbonyl]phenyl]-2,4-pyrimidinediamine | 1H NMR (DMSO-d6): δ 10.71 (s, 1H), 9.93 (bs, 2H), 8.32 (m, 1H), 8.19 (d, J = 4.8 Hz, 1H), 7.61-7.69 (m, 4H), 7.22-7.25 (m, 2H), 6.94 (d, J = 6.93 Hz, 1H), 3.60 (s, 3H), 3.44 (q, J = 6.9 Hz, 2H), 2.57 (t, J = 6.9 Hz, 2H), 1.41 (s, 6H); LCMS: purity: 97.5%; MS (m/e): 509.3 (MH+). | + | + | + | |
| 1303 | (S)-5-Fluoro-N2-[4-[N-(2-methoxycarbonylethyl)aminocarbonyl]phenyl]-N4-(2-methyl-3-oxo-2H,4H-benz[1,4]oxazin-6-yl)-2,4-pyrimidinediamine | 1H NMR (DMSO-d6): δ 10.83 (s, 1H), 10.32 (s, 1H), 10.13 (s, 1H), 8.39 (m, 1H), 8.25 (d, J = 4.8 Hz, 1H), 7.62-7.72 (m, 4H), 7.35 (s, 1H), 7.21 (dd, J = 2.4, 8.7 Hz, 1H), 6.96 (d, J = 8.7 Hz, 1H), 4.66 (q, J = 6.9 Hz, 1H), 3.59 (s, 3H), 3.43 (m, 2H), 2.57 (t, J = 7.6 Hz, 2H), 1.43 (d, J = 6.9 Hz, 3H); LCMS: purity: 90.1%; MS (m/e): 495.3 (MH+). | + | + | − | |
| 1304 | N4-(2,2-Difluoro-3-oxo-4H-benz[1,4]oxazin-6-yl)-5-fluoro-N2-[4-[N-(2-methoxycarbonylethyl)aminocarbonyl]phenyl]-2,4-pyrimidinediamine | 1H NMR (DMSO-d6): δ 12.15 (s, 1H), 9.85 (m, 2H), 8.31 (m, 1H), 8.20 (d, J = 4.2 Hz, 1H), 7.70-7.78 (m, 5H), 7.50 (d, J = 9.6 Hz, 1H), 7.27 (d, J = 9.90 Hz, 1H), 3.59 (s, 3H), 3.42 (m, 2H), 2.56 (t, J = 6.9 Hz, 2H); LCMS: purity: 88.5%; MS (m/e): 517.3 (MH+). | + | + | + | |
| 1305 | N4-(3,4-Dichlorophenyl)-5-fluoro-N2-[4-[N-(2-methoxycarbonylethyl)aminocarbonyl]phenyl]-2,4-pyrimidinediamine | 1H NMR (DMSO-d6): δ 9.82 (s, 1H), 9.77 (s, 1H), 8.36 (m, 1H), 8.24 (d, J = 3.9 Hz, 1H), 8.11 (d, J = 2.4 Hz, 1H), 7.65-7.79 (m, 5H), 7.56 (d, J = 8.7 Hz, 1H), 3.60 (s, 3H), 3.47 (q, J = 6.6 Hz, 2H), 2.57 (t, J = 6.6 Hz, 1H); purity 90.9%; MS (m/e): 478.2 (MH+). | + | + | + | |

-continued

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1306 | N4-(3,4-Dichlorophenyl)-5-fluoro-N2-[4-[N-(2-methoxycarbonylethyl)aminocarbonyl]phenyl]-N4-methyl-2,4-pyrimidinediamine | 1H NMR (DMSO-d6): δ 9.94 (s, 1H), 8.41 (m, 1H), 8.16 (d, J = 5.7 Hz, 1H), 7.64-7.75 (m, 6H), 7.36 (dd, J = 2.4, 8.7 Hz, 1H), 3.59 (s, 3H), 3.50 (s, 3H), 3.45 (m, 2H), 2.57 (t, J = 7.6 Hz, 2H); LCMS: purity: 88.5%; MS (m/e): 492.2 (MH+). | + | | | |
| 1307 | N2-[4-[1-(tert-Butoxycarbonylamino)methylenecarbonylamino]methylphenyl]-N4-(2,2-dimethyl-3-oxo-4H-benz[1,4]oxazin-6-yl)-5-fluoro-2,4-pyrimidinediamine | 1H NMR (DMSO-d6): δ 10.59 (s, 1H), 9.29 (s, 1H), 9.01 (s, 1H), 8.12 (m, 1H), 8.03 (d, J = 3.6 Hz, 1H), 7.56 (d, J = 9.0 Hz, 2H), 7.27 (dd, J = 2.1, 8.4 Hz, 1H), 7.21 (d, J = 2.4 Hz, 1H), 7.05 (d, J = 8.7 Hz, 2H), 6.90 (d, J = 9.0 Hz, 2H), 4.16 (d, J = 5.4 Hz, 2H), 3.54 (d, J = 5.4 Hz, 2H), 1.39 (s, 6H), 1.38 (s, 9H); LCMS: purity: 90.1%; MS (m/e): 566.5 (MH+). | + | + | + | |
| 1308 | (S)—N2-[4-[1-(tert-Butoxycarbonylamino)methylenecarbonylamino]methylphenyl]-5-fluoro-N4-(2-methyl-3-oxo-2H,4H-benz[1,4]oxazin-6-yl)-2,4-pyrimidinediamine | 1H NMR (DMSO-d6): δ 10.63 (s, 1H), 9.29 (s, 1H), 9.00 (s, 1H), 8.13 (m, 1H), 8.03 (d, J = 3.6 Hz, 1H), 7.29-7.57 (m, 3H), 7.21 (d, J = 2.1 Hz, 1H), 7.05 (d, J = 9.0 Hz, 2H), 6.90 (d, J = 8.4 Hz, 2H), 4.65 (q, J = 7.5 Hz, 1H), 4.16 (d, J = 5.7 Hz, 2H), 3.53 (d, J = 6.3 Hz, 2H), 1.43 (d, J = 6.6 Hz, 3H), 1.38 (s, 9H); LCMS: purity: 90.1%; MS (m/e): 552.4 (MH+). | + | + | | |
| 1309 | N2-[4-[1-(tert-Butoxycarbonylamino)methylenecarbonylamino]methylphenyl]-N4-(2,2-difluoro-3-oxo-4H-benz[1,4]oxazin-6-yl)-5-fluoro-2,4-pyrimidinediamine | 1H NMR (DMSO-d6): δ 9.52 (s, 1H), 9.08 (s, 1H), 8.13 (m, 1H), 8.09 (d, J = 3.3 Hz, 1H), 7.46-7.62 (m, 4H), 7.23 (d, J = 8.7 Hz, 2H), 7.07 (d, J = 8.4 Hz, 2H), 6.92 (m, 1H), 4.18 (d, J = 5.7 Hz, 2H), 3.54 (d, J = 5.7 Hz, 2H), 1.37 (s, 9H); LCMS: purity: 93.1%; MS (m/e): 574.4 (MH+). | + | + | − | |
| 1310 | N2-[4-[1-(tert-Butoxycarbonylamino)methylenecarbonylamino]methylphenyl]-N4-(3,4-dichlorophenyl)-5-fluoro-2,4-pyrimidinediamine | 1H NMR (DMSO-d6): δ 9.56 (s, 1H), 9.28 (s, 1H), 8.12-8.17 (m, 3H), 7.51-7.81 (m, 4H), 7.14 (d, J = 8.7 Hz, 2H), 6.93 (m, 1H), 4.20 (d, J = 6.3 Hz, 2H), 3.54 (d, J = 6.6 Hz, 2H), 1.38 (s, 9H); LCMS: purity: 94.1%; MS (m/e): 535.3 (MH+). | + | + | + | |
| 1311 | N2-[4-[1-(tert-Butoxycarbonylamino)methylenecarbonylamino]methylphenyl]-N4-(3,4-dichlorophenyl)-5-fluoro-N4-methyl-2,4-pyrimidinediamine | 1H NMR (DMSO-d6): δ 9.31 (s, 1H), 8.15 (m, 1H), 8.04 (d, J = 5.4 Hz, 1H), 7.55-7.66 (m, 4H), 7.30 (m, 1H), 7.08 (d, J = 8.7 Hz, 2H), 6.94 (m, 1H), 4.18 (d, J = 6.3 Hz, 2H), 3.54 (d, J = 6.3 Hz, 2H), 3.46 (s, 3H), 1.38 (s, 9H); LCMS: purity: 90.1%; MS (m/e): 549.3 (MH+). | + | | − | |
| 1312 | N2-[4-[N-(2-methoxycarbonylethyl)aminocarbonyl]phenyl]aminocarbonyl]phenyl]-2,4-pyrimidinediamine | LCMS: ret. time: 4.45 min. (9 min. method); purity: 95.3%; MS (m/e): 496.3 (MH+). | + | | | + |
| 1313 | N4-(2,2-Dimethyl-3-oxo-4H-5-pyrid[1,4]oxazin-6-yl)-5-fluoro-N2-(4-methoxycarbonylphenyl)-2,4-pyrimidinediamine | LCMS: ret. time: 4.00 min. (9 min. method); purity: 97.3%; MS (m/e): 439.3 (MH+). | + | | | |
| 1314 | N4-(2,2-Dimethyl-3-oxo-4H-5-pyrid[1,4]oxazin-6-yl)-5-fluoro-N2-(3-methoxycarbonylpyrid-2yl)-2,4-pyrimidinediamine | LCMS: ret. time: 4.00 min. (9 min. method); purity: 95.1%; MS (m/e): 440.4 (MH+). | + | | | |
| 1315 | N2-(4-Aminocarbonylphenyl)-N4-(2,2-dimethyl-3-oxo-4H-5-pyrid[1,4]oxazin-6-yl)-5-fluoro-2,4-pyrimidinediamine | LCMS: ret. time: 3.28 min. (9 min. method); purity: 98.1%; MS (m/e): 424.3 (MH+). | + | | | |
| 1316 | N2-(2-Aminocarbonylphenyl)-N4-(2,2-dimethyl-3-oxo-4H-5-pyrid[1,4]oxazin-6-yl)-5-fluoro-2,4-pyrimidinediamine | LCMS: ret. time: 3.98 min. (9 min. method); purity: 90.1%; MS (m/e): 424.5 (MH+). | + | | | |
| 1317 | N4-(2,2-Dimethyl-3-oxo-4H-benz[1,4]oxazin-6-yl)-5-fluoro-N2-(indazol-6-yl)-2,4-pyrimidinediamine Methanesulfonic Acid Salt | LCMS: ret. time: 8.50 min. (20 min. method); purity: 98.8%; MS (m/e): 420.1 (MH+). | | | | |
| 1318 | N4-(2,2-Difluoro-3-oxo-4H-benz[1,4]oxazin-6-yl)-5-fluoro-N2-[3-(N-methylamino)carbonyl]methyleneoxyphenyl]-2,4-pyrimidinediamine Methanesulfonic Acid Salt | LCMS: ret. time: 9.69 min. (20 min. method); purity: 98.4%; MS (m/e): 475.3 (MH+). | | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1319 | N4-(3-Chloro-4-methoxyphenyl)-5-fluoro-N2-(4-[N-[methoxycarbonylmethylene]aminocarbonyl]phenyl)-2,4-pyrimidinediamine | LCMS: ret. time: 3.17 min. (7 min. method); purity: 97.5%; MS (m/e): 460.3 (MH+). | | | | |
| 1320 | N4-(3-Chloro-4-methoxyphenyl)-5-fluoro-N2-(4-[2-[N,N-diethyl]amino]ethyleneaminocarbonyl]phenyl)-2,4-pyrimidinediamine | LCMS: ret. time: 2.64 min. (7 min. method); purity: 100%; MS (m/e): 487.3 (MH+). | | + | | + |
| 1321 | N2-(4-Aminocarbonylphenyl)-N4-(3-chloro-4-methoxyphenyl)-5-fluoro-2,4-pyrimidinediamine | LCMS: ret. time: 2.86 min. (7 min. method); purity: 100%; MS (m/e): 488.3 (MH+). | | + | | |
| 1322 | N4-(3-Chloro-4-methoxyphenyl)-5-fluoro-N2-(4-methoxycarbonylphenyl)-2,4-pyrimidinediamine | LCMS: ret. time: 4.02 min. (7 min. method); purity: 98.4%; MS (m/e): 403.3 (MH+). | | + | | |
| 1323 | N4-(3-Chloro-4-methoxyphenyl)-5-fluoro-N2-(4-[N-tert-butoxycarbonylaminomethylene]phenyl)-2,4-pyrimidinediamine | LCMS: ret. time: 3.83 min. (7 min. method); purity: 92.3%; MS (m/e): 474.3 (MH+). | | + | | |
| 1324 | N2-(4-Aminomethylenephenyl)-N4-(3-chloro-4-methoxyphenyl)-5-fluoro-2,4-pyrimidinediamine | LCMS: ret. time: 2.53 min. (7 min. method); purity: 96.6%; MS (m/e): 374.2 (MH+). | | + | | |
| 1325 | N4-(3-Chloro-4-methoxyphenyl)-5-fluoro-N2-(4-[N-[N-methyl]aminocarbonylmethylene]aminocarbonyl]phenyl)-2,4-pyrimidinediamine | LCMS: ret. time: 2.81 min. (7 min. method); purity: 100%; MS (m/e): 459.3 (MH+). | | | | |
| 1326 | 2-Chloro-5-fluoro-N4-(4-[N-[methoxycarbonylmethylene]aminocarbonyl]phenyl)-4-pyrimidineamine | LCMS: ret. time: 2.79 min. (7 min. method); purity: 100%; MS (m/e): 339.2 (MH+). | | − | | |
| 1327 | N4-[4-Aminocarbonylphenyl]-2-chloro-5-fluoro-4-pyrimidineamine | LCMS: ret. time: 2.40 min. (7 min. method); purity: 100%; MS (m/e): 267.1 (MH+). | | − | | |
| 1328 | 5-Fluoro-N2-(3-hydroxyphenyl)-N4-(4-[N-[methoxycarbonylmethylene]aminocarbonyl]phenyl)-2,4-pyrimidinediamine | LCMS: ret. time: 2.44 min. (7 min. method); purity: 94.9%; MS (m/e): 412.3 (MH+). | | + | | |
| 1329 | N2-(3,5-Dichloro-4-hydroxyphenyl)-5-fluoro-N4-(4-[N-[methoxycarbonylmethylene]aminocarbonyl]phenyl)-2,4-pyrimidinediamine | LCMS: ret. time: 9.92 min. (20 min. method); purity: 95.0%; MS (m/e): 482.0 (MH+). | | + | | |
| 1330 | N2-(3-Chloro-4-methoxyphenyl)-5-fluoro-N4-(4-[N-[methoxycarbonylmethylene]aminocarbonyl]phenyl)-2,4-pyrimidinediamine | LCMS: ret. time: 3.13 min. (7 min. method); purity: 95% MS (m/e): 460.3 (MH+). | + | + | | + |
| 1331 | N2-(2,2-Dimethyl-3-oxo-4H-benz[1,4]oxazin-6-yl)-5-fluoro-N4-(4-[N-[methoxycarbonylmethylene]aminocarbonyl]phenyl)-2,4-pyrimidinediamine | LCMS: ret. time: 2.80 min. (7 min. method); purity: 92.2%; MS (m/e): 495.3 (MH+). | + | + | | |
| 1332 | 5-Fluoro-N2,N4-bis(4-[N-[methoxycarbonylmethylene]aminocarbonyl]phenyl)-2,4-pyrimidinediamine | LCMS: ret. time: 2.77 min. (7 min. method); purity: 100%; MS (m/e): 511.4 (MH+). | + | + | | |
| 1333 | N2-(4-Aminocarbonylphenyl)-5-fluoro-N4-(4-[N-[methoxycarbonylmethylene]aminocarbonyl]phenyl)-2,4-pyrimidinediamine | LCMS: ret. time: 2.48 min. (7 min. method); purity: 97.6%; MS (m/e): 439.3 (MH+). | − | − | | |
| 1334 | N4-(4-Aminocarbonylphenyl)-5-fluoro-N2-(3-hydroxyphenyl)-2,4-pyrimidinediamine | LCMS: ret. time: 2.10 min. (7 min. method); purity: 100%; MS (m/e): 340.2 (MH+). | + | + | | |
| 1335 | N4-(4-Aminocarbonylphenyl)-N2-(3,5-dichloro-4-hydroxyphenyl)-5-fluoro-2,4-pyrimidinediamine | LCMS: ret. time: 8.72 min. (20 min. method); purity: 93.0%; MS (m/e): 410.0 (MH+). | + | + | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | fp_syk, 11 pt |
|---|---|---|---|---|---|---|
| 1336 | N4-(4-Aminocarbonylphenyl)-N2-(3-chloro-4-methoxyphenyl)-5-fluoro-2,4-pyrimidinediamine | LCMS: ret. time: 2.79 min. (7 min. method); purity: 100%; MS (m/e): 388.3 (MH+). | + | + | | |
| 1337 | N4-(4-Aminocarbonylphenyl)-N2-(2,2-dimethyl-3-oxo-4H-benz[1,4]oxazin-6-yl)-5-fluoro-2,4-pyrimidinediamine | LCMS: ret. time: 2.50 min. (7 min. method); purity: 100%; MS (m/e): 423.3 (MH+). | + | | | + |
| 1338 | N4-(Aminocarbonylphenyl)-5-fluoro-N2-(4-[N-[methoxycarbonylmethylene]aminocarbonyl]phenyl)-2,4-pyrimidinediamine | LCMS: ret. time: 2.52 min. (7 min. method); purity: 94.4%; MS (m/e): 439.3 (MH+). | + | + | | |
| 1339 | N2,N4-Bis(4-aminocarbonylphenyl)-5-fluoro-2,4-pyrimidinediamine | LCMS: ret. time: 2.26 min. (7 min. method); purity: 100%; MS (m/e): 367.3 (MH+). | − | − | | |
| 1340 | N4-(2,2-Dimethyl-3-oxo-4H-N4-oxo-5-pyrido[1,4]oxazin-6-yl)-5-fluoro-N2-(3,4,5-trimethoxyphenyl)-2,4-pyrimidinediamine | LCMS: ret. time: 3.48 min. (7 min. method); purity: 97.4%; MS (m/e): 487.3 (MH+). | + | + | | + |
| 1341 | N4-(4-Aminocarbonylphenyl)-5-fluoro-N2-(4-[3-methyl-1,2,4-oxadiazol-5-yl]methyleneoxyphenyl)-2,4-pyrimidinediamine | LCMS: ret. time: 2.72 min. (7 min. method); purity: 95.8%; MS (m/e): 436.3 (MH+). | + | + | | |
| 1342 | 5-Fluoro-N2-(4-[N-[methoxycarbonylmethylene]aminocarbonyl]phenyl)-N4-(4-[3-methyl-1,2,4-oxadiazol-5-yl]methyleneoxyphenyl)-2,4-pyrimidinediamine | LCMS: ret. time: 2.99 min. (7 min. method); purity: 95.1%; MS (m/e): 508.4 (MH+). | + | + | | + |
| 1343 | N2-(4-[2-[N,N-Diethylamino]ethyleneaminocarbonyl]phenyl)-5-fluoro-N4-(4-[3-methyl-1,2,4-oxadiazol-5-yl]methyleneoxyphenyl)-2,4-pyrimidinediamine | LCMS: ret. time: 2.58 min. (7 min. method); purity: 97.8%; MS (m/e): 535.4 (MH+). | + | + | | + |
| 1344 | N2-(3,5-Dichloro-4-hydroxyphenyl)-5-fluoro-N4-(4-[3-methyl-1,2,4-oxadiazol-5-yl]methyleneoxyphenyl)-2,4-pyrimidinediamine | LCMS: ret. time: 3.33 min. (7 min. method); purity: 95.0%; MS (m/e): 477.2 (MH+). | + | − | | |
| 1345 | N2-(3-Chloro-5-methoxyphenyl)-5-fluoro-N4-(4-[3-methyl-1,2,4-oxadiazol-5-yl]methyleneoxyphenyl)-2,4-pyrimidinediamine | LCMS: ret. time: 3.35 min. (7 min. method); purity: 96.4%; MS (m/e): 457.3 (MH+). | − | | | |
| 1346 | N2-(4-Aminocarbonylphenyl)-N4-(3,4-dichlorophenyl)-5-fluoro-N4-methyl-2,4-pyrimidinediamine | LCMS: ret. time: 3.86 min. (7 min. method); purity: 100%; MS (m/e): 406.2 (MH+). | + | + | | |
| 1347 | N2-(4-[2-[N,N-Diethylamino]ethyleneaminocarbonyl]phenyl)-N4-(3,4-dichlorophenyl)-5-fluoro-N4-methyl-2,4-pyrimidinediamine | LCMS: ret. time: 3.31 min. (7 min. method); purity: 100%; MS (m/e): 505.3 (MH+). | + | | | |
| 1348 | N4-(3,4-Dichlorophenyl)-5-fluoro-N2-(4-[N-[methoxycarbonylmethylene]aminocarbonyl]phenyl)-N4-methyl-2,4-pyrimidinediamine | LCMS: ret. time: 4.16 min. (7 min. method); purity: 95.8%; MS (m/e): 480.2 (MH+). | + | | | |
| 1349 | N2-(4-Aminocarbonylphenyl)-N4-(cyclopentyl)-5-fluoro-2,4-pyrimidinediamine | LCMS: ret. time: 2.26 min. (7 min. method); purity: 100%; MS (m/e): 316.3 (MH+). | − | | | |
| 1350 | N2-(4-[2-[N,N-diethylamino]ethyleneaminocarbonyl]phenyl)-5-fluoro-N4-(cyclopentyl)-2,4-pyrimidinediamine | LCMS: ret. time: 2.09 min. (7 min. method); purity: 97.3%; MS (m/e): 415.4 (MH+). | − | + | | |
| 1351 | N4-(Cyclopentyl)-5-fluoro-N2-(4-[N-[methoxycarbonylmethylene]aminocarbonyl]phenyl)-2,4-pyrimidinediamine | LCMS: ret. time: 2.62 min. (7 min. method); purity: 100%; MS (m/e): 388.3 (MH+). | + | + | | |
| 1352 | N2-(4-Aminocarbonylphenyl)-N4-(4-chloro-3-methoxyphenyl)-5-fluoro-2,4-pyrimidinediamine | LCMS: ret. time: 3.13 min. (7 min. method); purity: 96.4%; MS (m/e): 388.3 (MH+). | + | | | |

| Compound Number | Compound Name | Physical Data | LD Tryptase, CHMC, IgE, 3 pt | LD Tryptase, CHMC, IgE, 8 pt | LD Tryptase, CHMC, Iono, 3 pt | Tryptase, fp_syk, 11 pt |
|---|---|---|---|---|---|---|
| 1353 | N2-(4-Aminocarbonyl-3-chlorophenyl)-N4-(3-chloro-4-methoxyphenyl)-5-fluoro-2,4-pyrimidinediamine | LCMS: ret. time: 2.91 min. (7 min. method); purity: 89.5%; MS (m/e): 422.2 (MH+). | + | | | |
| 1354 | N2-(4-Aminocarbonyl-3-chlorophenyl)-N4-(4-chloro-3-methoxyphenyl)-5-fluoro-2,4-pyrimidinediamine | LCMS: ret. time: 3.14 min. (7 min. method); purity: 95.0%; MS (m/e): 422.2 (MH+). | + | + | | |
| 1355 | N4-(4-Chloro-3-methoxyphenyl)-N2-(4-[2-[N,N-diethylamino]ethyleneaminocarbonyl]phenyl)-5-fluoro-2,4-pyrimidinediamine | LCMS: ret. time: 2.80 min. (7 min. method); purity: 95.6%; MS (m/e): 487.4 (MH+). | + | + | | |
| 1356 | N4-(4-Chloro-3-methoxyphenyl)-5-fluoro-N2-(4-[N-[methoxycarbonyl]methyleneaminocarbonyl]phenyl)-2,4-pyrimidinediamine | LCMS: ret. time: 3.45 min. (7 min. method); purity: 94.6%; MS (m/e): 460.3 (MH+). | | | | |
| 1357 | N2-(4-Aminocarbonyl)phenyl)-5-fluoro-N4-phenyl-2,4-pyrimidinediamine | LCMS: ret. time: 2.58 min. (7 min. method); purity: 100%; MS (m/e): 424.3 (MH+). | + | + | | |
| 1358 | 5-Fluoro-N2-(3-hydroxyphenyl)-N4-(4-[3-methyl-1,2,4-oxadiazol-5-yl]methyleneoxyphenyl)-2,4-pyrimidinediamine hydrochloric acid salt | LCMS: ret. time: 2.72 min. (7 min. method); purity: 89.9%; MS (m/e): 409.3 (MH+). | | | | |

7.5 The Compounds are Effective for the Treatment of Autoimmunity

The in vivo efficacy of certain 2,4-pyrimidinediamine compounds towards autoimmune diseases was evaluated in the reverse passive Arthus reaction, an acute model of antigen-antibody mediated tissue injury, and in several disease models of autoimmunity and inflammation. These models are similar in that antibody to a specific antigen mediates immune complex-triggered (IC-triggered) inflammatory disease and subsequent tissue destruction. IC deposition at specific anatomic sites (central nervous system (CNS) for experimental autoimmune encephalomyelitis (EAE) and synovium for collagen-induced arthritis (CIA)) leads to activation of cells expressing surface FcγR and FcεR, notably mast cells, macrophages, and neutrophils, which results in cytokine release, and neutrophil chemotaxis. Activation of the inflammatory response is responsible for downstream effector responses, including edema, hemorrhage, neutrophil infiltration, and release of pro-inflammatory mediators. The consequences of these IC-triggered events are difficult to identify in autoimmune disorders; nonetheless, many investigators have demonstrated that inhibition of the FcγR signaling pathway in these animal models has resulted in a significant reduction in disease onset and severity.

7.5.1 The Compounds are Effective in Mouse Arthus Reaction

The in vivo efficacy of compounds 810, 944, 994 and 1007 to inhibit the IC-triggered inflammatory cascade was demonstrated in a mouse model of Reverse Passive Arthus Reaction (RPA reaction).

7.5.1.1 Model

Immune complex (IC)-mediated acute inflammatory tissue injury is implicated in a variety of human autoimmune diseases, including vasculitis syndrome, sick serum syndrome, systemic lupus erythematosus (SLE), rheumatoid arthritis, Goodpasture's syndrome, and glomerulonephritis. The classical experimental model for IC-mediated tissue injury is the reverse passive Arthus reaction. The RPA reaction model is a convenient in vivo method to study localized inflammation, induced by ICs, without systemic effects. Intradermal injection of antibodies (Abs) specific to chicken egg albumin (rabbit anti-OVA IgG), followed by intravenous (IV) injection of antigens (Ags), specifically chicken egg albumin (ovalbumin, OVA), causes perivascular deposition of ICs and a rapid inflammatory response characterized by edema, neutrophil infiltration and hemorrhage at the injection sites. Aspects of the mouse RPA reaction model resemble the inflammatory response of patients with rheumatoid arthritis, SLE and glomerulonephritis.

7.5.1.2 Study Protocol

In this model system, test compounds are administered at several timepoints prior to administration of Abs and Ags. A solution of rabbit anti-OVA IgG (50 μg in 25 μl/mouse) is injected intradermally, and immediately following is an intravenous injection of chicken egg albumin (20 mg/kg of body weight) in a solution containing 1% Evans blue dye. The degree of edema and hemorrhage is measured in the dorsal skin of C57BL/6 mice using the Evan's Blue dye as an indicator of local tissue damage. Purified polyclonal rabbit IgG is used as a control.

Pretreatment time, in which the test compounds are administered prior to Ab/Ag challenge, depends on the pharmacokinetic (PK) properties of each individual compound. Four hours after induction of Arthus reaction, mice are euthanized, and tissues are harvested for assessment of edema. This model system allows us to rapidly screen the in vivo activity of many inhibitors.

7.5.1.3 Results

All compounds tested were administered by the oral route.

Compound 994, when administered at a dose level of 100 mg/kg 90 minutes prior to Ab/Ag challenge in C57B16 mice, showed dose-dependent inhibition of edema formation (75%).

Compounds 1007 and 810 showed the efficacy of edema inhibition by 89.4% and 81.3%, respectively, when administered at 1.0 mg/kg, 30 minutes prior to challenge.

Compound 1007 showed 64.3%, 78.7%, 98.1% and 99.8%, inhibition of edema formation when administered at dose levels of 0.1 mg/kg, 0.5 mg/kg, 1.0 mg/kg and 5 mg/kg and a pretreatment time of 30, respectively. Results for the compounds tested are summarized in Table 2.

TABLE 2

Mouse Cutaneous Reverse Passive Arthus (RPA) Reaction Summary

| Compound Name | Compound Number | Dosage (mg/kg) | Pretreatment Time (hrs) | % inhibition to vehicle control Edema Size ± SEM | Satellite: At time of challenge Plasma Concentration ± SEM (ng/ml) | Exposure = Pretreatment Time + 4 hours Plasma Concentration ± SEM (ng/ml) | in vitro Potency (CHMC IgE) |
|---|---|---|---|---|---|---|---|
| 994 | | 100 | | 75.0 ± 6.2 | 78.6 ± 26.4 | 44.2 ± 8.9 | 0.047 |
| 1007 | | 1 | 0.5 | 89.4 ± 2.2 | | | |
| | | 3 | 0.5 | 86.3 ± 7.9 | | | |
| | | 10 | 0.5 | 97.8 ± 1.1 | | | |
| | | 30 | 0.5 | 88.2 ± 5.7 | | | |
| 1007 | | 0.1 | 0.5 | 64.3 ± 11.2 | 24.4 ± 9.6 | BLQ | |
| | | 0.5 | 0.5 | 78.7 ± 6.3 | 73.1 ± 14.5 | BLQ | |
| | | 1 | 0.5 | 98.1 ± 0.8 | 90.0 ± 11.0 | 2.3 ± 0.9 | |
| | | 5 | 0.5 | 99.8 ± 0.2 | 398.0 ± 30.2 | 19.8 ± 15.7 | |
| 810 | | 0.1 | 0.5 | 69.5 ± 19.6 | | | |
| | | 0.5 | 0.5 | 60.9 ± 9.6 | | | |
| | | 1 | 0.5 | 81.3 ± 8.4 | | | |
| | | 5 | 0.5 | 92.1 ± 3.1 | | | |
| 944 | | 2 | 1 | 39.3 ± 13.8 | NA | 4.3 ± 4.2 | |
| | | 5 | 1 | 48.4 ± 12.0 | NA | 3.5 ± 5.3 | |
| | | 15 | 1 | 56.1 ± 9.2 | NA | 29.7 ± 25.9 | |
| 944 | | 0.5 | 5 | −16.0 ± 17.3 | 22.1 ± 52.4 | 3.4 ± 9.1 | |
| | | 0.5 | 15 | 8.3 ± 13.4 | 1074.0 ± 492.3 | 85.1 ± 161.9 | |

7.5.2 The Compounds are effective in Mouse Collagen Antibody Induced Arthritis Model The in vivo efficacy of compounds towards autoimmune diseases can be demonstrated in a mouse model of collagen antibody-induced arthritis (CAIA).

7.5.2.1 Model

Collagen-induced arthritis (CIA) in rodents is frequently used as one of the experimental models for IC-mediated tissue injury. Administration of type II collagen into mice or rats results in an immune reaction that characteristically involves inflammatory destruction of cartilage and bone of the distal joints with concomitant swelling of surrounding tissues. CIA is commonly used to evaluate compounds that might be of potential use as drugs for treatment of rheumatoid arthritis and other chronic inflammatory conditions.

In recent years, a new technique emerged in CIA modeling, in which the anti-type II collagen antibodies are applied to induce an antibody-mediated CIA. The advantages of the method are: Short time for induction of disease (developing within 24-48 hrs after an intravenous (IV) injection of antibodies); arthritis is inducible in both CIA-susceptible and CIA-resistant mouse strains; and the procedure is ideal for rapid screening of anti-inflammatory therapeutic agents.

Arthrogen-CIA® Arthritis-inducing Monoclonal Antibody Cocktail (Chemicon International Inc.) is administered intravenously to Balb/c mice (2 mg/mouse) on Day 0. Forty-eight hours later, 100 µl of LPS (25 µg) is injected intraperitoneally. On Day 4, toes may appear swollen. By Day 5, one or two paws (particular the hind legs) begin to appear red and swollen. On Day 6, and thereafter, red and swollen paws will remain for at least 1-2 weeks. During the study, the clinical signs of inflammation are scored to evaluate the intensity of edema in the paws. The severity of arthritis is recorded as the sum score of both hind paws for each animal (possible maximum score of 8). The degree of inflammation with involved paws is evaluated by measurement of diameter of the paws. Body weight changes are monitored.

Animals can be treated at the time of induction of arthritis, beginning on Day 0. Test compounds and control compounds can be administered once a day (q.d.) or twice a day (b.i.d.), via per os (PO), depending on previously established PK profiles.

At the end of the study (1-2 weeks after induction of arthritis), mice are euthanized and the paws are transected at the distal tibia using a guillotine and weighed. The mean±standard error of the mean (SEM) for each group is determined each day from individual animal clinical scores, and hind paw weights for each experimental group are calculated and recorded at study termination. Histopathological evaluation of paws are obtained.

7.5.2.2 Results

Reduced inflammation and swelling should be evident in animals treated with compounds of the invention, and the arthritis would progress more slowly. Treatment with compounds should (b.i.d.) significantly reduce clinical arthritis compared with animals treated with vehicle only.

7.5.3 The Compounds can be Effective in Rat Collagen-Induced Arthritis

The in vivo efficacy of compounds of the invention towards autoimmune diseases can be demonstrated in a rat model of collagen-induced arthritis (CIA).

7.5.3.1 Model Description

Rheumatoid arthritis (RA) is characterized by chronic joint inflammation eventually leading to irreversible cartilage destruction. IgG-containing IC are abundant in the synovial tissue of patients with RA. While it is still debated what role these complexes play in the etiology and pathology of the disease, IC communicate with the hematopoetic cells via the FcγR.

CIA is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

7.5.3.2 Study Protocol

Syngeneic LOU rats were immunized on Day 0 with native chicken CII/IFA (performed at UCLA; E. Brahn, Principal Investigator). Beginning on the day of arthritis onset (Day 10), a total of 59 rats can be treated with either a vehicle control or a compound of the invention at one of four dose levels (1, 3, 10, and 30 mg/kg, q.d. by p.o. gavage).

7.5.3.3 Results

Hind limbs would be scored daily for clinical arthritis severity using a standardized method based on the degree of joint inflammation. High resolution digital radiographs of hind limbs can be obtained at the conclusion of the study (Day 28). These limbs can also be analyzed for histopathologic changes. IgG antibodies to native CII can be measured in quadruplicate by ELISA.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. A compound according to the structural formula:

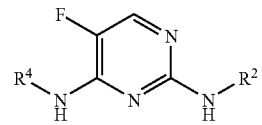

or a salt and/or N-oxide thereof, wherein:

$R^2$ is selected from the group consisting of (C1-C6) alkyl optionally substituted with one or more of the same or different $R^8$ groups, (C3-C8) cycloalkyl optionally substituted with one or more of the same or different $R^8$ groups, 3-8 membered cycloheteroalkyl optionally substituted with one or more of the same or different $R^8$ groups and 5-15 membered heteroaryl optionally substituted with one or more of the same or different $R^8$ groups;

$R^4$ is

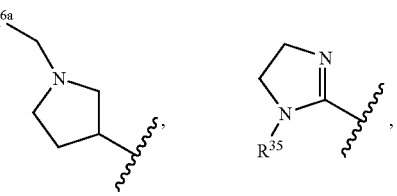

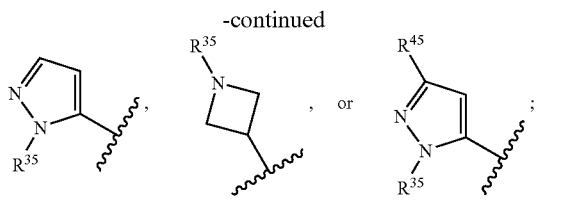

$R^{6a}$ is (C5-C10) aryl optionally substituted with one or more of the same or different $R^8$ groups;

$R^8$ is selected from the group consisting of $R^a$, $R^b$, $R^a$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—$(CH_2)_m$—$R^b$, —O—$CHR^aR^b$, —O—$CR^a(R^b)_2$, —O—$(CHR^a)_m$—$R^b$, —O—$(CH_2)_m$—$CH[(CH_2)_mR^b]R^b$, —S—$(CHR^a)_m$—$R^b$, —C(O)NH—$(CH_2)_m$—$R^b$, —C(O)NH—$(CHR^a)_m$—$R^b$, —O—$(CH_2)_m$—C(O)NH$(CH_2)_m$—$R^b$, —S—$(CH_2)_m$—C(O)NH—$(CH_2)_mR^b$, —O—$(CHR^a)_m$—C(O)NH—$(CHR^a)_m$—$R^b$, —S—$(CHR^a)_m$—C(O) NH$(CHR^a)_m$—$R^b$, —NH—$(CH_2)_m$—$R^b$, —NH—$(CHR^a)_m$—$R^b$, —NH[$(CH_2)_mR^b$], —N[$(CH_2)_mR^b$]$_2$, —NH—C(O)—NH—$(CH_2)_m$—$R^b$, —NH—C(O)—$(CH_2)_m$—$CHR^bR^b$, and —NH—$(CH_2)_m$—C(O)—NH—$(CH_2)_m$—$R^b$;

each $R^a$ is independently selected from the group consisting of hydrogen, (C1-C6) alkyl, (C3-C8) cycloalkyl, (C4-C11) cycloalkylalkyl, (C5-C10) aryl, (C6-C16) arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;

each $R^b$ is a group independently selected from the group consisting of =O, —$OR^d$, (C1-C3) haloalkyloxy, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —S(O)$R^d$, —S(O)$_2R^d$, —S(O)$_2OR^d$, —S(O)$NR^cR^c$, —S(O)$_2NR^cR^c$, —OS(O)$R^d$, —OS(O)$_2R^d$, —OS(O)$_2OR^d$, —OS(O)$_2NR^cR^c$, —C(O)$R^d$, —C(O)$OR^d$, —C(O)$NR^cR^c$, —C(NH)$NR^cR^c$, —C($NR^a$)$NR^cR^c$, —C(NOH)$R^a$, —C(NOH)$NR^cR^c$, —OC(O)$R^d$, —OC(O)$OR^d$, —OC(O)$NR^cR^c$, —OC(NH)$NR^cR^c$, —OC($NR^a$)$NR^cR^c$, —[NHC(O)]$_nR^d$, —[$NR^a$C(O)]$_nR^d$, —[NHC(O)]$_nOR^d$, —[$NR^a$C(O)]$_nOR^d$, —[NHC(O)]$_nNR^cR^c$, —[$NR^a$C(O)]$_nNR^cR^c$, —[NHC(NH)]$_nNR^cR^c$ and —[$NR^a$C($NR^a$)]$_nNR^cR^c$;

each $R^c$ is independently $R^a$, or, alternatively, each $R^c$ is taken together with the nitrogen atom to which it is bonded to form a 5-8-membered cycloheteroalkyl or heteroaryl which may optionally include one or more of the same or different additional heteroatoms and which is optionally substituted with one or more of the same of different $R^a$ or $R^b$ groups;

each $R^d$ is independently $R^a$;

each m is independently an integer from 1 to 3;

each n is independently an integer from 0 to 3;

$R^{35}$ is a hydrogen or a $R^8$; and $R^{45}$ is a (C3-C8) cycloalkyl optionally substituted with one or more of the same or different $R^8$ groups.

2. The compound of claim 1, wherein $R^2$ is cyclohexyl optionally substituted with one or more of the same or different $R^8$ groups.

3. The compound of claim 1, wherein $R^{35}$ is hydrogen.

* * * * *